United States Patent
Rosinko et al.

(10) Patent No.: US 11,529,466 B2
(45) Date of Patent: Dec. 20, 2022

(54) CLOUD-CONNECTED AMBULATORY PUMP INTEGRATION

(71) Applicant: Beta Bionics, Inc., Irvine, CA (US)

(72) Inventors: Michael J. Rosinko, Las Vegas, NV (US); Himanshu Patel, Rancho Santa Margarita, CA (US); Edward R. Damiano, Acton, MA (US); Firas H. El-Khatib, Allston, MA (US)

(73) Assignee: Beta Bionics, Inc., Irvine, CA (US)

( * ) Notice: Subject to any disclaimer, the term of this patent is extended or adjusted under 35 U.S.C. 154(b) by 0 days.

(21) Appl. No.: 17/657,086

(22) Filed: Mar. 29, 2022

(65) Prior Publication Data

US 2022/0305202 A1 Sep. 29, 2022

Related U.S. Application Data

(63) Continuation of application No. PCT/US2022/017368, filed on Feb. 22, 2022, which is a continuation-in-part of application No. PCT/US2021/012795, filed on Jan. 18, 2022, and a continuation-in-part of application No. PCT/US2021/064228, filed on Dec. 17, 2021, and a continuation-in-part of application No. PCT/US2021/072742, filed on Dec. 3, 2021, application No. PCT/US2021/064228, which is a continuation-in-part of application No. PCT/US2021/072742, filed on Dec. 3, 2021, which is a continuation of application No. 63/139,210, filed on Jan. 19, 2021, which is a continuation of application No. 63/128,428, filed on Dec. 21, 2020, which is a continuation of application No. 63/122,427, filed on Dec. 7, 2020.

(Continued)

(51) Int. Cl.
| | | |
|---|---|---|
| A61M 5/172 | (2006.01) | |
| G06Q 30/06 | (2012.01) | |
| G06Q 20/10 | (2012.01) | |

(52) U.S. Cl.
CPC ......... *A61M 5/1723* (2013.01); *G06Q 20/102* (2013.01); *G06Q 30/0633* (2013.01); *A61M 2205/3553* (2013.01); *A61M 2205/52* (2013.01); *A61M 2209/01* (2013.01); *A61M 2230/201* (2013.01)

(58) Field of Classification Search
None
See application file for complete search history.

(56) References Cited

U.S. PATENT DOCUMENTS

| | | |
|---|---|---|
| 4,585,439 A | 4/1986 | Michel |
| 11,238,133 B1 | 2/2022 | Brewer et al. |

(Continued)

OTHER PUBLICATIONS

International Search Report and Written Opinion dated May 31, 2022 in application No. PCT/US2022/017368.

*Primary Examiner* — Manuel A Mendez
(74) *Attorney, Agent, or Firm* — Knobbe, Martens, Olson & Bear, LLP

(57) ABSTRACT

Ambulatory medical devices, which includes ambulatory medicament pumps, and blood glucose control systems that provide therapy to a subject, such as blood glucose control, are disclosed. Disclosed systems and devices can implement one or more features that improve the user experience, such as prompting and/or facilitating the user to order additional infusion sets, sensors, and/or other components to facilitate treatment.

30 Claims, 84 Drawing Sheets

Related U.S. Application Data

(60) Provisional application No. 63/264,645, filed on Nov. 29, 2021, provisional application No. 63/263,602, filed on Nov. 5, 2021, provisional application No. 63/276,481, filed on Nov. 5, 2021, provisional application No. 63/249,975, filed on Sep. 29, 2021, provisional application No. 63/261,290, filed on Sep. 16, 2021, provisional application No. 63/239,365, filed on Aug. 31, 2021, provisional application No. 63/238,670, filed on Aug. 30, 2021, provisional application No. 63/216,177, filed on Jun. 29, 2021, provisional application No. 63/215,857, filed on Jun. 28, 2021, provisional application No. 63/212,521, filed on Jun. 18, 2021, provisional application No. 63/194,126, filed on May 27, 2021, provisional application No. 63/183,900, filed on May 4, 2021, provisional application No. 63/169,112, filed on Mar. 31, 2021, provisional application No. 63/168,203, filed on Mar. 30, 2021, provisional application No. 63/167,563, filed on Mar. 29, 2021, provisional application No. 63/157,541, filed on Mar. 5, 2021, provisional application No. 63/152,744, filed on Feb. 23, 2021, provisional application No. 63/152,716, filed on Feb. 23, 2021, provisional application No. 63/151,565, filed on Feb. 19, 2021.

(56) References Cited

U.S. PATENT DOCUMENTS

| | | |
|---|---|---|
| 2010/0198143 A1 | 8/2010 | Estes |
| 2011/0152756 A1 | 6/2011 | Drew |
| 2014/0058349 A1 | 2/2014 | Bazargan et al. |
| 2016/0317744 A1 | 11/2016 | Estes et al. |
| 2017/0258986 A1 | 9/2017 | Tsoukalis |

CLOUD-CONNECTED AMBULATORY PUMP INTEGRATION

INCORPORATION BY REFERENCE

This application is a continuation of PCT Application No. PCT/US2022/17368, filed Feb. 2, 2022, which claims priority to U/S. Provisional Patent No. 63/167,563, filed Mar. 29, 2021; 63/216,177, filed Jun. 29, 2021; 63/239,365, filed Aug. 31, 2021; 63/169,112, filed Mar. 31, 2021; 63/151,565, filed Feb. 19, 2021; 63/261,290, filed Sep. 16, 2021; 63/152,744, filed Feb. 23, 2021; 63/157,541, filed Mar. 5, 2021; 63/152,716, filed Feb. 23, 2021; 63/168,203, filed Mar. 30, 2021; 63/212,521, filed Jun. 18, 2021; 63/238,670, filed Aug. 30, 2021; 63/276,481, filed Nov. 5, 2021; 63/215,857, filed Jun. 28, 2021; 63/183,900, filed May 4, 2021; 63/249,975, filed Sep. 29, 2021; 63/194,126, filed May 27, 2021; 63/263,602, filed Nov. 5, 2021; 63/264,645, filed Nov. 29, 2021, and 63/295,361, filed Dec. 30, 2021.

The PCT Application No. PCT/US2022/17368 is a continuation-in-part of PCT Application No. PCT/US2021/072742, filed Dec. 3, 2021, which claims priority to U.S. Provisional Patent No. 63/122,427, filed Dec. 7, 2020; 63/169,112, filed Mar. 31, 2021; 63/151,565, filed Feb. 19, 2021; 63/261,290, filed Sep. 16, 2021; 63/128,428, filed Dec. 21, 2020; 63/152,744, filed Feb. 23, 2021; 63/157,541, filed Mar. 5, 2021; 63/152,716, filed Feb. 23, 2021; 63/168,203, filed Mar. 30, 2021; 63/212,521, filed Jun. 18, 2021; 63/139,210, filed Jan. 19, 2021; 63/276,481, filed Nov. 5, 2021; 63/215,857, filed Jun. 28, 2021; 63/183,900, filed May 4, 2021; 63/167,563, filed Mar. 29, 2021; 63/216,177, filed Jun. 29, 2021; 63/249,975, filed Sep. 29, 2021; 63/194,126, filed May 27, 2021; 63/239,365, filed Aug. 31, 2021; 63/263,602, filed Nov. 5, 2021; 63/264,645, filed Nov. 29, 2021, and 63/238,670, filed Aug. 30, 2021.

The PCT Application No. PCT/US2022/17368 is a continuation-in-part of PCT Application No. PCT/US2021/064228, filed Dec. 17, 2021, which claims priority to U.S. Provisional Patent No. 63/128,428, filed Dec. 21, 2020; 63/167,563, filed Mar. 29, 2021; 63/216,177, filed Jun. 29, 2021; 63/239,365, filed Aug. 31, 2021; 63/169,112, filed Mar. 31, 2021; 63/151,565, filed Feb. 19, 2021; 63/261,290, filed Sep. 16, 2021; 63/152,744, filed Feb. 23, 2021; 63/157,541, filed Mar. 5, 2021; 63/152,716, filed Feb. 23, 2021; 63/168,203, filed Mar. 30, 2021; 63/212,521, filed Jun. 18, 2021; 63/139,210, filed Jan. 19, 2021; 63/238,670, filed Aug. 30, 2021; 63/276,481, filed Nov. 5, 2021; 63/215,857, filed Jun. 28, 2021; 63/183,900, filed May 4, 2021; 63/249,975, filed Sep. 29, 2021; 63/194,126, filed May 27, 2021; 63/263,602, filed Nov. 5, 2021, and 63/264,645, filed Nov. 29, 2021. The PCT Application No. PCT/US2021/064228 is a continuation-in-part of PCT Application No. PCT/US2021/072742.

The PCT Application No. PCT/US2022/17368 is a continuation-in-part of PCT Application No. PCT/US2022/012795, filed Jan. 18, 2022 which claims priority to U.S. Provisional Patent No. 63/139,210, and filed Jan. 19, 2021; 63/238,670, filed Aug. 30, 2021. The entire contents of each application referenced in this paragraph are hereby incorporated by reference herein for all purposes and made part of this specification. Any and all applications for which a foreign or domestic priority claim is identified in the Application Data Sheet as filed with the present application are hereby incorporated by reference under 37 CFR 1.57.

BACKGROUND

Technical Field

This disclosure relates to glucose control systems, including medical devices that provide glucose control therapy to a subject, glucose level control systems, and ambulatory medicament pumps that deliver medicament to the subject to control glucose level in the subject.

Description of Related Art

Sustained delivery, pump driven medicament injection devices generally include a delivery cannula mounted in a subcutaneous manner through the skin of the subject at an infusion site. The pump draws medicine from a reservoir and delivers it to the subject via the cannula. The injection device typically includes a channel that transmits a medicament from an inlet port to the delivery cannula which results in delivery to the subcutaneous tissue layer where the delivery cannula terminates. Some infusion devices are configured to deliver one medicament to a subject while others are configured to deliver multiple medicaments to a subject. The medicament and/or supplies (infusion sets, analyte sensors, transmitters, and/or other components), must be monitored and periodically replaced, which requires the subject keep track of the amount of medicament and/or supplies left. Failure to maintain an adequate supply of medicament and other supplies can disrupt treatment.

Healthcare providers and payers are generally interested in therapy reports that include outcomes of glucose control therapy provided to a group of subjects each receiving glucose control therapy by a glucose level control system. Such therapy reports may provide useful information for improving the quality of glucose control therapy provided to a group of subjects and/or reducing the cost glucose level control therapy.

SUMMARY

Glucose level control system and ambulatory medical devices that provide therapy to a subject, such as glucose level control, are disclosed. Disclosed systems and devices can implement one or more features that improve the user experience, such as software update techniques that avoid interrupting delivery of therapy, gesture-based control of therapy delivery, automatic resumption of therapy after a user-initiated pause, improved alarm management, display of autonomously calculated dosing recommendations, wide area network connectivity, security features, automatically detecting when additional medicament and/or supplies (infusion sets, analyte sensors, transmitters, and/or other components) are needed, automatically prompting and/or facilitating the process for ordering additional medicament and supplies, modifying glucose control therapy remotely via a wireless connection, and allowing modification of glucose level control therapy based on requests received via voice/verbal commands.

Some embodiments described herein pertain to glucose level control systems (GLCSes) for providing, managing, and facilitating glucose control therapy. In some cases, the disclosed GLCSes may include interconnected remote computing systems, mobile electronic devices, and medicament delivery devices that cooperatively improve the glucose control therapy provided to a subject by facilitating various tasks associated with glucose therapy delivery, such as software update, controlling and modifying therapy delivery, monitoring and ordering supply and medicament. Additionally or alternatively, the disclosed GLCSes may include automated systems that autonomously calculate dosing recommendations, monitor medicament and/or supplies, order additional medicament and/or supplies, and modify glucose control therapy.

Additionally, some of the disclosed systems and methods can be implemented by a computing system to generate and share aggregate reports that include a summary of glucose control therapy provided to a group of subjects by the glucose level control systems or ambulatory medicament pumps, the resulting glycemic control of the subjects, comparative assessments, and evaluation of the therapy outcomes with respect to reference data and selected evaluation criteria. Such therapy reports may be used to: evaluate a performance of the glucose level control systems, modify a control parameter of the glucose level control systems, evaluate the glycemic control of different groups of subjects receiving glucose control therapy from the same or different types of glucose level control systems, and any other assessment.

BRIEF DESCRIPTION OF THE DRAWINGS

The systems, methods, and devices of this disclosure each have several innovative aspects, no single one of which is solely responsible for all of the desirable attributes disclosed herein. Details of one or more implementations of the subject matter described in this specification are set forth in the accompanying drawings and the description below.

DETAILED DESCRIPTION

Figure 1A:
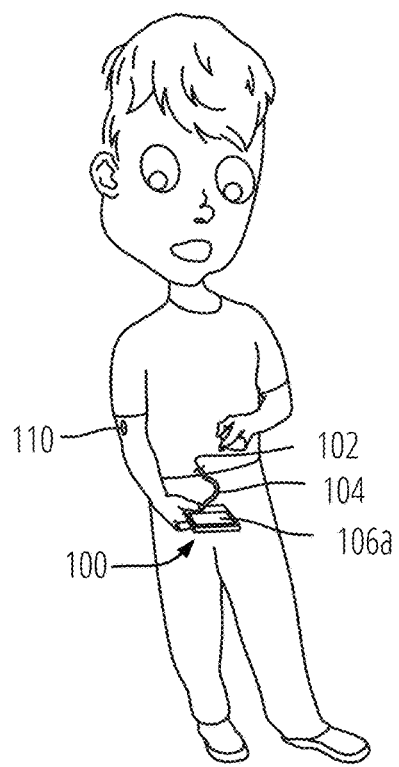
FIG. 1A illustrates an example glucose level control system that provides glucose level control via an ambulatory medicament pump.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to methods of manufacturing infusion systems and components thereof. Some embodiments pertain to methods of using any of the foregoing systems or components for infusing one or more medicaments (e.g., pharmaceutical, hormone, etc.) to a subject. As an exemplary illustration, an infusion system may include an infusion pump, which can include one or more medicament cartridges or can have an integrated reservoir of medicament. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. A glucose level control system can operate in conjunction with an infusion system to infuse one or more medicaments, including at least one glucose level control agent, into a subject. An infusion system may include a user interface that allow modifying one or more control parameters that control medicament delivery to a subject. An infusion system may include a wireless transceiver that allows data communication between the infusion system and one or more electronic devices.

Some embodiments described herein pertain to computing systems for generating aggregate reports. Some embodiments pertain to a computing system (e.g., a computing system in patient data network) that requests and receives therapy data from a plurality of Glucose Level Control Systems (GLCSes) or Ambulatory Medicament Pump (AMPs) that provide glucose level control therapy to a group of subjects. The computing system may request and receive the therapy data via data connections (e.g., wireless data connections) established with the GLCSes. As an exemplary illustration, the computing system may include an electronic processor, a memory that stores machine readable instructions usable by the electronic processor, and reference data associated with glycemic control of a subject and/or performance of a GLCS. The processor may process the received therapy data to generate aggregate therapy data, determine the values of one or more biometric parameters, and to generate a comparative assessment and an evaluation using the reference data, aggregate therapy data and aggregate biometric data. Subsequently, the computing system generates an aggregate report that may include representations (e.g., graphical and/or textual representations) of the aggregate therapy data, the aggregate biometric data, the comparative assessment, and the evaluation. In some cases, the computing system may share the aggregate report with a display system in response to receiving a report request. In some cases, the computing system may generate and share a customized aggregate report with a display system upon receiving a customized report request.

Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

Glucose Level Control System Overview

A glucose level control system (GLCS) is used to control glucose level in a subject. In some cases, glucose level may comprise blood glucose level, or glucose level in other parts of fluids on subjects body. In some examples, glucose level may comprise a physiological glucose level of the subject that can be a concentration of glucose in subject's blood or an interstitial fluid in part of the subject's body (e.g., expressed in milligram per deciliter (mg/dl)). Glucose level control systems (GLCSes) or glucose control systems, which are sometimes referred to herein as glucose level systems, can include a controller configured to generate dose control signals for one or more glucose control agents that can be infused into the subject. Glucose control agents can be delivered to a subject via subcutaneous injection, via intravenous injection, or via another suitable delivery method. In the case of glucose control therapy via an ambulatory medicament pump, subcutaneous injection is most common. Glucose control agents may include regulatory agents that tend to decrease a glucose level (e.g., blood glucose level) of the subject, such as insulin and insulin analogs, and counter-regulatory agents that tend to increase a glucose level of the subject, such as glucagon or dextrose. A glucose level control system configured to be used with two or more glucose control agents can generate a dose control signal for each of the agents. In some embodiments, a glucose level control system can generate a dose control signal for an agent even though the agent may not be available for dosing via a medicament pump connected to the subject.

In some embodiments, a GLCS may include or can be connected to an ambulatory medicament pump (AMP). An ambulatory medicament pump is a type of ambulatory medical device ("AMD"), which is sometimes referred to herein as an ambulatory device, an ambulatory medicament device, or a mobile ambulatory device. In various implementations, ambulatory medical devices include ambulatory medicament pumps and other devices configured to be carried by a subject and to deliver therapy to the subject. Multiple AMDs are described herein. It should be understood that one or more of the embodiments described herein with respect to one AMD may be applicable to one or more of the other AMDs described herein. In some cases, a GLCS can include a therapy administration system and an AMD that is in communication with the therapy administration system. In some cases the AMD may comprise an AMP.

In some embodiments, a GLCS implements algorithms and medicament or glucose control functionality discussed herein to provide medicament or glucose control therapy without being connected to an AMD. For example, the GLCS can provide instructions or dose outputs that direct a user to administer medicament to provide glucose control therapy. In some implementations, the user may use, for example, a medicament pen to manually or self-administer the medicament according the GLCS's dose outputs. In some implementations, the user may also provide inputs such as glucose level readings into the GLCS for the GLCS to provide dose outputs. The user inputs into the GLCS may be in combination with inputs from other systems or devices such as sensors as discussed herein. In some implementations, the GLCS can provide glucose control therapy based on user inputs without other system or device inputs.

In some embodiments, the GLCS includes a memory that stores specific computer-executable instructions for generating a dose recommendation and/or a dose control signal. The dose recommendation and/or the dose control signal can assist with glucose level control of a subject via medicament therapy. The dose recommendation or dose output of the GLCS can direct a user to administer medicament to provide medicament therapy for glucose level control, including manual administration of medicament doses. In additional embodiments, the GLCS includes the memory and a delivery device for delivering at least a portion of the medicament therapy. In further embodiments, the GLCS includes the memory, the delivery device, and a sensor configured to generate a glucose level signal. The GLCS can generate the dose recommendation and/or the dose control signal based at least in part on the glucose level signal. In certain embodiments, the dose recommendation and/or the dose control signal can additionally be based at least in part on values of one or more control parameters. Control parameters can include subject-specific parameters, delivery device-specific parameters, glucose sensor-specific parameters, demographic parameters, physiological parameters, other parameters that can affect the glucose level of the subject, or any combination of one or more of the foregoing.

In some examples, the ambulatory medical device (AMD) is an electrical stimulation device, and therapy delivery includes providing electrical stimulation to a subject. An example of an electrical stimulation device is a cardiac pacemaker. A cardiac pacemaker generates electrical stimulation of the cardiac muscle to control heart rhythms. Another example of an electrical stimulation device is a deep brain stimulator to treat Parkinson's disease or movement disorders.

Figure 1B:
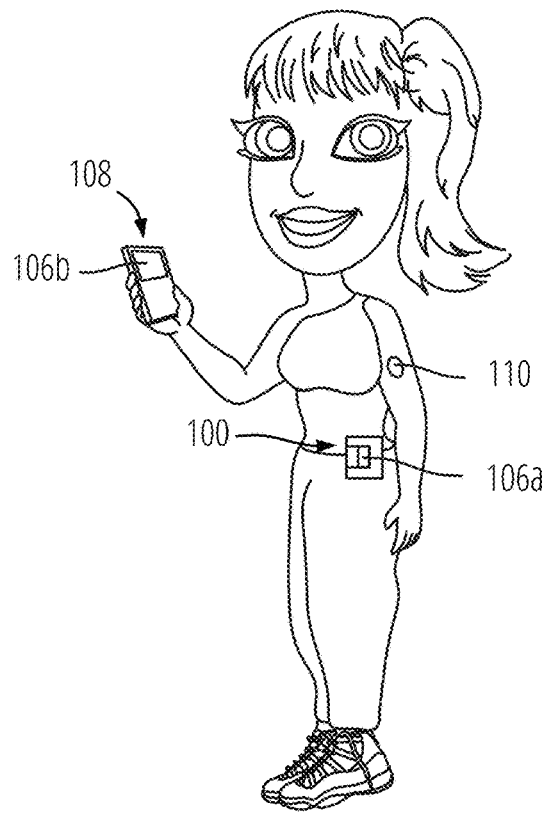
FIG. 1B illustrates another example glucose level control system that provides glucose level control via an ambulatory medicament pump.
Figure 1C:
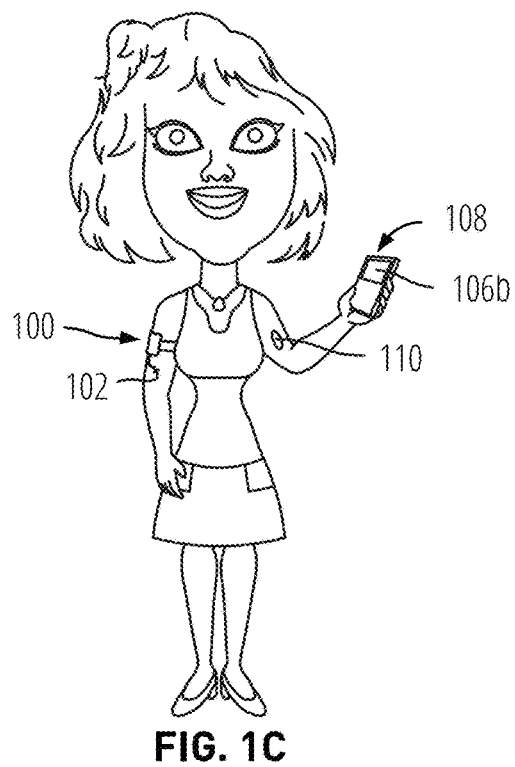
FIG. 1C illustrates a further example glucose level control system that provides glucose level control via an ambulatory medicament pump.

FIG. 1A-FIG. 1C show examples of glucose level control systems that provide glucose level control via an ambulatory medical device or AMD, such as an ambulatory medicament pump (AMP), connected to a subject.

In FIG. 1A, the AMD 100 is connected to an infusion site 102 using an infusion set 104. The AMD 100 may include a medicament pump and an integrated user interface 106*a* that permit a user to view pump data and change therapy settings via user interaction with the user interface elements of the user interface 106*a*. An analyte sensor 110, such as a glucose level sensor, generates a glucose level signal that is received by the glucose level control system. In some variants, the analyte sensor 110 can include an insulin level sensor that can generate an insulin level signal that can be received by the glucose level control system. In some variants, the analyte senor 110 can include a glucose level sensor and/or an insulin level sensor. In some variants, the analyte senor 110 may include a continuous glucose monitor (CGM).

In FIG. 1B, the glucose level control system includes the AMD 100 (e.g., an medicament pump) communicates with an external electronic device 108 (such as, for example, a smartphone) via a wireless data connection. At least some of the pump controls can be manipulated via user interaction with user interface elements in the user interface 160b of the external electronic device 108. The glucose level sensor 110 can also communicate with the AMD 100 (that includes a medicament pump) via a wireless data connection.

In FIG. 1C, the AMD 100 (e.g., a medicament pump) includes an integrated cannula that inserts into the infusion site 102 without a separate infusion set. At least some of the pump controls can be manipulated via user interaction with user interface elements 106b of an external electronic device 108. In some instances, pump controls can be manipulated via user interaction with user interface elements generated by a remote computing environment (not shown), such as, for example, a cloud computing service, that connects to the AMD 100 (medicament pump) via a direct or indirect electronic data connection.

Glucose level control systems typically include a user interface configured to provide one or more of therapy information, glucose level information, and/or therapy control elements capable of changing therapy settings via user interaction with interface controls. For example, the user can provide an indication of the amount of the manual bolus of medicament from an electronic device remote from the medicament pump. The user interface can be implemented via an electronic device that includes a display and one or more buttons, switches, dials, capacitive touch interfaces, or touchscreen interfaces, or voice interfaces. In some embodiments, at least a portion of the user interface is integrated with an ambulatory medicament pump that can be tethered to a body of a subject via an infusion set configured to facilitate subcutaneous injection of one or more glucose control agents. In certain embodiments, at least a portion of the user interface is implemented via an electronic device separate from the ambulatory medicament pump, such as a smartphone.

Figure 2A:
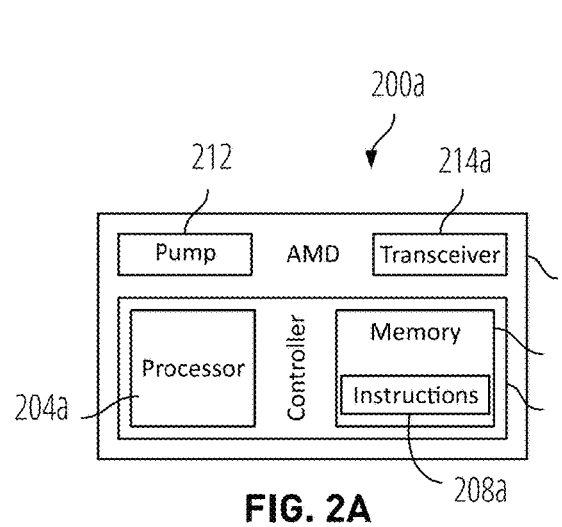
FIG. 2A shows a block diagram of an example glucose level control system.

FIG. 2A-FIG. 2D illustrate block diagrams showing example configurations of four different embodiments (200a/200b/200c/200d) of a glucose level control system. As shown in FIG. 2A, a glucose level control system 200a may comprise an ambulatory medical device (AMD) 100 that includes a controller 202a having an electronic processor 204a and a memory 210a that stores instructions 208a executable by the electronic processor 204a. The controller 202a and a pump 212 (e.g., a medicament pump) can be integrated into AMD) 100. In some cases, the pump 212 can be an infusion pump for administering regulatory agent and/or counter-regulatory agent. In some implementations, the AMD 100 can include at least one pump 212. In some implementations, the AMD 100 may include at least one pump and a wireless connection interface or a transceiver. The AMD 100 can include a wireless electronic communications interface (e.g., the transceiver 214a) for wireless data (e.g., digital data) communications with external electronic devices. When the instructions 208a stored in the memory 210a are executed by the electronic processor 204a, the controller 202a can implement at least a portion of a control algorithm that generates dose control signals for one or more glucose control agents based on time-varying glucose levels of the subject (e.g., received from a glucose level sensor 110 that is in communication with the AMP 100) and one or more control parameters. The dose control signals, when delivered to the pump 212, result in dosing operations that control a glucose level of the subject. The pump 212 may be controlled by at least one pump controller. In some examples, the pump controller may be included in the pump 212. The pump controller receives the dose control signals and controls the operation of the pump 212 based on the received dose control signals. In some embodiments the pump controller may be integrated with the pump. In various implementations, the controller may be included in the AMP 100, or in an external electronic device 108 or a remote computer 206, that are connected to the AMP 100 via wired or wireless communication links.

As illustrated in FIGS. 2A-2D, in some embodiments, a glucose level control system may comprise an ambulatory medicament pump AMP 100 (also referred to as ambulatory medicament pump or AMP) that includes a medicament pump, and at least one controller that controls the medicament pump. In various implementations, the controller may be included in the AMD 100, or in an external electronic device 108 or a remote computer 206, that are connected to the AMD 100 via wired or wireless communication links.

Figure 2B:
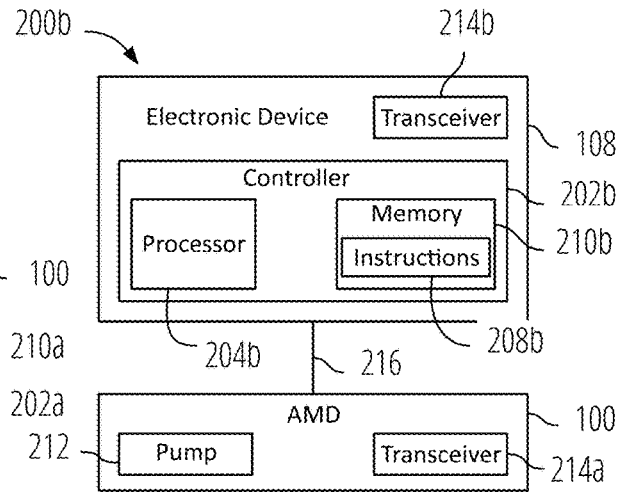
FIG. 2B shows a block diagram of another example glucose level control system.

As shown in FIG. 2B, a glucose level control system 200b can operate at least partially via execution of instructions 208b by an electronic processor 204b of an external electronic device 108 separate from the AMD 100. The external electronic device 108 can include a transceiver 214b capable of establishing a wireless data connection to the AMD 100, and a controller 202b can implement at least a portion of a control algorithm via execution of instructions 208b stored in memory 210b. When the instructions 208b stored in memory 210b are executed by the electronic processor 204b, the controller 202b can implement at least a portion of a control algorithm that generates dose control signals for one or more glucose control agents based on time-varying glucose levels of the subject and one or more control parameters. The dose control signals, when delivered to the pump controller of the pump 212, result in dosing operations that control the glucose level of a subject. In some embodiments, the dose control signals are transmitted from the electronic device transceiver 214b to the AMD transceiver 214a over a short-range wireless data connection 216. The AMD 100 receives the dose control signals and passes them to the pump controller of the pump 212 for dosing operations.

Figure 2C:
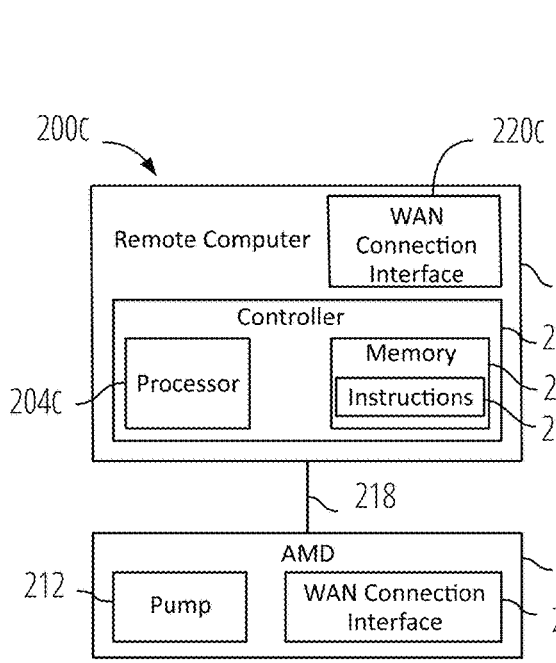
FIG. 2C shows a block diagram of another example glucose level control system.

As shown in FIG. 2C, a glucose level control system 200c may include a remote computer 206 that is in communication with the AMD 100 (e.g., an ambulatory medicament pump). In some cases, the glucose level control system 200c can operate at least partially via execution of instructions 208c by an electronic processor 204c integrated with the remote computer 206, such as, for example, a cloud service (e.g., remote computing environment). When the instructions 208c stored in memory 210c are executed by the electronic processor 204c, the controller 202c can implement at least a portion of a control algorithm that generates dose control signals for one or more glucose control agents based on time-varying glucose levels of the subject and one or more control parameters. The dose control signals, when received by the pump controller of the pump 212, may result in dosing operations that control the glucose level of a subject. In some embodiments, the dose control signals are transmitted from the remote computer 206 from wide area network (WAN) connection interface of the remote computer 206 (e.g., WAN connection interface 220c) to a WAN connection (e.g., WAN connection interface 220a) of the AMD 100 over an end-to-end wireless data connection 218. The AMD 100 receives the dose control signals and passes them to the pump 212 (or the controller that controls the pump 212) for dosing operations.

Figure 2D:
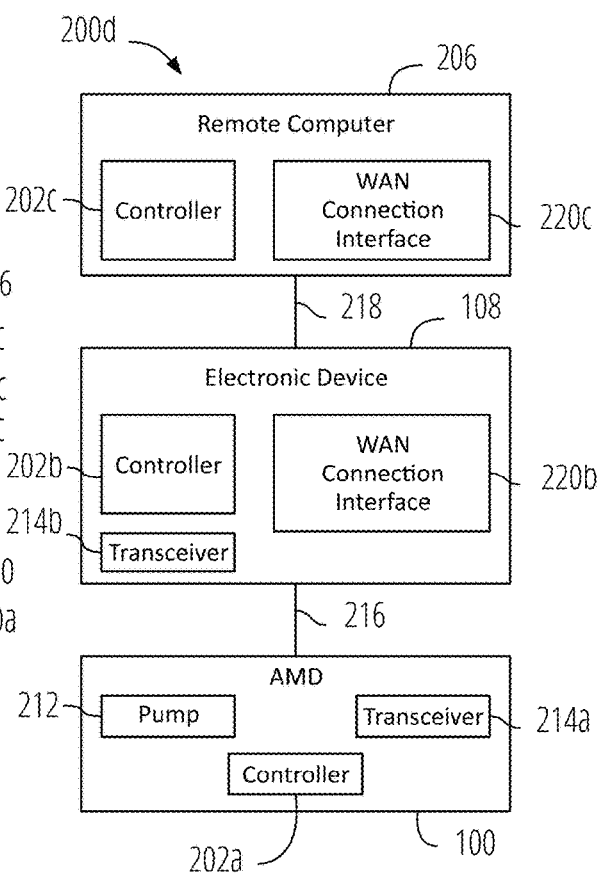
FIG. 2D shows a block diagram of another example glucose level control system.

As shown in FIG. 2D, a glucose level control system 200d that includes a remote computer 206 that is in communication with an external electronic device 108 (e.g., an electronic device of the subject), and the AMD 100, which is in communication with the electronic device 108. In some implementations, the glucose level control system 200d can have two or more controllers 202a, 202b, 202c (e.g., located in different subsystems) that cooperate to generate a dose control signal for dosing operations by the pump 212. For example, the remote computer 206 can transmit or receive data or instructions passed through a WAN connection interface 220c via an end-to-end wireless data connection 218 to a WAN connection interface 220b of the external electronic device 108. The external electronic device 108 can transmit or receive data or instructions passed through a transceiver 214b via a short-range wireless data connection 216 to a transceiver 214a of an AMD 100. In some embodiments, the electronic device 108 can be omitted, and the controllers 202a, 202c of the AMD 100 and the remote computer 206 cooperate to generate dose control signals that are passed to the pump 212 (or the pump controller that controls pump 212). In such embodiments, the AMD 100 may have its own WAN connection interface to support a direct end-to-end wireless data connection to the remote computer 206.

Figure 3:
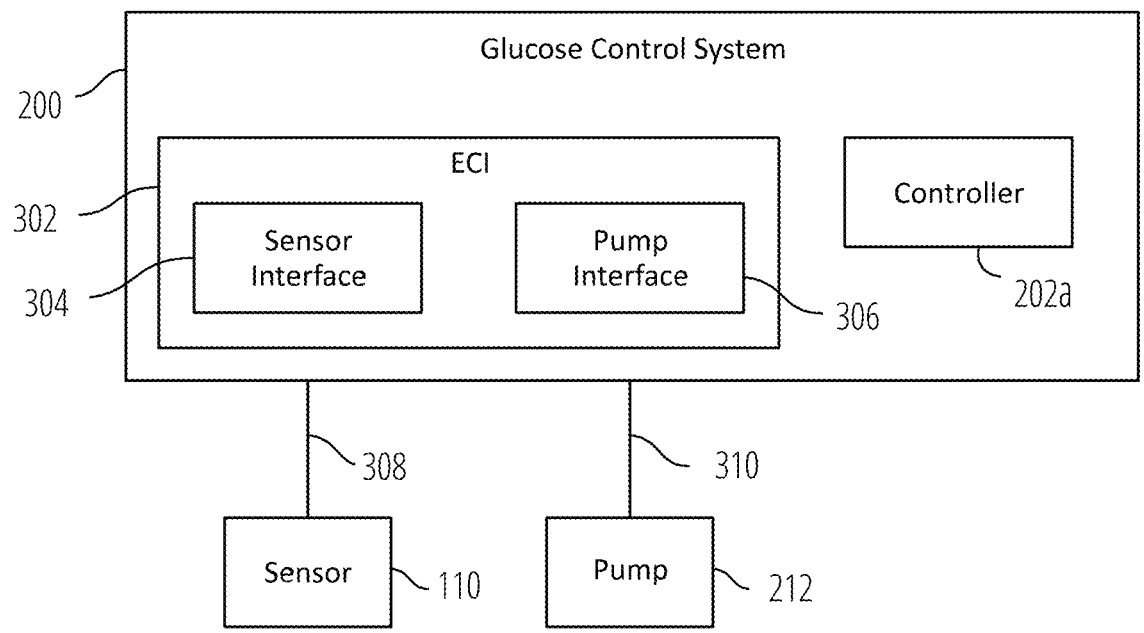
FIG. 3 is a schematic of an example glucose level control system that includes an electronic communications interface.

As shown in FIG. 3, in some embodiments, a glucose control system 200 (e.g., AMD 100), may include circuitry that implements an electronic communications interface (ECI) 302 configured to send and receive electronic data from one or more electronic devices. The ECI includes a sensor interface 304 (e.g., a glucose sensor interface) configured to receive a glucose level signal from a sensor 110 (e.g., an analyte sensor or a glucose level sensor) such as a continuous glucose monitor (CGM). In some cases the sensor 110 can be a continuous glucose monitor (CGM). Some CGMs may generate glucose level signals at fixed or periodic measurement intervals, such as five-minute intervals. The sensor 110 can be operatively connected to a subject in order to generate a glucose level signal that corresponds to a glucose level estimate or measurement of the subject. The glucose level signal can be used by the controller 202a to generate a dose control signal. The dose control signal can be provided to a pump 212 via a pump interface 306 (or a delivery device interface). In some embodiments, the sensor interface 304 connects to the sensor 110 via a short-range wireless connection 308. In some embodiments, the pump interface 306 connects to the pump 212 via a short-range wireless connection 310. In other embodiments, the pump interface 306 connects to the pump 212 via a local data bus, such as when the controller 202a, the ECI 302, and the pump 212 are integrated into an AMD 100. In some variants, the sensor 110 can be an insulin level sensor that can detect insulin levels. The sensor interface 304 can be configured to receive an insulin level signal from the sensor 110, which can correspond to an insulin level estimate or measurement of the subject (e.g., a concentration of insulin in subject's blood). The insulin level signal can be used by the controller 202a to generate a dose control signal, which can be provided to the pump 212 via the pump interface 306. In some variants, the sensor 110 can include a glucose sensor and an insulin sensor.

The controller 202a can be configured to generate the dose control signal using a control algorithm that generates at least one of a basal dose, a correction dose, and/or a meal dose (or food intake). Examples of some control algorithms that can be used to generate these doses are disclosed in U.S. Patent Application Publication Nos. 2008/0208113, 2013/0245547, 2016/0331898, and 2018/0220942 (referenced herein as the "Controller Disclosures"), or in the PCT Patent Application Publication No. WO 2021/067856, the entire contents of which are incorporated by reference herein and made a part of this specification. The correction dose can include regulatory or counter-regulatory agent and can be generated using a model-predictive control (MPC) algorithm and/or other algorithms such as those disclosed in the Controller Disclosures. The basal dose can include regulatory agent and can be generated using a basal control algorithm such as disclosed in the Controller Disclosures. The meal dose can include regulatory agent and can be generated using a meal control algorithm such as disclosed in the Controller Disclosures. In some cases, a meal dose can be generated by the subject via a user interface of the glucose level control system 200a/200b/200c/200d. Additional aspects and improvements for at least some of these controllers are disclosed herein. The dose control signal can be transmitted to pump interface 306 via the ECI 302 or can be transmitted to the pump interface 306 via an electrical conductor when the controller 202a is integrated in the same housing as the pump interface 306.

Figure 4A:
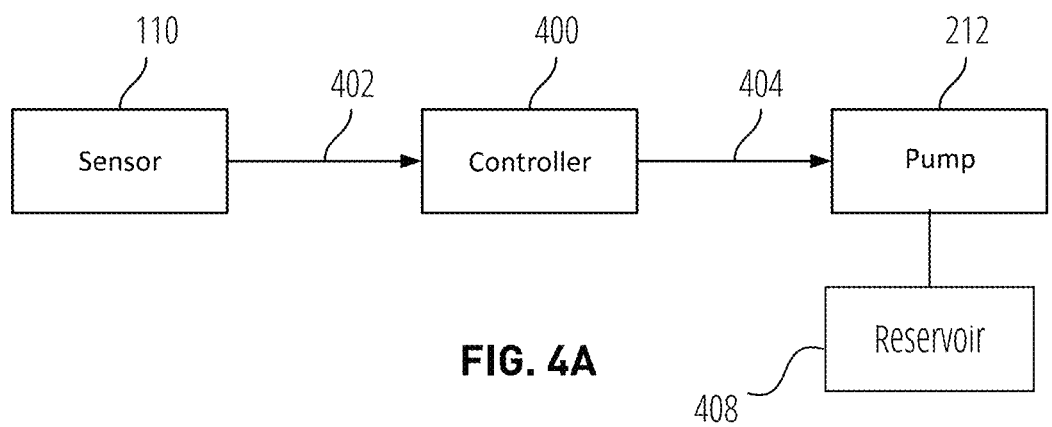
FIG. 4A shows a block diagram of an example glucose level control system in online operation mode.

FIG. 4A shows a block diagram of an example glucose level control system in online operation mode. In the example shown, the controller 400 can be configured to operate in "online mode" (or "automatic mode") during time periods when the controller 400 receives a glucose level signal 402 from the sensor 110 (e.g., a glucose level sensor) and/or an insulin level signal 402 from the sensor 110 (e.g., an insulin level sensor). In online mode, the control algorithm generates a dose control signal 404 that implements regular correction doses based on values of the glucose level signal 402 and/or insulin level signal 402 and control parameters of the control algorithm. The pump 212 is configured to deliver at least correction doses and basal doses to the subject without substantial user intervention while the controller 400 remains in online mode. In some examples, the ambulatory medicament pump 212 can include one or more medicament cartridges or can have an integrated reservoir 408 of medicament. The reservoir 408 may be integrated with the pump 212. A medicament stored in the reservoir 408 can be delivered to the subject by operation of the pump 212. In various embodiments, the operation of the pump 212 can be controlled by the controller 400. In some cases, the online mode, the controller 400 may generate the dose control signal 404 using a control scheme such as described in U.S. Pat. No. 7,806,854, the contents of which are hereby incorporated by reference in its entirety herein.

Figure 4B:
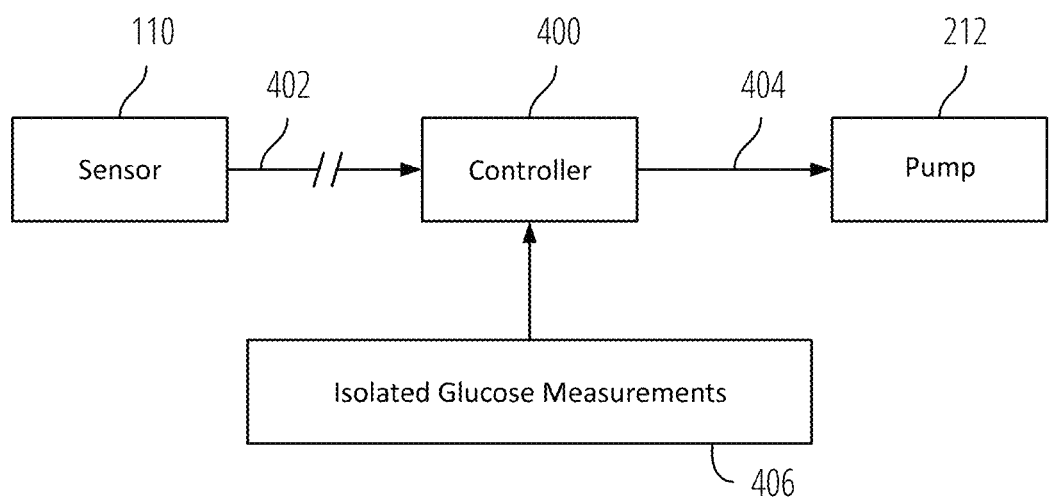
FIG. 4B shows a block diagram of an example glucose level control system in offline operation mode.

FIG. 4B shows a block diagram of an example glucose level control system in offline operation mode. In this example, the controller 400 can be configured to operate in "offline mode" during time periods when the controller does not receive a glucose level signal 402 and/or insulin level signal 402 from a sensor 110, at least during periods when the glucose level signal 402 is expected but not received. In the offline mode, the controller may generate dose control signals as described in U.S. Pat. No. 10,543,313, the entire contents of which are hereby incorporated by reference in its entirety herein. In offline mode, the control algorithm generates a dose control signal 404 that implements correction doses in response to isolated glucose measurements 406 (such as, for example, measurements obtained from the subject using glucose test strips) and/or insulin measurements 406 and based on control parameters of the control algorithm. The pump 212 is configured to deliver basal doses to the subject without substantial user intervention and can deliver correction doses to the subject in response to isolated glucose measurements 406 and/or isolated insulin measurements 406 while the controller 400 remains in offline mode.

Example Ambulatory Medical Device (AMD)

In some embodiments, the ambulatory medical device (AMD) can be a portable or wearable device (e.g., an insulin or bi-hormonal medicament pump) such as an ambulatory medicament pump (AMP) that provides life-saving treatment to a subject by delivering one or more medicaments (e.g., insulin and/or glucagon) to a subject. Some AMDs may continuously monitor the health condition of a subject (e.g., glucose level, insulin level, heart rate, etc.) using a sensor (e.g., a glucose level sensor that can measure values corresponding to the glucose level, or a blood insulin level sensor that can measure values corresponding to the blood insulin level, etc.) and deliver therapy (e.g., one or more medicaments) to the subject based on the health condition of the subject. For example, an AMP (e.g., an insulin pump or a bi-hormonal pump) may monitor the glucose level in a subject using a Continuous Glucose Monitor (CGM) and adjust the dose or frequency of the medicament delivery (e.g., insulin or glucagon) accordingly. Certain AMDs may be worn by subjects constantly (e.g., all day), or for a large portion of the day (e.g., during waking hours, during sleep hours, when not swimming, etc.) to enable continuous monitoring of the health condition of the subject and to deliver medicament as necessary. In some embodiments, an AMD may be an ambulatory medicament device such as a medicament delivery pump. In some examples, an AMD may be a device that provides therapy in the form of electrical stimulation based on a health condition of a subject (e.g., heart rhythm or brain activity) determined using signals received from one or more sensors (e.g., heartbeat monitor or electrodes monitoring activity of the brain).

Figure 5A:
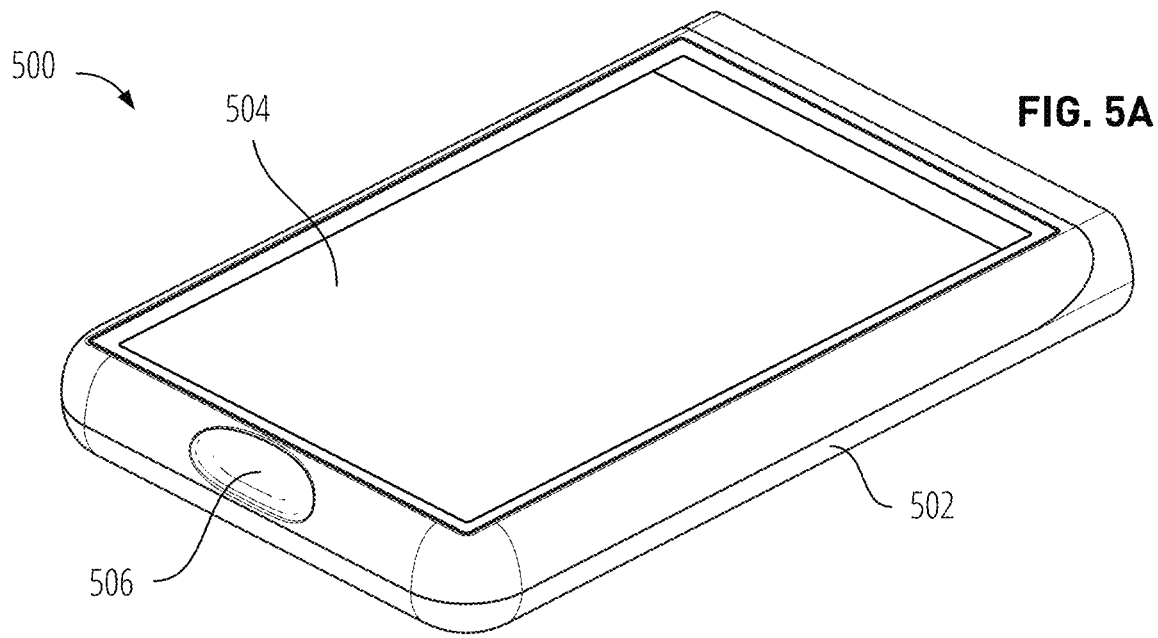
FIG. 5A illustrates a perspective view of an example ambulatory medical device.
Figure 5B:
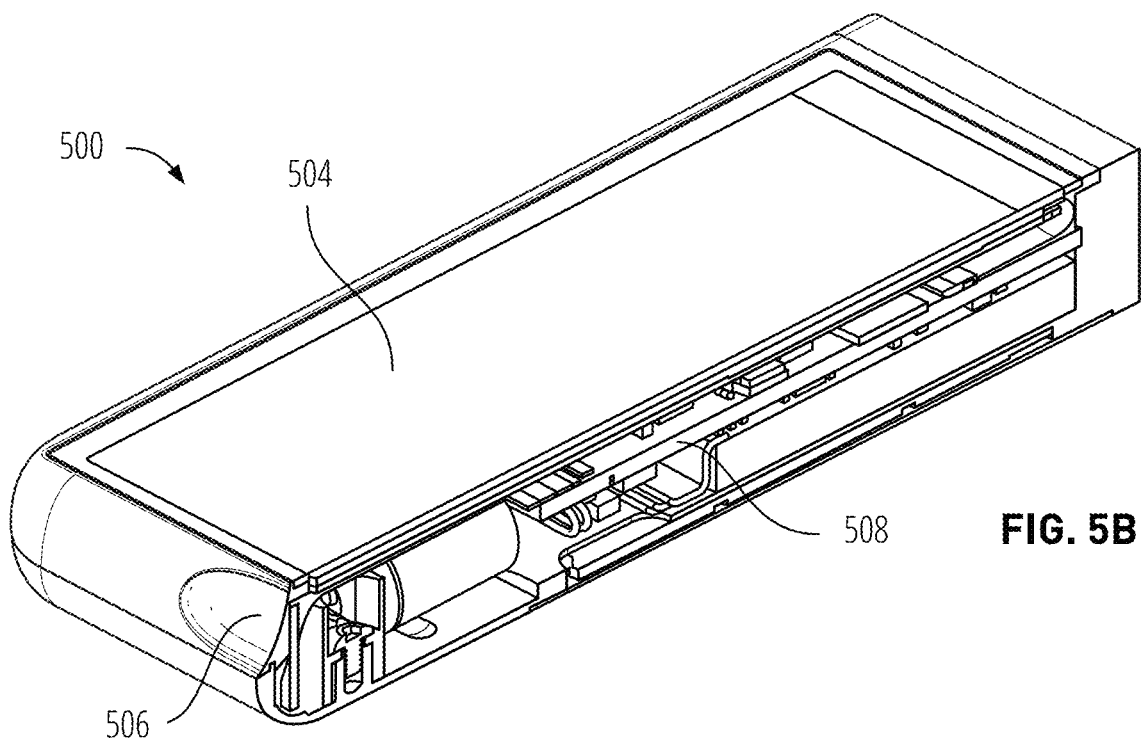
FIG. 5B illustrates a cross sectional view of the ambulatory medical device shown in FIG. 5A.

FIG. 5A illustrates a three-dimensional (3D) view of an example ambulatory medical device 500 (such as an ambulatory medicament pump) comprising a housing 502 with a wake button 506 and a touchscreen display 504. FIG. 5B is an illustration of a cross sectional view of the ambulatory medical device 500 shown in FIG. 5A. In this example, all the electronic systems 508 are included inside the housing, for example, as a single integrated electronic board. The wake button 506 may be any type of button (e.g., capacitive, inductive, resistive, mechanical, etc.) that registers an input generated by user interaction with the wake button 506 to generate a wake signal. A wake signal may be a signal that activates a user interface of the AMP (e.g., a touchscreen display). The wake button 506, if touched, pressed, or held for a period, may generate the wake signal that activates the touchscreen display 504. In some embodiments, the wake signal is generated by a sensor (e.g., a biometric sensor such as a fingerprint reader or a retinal scanner, an optical or RF proximity sensor, and the like). In various embodiments, the wake signal may be generated by user interaction with the touch screen display 504 or with an alphanumeric pad (not shown). In some examples, wake signal may be generated based on facial recognition or other biometric indicia. In some examples, the wake signal may be generated by a wireless signal such as a signal generated by an RFID system or Bluetooth signals received from an electronic device or by detection of movement using one or more motion sensors such as an accelerometer. The wake button 506, if touched, pressed, or held for a certain period of time, may generate a wake signal that activates the touchscreen display 504. In some examples, touches on the touchscreen display 504 are not registered until the wake button activates the touchscreen display. In some such examples, the AMD remains locked from accepting at least certain types of user interaction or settings modification until a gesture (such as, for example, any of the gesture interactions described with reference to any of the embodiments disclosed herein) is received after the touchscreen display 504 is activated by the wake button 506. In some examples, after the touchscreen display 504 has been activated by the wake signal, a passcode may be required to unlock the touchscreen display. In some examples, the AMD 500 includes a microphone and a speaker for receiving a sound (e.g., user's voice) and outputting a sound, respectively. In this case, a user can wake up the touchscreen by a voice input.

Figure 6:
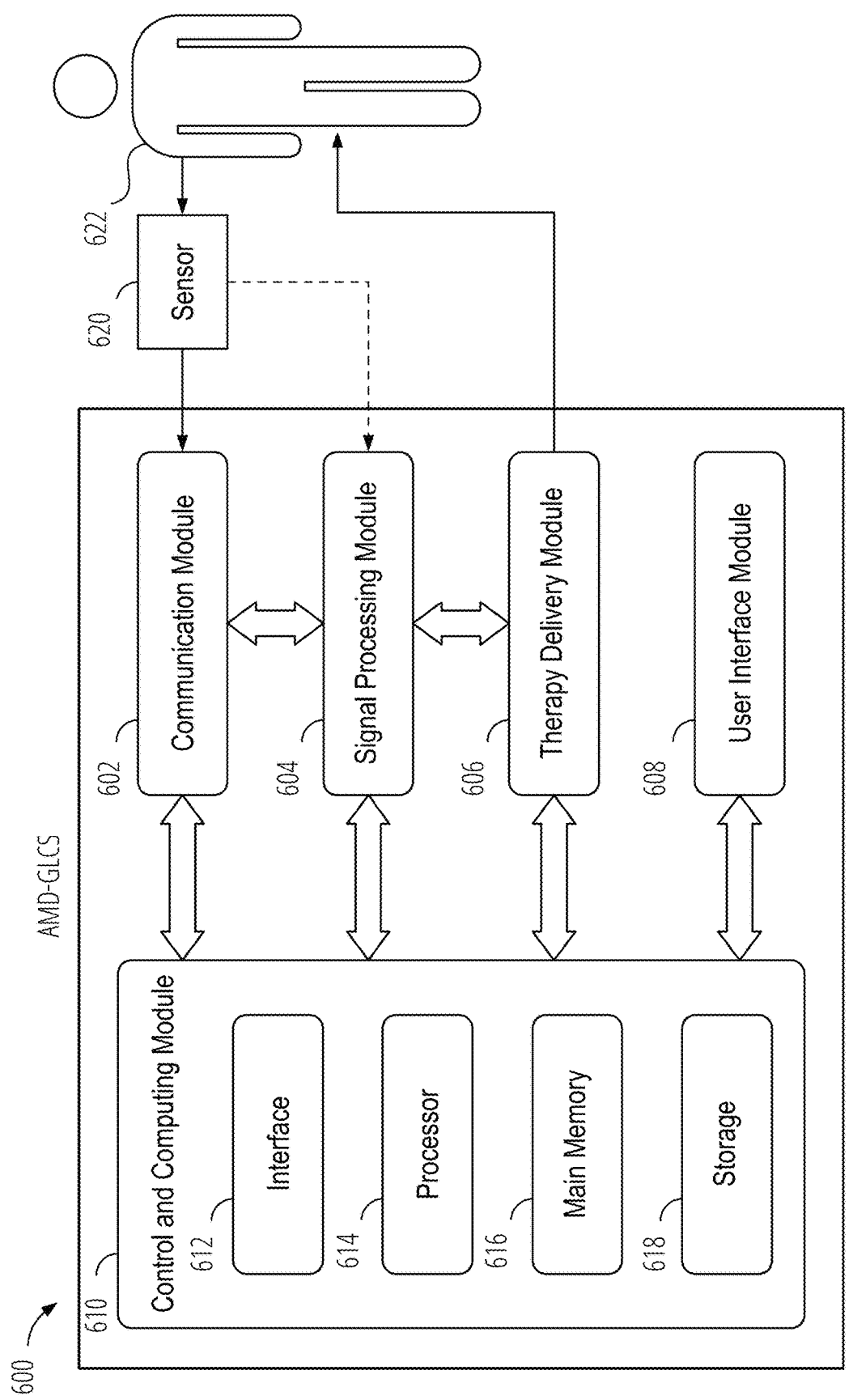
FIG. 6 illustrates different modules that may be included in an example ambulatory medical device.

FIG. 6 illustrates different modules or systems that may be included in an example ambulatory medicaments device (AMD) or an example glucose level control system (GLCS). As mentioned above, in some examples, the AMD (or GLCS) 600 may comprise a complete glucose level control system (e.g., glucose level control system 200a/200b/200c/200d), or can include one or more components of a complete glucose level control system (e.g., a medicament pump, a transceiver, and/or a controller). In some implementations, the AMD 600 may include one or more modules or systems that can facilitate monitoring a subject's glucose level (e.g., glucose level in an interstitial fluid of the subject, or subject's glucose level), monitoring a subject's insulin level, managing the subject's diabetes, tracking a condition of the AMD 600, tracking usage of infusion sets, tracking usage of analyte sensors, and/or communicating with one or more computing systems (e.g., remote computing systems). For example, the AMD (or GLCS) 600 may include a mono-hormonal or bi-hormonal medicament pump configured to administer one or more types of insulin and, in some cases, counter-regulatory agent (e.g., Glucagon or other medicament that can reduce or address hypoglycemia). As another example, the AMD 600 may include one or more alarm generators, transceivers, touchscreen controllers, display controllers, encryption modules, etc. In some examples, two or more of the modules or systems may be integrated together inside a single housing 502 (as shown in FIGS. 5A and 5B). In some examples, one or more modules may be individual modules contained in separate housings that communicate with other modules and/or the main unit via a wired or wireless communication link (e.g., Bluetooth). The modules included in the AMD 600 may include a communication module 602, signal processing module 604, a medicament delivery or therapy delivery module 606, a user interface module 608, and a control and computing module (CCM) 610. In some cases, the control and computing module 610 can be the same or similar in at least some respects to the other glucose control system controllers described herein, including, for example, the controllers 202a-c, and 400 described with reference to FIGS. 2A-D and 4A-B. In some embodiments, one or more modules may comprise one or more single purpose or multipurpose electronic systems. In some such examples, one or more electronic systems may perform procedures associated with different features of the AMD 600. In some embodiments, one or more modules or systems may comprise a non-transitory memory that stores machine readable instructions and a processor that executes instructions stored in the memory. The memory may be a non-volatile memory, such as flash memory, a hard disk, magnetic disk memory, optical disk memory, or any other type of non-volatile memory. Further, types of memory may include but are not limited to random access memory ("RAM") and read-only memory ("ROM"). In some such examples, a system can be programed to perform different procedures each implemented based on a different set of instructions.

In some embodiments, the therapy delivery module 606 may be an external medicament delivery system that is in communication with the control and computing module 610, e.g., via the communication module 602 (e.g., via a wired or wireless link). In some embodiments, the therapy delivery module 606 may be included in the same housing as other systems and subsystems of the AMD 600. In some cases, AMD 600 may include a therapy delivery interface configured to transmit dose control signals to the external therapy delivery system and receive signals indicating the status of the external therapy delivery system and/or medicament delivery. In some case, the therapy delivery interface may be included in the communication module 602. In some cases, the external therapy delivery module may communicate with the AMD 600 using a wireless transceiver included in the external therapy delivery module.

The control and computing module 610 may include one or more processors 614, a main memory 616, a storage 618 that may comprise one or more non-transitory and/or non-volatile memories and an interface 612 that enables data and signal communication among the systems within the control and computing module 610 as well as communication between the control and computing module 610 and all other modules of the AMD 600. The main memory 616 and the storage 618 each may be divided into two or more memory locations or segments. The main memory 616 may communicate with the other components of the control and computing module 610 as well as other modules via the interface 612. Instructions may be transmitted to the main memory (e.g., from the storage) and the processor 614 may execute instructions that are communicated to the processor through the main memory 616. The storage 618 may store data while the control and computing module 610 is powered or unpowered. The storage 618 may exchange data with subsystems within the control and computing module 610 as well as other systems (e.g., via the interface 606). In some cases, the storage 618 may exchange data with the main memory directly or through the interface 612. The main memory 616 can be any type of memory that can store instructions and communicate them to the processor 614 and receive executed instructions from the processor 614. Types of main memory include but are not limited to random access memory ("RAM") and read-only memory ("ROM"). The processor 614 may be any type of general purpose central processing unit ("CPU"). In some embodiments, the control and computing module may include more than one processor of any type including, but not limited to complex programmable logic devices ("CPLDs"), field programmable gate arrays ("FPGAs"), application-specific integrated circuits ("ASICs") or the like. The storage 618 can be any type of computer storage that can receive data, store data, and transmit data to the main memory 616 and possibly other modules of AMD 600. Types of storage 618 that can be used in the control and computing module 610 include, but are not limited to, magnetic disk memory, optical disk memory, flash memory and the like. The interface 612 may include data transfer buses and electronic circuits configured to support data exchange among different components within the control and computing module 610. In some examples, in addition to data exchange between any of the systems and the control and computing module 610, the interface 612 may also support data and signal exchange among other modules as well as data exchange between any of the modules and the control and computing module 610.

The signal processing module 604 may include a plurality of interconnected electronic modules for signal conditioning and signal conversion (e.g., A-to-D or ADC conversion and D-to-A conversion of DAC conversion) configured to support communication and data exchange between different modules. For example, the signal processing module 604 may convert an analog signal received from the communication module 602 and convert it to a digital signal that can be transmitted to the control and computing module 610 (e.g., via the interface 612). In some cases, the control and computing module 610 may further process the digital signal and control one or more modules based on the processed signal. As another example, the signal processing module 604 may receive a digital control signal from the control and computing module 610 and convert it to a dose control signal (e.g., an analog signal) that can be transmitted to the therapy delivery module 606, for example, to control one or more infusion pumps included in the therapy delivery module 606.

In some embodiments, the therapy delivery module 606 may comprise one or more infusion pumps configured to deliver one or more medicaments (e.g., insulin, glucagon, etc.) to a subject 622 and a pump controller that may activate the infusion pumps upon receiving dose control signals. In some examples, the medicaments may be stored in one or more medicament cartridges housed in the therapy delivery module 606. In some examples, the medicaments may be stored in a cavity of the therapy delivery module 606 or in a cartridge inserted in a cartridge receptacle of the therapy delivery module 606. In some examples, the therapy delivery module 606 may include electronic and mechanical components configured to control the infusion pumps based on the signals received from control and computing module 610 (e.g., via the signal processing module 604 or the interface 612). In some examples, the therapy delivery module 606 may include a pump controller that controls the infusion pumps upon receiving dose control signals from the control and computing module 610.

The user interface module 608 may include a display to show various information about the AMD 600, for example, medicament type and delivery schedule, software status, and the like. The display may show graphical images and text using any display technology including, but not limited to OLED, LCD, or e-ink. In some embodiments, the AMD 600, may include a user interface (e.g., an alphanumeric pad) that lets a user enter information or interact with the AMD 600 to modify the settings of the AMD 600, respond or submit to request(s) for certain actions (e.g., ordering infusion sets, sensors, transmitters, replacement components, a replacement pump, etc.) and the like. The alphanumeric pad may include a multitude of keys with numerical, alphabetical, and symbol characters. In different embodiments, the keys of the alphanumeric pad may be capacitive or mechanical. The user may be a subject 622 receiving medicament or therapy, or may be another user, such as a clinician or healthcare provider, or a parent or guardian of the subject 622. In some embodiments, the AMD 600 may include a touchscreen display that produces output and also accepts input enabling a two-way interaction between the user and the AMD 600. The touchscreen display may be any input surface that shows graphic images and text and also registers the position of touches on the input surface. The touchscreen display may accept input via capacitive touch, resistive touch, or other touch technology. The input surface of the touchscreen display can register the position of touches on the surface. In some examples, the touchscreen display can register multiple touches at once. In some embodiments, the keypad may be a display of a keypad. For example, an alphanumeric pad comprising user-selectable letters, numbers, and symbols may be displayed on the touchscreen display. In some examples, the touchscreen may present one or more user-interface screens (e.g. as described in reference to FIGS. 50-52) to a user enabling the user to modify one or more therapy settings of the ambulatory medicament device, order additional infusion sets, order additional analyte sensors, order a replacement AMD, etc. In some examples, a user-interface screen may comprise one or more parameter control elements. Further, a user-interface screen may include one or more user input elements displayed on the screen that enable a user to interact with the AMD 600. In some examples, a user-interface screen may comprise one or more therapy control elements (e.g., displayed on the touchscreen display) enabling a user or the subject to access therapy change controls and modify therapy settings by interacting with these control elements. For example, the user can modify the therapy settings by changing one or more control parameters using the corresponding therapy control elements. In some embodiments, a therapy control parameter comprise any parameter that controls or affects the volume, duration and/or the frequency of medicament doses delivered to the subject.

In some embodiments, the user interface module 608 may include an audio or auditory sensor and system such as a speaker and a microphone for voice recognition. In this case, a user can verbally interact with the AMD 600 without contacting the device. In addition, the verbal interaction may reduce gesture motion of the user for controlling the AMD 600. In various embodiments, "voice recognition" refers to identifying the speaker. Recognizing the speaker can simplify the task of translating speech in systems that have been trained on a specific user's voice or it can be used to authenticate or verify the identity of a speaker as part of a security process.

In some examples, voice recognition (or also known as speech recognition) may be carried out according to any of the methods known in the art. In particular, a voice recognition method may be based on hidden Markov models using cepstral coefficients. The employed hidden Markov model may further involve context dependency for phonemes, cepstral normalization to normalize for different speakers and/or recording conditions, vocal tract length normalization (VTLN) for male/female normalization, and/or maximum likelihood linear regression (MLLR) for more general speaker adaptation. A voice recognition system based on hidden Markov models may further be adapted using discriminative training techniques, such as maximum mutual information (MMI), minimum classification error (MCE) and minimum phone error (MPE). As an alternative to hidden Markov models, the voice recognition method may be based on dynamic time warping (DTW). Other methods, which may be used for detecting a voice signal in the microphone signal using voice recognition include, but are not limited to, e.g., power spectral analysis (FFT), linear predictive analysis (LPC), perceptual linear prediction (PLP), mel scale cepstral analysis (MEL), relative spectra filtering (RASTA) may be used.

Detecting a voice signal may further comprise detecting voice/speech activity of at least two different human speakers using voice recognition based on speaker recognition methods. Voice recognition may be used by the voice command device to authorize operation of the voice command device. In various embodiments, the voice recognition adapts as automatic speech recognition (ASR), computer speech recognition or speech to text (STT). A large number of additional units known for voice command devices such as Amazon's Echo may be part of the system of the embodiments. Additional processor units, volatile and non-volatile memory units, storage units, FFT/IFFT units, matrixing units, amplifiers, A/D and D/A converters and the like may be implemented.

In some embodiments, the user may wake the AMD by verbal communication. In some cases, the user interface may be incorporated into a sensor for recognizing a voice. When there is a specific verbal command (e.g., voice command "Alexa" is used for waking up Amazon Echo devices, the AMD receives a wake signal and is triggered to prompt the user predefined questions (e.g., "what can I do for you?"). In this case, the voice command system may thus constantly monitor the acoustic space for speech signals. As a result of a detected keyword or key phrase, each voice command device may analyze the detected speech signal or transmit the speech signal. The user can directly request the AMD to perform the functions (e.g., "hey pump, please start therapy delivery," "pump, change the time of therapy deliver," etc.). In some examples, the user can set the wake-up command. For example, when the wake-up command is set as "hey, pump," the user can change to the specific name of the pump. In some cases, the pump may be configured to recognize only a specific user. Other users are prohibited from waking-up and/or controlling the AMD. In this case, voice recognition requires "training" (e.g., "enrollment") where an individual speaker reads text or isolated vocabulary into the voice recognition system of the AMD. The voice recognition system analyzes the user's specific voice and uses it to fine-tune the recognition of the user's voice, resulting in increased accuracy.

In some embodiments, the communication module 602, may include one or more wireless transceivers, one or more antennas and in or more plurality of electronic systems (e.g., front end modules, antenna switch modules, digital signal processors, power amplifier modules, etc.) that support communication over one or more communication links and/or networks. In some examples, each transceiver may be configured to receive or transmit different types of signals based on different wireless standards via the antenna (e.g., an antenna chip). The transceiver may support communication using a low power wide area network (LPWAN) communication standard. In some examples, the transceiver may support communication with wide area networks (WAN) such as a cellular network transceiver that enables 3G, 4G, 4G-LTE, or 5G. Further, the transceiver may support communication via a Narrowband Long-Term Evolution (NB-LTE), a Narrowband Internet-of-Things (NB-IoT), or a Long-Term Evolution Machine Type Communication (LTE-MTC) communication connection with the wireless wide area network. In some cases, the transceiver may support Wi-Fi® communication. In some cases, one or more transceivers may support data communication via Blue tooth or Blue Tooth Low Energy (BLE). In some examples, the transceiver may be capable of down-converting and up-converting a baseband or data signal from and to a wireless carrier signal. In some examples, the communication module may wirelessly exchange data between other components of the AMD 600 (e.g., an analyte sensor such as a glucose level sensor or insulin level sensor), a mobile device (e.g., smart phone, a laptop, a tablet, and the like), a Wi-Fi network, WLAN, a wireless router, a cellular tower, a Bluetooth device, and the like. The antenna may be capable of sending and receiving various types of wireless signals including, but not limited to, Bluetooth, LTE, or 3G. In some examples, the communication module 602 may support direct communication between the AMD and a server or a cloud network. In some examples the AMD 600 may communicate with an intermediary device (e.g., a smart phone or other mobile devices, a personal computer, a notebook, a tablet, and the like). In some embodiments, the AMD 600 may include an eSIM card that stores information that may be used to identify and authenticate a mobile subscriber. The eSIM card may enable the AMD 600 to function as an IoT device that can communicate over a network that supports communication with IoT devices. In other embodiments, the AMD 600 may be configured to transmit data using a narrowband communication protocol such as 2G or EDGE. Using the cellular connection the AMD 600 may be paired with the mobile device at inception and permit real-time data access to the AMD 600 by a healthcare provider. In certain implementations, the AMD 600 may include a geolocation receiver or transceiver, such as a global positioning system (GPS) receiver. In some embodiments, the communication module 602 may include a Near Field Communication (NFC) sub-system that enables contactless data exchange between the AMD 600 and an electronic device located in the vicinity of the AMD 600. In some cases, a glucose sensor interface in the communication module 602 may be configured to receive glucose level signals from an analyte sensor, a glucose level sensor, and/or insulin level sensor, hereinafter referred to as "subject sensor" 620. In some cases, the subject sensor 620 can be a wearable continuous glucose monitor (CGM) that is operatively connected to the subject 622. For example, the subject sensor 620 may be attached to a site on subject's body using adhesive patch holds and may include a cannula that penetrates the subject's skin allowing the sensor to take glucose readings in interstitial fluid and generate glucose level signals that indicate the level of glucose in subject's blood. In some cases, the glucose sensor interface may receive the glucose level signals from the subject sensor 620 via a wired or wireless link. As previously stated, each of the AMDs described herein may include one or more of the embodiments described with respect to the other AMDs unless specifically stated otherwise.

Example Operation of the AMD or GLCS

In some embodiments, the AMD (or GLCS) 600 may continuously, periodically (e.g., every 5 minutes, every 10 minutes, etc.), or intermittently receive information associated with one or more parameters (e.g., parameter values) that are correlated with a health condition of the subject 622 (e.g., glucose level, glucose level trend, insulin level, insulin level trend, heart rate, body movement indicia, etc.). This information may be encoded to a signal provided to AMD 600 by an analyte sensor (e.g. a glucose sensor), which can be the subject sensor 620 that is connected to the AMD 600 via a wired or wireless link (e.g., Bluetooth). For example, AMD 600 may receive glucose level signals that carry encoded glucose level data usable to determine a glucose level of the subject 622, from a continuous glucose monitor (CGM). In some examples, a CGM may be a wearable biomedical sensor that measures a glucose level in an interstitial fluid of the subject. A glucose level signal may comprise an electronic signal indicative of a measured glucose level of the subject 622. In some cases, the measured glucose level associated with a glucose level signal may be correlated with a physiological glucose level of the subject. The physiological glucose level of the subject can be a concentration of glucose in subject's blood or an interstitial fluid in part of the subject's body (e.g., expressed in milligram per deciliter (mg/dl)). In some cases, the glucose level of the subject may comprise a measured glucose level of the subject. In some examples, the measured glucose level of the subject may be associated with a measured concentration of glucose in an interstitial fluid of a subject's body. The concentration of glucose in the interstitial fluid of the subject's body may be correlated to a glucose level of the subject. Measured glucose level may be referred to herein as "glucose level of the subject" or "glucose level".

As described above, the AMD (or GLCS) 600 may continuously, periodically or intermittently receive glucose level signals from the subject sensor 620 (e.g. a glucose level sensor) via a glucose sensor interface (e.g., via a wired or a wireless data connection). In some cases, the glucose sensor interface may be included in the communication module 602. In some cases, the glucose sensor interface may be separate from the communication module 602. In some examples, the glucose level signal sent by the subject sensor 620 may be received by the communication system 602 and transmitted to control and computing module 610 where the signal may be analyzed to determine whether medicament should be delivered to the subject 622. In some examples, a second communication system may be included in the AMD (or GLCS) 600 to communicate with the subject sensor 620. If it is determined that medicament should be administered to the subject, the control and computing module 610 may determine the dosage and type of medicament to administer based on the information received from the subject sensor 620, generate a dose control signal, and send it to therapy delivery module 606 to initiate the medicament delivery to the subject. In some examples, the dose control signal may be received by the pump controller that controls the operation of the infusion pump.

In some embodiments, the control and computing module 610 may perform one or more procedures using the processor 614 (or a plurality of processors) that execute the instructions stored in the main memory 616. These procedures include, but are not limited to, determining the need for delivering medicament, determining the type of medicament and the required dose, determining the rate of delivery during a therapy session, providing information (e.g., device status, next delivery time, level of certain analytes in the subject's blood and the like) via the user interface module 608, processing the data received from the subject 620, managing access to control parameters (e.g., by controlling one or more therapy change controls that may be provided by the user interface module 608).

In some cases, an amplitude of the glucose level signal (e.g., an analog electronic signal) may be proportional to or correlated to the glucose level of the subject. In some cases, a glucose level signal may carry glucose level data (e.g., measured glucose level values or information usable to determine glucose level values). In these cases, the glucose level signal, generated by the glucose sensor (e.g., subject sensor 620), may comprise encoded glucose level data. In some examples, the glucose level signal may comprise glucose level data encoded onto a carrier signal, for example, using amplitude modulation, frequency modulation, and/or phase modulation. In some examples, the glucose level signal can be an analog signal encoded with data associated with the glucose level data. The glucose level signal can be transmitted via a wireless link (e.g., a Bluetooth link, a Wi-Fi link, a cellular data link, and/or other wireless network infrastructure) and received by a wireless receiver included in a glucose sensor interface. In some cases, the glucose sensor interface can be included in the communication module 602. In some cases, the glucose sensor interface can a separate module or system in the AMD 600. Subsequently, the glucose sensor interface may direct the glucose level signal to the control and computing module 610. In some examples, the control and computing module 610 may decode the glucose level data from the glucose level signal. In some embodiments, the glucose level data may be decoded by the glucose sensor interface. In other embodiments, the glucose level signal sent by the subject sensor 620 may be received by the communication module 602 and transmitted to the control and computing module 610.

The control and computing module 610 may determine a dose and a delivery time of a medicament (e.g., insulin or glucagon) based at least in part on the glucose levels of the subject 622 decoded from the received glucose level signals. Subsequently, the control and computing module 610 may generate a dose control signal and transmit the dose control signal to the therapy delivery module 606 of the AMD 600, to cause the delivery of the determined dose of medicament at the determined delivery time to the subject 622. The control and computing module 610 may generate the dose control signal using a control algorithm. In some cases, the control algorithm may comprise a model-predictive control (MPC) algorithm and/or a basal control algorithm.

In some examples, the signal (e.g., the glucose level signal) sent by the subject sensor 620 may be received by the communication module 602 (e.g., a sensor interface in the communication module 602) and transmitted to a signal processing module 604 that converts the signal to a machine-readable signal (e.g., a digital signal). In some examples, a second communication module separate from the communication module 602 may be included in the AMD 600 to communicate with the subject sensor 620. In some examples, the signal processed by the signal processor module 604 may be transmitted to the control and computing module 610 where the signal may be analyzed to determine whether medicament should be delivered to the subject 622. If it is determined that medicament should be administered to the subject 622, the control and computing module 610 may determine the dosage and type of medicament to administer based on the information received from the subject sensor 620, generate a dose control signal and send a dose signal to the therapy delivery module 606 (e.g., directly or via the signal processing module 604) to initiate the medicament delivery to the subject (e.g., using an infusion pump of the therapy delivery module 606).

In some embodiments, one or more procedures within the control and computing module 610 may be executed by the processor 614 (or a plurality of processors) based on instructions provided by one or more software applications installed in one of the memories (e.g., the main memory 616) of control and computing module 610. These procedures include, but are not limited to, determining the need for delivering medicament, determining the type of medicament and the required dose, determining the rate of delivery during a therapy session, providing information (e.g., device status, infusion set usage, infusion set status, subject sensor usage, transmitter status, transmitter usage, subject sensor 620 status, next delivery time, level of certain analytes in the subject's blood and the like) via the user interface module 608, processing the information received from a subject sensor 620 via the user interface module 608, managing access to control parameters (e.g., by controlling one or more therapy change controls that may be provided by the user interface module 608, and the like). In some embodiments, a first software application may control the AMD 600 and may be installed on the main memory 616 while a second software application (e.g., different version) may be stored in the storage 618. In some examples, the first and second software applications may be both installed in the main memory 616 but in different locations or segments. In some such examples, if needed, the control of the device can be switched from the first software application to the second software application.

In some embodiments, the AMD 600 may deliver multiple types of therapies that are selectable by a user or the control and computing module 610. For example, the AMD 600 may deliver the therapy of infusing insulin into a user and may also deliver the therapy of infusing glucagon into a user. In some examples, the user interface may include an option for the user to select an infusion of insulin, glucagon, or both insulin and glucagon. In other embodiments, other hormones, liquids, or therapies may be delivered. In some examples, the software application executed by the control and computing module 610, may determine the type of hormone that needs to be delivered, at least partly based on the information received from the subject sensor 620.

In some embodiments, the AMD 600 may allow the user or the subject 622 to announce to AMD 600 that the infusion set has been replaced. For example, upon user's request via a main menu, the user interface module 608 may generate a user interface on a touch screen display that allows the user or the subject 622 to enter a time and a date at which the infusion set has been replaced.

In some embodiments, the AMD 600 may provide the user or the subject 622 a user interface (e.g., via a touch screen display) that allows delivery of glucose therapy to the subject 622 upon request. For example, upon the user's request via a menu, the user interface module 608 may generate a medicament bolus or medicament burst user interface on a touch screen display that allows the user to enter a dose of a medicament for immediate delivery. In some cases, a regulatory medicament bolus can be a meal bolus requested and delivered in anticipation of food intake. In some cases, a counter-regulatory medicament bolus can be delivered in anticipation of physical activity (e.g., swimming or running), or similar to how a meal bolus can be delivered in anticipation of food intake. In some embodiments, a medicament bolus may be requested and delivered to maintain the glucose level of the subject 622 within a set range during a period of time when the subject 622 does not receive therapy from the AMDs 600. For example, the subject 622 may request a medicament bolus via the medicament burst user interface when he or she expects to be disconnected from the AMDs 600 for a period.

Communication and Networking

Figure 7:
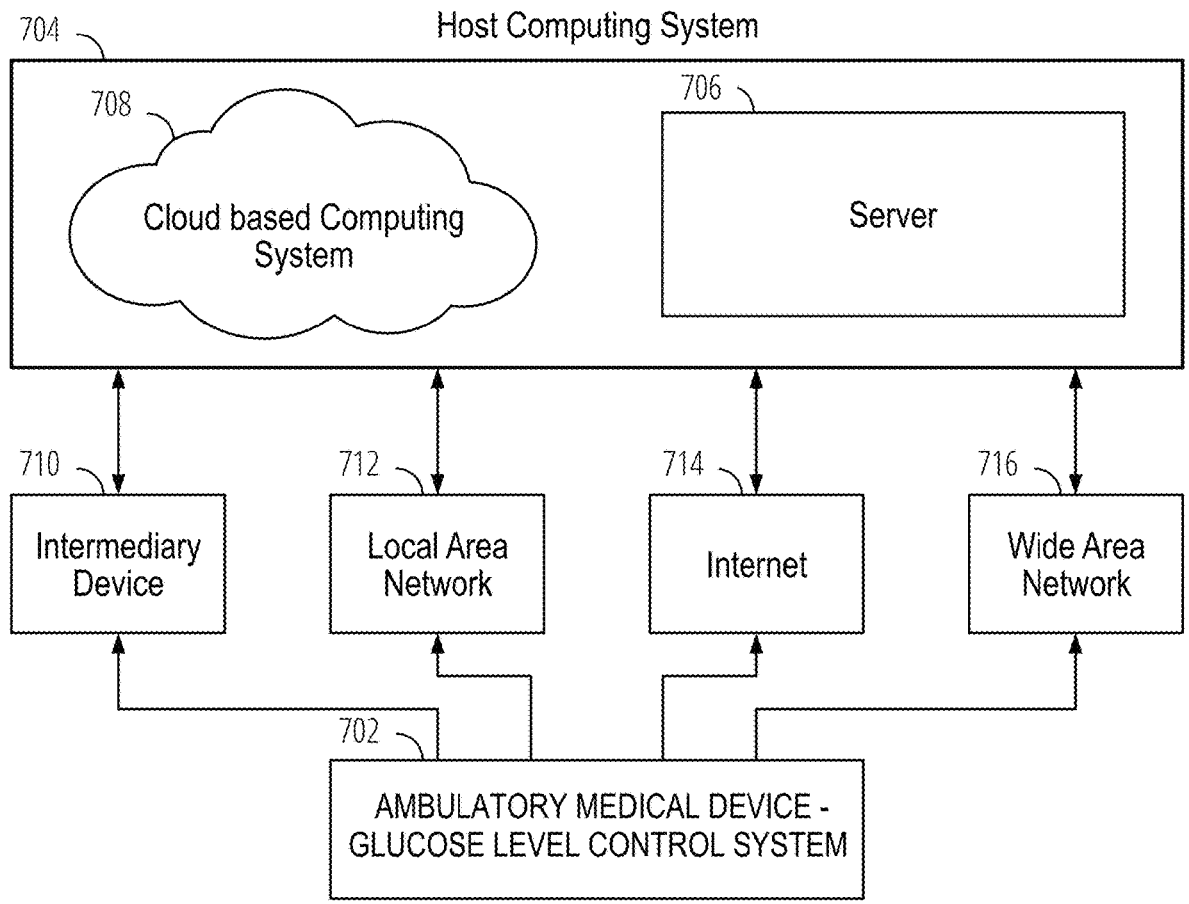
FIG. 7 illustrates various methods and links that an ambulatory medical device (AMD) may establish a connection with a host computing system.

FIG. 7 illustrates various methods and links or communication paths that an AMD (or GLCS) 702 may use to communicate (e.g., by establishing a connection) with a host computing system 704 (e.g., a remote computing environment), for example, to obtain an application update, send and/or receive therapy reports, facilitate ordering of infusion sets, analyte sensors, transmitters, and/or a new AMD, receive passcodes, send and receive electronic requests, receive values of control parameters, send or receive aggregate reports, and the like. In some examples, the host computing system 704 may be a server 706 or a computing system within a cloud based computing systems 708, or other networked computing environments, that provide networking computing services (e.g., network storage, application hosting, and/or network processing services). In some examples, the host computing system 704 may be part of a data center (e.g., the data center of a healthcare provider).

In some cases, the host computing system 704 may be a computing system of a healthcare provider, a healthcare professional, a manufacturer, or a payer (e.g., an insurance company). In some examples, the host computing system 704 may be part of a patient data network or be connected to a patient data network. The patient data network may comprise a local storage of patient data or a cloud storage. In some cases, the host computing system 704 may be in communication with a data center of a healthcare provider, a health institute, or a payer.

In some embodiments, the AMD (or GLCS) 702 may establish a connection (e.g., using the communication module 602) with the host computing system 704 through an intermediary device 710 (e.g., a smart phone or other mobile devices, a personal computer a notebook or the like). In some cases, the server 706 can be an electronic device can be a desktop computer, a mobile phone, a notebook, or any electronic device capable of establishing a data connection with the AMD 702 and receiving data from the AMD 702.

In some such examples, the AMD 702 may receive an application update from an intermediary device 710 of a user (e.g., a clinical computer, a subject's home computer, a smartphone, etc.) that has obtained a copy of the application update from the host computing system directly or via internet 714. In some examples, the AMD 702 may communicate with the host computing system 704 through a local area network (LAN) and/or through a Wi-Fi connection. Alternatively, or in addition, the AMD 702 may establish a communication connection to the host computing system 704 via a wide area network (WAN) 716. In some examples, the communication between the AMD 702 and the host computing system 704 may be encrypted.

In some embodiments, the AMD 702 may establish a direct end-to-end communication connection over a wide area network (WAN) 716 (e.g., a cellular network) with the host computing system 704. In some cases, a direct-end-to-end communication connection may be a connection that does not involve a local device, a device that is accessible by the user or the subject (besides the AMD 702), a Wi-Fi network, a short range wireless link (e.g., Bluetooth), or the like. In some such cases, the direct end-to-end communication may pass through one or more wireless systems (e.g., receivers, transmitters or antenna) of a WAN.

In some examples, the host computing system 704 may establish the end-to-end connection by receiving a public key from the AMD 702. In some examples, the public key and a private key stored in the host computing system 704 can be used to permit the host computing system 704 to decrypt data communications transmitted by the AMD 702. In some examples, the host computing system 704 may send a public key to the AMD 702 that allows the AMD 702 to encrypt data (e.g., therapy data). Up one receiving the encrypted data from the AMD 702 the host computing system 704 may use a private key stored in its memory, to decrypt the data.

In some implementations, the host computing system 704 may establish a direct end-to-end data connection with the AMD 702 based on receiving a device identifier associated with the AMD 702. The device identifier may be a unique identifier specific to the AMD 702. In some implementations, establishing the direct end-to-end data connection may include determining that the AMD 702 is permitted to communicate with the host computing system 704 based at least in part on the device identifier. In some examples, the device identifier may be initially provided to the networked-computing environment prior to provisioning of the AMD 702 to the subject. For example, the device identifier may be initially provided to the networked-computing environment as part of a manufacturing process for manufacturing the AMD 702. In some examples, the device identifier may include or may be based on one or more of an Internet Protocol (IP) address, a Media Access Control (MAC) address, a serial number, or a subject identifier of a subject that receives therapy from the AMD 702.

In some cases, the subject 622 or a user may establish or initiate establishing the direct end-to-end data connection with the host computing system 704. In some cases, the direct end-to-end data connection may be initiated or established without any action by the subject or the user. For example, the direct end-to-end data connection may be established automatically at particular times and/or when the AMD 702 is in a particular location. In some such cases, this automatic connection may occur using information supplied to the AMD 702 at a time of manufacture, shipment, sale, or prescription to the subject. Alternatively, or in addition, a subject or other user may configure the AMD 702 to automatically connect to the host computing system 704 at particular times and/or locations. In some cases, the local area networks 712 or wide area networks 716 include, or may communicate with, the Internet 714.

In some embodiments, the AMD 702 may be configured to communicate via the wide area network 716 during manufacture or prior to being provisioned to the subject. For example, a manufacturer can register the AMD 702 with a wireless wide-area network provider (e.g., T-Mobile, Verizon, etc.) and provide an International Mobile Equipment Identity (IMEI) number or serial number for the AMD 702 to the network provider. Moreover, fees can be negotiated between the manufacturer and the network provider or between the subject's health insurance and the network provider. Similarly, fees may be paid by the manufacturer or health insurance provider, or other entity, without subject involvement. Thus, the subject's AMD 702 may be configured to communicate via the network of the network provider without any action by the subject or the user. In some cases, the subject may be responsible for obtaining wireless service to connect the AMD 702 to a wide area network 716 (e.g., a cellular network).

In some examples, the AMD 702 may be pre-registered or authenticated with a computing network of the cloud services provider as part of the manufacturing process or before AMD 702 is provided to the subject. This enables the AMD 702 to communicate over the wide area network 716 with the computing system of the cloud services provider from day one without any or with minimal configuration by the subject. In some cases, a user, such as a healthcare provider may register or associate the AMD 702 with the subject at the computing network of the cloud services provider.

In some embodiments, the AMD 702 may use a whitelist, or approved list, that identifies via a unique identifier (e.g., via an IP address, a MAC address, or a URL) one or more permitted cloud servers or computing systems of the cloud based computing system 708 that the AMD 702 is permitted to access. By restricting access to an approved set of computing systems, the risk of malicious actors accessing the AMD 702 is reduced.

The whitelist may be stored in a memory of AMD 702 and/or in a memory of a trusted computing device that is accessible by the AMD 702. The trusted computing device can include any computing device that a manufacturer of the AMD has identified as trusted. Alternatively, or in addition, the trusted computing device can include any computing device that a subject or user that helps caste for the subject (e.g., parent, guardian, healthcare provider) has identified as a trusted computing device that is designated to store the whitelist. In some examples, the whitelist may be configured during manufacture of the AMD 702. For example, the whitelist may be configured with connection information to establish communication with one or more computing systems of a networked-computing environment. In some examples, the AMD 702 may be configured to execute the specific computer-executable instructions to at least obtain an address of a computing system from the whitelist and to establish a direct end-to-end data connection to the computing (e.g., a computing system in the networked-computing environment), via a wireless wide area network using the address. In some embodiments, the AMD 702 may be configured to execute the specific computer-executable instructions to at least receive a public key from the computing system of the networked-computing environment.

Moreover, in some cases, the AMD 702 may include a blacklist, or restricted list, that identifies systems the AMD 702 is not permitted to access. The blacklist may be updated as more restricted or unsafe websites, network accessible systems, or computing systems are identified. Similarly, the whitelist may be updated over time if approved systems are added or removed.

Further, the cloud based computing system 708 service may have a whitelist, or approved list, that uses unique identifiers to specify AMD 702 and/or other computing systems (e.g., remote display systems) that are permitted to communicate with the cloud based computing system 708. Moreover, as with the AMD 702, the cloud based computing system 708 may have a blacklist or restricted list that identifies AMDs, or other computing devices, that are not permitted to access the cloud computing services. An AMD may be added to the restricted list if it is decommissioned, damaged, or is no longer in possession of the subject. It may be desirable to remove an AMD's access to the cloud computing service to help protect private or personal data of a subject.

Advantageously, establishing a connection based on a whitelist may enhance the security of the communication link established between AMD 702 and the cloud based computing system 708 or other computing systems. In addition to the identifiers that identify permitted computing systems for access by the AMD 702 and/or permitted AMDs for access by a cloud or networked computing service, the whitelist may include any information that may facilitate access to the systems identified on the whitelist. For example, the whitelist may include access information (e.g., usernames, passwords, access codes, account identifiers, port identifiers, a shared secret, public keys, etc.). It should be understood that the whitelist may include different information depending on whether the whitelist is publicly accessible, accessible by only the AMD, accessible by authorized users or devices, etc. For example, a publicly accessible whitelist or a whitelist accessible by more than one authorized system or user may not include passwords or access codes.

Software Update of Ambulatory Medical Device

It is often the case that a computer application is updated after it is released. In some cases, the application is updated to patch bugs or vulnerabilities. In other cases, the application is updated or replaced with a new version to introduce new features or improve existing features. Regardless of the reason, it is often the case that an application is shutdown or is not executing while the application is updated. For most applications, there is minimal to no harm in shutting down or not executing an application while it is updated or otherwise replaced. For example, it is inconsequential that a video game, word processing, or edutainment application is not executing while it is updated.

However, it can be inconvenient, harmful, or, in some cases, life-threatening to cause an application on an ambulatory medical device to cease executing while it is updated or replaced by a new version of the application. If a subject or subject that is receiving therapy from the ambulatory medical device enters a state where therapy is desired or needed while an application or control software of the ambulatory medical device is being updated or replaced, harm may occur to the subject. For example, suppose the ambulatory medical device is an insulin pump, such as those that may be used by a type-1 diabetic. If the insulin pump becomes inoperative due to a software update process occurring at a time when a subject's glucose level exceeds a set-point or target range, the user may not receive a necessary insulin bolus from the ambulatory medical device. Thus, it is desirable to modify reduce or eliminate disruption to subject care or therapy when updating applications, such as control software, of an ambulatory medical device.

In some embodiments, an ambulatory medical device includes a computer-implemented method of updating an application executing on the ambulatory medical device without interrupting, or while causing minimal interruption, to therapy provided by the ambulatory medical device to a subject or subject. The method may generally be performed by a hardware processor, (e.g., a controller, and the like), included in an ambulatory medical device and based on a set of instructions that may be stored, for example, in a non-transitory memory of the AMD. The application update may be a new version of the application, a replacement or substitute application, or an application patch. In some examples, the application may be an older version of the application that has been used by instances of the ambulatory medical device for more than a threshold period of time and has experienced less than a threshold number of faults. The application update may be stored in one or more host computing systems. The application update may be pushed to the host computing systems by a company that manages or manufactured the ambulatory medical device or other software company that is authorized by the manufacturer or licensee of the device.

Figure 8:
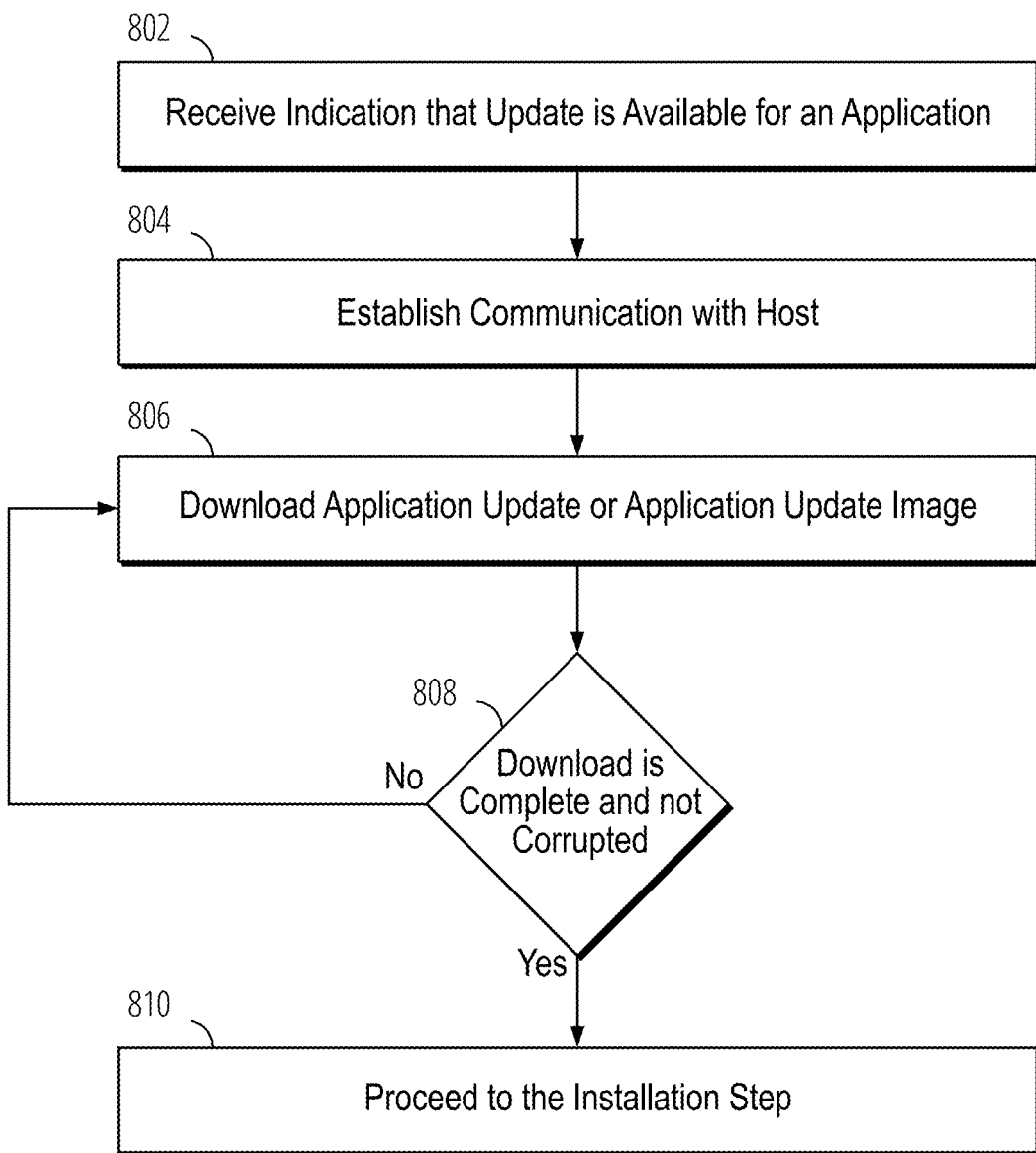
FIG. 8 is a flow diagram showing an example of a computer-implemented method that may be used by an AMD in order to detect and download an application update.

FIG. 8 is a flow diagram showing an example of a computer-implemented method that may be used by the AMD in order to detect and download an application update from a host computing system or other computer readable media in which a copy of the application update is stored. In certain aspects, an ambulatory medical device, such as a medicament delivery device or a medicament pump may receive an indication 802 that an update is available for an application, such as control software or other software that controls or facilitates the operation of the ambulatory medical device. The software update may include a binary executable file for various processors of the ambulatory medical device. In some embodiments, the indication may be a determination made by a software or hardware module included in an ambulatory medical device of AMD. For example, the AMD may access a particular host computing system (e.g., using its communication module) to determine whether an update is available, based on set of update trigger conditions stored in a memory of AMD. The set of update trigger conditions may be defined/changed by a user and/or received by AMD from a host computing system. For example, a trigger condition may push the AMD to periodically search for an update at time intervals set by the user or received from a host computing system. Alternatively, or in addition, in response to a trigger (such as a user command, the replacement of medicament within the ambulatory medical device, the connecting to a particular network, or the connecting to a network using a particular communication transceiver (e.g., Wi-Fi) or the like), the ambulatory medical device may access a particular host computing system to determine whether an update is available to an application installed on the AMD. The software to be updated on the AMD may be currently executing on the ambulatory medical device or may be executed in future.

In some embodiments, the indication may a query received from the host computing system that may access the AMD to read and compare the software versions and the hardware configuration (and warranty) to determine the eligibility of the ambulatory medical device for a software upgrade. The serial number, the model number, and/or the software version may be used to determine software upgrade eligibility. In some embodiments, the eligibility may be determined based on the geoposition of the device and/or whether the device is connected to a local area network (such as for example, a Wi-Fi network) or a wide area network (such as, for example, a cellular network). In various embodiments, the ambulatory medical device may have an antenna that provides the device with GPS, text or picture messaging, telephone calling, and data transfer capabilities. Software update may be provided on a limited release with test groups of varying sizes, e.g., 1-100 or 1-1000 or 1-10000. There may be a phase rollout of the software updates. In some embodiments, the AMD may respond to an upgrade eligibility request with a version of the first software or a model identification information of the ambulatory medical device or a manufacturing date of the ambulatory medical device.

If it is determined that an update is available to the application executing on the ambulatory medical device, the ambulatory medical device may establish a connection 804 to a host computing system that hosts the update to the application. Such connection may be established via one or more links or methods discussed above with reference to FIG. 7.

Once a connection is established, the ambulatory medical device may download the application update or application update from the host computing system over the connection 806. In some examples, the ambulatory medical device may download an image of the application update from the host computing system. While the application update is being downloaded, an existing version of the application on the ambulatory medical device may continue to execute. Thus, there is little or no interruption to therapy provided by the ambulatory medical device while the application update is being obtained by the ambulatory medical device.

Once the application update is obtained, the ambulatory medical device (using its control and computing module) may perform one or more operations to confirm that the application update was successfully downloaded from the application host system and that the download was not corrupted 808. For example, the ambulatory medical device may calculate a hash or checksum value from the downloaded application update. This hash or checksum value may be compared with one received from the application host system. If the calculated hash or checksum value matches the received hash or checksum value, then it may be determined that the download is both complete and not corrupt. Further, the ambulatory medical device may use the checksum, a tag, a payload size, or any other method to confirm that the download of the application update is complete and not corrupt. If it is determined that the download is corrupt 808, the AMD discards the corrupt copy and downloads another copy of the update. If it is determined that the download is complete and not corrupt, the AMD may proceed to the installation step 810 wherein the application update may be installed on the AMD without interrupting the ongoing or upcoming therapy sessions.

Figure 9:
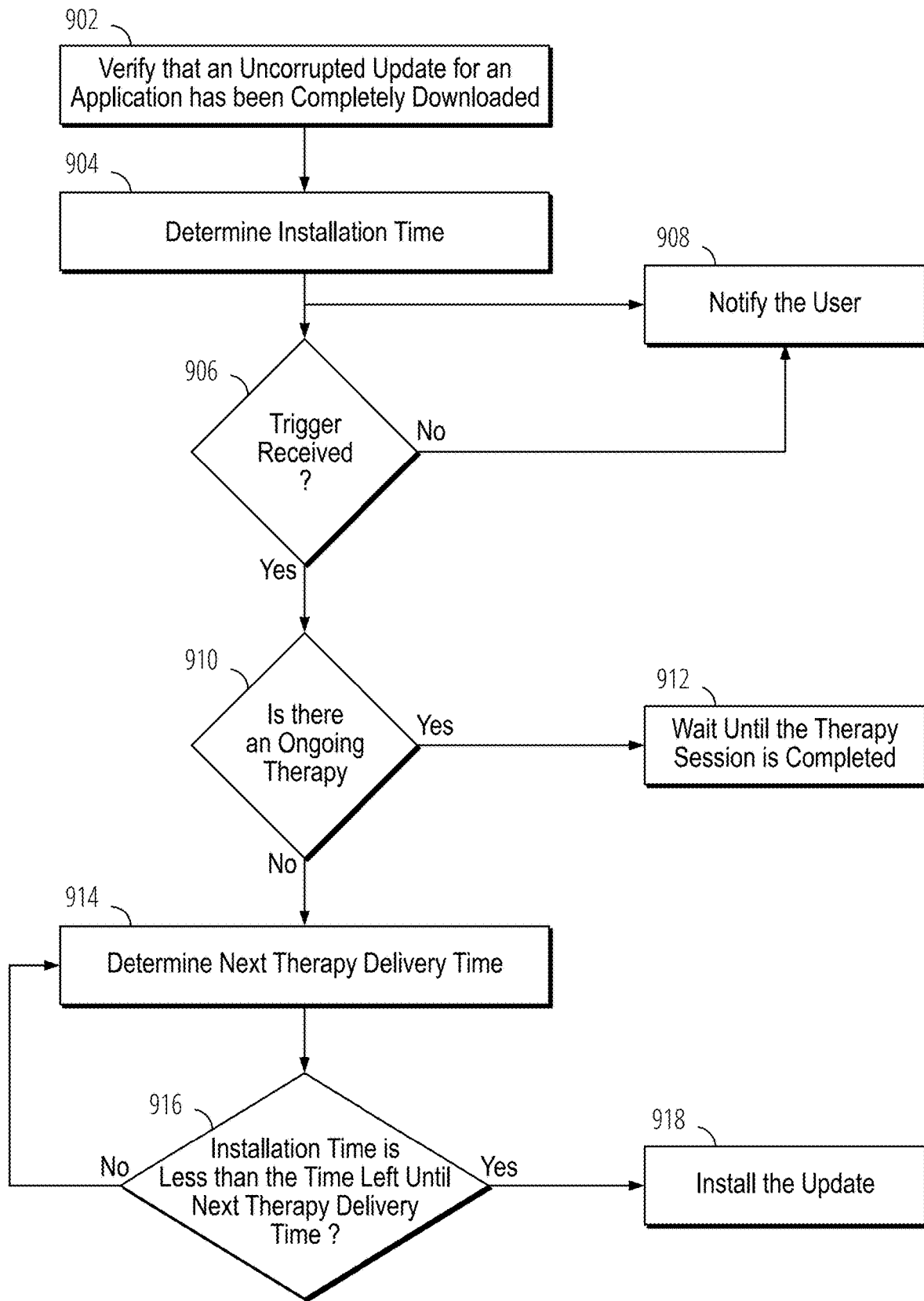
FIG. 9 is a flow diagram showing an example of a computer-implemented method that may be used by an AMD to install a down-loaded application update without interrupting the therapy provided to a subject.
Figure 10:
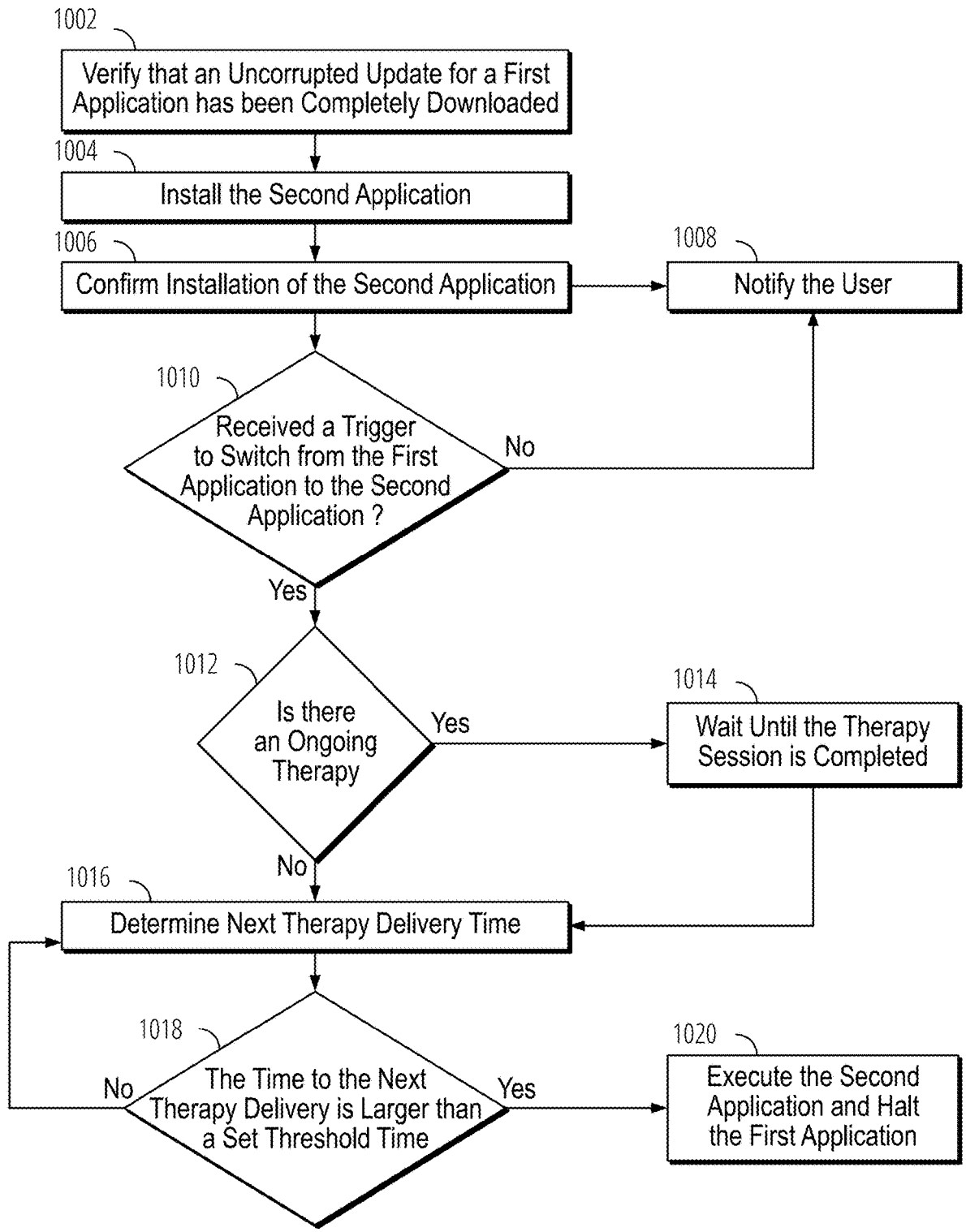
FIG. 10 is a flow diagram showing an example of a computer-implemented method that may be used by an AMD to install a second update downloaded from a host computing system and switch control of the AMD from a first application to the second application without interrupting the therapy provided to a subject.
Figure 11:
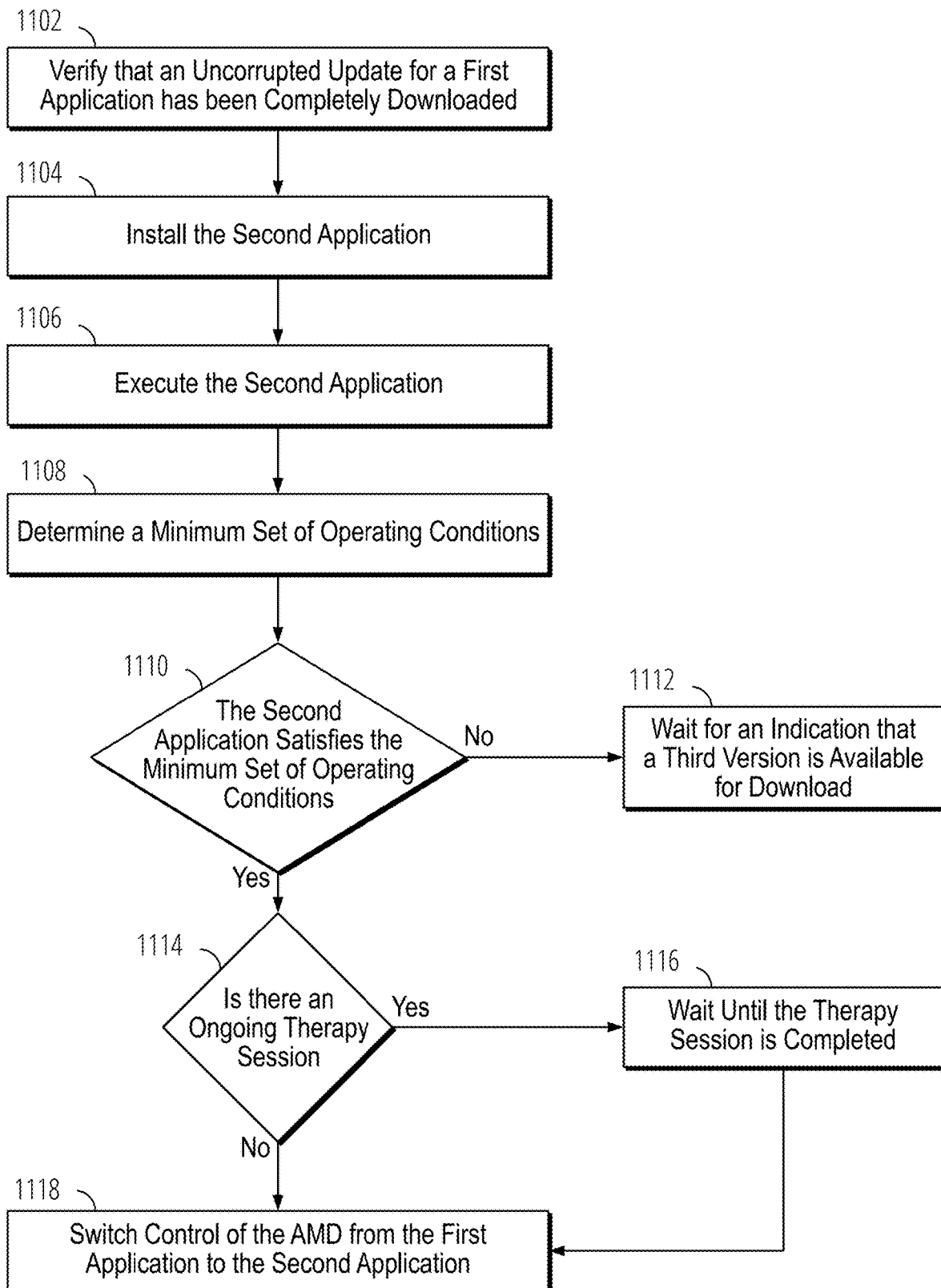
FIG. 11 is a flow diagram showing an example of a computer-implemented method that may be used by an AMD to install a second application downloaded from a host computing system, verify and switch control of the AMD from a first application to the second application without interrupting the therapy provided to a subject, only if the second application satisfies a minimum set of operation conditions.

FIG. 9-FIG. 11 are flow diagrams illustrating examples of computer-implemented methods that may be used by the AMD to install a downloaded application update without disrupting the therapy provided to a subject.

In the example method illustrated in FIG. 9, if it is verified that an uncorrupted copy of the update for an application is successfully downloaded 902 (e.g., using the procedure described above with reference to FIG. 8), the control and computing module (CCM) of the AMD 600 may determine the amount of time required to install the application update 904 and wait for a trigger signal 906 to initiate installation process. In some examples, the CCM 610 may notify to the user 908 through a user interface (e.g., a touchscreen display), that an update is ready for installation. The notification may include the installation time and information about the update. In such examples, if a trigger is not received, CCM 610 may send one or more notifications to the user indicating that a new update is ready for installation. In some examples, the trigger may be the confirmation that the application was successfully downloaded. Alternatively, or in addition, the trigger may be a user command received based on an interaction by a user or subject with a user interface that is part of or that communicates with the ambulatory medical device.

The installation time may be determined by the CCM based on data or metadata provided with the downloaded application update. For example, the application update may include a file (e.g., a text file or configuration file) that includes the install time. The installation time may be determined by the manufacturer of the ambulatory medical device or the publisher of the application update. For example, the developer of the software update may average the install time across several test devices to determine the install time metadata that is provided with the software update. General purpose computers have a wide variety of configurations and the performance of a general purpose computer may vary depending on the applications executing at a particular time. Thus, the determination of install time for an application based on the measurement of install time on a test device is typically unreliable. However, as an ambulatory medical device is often a special-purpose device that is designed to perform a specific function (e.g., provide insulin to a subject), an install time determined during testing by a manufacturer may in many cases be a reliable determination of install time on an ambulatory medical device of a subject. Alternatively, or in addition, to determining the install time based on testing by a manufacturer, the install time of an application update may be determined or estimated based on a size of the application update. In some cases, the provided or estimated install time may include a buffer. In other words, an additional amount of time may be added to the install time to account for variances in operating condition of the ambulatory medical device or inaccuracies in the estimated install time.

If a trigger is received 906, the CCM may check for any ongoing therapy session 910. If the no therapy is currently being administered, the CCM determines the next therapy time 914 (or the time left until the next therapy session). If therapy is currently being administered the installation will be delayed 912 until the therapy session is compete. Once the current therapy session is complete, the CCM may determine the time remaining until next therapy session 914 (e.g., during which medicament, such as insulin is delivered to a subject).

In some cases, the determination of the next time that therapy is to be delivered may be an estimate based on historical delivery of therapy, a present condition of the subject (e.g., when a glucose level is of a subject is at the center of a desired range, the next therapy delivery time may be estimated to be further off than when the glucose level is at the edge of the desired range), and/or an indication provided by a user or subject (e.g., an indication that the user is planning to have a meal, to exercise, or to go to sleep). Alternatively, or in addition, the determination of the next time that therapy is to be delivered may be based on a scheduled delivery of therapy (e.g., every 5 minutes or every hour).

As previously described, it is desirable to prevent disruption to therapy during the application update process. Thus, after the next therapy time is determined 914, the estimated install time may be compared 916 to the determined or estimated next therapy delivery time to determine whether the installation of the application update can be completed before the next therapy delivery to the subject. If it is determined that the time left until the next therapy session is sufficiently longer than the determined time for completing the installation, installation of the application updated may be initiated 918. In some examples, the determined time to the next therapy session has to be longer than the determined installation time by a threshold value. Such threshold value may be different for different application updates and/or the type of next therapy session. If it is determined that the application installation cannot be completed before the next therapy delivery (or the time left until the next therapy is not larger than that estimated installation time by a threshold value), the installation of the application may be delayed, regardless of receipt of the trigger. In this case, the CCM may wait for the next therapy to be completed and then determine a new therapy time 914. This process may be repeated until CCM determines that the update can be installed without interrupting an expected or scheduled therapy by the ambulatory medical device. In some examples, a new determination may be made before completion of the next therapy, to determine whether installation may be completed prior to a subsequent therapy time after the next therapy time.

In some cases, a time when the application can be installed without interrupting therapy may not be identified. In some such cases, a user (e.g., a clinician or other medical provider, or a subject) may be provided with an alert that an application update is available and/or that the application update cannot be installed without interrupting therapy. The user may be provide with an option as to whether to permit the update and/or when to install the application update. The option may include presenting the user with the estimated install time enabling the user to schedule the application update at a time when interruptions to therapy may be minimal or when an alternative source of therapy (e.g., injection therapy) can be utilized.

In some embodiments, once it is verified that an uncorrupted copy of the update for an application is successfully downloaded 902, the AMD's control and computing module (CCM) may notify the user and wait for a trigger signal before determining the installation time. Once the trigger has been received, the CCM initiates the installation process of the downloaded copy of the application update without interrupting therapy provided by the ambulatory medical device to the subject. In such embodiments, the application update may be installed in a different memory location than the memory location where the original application is installed and executed.

FIG. 10 is flow diagram illustrating an example of a computer-implemented method that may be used by the AMD in order to install a second application that is an update to a first application executing on the ambulatory medical device, without disrupting the therapy provided to a subject. In this example, once the control and computing module (CCM) of the AMD verifies that an uncorrupted copy of the second application is successfully downloaded 1002 (e.g., using the procedure described above with reference to FIG. 8), the CCM may initiate the installation process of the second application 1004 without interrupting the execution of the first application. The CCM may confirm 1006 the successful installation of the second application and wait for a trigger signal 1010 to initiate the execution of the second application in place of the first application. In some examples, the installation of the second application may be confirmed by sending a notification the user 1008 via a user interface of the AMD. In some examples, the CCM may determine the amount of time required for switching the control of AMD to from the first application to the second application. The notification may include information about the update and the time required for switching between the applications. In some examples, the trigger may be a user command received based on an interaction by a user or subject with a user interface that is part of or that communicates with the ambulatory medical device. In such examples, if a trigger is not received the AMD may send one or more notifications to the user indicating that a new update is ready for installation. If a trigger is received, the CCM may check for any ongoing therapy session 1012. If the no therapy is currently being administered, the CCM determines the next therapy time 1016 (or the time left until the next therapy session). If therapy is currently being administered the installation will be delayed 1014 until the therapy session is compete. Once the current therapy session is complete, the CCM may determine the time remaining until next therapy session 1016. The estimated next therapy delivery time may be compared to a set threshold time to determine whether the switching from the first application to the second application can be performed without interfering with the next therapy session. If it is determined that the time left until the next therapy session is longer than the set threshold time 1018, the execution of the second application will be initiated and the execution of the first application will be halted 1020. In some examples, the set threshold time may be determined by the CCM at least partly based on the time required to execute of the second application and halt the first application. In some examples, the set threshold time may be received from a host computing system.

In some embodiments, the performance of an application update may be tested before switching control of the AMD to the application update. FIG. 11 illustrate an example method that may be used by such embodiment. First the AMD verifies that an uncorrupted copy of the update for a first application is successfully downloaded 1102 (e.g., using the procedure described above with reference to FIG. 8). Next the AMD may install 1104 and execute 1106 the downloaded copy of the second application without interrupting the execution of the first application and therefore the therapy that might be provided by the ambulatory medical device to the subject. In some examples, the second application update may be installed to a separate portion (e.g., a separate execution space or separate memory) from the portion where the first application is installed and is being executed. The Control and computing module (CCM) of the AMD may determine that a minimum set of operating conditions 1108 are satisfied by the second application 1110, wherein the minimum set of operating conditions relate to maintaining therapy provided by the ambulatory medical device to the subject. If it is determined that the minimum set of operating conditions are not satisfied by the second application, the AMD may wait for an indication that a third application is available 1112 and repeat the procedure described above to evaluate the performance of the third application. If it is determined that the minimum set of operating conditions are satisfied by the second application, the AMD may check for an ongoing therapy session 1114. If it is determined that currently no therapy is provided to a subject, CCM may switch the control of the ambulatory medical device from the first application to the second application 1118. If currently therapy is provided to a subject, the CCM may wait until the therapy session is competed 1116 and then switch the control of the AMD from the first application to the second application.

In some cases, the ambulatory medical device may be updated (or downgraded) to add (or remove) features from the ambulatory medical device. For example, the ambulatory medical device may initially provide only insulin therapy. At some point in time, the ambulatory medical device may be upgraded to include bi-hormonal control (e.g., to provide both insulin therapy and counter-regulatory agent (e.g., Glucagon) therapy). The upgrade may be based on newly available features and/or based on a decision by a user to purchase or otherwise obtain additional features. Similarly, a user may opt to downgrade therapy from bi-hormonal to insulin-only therapy. Alternatively, the upgrade or downgrade may be made based on the availability of medicament. In some examples, a first update can be a first application version comprising a first feature set (e.g., providing insulin therapy) and a second update can be a second application version comprising a second feature set (e.g., provide both insulin therapy and Glucagon therapy). In some such examples the first feature set may comprise a subset of the second feature set. In some examples, the first feature set may comprise a partially overlapping set of features with the second feature set.

In some examples a computer-implemented method that may be used by the AMD in order to detect, download and install an update to an application executing on the ambulatory medical device wherein the application comprises one of a first application version comprising a first feature set or a second application version comprising a second feature set. In some examples, the first feature set may comprise partially overlapping set of features with the second feature set. In some examples, the first feature set may comprise partially overlapping set of features with the second feature set. The AMD may receive an indication of availability of the application update, download the application update and verify that an uncorrupted image of the application update is successfully downloaded (e.g., using the procedure described above with reference to FIG. 8). Next, the control and computing module (CCM) of the AMD may initiate the installation process of the application update image without interrupting the execution of the application. In some examples, the indication received by the AMD (with reference to FIG. 8), may include information about application update being an update to the first application version or to the second application version. In some such examples, the CCM may determine the version of the application update and download the application update image based on the determined version In some embodiments, any downloaded application update may be installed to a separate portion (e.g., a separate execution space or separate memory) from a currently executing version of the application. Once installation of the application is complete and the application is verified as being successfully installed, the active version of the application can be switched. For example, control of the ambulatory medical device can be provided to the updated application, the previously executing application can be ceased or halted. The old application can then be removed, or kept as backup. Determining when to switch which version of the application is active may follow a similar process as previously described for identifying a next therapy delivery time and selecting a time to switch active versions of the application when there will not be an interruption to the therapy provided by the ambulatory medical device.

In some embodiments, the ambulatory medical device may be configured to store multiple instances of an application (e.g., ambulatory medical device control software). For example, the ambulatory medical device may have a current, or first, version of the application that it is installed in a first memory location (e.g., in the main memory 616) and is executing to, for example, control therapy provided by a subject. Further, the ambulatory medical device may include an updated, or second version of the application installed in a second memory location (e.g., in the main memory 616). The update of the second version may have been downloaded and installed (e.g., in a prior to detection of the fault). In such embodiments, when a fault is detected during execution of the first version of the application, the ambulatory medical device may initiate the execution of the second version of the application and then switch control of the AMD to the second version of the application to maintain therapy to the subject.

Figure 12:
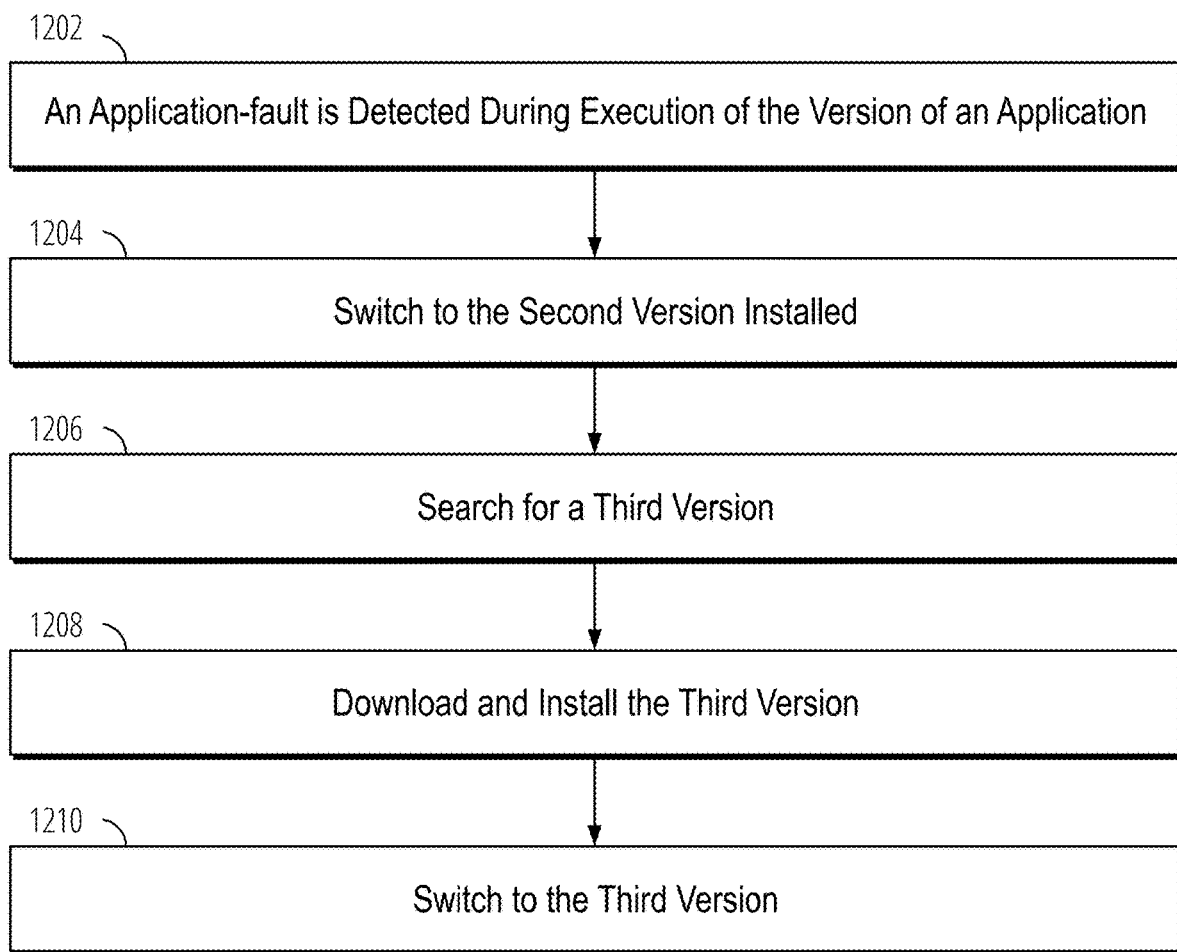
FIG. 12 is a flow diagram showing an example of a computer-implemented method that may be used to respond to detection of an application fault during the execution of a first version of an application and switching control of the AMD to a second version an application installed on the AMD.

In some examples, the second version of the application installed on the AMD may be a version older than the first version, or version that may not have track a record of stability and reliability. FIG. 12 is a flow diagram for such examples. Once an application-fault is detected during execution of the first version 1202, the control and computing module (CCM) of the AMD may switch the control of the AMD to the second version of the application 1204 while searching for a third update 1206. In some examples, the CCM may establish a connection with a host computing system configured to host a third update and download and install the third update 1208. The third version of the application may be a new version, a version prior to the first version, an update to the first application that addresses the detected application-fault or an older version that satisfies the conditions to be classified as a "safe version" (e.g., less than a threshold number or rate of faults over a minimum period of time). The second version (installed in the device) may control the AMD while the third version is being downloaded and installed 1208 without interrupting the therapy. Once the download of the third version is complete, the CCM may initiate the installation process of the downloaded copy of the third application and switch control of the ambulatory medical device form the second application to the third application 1210 without interrupting therapy provided by the ambulatory medical device to the subject In yet other embodiments, a "safe version" of the application may have been installed on the ambulatory medical device prior to detection of a fault. The safe version of the application may include a version of the application that has been used by instances of the ambulatory medical device for more than a threshold period of time and has experienced less than a threshold number of faults. For example, the safe version of the application may be a two-year old version of the application that has demonstrably had less than a threshold number of faults occur over the period of two years. This safe version of the application may have less features than the first or second version of the application. However, when a fault is detected during execution of the first or second version of the application, the ambulatory medical device may switch control of the device to the safe version of the application to maintain therapy to the subject.

In some cases, if there is an issue installing an updated version of the application, the ambulatory medical device may revert to the current version or a safe version installed on the AMD.

In some examples, the AMD may be triggered to establish a connection with the host computing system and search for the second version once a fault is detected during execution of the first version. In these examples, the ambulatory medical device may revert to the safe version (installed in the device) while downloading and installing the second version without interrupting the therapy.

Figure 13:
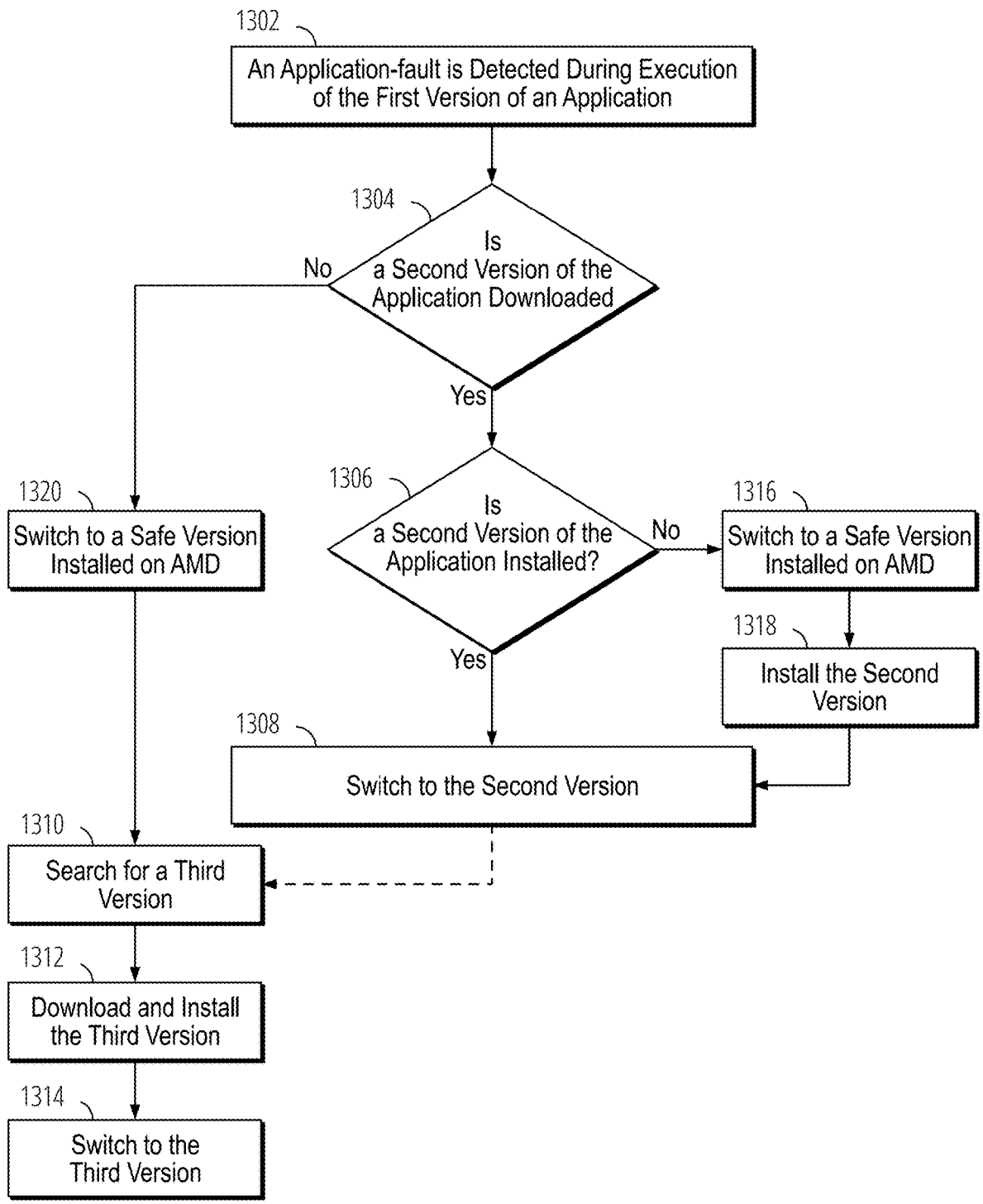
FIG. 13 is a flow diagram showing an example of a computer-implemented method that may be used to respond to detection of an application fault during the execution of a first version of an application and switching control of the AMD to a second version an application installed on the AMD and/or downloading a third version of the application.

FIG. 13 is a flow diagram illustrating yet another example of a method of responding to a fault detection by the AMD. In this example, once an application-fault is detected during execution of the first version of an application 1302, the control and computing module (CCM) of the AMD may look for a second version of the application 1304 in the main memory or the storage. If it is determined that the second version has been already downloaded, the CCM will determine 1306 whether the second version of the application is installed in a memory location and is ready to be executed. If it is determined that the second version of the application is installed, the control of the AMD will be switched to the second version of the application 1308. With reference to block 1306, if CCM determines that the second version exists in the memory but it is not installed, it will switch the control of the AMD to a safe version that may be already installed 1316 and then initiates the installation 1318 of the second version. Once the installation of the second version is complete, the CCM may switch control of the AMD from the safe version of the application to the second version of the application. In some embodiments, after the control of the AMD is switched to the second version of the application, the CCM may search for a third version of the application 1310 that may be an update to the previously downloaded second version. If a third version is found, the CCM may download and install the third version 1312 and switch the control of the AMD to the third version 1314. With reference to block 1304, if the CCM cannot find a second version of the application in a memory or storage location, it will switch the control of the AMD to a safe version of the application 1320 that may be installed in a memory location (e.g., in the main memory or in the storage) and then search for a third version of the application 1310. If a third version is found, the system may download and install the third version 1312 and switch the control of the device to the third version 1314.

In some embodiments, when an application-fault of an application executing on the ambulatory medical device is detected, the AMD may transmit an indication of the application-fault to the host computing system of a manufacturer or maintenance service of the ambulatory medical device. In some embodiments, the AMD may notify the user when an application-fault occurs through a user interface of the AMD or user interface communicating with the AMD.

Direct Network-Connected Medical Device Communication and Remote Viewing

An ambulatory medical device, such as an ambulatory medicament device (e.g., glucose level control system (e.g., an insulin pump or a bi-hormonal pump that includes insulin and a counter-regulatory agent), a pacemaker, or any type of medical device that may be connected to a subject to provide therapy to the subject, can generate a significant amount of data related to therapy provided to a subject (therapy data). This therapy data may be useful for the subject, a healthcare provider, or other users (e.g., parent or guardian) to actively manage the subject's health condition. For example, the therapy data may be useful to determine whether a modification to therapy may be desirable or to confirm that intended therapy is being delivered at the right time. In other examples the data may be used to generate an alerts about the health condition of the subject when therapy data indicates that immediate attention is needed with regards to subject' health condition.

Various aspects of accessing the therapy data or other types of data stored in a memory of the AMD needs proper management in order to provide uninterrupted, secure, and easy access to authorized users. As described above, the procedures and task performed by an AMD, including those associated with data transfer management, may be associated with certain computer-executable instructions stored and executed by the control and computing module 610 of the AMD 600. As such, different AMD configurations used for various data transfer management tasks, may be configurations of the control and computing module 610 of the AMD 600.

Accessing the data from the ambulatory medical device can be problematic in some cases. For example, accessing the data may require a user to connect the ambulatory medical device to a computer to upload the data. This places a burden on the user to remember to connect the ambulatory medical device. Further, during the period when the device is connected to the computer, the subject may not be receiving therapy from the ambulatory medical device. In some cases, the subject may not be capable of connecting the device to the computer (e.g., when the AMD is not within range of the local device) and may not have someone available to assist the subject. Thus, a direct end-to-end connection to a computing system that (e.g., computing system of a healthcare provider) can safely share data (e.g., therapy data) with authorized users may facilitate data management and access.

Figure 14:
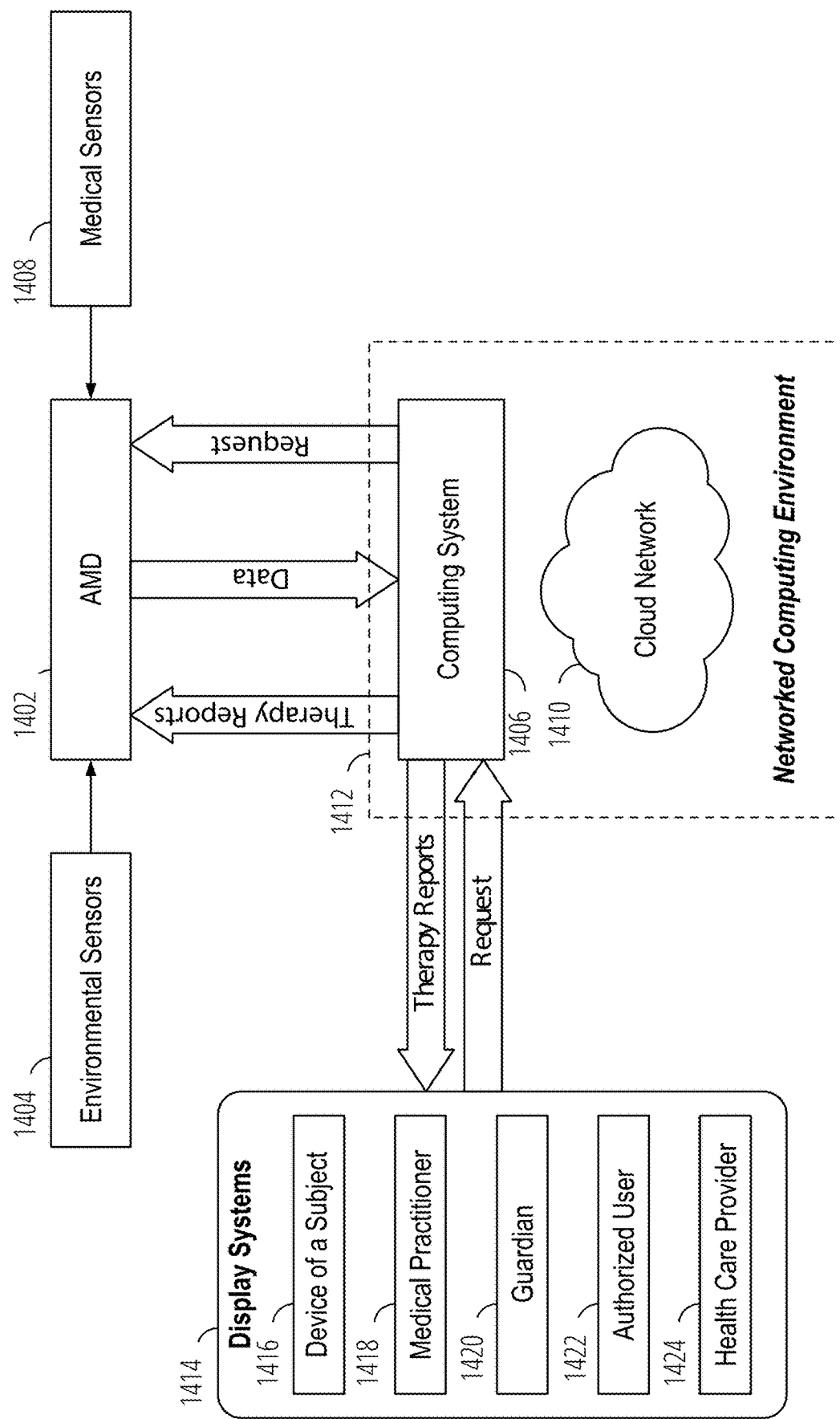
FIG. 14. is a block diagram, illustrating an example network configuration wherein the AMD is directly connected to a computing system and the computing system shares the therapy reports with one or more display systems and the AMD.

FIG. 14 is a block diagram illustrating an example network configuration wherein the AMD 1402 is directly connected to a computing system 1406 in addition to environmental sensors 1404 and medical sensors 1408. The computing system 1406 may be part of networked computing environment 1412 (e.g., a data center, networked computing system), or cloud network 1410 or cloud computing system of a cloud service provider. The computing system may include one or more non-transitional memories and one or more hardware processors configured to execute the computer-executable instructions stored in one or more non-transitional memories. In some such examples, the procedures performed by the computing system may be associated with the execution of certain computer-executable instructions stored in a memory of the computing system by a hardware processor of the computing system.

In some examples, the direct end-to-end data connection may be supported by one or more transceivers in AMD's communication module 602. For examples, a direct connection may be established between the AMD 1402 and the computing system 1406 over a wide area network (e.g., a cellular network) without using an intermediary system using various wireless standards and technologies (e.g., 4G, 5G and the like). In some examples, the transceiver may support communication via communication standards, including but not limited to, low power wide area network (LPWAN), Narrowband Long-Term Evolution (NB-LTE), Narrowband Internet-of-Things (NB-IoT), or Long-Term Evolution Machine Type Communication (LTE-MTC). In some cases, the transceiver is always on, and in other cases, the transceiver may be activated when a data transfer is scheduled, requested, or activated. In some cases, the capability of the ambulatory medical device 1402 to communicate with the computing system may be activated during manufacture or before providing the device to a subject.

In some cases, the subject or a user establishes or initiates establishing the direct end-to-end data connection with the computing system. For example, the subject may interact with a user interface to cause the ambulatory medical device to communicate with the cloud computing service. In other cases, the direct end-to-end data connection may be initiated or established without action by the subject or the user. For example, the direct end-to-end data connection may occur automatically at particular times or when the ambulatory medical device is in particular locations. This automatic connection may occur using information supplied to the ambulatory medical device at a time of manufacture, shipment, sale, or prescription to the subject. Further, in some cases, the ambulatory medical device can communicate with the computing system without having access to a Wi-Fi network or a local area network (LAN). For example, the ambulatory medical device may communicate using a cellular or other wide area network. Further, in some cases, the interaction by the user with the ambulatory medical device may be relatively minimal or simple compared to traditional network communication. For example, a user may push a single button (e.g., an "upload" button) to trigger establishing of a connection with the cloud computing service and causing data to be provided from the ambulatory medical device to the cloud computing service.

In some cases, the ambulatory medical device may be turned on and paired with the wireless wide area network (e.g., a cellular network) at the time of manufacture, or prior to being provided to a subject. Further, the ambulatory medical device may be authenticated with the networked-computing environment as part of the manufacturing process Further, establishing the direct end-to-end data connection may include determining that the ambulatory medical device is permitted to communicate with the computing system based at least in part on the device identifier.

In some implementations, establishing the direct end-to-end data connection may include determining that the ambulatory medical device is permitted to communicate with the computing system based at least in part on a device identifier associated with the ambulatory medical device. The device identifier may be a unique identifier specific to the ambulatory medical device. The device identifier may include or may be based on one or more of an Internet Protocol (IP) address, a Media Access Control (MAC) address, a serial number, or a subject identifier of a subject that receives therapy from the ambulatory medical device.

Further, establishing the direct end-to-end data connection may include determining that the ambulatory medical device is permitted to communicate with the computing system based at least in part on the device identifier. The device identifier may be initially provided to the networked-computing environment prior to provisioning of the ambulatory medical device to the subject. For example, the device identifier may be initially provided to the networked-computing environment as part of a manufacturing process for manufacturing the ambulatory medical device. The request may include a device identifier associated with the ambulatory medical device.

The ambulatory medical device may be configured to at least identify a computing system 1406 of a networked computing environment 1412 based on a whitelist of one or more approved computing systems. The whitelist may be stored in a memory of the AMD 1402 (e.g., a memory in the control and computing module of the AMD). Further, the whitelist may be configured during manufacture of the ambulatory medical device. For example, the whitelist may be configured with connection information to establish communication with one or more computing systems of a networked-computing environment. Further, the ambulatory medical device may be configured to at least obtain an address of the computing system from the whitelist and to establish a direct end-to-end data connection to the computing system of the networked-computing environment via a wireless wide area network using the address. The whitelist may include unique identifiers, such as MAC addresses or static IP addresses that are associated with computing systems of the cloud services provider.

To enhance security, the ambulatory medical device may use a whitelist that identifies via a unique identifier (e.g., via an IP address, a MAC address, or a URL) permitted cloud servers or computing systems in networked computing environment. Further, the cloud computing service may have a whitelist that uses unique identifiers to specify ambulatory medical devices and/or other computing systems (e.g., remote display systems) that are permitted to communicate with the cloud computing system.

When the AMD communicates data over a network, there is a risk of a data breach. Thus, to improve security, all communication between the ambulatory medical device and the computing may be based on a secure data transmission method. For example, the ambulatory medical device may encrypt all data using an asymmetric key.

In some examples, the therapy data may be encrypted before being transferred to the computing system. In these examples, AMD may have a public key and a private key stored in one of its memories permitting the AMD to encrypt data communications transmitted by the ambulatory medical device to the computing system. In these examples, AMD may transmit the public key along with the therapy data to the computing system. The public key provided by the AMD and a private key stored on the computing system may permit the computing system to decrypt the data received from the ambulatory medical device. In some such cases, the public key may timeout and a new public key may be obtained from the ambulatory medical device to facilitate decrypting subsequent communications from the ambulatory medical device. In some cases, the public key may be associated with a time-to-live (TTL) value. In some such cases, the public key may timeout and a new public key may be obtained from the ambulatory medical device to facilitate decrypting subsequent communications from the ambulatory medical device.

Moreover, the secure data transmission may include generating a shared secret based at least in part on the public key and the private key. In some such cases, decrypting the encrypted data comprises using the shared secret to decrypt the encrypted data. In some examples, shared secret may be established using public key exchange algorithm (e.g., Diffie-Hellman key exchange algorithm).

In some cases, the computing system may be configured to transfer the data after receiving a request to transfer data stored on the ambulatory medical device to the computing system over the direct end-to-end data connection via the wireless wide area network. Responsive to receiving the request to transfer data stored on the ambulatory medical device to the computing system, the computing system may be configured to receive, via the direct end-to-end data connection.

Once a connection is established and the therapy data is transferred to the computing system, the computing system may analyze the therapy data received from the ambulatory medical device and generate a therapy report. Further, the computing system may detect an alarm condition, based on therapy data analysis, and generate an alarm that may be provided to the subject, authorized user (e.g., healthcare provider). In some cases, the therapy data may trigger an automatic response by the computing system. For example, the AMD may determine that a medicament or another disposable is running low based on the received data and may automatically reorder the medicament or the disposable.

In some cases, the computing system may periodically receive data from the ambulatory medical device based on a regular schedule. Alternatively, or in addition, the data may be received in response to a command or when the ambulatory medical device determines it is within a certain location. For example, when the ambulatory medical device determines it is within a subject's home or at a healthcare provider's office based on a local area network connection or based on a geolocation system (e.g., a global positioning system (GPS)). In some implementations, additional encrypted data is received from the ambulatory medical device on an intermittent basis. Alternatively, or in addition, additional encrypted data is received from the ambulatory medical device on a continuous basis for at least a time period. The ambulatory medical device may be configured to transmit data as it is generated, or shortly thereafter, (e.g., in real or near real-time (e.g., within a few millisecond, seconds, or minutes of the data being generated)), or in bulk at specified periods of time. Transmitting the data in bulk at particular time periods may extend battery life, but may provide for less up-to-date analysis. Data can be made available on-demand by keeping the transceiver always on, but this may consume more power. Thus, the scheduling of data transfer may be balanced based on different considerations, such as: (1) power consumption and (2) need to share information with authorized users or systems.

In some cases, the computing system may be used as a backup for the ambulatory medical device. For example, the ambulatory medical device can backup data to the computing system every night, when it is charging, or when it is in proximity to home or a physician's office (e.g., when subject is in waiting room, the device may upload data that the physician can then access). Moreover, if the ambulatory medical device is replaced (e.g., for a new model or to replace a damaged device), the device can automatically synchronize with the computing system to obtain subject-specific configuration or therapy control data.

Therapy Data and Therapy Report

In some examples, the therapy data comprises dose or dosage data corresponding to one or more doses of medicament provided by the ambulatory medical device to the subject. Further, the therapy data may comprise subject data corresponding to a medical or physiological state of the subject as determined by the ambulatory medical device.

In other examples, the data provided to computing system may include any type of data that may be measured or obtained by the ambulatory medical device and may include a record of therapy provided by the ambulatory medical device. For example, the data may include a time that therapy was provided, an amount of medicament provided as part of the therapy, a measure of one or more vital signs of the subject, a measure of glucose levels (e.g., blood glucose levels) at different times for the subject, a location of the subject, and the like.

In some cases, the therapy data may be used to track the use of disposables, such as insulin or other medicament, or insulin pump site kits. In some cases, the computing system may automatically order or reorder disposables at a particular time based on tracking the use of the disposable. Alternatively, or in addition, the reordering of the disposables may be initiated or performed from the ambulatory medical device (e.g., via a wireless wide area network or via a local connection through a separate electronic device).

In some cases, the data transferred to the computing systems may comprise operation data corresponding to operation of the ambulatory medical device. Alternatively, or in addition, the data may further comprise error data corresponding to an error in operation of the ambulatory medical device.

In some examples, the data, therapy data and/or the therapy report may be stored in a memory of the computing system and/or at a storage of the networked-computing environment.

In some cases, the method may include converting the therapy data from one format to another format. For example, the method may include converting the therapy data from a format used to store and/or present data on ambulatory medical device to a format that can be stored or processed on the computing system. In some cases, the therapy data is converted from a machine-readable format to a human-readable format. The data may be stored in a more easily interpreted format that can be understood by different types of users. For example, the data may be presented in one format for a healthcare provider (e.g., sensor readings), a simplified format for a subject or parent of a subject, other data formats for displaying data to different types of users.

In some examples, the therapy data collected from different AMDs associated with plurality of subjects may be aggregated for a group of subjects based on their association with an institution or organization (e.g., a clinic, an insurance company, and the like)

In some examples, a therapy report based at least in part on the therapy data may be generated by the computing system. The therapy report may comprise time-series therapy data relating to the therapy delivered by the ambulatory medical device over a particular time period.

In some examples, the therapy report may be sent to AMD wherein the subject can see the report via a user interface (e.g., a touchscreen display).

In some cases, the ambulatory device data and/or data generated by the computing system based on the ambulatory device data can be viewed on a secondary display system from the computing system. For example, a clinician or parent can access the data from their personal device. The communication between the computing systems and the viewing device may be encrypted. Moreover, permission for sharing of end user data with a 'follower' (e.g., family member) or clinician may be granted or controlled by the end user (e.g., the subject or a guardian).

An association between a subject, a clinic, and/or an ambulatory medical device may be performed by association of a device serial number of the ambulatory medical device with the subject and/or clinic. Further, a user (e.g., a subject, clinician, or parent) can access therapeutic recommendations through the cloud in case either the ambulatory medical device (e.g., an insulin pump) or the CGM sensor fails to function.

In some cases, the computing system may be configured to at least receive a request from one or more display systems 1414 that are separate from the networked computing environment to access the therapy report, therapy data or other data received by or stored in the AMD. In some cases, the display system may be a computing system of a medical practitioner 1418 (e.g., such as a doctor or a nurse), a guardian of the subject 1420 (e.g., subject's parents), an authorized user 1422 (e.g., a user authorized by the subject such as spouse, relative, friend, and the like), a health care service provider 1424, or a device of the subject 1416 (e.g., cell phone, personal computer, tablet, and the like).

In some examples, the display system can be a therapy data management system that analyses a therapy data associated with a specific type of health problem (e.g., data associated with managing diabetes) and provides useful information to the subject or an authorized user to monitor and manage the corresponding ailment.

The request may comprise an account identifier associated with a user that generated the request. In some examples, the account identifier may comprise a unique identifier associated with the subject. Alternatively, or in addition, the account identifier comprises a unique identifier associated with a user that is authorized to access the therapy report. The user may or may not be the subject. In some aspects of the present disclosure, the method may further include associating the therapy data with the account identifier at a storage of the networked-computing environment. Further, the computing system may be configured to determine whether an account associated with the account identifier is permitted to view the therapy report. In some examples, account permissions may be granted and/or modified by the subject. For example, the subject can access an account at a networked computing environment 1412, for example, a cloud service provider associated with the subject, and provide one or more identifiers associated with one or more other users to give them permission to access the subject's therapy data or report stored on the computing system.

Responsive to determining that the account is permitted to view the therapy report, the hardware processor may be configured to transmit the therapy report to the display system over an encrypted communication channel.

In some cases, the method may include receiving an identity or identification information of one or more users that are authorized to access therapy data stored at the networked-computing environment. For example, a user or subject may authorize a clinician or other healthcare provider, a parent or guardian, or other users that the subject desires to have access to the therapy data. The identity information of the one or more users may include any type of information that may identify the user or enable the user to be authenticated. For example, the identity information may include a name, unique identifier (e.g., social security number), an email, an address, a phone number, account information for the user at the networked-computing environment, or any other identifying information.

Figure 15:
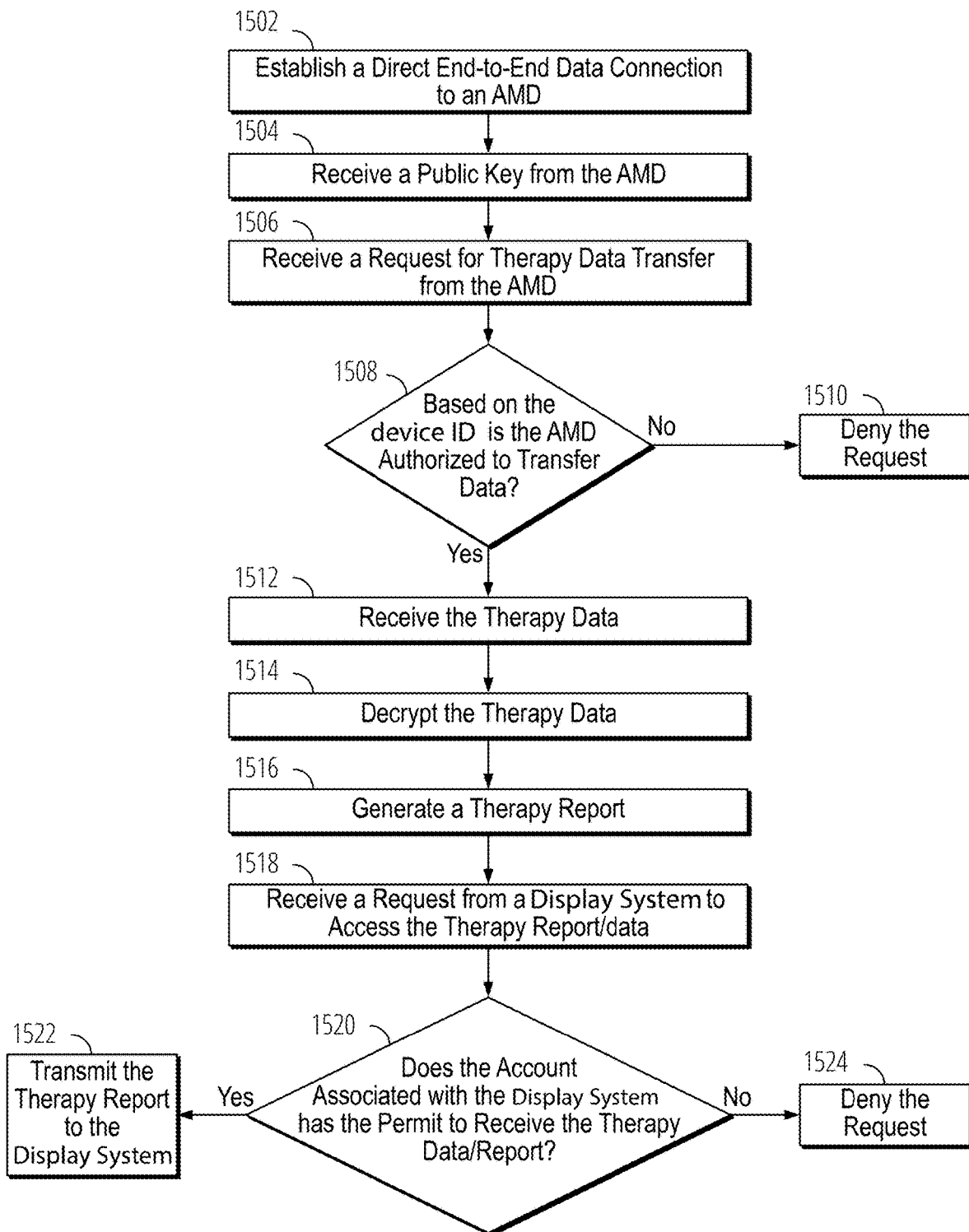
FIG. 15 is a flow diagram illustrating an example method that may be used by a computing system, to generate and share a therapy report based on encrypted therapy data received from an AMD.

FIG. 15 is a flow diagram that illustrates an example method that may be used by computing system 1406, to generate and share a therapy report based on encrypted therapy data received from an AMD 1402. In some examples, the AMD 1402 may generate the encrypted therapy data using a public key and a private key. The method may include establishing a direct end-to-end data connection 1502 to an ambulatory medical device, for example, via a wireless wide area network (WAN) using a Narrowband Long-Term Evolution (NB-LTE) transceiver included in the AMD 1402. Once a direct end-to-end data connection between the AMD 1402 and the computing system 1406 is established, the computing system may receive a public key 1504 (e.g., associated with encrypted data), from the AMD 1402 over the established connection. Next, the computing system may receive a request from the AMD 1506 to transfer data (e.g., therapy data) stored on the AMD 1402 to the computing system 1406 over the direct end-to-end data connection. In some examples, the computing system 1406 may use the device ID associated with the AMD 1402 to determine whether the AMD 1402 is authorized to transfer data to the computing system 1508. If, based on the device ID, it is determined that the AMD 1402 is authorized to transfer data to the computing system, the encrypted therapy data may be transferred 1512 to the computing system. If, based on the device ID, it is determined that the AMD 1402 is not authorized to transfer data to the computing system, the request may be denied 1510. The computing system may decrypt the encrypted therapy data 1514 using a private key (e.g., stored in a memory of the computing system) and a public key received from the AMD 1402. In some examples, the therapy data may be used to generate a therapy report 1516. In some examples, the decrypted therapy data and/or therapy report may be stored in a memory of the computing system 1406.

The example method may further include receiving a request from a display system 1414 that is separate from the networked computing environment, to access the therapy report 1518. The request may comprise an account identifier associated with a user that generated the request. The method may include determining using the account identifier to determine whether the account associated with the account identifier is permitted to view the therapy report 1520. In the computing system determines that the account associated with the received account identifier does not have the required permission, the request will be denied 1524. Responsive to determining that the account is permitted to view the therapy report, the method may include transmitting the therapy report to the display system 1522 over an encrypted communication channel.

In certain implementations, the method may further include determining that the therapy data or other data received from the AMD satisfy an alert threshold condition. In these implementations, it is determined that the therapy data or other data received from the AMD satisfy an alert threshold condition, the computing system may send an alert to one or more display systems designated to receive alerts from the computing system.

In some examples, alert threshold condition may be associated with the health condition of the subject. For example, alert threshold condition may include subject's glucose level is above or below a set value (hyperglycemia or hypoglycemia). In some examples the alert threshold condition may be associated with the operation of the AMD. For example, alert threshold condition may include the rate of therapy (e.g., the rate at which insulin is provided to a subject) being above or below a set value.

In some examples, alert threshold condition may be associated with the temporal behavior of therapy data over a period of time. For example, the alert threshold condition may include the fluctuations or variations of the subject's glucose level being above a set value.

In some examples, the alert threshold condition may be defined or set by health provider. In some such examples, the health provider may change one or more alert threshold conditions based on the health condition of the subject.

Figure 16:
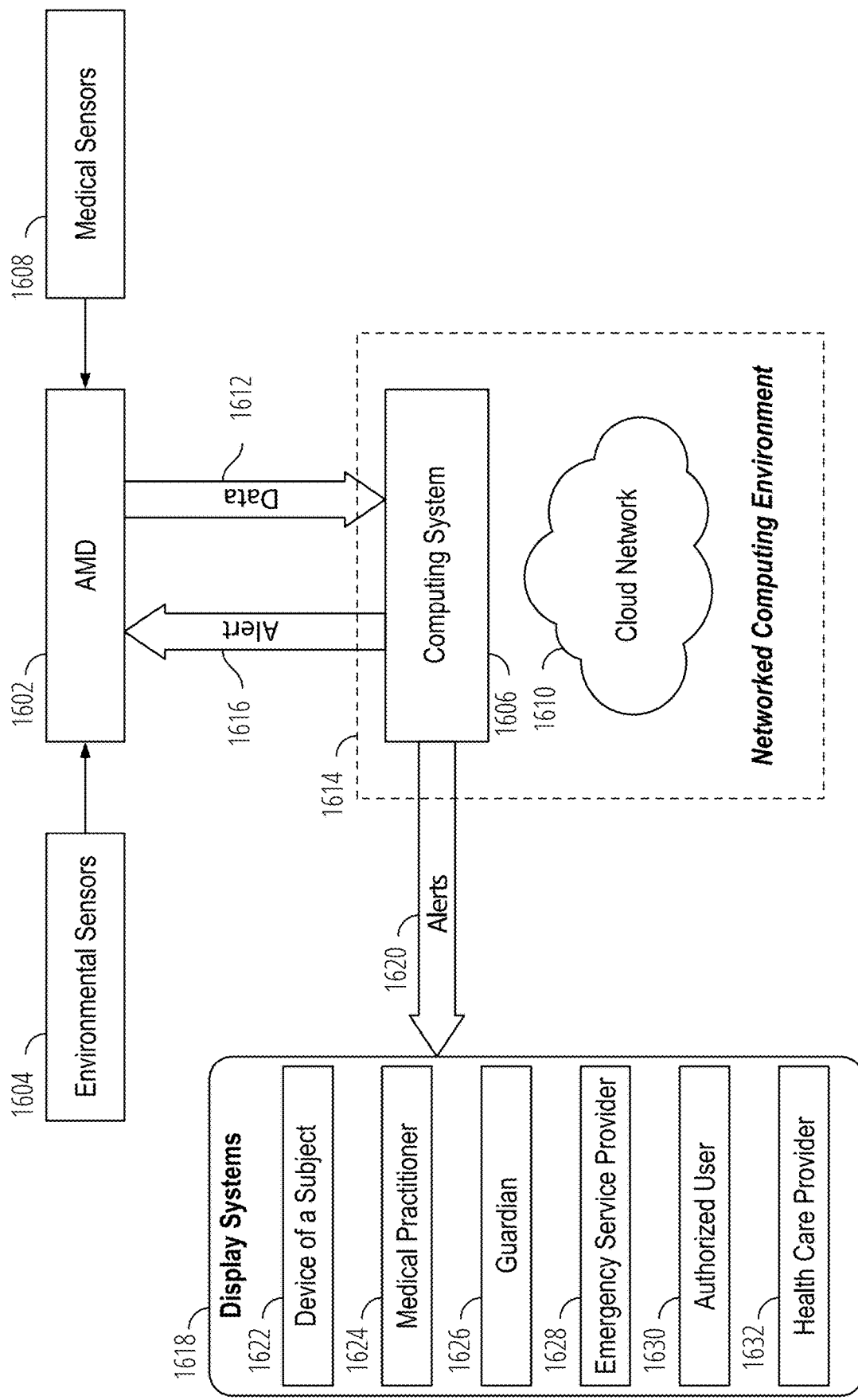
FIG. 16. is a block diagram, illustrating an example network and data flow configuration wherein the AMD is directly connected to a computing system and the computing system generates and sends alerts to one or more display systems and the AMD.

FIG. 16 is block diagram, illustrating an example network and data flow configuration where an AMD 1602, which is directly connected to a computing system 1606 (e.g., computing system within a cloud network 1610), may generate and send alerts 1616 (e.g., alert messages, alert signals, and the like) upon determining that data 1612 received from the AMD satisfies a threshold condition. The computing system 1606 may be part of networked computing environment 1614 (e.g., a data center, networked computing system), or cloud network 1610 or cloud computing system of a cloud service provider. The computing system may include one or more non-transitional memories and one or more hardware processors configured to execute the computer-executable instructions stored in one or more non-transitional memories. The AMD may receive data from one or more medical sensors 1608 (e.g., analyte sensor, temperature sensor, heart beat sensor, and the like) and/or one or more environmental sensors (e.g., geolocation receiver, motions sensor, accelerometer and the like.). These sensors may be included in the AMD unit or may be connected to the AMD via a wired or wireless link.

In some cases, the display systems receiving the alert 1620, may be display systems that have already received therapy reports from the computing system 1606. In other examples, a group of display systems may be selected and authorized by the subject, who is receiving therapy from the AMD, to receive alerts 1620. The display systems that may receive alerts 1620 from the AMD may include: a medical practitioner 1624 (e.g., such as a doctor or nurse), a guardian of the subject 1626 (e.g., subject's parents), an emergency service provider 1628, an authorized user 1630 (e.g., a user authorized by the subject such as spouse, relative, friend, and the like), a healthcare provider 1632, or a device of a subject 1622 (e.g., cell phone, personal computer, tablet, and the like). In some examples, when it is determined that received data 1612 the AMD satisfies a threshold condition, in addition to sending a alerts to one or more display systems 1618, the computing system 1606 may send an alert 1616 to the AMD 1602.

In some examples, the AMD 1602 may be configured to establish a connection to support continuous data transfer to the computing system 1606 for a given period of time (e.g., provided to the AMD by the subject), in order to capture any data that is generated over that period and satisfies an alert threshold condition. For example, the subject may request a continuous connection between AMD and the computing system when going for hike alone to make sure that if his/her health condition deteriorate during the hike, an alert is sent to authorized display systems.

In some examples, a geolocation sensor (e.g., a Global Positioning System (GPS) receiver) and/or a proximity sensor can be used to enable location-activated features such as automatic upload of data at certain locations.

In some cases, the ambulatory medical device may include or be connected to an accelerometer or a geolocation system. This velocity of the ambulatory medical device may be determined based at least in part on the accelerometer or geolocation system. Using the data obtained 1612 from the ambulatory medical device 1602 including the location and/or velocity information, the computing system 1606 can provide intelligent alerts. For example, if the data indicates that a user is travelling at a high rate of speed (e.g., likely in a car) and the user's glucose level is low (e.g., below 55 mg/dl), the computing system may automatically alert emergency service providers 1628 that a subject is at risk of hypoglycemia and may be driving. Further, the computing system can provide a location of the subject to the emergency service provider 1628.

In some examples, the computing system can generate alerts based on a trend of the aggregated therapy data or based on therapy data that is an outlier to the aggregate therapy data or an outlier to a time-based average of the therapy data.

Further, the geolocation sensor and/or a motion sensor (e.g., an accelerometer) can be used to detect velocity of a subject to enable intelligent motion-sensitive alerts. For example, if the subject is moving at 60 mph and experiences low glucose level, the system may enable a set of driving alerts and schedule possibly therapy in the future. The driving alerts may inform the subject to pull over immediately due to a risk of a hypoglycemic event. Further, an emergency responder may be informed of a subject location using based on information obtained from the geolocation sensor. If the subject is moving at 6-7 mph, exercise alerts may be enabled to, for example, alert the user to pause exercising and attend to low glucose level. If the subject hasn't moved for 3 hours and has low glucose level, the system can enable automatic notification to emergency services. Further, a determination of the subject's motion can be used to automatically adjust setpoint (e.g., raise setpoint during exercise). The activity level of the subject can be sensed and use to improve alerts and therapy.

Additionally, the cloud server can send a text message or call to a follower's and/or end user's phone or smart device in case the therapy data satisfies an alert threshold. These messages may be provided from the cloud computing system to a third-party device in case roaming or disabling of the data plan on the ambulatory medical device occurs (e.g., no TCP/IP available). Further, the cloud computing service may send a text message or call 911 in case of a detected emergency. The cloud server can track, for example, via GPS, the end user's most recent location and share that information with a follower and/or emergency personnel. Moreover, the cloud computing system may enable an end user to order and re-order medical supplies directly from the viewing device.

Moreover, the computing system can generate notifications (e.g., generate a message when there is a risk of hypoglycemia). Further, more detailed processing in the cloud can result in improved recommendations (e.g., Tmax, setpoint, or other control parameters)

Figure 17:
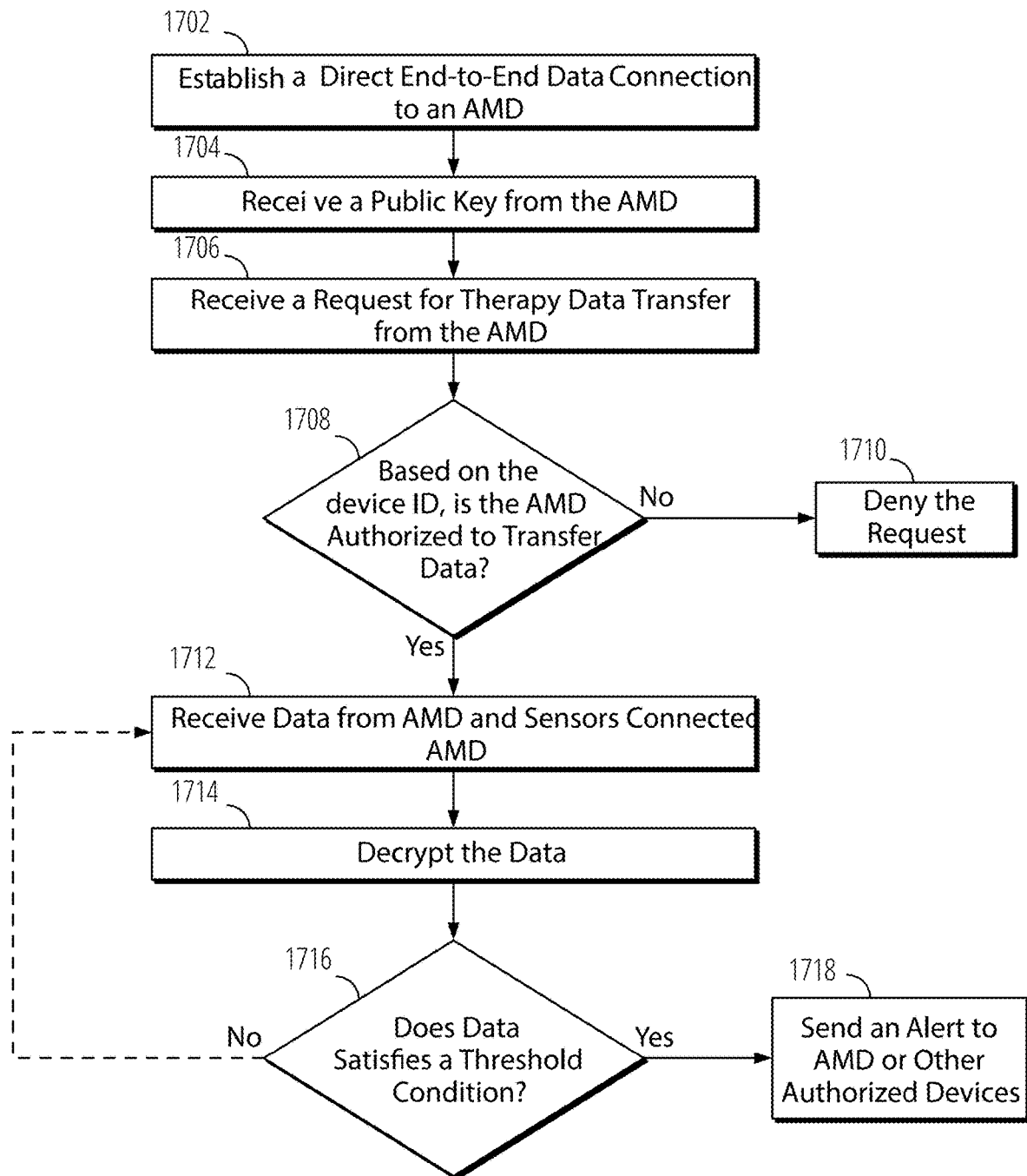
FIG. 17 is a flow diagram illustrating an example method that may be used by a computing system, to generate and send an alert to one or more authorized devices.

FIG. 17 is a flow diagram illustrating an example method that may be used by computing system 1606, to generate and send alerts (e.g., alert messages, alert signals, and the like) to one or more authorized devices and to the AMD. The method may include establishing a direct end-to-end data connection 1702 to an ambulatory medical device, for example, via a wireless wide area network (WAN) using a Narrowband Long-Term Evolution (NB-LTE) transceiver included in the AMD 1602. In some examples, the direct end-to-end connection may be established for a given period of time set by the subject or an authorized user (e.g., a guardian of the subject). Once a direct end-to-end data connection between the AMD 1602 and the computing system 1606 is established, the computing system may receive a public key 1704, from the AMD 1602 over the established connection. Next, the computing system may receive a request from the AMD 1706 to transfer data (e.g., therapy data, medical sensor data or environmental sensor data) generated by the AMD 1602 to the computing system 1606 over the direct end-to-end data connection. In some cases, the request may include a time period during which AMD continuously transmits any data generated by the AMD 1602 or obtained from one or more sensors (e.g., environmental sensors 1604 or medical sensors 1608), to the computing system 1606. In some such cases, the time period for continuous data transfer from the AMD 1602 to the computing system 1606, may be provided by the subject or a guardian of the subject to the AMD. In some examples, the computing system 1606 may use the device ID associated with the AMD 1602 to determine whether the AMD 1602 is authorized to transfer data 1708 to the computing system 1606. If, based on the device ID, it is determined that the AMD 1602 is authorized to transfer data to the computing system 1606, the encrypted therapy data may be transferred 1712 to the computing system 1606. If, based on the device ID, it is determined that the AMD 1602 is not authorized to transfer data to the computing system, the request may be denied 1710. The computing system 1606 may decrypt the received data 1714 using a private key (e.g., stored in a memory of the computing system 1606) and a public key received 1702 from the AMD 1602. In some examples, the computing system 1606 may determine whether the received data (e.g., therapy data, medical sensor data or the environmental sensor data), satisfies a threshold condition 1716. In some cases, the threshold condition may be provided to the AMD by the subject or an authorized user (e.g., a guardian of the subject). In some examples, the threshold condition may be provided by a healthcare provider. In some such examples, the threshold condition may be stored in a memory of the AMD. If it is determined that the data satisfies a threshold condition, an alert may be generated and sent 1718 to one or more display systems 1618 that are authorized (e.g., by the subject or a guardian of the subject) to receive alerts. In some examples, the subject or the guardian may authorize one or more display systems 1618 to receive alerts by providing the account IDs of the one or more displays systems to the computing system 1606 or the networked computing environment 1614.

Preventing Inadvertent Therapy Changes

As described above, the ambulatory medicament device may include a user interface (e.g., touchscreen interface or a non-touchscreen interface) that may present one or more user-interface screens to a user enabling the user to modify one or more therapy settings of the ambulatory medicament device, such as a quantity of medicament delivered when a condition is met or the condition that triggers the delivery of medicament to a subject. The user may be a subject receiving medicament or therapy, or may be another user, such as a clinician or healthcare provider, or a parent or guardian. For ambulatory medicament devices that include a user interface, there is a risk that a setting is accidentally modified or is modified (intentionally or unintentionally) by a user that does not fully comprehend his or her action (e.g., a child or a user with a reduced mental capacity). Further, ambulatory medicament devices may accidentally have settings modified by inadvertent interactions with a user interface, such as may occur when an ambulatory medicament device is worn against the body of a subject.

This section relates to an ambulatory medical device (AMD) to prevent an inadvertent modification in medicament deliver, for example, in the event of a setting of the AMD being accidentally modified by a user or inadvertent interactions with a user interface.

As mentioned above, in some embodiments the user may modify the control or configuration the AMD using a user interface. There is a possibility that the control or configuration of the AMD is accidentally modified through the user interface. For example, as the user may transport the ambulatory medical device, there is a danger that the user will inadvertently activate input in the ambulatory medical device that initiates a therapy change input (e.g., by applying pressure on the ambulatory medical device that may be placed in the jacket pocket of the user).

Figure 18:
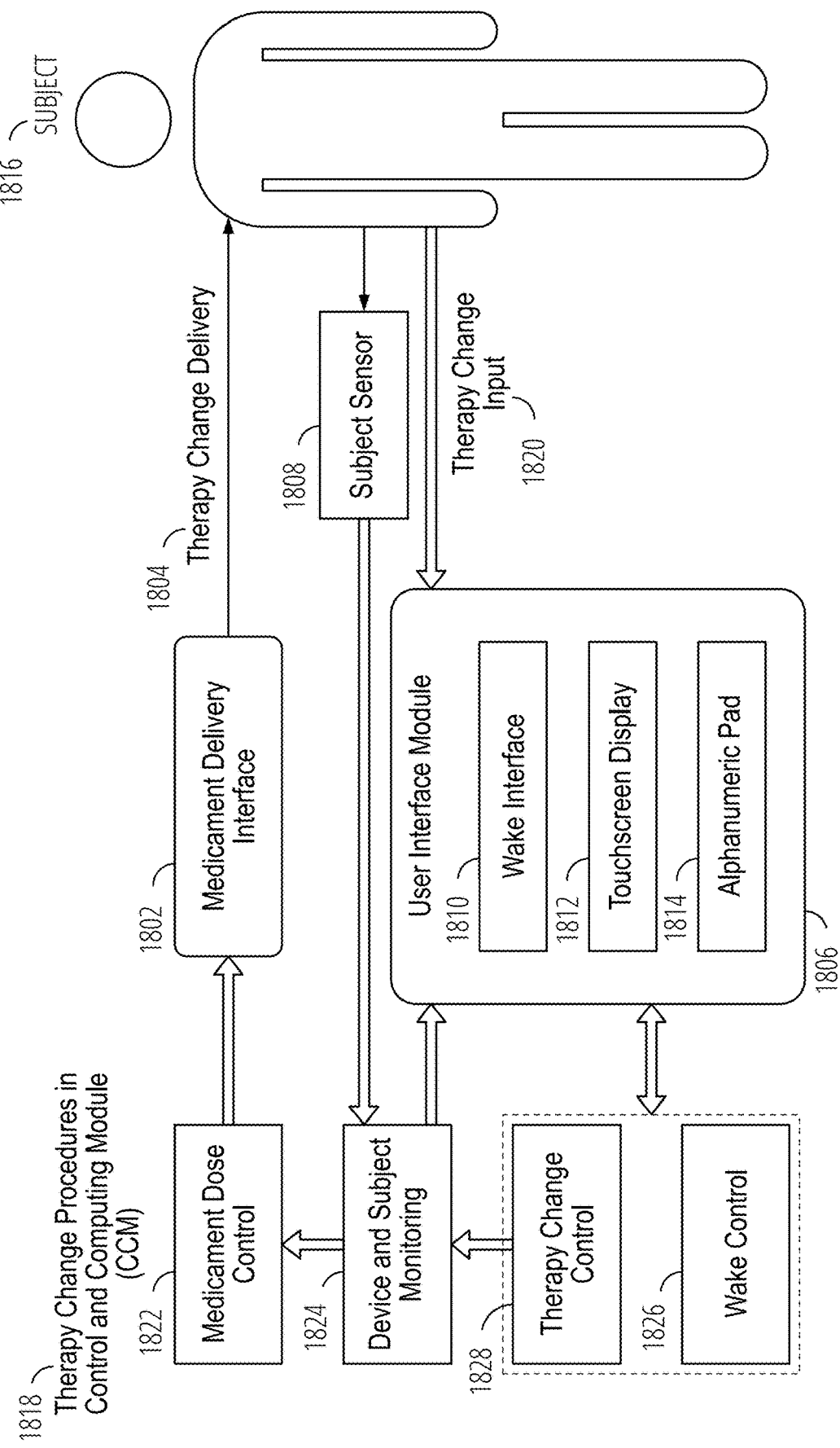
FIG. 18 illustrates the interconnection among modules and procedures in AMD involved in receiving, accepting and/or canceling therapy change request.

With reference to FIG. 18, in some such embodiments, the control and computing module (CCM) of the AMD may include a set of therapy change procedures 1818 implemented to prevent therapy change inputs 1820 that are inadvertent. The therapy change procedures 1818 may be implemented as instructions stored in a memory of control and computing module 610 (e.g., the main memory 616) and executed by the processor 614. The therapy change input 1820, received from a subject 1816, may be verified by the therapy change procedures 1818 before the AMD 600 provides the therapy change delivery 1804. All the user interactions with the user interface module 1806 may be controlled and analyzed by the control and computing module 610 (CCM) via one or more therapy change procedures 1818.

In these embodiments, the subject 1816 may wake or unlock the AMD by interacting with a wake interface 1810. The wake interface 1810 can be any of the additional user interfaces mentioned above, configured to generate a wake input to the CCM 610 when detecting a pre-set user interaction.

The therapy change input 1820 can be an input provided by the subject 1816 to change a therapy that is currently being delivered to the subject 1816. In some embodiments, the therapy change input 1820 may cause the insulin or glucagon infusion pump to start infusing an amount of insulin or glucagon into the subject 1816. Alternatively, the therapy change input 1820 may modify the rate of insulin or glucagon infusion into the subject 1816. The therapy change input 1820 may also cancel insulin or glucagon infusion into the subject 1816 from the insulin or glucagon infusion pump.

When a wake action is detected by the wake interface 1810, a wake input is sent to the control and computing module 610 wherein it imitates a wake control procedure 1826 that generates a wake signal to wake/unlock the user interface (e.g., a touch screen display).

When in the wake and/or unlocked state, a user may interact with the touchscreen display 1812, alphanumeric pad 1814 or other types of user interfaces that may be included in the user interface module 1806, to obtain access to therapy change user interface.

The therapy change user interface may be activated by a first user interaction with the user interface (e.g., touchscreen display 1812). When the first user interaction is detected, the user interface module user interface module 1806 sends an input signal to the control and computing module 610 wherein it is analyzed by a therapy change control procedure 1828. If it is determined that the first user interaction satisfies a set of predefined conditions, the therapy change control procedure 1828 generates a signal to the user interface module user interface module 1806 to activate the therapy change user interface.

In some embodiments, the therapy change user interface may be limited based on the first user interaction. For example, the therapy change control procedure 1828 may send one of two signals to the user interface module user interface module 1806. The therapy change user interface may then unlock one of two different therapy change user interfaces that result in different options of therapy change selections for the subject 1816. In an implementation of this example, a therapy change selection to make a significant therapy change, such as dramatically increase the rate of insulin or glucagon infusion rate, requires a first user interaction that is different from the first user interaction that would be required for an insulin or glucagon infusion at a normal or prescribed rate. In some examples, the first user interaction may be a simple interaction (e.g., a simple gesture) that unlocks a therapy change user interface with therapy change selections that are limited. Another first user interaction may be a complicated interaction (e.g., a series of complex gestures) that unlocks a therapy change user interface with therapy change selections that have no limits. An example of this implementation may be useful for child users. The child user may perform the first gesture that is made up of a series of simple inputs to unlock therapy change selections that are limited. An adult user may perform the first gesture that is made up of a series of complex inputs to unlock the therapy change user interface with therapy change selections that have no limits.

Once activated, the therapy change user interface that may provide one or more control or configuration elements that enable the user to modify the control or configuration of the ambulatory medicament device. The control or configuration element may include any type of user interface screen on the touchscreen, or other type of user interface in the non-touchscreen context, that enables or permits a user to change a configuration of the ambulatory medicament device. This change in configuration of the ambulatory medicament device may relate to a change in the therapy provided or in the detection of a triggering event that causes therapy (e.g., medicament) to be provided to a subject. For example, the change in configuration may include a selection between one or more hormones that regulate glucose level (e.g., insulin or glucagon) of a user, an amount of the one or more hormones that regulate glucose level of the user.

In some cases, a change to the configuration of the ambulatory medicament device is automatically and/or instantly recognized or implemented by the ambulatory medicament device, and/or transmitted to the ambulatory medicament device. In other cases, a confirmation of the change may be required before the change is implemented by or transmitted to the ambulatory medicament device.

This confirmation may be entered based on a second user interaction with a user interface (e.g., touchscreen display 1812). When the second user interaction is detected, the user interface module user interface module 1806 sends an input signal to the control and computing module 610 wherein it is analyzed by a therapy change control procedure 1828. If it is determined that the second user interaction satisfies a set of predefined conditions, the therapy change control procedure 1828 implements the change to the configuration of the AMD.

The first and/or second user interactions may include the selection of an icon, a series of taps or inputs, one or more gestures (e.g., a linear swipe, an arcuate swipe, a circular swipe, or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. Gesture interactions can be guided by visual indicia displayed or printed on the AMD. In some embodiments, the visual indicia can include animations that suggest or guide user interactions with a touchscreen. For example, the first user interaction can include an arcuate swipe around at least a portion of a generally circular icon or logo. In some examples, the first and/or second user interactions may include a predetermined sequence of numerical or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds.

Further, one or more of the interactions may include interacting with a sensor as an optical sensor (e.g., visible light or IR sensor), biometric sensor (e.g., a fingerprint or retinal scanner), a proximity sensor, a gyroscope, or a combination of accelerometer and gyroscope, and the like. Also, in an exemplary embodiment, the second user interaction may be made through a wireless signal such as RFID or Bluetooth. In some embodiments, the second user interaction may include receiving a selection of an indicator box that correspond to either insulin or glucagon and receiving a predetermined sequence of numerical inputs in order to deliver the therapy change selection.

The type of user interaction that unlocks the touchscreen, provides access to a configuration screen, and/or confirms a change to the configuration of the ambulatory medicament device may be the same or may differ.

In an exemplary embodiment, the system may have a time-out such that if no interaction occurs for a set period of time, the user interface will turn off and the therapy change request process has to start again. In one implementation of the time-out, if no interaction occurs for more than 30 seconds after the system is waked/unlocked before the second user interaction is received by the user interface, the user interface will be deactivated.

Once the configuration change is confirmed, implemented, or transmitted, the ambulatory medicament device may begin operating with the changed configuration.

This operation may include triggering therapy based on the new configuration or providing therapy based on the new configuration. For example, the ambulatory medicament device may generate a dose control signal based at least in part on the modified configuration or control parameter, or may detect a trigger based at least in part on the modified configuration or control parameter that leads to the provisioning of therapy.

With reference to FIG. 18, in some embodiments, the changes made through the therapy change user interface are sent to CCM wherein the therapy change control procedure 1828 in CCM transfers the changes to the device and subject monitoring procedure 1824. The device and subject monitoring procedure 1824 may be implemented in the CCM 610 to monitor the status of the AMD (e.g., therapy delivery configuration) and the health condition of the subject 1816 (or a subject). For example, the subject monitoring procedure 1824 may receive information about a therapy change requested by a subject 1816 through a user interface (a touchscreen display 1812 or alphanumeric pad 1814) or information about subject's glucose level from the subject sensor 1808. Subsequently, the device and subject monitoring procedure 1824 may transmit the information pertaining a health condition of the subject and/or the AMD configuration, to the medicament dose control procedure 1822. In some examples, the parameters in the medicament dose control procedure 1822 may be adjusted based on the changes and/or information captured by the device and subject monitoring procedure 1824. The medicament dose control procedure 1822, controls the medicament delivery interface 1802 by providing a medicament dose signal. The medicament does control may be generated based on detected conditions or physiological characteristics of the subject (e.g., provided by the readings of the subject sensor 1808) and according to parameter values received from the therapy change control procedure 1828. The medicament delivery interface 1802 may provide a therapy change delivery to the user according to the information received by device and subject monitoring procedure 1824.

In some examples, the dose control signals may be produced based on time (e.g., medicament may be delivered on a periodic basis), one or more a command, indication that the subject is planning to engage or is engaging in a particular activity (e.g., eating a meal, exercising, sleeping, fasting, etc.), or any other factor that may relate to or cause the triggering of therapy (e.g., medicament delivery).

Figure 19:
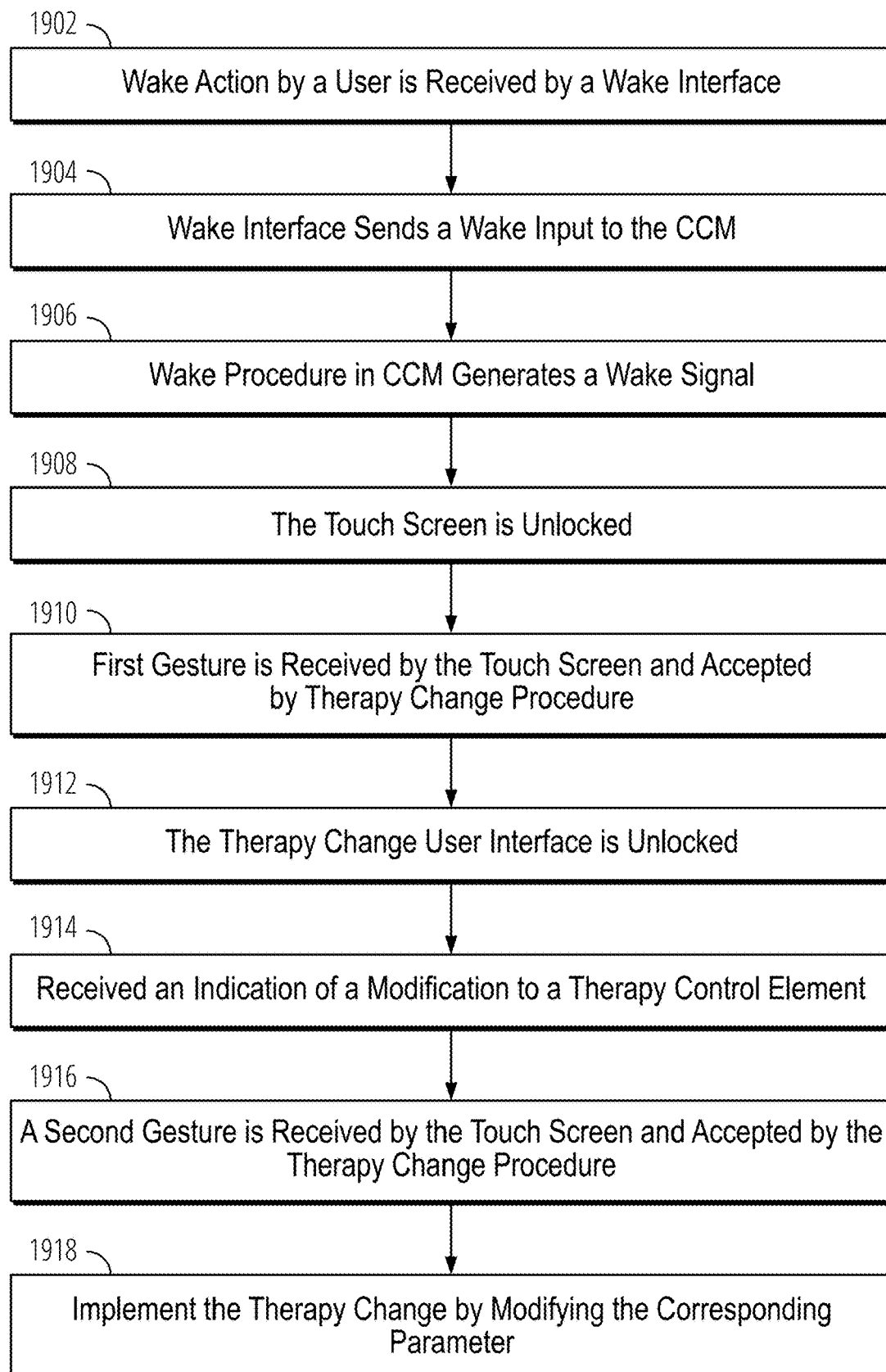
FIG. 19 is a flow diagram illustrating an example method that may be used by an AMD to allow a user to change the configuration of the ambulatory medicament device using a touch screen user interface.

FIG. 19 is a flow diagram illustrating an example method that may be used by an AMD to allow a user to change the configuration of the ambulatory medicament device using a touch screen user interface. The user may initiate the configuration change process by waking/unlocking the touch screen using a wake action. Once the wake action is received by the wake interface 1902, the wake interface sends a wake input to CCM 1904. Within CCM, the wake procedure generates a wake signal 1906 that unlocks the touch screen 1908. Next, in response to receiving a first gesture by the user 1910, the therapy change user interface is unlocked 1912. Using one or more therapy control or configuration elements provided in the therapy change user interface, the user may change the therapy configuration 1914. The user may confirm the changes made, by providing a second gesture on the touch screen 1916. Once the confirmation is received 1916 the requested changes will be implemented 1918, and the ambulatory medicament device may begin operating with the changed configuration. In some examples, once the user confirms the changes made, a dose control signal may be sent to the medicament delivery interface 1802 that triggers a therapy change delivery to the subject.

In some cases, the ambulatory medicament device, or a control device that enables a user to modify a configuration of the ambulatory medicament device, may have a timeout feature. The timeout feature may cause the ambulatory medicament device or the control device to enter a sleep or locked state after a period of time of inactivity by the user. In some cases, the timeout feature may cause the ambulatory medicament device or the control device to enter a sleep or locked state after a particular period of time regardless of whether the user is interacting with the ambulatory medicament device or control device. Thus, a user may have a limited period of time to modify he configuration of the ambulatory medicament device.

In some examples, the therapy change made by a user may trigger the delivery of a medicament according to the therapy change received and confirmed by a user. This therapy change delivery may occur after a set time from period from receiving the confirmation.

In some embodiments of the AMD, an alarm status indicator may be presented to the user via the user interface. The alarm status indicator can be an alert message or an alert symbol. The alarm status indicator may be related to a configuration change made by a user, a change in the status of the AMD not related to a user input, or the condition of the subject (e.g., detected by the subject sensor).

Figure 20A:
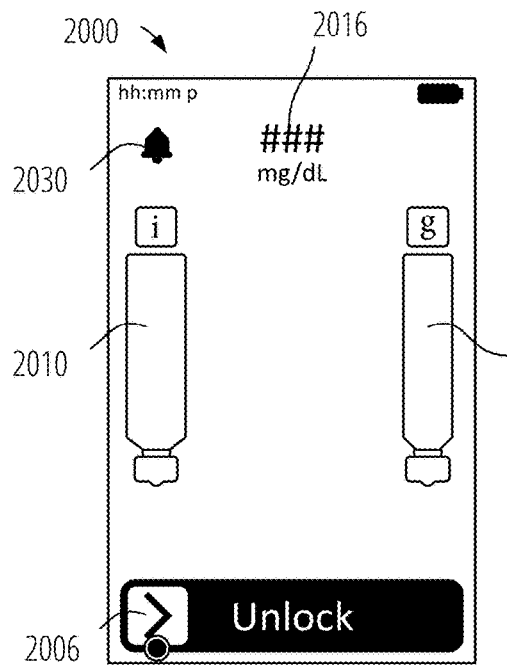
FIG. 20A is an illustration of the touchscreen display of an example AMD after the touch screen is waked/unlocked by a wake action of a user and before the first user gesture is received.

FIG. 20A is an illustration of the touchscreen display 2000 of an example AMD after the touch screen is waked/unlocked by a wake action of a user and before the first user gesture is received. Even while the touchscreen display is locked, the touchscreen display 2000 may display any images, animations, text, or other graphics. The first gesture prompt 2006 displays to the subject 1816 the input required to unlock the therapy change user interface. Here, the first gesture prompt 2006 shows the subject 1816 that a touch movement that begins at the greater-than symbol and moves right across the "Unlock" text is the acceptable first gesture. In addition to the first gesture prompt, the refill status of the AMD 600 is shown in a graphic representation 2010. Here, the graphic representation 2010 shows that the insulin cartridge in the AMD 600 is almost full. A current glucose level 2016 is shown at the top of the touchscreen display 2000, which can inform the subject 1816 of the need for a hormone that regulates glucose levels. The touchscreen display 2000 also shows a graphic representation of a cartridge of glucagon 2024. The graphic representation of an alarm 2030 in the touchscreen display 2000 shows that an alert is set on the AMD 600.

Figure 20B:
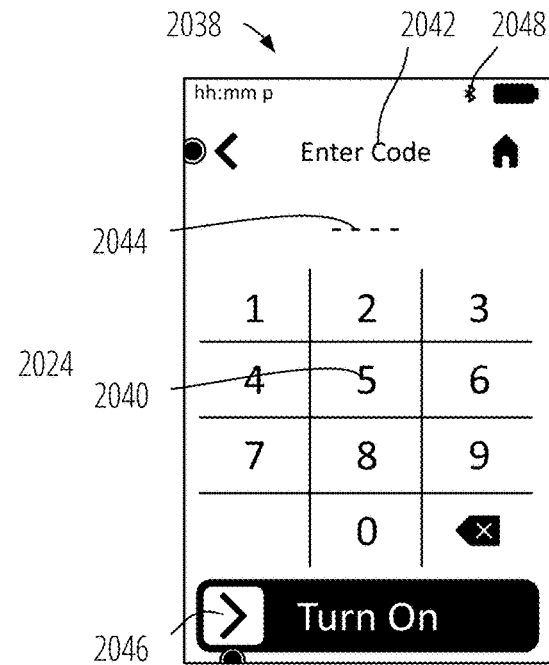
FIG. 20B is an illustration of an example touchscreen display that may prompt the user to enter a predetermined series of inputs for the first gesture or second gesture.

FIG. 20B is an illustration of an example touchscreen display 2038 that may prompt the user to enter a predetermined series of inputs for the first gesture or second gesture. In various embodiments, such as the embodiment shown in FIG. 20B, the touchscreen display 2038 may display touchable number keys 2040. In various embodiments, the touchscreen display 2038 prompts the subject 1816 to enter the series of inputs that complete the first gesture or second gesture. The text Enter Code 2042 prompts the subject 1816 to enter a predetermined or preselected numerical sequence as part of the first gesture or second gesture. The numerical sequence being typed by the subject 1816 is displayed in field 2044 as it is entered as an aid to the subject 1816. The input 2046 of the touchscreen display 2038 shows that a touch movement of a swipe right across the bottom of the screen is required to complete the predetermined series of inputs for the first gesture or second gesture. A Bluetooth connection symbol 2048 shows that the AMD 600 is paired or can be paired to another electronic device.

Figure 20C:
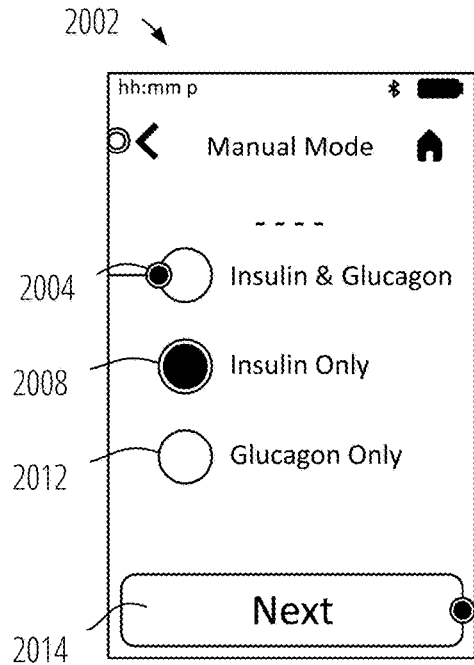
FIG. 20C is an illustration of an example therapy change user interface.

FIG. 20C is an illustration of an example therapy change user interface (in this case a touchscreen display 2002). The touch screen display may the subject 1816 prompt to select a hormone that regulates glucose level. The touchscreen display 2002 presents the subject 1816 with an option to select between two hormones. The touchscreen display 2002 aids the subject 1816 by showing the selected hormone 2008 for the subject 1816. The selected hormone 2008 is "insulin Only". The subject 1816 is also given the options of selecting the hormone Glucagon Only button 2012 or both Insulin & Glucagon button 2004 to regulate glucose level. Once the subject 1816 selects between the one or more hormones that regulate glucose level. The Next button 2014 may be selected to complete the therapy change selection or select more options. In one embodiment, to select more options, the therapy change user interface prompts the subject 1816 to select an amount of the one or more hormones that regulate glucose level of the subject 1816. In other embodiments, the subject 1816 may be prompted to select a glucose level and the ambulatory medical device 200 may choose the hormone and the amount of the hormone.

Figure 20D:
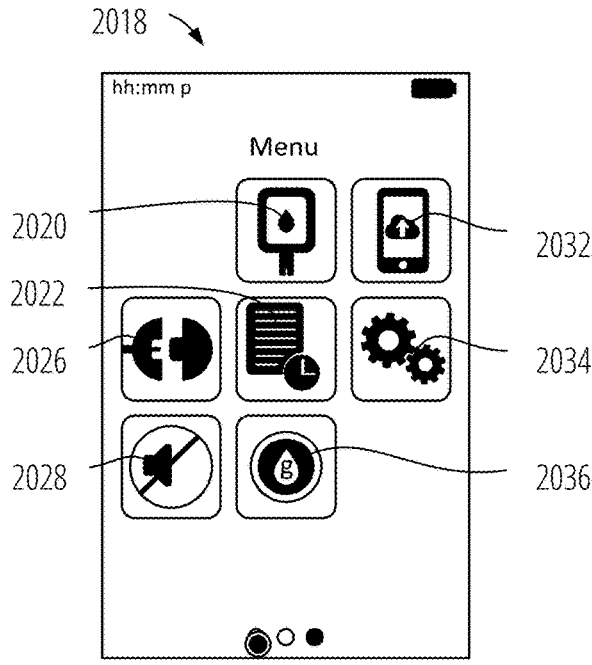
FIG. 20D is an illustration of another therapy change user interface on a touchscreen display.

FIG. 20D is an illustration of another therapy change user interface on a touchscreen display 2018. Here, the subject 1816 is given a multitude of options. One or more options in the therapy change user interface allow the subject 1816 to make a therapy change selection. Other options are related to the therapy change selection. A Deliver Hormone button 2036 allows the subject 1816 to select a therapy change that delivers a hormone that regulates blood glucose to the subject 1816. A Test glucose button 2020 allows the subject 1816 to test the glucose level of the subject 1816. A Generate Report button 2022 generates a document that reports the therapy changes that have been delivered to the subject 1816. A Refill Cartridge button 2026 allows the subject 1816 to fill a cartridge in the AMD 600 with medicament. An Upload to Cloud button 2032 allows the subject 1816 to transmit therapy change information to a cloud-based server. A Sound Control button 2028 allows the subject 1816 to control the sounds emitted by the AMD 600. A Settings button 2034 allows the subject 1816 to manipulate other settings of the AMD 600.

As mentioned above, in some embodiments of the AMD, an alarm status indicator may be presented to the user via the user interface to alert the user about a change made or occurred in the AMD configuration.

For example, with reference to FIG. 18, the subject 1816 may make a therapy change input 1820 using the user interface and based on the procedure illustrated in FIG. 19. Once therapy change control procedure 1828 implements the therapy change, the AMD may alert the user that a therapy change is implemented. The alert message or symbol may be presented on a user interface (e.g., touch screen display) before and/or during the therapy change delivery 1804. For example, alarm indicator may inform the subject 1816 that a therapy change is about to occur. Any number of details of the therapy change may be displayed as part of the alert message or symbol. In some cases, the alarm status indicator may appear after the user unlocks or wakes the user interface using a wake action.

Figure 21:
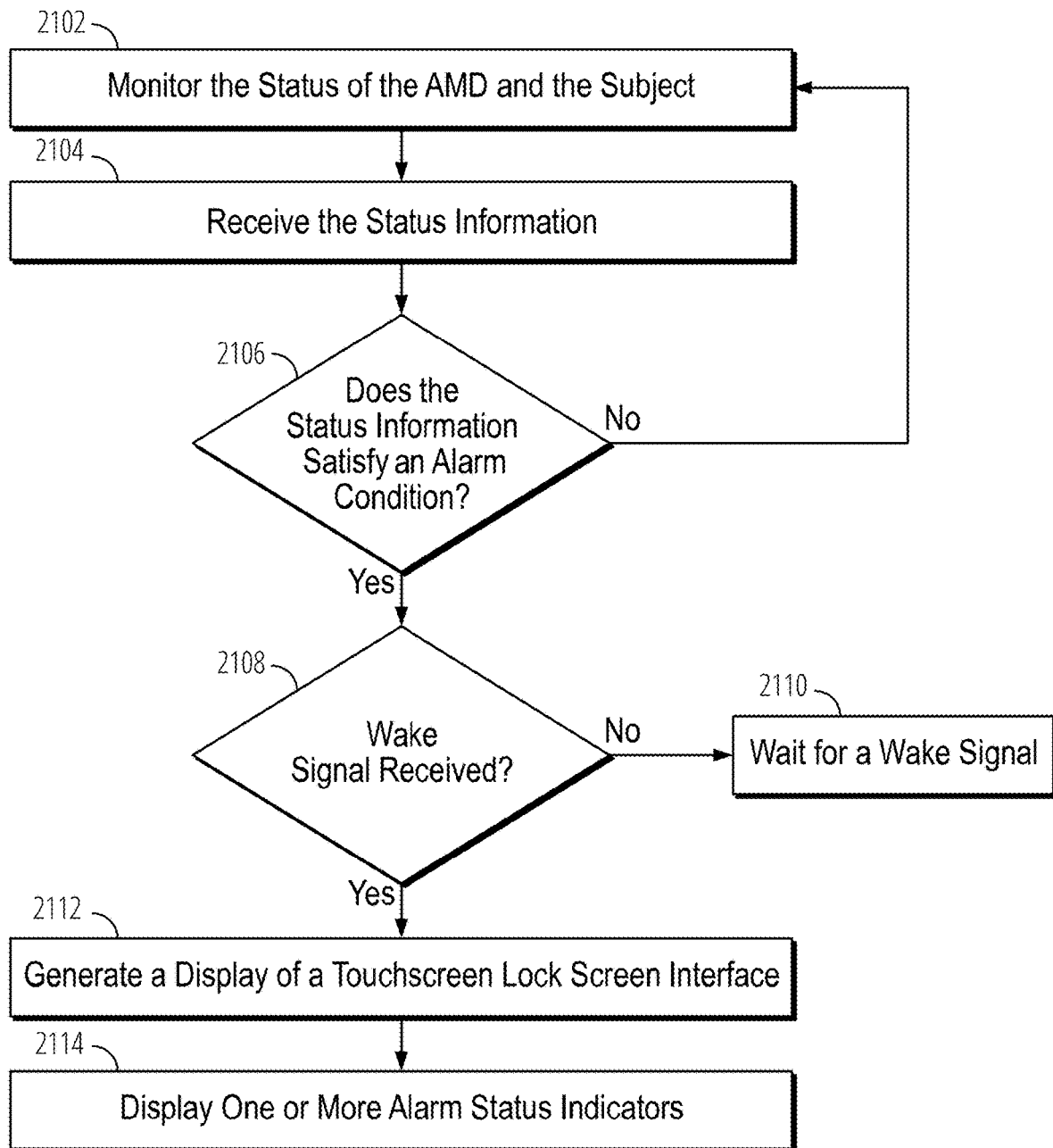
FIG. 21 is a flow diagram illustrating an example method that may be used by an AMD to generate an alarm status indicator.

FIG. 21 is a flow diagram illustrating an example method that may be used by an AMD to generate an alarm status indicator. In some embodiments the device and subject monitoring procedure (excused within CCM), may continuously monitor the status of the AMD (e.g., the user interface, different modules of the AMD and the like) as well as the health condition of a subject (e.g., using various subject sensors such as analyte sensors) 2102. Once a status information is received 2104, the device and subject monitoring procedure may determine whether the received status information satisfies an alarm condition 2106. If the received status information does not satisfy an alarm condition, no cation will be taken and device and subject monitoring procedure continuous monitoring the AMD and the subject. If it is determined that the received status information satisfies an alarm condition, the system search for a wake signal 2108. If no wake signal is detected, the system waits for a wake signal to be received 2110. Once a wake signal is received via one or more user interfaces or sensors, the CCM may generate a display of a touchscreen lock screen interface 2112 and display one or more alarm status indicators 2114, corresponding to the detected alarm condition, on the lock screen.

Figure 22:
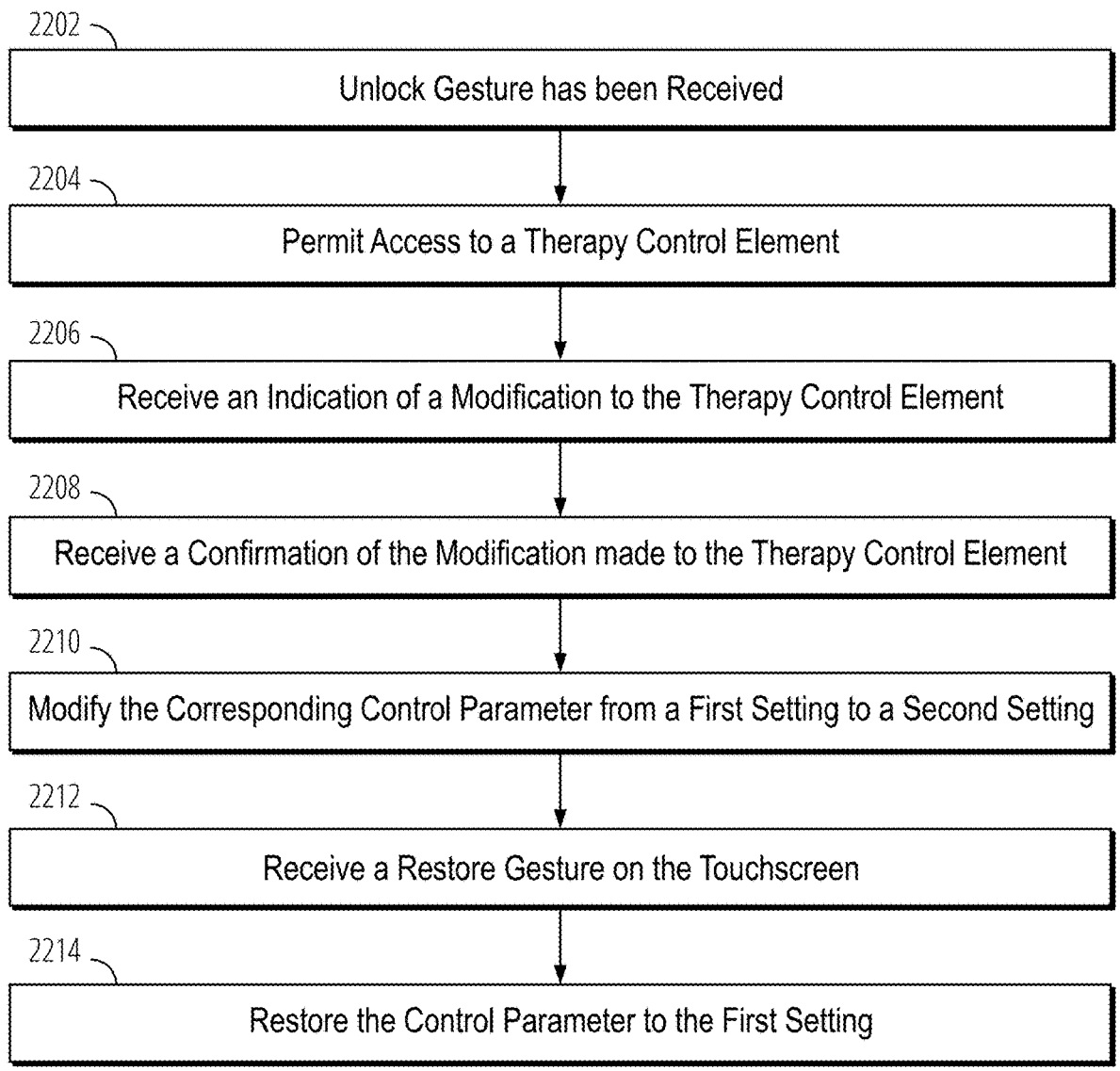
FIG. 22 is a flow diagram illustrating an example method that may be used to cancel a therapy change using a touchscreen interface.

In some embodiments, the AMD may allow the user to provide a therapy change and then cancel the therapy change. FIG. 22 is a flow diagram illustrating an example method that may be used to cancel a therapy change using a touchscreen interface. The user may unlock the touchscreen display 2202 using a wake action and get access to a therapy change user interface 2204 (e.g., using a first gesture) and a therapy control element therein, where one or more therapy control elements may be displayed. Next, an indication of a modification to a therapy control element may be received 2206 by the user interface followed by a confirmation of the modification made 2208 (e.g., a second gesture). In response to receiving an indication and confirmation of a modification to a therapy control element, the corresponding control parameter may be changes from a first setting to a second setting 2210. In some examples, once the change is implemented 2210, the user may decide to cancel it, for example, after realizing that requested change is erroneous. In these examples the user may provide a third gesture 2212 on the touch screen. In response to receiving the third gesture from the user interface the therapy change procedure may restore the modified control parameter to the first setting 2214. In some examples the third gesture may a restore gesture. In some cases, the restore gesture may be a swipe gesture. In some examples the swipe gesture may be performed near or in a region of the therapy change user interface that is occupied by the therapy control element. An example of a restore swipe gesture may be performed from a starting swipe position to an ending swipe position located closer to a left edge of the touchscreen than the starting swipe position. In some embodiments, the restore gesture is received on a different user interface screen than a therapy change user interface wherein one or more therapy control element are provided. In various examples, the restore gesture is performed in the opposite direction from a therapy change confirmation gesture that confirms the modification to the therapy control element.

In some examples, in order to cancel a therapy change request, the restore gesture has to be provided within a set time period after the confirmation gesture is received by the user interface. In some such examples, during the set time period one or more dose control signals may be provided to the medicament delivery interface resulting in one or more therapy change deliveries.

In some cases, the system may allow the user, to modify a therapy change before confirmation. In these cases, the user may modify a therapy control element for a second time to change the corresponding control parameter from a second setting to a third setting.

In some examples, the third setting may be the same as the first setting. In some cases, the first setting or the third setting may be a default setting. In some cases, the first setting or the third setting may be a restore setting.

Figure 23A:
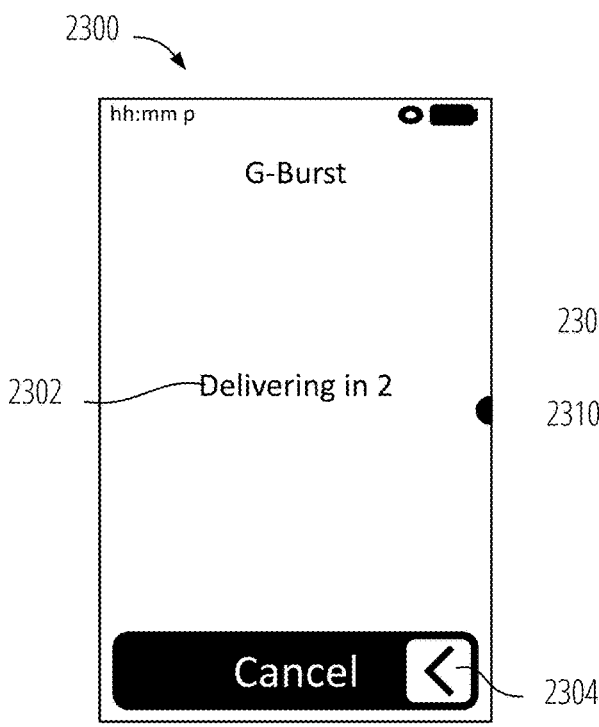
FIG. 23A is an illustration of a touchscreen display alerting the user that the delivery of one or more medicaments will occur.

FIG. 23A is an illustration of a touchscreen display 2300 alerting the user that the delivery of one or more medicaments will occur. The alert may be accompanied by sound or vibration effects. Here, the alert informs the subject 1816 a delivery of medicament will occur in 2 seconds 2302. The touchscreen display 2300 is further allowing the subject 1816 to perform a gesture to cancel the therapy change. The gesture to cancel the delivery is a touch movement that starts at the less-than symbol 2304 and swipes left across the "Cancel" text. In the embodiment shown in FIG. 23A, a single gesture by the subject 1816 may cancel the therapy change. In an exemplary embodiment, input of the wake signal, the first gesture, the therapy change selection, and the second gesture are all required to cancel a therapy that is being delivered.

In some examples, the user may be able to cancel a therapy change delivery triggered based on therapy change made by the user. In these examples, the user may get access to the user interface using a wake action and provide a gesture to cancel the ongoing therapy corresponding to a therapy change delivery.

Figure 23B:
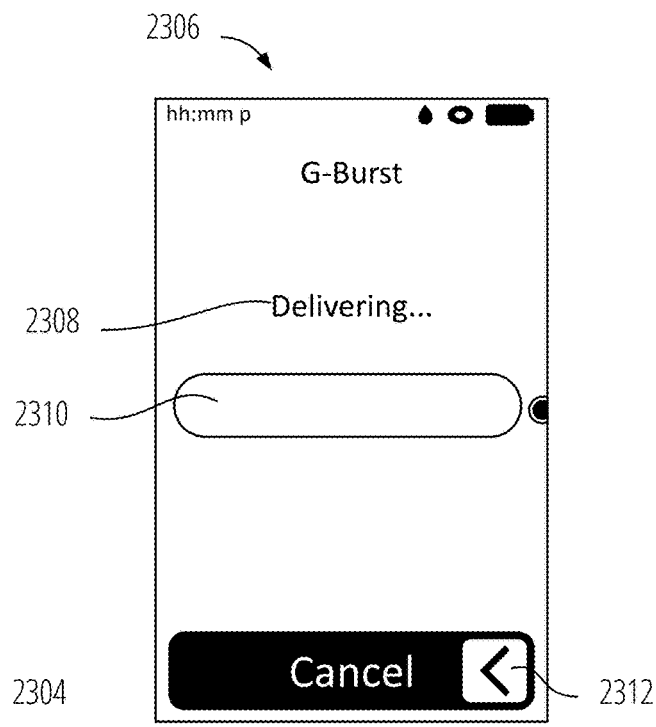
FIG. 23B is an illustration of a touchscreen display showing that a medicament is being delivered to the user.

FIG. 23B is an illustration of a touchscreen display 2306 showing that a medicament is being delivered to the subject 1816. The text Delivering 2308 informs the subject 1816 that a medicament is currently being delivered to the subject 1816. The progress bar 2310 is a graphic representation of the progress of the delivery. As shown in FIG. 23B, the delivery is only starting and zero progress has been completed. The touchscreen display 2306 is allowing the subject 1816 to perform a gesture to cancel the delivery, which includes interrupting and discontinuing the delivery if it had already begun but has not yet been completed. The gesture to cancel the delivery is a touch movement that starts at the less-than symbol 2312 and swipes left across the "Cancel" text. In an exemplary embodiment that is shown in FIG. 23B, the therapy change delivery 1804 may be canceled by an input by the subject 1816. The input to cancel a therapy change delivery 1804 may be any input such as a wake signal input or a series of touch inputs such as a gesture.

Additional embodiments relating to interacting with an ambulatory medicament device that can be combined with one or more embodiments of the present disclosure are described in U.S. Provisional Application No. 62/874,950, which was filed on Jul. 16, 2019 and is titled "PREVENTING INADVERTENT THERAPY CHANGES ON AN AMBULATORY MEDICAL DEVICE," the disclosure of which is hereby incorporated by reference in its entirety herein for all purposes, and in U.S. Provisional Application No. 62/874,954, which was filed on Jul. 16, 2019 and is titled "CAPACITIVE TOUCH WAKE BUTTON FOR AN AMBULATORY MEDICAL DEVICE," the disclosure of which is hereby incorporated by reference in its entirety herein for all purposes.

Automatic Resumption of Medicament Delivery Following Manual Suspension

In some cases, it may be desirable to suspend operation of the ambulatory medicament device or to suspend at least the delivery of medicament by the ambulatory medicament device for a period of time. For example, it may be desirable to suspend an operation associated with the delivery of medicament when the medicament reservoir or cartridge in the ambulatory medicament device is empty or needs replacing. As another example, it may be desirable to suspend delivery of medicament when the ambulatory medicament device is removed or is being moved to another site on the subject. In yet another example, it may be desirable to suspend delivery of the medicament when the subject is taking or ingesting another medicament that may produce a contraindication with the medicament provided by the ambulatory medicament device. In some cases, when a subject suspends the treatment delivered by a medical device, the subject may forget to resume the treatment delivered by the medical device. In other cases, the health condition of the subject may deteriorate during the suspension period requiring therapy delivery prior to end of the suspension period. As such, there is a need for AMDs that allows subjects to safely suspend treatment for temporary amounts of time.

In some embodiments, the AMD may support a therapy suspension and resumption procedure allowing a user to suspend all therapies or a subset of therapies for a period of time defined by the user as well as automatic resumption of one or more therapies at the end of the requested suspension period or when a threshold condition is met (e.g., a threshold condition associated with the health condition of the subject).

In AMDs that support therapy suspension, inadvertent activation and/or resumption of therapy delivery can be dangerous (e.g., when the AMD is an insulin and/or glucagon infusion device). In some examples to mitigate this risk, the AMD may be configured to avoid inadvertent suspension or resumption of therapies. For example, inadvertent activations of suspensions of medicament delivery may be prevented by requiring a user to perform gestures to activate suspension on the ambulatory medical device. The gestures must be entered at a particular prompt to activate a therapy suspension.

One particular application of the therapy suspension with automatic resumption feature in an AMD can be in the field of diabetes drug delivery. For example, the may need the ability to suspend delivery of insulin during situations such as exercise, which has a blood glucose lowering effect. Suspension of insulin delivery can prevent a subject from entering a hypoglycemic state (extreme low blood glucose), which carries severe complications. Once the therapy is suspended the user many at the risk of entering a hyperglycemic state (high blood glucose that may result in complications such as diabetic ketoacidosis or neurovascular complications), if the user forgets to reactivate the drug delivery after exercise. Further, the subject's glucose level may raise above or below a dangerous level during the period of exercise. In these situations, the automatic medicament delivery resumption may improve the health of the subject.

In certain cases, the AMD may suspend one or more therapy deliveries when the AMD receives an indication that therapy (e.g., delivery of medicament) is to be suspended. The indication that therapy is to be suspended may be a command from a user. Often the user is the subject, but the user may also include other users that may have a say or interest in the care of the subject. For example, the user may be a clinician or other healthcare provider, or a parent or guardian.

In some examples, the indication that the therapy or medicament delivery is to be suspended may be a command received via an interface of the ambulatory medicament device or from another device that provides the user with an interface to request that medicament delivery be suspended. For example, the device may be a smartwatch, smartphone, laptop or desktop, or other control device that can communicate via a wired or wireless connection with the ambulatory medical device.

In some cases, the indication that the therapy or medicament delivery is to be suspended may be received from the ambulatory medicament device itself. For example, if the quantity of medicament available to the ambulatory medicament device drops below a threshold (e.g., the cartridge or reservoir is empty or below a minimum dosage amount), a signal may be generated to suspend medicament delivery. In some embodiments, suspension of therapy occurs based on a loss of a sensor signal, such as the loss of a glucose level signal.

Figure 24:
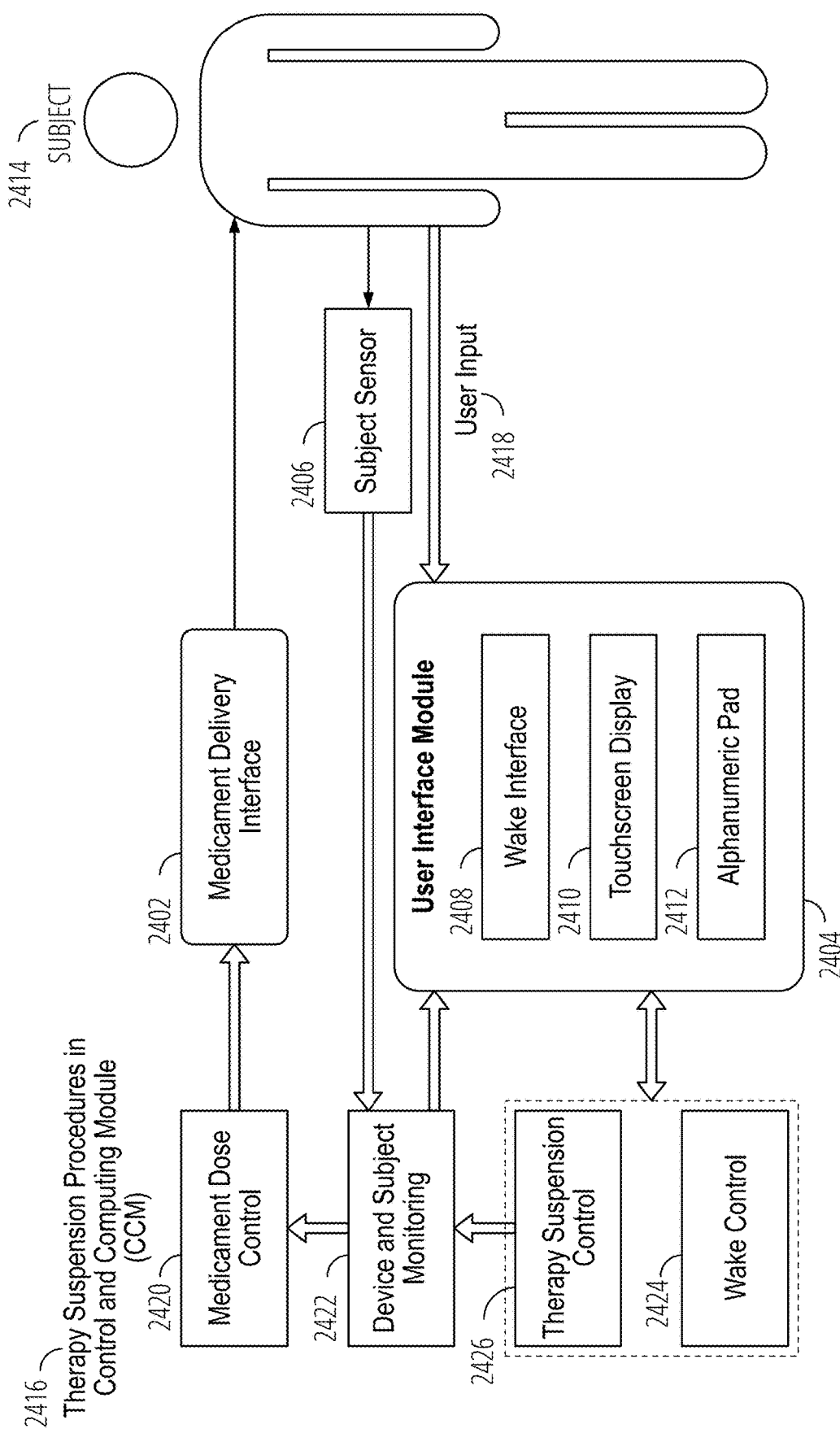
FIG. 24 is a block diagram illustrating the interconnection among modules and procedures in AMD involved in receiving, accepting and/or canceling a therapy suspension request.

FIG. 24 illustrates the interconnection among modules and procedures involved in receiving, accepting and/or canceling a therapy suspension request, in an example AMD. In some embodiments, a request for suspending one or more therapies (e.g., delivery of one or more medicament to the subject) can be made by a subject 2414 by providing a user input 2418 (e.g., the start and stop time for therapy suspension, selecting the type of therapy that should be suspended, and the like), through a therapy suspension user interface provided by the user interface module 2404. The therapy suspension user interface sends the suspension request along with the corresponding information to CCM wherein the therapy suspension control procedure 2426 implemented in CCM, processes and sends a therapy suspension signal to the device and subject monitoring procedure 2422. To prevent therapy suspension request based on user inputs 2418 that are inadvertent, the therapy suspension control procedure may include a therapy suspension request verification procedure to verify the therapy suspension request.

The device and subject monitoring procedure 2422 may be implemented in the control and computing module 2416 to monitor the status of the AMD (e.g., therapy delivery configuration) and the health condition of the subject 2414 (or a subject). For example, when the device and subject monitoring procedure 2422 receives the request for therapy suspension, it may send a signal to the medicament dose control procedure 2420 indicating that no does control signal should be send to the medicament delivery interface 2402 during the period request by the subject 2414. In some cases, if during the suspension period, certain pre-set conditions are satisfied, the device and subject monitoring procedure 2422 automatically resumes the therapy delivery by sending a signal to the medicament dose control procedure 2420. For example, if during the suspension period the subject sensor 2406 detects an elevation of the level of one or more analytes in subject's blood and/or interstitial fluid beyond a set threshold, it may resume the medicament delivery to the subject 2414 by a sending a dose control signal to the medicament delivery interface 2402.

In order to prevent inadvertent activation of a suspension, the user may initiate a therapy suspension request starting with a wake action (e.g., received by the wake interface 2408 and processed by the wake control procedure 2424), that activates the user interface module 2404. Using a first interaction with a user interface (e.g., a touchscreen display 2410 or alphanumeric pad 2412) the user may unlock a therapy suspension user interface where the information pertaining therapy suspension is provided. Next, the user may confirm the requested therapy suspension using a second interaction with the user interface. In some examples, the system may allow access to the therapy suspension user interface and accept the suspension request, only if the first and second interaction with the user interface are verified by the therapy suspension control procedure 2426.

In some examples, the therapy suspension control procedure 2426 may receive the request for suspension and suspension information from another device connected to the AMD 600 (e.g., through the communication module).

The suspension information provided by the user may include a set of parameters needed for a suspension. For example, the suspension information may include the dates and/or times for starting and ending the therapy suspension, threshold values needed to define a threshold condition that may trigger an early resumption of the therapy delivery, and the like. In some examples, suspension information may indicate that the suspension of therapy should happen at a particular time or after a particular event (e.g., after the next dose of medicament is delivered or after the condition of the subject reaches a particular state, such as the middle of a desired blood glucose range). In some examples, the threshold values may be associated with input provided by the subject sensor 2406 or other types of sensors that may be used to monitor one or more parameters associated with the health condition of the subject 2414.

The parameters for a suspension may include the start and stop conditions for a suspension. The start condition for a suspension may be a condition that, when met, activates a suspension. In some such examples, the start condition is met when a timer runs out. Similarly, the stop condition is a condition that, when met, ends the suspension. In one example, the stop condition is met when a timer runs out. In another example, the stop condition is met when a threshold is met. A threshold may be related to a measurement taken by ambulatory medical device (e.g., by a subject sensor 2406), such as a glucose concentration of the blood of a user. The threshold may be met if the glucose concentration goes above, goes below, or matches a set concentration. Multiple conditions may be set by the suspension request interface component. For example, a time condition and a threshold condition may be set simultaneously. A user may specify that a suspension will end after a set time. However, the suspension may end sooner than the set time if the glucose concentration of the user meets a threshold.

In some cases, the request to suspend therapy may include an indefinite suspension period. In other words, the request may not include a time period specified by a user or an identity of a resumption condition. In some cases, the indication may include a request to temporarily suspend delivery of therapy for a defined period of time or until a further interaction or event occurs. Thus, the resumption condition can include an expiration of time or an active event (e.g., a command or a determined condition of a subject). Further, the therapy to be suspended may include any type of therapy. For example, the therapy to be suspended may be the suspension of the delivery of medicament, which may include insulin, counter-regulatory agent (e.g., Glucagon), or both insulin and a counter-regulatory agent. In some cases, the ambulatory medicament device may be capable of and/or configured to administer multiple medicaments (e.g., both insulin and a counter-regulatory agent). In some such cases, the request to suspend therapy may include a request to suspend one (e.g., insulin or the counter-regulatory agent) or both of the medicaments.

The interactions with the user interface may include the selection of an icon, a series of taps or inputs, one or more gestures (e.g., a swipe or other simple or complex movement across the touchscreen), performing a pattern or sequence on the touchscreen (e.g., drawing an image), a multi-touch or multi-input interaction, a combination of the foregoing, or any other type of interaction with a touchscreen, or portion thereof. The series of inputs may be any combination of touch movements, touch points, numerical characters, alphabetical characters, and other symbols. In some examples, the first and/or second user interactions may include a predetermined sequence of numerical or alphabetical inputs. In some examples, a series of multiple inputs, the range of parameters for an input may be dependent on other inputs in the series. For example, required start position of a touch movement may be dependent on the position of the previous touch movement. The time that the series of inputs are entered may also be a part of the range of parameters. For example, a series of inputs may need to be entered in no less than 3 seconds or more than 3 seconds, and no more than 15 seconds or less than 15 seconds. In some cases, a visual guide may assist the user in generating the user interaction. For example, one or more arrows or images may be presented to the user to guide the user in providing the command to suspend the delivery of therapy.

Further, one or more of the interactions may include interacting with a sensor as an optical sensor (e.g., visible light or IR sensor), biometric sensor (e.g., a fingerprint or retinal scanner), a proximity sensor, a gyroscope, or a combination of accelerometer and gyroscope, and the like. Also, in an exemplary embodiment, the second user interaction may be made through a wireless signal such as RFID or Bluetooth. In some embodiments, the second user interaction may include receiving a selection of an indicator box that correspond to either insulin or glucagon and receiving a predetermined sequence of numerical inputs in order to deliver the therapy change selection.

The type of user interaction that unlocks the touchscreen, provides access to a therapy suspension user interface, or confirms a suspension request may be the same or may differ.

In an exemplary embodiment, the system may have a time-out such that if no interaction occurs for a set period of time at each step during the therapy suspension request process, the user interface will turn off and the therapy suspension request process has to start again. In one implementation of the time-out, if no interaction occurs for more than 30 seconds after the system is waked/unlocked before the second user interaction is received by the user interface, the user interface will be deactivated.

Figure 25:
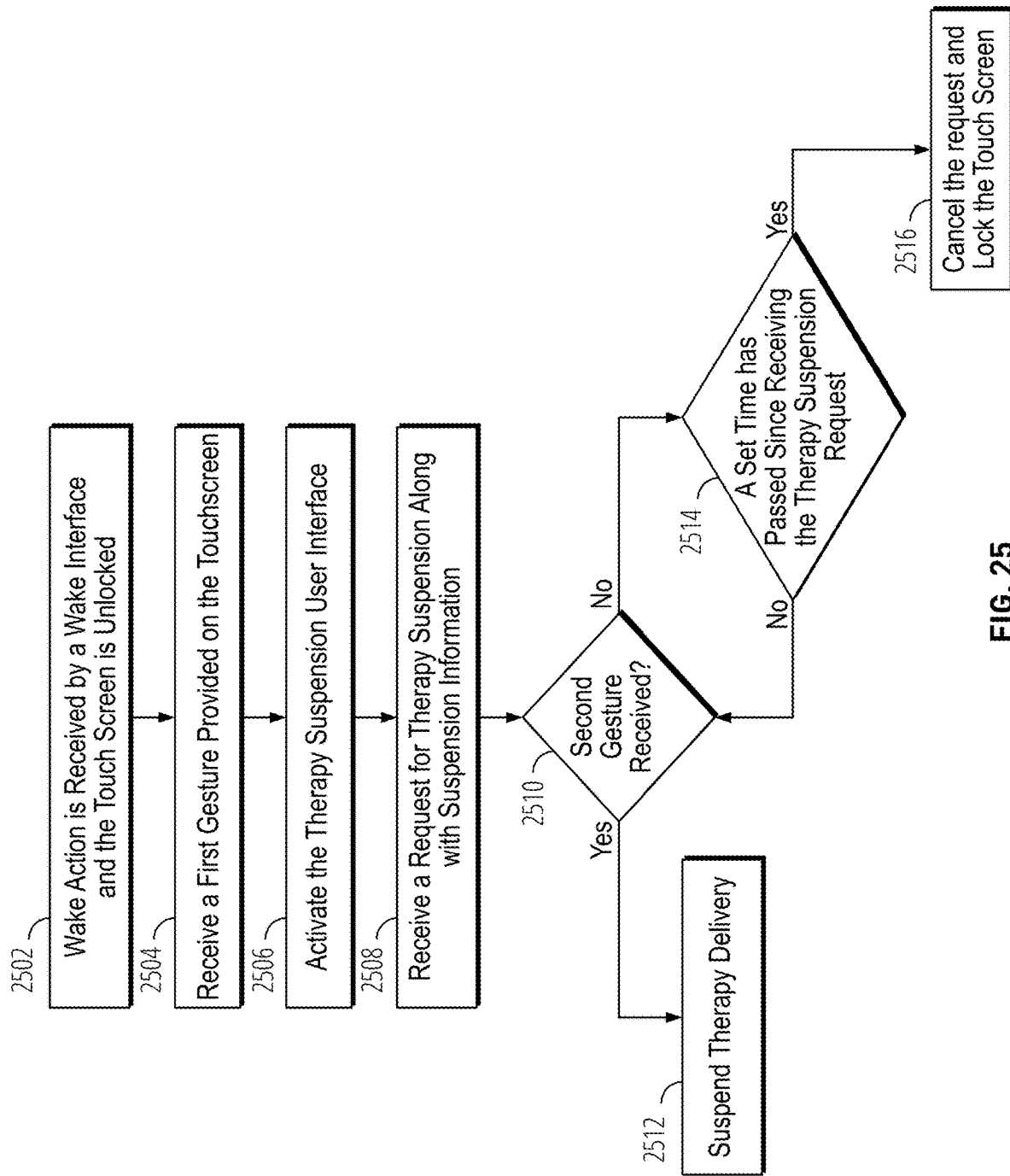
FIG. 25 is a flow diagram illustrating an example method for receiving and implementing a suspension request, which may be implemented by an AMD.

FIG. 25 is a flow diagram illustrating an example method for receiving and implementing a suspension request, which may be implemented by an AMD. In this example the user may use a touchscreen interface to request and confirm a therapy suspension. Once the user activates the touchscreen using a wake action 2502, the AMD may wait for a first gesture on the touchscreen. After the user provides the first gesture and the gesture is verified by the therapy suspension control procedure 2426, a therapy user interface may be activated 2506 where the user can request a therapy suspension and provide 2508 the suspension information (e.g., a start day/time and stop day/time and/or a resumption condition). Next, the AMD may wait for second gesture on the user interface 2510. If the second gesture is received and verified by the therapy suspension control procedure 2426, the therapy delivery will be suspended 2512. If the second gesture is not received or not verified by the therapy suspension control procedure 2426, the therapy suspension control procedure 2426, may determine if a set time has passed since receiving the therapy suspension request 2514. If it is determined that a set time has passed since receiving the therapy suspension request, the request will be canceled and the touch screen will be locked 2516. If it is determined that time from receiving the therapy suspension is less than a set time the AMD may wait for the second gesture to be received.

In some examples, once a wake action is received 2502, the AMD may automatically activate a therapy suspension user interface 2506, without the need for a first gesture 2504. In these examples, once the request for therapy suspension is received 2508, a gesture (e.g., a first gesture) may be required to verify the request. In some such examples, once the therapy delivery is suspended, a second gesture may stop a suspension before any of the conditions of the stop parameter are met. This allows the user the versatility of being able to modify a suspension that has been activated.

Figure 26:
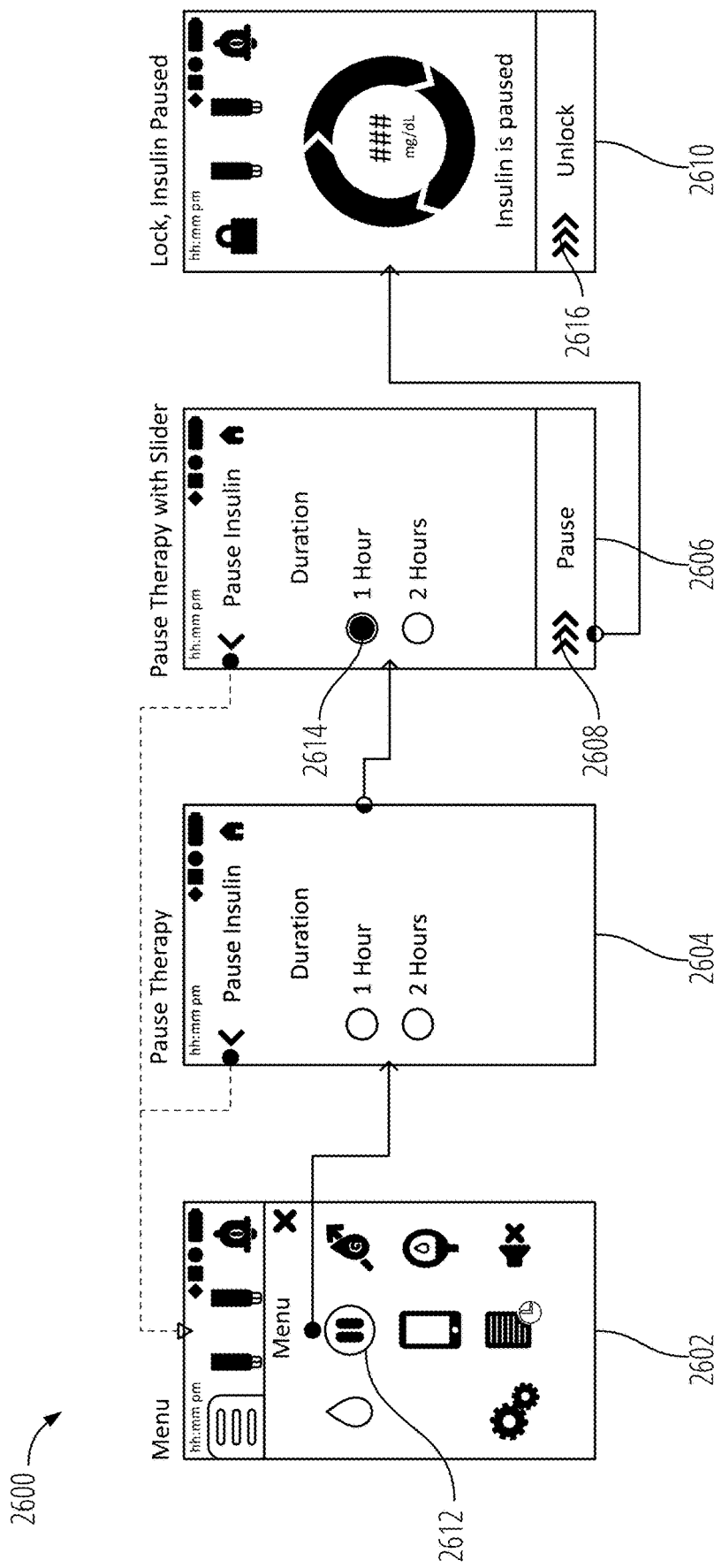
FIG. 26 illustrates a plurality of screens that the ambulatory medical device may display when a user pauses therapy.

FIG. 26 is an illustration of a plurality of screens 2600 that the ambulatory medical device may display when a user activates a therapy suspension user interface. Screen 2602 shows a user interface that an ambulatory medical device may display to a subject 2414. The display may be a touchscreen display 2410 that can accept input that includes the first and second gestures. The therapy suspension system (AMD 600) is not limited to the displays shown in FIG. 26. Various displays may communicate, to the subject 2414, the same information shown in FIG. 26. The screen 2602 allows the subject 2414 to select various functions. The pause button 2612, shown on screen 2602 is a function that suspends the delivery of a medicament to the subject 2414. When the pause button 2612 is selected, the subject 2414 is treated to the pause screen 2604. The pause screen 2604 allows the subject 2414 to select a duration of the medicament suspension. The AMD 600 may display various interfaces to allow the subject 2414 to select a duration of the medicament suspension. The pause screen 2604 shows a simple interface, giving the subject 2414 one of two duration options.

When the subject 2414 has made a duration selection on the pause screen 2604, the pause screen 2606 shows the subject 2414 the duration 2614 that the subject 2414 selected (e.g., in the figure the subject 2414 selected 1 hour. Thus, the medicament delivery is suspended for 1 hour after the suspension begins). The pause screen 2606 has a prompt 2608 for the user to make a gesture to confirm the requested suspension before the medicament suspension begins. As shown by the prompt 2608, the subject 2414 is being prompted to swipe right across the bottom of the screen. Once the subject 2414 performs the gesture to begin the medicament suspension, the suspension screen 2610 is displayed on the touchscreen. The suspension screen 2610 informs the subject 2414 that the medicament is paused. The subject 2414 has the option of performing another gesture to unlock the ambulatory medical device. The prompt 2616 for the subject 2414 to unlock the device forces the user to perform another swipe to execute more functions on the AMD 600.

Suspending the medicament delivery may occur by not generating a dose control signal to deliver a dose of medicament. Alternatively, or in addition, suspending the medicament delivery may occur by sending a signal to the medicament pump to cease providing therapy or medicament to the subject.

In some cases, the ambulatory medicament device may not immediately suspend therapy upon receiving a command to suspend therapy. For example, if the ambulatory medicament device is in the process of delivering medicament or determines that a condition of the subject indicates that medicament may soon be required to maintain the subject's condition (e.g., blood glucose) within a particular state (e.g., within a desired blood glucose range), the suspension of therapy may be delayed until at least such time that medicament is not being delivered, is predicted to not be required during the suspension period, or the next therapy has been delivered. In some such cases, the ambulatory medicament device may inform that user that the suspension of therapy is being delayed. Further, the ambulatory medicament device may indicate the reason for the delay. In some cases, the user may be able to override the delay and request immediate suspension of therapy. For example, if the user is replacing the medicament cartridge, the user may override an indication that the suspension of therapy should be delayed. In some cases, the requested start time may be overridden by a determined condition of the subject.

The suspension of therapy or the suspension of the delivery of medicament may continue until a resumption condition occurs. In certain cases, when a resumption condition is met, the suspension period may automatically end without action by the user or subject.

The resumption condition may include the expiration of a time period, a command from a user (e.g., the subject), detection that the ambulatory medicament devise satisfies a condition (e.g., that medicament has been refilled), that the condition of the subject meets certain criteria (e.g., the subject's glucose level drops below a threshold range or rises above a threshold range), or any other condition that may satisfy the reason for suspension of therapy or that overrides the request for suspension of therapy. For example, the drug delivery device may be configured to automatically resume drug delivery when a glucose threshold is reached or exceeded. This threshold could be set to 300 mg/dl for example. The resumption condition may include detection of an impending risk of hypoglycemia or hyperglycemia, or a hypoglycemia or hyperglycemia event. Further, the resumption condition may include a meal announcement, or an "exercise concluded announcement," a motion sensing event, a pause of other administered medicament, a conclusion of an undefined suspension length (e.g., during cartridge change), a speed-based resumption event, a location-based resumption, a remote resumption in case of an emergency (e.g., commanded from caregiver admin software or clinician), or any other type of resumption event. In some cases, the resumption condition can include a combination of criteria.

In some cases, automatically resuming therapy may include discontinuing the suspension of therapy before the expiration of the suspension period. For example, if a condition that caused therapy to be suspended is resolved prior to the expiration of the suspension period, therapy may be resumed.

In some cases, when a resumption condition (provided by the user) is met, the ambulatory medicament device may confirm that one or more additional condition of the ambulatory medicament device are satisfied before therapy is resumed. For example, if the ambulatory medicament device determines that medicament has not been refilled or if there is a problem with the refill (e.g., cartridge is incorrectly installed), the ambulatory medicament device may continue to maintain the suspension of therapy despite the trigger to resume therapy.

In some examples, a therapy suspension may be ended if a third interaction with a user interface (e.g., a gesture) is detected. The third user interface interaction may be detected by the user interface module 2404 and sent to the therapy suspension control procedure 2426. If the therapy suspension control procedure 2426 verifies that third interaction with the user interface is a predetermined third user interface interaction, it may send a signal to the device and subject monitoring procedure 2422 to activate the medicament dose control procedure 2420. This allows the user the versatility of being able to end a suspension that has been activated, during the suspension period set by the user before the confirmation (second interface with the user interface). In some cases, a user may decide to end a therapy suspension to modify one or more suspension conditions set prior to activation of the current therapy suspension. In some examples, user may decide to end a therapy suspension due to change in user's health condition not included in one or more therapy resumption conditions provided before activating the current therapy suspension.

Figure 27:
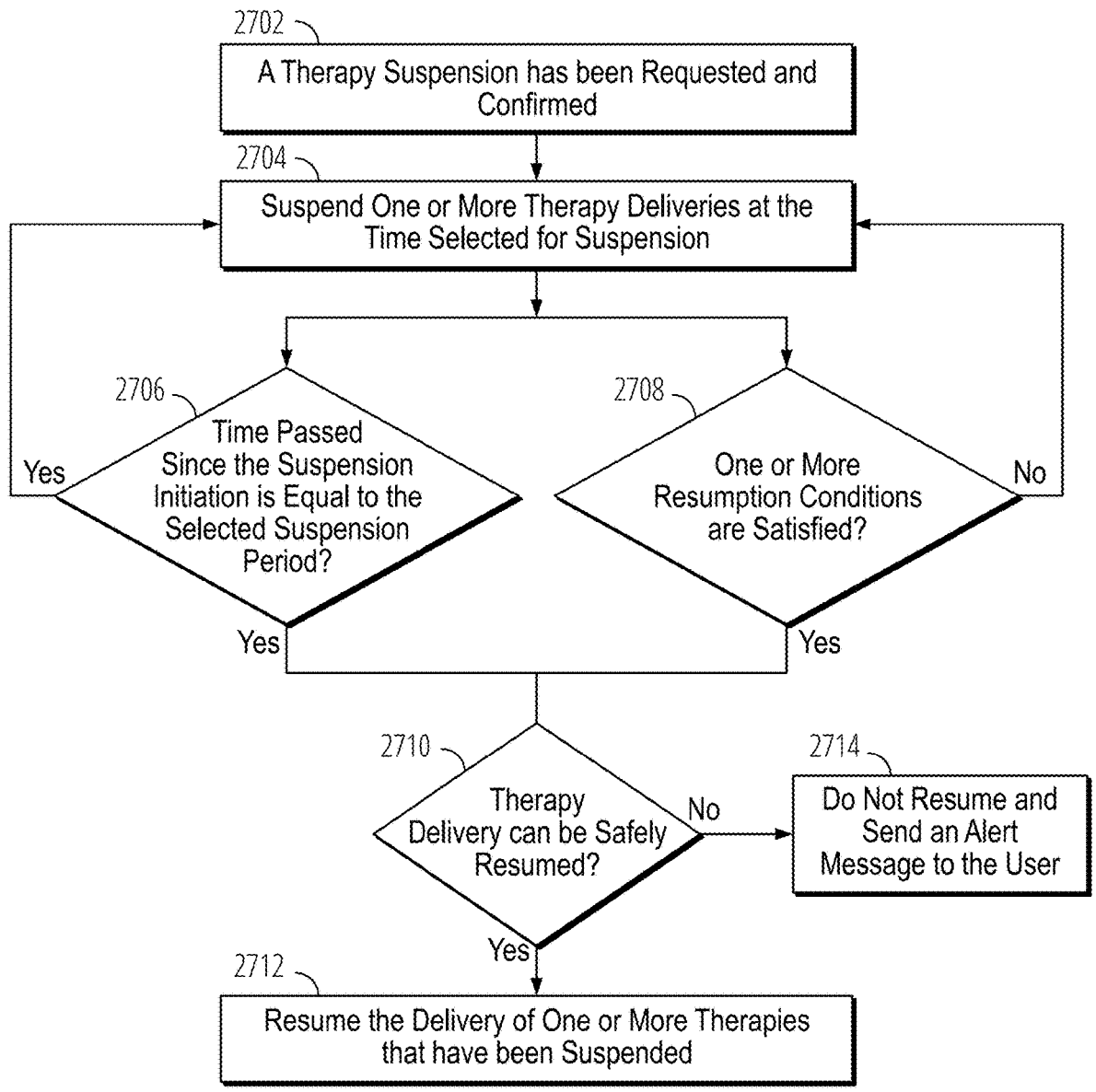
FIG. 27 is a flow diagram illustrating an example method of resuming a suspended therapy that may be implemented by an AMD.

FIG. 27 is a flow diagram illustrating an example method of resuming a suspended therapy that may be implemented by an AMD. Once a therapy suspension has been requested and confirmed by a user (e.g., using the procedure illustrated in FIG. 10) 2702, the AMD suspends one or more therapies selected for suspension 2704 at suspension initiation time received as part of the suspension information. For example, therapy suspension control procedure 2426 deactivates the medicament dose control procedure 2420 using the device and subject monitoring procedure 2422. During the suspension period, the therapy suspension control procedure 2426 continuously monitors the system clock and the subject and device condition (e.g., using medicament dose control procedure 2420).

If the therapy suspension control procedure 2426 determines that the time passed since the suspension initiation is less than the requested suspension time period 2706 and none of condition for resumption has been met 2708, the therapy suspension continues.

If the therapy suspension control procedure 2426 determines that the time passed since the suspension initiation is equal to the requested suspension time period 2706, or one or more resumption conditions have been met 2708, it may check other AMD or subject conditions (not included in the therapy suspension information), in order to determine whether the therapy delivery can be safely resumed 2710. If it is determined that the therapy delivery cannot be safely resumed, an alert message will be sent to the user interface to inform the about the reason for such determination 2714. If it is determined that the therapy delivery can be safely resumed, the one or more suspended therapies will be resumed 2712.

Figure 28:
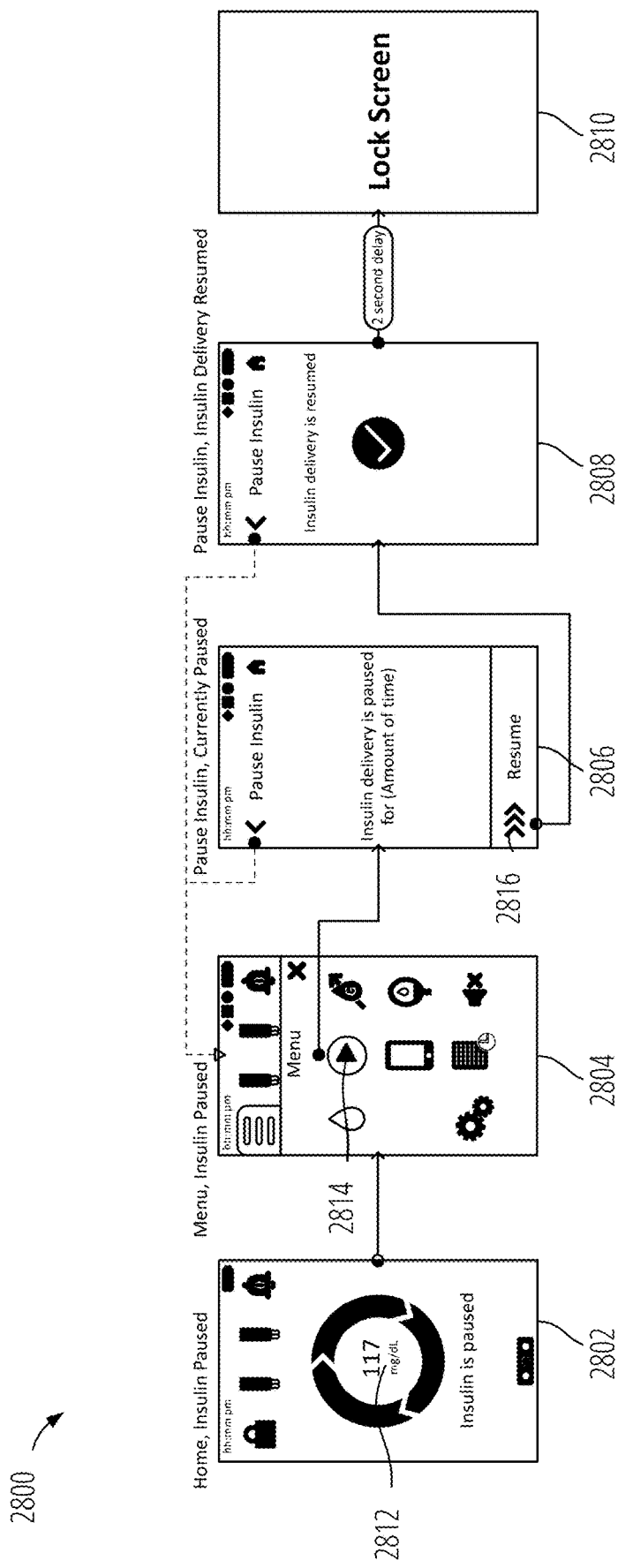
FIG. 28 illustrates a plurality of screens that the ambulatory medical device may display when a user resumes therapy.

FIG. 28 is an illustration 2800 of a plurality of screens that may be displayed, for example, on a touchscreen display when a subject 2414 resumes a suspended therapy. Screen 2802 informs the user that the delivery of medicament is currently in a suspended mode. The screen 2812 also shows the subject 2414 the current glucose concentration of the blood of the subject 2414. The AMD 600 may display various vital measurements that are useful to the subject 2414. In one implementation, the medicament suspension ends if the glucose concentration of the blood of the user meets or passes a threshold.

The interface screen 2804 allows the subject 2414 to select and execute various functions on the AMD 600. The resume button 2814 is a function that ends a medicament suspension. When the resume button 2814 is selected, the AMD 600 displays a resume screen 2806. The resume screen 2806 has a prompt 2816 that prompts the subject 2414 to perform a gesture. In the examples shown, the subject 2414 receives a prompt 2816 in the resume screen to swipe right across the bottom of the resume screen 2806. The requirement to perform the gesture to resume medicament delivery prevents the subject 2414 from inadvertently resuming medicament delivery in the AMD 600.

Once the subject 2414 performs the gesture to resume medicament delivery, the medicament suspension ends. The resumption screen 2808 shows the subject 2414 that the regular medicament delivery has resumed. Once the resumption screen 2808 has been displayed to the subject 2414 for a sufficient amount of time to inform the subject 2414 that the suspension is ending, the AMD 600 may display a lock screen 2810. The lock screen 2810 prevents the subject 2414 from inadvertently executing more functions on the AMD 600.

In one embodiment, the AMD 600 must receive a second gesture to end the suspension before the one or more conditions to end the suspension are met. The purpose of the second gesture is to ensure that the subject 2414 does not inadvertently end the suspension. Like the first gesture, the second gesture may be simple or complex.

With reference to FIG. 24, once the AMD device is instructed to resume therapy and/or determines that therapy is to be resumed, the ambulatory medicament device may determine whether a dose of medicament should be supplied to the user based on a control algorithm used by the ambulatory medicament device to control the provisioning of medicament to the subject. For example, the therapy suspension control procedure 2426 may determine a resumption condition has been satisfied or receive a user input from the user interface module 2404 (a third interaction with a user interface) indicating that therapy suspension should be ended. Subsequently the therapy suspension control procedure 2426 may send a signal to the device and subject monitoring procedure 2422 to activate the medicament dose control procedure 2420. If medicament is to be supplied, the medicament does medicament dose control procedure 2420 may generate and send a dose control signal to the medicament delivery interface 2402.

In some cases, the ambulatory medicament device may alert the user and/or the subject that therapy is being resumed. This alert may occur before generating a dose control signal and/or after a resumption condition is satisfied (e.g., a suspension time expires). In some cases, the user may request that the suspension of therapy end early. The user may request the early resumption of therapy be interacting with the aforementioned user interface using one or more of the previously described interaction methods (e.g., gestures or taps).

Additional embodiments relating to suspending medicament delivery to a subject that can be combined with one or more embodiments of the present disclosure are described in U.S. Provisional Application No. 62/910,970, which was filed on Oct. 4, 2019 and is titled "METHOD FOR SUSPENDING DELIVERY OF A DRUG INFUSION DEVICE WITH AUTOMATIC RESUMPTION OF DELIVERY," the disclosure of which is hereby incorporated by reference in its entirety herein for all purposes.

AMD with Security Functionality

An ambulatory medicament device (AMD), such as, but not limited to, an insulin pump, that provides life-saving treatment to subjects or subjects based on the condition of the subject, may include a user interface (e.g., a touchscreen display) that lets a user to modify the settings of the ambulatory medicament device. The setting may include, but not limited to, a condition that triggers the delivery of medicament to a subject, the quantity of medicament delivered when a condition is met, type of the medicament and the like. The setting may also include features of the AMD that may not be directly related to the medicament delivery (e.g., the screen brightness, an alarm sound, and the like). In some examples, it is desirable to manage access to various settings of AMD in order to avoid inadvertent changes while enabling changes that may be necessary for uninterrupted and proper operation of the AMD. For example, it may be desirable to limit the access to some settings to certain authorized users (e.g., a healthcare provider) while enable access to some other settings other authorized users (e.g., the subject, a guardian or parent of the subject).

In many cases, a healthcare provider can modify the settings of the ambulatory medicament device. However, it is often desirable that a non-healthcare provider modify at least some settings of the ambulatory medicament device. For example, when the ambulatory medicament device runs out of or has below a threshold amount of medicament, it is often desirable that a user be able to refill or change a medicament cartridge without visiting a healthcare provider. In some cases, changing the medicament cartridge may include interacting with a user interface and/or one or more settings of the ambulatory medicament device. Another example of when it is desirable for a non-healthcare user (e.g., a subject, parent, or guardian) to modify settings of the ambulatory medicament device is when the initial settings of the ambulatory medicament device are not providing the desired effect (e.g., sufficient medicament, too much medicament, providing the medicament too slowly or too fast, etc.). In some cases, normal maintenance of the ambulatory medicament device and/or subject may require interaction with the ambulatory medicament device settings and/or controls. For example, negative consequences may being to occur when an ambulatory medicament device remains connected to a subject at the same site for more than a threshold period of time (e.g., for more than 2-3 days, more than 5 days, more than a week, etc.). Thus, the ambulatory medicament device may need to be periodically moved from one site on the subject to another site on the subject (e.g., from left-side to right-side, from arm to leg, from stomach to back, etc.). The change in site location may require interaction with settings of the ambulatory medicament device (e.g., pausing operation until the site change is completed).

Although, as explained above, there are a number of reasons it is desirable to enable a user other than a healthcare provider (e.g., the subject receiving therapy, a parent, or a guardian) to have access to at least some user settings of an ambulatory medicament device, it is also desirable to regulate access to at least some of the ambulatory medicament device settings. For example, it is generally undesirable that a child (subject or otherwise), or a user below a particular age, have access to ambulatory medicament device settings that could cause harm to the subject if modified. Further, it may be undesirable for certain subjects who have diminished mental capacity regardless of age to have access to at least some ambulatory medicament settings.

The user may be a subject receiving medicament or therapy, or may be another user, such as a clinician or healthcare provider, or a parent or guardian of the subject. In some examples, the passcode required for changing one or more setting via an intermediary device may be different that the passcode required for changing the same settings directly using the AMD's user interface.

One solution to regulating access to settings of the ambulatory medicament device is to implement a lock feature to require that a user provide a passcode, a passcode, or other information before the user is permitted to modify a setting of the AMD, such as a control parameter. To simplify discussion, the disclosure will describe using a passcode. However, it should be understood that the passcode can be substituted for a passcode or any other type of secret or semi-secret information. In some examples, when the AMD is in the locked state, it may continue delivering therapy to the subject at the same rate as unlocked state.

The lock feature may be activated by default or may be activated by a user. In some examples, the lock feature can be enabled through a setting in a control menu of the AMD device provided on a user interface (i.e., touchscreen display). The setting may include an on/off toggle (e.g., a software interface element or a hardware interface element) so when the toggle is on, a passcode (e.g., 4 to 8 numeric digits) may be required. In some cases, if the lock feature is on, the passcode (e.g., a 4 to 8 numeric digit code) may be required to turn the lock feature off. When the lock feature is activated, the user may program the ambulatory medicament device with a user passcode selected by the user. Alternatively, or in addition, the user passcode may be set in response to a passcode change request. In some cases, a user passcode may expire. In such cases, a user may be required to generate a new passcode after the previous passcode expires or before the previous passcode is permitted to expire. In other cases, the ambulatory medicament device may periodically generate a new passcode (e.g., an override passcode), or may generate the passcode at a time when a user supplies the passcode.

In some cases, the user interface element used for accessing a user interface that enable changing one or more settings of the AMD may differ from the user interface for modifying the control parameters associated with that setting. For example, a keypad may be used to enter a passcode for unlocking a user interface for changing a control parameter and a touchscreen may be used to modify the control parameter.

When the lock feature is enabled, the user interface screen may look and function the same as if the lock feature were not enabled. If the lock feature is enabled, when a visual guide for unlocking the device (such as, for example, a linear unlock slider, an arcuate unlock slider, or another unlock user interface element) is activated, a passcode entry interface (e.g., a keypad user interface element) may be displayed. If either the user passcode or the global override passcode is entered, the user interface may proceed as normal. Otherwise, the user interface may revert back to the original lock screen.

In some examples, the user action that permits a user to change one or more settings of the AMD may be different from the wake action that activates a user interface. For example, a wake action may be used to activate a touchscreen display that may display a plurality of user selectable elements some of which may be accessible without a passcode. In such examples, a subset of the user selectable elements, for example those allowing the user to change therapy control parameters, may require a passcode. In some cases, access to each user parameter control element may require a different passcode. In some examples, providing a passcode may to an AMD in locked state, may directly enable access to a subset of control parameter elements.

To help recall the passcode, the passcode may be set by the user enabling the user to select a passcode the user is more likely to remember. However, regardless of who sets the passcode, there is a risk that the user will not remember the passcode. Due to the nature of the device (e.g., a device that may provide life-saving treatment), it is desirable that certain users not be restricted from accessing particular settings of the ambulatory medicament device, and be able to quickly (e.g., within seconds, minutes, prior to a next therapy event, or before harm may occur to the subject) obtain access to the particular settings when required. Thus, while some non-medical devices may implement lockout periods or other restrictions to prevent a malicious user from trying to brute-force determine a passcode for a device, such features are generally undesirable for an ambulatory medicament device. Accordingly, embodiments disclosed herein include an ambulatory medicament device that includes an override passcode that enables access to the ambulatory medicament device (or control settings thereof) regardless of whether the user passcode is provided.

In some examples the passcode or the override passcode can be a series of taps, series of inputs, a complex or a simple gesture (e.g., a swipe or other movement across the touchscreen), The series of inputs may be any combination of touch movements, touch points, numerical characters, alphabetical characters, and other symbols. In some examples, the time that the series of inputs are entered may also be a part of the range of parameters. For example, a series of inputs may need to be entered in no less than 3 seconds or more than 3 seconds, and no more than 15 seconds or less than 15 seconds. One example of the complex gesture is a swipe.

In some examples the passcode or the override passcode can be a complex or a simple gesture (e.g., a swipe or other movement across the touchscreen), performing a pattern or sequence on the touchscreen (e.g., drawing an image), a multi-touch interaction, a combination of the foregoing, or any other type of interaction with a touchscreen, or portion thereof. Another example of a complex gesture is entering a predetermined sequence of touches. In some cases, the passcode may include a quiz or set of questions, In some examples, the ambulatory medicament device may be configured to receive therapy settings or modifications to therapy settings from an intermediary device via a communication connection. In some cases, this feature may be supported in addition to providing the user with option of modifying one or more settings with a user interface of the AMD. The communication connection between the intermediary device and the AMD may be a direct connection via, for example, Bluetooth®, or a connection via a network, such as over a local area network or a wide area network. In some such cases, the ambulatory medicament device may include a wireless transceiver, such as an NB-LTE transceiver, a Wi-Fi transceiver, or a Bluetooth transceiver. The intermediary device, that provides the user with a user interface to modify settings of the AMD, include any type of device (e.g., a computing device) that can communicate with an ambulatory medicament device. For example, the intermediary device may be a laptop or desktop computer, a smartwatch, a smartphone, or a hardware control device that may be configured to interact with the ambulatory medicament device. Embodiments disclosed herein are applicable regardless of whether the user interface for modifying therapy settings or the configuration of the ambulatory medicament device is generated or presented by the ambulatory medicament device to the user or via another device. In some such cases, a user may provide a user-generated passcode or an override passcode via an interface of the computing device. The computing device may then provide the user-generated passcode or the override passcode to the ambulatory medicament device via the network connection between the devices.

In some examples, even if the AMD is in locked state, certain intermediary devices may have access to user interfaces that may be used to change one or more settings (e.g., therapy settings) of the AMD. For example, the smart phone of a guardian or a parent of the subject may be used to change one or more settings of the AMD while the AMD is in the locked state.

In some examples, the AMD may be configured to receive a passcode from or via a computing systems (e.g., a cloud computing system). In these examples, the AMD may receive passcode through a direct end-to-end connection (e.g., a wireless connection over a wide area network) stablished with the computing system. In some such examples, another computing device (e.g., a smartphone, a laptop, a personal computer, and the like) connected to the computing system, may send a passcode to the AMD and be able to change one or more settings of the AMD if the passcode is validated by the AMD.

In cases where the user cannot recall the user passcode, the user can obtain access to the user interface that permits modification of the control parameter by supplying an override passcode. In some examples, the override passcode may be a universal fixed passcode (e.g., an 8-digit override passcode) that can be used instead of the user set passcode. The override passcode can be stored in the ambulatory medicament device at the time of manufacture and may be shared among multiple ambulatory medicament devices (e.g., a global override passcode), or may be unique to a particular ambulatory medicament device. The override passcode may be managed by the manufacturer or by a third-party service. To obtain the override passcode, the user may contact the manufacturer or passcode managing service. Generally, enabling the passcode may exist to prevent a user with a diminished mental capacity (e.g., a child) from modifying settings of the ambulatory medicament device. Thus, security may be less of a concern and any user can contact the manufacturer or passcode managing service to obtain the override passcode. In some such cases, a single global override may be used for all devices produced by the manufacturer. However, in some cases, a level of security may be desired. In some such cases, it may be necessary for the user to authenticate him or herself. Further, the user may be required to provide a serial number of the ambulatory medicament device. In some cases, each model or each unit of the ambulatory medicament device may have a different override passcode. The user may provide authorization information and a serial number of the ambulatory medicament device to the manufacturer or passcode managing service to obtain the override passcode.

In some examples, may periodically generate a new override passcode or may generate an override passcode at a time when a user supplies the passcode. In these examples, the ambulatory medicament device may use the same parametric values to generate the override passcode as another device may use thereby ensuring a match between the override passcodes. Advantageously, in some cases, by using an algorithm to generate the override passcode, the override passcode can be obtained regardless of whether a user is able to contact a manufacturer or other passcode managing service. In some cases, the user may generate the override passcode without access to a network or phone using, for example, a computing device that can access a common parameter value as the ambulatory medicament device.

In some cases, the override passcode may change over time or be a rotating passcode. For example, in some cases, the override passcode may change every thirty seconds, every minute, every hour, etc. In some such cases, the override passcode may be determined from an algorithm executed by an application. The ambulatory medicament device may store a copy of the algorithm in a memory of the ambulatory medicament device and may execute the algorithm to determine the override passcode that is currently valid. A copy of the algorithm may be executed by another computing device accessible by the user. The output of the algorithm may be based on a value that is commonly accessible by the ambulatory medicament device and the copy of the algorithm accessible by the computing device. For example, the output of the algorithm may be generated based on a time, a user identifier, a provided value, or any other factor that may be used to repeatedly generate the same output. In some cases, the override passcode may be calculated based on a combination of factors. For example, the override passcode may be calculated based on a portion of a serial number or model number for the ambulatory medicament device and the time. The determination of the override passcode may be calculated by the ambulatory medicament device, a computer server, and/or an application on a user device.

In some cases, the override code can be automatically received by the ambulatory medicament device. Thus, a user may not need to see or enter the override code. In some cases, the override code may be transmitted to another device of the user (e.g., a smartphone or laptop). For example, the override code can be texted to a user's smartphone. In some cases, the override code may be received in a coded manner that may not be understandable by a child or user with diminished mental capacity.

In some cases, the override passcode may be linked to a location. For example, the override passcode may only be enterable at a healthcare provider's office or at the subject's place of residence. The determination of the location of the ambulatory medicament device may be based on a geolocation system (e.g., a Global positioning System (GPS)) available to the ambulatory medicament device.

In some examples, at least for a subset of therapy settings, the passcode may provide a second level of security in addition to other interactions with the user interface (e.g., a first and a second gesture on a touchscreen display) that may be used to change the therapy settings and/or accept the change made to a therapy setting. In some examples, at least for a subset of settings, the passcode may be used instead of other interactions with the user interface (described above).

As mentioned above, interacting with the user interface may cause the ambulatory medicament device, or other device that can modify a control of the ambulatory medicament device, to present a passcode input screen to the user. The user may enter the passcode to unlock additional user interface features including, for example, a user interface that enables the user to modify at least one control parameter of the ambulatory medicament device. The control parameter can be modified based on an interaction with a parameter control element of the user interface. Further, modification of the control parameter may cause modification of the generation of a dose control signal that is generated by a control algorithm based at least in part on the control parameter.

In some embodiments, the ambulatory medicament device may have an advanced therapy screen, or other user interface, that permits a healthcare provider, or other user, to obtain additional details relating to therapy provided by the ambulatory medicament device. Although the advanced therapy screen may generally be intended for a knowledgeable user, such as a clinician, in some cases, any user may obtain access to the advanced therapy screen. The advanced therapy screen may permit the healthcare provider to modify control parameters that may not be modifiable by other users. For example, the healthcare provider may be able to control parameters that relate to the calculation of a rate of insulin accumulation, the rate the insulin diminishes within the blood of the subject, the setting of a glucose setpoint, an aggression level or factor of therapy relating to an amount of insulin provided when the subject's glucose level is outside the setpoint range, or when the insulin reaches a point of maximum concentration within the blood of the subject (e.g., $T_{max}$).

Access to the advanced therapy screen may be limited by requirement of a passcode, which may be referred to as a clinician passcode to distinguish it from the user-generated passcode and/or the override passcode. This clinician passcode may or may not be user-generated. However, the clinician passcode may be a separate passcode from the user-generated passcode that permits access to the non-advanced therapy screen interface. Further, the clinician passcode may be separate from the override passcode that permits a user to override the user-generated passcode to obtain access to the non-advanced therapy screen interface. In some cases, the clinician passcode may be used as an override passcode. In some example the clinician passcode can be valid for period of time (e.g., set by a subject or another authorized user such as the guardian or apparent of the subject). For example, the clinician passcode may be valid for a day, a week or a month. In some examples, the AMD may allow certain authorized users to terminate the clinician access at any time.

In some cases, access to the advanced therapy screen may be limited to a particular period of time. After the time period expires, the ambulatory medicament device may automatically restrict access to the advanced therapy screen. In some cases, the window of access may be extended. For example, if the healthcare provider is continuing to interact with the advanced therapy screen, the screen may remain accessible.

In some cases, the advanced therapy screen may provide additional features. For example, while a user may be able to indicate that an amount of insulin provided for a meal or as a correction factor should be higher or lower, the healthcare provider may be able to specifically adjust the amount of insulin. Moreover, while a user's direction may or may not be followed depending, for example, if the request exceeds a threshold or may cause blood glucose to not satisfy a setpoint range, an indication provided via the advanced therapy screen may be followed regardless, or may have a wider range or different threshold that may control whether the instruction is followed. Further, the advanced therapy screen may be used to temporarily pause therapy and/or may prevent subject access.

In some cases, the manufacturer of the ambulatory medicament device may provide a remote unlock signal that can be used to unlock access to the ambulatory medicament device and/or to an advanced therapy screen of the ambulatory medicament device.

As described above, the passcode may be desired to prevent particular users from inadvertently changing certain control parameters of the ambulatory medicament device. However, features of the ambulatory medicament device that do not affect therapy may remain accessible to a user when the ambulatory medicament device is in a locked state. For example, a user may be able to access therapy history, screen brightness settings or colors, or any other feature that is unlikely to harm a subject if modified in a particular manner. Further, as the passcode feature is generally to prevent control parameter changes, the ambulatory medicament device may provide therapy and continue to provide therapy at the same rate and under the same condition, whether or not the ambulatory medicament device is locked or unlocked.

When the ambulatory medicament device receives the user passcode or the override passcode, the ambulatory medicament device validates the passcode. The passcode may be validated by comparing the received passcode to a passcode stored in a memory of the ambulatory medicament device or generated by the ambulatory medicament device. If the passcode received from the user is successfully validated, the user may be granted access to a user interface to modify one or more control parameters. In some cases, the user may be requested to re-enter a passcode to confirm a change to a control parameter. In some examples, the user may be requested to provide a gesture on a touchscreen to confirm a change to a control parameter.

If the passcode is not validated, the ambulatory medicament device, or other control device that can provide access to control parameters of the ambulatory medicament device, may prevent access to the user interface to modify the one or more control parameters. In some cases, the user interface that presents the user with the ability to enter the passcode may permit the user a particular number of tries or a particular number of tries within a particular time period to enter the user passcode. If the correct user passcode is not entered within the provided number of tries or within the particular time period, the user interface may enter a lock state (e.g., the screen will be turned off) and prevent further attempts to enter a passcode for at least a period of time. In some cases, the user passcode option may be indefinitely locked or blocked. In some such cases, the control parameters of the ambulatory medical device may only be accessible if the override passcode is provided. Alternatively, or in addition, a user passcode of a different user may be used to provide access to the control parameters of the ambulatory medical device. In some examples, if the correct override passcode is not entered within the provided number of tries or within the particular time period, the user interface may block any attempt to change the override passcode for at least a period of time.

In some cases, once the passcode is successfully entered or validated, a user may deactivate the passcode feature of the ambulatory medicament device. Deactivating the passcode feature may require use of a separate passcode or the override passcode in addition to the user passcode.

In some cases, the passcode may be optional or omitted based on the computing device connected to the ambulatory medicament device. For example, if the end-to-end connection is established between a smartphone registered to a particular user (e.g., a parent of the subject), the ambulatory medicament device may unlock automatically without requiring a passcode. In other cases, the smartphone, or other computing device, may automatically provide the user-generated passcode or the override passcode to the ambulatory medicament device upon establishing a connection. In some cases, the ambulatory medicament device may automatically be unlocked when connected to a charger or when in a particular geographic area. For example, a geofence may be configured in one or more locations, such as the subject's house or the clinician's office. When the ambulatory medicament device determines it is within the geo-fence, the ambulatory medicament device may automatically be unlocked. Similarly, when the ambulatory medicament device determines that it is not within the geo-fenced region, it may automatically be locked. The determination of the location of the ambulatory medicament device may be made based on a geo-location system, such as the Global Positioning System (GPS).

Figure 29:
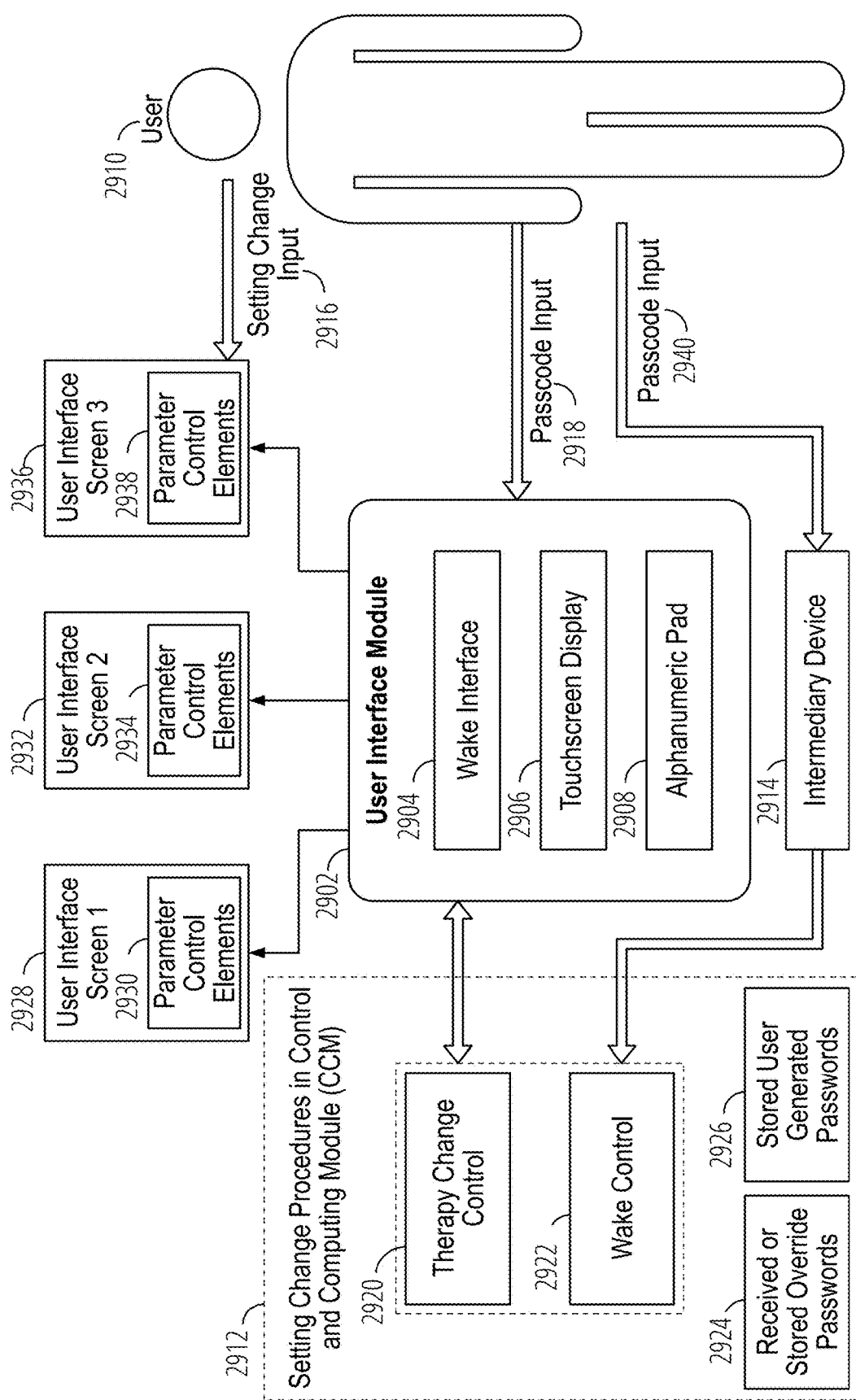
FIG. 29 is a block diagram illustrating the interconnection among modules and procedures in AMD involved in changing the settings of the AMD.

In some cases, after a certain number of unsuccessful passcodes are entered (e.g., after 5 tries), the user interface screen may be turned off or may accept only the global override passcode Example AMD with Security Codes FIG. 29 is a block diagram illustrating the interconnection among modules and procedures in AMD involved in changing the settings of the AMD. In some cases, one or more settings of the AMD may be changed using a setting change input 2916 to one or more parameter control element parameter control elements 2930/2934/2938 presented on one or more setting user interface screens 2928/2932/2936 provided by the user interface module 2902. In some examples, when the lock feature is activated, access to one or more setting control screens 2928/2932/2936 and/or one or more parameter control element 2930/2934/2938, may be protected by a passcode. In order to change a parameter control element 2930/2934/2938, the user may provide a passcode input 2918 (e.g., a user generated passcode or an override passcode), via the user interface module 2902 (e.g., using a touchscreen display 2906 or alphanumeric pad 2908). Alternatively or in addition, the user 2910 may provide a passcode 2940 using an intermediary device (e.g., a laptop, a smart phone and the like) that is connected to the AMD (e.g., via a wireless link). In some examples, the access to one or more setting user interface screens 2928/2932/2936 and/or parameter control element parameter control elements 2930/2934/2938, may be managed by setting change procedures 2912 stored in a memory in the control and computing module of the AMD. A hard processor may execute the machine readable instructions associated with the setting change procedures 2912.

In some examples, the option to provide a passcode may become available, when the user 2910 performs a wake action on a wake interface 2904. In these examples if the wake control procedure 2922 of the CCM determines that a valid wake action is performed, it may present selectable elements associated with the setting user interface screens 2928/2932/2936, for example, on a touchscreen display. In some examples, the first screen presented on the touchscreen display, may provide other selectable elements including an element to change the settings of the AMD. In such examples, selecting element associated with settings change may activate a second screen that presents selectable elements associated with the setting user interface screens 2928/2932/2936. When the lock feature is activated, access to any of the setting user interface screens 2928/2932/2936 and/or parameter control element 2930/2934/2938 may require a passcode. In some examples, each one of the user interface screens 2928/2932/2936 and/or parameter control element 2930/2934/2938 may require a different passcode. In some examples, one or more user interface screens 2928/2932/2936 and/or parameter control element 2930/2934/2938 may not require a passcode. For example, access to the first user interface screen 2928 may require a first passcode, the access to the second user interface screen 2932 may require a second passcode and the access to the third user interface screen 2936 may not need a passcode. In yet another examples, all the user interface screens 2928/2932/2936 may be presented without the need for providing a passcode, but access to the one or more control elements in a control screen may require a passcode. For example, the user may select the second user interface screen 2932 without entering a passcode but in order to select one or more parameter control element 2934 on that screen, the user may need to enter one or more passcodes.

In some examples, once a passcode or override passcode received from the intermediary device 2914 or the user interface module 2902, the passcode may be transmitted to the control and computing unit of the AMD where the setting change procedures 2912 (therapy change control procedure 2920 and wake control procedure 2922) determine the validity of the passcode by comparing it to the one or more stored user generated passwords 2926 or received or stored override passwords 2924 stored in a memory of the CCM.

Figure 30:
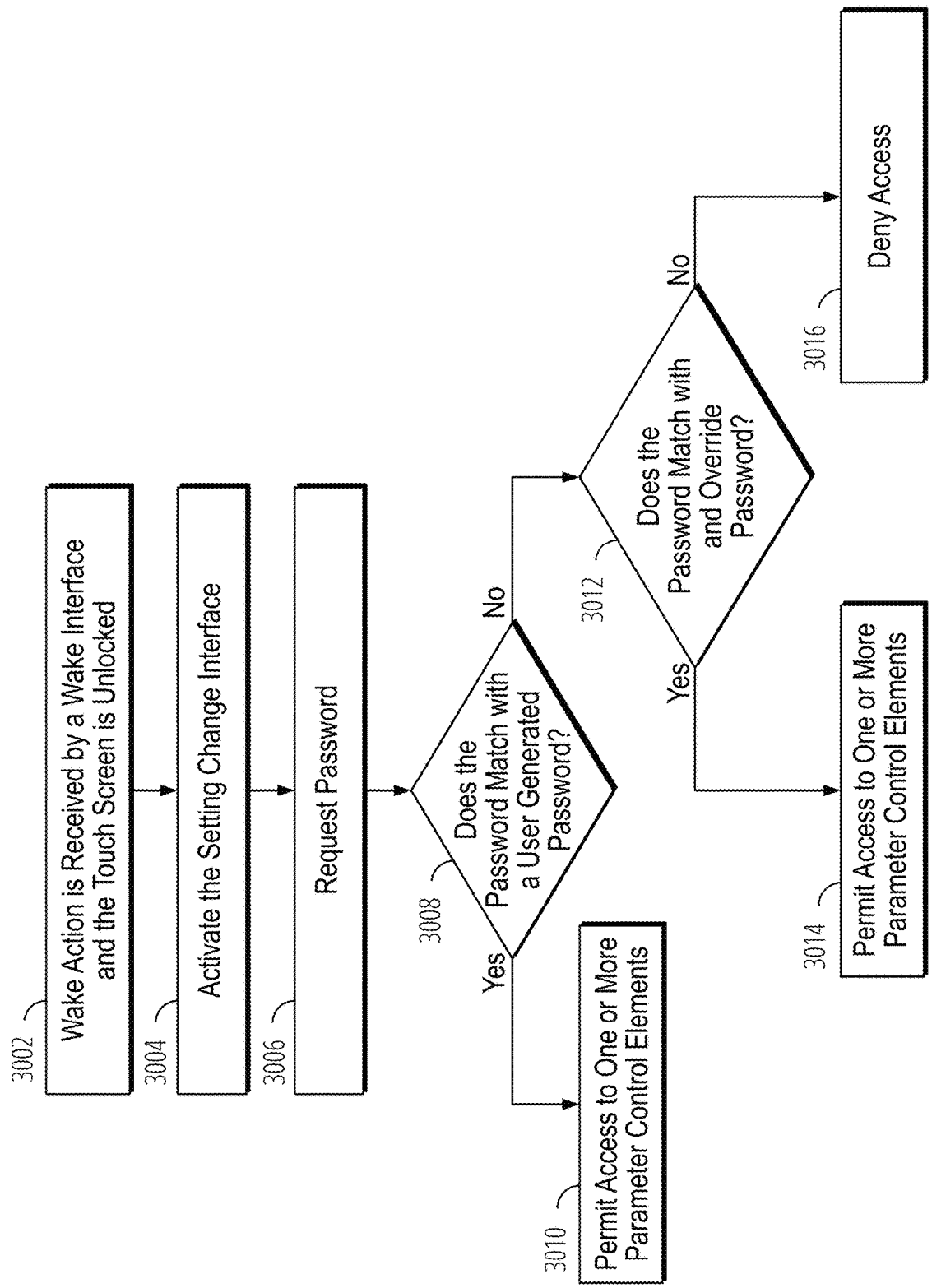
FIG. 30 is a flow diagram illustrating an example method that may be used by an AMD to allow a user to change a setting of the AMD using a user generated passcode or an override passcode.

FIG. 30 is a flow diagram illustrating an example method that may be used by an AMD to allow a user to change a setting of the AMD using a user generated passcode or an override passcode. Once the AMD (e.g., the wake action procedure in the CCM) receives a valid wake action 3002, a user interface may be activated. In some examples, the wake action may directly activate a setting change interface 3004 (e.g., a setting change screen presented on a touchscreen display). In some examples, a specific wake action may activate the setting change interface. On the setting change interface 3006, the AMD (e.g., the setting change procedure in the CCM) may request a passcode (e.g., by presenting a window to enter a passcode). Once a passcode is received, the AMD (e.g., the setting change procedure in the CCM) may determine whether the passcode matches a user generated passcode 3008. If it is determined the passcode matches with a user generated passcode, the AMD may provide access 3010 to one or more control parameter elements associated with the received passcode. If the received passcode dose not match with any of the stored user generated passcode, the AMD may determine whether the passcode matches with an override passcode 3012. If it is determined the passcode matches an override passcode stored in a memory of AMD or a memory of an authorized computing device, the AMD may provide access 3014 to one or more control parameter elements associated with the received override passcode. If it is determined the passcode does not match an override passcode, the AMD denies access 3016 to one or more passcode protected control elements.

Figure 31:
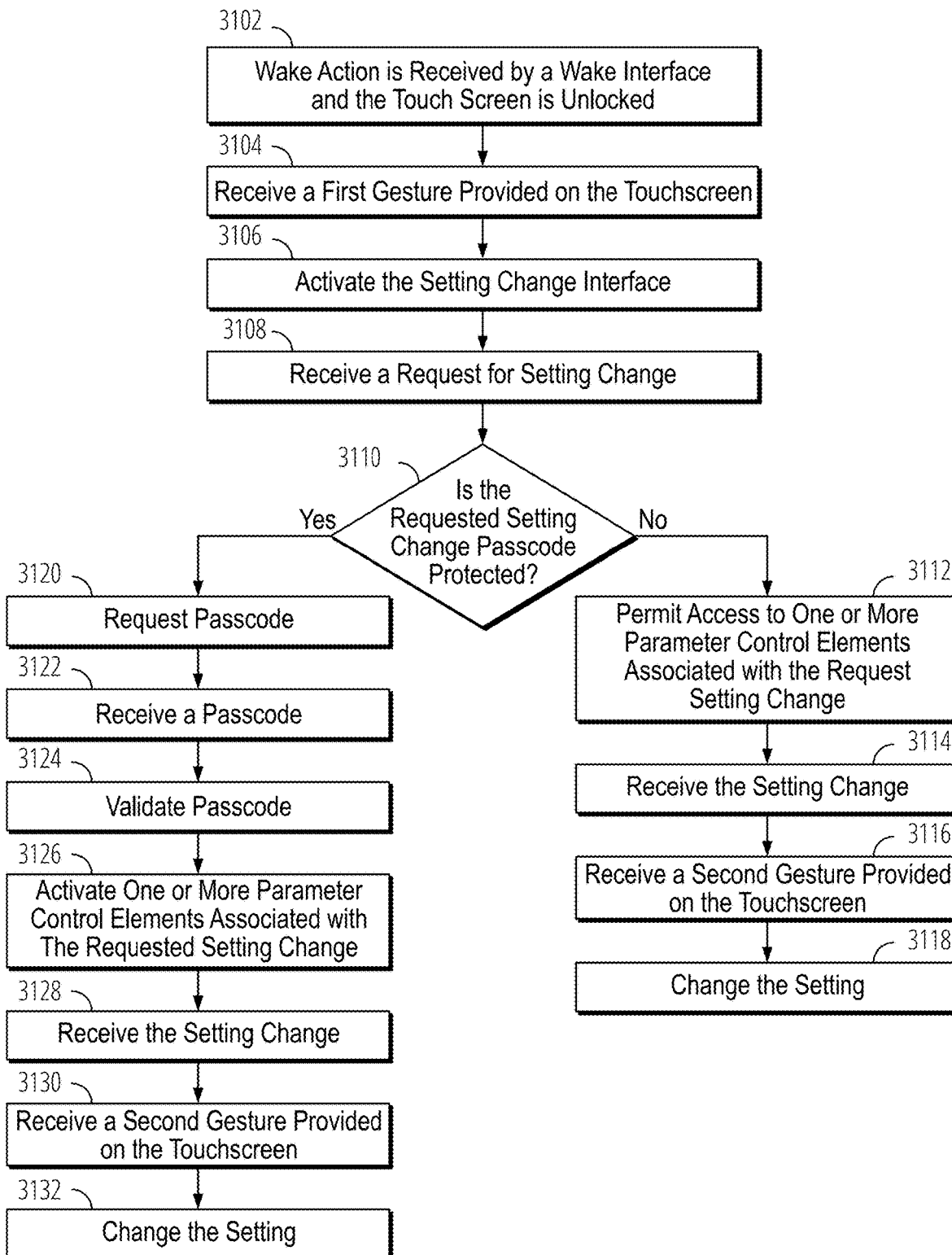
FIG. 31 is a flow diagram illustrating an example method that may be used by an AMD to allow a user to change a setting of the AMD using a user generated passcode or an override passcode.

FIG. 31 is a flow diagram illustrating another example method that may be used by an AMD to allow a user to change a setting of the AMD using a user generated passcode or an override passcode. Once the AMD (e.g., the wake action procedure in the CCM) receives a valid wake action 3102, the AMD may provide a user interface (e.g., a touchscreen display) on which the user can provide a first gesture to activate a setting change interface or screen. When a first gesture is received from a user or subject 3104, the AMD may activate a setting change interface 3106 or a screen. In some examples, the setting change interface or a screen may include one or more parameter control elements associated with one or more settings of the AMD. In some examples, the setting change interface or a screen may include one or more selectable elements each associated with a setting change screen (e.g., a screen provided on a touchscreen display) that may include one or more control parameters. When a request for setting change is received 3108, the AMD may determine whether the requested setting change is passcode protected or not 3110. In some examples, the request for setting change may include selecting a parameter control element. In some examples, the request for setting change may include selecting a list of parameter control elements (e.g., included in a separate screen provided on a touchscreen display).

If the AMD determines that the requested setting change is not protected by a passcode, it may permit access to one or more parameter control elements associated with the requested setting change 3112. In some examples, once the changes are received via parameter control elements 3114, the user may need to provide a second gesture on the user interface (e.g., touchscreen display) to confirm the changes made. In response to receiving the second gesture 3116, the AMD may change one or more settings 3118 according to the requested and confirmed changes.

If the AMD determines that the requested setting change is protected by a passcode, it may request a passcode 3120 via a passcode display (e.g., provided on a touchscreen display). In some examples, the request for the passcode may be presented on a display but the passcode may be received via a physical keypad. Once a passcode is received 3122 from the user or subject, the AMD may validate the passcode 3124 by comparing it with one or more user generated passcodes or an override passcode. If it is determined that the passcode matches with a user generated passcode or an override passcode, the AMD may activate 3126 one or more parameter control elements associated with the requested setting change. Subsequently, the AMD may receive a setting change via the selected control parameter element 3128. In some examples, the user may need to provide a second gesture on the user interface (e.g., touchscreen display) to confirm the changes made. In response to receiving the second gesture 3130, the AMD may change one or more settings according to the requested and confirmed changes 3132.

AMD with Alarm System

In some cases, a condition may occur that impacts the operation of the ambulatory medicament device. This condition may be associated with the ability of the ambulatory medicament device to operate as intended by the manufacturer, a subject receiving therapy from the ambulatory medicament device, and/or user (e.g., healthcare provider, parent, or guardian of the subject). In some cases, the ambulatory medicament device may be operating as intended, but the condition of the subject may not satisfy a desired level of health. In either case, it is generally desirable to generate an alarm to inform the subject and/or one or more users of the condition of the ambulatory medicament device and/or the subject. Moreover, it is desirable to track the alarm until the condition that caused the alarm is resolved. Further, it is desirable to issue different types of alarms for different conditions to enable a subject or user to easily distinguish the severity of the condition that triggered the alarm. The user may be a subject receiving medicament or therapy, or may be another user, such as a clinician or healthcare provider, or a parent or guardian.

This section of the disclosure relates to an ambulatory medicament device, such as an insulin pump or a combined insulin and counter-regulatory agent (e.g., Glucagon) pump, configured to generate a dose control signal configured to cause a medicament pump to infuse medicament into a subject. Moreover, the present disclosure relates to an ambulatory medicament device configured to detect a condition of the ambulatory medicament device and/or the subject, and to generate an alarm when it is determined that the detected condition satisfies an alarm condition.

As mention above, an ambulatory medicament device may include an alarm system configured to monitor the ambulatory medicament device and/or the subject, and to generate an alarm when it is determined that a condition has been detected that satisfies an alarm condition. In some examples, the alarm system that may organize a list of alarms, notifying a user of these alarms, and allowing the user to acknowledge alarms.

In some embodiments, the alarm system may comprise a plurality of sensors that monitor the AMD or the subject, a monitoring system interface that receives the data from sensors, and alarm generation module that process the received data and generate alarms if an alarm condition is met. In some examples, the monitoring system interface and the alarm generation module are implemented using one or more hardware processors and machine readable. In some examples, the monitoring system interface and the alarm generation module are separate hard ware modules.

Figure 32:
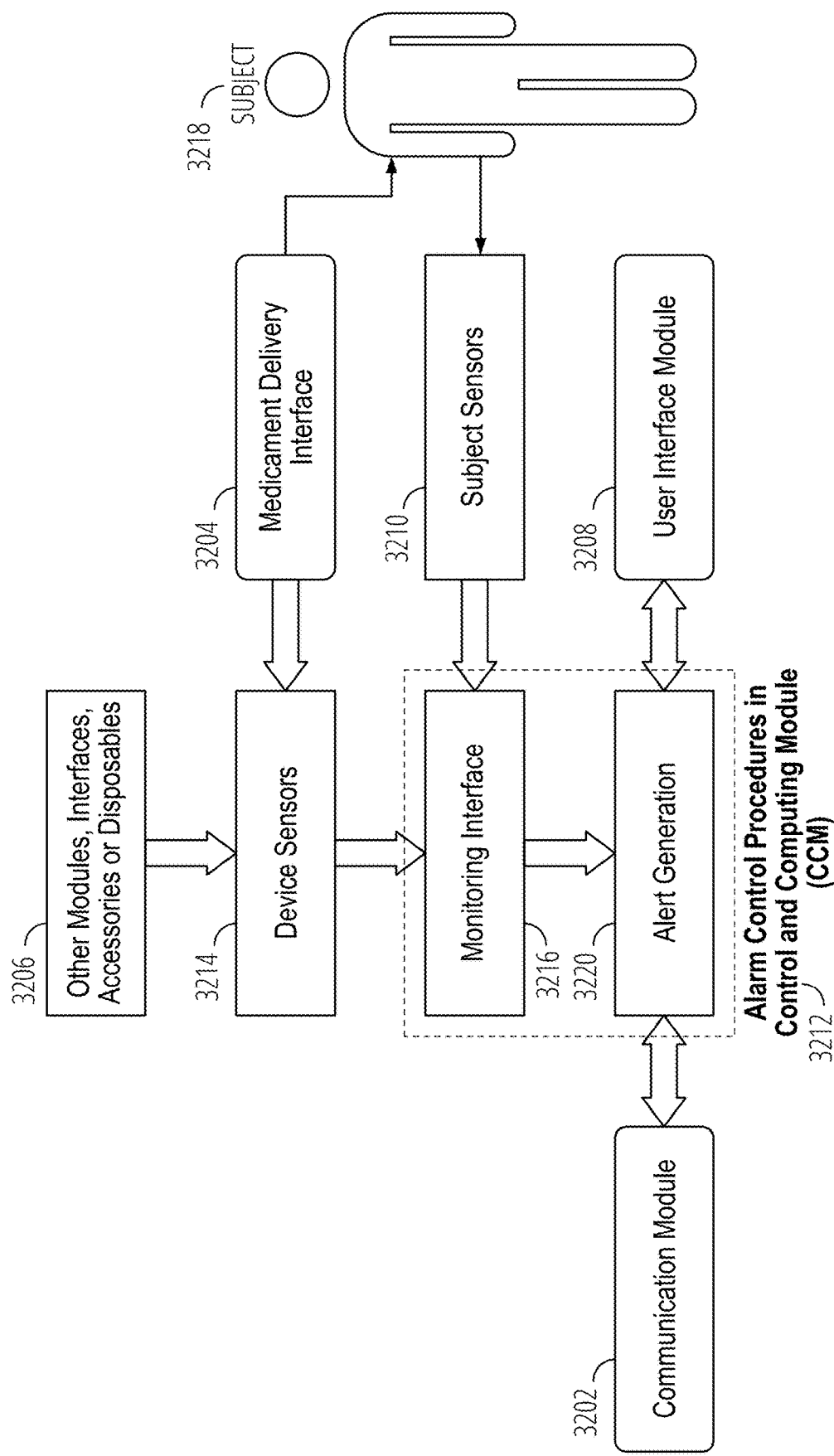
FIG. 32 is a schematic diagram illustrating the interconnection among modules and procedures in AMD involved in monitoring the status of the AMD and/or the subject and generate alarms when an alarm condition is met.

With reference to FIG. 32, in some embodiments, an alarm control procedure 3212 implements alarm control procedures in the control and computing module 610 (CCM) of the AMD. The alarm control procedure 3212 can be implemented as instructions stored in a memory of the CCM (e.g., the main memory 616) and executed by a hardware processor 614 to generate an alarm upon detection of a condition of the ambulatory medicament device and/or the subject. In some cases, the hardware processor of the monitoring system is a hardware processor of the ambulatory medicament device that controls medicament delivery. In other cases, the hardware processor of the monitoring system may be a separate hardware processor.

In some examples, the alarm control procedure 3212 includes a monitoring interface 3216 and an alert generation 3220 system. The monitoring interface 3216 monitors the condition or status of the AMD and/or the subject at least partially based on signals or status values received form a set of device sensors 3214 and a set of subject sensors 3210. In some examples, the device sensors may be configured to track the status of the components or the elements of the ambulatory medicament device, and the subject sensors can be configured to obtain measurements of one or more physiological characteristics of the subject In some examples, a device sensor 3214 is a sensor that generates a signal or status value associated with the condition of modules, interfaces, accessories, other modules, interfaces, accessories, or disposables 3206 of the AMD. In some examples, a device sensor 3214 may generate a signal that corresponds to a parameter associated with a component in a module or interface. For example, one device sensor may record the voltage of a battery and another device sensor may record the follow rate of a pump the medicament delivery interface 3204.

In some examples, a subject sensor 3210 may be any sensor that generates a signal or status value associated with one or more physiological indicators (or parameters) of a subject (e.g., heart rate, blood pressure, body temperature, level of blood glucose, serum levels of various hormones or other analytes). In some cases, the monitoring interface 3216 may continuously receive and analyze signals from device sensors 3214 and subject sensors 3210 to determine the condition of the ambulatory medicament device, the subject 3218, a sensor, and/or other accessories.

In some cases, a single sensor may be used to monitor both the condition of the subject and the ambulatory medicament device or accessories, and sensors connected to AMD. For example, a continuous glucose monitoring CGM sensor may be used to monitor the condition of the subject, and may also be monitored to determine whether the condition of the CGM satisfies an alarm condition (e.g., to alarm a user that the CGM should be replaced).

Although described as sensors of the ambulatory medicament device, one or more of the sensors may be accessories that may or may not be part of the ambulatory medicament device, but that may communicate with the ambulatory medicament device.

In some examples, alarm control procedure 3212 implements procedures for allowing a user or the subject 3218 to change the alarm settings and/or acknowledging an alarm annunciation via the user interface module 3208. In some examples, the subject 3218 or the user may be able to see one or more alarms annunciated on a user interface (e.g., as a list of alarms), even if the AMD is in locked state. In these examples, the user may not be able to acknowledge or respond to alarm when the AMD is in locked state.

In some such examples, a subject 3218 or the subject may get access to an alarm setting screen or acknowledge an alarm annunciation by providing a wake signal and a first gesture (e.g., on a touchscreen display). In some cases, the first gesture may be created by entering predetermined characters on the alphanumeric pad. In some such examples, the alarm control procedure 3212 distinguishes inadvertent alarm control inputs from intentional alarm control inputs. An inadvertent alarm control input is an alarm acknowledgment input that was made without the intent of the subject 3218 to acknowledge the alarm that the AMD 600 is delivering to the subject 3218.

In some examples, the alarm control procedure 3212 implements processes for determination and categorization of an alarm condition based on its severity level (e.g., a severity level between 0 and 5), according to the information received through the monitoring interface 3216.

In some examples, the alarm control procedure 3212 implements procedures for controlling the annunciation of alarm conditions via the user interface module 3208, at least partially, based on their severity level. In some such examples, a user interface (e.g., a touchscreen display) may be configured to allow the subject 3218 to navigate directly to the issue or fault for which an alarm is being delivered. This capability provides the subject 3218 with access to address the fault causing the alarm so that it could be corrected thereby stopping the alarm.

Alarm Conditions

In some examples, monitoring interface 3216 may provide the status information received from the device sensor 3214 and/or subject sensors 3210 to the alert generation 3220 system. In some examples, the status information may comprise one or more status values. In some such examples, the alert generation 3220 system is configured to determine based at least in part on the status information received from the subject monitoring interface 3216, whether an alarm condition is satisfied.

Determining whether the alarm condition is satisfied may include comparing one or more status values associated with the ambulatory medicament device and/or the subject to one or more alarm thresholds or alarm conditions. In some cases, each alarm threshold or alarm condition may be associated with an alarm profile. In some such cases, determining whether the alarm condition is satisfied may include comparing the status information to one or more alarm thresholds or alarm conditions included in one or more alarm profiles. In some examples, the alarm profile may be stored in the storage 618 of the control and computing module 610. In some such examples, at least some of the alarm profiles may be provided to the CCM by an authorized user or the subject via a user interface or directly transferred from another device to the storage (e.g., from USB drive, a laptop, smart phone, PC, and the like). In some examples, at least some of the alarm profiles may be stored in the storage 618 at the time of manufacture, Each of the alarm profiles may indicate the characteristics or status of the ambulatory medicament device and/or subject that triggers an alarm corresponding to the alarm profile. For example, at least some alarm profiles may indicate the threshold status values below of above which an alarm should be triggered. For example, one alarm profile may indicate that when a glucose level of the subject exceeds a particular threshold, a particular alarm is to be generated and/or annunciated. As another example, an alarm profile may indicate that when an available amount of medicament is below a particular threshold, a particular alarm is to be generated and/or annunciated. The type of alarm and/or the alarm frequency or intensity associated with the medicament level may differ from the alarm triggered based on the glucose level. Although the previous examples, described a single condition associated with a single alarm profile, it should be understood that multiple conditions may be associated with an alarm profile. For example, a glucose level that exceeds an upper threshold or is below a lower threshold may be associated with different alarm profiles or the same alarm profile. As another example, a glucose level that is above an upper threshold or a medicament pump that is unable to supply insulin may be associated with the same alarm profile. On the other hand, a medicament pump that is unable to supply insulin due to an empty insulin cartridge may be associated with a different alarm profile than if the medicament pump is unable to supply insulin due to damage to the medicament pump.

Some non-limiting examples of conditions of the ambulatory medicament device or of the subject that may be associated with an alarm profile include conditions relating to a battery capacity (e.g., below a threshold charge capacity or below a capacity associated with a particular amount of operating time (e.g., one day)), a battery condition (e.g., high temperature or low voltage), a medicament or drug delivery condition (e.g., medicament is empty or below a threshold, motor is stalled, catheter is occluded, etc.), subject sensor condition (e.g., blood glucose sensor is expiring, or signal was not received from sensor), calibration failure, high or low glucose levels, network (e.g., Bluetooth® or BN-LTE) communication errors, haptic interface errors (e.g., motor non-responsive), speaker errors (e.g., noise or low volume), medicament cartridge errors (e.g., empty cartridge, cartridge detection error, etc.), and the like. As explained below, each of these errors or conditions may be associated with different severity levels that cause the annunciation of different alarms.

In some cases, each alarm profile may be associated with a severity level of the alarm. The severity level may be associated with how urgently the condition that triggered the alarm should be addressed or resolved. Further, the severity level may be associated with an amount of harm that may be caused to a subject if the condition that triggered the alarm is not resolved or is not resolved within a particular time period. The number of severity levels may vary based on the type of ambulatory medicament device. Generally, there is no limit to the number of severity levels. However, there may be a point of diminishing returns as the number of severity levels exceeds a particular number because, for example, it may be difficult for a user to distinguish between the different numbers of severity levels or to identify with which severity level a particular alarm is associated. Thus, the number of severity levels may be limited to a particular number, such as 3, 5, 6, 9, or some number in between. However, it is possible for there to be more than 9 severity levels.

There may be multiple alarm profiles associated with the severity level. Or each condition of the ambulatory medicament device and/or subject that is associated with the same severity level may be associated with the same alarm profile.

The ambulatory medicament device may determine a severity of an alarm condition based on the condition of the ambulatory medicament device and/or the subject that triggered the alarm condition. In some cases, the ambulatory medicament device may determine the severity of the alarm condition based at least in part on an alarm profile associated with the alarm condition.

Generally, if the alarm condition does not prevent the ambulatory medicament device from providing therapy, the ambulatory medicament device may continue to provide therapy. However, if the alarm condition interferes with the delivery of therapy, operation of the ambulatory medicament device may be suspended or partially suspended. Generally, alarm conditions that interfere with the provisioning of therapy may be associated with a higher severity level. However, some alarm conditions that interfere with the provisioning of therapy may be associated with lower severity levels. For example, a determination that the ambulatory medicament device cannot supply insulin may normally be associated with a highest severity alarm. But if a user indicates that the site location is currently in process of being changed, the alarm condition may be associated with a lower severity level (e.g., an informational alarm reminding the user that insulin cannot be delivered during site change).

Alarm Annunciation

The alert generation 3220 system can implement an annunciation pattern selected based at least in part on the status information generated by and received from the monitoring interface 3216, whether an alarm condition is satisfied. Determining whether the alarm condition is satisfied may include comparing one or more status values associated with the ambulatory medicament device and/or the subject to one or more alarm thresholds or alarm conditions associated with an alarm profile.

Upon verifying that an alarm condition associate with an alarm profile is satisfied, the alert generation 3220 system annunciates the alarm condition.

In some examples, the alarm system may generate a list of pending alarm conditions and store it in a memory of the AMD (e.g., storage 618 in control and computing module 610). In these examples, any time an alarm condition associated with an alarm profile is satisfied, the alarm system may update the list of pending alarm condition by adding the new alarm condition to the list of pending alarm conditions.

In some examples, the list of pending alarm conditions may be sorted according to the severity level associated with the alarm conditions.

In some examples, the alarm system may annunciate the alarm conditions via the user interface module 3208 of the AMD 600. For example, the alarm condition may be annunciated via one or more user interfaces (e.g., a display, a speaker, and the like). In some such examples, an alarm may comprise an audio alarm, a text message, a graphical message, a text or graphical message with audio, vibrations, flashing light and any combination of these.

In some examples, the alarm conditions may be transmitted to other devices, via the communication module 3202 of the AMD where, for example, an authorized user or the subject 3218 (e.g., guardians or parents of the subject), the subject or an emergency provider can view the alarm condition. In yet other examples, the alert generation 3220 system, may establish a direct end-to-end connection with a computing system (e.g., a cloud computing system) using the communication module 3202 and send the alarm condition to the computing system through the end-to-end connection.

Based on the severity of the alarm condition and/or the alarm profile corresponding to the alarm condition, an alarm may be generated and/or annunciated that is associated with the severity of the alarm condition and/or the type of alarm condition. Different alarm conditions and/or alarm profiles may result in different types of alarms or different annunciations of the alarm. For example, an alarm associated with the highest severity level may include an audible alarm with a loudness that exceeds a particular decibel level (e.g., above 70 or 80 decibels), a visible alarm (e.g., a flashing or steady light) with a luminance above a particular luminance value (e.g., a luminance between $10^5$ or $10^6$ candelas per square meter), and/or a vibrational alarm. Further, the alarm associated with the highest severity level may not be snoozed or dismissed. Alternatively, the alarm associated with the highest severity level may be snoozed for a shorter time period than alarms of lower severity levels (e.g., for 5 minutes, for 10 minutes, etc.). An alarm associated with a different severity level than the highest severity level may include a different combination of audible, visible, and vibrational alarms. Not only may the existence of audible, visible, and vibrational alarms differ for different severity levels, but so may the characteristics of each of the alarm types. For example, audible alarms may have different sound patterns, loudness, frequencies, etc. Visible alarm may be of different intensity, color, pattern, etc. Vibrational alarms may be of different pattern, intensity, etc. Further, an alarm with a different severity level than the highest severity level may be permitted to be snoozed or dismissed or snoozed for a longer period of time. In some examples, the severity of the alarm condition may determine the type of type of the alarm generated (e.g., audio, text, graphical, or any combination of these).

Further, the display of alarm conditions on the user interface may include an icon for each type of alarm condition. The user interface may display the number of alarm conditions and/or the number of alarm conditions of a particular type or severity level. In some cases, a duplicate alarm may be omitted from the list of alarms. In other cases, a count of the occurrence of alarms may be increased to reflect the duplicate alarm. In some cases, a duplicate alarm may result in the annunciation of the duplicate alarm. In other cases, the duplicate alarm is ignored. In some cases, the occurrence of a duplicate alarm may cause an escalation of the existing alarm. For example, if an alarm condition that causes an annunciation of an alarm with a first severity level is detected as occurring a second time, the alarm may be annunciated with a second severity level that indicates a greater degree of severity that the first severity level. It should be understood that an alarm occurring after an alarm condition is resolved may not be considered a duplicate alarm, but instead may be a reoccurrence of the alarm condition and/or an indicator that the resolution for the alarm condition failed (e.g., an insulin cartridge replacement is faulty or is empty).

In some cases, the list of alarms may be accessed when the ambulatory medicament device is locked. Further, details about the alarms may be accessible when the ambulatory medicament device is locked.

Each of the alarm conditions, or information associated therewith, may be added to an indicator or user interface (e.g., a list, or other data structure or user interface element) that may be accessed by a user. This user interface may maintain the alarm condition on the user interface until the alarm condition is resolved. Further, the alarm conditions may be sorted or ranked based on the severity level of the alarm condition, the time that the alarm condition occurred, whether the alarm condition relates to the subject or the ambulatory medicament device, any combination of the foregoing, or any other factor for sorting or ranking the alarm conditions.

In some cases wherein the alarm is presented on a display, the displayed information may include details about what caused the alarm, the severity of the alarm, how to respond to or address the alarm, or any other information that may be informative regarding why the alarm was generated and/or how to respond to the alarm. In some cases, the information may provide a workflow or instructions on how to respond to the alarm. The instructions may include a link to a workflow provided by a manufacturer of the ambulatory medicament device or of another entity, such as an entity that provides medicament or site changing kits.

In some cases, different views of an alarm or different information associated with the alarm may be provided based on an identity of the user, or a role of the user, viewing the alarm. For example, a child may be instructed to contact a parent to address an alarm. But a parent may be provided with information to resolve the alarm. The parent may receive simplified information (e.g., glucose level is high)

about what caused the alarm, but a healthcare provider may receive more detailed information regarding the alarm (e.g., internal control parameter values, insulin flow rates, curvature of insulin diminishment predictions, etc.) that facilitates the healthcare provider caring for the subject.

The alarm conditions may be displayed on a display of the ambulatory medicament device. Alternatively, or in addition, the alarm conditions may be displayed on a remote display that is separate from the ambulatory medicament device. The remote display may be a display that is authenticated or associated with a computing device that is authenticated to access data, such as alarm conditions, from the ambulatory medicament device. In some cases, the list of alarms may be presented on a mobile device (e.g., a smartwatch or smartphone) or on a computing device (e.g., a laptop or desktop) that can obtain data directly or indirectly from the ambulatory medicament device.

In some cases, annunciating the alarm may include contacting a manufacturer and/or user (e.g., a healthcare worker, a parent or guardian, or other registered user). Further, the alarm may include instructions on repairing the ambulatory medicament device and/or on addressing the alarm condition. For example, the alarm may provide a user with instructions to replace the insulin cartridge and how to replace the insulin cartridge. As another example, the alarm may provide instructions on how to change the battery of the device or on how to change a site where the insulin pump connects to the subject. In some cases, the alarm may include one or more operations associated with the alarm. For example, the alarm may trigger reordering of insulin or may request that the user confirm a reorder request to reorder insulin.

A user may be able to acknowledge and/or snooze alarms. Certain alarms, such as informational alarms, may be dismissible. However, generally the alarm may remain on the alarm list until the condition that caused the alarm is resolved.

Resolving the alarm may include any action that addresses the condition that caused the alarm to be generated. For example, resolving the alarm may include replacing an insulin cartridge, changing a site where the ambulatory medicament device is connected to the subject, charging a battery of the ambulatory medicament device, providing insulin or a counter-regulatory agent to the subject and/or the ambulatory medicament device, or any other action that may be performed to address an alarm condition. In some cases, the resolution action may be acknowledging the alarm. For example, if the alarm is informational (e.g., to inform the user that more insulin has been ordered), acknowledging the alarm may be a sufficient resolution action.

In some cases, whether the alarm condition is resolved may depend on an identity of the user. For example, if a child interacts with an alarm related to reordering of insulin, the alarm may remain until a parent or guardian acknowledges the alarm. However, the child may be able to snooze the alarm. In some cases, a user interface that displays alarms may differ based on who is viewing the alarm. For example, a child may view the alarms, but may not be able to interact with the alarms. However, a parent or guardian may be able to snooze or dismiss an alarm. Further, a child may be instructed to bring the device to a parent or adult to address an alarm. In some cases, the child may be informed of how urgently to contact the parent (e.g., contact a parent immediately, within a day, within a week, etc.). Moreover, a designated adult may separately be alarmed (e.g., via a text or email alarm). The parent or guardian may receive additional information not provided to the child or subject (e.g., a link to repair instructions or a workflow to address the alarm condition).

In some cases, certain conditions may self-resolve over time. For example, a low battery alarm may resolve as the battery is charged. In such cases, the alarm may be cancelled automatically as the battery charge level exceeds a particular threshold. Further, in some cases, one or more alarms and/or the alarm list can be viewed and/or accessed on a home screen, a main screen, or other non-alarm based user interface screen in addition to a user-interface screen designated for display alarms. The alarm list may be accessed from the ambulatory medicament device and/or a computing system in communication with the ambulatory medicament device.

However, in some cases, the alarm condition may or may not be resolvable when the ambulatory medicament device is locked.

A user may interact with the alarms generated based on the alarm condition. In some cases the user can only interact with the alarms when the ambulatory medicament device is unlocked. In other cases, the user can interact with the alarms to snooze them or to obtain further information. However, the user may not be able to dismiss the alarm without unlocking the ambulatory medicament device. Interacting with the alarms may include providing information associated with the alarm to a user in response to the user interacting with the alarm, or an indicator representative of the alarm.

Example AMD with Alarm Management System

Figure 33:
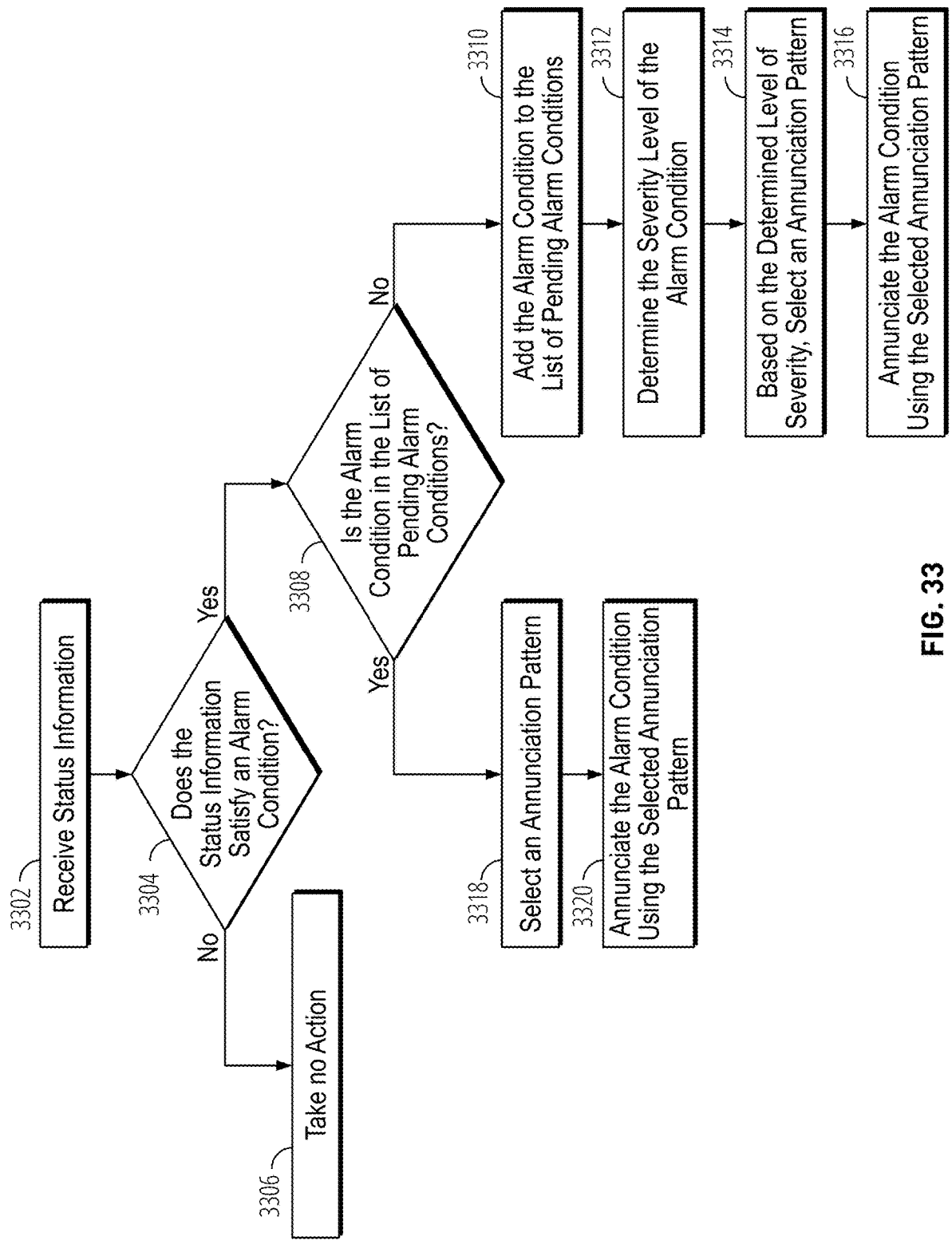
FIG. 33 is a flow diagram illustrating an example procedure that may be used by the alarm system of an AMD to annunciate an alarm condition upon receiving a status information that satisfies an alarm condition.

FIG. 33 shows a flow diagram illustrating an example procedure that may be used by the alarm system of an AMD to annunciate an alarm condition upon receiving a status information that satisfies an alarm condition. In some examples, the alert generation 3220 system implements an annunciation process by execution of instructions by a processor in CCM of the AMD, where the instructions can be stored in the main memory, storage of the AMD, or in a memory of a connected electronic device or computing system.

The alarm system may receive status information 3302 using the monitoring interface 3216, one or more device sensors and/or one or more subject sensors. In some examples, the alert generation 3220 system determines whether the received status information satisfies an alarm condition 3304. In some examples, the alarm condition may be an alarm condition in an alarm profile. If the received status information does not satisfy an alarm condition, no action may be taken 3306. If the received status information satisfies an alarm condition, the alarm system may determine whether the alarm condition is already present in the list of pending alarm conditions or not 3308. If the alarm condition is not present in the list of pending alarm conditions, the alarm system may add the alarm condition to the list of pending alarm conditions 3310. Next the alarm system, may determine the severity of the alarm condition 3312. Based on the determined level of severity, the alert generation 3220 system can select an annunciation pattern 3314 and annunciate the alarm condition using the selected annunciation pattern 3316. If the alarm condition is present in the list of pending alarm conditions, the alarm system may select an annunciation pattern 3318 and annunciate the alarm condition using the selected annunciation pattern 3320. In some examples, the annunciation pattern selected at block 3318, may be an annunciation pattern that is different than the previously used annunciation patterns for the alarm condition. In some such examples, the annunciation pattern selected at block 3318, may be selected based on number of times that the same alarm condition is satisfied by a received status information. The process of the alarm detection and control function may repeat each processing cycle so long as the ambulatory medical device is in use. In some examples, after an alarm is annunciated, the alarm system may wait for user acknowledgment of the alarm. If the user acknowledges the alarm, the system proceeds to perform alarm processing. However, if the user fails to acknowledge the alarm, the annunciation continues and may escalate depending on the level of the alarm.

As mentioned above, the alarm conditions may be categorized based and annunciated based on their severity level. In some examples, the alarms are categorized numerically in descending order with the highest priority fault displayed at the top of the list.

In some examples, a level 0 severity, may be for a trivial fault that does not require any action by the user thus not warranting an alarm notification. In some examples, a level 1 severity may be an informational type of notification that repeats at a certain frequency (e.g. every 30 minutes) until acknowledged by user which results in it being reset. The annunciation may include a brief vibration and a beep, for example. In some examples, a level 2 severity, may be one relating to an imminent loss of system function. Thus, such an annunciation may include two brief vibrations and two beeps, for example, and repeating at a certain frequency (e.g. every 30 minutes). Thus, the user would still need to address the situation creating the fault to completely stop the annunciation. In some examples, a level 3 fault may be for when the system is no longer fully functional thus requiring user intervention to correct the issue. The annunciation may begin with a base level intensity with three brief vibrations and three audio beeps, for example, and repeating at a certain frequency (e.g., every 5 minutes). The annunciation escalates at a second frequency, e.g. every 30 minutes, up to a maximum intensity level. The escalation may be a change in vibration intensity and/or audio level, for example. The escalation may be cleared to base level when the user acknowledges the fault; however, the base alarm remains if underlying condition persists. Thus, the user would still need to address the situation creating the fault to completely stop the annunciation. In some examples, a level 4 severity, may be for when the system is no longer functional and not correctable by the user. The annunciation may begin with a base level intensity with three audio beeps, for example, and repeating at a certain frequency (e.g. every 5 minutes). The annunciation escalates at a second frequency, e.g. every 30 minutes, up to a maximum intensity level. The escalation may be a change in audio level, for example. The escalation may be cleared when the user acknowledges the fault; however, the base alarm remains because the underlying condition persists. In some examples, a level 5 severity, may be for high priority alarms per IEC 60601-1-8. The annunciation when activated may be cleared only when the underlying issue is resolved, e.g., glucose level is raised.

Additional embodiments relating to determining a severity of an alarm condition and annunciating the alarm based at least in part on the severity of the alarm condition that can be combined with one or more embodiments of the present disclosure are described in U.S. Provisional Application No. 62/911,017, which was filed on Oct. 4, 2019 and is titled "ALARM SYSTEM AND METHOD IN A DRUG INFUSION DEVICE," the disclosure of which is hereby incorporated by reference in its entirety herein for all purposes.

Non-Critical AMD Condition Management

In some cases, a condition may occur that impacts the operation of the ambulatory medicament device. This condition may be associated with the ability of the ambulatory medicament device to operate as intended by the manufacturer, a subject receiving therapy from the ambulatory medicament device, and/or user (e.g., healthcare provider, parent, or guardian of the subject). In some cases, the condition or malfunction of the ambulatory medical device may prevent the ambulatory medical device from providing therapy to the subject. In other cases, the condition or malfunction may permit, at least for a period of time, the ambulatory medical device to continue providing at least partial therapy to the subject. In either case, it is generally desirable to generate an alert to inform the subject and/or one or more users of the condition of the ambulatory medical device and/or the subject. Moreover, it is desirable to track the alert until the condition that caused the alert is resolved. Further, it is desirable to issue different types of alerts for different conditions to enable a subject or user to easily distinguish the severity of the condition that triggered the alert.

In many cases, if the nature of the alert is non-critical, it may be safer to continue the underlying therapy and notify the user of the condition than to cease therapy. In some such cases, the best response to a problem with the device for a subject is to notify the device manufacturer, or other user that can address the problem, while the subject continues to receive therapy until a replacement device can be obtained or a repair can be made.

Additionally, alert fatigue can be an issue with medical devices due to excessive alerts which do not necessarily require user interaction. Alert fatigue can be dangerous because it can lead users to ignore serious alerts or alerts that require action in the short term.

The method described herein may be performed by an AMD (e.g., by one or more processor of the AMD) to detect device malfunctions for the AMD and that can generate alerts corresponding to the ambulatory medical device and prioritize the alerts to enable the subject or user to quickly and easily determine whether the device malfunction will impact therapy, should be addressed in the short-term (e.g., immediately, in 1-2 hours, within the day, etc.), and/or can be addressed at the subject's convenience (e.g., within a month, or more). In some cases, the method may be used by other systems.

In certain embodiments, the system disclosed herein can detect a condition in which the ambulatory medical device does not meet a manufacturer's specification (e.g. a failure of a haptic annunciator, a Bluetooth® radio malfunction, glucagon or insulin runs out, there is a medicament delivery malfunction, a touchscreen failure, etc.). In some cases, there can be several tiers of critical and/or non-critical faults. If it is determined that the underlying condition is not sufficient to stop therapy (e.g., delivery of insulin is not stopped), the fault may be deemed non-critical. In some cases, the fault may not be a fault of the device, but may be indicative of required maintenance (e.g., recharge battery indicator, order more medicament indicator, etc.). The condition may be annunciated to the user with appropriate instructions (e.g., call manufacturer for replacement medicament or parts) for addressing the fault or issue.

After the annunciation is acknowledged, the alert may be re-annunciated as a reminder at some later period in time (e.g. the alert may be re-annunciated daily at 4:00 PM or on Saturdays at noon). The length of time between annunciations may depend on the severity of the fault. In some cases, the re-annunciation cannot be stopped by the user, but may only cease if the underlying condition is resolved.

The method may include detecting a condition of the ambulatory medical device. The condition of the ambulatory medical device may be determined by one or more sensors of the ambulatory medical device. Further, the condition of the ambulatory medical device may be determined by the presence or absence of one or more errors when performing one or more functions of the ambulatory medical device. For example, if the ambulatory medical device fails to establish a communication connection with a control system or a data storage system, it may be determined that there is a possible malfunction with the ambulatory medical device. As another example, if the ambulatory medical device fails to deliver medicament or detects an error when attempting to deliver medicament, there may be a malfunction with the medicament pump. In some cases, the condition of the ambulatory medical device may be determined based on one or more configuration values being outside a normal operating range. For example, if the speed of delivery of medicament is faster or slower than a configured operating range, then it may be determined that there is a malfunction with the medicament pump or a connection with a medicament delivery tube (e.g., a catheter).

The method may include comparing the detected condition of the ambulatory medical device to a set of normal operating parameters. The set of normal operating parameters may be the specifications set by the manufacturer for when the ambulatory medical device is operating as intended by the manufacturer. In some cases, the normal operating parameters may be associated with a range of values. For example, the operating parameter for a speed of medicament delivery may be associated with a range of speeds, which may vary based on user settings, medicament type, site location of medicament delivery, or manufacturing tolerances, among other parameters. Comparing the detected condition of the ambulatory medical device to the set of normal operating parameters may include comparing each operating parameter in the specification to a corresponding detected operating parameter of the ambulatory medical device. The ambulatory medical device may generate a user alert based on the determined condition of the ambulatory medical device. For example, the AMD may generate an alert when the detected condition of the ambulatory medical device does not satisfy a set of normal operating parameters.

The method may further include determining whether the detected condition satisfies a minimum set of operating parameters. In some cases, the minimum set of operating parameters may match the normal operating parameters. However, typically the minimum set of operating parameters differ from the normal operating parameters. The minimum operating parameters may include the minimum specifications, minimum parameters, or minimum condition required by the ambulatory medical device to maintain or continue providing therapy to the subject. In other words, the minimum operating parameters are the operating parameters sufficient to provide therapy. However, the minimum operating parameters may not be sufficient to enable all features of the ambulatory medical device. For example, the minimum operating parameters may permit the ambulatory medical device to deliver insulin to the subject, but may not be sufficient to deliver the insulin at a normal delivery speed for the particular ambulatory medical device. As another example, the minimum operating parameters may permit the delivery of therapy, but may not be sufficient to track a log of therapy or to transmit a therapy log to another computing system. In some cases the normal operating parameters and/or minimum operating parameters may be specified by a subject or healthcare provider (e.g., the minimum amount of medicament that is to be provided in each bolus may be specified by a healthcare provider). In some cases, the normal or minimum operating parameters may be modified.

When it is determined that the condition of the ambulatory medical device satisfies at least the minimum operating parameters, the ambulatory medical device may be configured to maintain delivery of therapy to the subject. Maintaining delivery of therapy may include maintaining therapy at the same rate, at a reduced rate (e.g., providing only basal therapy and therapy responsive to a meal announcement), or at a minimum maintenance rate (e.g., providing only basal insulin). Advantageously, the ability of the ambulatory medical device to distinguish between a minimum set of operating parameters and a normal set of operating parameters enables an ambulatory medical device with a malfunction to continue providing therapy, which sometimes includes life-saving treatment, to a subject until the ambulatory medical device can be repaired or until the condition of the device worsens to a point where the minimum operating parameters cannot be maintained. In some cases, the ambulatory medical device may temporarily maintain delivery of therapy. Temporarily maintaining therapy may provide a subject time to address the issue that caused the ambulatory medical device to not satisfy the normal operating parameters before the subject loses access to therapy. In some cases, the ambulatory medical device temporarily maintains therapy until the device condition makes it no longer possible to maintain therapy.

Figure 34:
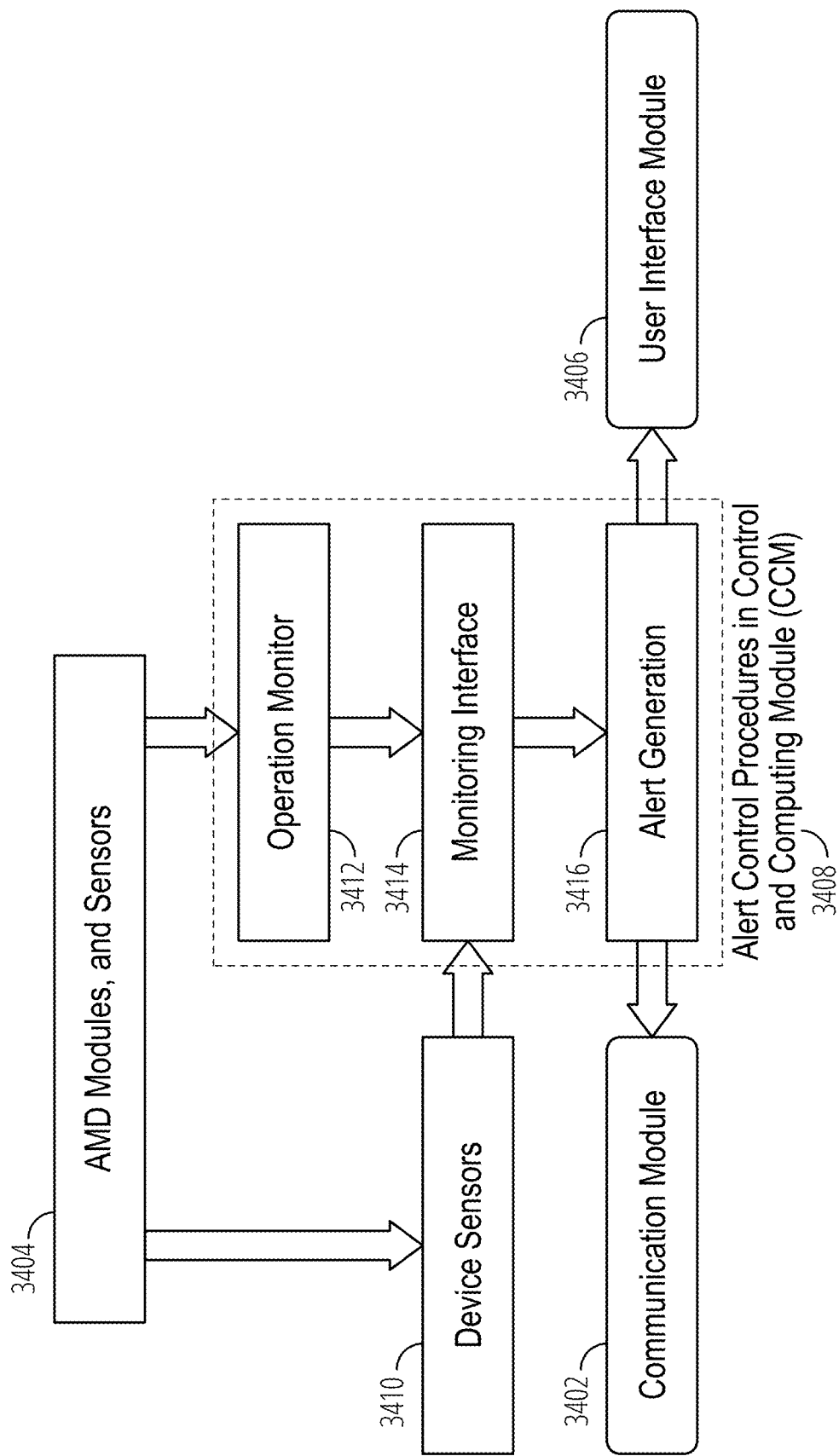
FIG. 34 is a block diagram illustrating the interconnection among modules and procedures in AMD involved in monitoring the condition of the AMD and generating alerts when a device malfunction is detected.

FIG. 34 is a block diagram illustrating the interconnection among modules and procedures in AMD involved in monitoring the condition of the AMD and generating an alert when a device malfunction is detected. In some examples, the condition of AMD may include the status of the modules and components of the AMD, such as AMD modules and sensors 3404 and/or operation of modules and procedures of the AMD. In some embodiments, the alert system may be implemented as a set of alert control procedures 3408 in the control and computing module 610 (CCM) of the AMD. The alert control procedures 3408, may be implemented as instructions stored in a memory of CCM (e.g., the main memory 616) and executed by a hardware processor 614 to generate an alert upon detection of a malfunction of the ambulatory medicament device. In some cases, the hardware processor may be a hardware processor of the ambulatory medicament device that controls medicament delivery. In other cases, the hardware processor of the monitoring system may be a separate hardware processor.

In some examples, the alert control procedures 3408 may include a monitoring interface 3414, an operation monitoring procedure 3412 and alert generation procedure 3416. The monitoring interface 3414 may monitor and evaluate the condition of the AMD and/or the subject at least partially based on the information received from the operation monitoring procedure 3412 and device sensors 3410. In some examples, the device sensors may be configured to track the status of the components or the modules of the ambulatory medicament device and the operation monitoring procedure 3412 may be configured to monitor the operation of the modules and other procedures. In some examples, the detected of the AMD may be provided to the alert generation procedure monitoring interface. The alert generation procedure 3416 may compare the detected condition of the AMD with a set of normal operating parameter. In some examples, the alert generation procedure may also determine whether the detected condition of the AMD satisfies a minimum set of operating parameters. In some examples, if it is determined that the detection condition of the AMD does not satisfy the normal operating parameters, the alert generation procedure may generate an alert. In some examples, the alert may be transmitted to the user interface module 3406 and displayed on a display of the AMD (e.g., a touchscreen display). In some examples, once an alert is generated the AMD may establish a connection (e.g., a wireless connection) with another device. This other device may include a local device (e.g., a laptop, smartphone, or smartwatch of the user) or a computing system of a cloud-based service. In some such examples, the alert may be transmitted by the communication module 3402 to the computing systems where it may be displayed on user interface associated with the computing system. In some cases, the additional device may receive data from the ambulatory medical device enabling it to monitor the condition of the ambulatory medical device.

The type of the alert, and the frequency at which the alert is repeated, or whether an alert is dismissible or not, may be determined by the alert generation procedure based on the detected condition of the AMD and the alert information stored in a memory of the AMD. In some examples, the alert information may be provided by the subject, an authorized user, or a healthcare provider. In some examples, the alert information may be stored in the AMD at time of manufacturing.

In some examples, upon determination that the detected AMD condition does not satisfy a set of normal operating parameters, the alert generation procedure may cause the medicament delivery interface, such as the therapy delivery module 606, to stop therapy delivery or modify one or more delivery parameters (e.g., therapy delivery rate). In some examples, upon determination that the detected AMD condition does not satisfy a set of normal operating parameters, but satisfies a set of minimum operating parameters, the therapy delivery may be maintained at a normal rate.

The alert may include any type of alert. For example, the alert may be a visual alert (e.g., a light or changing light), an audible alert (e.g., a beep or series of beeps), a haptic or vibration alert, an email alert, a text alert, or any other type of alert. Different device conditions may be associated with or may trigger different alerts. Thus, the user alert may enable the user to determine the device condition of the ambulatory medical device based on the alert. For example, an indication that the ambulatory medical device failed to deliver a medicament may trigger one type of alert while an indication that the ambulatory medical device has below a particular level of medicament available may trigger a different alert. In some cases, the user alert is dismissible and/or may be snoozed by the user. In other cases, such as when the ambulatory medical device fails to satisfy a set of minimum operating parameters, the user alert may not be dismissible or cannot be snoozed.

A dismissible alert may be scheduled to repeat on a particular schedule until an alert modification condition occurs. The frequency with which the dismissible alert repeats may depend on the severity of the condition or the particular operating parameters that do not satisfy normal or minimum operating parameters. More urgent device conditions may result in alerts that repeat more frequently. Further, alerts may vary based on when the condition was detected, the time of day, or the detected activity of a subject (e.g., sleep, abnormal activity, or elevated activity, such as exercise). Similarly, the snooze options may vary for different alerts or any of the aforementioned conditions. In some cases, the ambulatory medical device may escalate an alert if it detects that the condition of the ambulatory medical device has become more critical.

The alert frequency may be for a static time period (e.g., every 5 hours) or may ramp towards more frequency (e.g., every 5 hours for 1 to 3 reminders, every 4 hours for 3 to 6 reminders, etc.), or may change based on time of day (e.g., snooze alerts during sleeping hours for non-urgent alerts), etc.

The alert modification condition may include any action that causes the operating parameters of the ambulatory medical device to return to normal operating parameters. For example, the alert modification condition may be a repair or replacement of a faulty component. In some cases, the alert modification condition may comprises an acknowledgement of the alert. In other cases, the alert modification condition may include a worsening of the ambulatory medical device condition. In such cases, the modification to the alert may include the substitution of the alert to a different alert that indicates a different or more serious condition of the ambulatory medical device. For example, an urgent condition may become critical if the detected malfunction is addressed after generating certain number of alerts. When an urgent condition becomes critical, it may trigger a different alert type (e.g., a louder sound, or brighter image) and/or escalation in the alert frequency. For example, the audible alert may become louder and may be combined with a vibration alert from a haptic annunciator. Moreover, if the condition reaches a critical state, the ambulatory medical device may cease providing therapy to the subject.

In some cases, generating the alert may further include contacting a manufacturer and/or healthcare provider (e.g., clinician). Further, generating the alert may include ordering replacement parts. In some cases, the alert may instruct a subject or user on how to repair the ambulatory medical device.

Once the malfunction is addressed, the ambulatory medical device is repaired, or the condition that caused the alert is resolved, a user may permanently (or until the next time a device condition triggers the alert) dismiss the alert. Alternatively, or in addition, the ambulatory medical device may automatically dismiss the alert if it senses that the device condition that caused the alert has been resolved. In some cases, the ambulatory medical device may periodically recheck the device condition to determine whether the alert condition has been resolved.

In some cases, the manufacturer or healthcare provider may remotely clear or stop an alert using, for example, an NB-LTE connection. In some cases, only the manufacturer and/or healthcare provider can clear or stop the alert. Further, in some cases, a manufacturer and/or a healthcare provider may notify a user (e.g., a subject, or parent or guardian) of an issue or impending issue with the ambulatory medical device. The notification may be received by the ambulatory medical device via the NB-LTE connection. Alternatively, or in addition, the notification may be received via a computing device, such as a smartphone or laptop.

Figure 35:
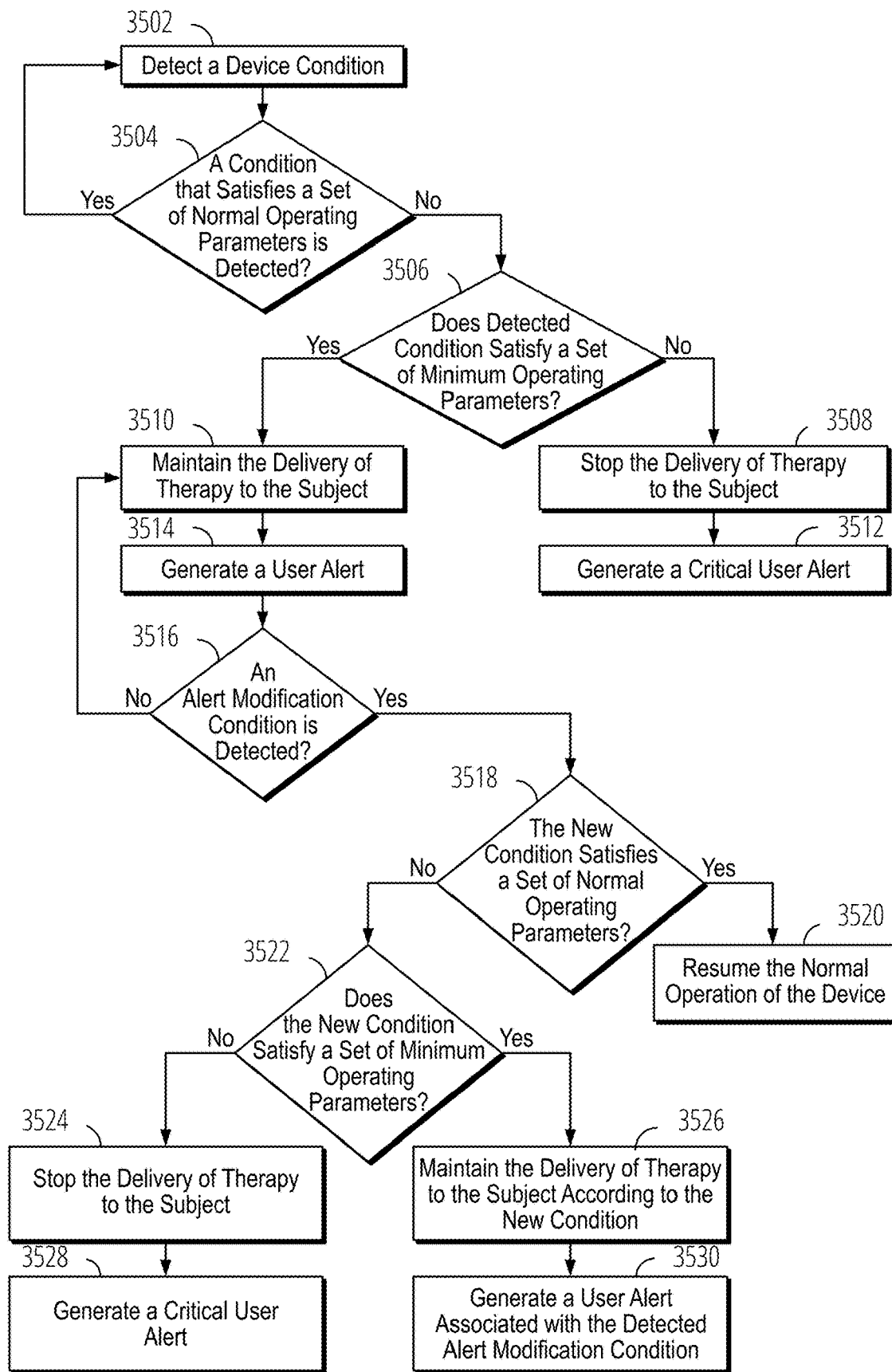
FIG. 35 is a flow diagram illustrating an example procedure that may be used by the alert system of an AMD to monitor the operation of an AMD and generate alerts when a device malfunction is detected.

FIG. 35 is a flow diagram illustrating an example procedure that may be used by the alert system of an AMD to monitor the operation of an AMD and generate alerts when a device malfunction is detected. In some examples, the alert system continuously monitors the status of all modules and components associated with AMD as well as the operation of all modules and procedures of the AMD. When a device condition is detected 3502, the alert system may determine whether the detected device condition satisfies a set of normal operating parameters 3504. If it is determined that the detected device condition satisfies a set of normal operating parameters, the alert system takes no action and continuous monitoring the AMD. If it is determined that the device condition does not satisfy a set of normal operating parameters, the alert system determines whether the detected device condition satisfies a set of minimum operating parameters. If, at block 3506, it is determined that the device condition does not satisfy a set of minimum operating parameters, the alert system may send a signal to the therapy delivery module to stop delivery of therapy to the subject 3508, and immediately generate a critical user alert 3512 indicating that immediate action is required. In some examples, upon generation of a critical alert the alarm system of the AMD, may contact a healthcare provider or certified user (e.g., parent or guardian of the subject) and also send the critical alert to one or more computing devices (e.g., laptop, cell phone, personal computer, and the like) of the healthcare provider or certified user. If, at block 3506, it is determined that the device condition satisfies a set of minimum operating parameters, the alert system may maintain the delivery of therapy to the subject 3510 and generate a user alert 3514. In some such examples, the alert system may maintain the delivery of the therapy at rate associated with the detected condition of the AMD (e.g., normal rate or minimum maintenance rate) until an alert modification condition is detected 3516. Upon detection of an alert modification condition 3516, the alert system may determine whether the new device condition satisfies a normal set of parameters 3518. If, at block 3518, it is determined that the new device condition satisfies a set of normal operating parameters, the alert system may resume the normal operation of the AMD 3520 (e.g., deliver the therapy at a normal rate). If, at block 3518, it is determined that the new device condition does not satisfy a set of normal operating parameters, the alert system may determine whether the new device condition satisfies a minimum set of parameters 3522. If, at block 3522, it is determined that the new device condition satisfy a set of minimum operating parameters. The alert system may maintain or modify the rate of therapy delivery according to the new device condition 3526 and generate a user alert 3530 according to the according to the new device condition. If, at block 3522, it is determined that the new device condition does not satisfy a set of minimum operating parameters, the alert system may send a signal to the therapy delivery module to stop delivery of therapy to the subject block 3524, and immediately generate a critical user alert 3528 indicating that immediate action is required. In some examples, upon generation of a critical alert the alarm system of the AMD, may contact a healthcare provider or certified user (e.g., parent or guardian of the subject) and also send the critical alert to one or more computing devices (e.g., laptop, cell phone, personal computer, and the like) of the healthcare provider or certified user.

Managing Doses of Glucose Control Agents

Ambulatory medical devices allow subjects the freedom to treat themselves while being mobile. Self-managed medical treatment comes with inherent risks to the subject.

An automated glucose level control system may automatically provide insulin and/or a counter-regulatory agent (e.g., Glucagon) to a subject to help control the glucose level of the subject. Generally, a control algorithm is implemented by an automated glucose level control system (GLCS) to determine when to deliver one or more glucose control agents and how much agent to provide to the subject. Further, the control algorithm may control both an ongoing or periodic delivery of insulin (e.g., a basal dose), and a correction bolus that may be provided to adjust a subject's glucose level to within a desired range. The control algorithm may use glucose level readings obtained from a sensor, such as a continuous glucose monitoring (CGM) sensor, that obtained automated blood glucose measurements from the subject. Moreover, in some cases, the control algorithm may deliver a bolus of insulin in response to an indication of a meal to be consumed or being consumed by the subject.

Insulin may be administered subcutaneously into blood of a subject. There is often a delay between when the insulin is provided and when the amount of insulin in the subject's blood plasma reaches maximum concentration. This amount of time may vary based on the type of insulin and on the physiology of the particular subject. For example, with a fast-acting insulin, it may take approximately 65 minutes for a bolus of insulin to reach maximum concentration in the blood plasma of the subject. For some other types of insulin, it may take anywhere from 3-5 hours to reach maximum concentration in the blood plasma of the subject. Accordingly, the glucose level control system may implement a predictive algorithm that implements a bi-exponential pharmacokinetic (PK) model that models the accumulation of insulin doses in the blood plasma of the subject. The glucose level control system may modify its predictions based on the type of insulin, one or more glucose level readings, and/or characteristics of the subject.

In some cases, a subject may receive a manual bolus of insulin or medicament. For example, a user (e.g., healthcare provider, parent, or guardian) or subject may inject a dose of insulin into the subject. As another example, the user or subject may manually direct the automated glucose level control system to provide a bolus of insulin to the subject.

It is generally undesirable to have too much insulin. An excess of insulin can lead to Hypoglycemia. As described above, it may take time for insulin to reach maximum concentration in the blood plasma of the subject. Thus, a glucose level reading from a sensor may not immediately, or even after a particular period of time, reflect the amount of insulin within a subject. Thus, a manual bolus of insulin may not be detected by the automated glucose level control system. As a result, if the automated glucose level control system is operating during delivery of a manual bolus or is configured to operate on the subject prior to glucose level readings reflecting the effect of the manual bolus on the subject, the automated glucose level control system may unnecessarily administer additional insulin to the subject potentially leading to hypoglycemia.

The present disclosure relates to an automated glucose level control system configured to provide automatic delivery of glucose control therapy to a subject and receive information about manual glucose control therapy provided to the subject. Using the received information about the manual glucose therapy, the automated glucose level control system can adjust the glucose level control algorithm to account for the manual dosing of insulin (or counter-therapy agents). The manual glucose control therapy may be provided by injection therapy, or it may be provided by an insulin pump.

In some cases, the automated glucose level control system may receive an indication of insulin or medicament to administer to a subject in place of an automatically calculated dose of insulin. For example, the automated glucose level control system may receive an indication that a subject is consuming or will consume a meal. The indication may include a type of meal to be consumed (e.g., breakfast, lunch, or dinner) and an estimate of the quantity of food or carbohydrates to be consumed (e.g., less than usual, a usual amount, more than usual, 30-40 grams of carbohydrates, 45-60 grams of carbohydrates, etc.). Based on the indication, or meal announcement, the automated glucose level control system may calculate an amount of insulin to administer to the subject. The calculation may be based on an insulin to carbohydrate ratio provided by a clinician and/or determined by the automated glucose level control system. Moreover, the calculation may be based at least in part on a history of glucose level measurements for the subject when consuming particular meals.

The calculated amount of insulin for the meal announced by the user may be presented to the user. The user (e.g., the subject) may modify the amount of insulin to administer. For example, the user may determine that for the size meal the subject is consuming or planning to consume, more or less insulin should be administered. In such cases, the user may modify the calculated insulin dosage to match the user's determination of the amount of insulin to administer. In some cases, the automated glucose level control system may modify its control algorithm based on the user's input. Thus, future meal announcements may result in a calculation of insulin that satisfies the subject's insulin needs and/or preferences.

In some cases, the indication of an amount of a manual bolus may be received by a user entering a numerical value (e.g., an amount of insulin, a number of carbohydrates, or another calculation) associated with administering insulin. As described above, the automated glucose level control system may automatically-calculate a meal dose of insulin and present it to a user via a user interface where a user may provide the manual bolus information. At the time of making the meal announcement, the user may have an option to enter the manual bolus. The meal controller of the glucose level control system can provide a recommendation against the manual entry if there is a prior history of online operation or a basis for making the recommendation.

The information may be received from a user via a user interface. This user interface may be provided by the automated glucose level control system. Alternatively, or in addition, the user interface may be generated by another device, such as a laptop or desktop, a smartphone, a smartwatch, or any other computing device that can communicate via wired or wireless communication with the automated glucose level control system. The information may include one or more of: an indication of delivery of a manual bolus (e.g., via injection therapy), an amount of the manual bolus, a type of the insulin (or other medicament), a time when the manual bolus was delivered, a general location that the manual bolus was administered to the subject (e.g., back, stomach, arm, leg, etc.), a reason for the manual bolus (e.g., a meal, a maintenance dose, a glucose level reading, in advance of exercise, etc.), and any other information that may be useable by the glucose level control system in controlling the glucose level of the subject.

Advantageously, in certain embodiments, providing manual dosing information to the automated glucose level control system can help the glucose level control system maintain the glucose level of the subject within a desired range when the automated features of the glucose level control system are active or operational. For example, if the automated glucose level control system determines from a CGM sensor reading that a subject's glucose level is high, the automated glucose level control system might normally administer a bolus of insulin. However, if the automated glucose level control system receives an indication that a manual bolus of insulin was administered recently (e.g., within the past thirty minutes), the automated glucose level control system may reduce or not administer a bolus of insulin, thereby preventing a Hypoglycemic event. In some such cases, the automated glucose level control system may continue monitoring the glucose level of the subject and may administer additional insulin at a later time if the glucose level readings do not reflect an expected glucose level based on the reported manual bolus of insulin.

In some cases, it may be unnecessary to receive an indication of the manual bolus because, for example, a user may cause the automated glucose level control system to provide the manual bolus. In such cases, the automated glucose level control system may track the amount of insulin delivered and the timing of the administering of the bolus. To track the manual bolus, the automated glucose level control system may store the information associated with the manual bolus in a therapy log. Accordingly, when the automated glucose level control system is operating in an automatic mode, the automated glucose level control system can access the therapy log to determine whether any manual bolus was administered and, if so, the timing and amount of the manual bolus.

In some cases, the automated glucose level control system may model the diminishing of insulin, or other medicament, in the blood plasma over time based on the information associated with the manual bolus. Modeling the diminishing of medicament over time may be used to estimate a future effect of the medicament previously administered. In some cases, the model may account for previously administered medicament by the automated glucose level control system. Further, in some cases, the model may account for physiological characteristics of the subject, such as the subject's weight or an input parameter related to the subject's weight (e.g., body mass index). Moreover, the model may account for perfusion over time of the medicament bolus from a subcutaneous infusion site into the blood plasma of the subject. Further, the automated glucose level control system may model an accumulation of insulin, model time course of activity of insulin, or model a finite rate of utilization of insulin.

Based on the model, the automated glucose level control system may adjust the automated administering of insulin, or other medicament when operating in an automatic mode. Further, the automated glucose level control system may operate the administering of medicament (e.g., by controlling a medicament pump) based on a glucose level of the subject and the modeled concentration of medicament in the subject.

In some cases, the automated glucose level control system may confirm that the manual bolus was delivered to the subject. The confirmation may be determined based at least in part on whether glucose level readings by the CGM sensor match or are within a threshold level anticipated by the automated glucose level control system based on the manual dosing information. Alternatively, or in addition, the automated glucose level control system may request, via a user interface, that a user confirm that the manual bolus was delivered. In cases where the manual bolus in delivered by the automated glucose level control system, a user may be requested to confirm the administering of the manual bolus by using a particular gesture or sequence of interactions with a user interface (e.g., a touchscreen) of the automated glucose level control system or of a device (e.g., laptop or smartphone, etc.) that communicates with the automated glucose level control system.

As previously described, in some cases, the information relating to the manual bolus may include an amount of insulin and a reason the manual bolus was administered (e.g., for a meal of a particular size). In some such cases, the automated glucose level control system may determine an amount of insulin the automated glucose level control system would administer in an automatic operating mode based on the manual dosing information if the manual bolus had not been supplied. If the automated glucose level control system determines it would have supplied a different quantity of the medicament, and if the difference exceeds a threshold, the automated glucose level control system may adjust a glucose level control algorithm to account for the difference. For example, the automated glucose level control system may change the operating setpoint or range of insulin the automated glucose level control system attempts to maintain in the subject. As another example, the automated glucose level control system may supplement the manual bolus with additional insulin to account for an under-administering of insulin or may reduce a subsequent dosage of insulin to account for an over-administering of insulin.

As previously indicated, the automated glucose level control system may maintain a therapy log of manual insulin therapy. This therapy log may be maintained based on the use of the automated glucose level control system to provide a manual bolus, or based on information provided by the user based on manual administering of insulin (e.g., via injection). The manual boluses may be supplied when the automated glucose level control system is not operating, is not operating in an automatic mode, or is not connected to the subject. Once the automated glucose level control system is connected to the subject and is configured in automatic mode, the automated glucose level control system may determine therapy, if any, to provide to the subject based on a combination of the therapy log and the glucose control algorithm implemented by the automated glucose level control system.

The automated glucose level control system may generate a dose control signal based on the determined therapy. This dose control signal may be supplied to a medicament pump, which may control delivery of the medicament (e.g., insulin) to the subject.

In some cases, a user may control whether the automated glucose level control system is operating in a manual mode or an automatic mode by interacting with a user interface of the automated glucose level control system or of a device that communicate with the automated glucose level control system. The user interaction may include any type of user interaction with a user interface. For example, the user interaction may include interaction why physical buttons or interactions with a touchscreen including gestures or taps on the touchscreen.

Additional embodiments relating to managing meal medicament doses and manual dosing that can be combined with one or more embodiments of the present disclosure are described in U.S. Provisional Application No. 62/911,143, which was filed on Oct. 4, 2019 and is titled "SYSTEM AND METHOD OF MANAGING MEAL DOSES IN AN AMBULATORY MEDICAL DEVICE," the disclosure of which is hereby incorporated by reference in its entirety herein for all purposes.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method including: providing an option to a user to select between receiving medicament using a manual delivery component or an automated delivery system. The method also includes receiving, by the automated delivery system, subjective information regarding the activity or action that may alter the glucose level. The method also includes receiving, by the manual delivery component, an amount of the medicament to be infused. The method also includes storing a time and the amount of medicament that is infused into the automated delivery system that controls glucose level. Other embodiments of this aspect include corresponding computer systems, apparatus, and computer programs recorded on one or more computer storage devices, each configured to perform the actions of the methods.

Implementations may include one or more of the following features. The method where the automated delivery system modifies medicament delivery based on the time and the amount of medicament that was received from either the manual delivery component or the automated delivery system. The method where the manual delivery component includes a keypad which allows the user to type in the dosage amount of the desired medicament. The method where providing the option to select is provided prior to a user performing the activity that may alter the glucose level. The method where the activity that may alter the glucose level includes of consuming food or exercising. The method where the subjective information regarding the activity of consuming food includes the approximate relative size of the food that is to be digested. The method where the approximate relative size of the food is compared to the recommended meal doses for the user and depending on whether the approximate relative size is the same, larger, or smaller than the recommended doses, the model predictive control component is able to determine the actions that is required to regulate the glucose level of the subject (e.g., in subject's blood stream). The method where the subjective information regarding the activity of exercising includes the intensity and the duration of the exercise. The method where the intensity and the duration of the exercise is compared to the recommended intensity and duration, and depending on whether it is the same, larger, or smaller than the recommended intensity and duration, the automated delivery system is able to determine the actions that is required to regulate the glucose level of the subject (e.g., in subject's blood stream). Implementations of the described techniques may include hardware, a method or process, or computer software on a computer-accessible medium.

One general aspect includes a system having a medical device configured to provide an option to a user to select between receiving medicament using a manual delivery component or an automated delivery system. The system also includes automated delivery system configured to receive subjective information regarding the activity that may alter the glucose level. The system also includes a manual delivery component configured to receive an amount of the medicament to be infused. The system also includes where the medical device storing a time and the amount of medicament that is infused into an automated delivery system that controls glucose levels. Other embodiments of this aspect include corresponding computer systems, apparatus, and computer programs recorded on one or more computer storage devices, each configured to perform the actions of the methods.

Upon utilizing an ambulatory medical device to request for a therapy change, users may have different preferences. Therefore, it is desirable for modern technology, specially the ambulatory medical devices to be equipped with optionality features. These optionality features may fulfill the different preferences of the users and subjects. The optionality features may allow users to control the therapy changes more closely and may allow them to be more engaged with the medical assistance of the ambulatory medical device.

In order to fulfill the variety of preferences, an ambulatory medical device needs to provide options which allows the user to either manually request the amount of the desired medicament or chose an automated delivery system that automatically delivers the right amount of the medicament at the right time without further assistance. For the manual component, the user may personally input the desired amount on a keypad that is provided by the medical device. The medical device further confirms and delivers the requested medicament. After the medicament is infused through a manual delivery component, the data is stored into a model predicative control component which is further used to control and regulate the glucose level. However, if the user decides to use the automated delivery system, the user must provide subjective information regarding the activity or the action that may alter the glucose level. For example, if the glucose level changing activity is consuming food, the user must provide the time and the dosage amount of the food that is going to be digested. This information is tied to the automated delivery system, and the subjective information is further stored into a model predicative control component.

Embodiments described herein include an ambulatory medical device that has a keypad which allows a user to type in a dose of insulin or glucagon to be administered to a user. A user may wish to receive a single dose of insulin prior to consuming food and decide how much insulin need to be administered. In other embodiments, the user may choose to receive a burst of glucagon due to low glucose level because of physical activities. Embodiments may include the options for manual inputs of medicament and automated delivery system of medicament. In various implementations, the automated delivery system of medicament is driven by the glucose level or related trends. Embodiments herein address a problem that may arise when the user has just received a manual dose and has switched on the automated delivery system. In such cases, the automated delivery system may be made aware of all manual medicament infusion amounts and the timing of such infusions. Accordingly, the manual delivery component may inform the automated delivery system upon delivering any medicament the type of medicament delivered, the amount of medicament and the timing of the medicament delivered. By having the above information, the automated delivery system may determine the amount of medicament that is the user's blood stream and adjust the automated delivery of medicament and the timing of the automated delivery. Accordingly, embodiments are directed to allows for a risk free transition from the manual delivery component and the automated delivery system.

Differences from other system may include that the manual delivery may be tied to an automated delivery system, the dose input from the user is then stored into the MPC algorithm (Model Predictive Control) instead of the meal delivery algorithm and is handled by the MPC algorithm. Other embodiments may include selection being able to have a relativistic algorithmically tuned value. Other embodiments may include a learning algorithm that includes a usual size meal or larger size meal or small size meal. Embodiments may include correlating the manual inputs to asking the user what was the size of the meal and learning how the insulin affects the user. Embodiments may include correlating the manual inputs to asking the user what activity the user performed and learning how the glucagon affects the user for a particular activity.

GLCS with Manual Dose Management

Figure 36:
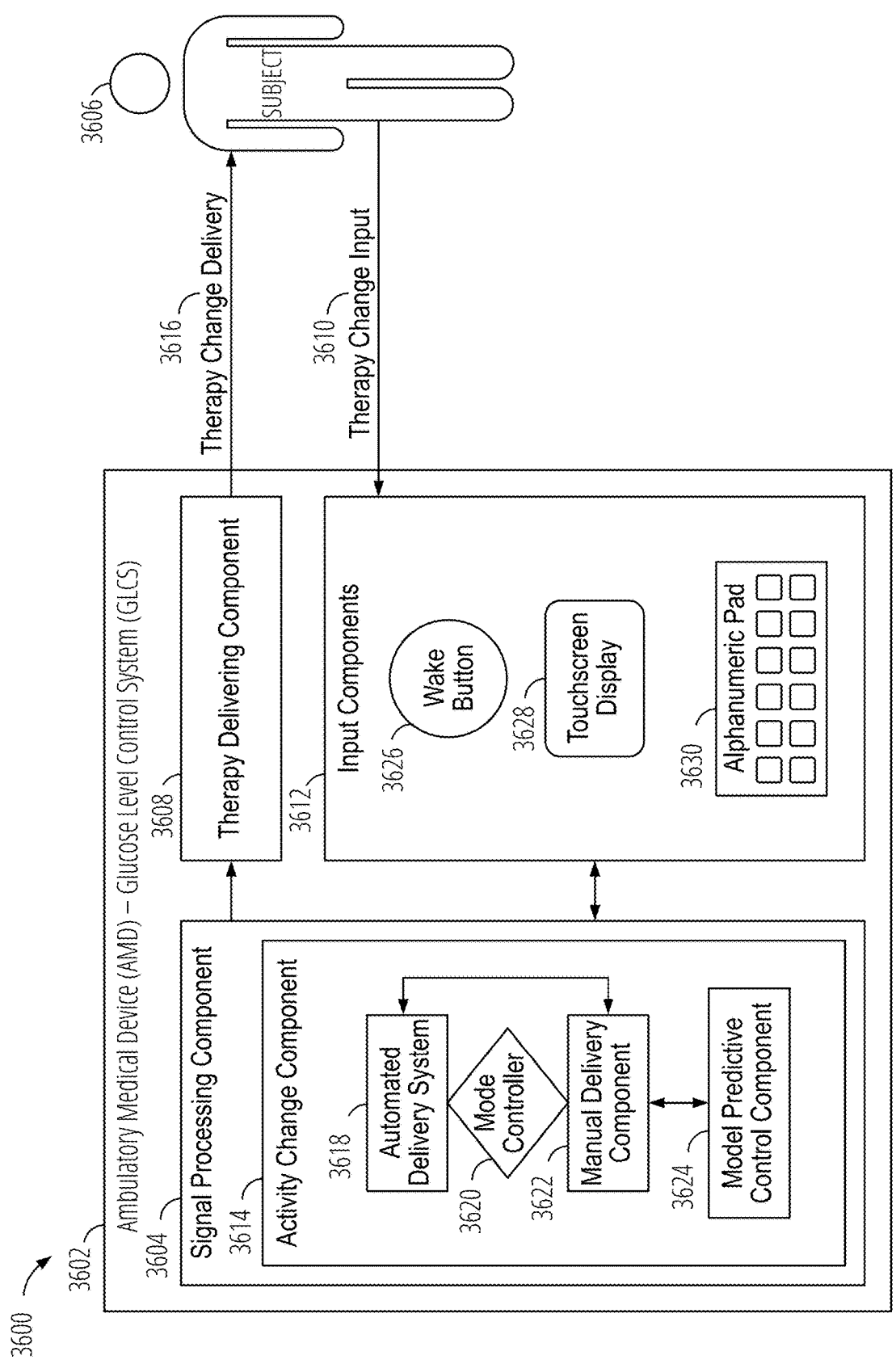
FIG. 36 is a schematic diagram illustrating an ambulatory medical device that provides the user with various options for providing medicament.

FIG. 36 illustrates a schematic of the therapy change delivery system 3600 in an ambulatory medical device (or glucose level control system) 3602 that allows the user the choice of receiving manual delivery of medicament or automated delivery of medicament. Moreover, the therapy change delivery system 3600 allow the user to transition between the manual mode and the automated mode with ease. The therapy change delivery system 3600 includes the ambulatory medical device 3602, a signal processing component 3604, a subject 3606, a therapy delivering component 3608, a therapy change input 3610, input components 3612, activity change component 3614, and a therapy change delivery 3616. When the user intends to receive a therapy from an ambulatory medical device 3602, the subject 3606 may initiate a therapy change input 3610 to request the manual or automated medicament.

The ambulatory medical device 3602 is any medical device that a subject 3606 may carry around and use with the approval of a medical professional. There are many different types of ambulatory medical devices 3602. In one embodiment, the ambulatory medical device 3602 is an insulin and/or glucagon infusion device for subject 3606 that have type I diabetes. Ambulatory medical devices 3602 allow subjects 3606 the freedom to receive medical care in any setting at their convenience. However, the drawback of using an ambulatory medical device 3602 could be the subject 3606 making mistakes when the user is away from the medical professionals. One possible issue may be caused the subject 3606 switches from a manual delivery mode to an automated delivery mode when the automated delivery mode is unable to determine the amount of medicament in the user's blood stream. Embodiments are directed to the manual medicament delivery information being provided to the automated medicament delivery system so that it can adjust its operations based on the current and future medicament in the user's blood stream. In some cases, such as the embodiment where the ambulatory medical device 3602 is an insulin and/or glucagon infusion device, doing automated delivery of medicament can be problematic.

The ambulatory medical device 3602 includes a signal processing component 3604, a therapy delivering component 3608, and input components 3612. The signal processing component 3604, therapy delivering component 3608, and input components 3612 may be physically connected, wirelessly connected, connected via a cloud-based computer system, or connected in any other way.

The signal processing component 3604 is a computing system that performs the computing functions for the ambulatory medical device 3602. The signal processing component 3604 includes a processor, memory, and storage. The signal processing component 3604 may be a single computing system or may be made up of several computing systems. The signal processing component 3604 may perform the computing functions for a single ambulatory medical device 3602 or many ambulatory medical device 3602. The signal processing component 3604 receives signals from the therapy delivering component 3608 and from the input components 3612. The signal processing component 3604 also transmits signals to the therapy delivering component 3608 and the input components 3612. Signals of the therapy change input 3610, the therapy change delivery 3616, and all steps of the activity change component 3614 may be received or transmitted by the signal processing component 3604.

The subject 3606 is any individual that uses the ambulatory medical device 3602. In one embodiment the subject 3606 is an individual with diabetes that requires a periodic infusion of insulin or glucagon to maintain healthy glucose levels. In various embodiments, the ambulatory medical device 3602 infuses insulin or glucagon into the subject 3606. The subject 3606 may transport the ambulatory medical device 3602. Thus, as the subject 3606 moves around, there is a danger that the subject 3606 will inadvertently activate input in the ambulatory medical device 3602 that initiates a therapy change input 3610.

The therapy delivering component 3608 provides medicaments to the subject 3606. Signals received from the signal processing component 3604 are executed by the therapy delivering component 3608 to change therapy such as starting, modifying, or stopping a therapy. The therapy delivering component 3608 may have a computing component for interpreting and executing instructions from the signal processing component 3604. Thus, the therapy delivering component 3608 can follow a program that is controlled by the signal processing component 3604. In one embodiment, the therapy delivering component 3608 is one or more infusion pumps. An infusion pump is capable of delivering fluids at varying rates to a subject 3606. The infusion pump may deliver any fluid, including medicaments. The infusion pump may be connected to a subject 3606 through any means. In one example, the infusion pump is connected to the body through a cannula. In an exemplary embodiment, the therapy delivering component 3608 is an insulin infusion pump. Also, in an exemplary embodiment, the therapy delivering component 3608 is an insulin and glucagon infusion pump. Signals received from the signal processing component 3604 may be interpreted by an insulin and glucagon pump to start, stop, or change the rate of insulin and glucagon being delivered into a subject 3606.

In an exemplary embodiment, the therapy delivering component 3608 is an electrical stimulation device. An example of an electrical stimulation device is a cardiac pacemaker. A cardiac pacemaker stimulates the cardiac muscle to control heart rhythms. Instructions received from the signal processing component 3604 may be interpreted by a cardiac pacemaker to start stimulating a cardiac muscle, stop stimulating a cardiac muscle, or change the rate of stimulation of a cardiac muscle. Another example of an electrical stimulation device is a deep brain stimulator to treat Parkinson's disease or movement disorders. Instructions received from the signal processing component 3604 may be interpreted by the deep brain stimulator to start, stop, or modify the stimulation of the brain.

The therapy change input 3610 is an input provided by the subject 3606 to change a therapy that is currently being delivered to the subject 3606. The change of therapy may be to start a therapy, modify a therapy, or cancel a therapy. There are many types of possible therapy changes, and the types of therapy changes are dependent on the type of ambulatory medical device 3602. In one embodiment, the ambulatory medical device 3602 is an insulin or glucagon infusion device. However, there are many possible embodiments of ambulatory medical devices 3602 for the disclosed subject matter. The therapy change input 3610 in an insulin or glucagon infusion device may be an instruction, that when executed, causes the insulin or glucagon infusion device to start infusing an amount of insulin or glucagon into the subject 3606. Alternatively, the therapy change input 3610 may be an instruction to modify the rate of insulin or glucagon infusion into the subject 3606. The therapy change input 3610 may also be an instruction to cancel insulin or glucagon infusion into the subject 3606 from the insulin or glucagon infusion device. In an exemplary embodiment, the ambulatory medical device 3602 is an electrical implant, that when operated, stimulates a part of the body. An example is an electrical brain implant for subjects 3606 with Parkinson's disease or for pain management. The implementation of the therapy change can be to modify the rate of electrical stimulation to the body.

Figure 43:
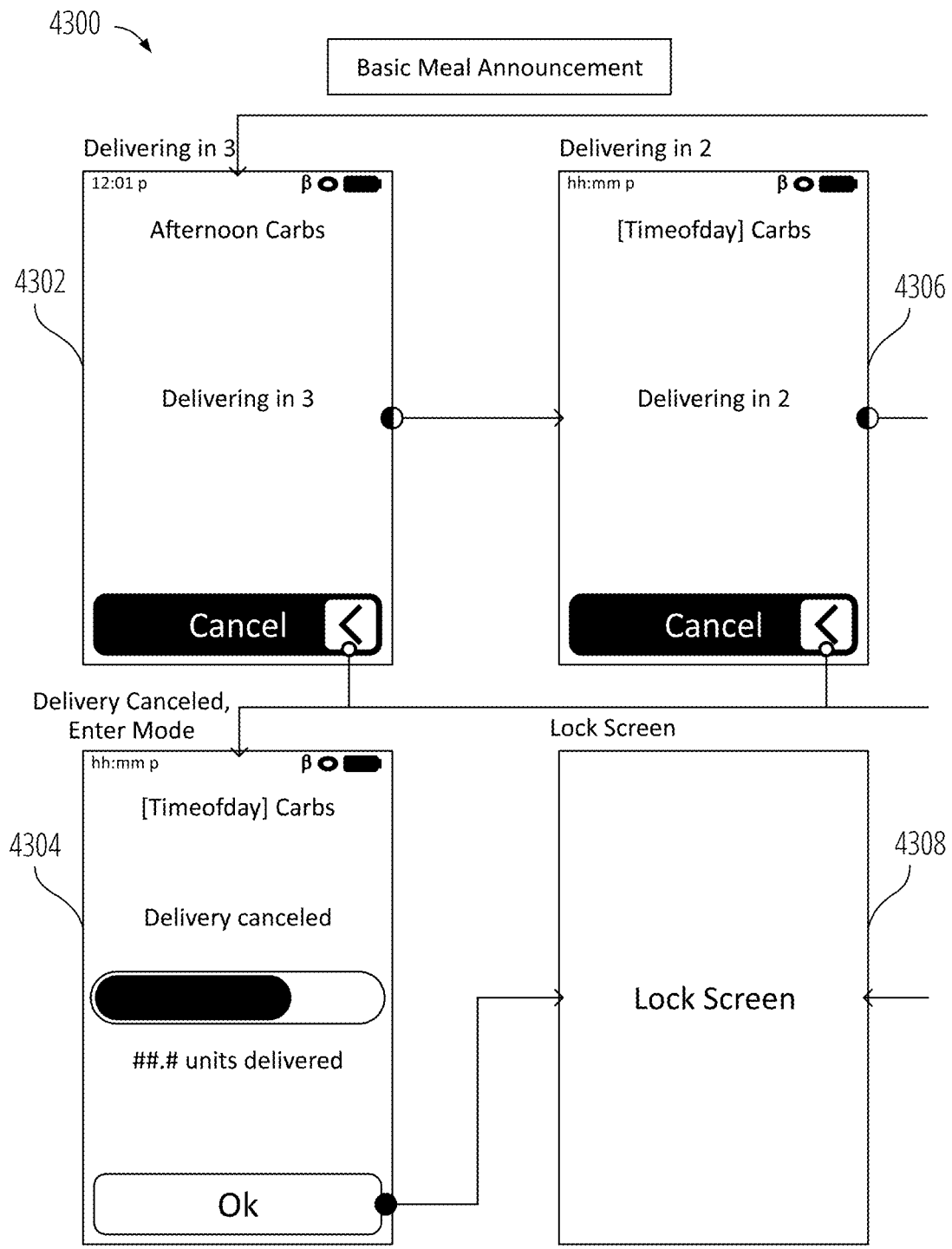
FIG. 43 is a series of screen displays showing an ambulatory medical device delivering the units and cancelling the delivery of the units.

The therapy change delivery 3616 is the performance, by the ambulatory medical device 3602, of the therapy change input 3610 that was verified by the 3614. The therapy change that is delivered by the therapy change delivery 3616 corresponds to the therapy change selection made by the subject 3606. In one embodiment, the ambulatory medical device 3602 alerts the subject 3606 that it is performing a therapy change delivery 3616. In an example of various embodiments, the ambulatory medical device 3602 displays the therapy change during the therapy change delivery 3616. Any number of details of the therapy change may be displayed during the therapy change delivery 3616. As shown in FIG. 43, a simple message of "Delivering" may be displayed during the therapy change delivery 3616. Alternatively, more exact details, such as "Delivering 2 units of insulin" or "Delivering insulin at 2 units per minute" may be displayed. In another example, the ambulatory medical device 3602 plays a sound effect during the therapy change delivery 3616. In an exemplary embodiment that is shown in FIG. 43, the therapy change delivery 3616 may be canceled by an input by the subject 3606. The input to cancel a therapy change delivery 3616 may be any input such as a wake signal input or a series of touch inputs such as a gesture.

The input components 3612 allow the subject 3606 to interact with and control the ambulatory medical device 3602. The amount of control that a subject 3606 has may vary based on the type of ambulatory medical device 3602 and the subject 3606. For example, an ambulatory medical device 3602 that delivers pain medication may allow the user more control than an ambulatory medical device 3602 that controls heart rhythms. In another example. a subject 3606 that is a young child (less than about 10, 11 or 12 years) may be allowed less control over an ambulatory medical device 3602 than a subject 3606 that is a teen or an adult. The input components 3612 include a wake button 3626, a touchscreen display 3628, and an alphanumeric pad 3630.

The wake button 3626 is activated by a subject 3606 to create a wake signal input to unlock an ambulatory medical device 3602. The wake button 3626 may be any input button. In one embodiment, the wake button 3626 is a capacitive button that detects a change in capacitance. The wake button 3626 may have a computing component for interpreting and executing instructions from the signal processing component 3604. Thus, the wake button 3626 can follow a program that is dictated by the signal processing component 3604.

The touchscreen display 3628 may display a therapy change user interface for the subject 3606 and receive subject 3606 inputs on the touchscreen display 3628 input surface. Inputs on the touchscreen display 3628 may be registered by any touch technology including, but not limited to capacitive and resistive sensing. The touchscreen display 3628 may be a part of a mobile computing device, such as a cellular phone, tablet, laptop, computer, or the like. The touchscreen display 3628 may have a computing component for interpreting and executing instructions from the signal processing component 3604. Thus, the touchscreen display 3628 can follow instructions that are directed by the signal processing component 3604. To receive input, the touchscreen display 3628 may display buttons, alphanumeric characters, symbols, graphical images, animations, or videos. The touchscreen display 3628 may display an image to indicate when the ambulatory medical device 3602 is locked or inaccessible via the touchscreen display 3628. The touchscreen display may receive the series of inputs that make up the first gesture and the second gesture.

The alphanumeric pad 3630 registers numerical inputs, alphabetical inputs, and symbol inputs. The alphanumeric pad 3630 includes a multitude of keys corresponding to numerical, alphabetical, and symbol inputs. The alphanumeric pad 3630 may have a computing component for interpreting and executing instructions from the signal processing component 3604. Thus, the alphanumeric pad 3630 can follow instructions that are dictated by the signal processing component 3604. The alphanumeric pad 3630 may be configured to provide haptic feedback from its keys. The alphanumeric pad or pads 3630 may have any number of keys and any number of characters and may span multiple screens that the subject 3606 can toggle between in order to find all of their sought-after characters. In one embodiment, the wake button 3626 is incorporated into the alphanumeric pad 3630. In various embodiments, the wake button 3626 may be any one or more keys of the alphanumeric pad 3630. In an exemplary embodiment, the alphanumeric pad 3630 is displayed as part of the touchscreen display 3628. Characters from the alphanumeric pad 3630 may be used as input for the wake signal input, first gesture, therapy change selection, and second gesture. In an exemplary embodiment, the first gesture and/or second gesture are created by entering predetermined characters on the alphanumeric pad 3630.

The activity change component 3614 may be part of a specialized software that is executed on an ambulatory medical device or include a specialized hardware that performs the various functions described here. The activity change component 3614 may receive inputs from the user regarding weather the user is about to conduct activities that will change the glucose level of the user. For example, the user may provide input using the input components 3612 that the user is about to perform exercise that may lower their glucose level (e.g., blood glucose level) or eat a meal that will increase their glucose. Upon receiving the activity change from the input components 3612, the activity change component 3614 offers the user the option via the mode controller 3620 to select between the automated delivery system 3618 or the manual delivery component 3622. As shown in FIG. 36, the manual delivery system may inform the automated delivery system 3618 and the model predictive control component 3624 regarding any manual medicament deliveries of insulin or glucagon.

In various embodiments, the user may choose the dosage amount, the drug type (insulin or glucagon; fast or slow acting) and the time of the delivery and the manual delivery component 3622 may receive such information and deliver the medicament(s) accordingly. In one embodiment, the manual delivery component 3622 may inform the automated delivery system 3618 and the model predictive control component 3624 regarding the drug type (insulin or glucagon; fast or slow acting) and the time of the delivery.

When the user activates the automated delivery system 3618, the data from previous manual medicament infusions can be readily available so that the automated delivery system 3618 may be able to determine how much medicament is still in the user's blood stream. The automated delivery system 3618 may make that determination by tracking the finite rate of utilization of infused insulin by the subject based on the time and amount of any manual medicament infusions reported to the automated delivery system 3618.

Figure 37:
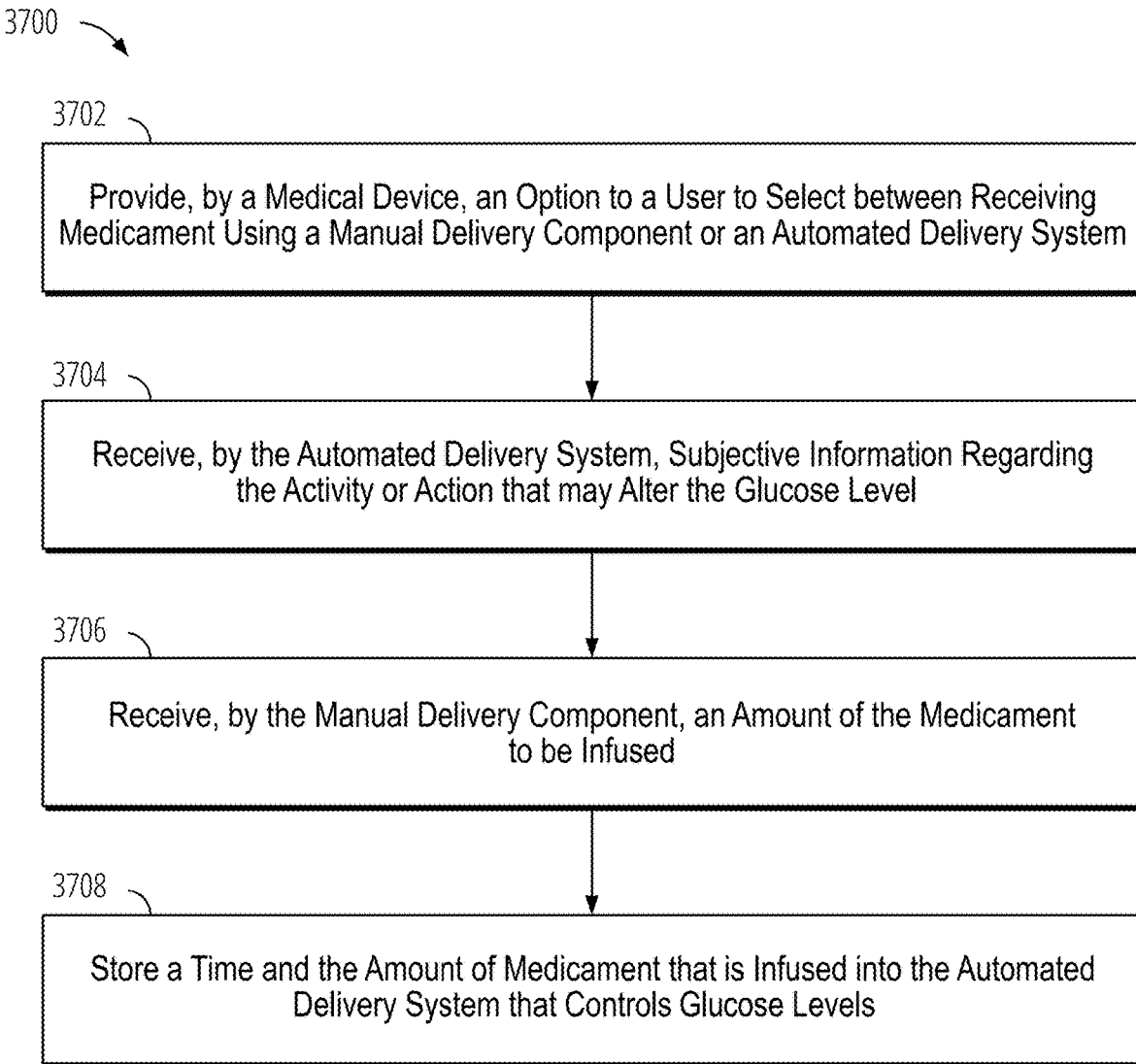
FIG. 37 is a flow diagram of a process for providing options for meal dosage selection on an ambulatory device.

FIG. 37 is a flow chart of a process 3700 detailing a medicament selection process, according to an exemplary embodiment. In step 3702, the medical device provides an option to a user to select between receiving medicament using a manual delivery component or an automated delivery system. By using the mode controller 113, the user can select the method for the therapy change request between manual delivery component and the automated delivery system.

In step 3704, the medical device may receive subjective information regarding the activity or action that may alter the glucose level. Subjective information may include the size of the meal and/or the type of physical activity. In step 3706, the manual delivery component may receive an amount of the medicament to be infused. The medicament may be a plurality of hormones, including but not limited to, glucagon or insulin. At step 3708, the medical device may store a time and the amount of medicament that was infused into the automated delivery component that controls the glucose level. The systems that are disclosed in FIG. 36 will be utilized to accomplish each and every step from steps 3702, 3704, 3706 and 3708.

Figure 38:
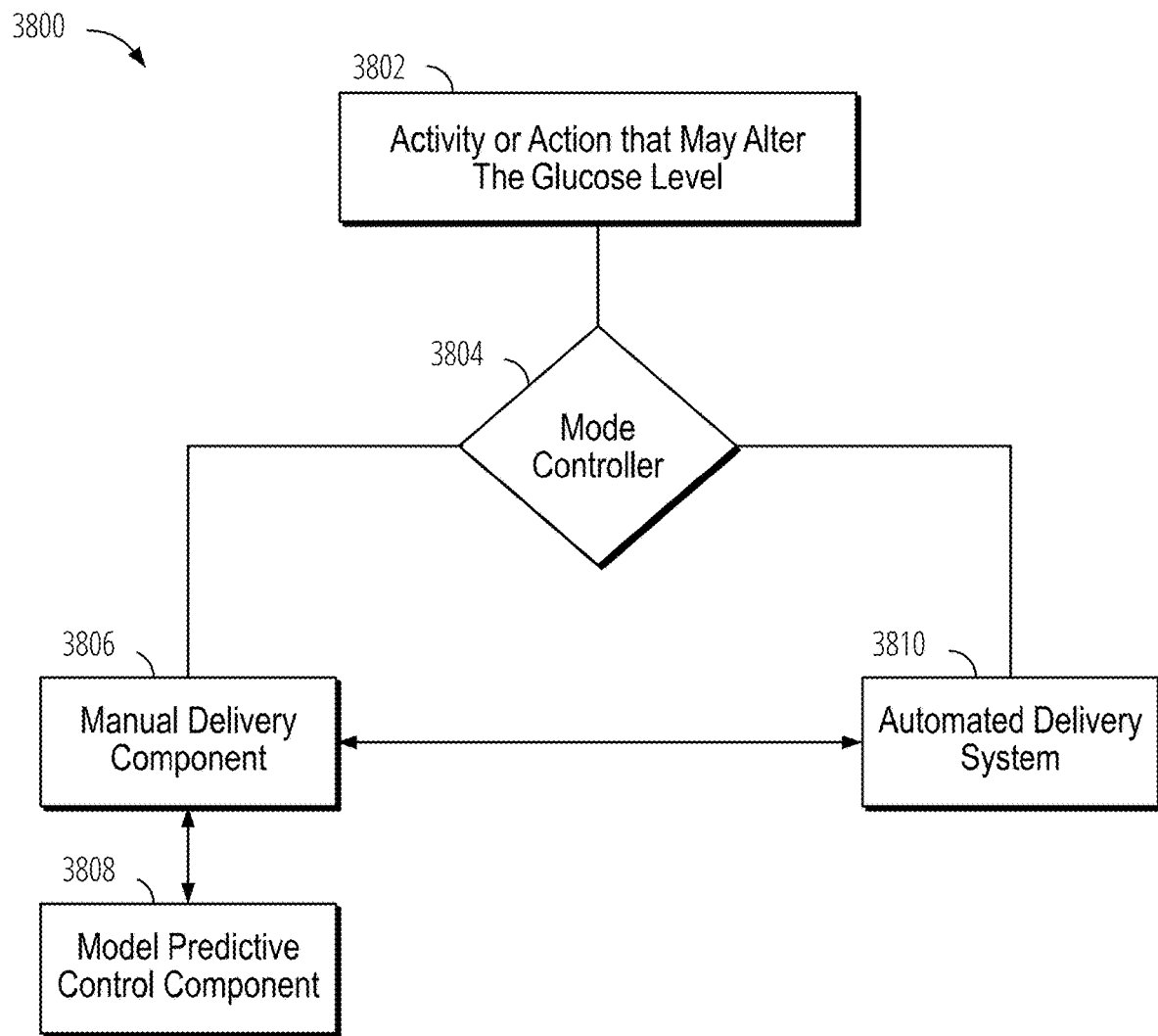
FIG. 38 is another flow diagram of a process for providing options for meal dosage selection on an ambulatory device.

FIG. 38 is another flow diagram of a process 3800 for providing options for meal dosage selection or physical activity of the user on an ambulatory device. Embodiments described herein include an ambulatory medical device that has a keypad which allows a user to type in a dose of insulin or glucagon to be administered to a user. A user may wish to receive a single dose of insulin prior to consuming food and decide how much insulin need to be administered. In other embodiments, the user may choose to receive a burst of glucagon due to low glucose level (e.g., low blood glucose level) because of physical activities. Embodiments may include the options for manual inputs of medicament and automated delivery system of medicament. In various implementations, the automated delivery system of medicament is driven by the glucose level or related trends. Embodiments herein address a problem that may arise when the user has just received a manual dose and has switched on the automated delivery system. In such cases, the automated delivery system may be made aware of all manual medicament infusion amounts and the timing of such infusions. Accordingly, the manual delivery component may inform the automated delivery system upon delivering any medicament the type of medicament delivered, the amount of medicament and the timing of the medicament delivered. By having the above information, the automated delivery system may determine the amount of medicament that is the user's blood stream and adjust the automated delivery of medicament and the timing of the automated delivery. Accordingly, embodiments are directed to allows for a risk free transition from the manual delivery component and the automated delivery system.

At block 3802, the user may inform the activity change component 3614 that the user is about to engage in activities that may alter the glucose level of the user. The mode controller 3620 may be activated at decision block 3804 and ask whether the user wants to use the manual delivery component 3806 or the automated system 3810. If the user chooses to use the manual delivery component 3806 and the user provides an input to infuse medicament, the ambulatory device 3602 may delivery the medicament to the user. Upon the manual delivery process completion, the manual delivery component 3806 may inform at least one of the model predictive control component 3808 and the automated delivery system 3810 regarding the type of medicament, amount of medicament and the time when the medicament was delivery. The predictive control component 3808 and automated delivery system 3810 may track these manual infusions of medicament and determine that based on the rate of decay or the half-life of the medicament the total amount of medicament that remains in the user's blood stream at a particular time or a period of time. Accordingly, when the automated delivery system 3810 is activated by the user, the automated delivery system 3810 may change its medicament infusion based on the medicament that remains in the user's blood stream after a manual infusion by the user.

Differences from other system may include that the manual delivery may be tied to an automated delivery system, the dose input from the user is then stored into the MPC algorithm (Model Predictive Control) instead of the meal delivery algorithm and is handled by the MPC algorithm. Other embodiments may include selection being able to have a relativistic algorithmically tuned value. Other embodiments may include a learning algorithm that includes a usual size meal or larger size meal or small size mean. Embodiments may include correlating the manual inputs to asking the user what was the size of the meal and learning how the insulin affects the user. Embodiments may include correlating the manual inputs to asking the user what activity the user performed and learning how the glucagon affects the user for a particular activity.

Figure 39:
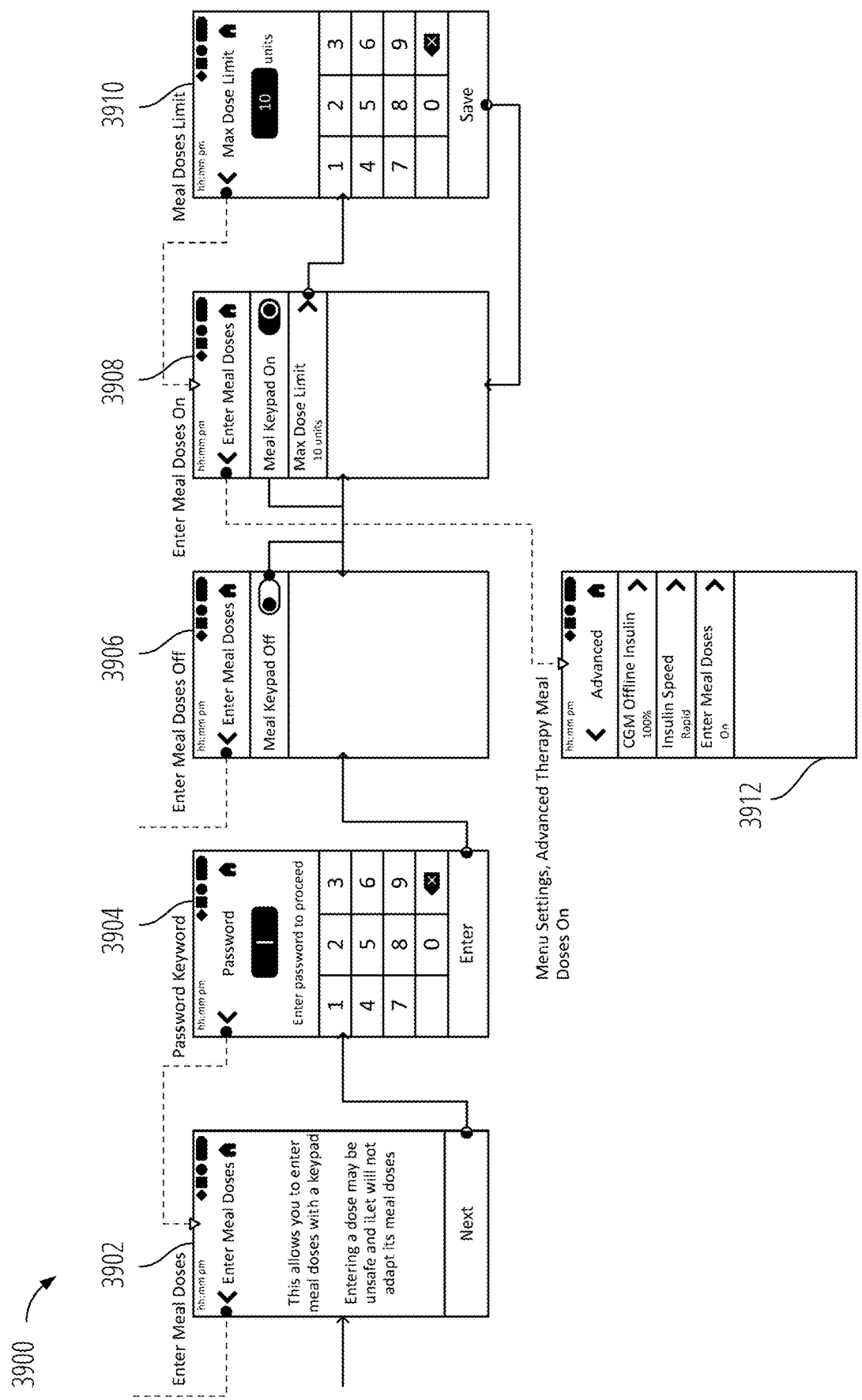
FIG. 39 is a series of screen displays showing a user initiating the activation of meal dosage on an ambulatory device.

FIG. 39 illustrates a plurality of screens 3900 that may be produced by the ambulatory medical device 3602. The plurality of screens 3900 demonstrates a process that a user may take in order to enter meal doses. When the mode controller 3620 is activated, the enter meal doses screen 3902 may be displayed. Once the screen 3902 is displayed, a warning text may be displayed for the user to ensure safety. The warning text states that entering a dose may be unsafe and the device will not adapt its meal doses. This warning text cautions the user of the risks that may be involved in the process of using the ambulatory medical device 3602. After a user acknowledges the warning sign and choses to proceed, a password screen 3904 may be displayed. Once the password screen 3904 is displayed, a keypad is provided for the user to enter a predetermined sequence of numbers to ensure that the user is the actual registered user of the ambulatory medical device 3602. When the ambulatory medical device 3602 receives the correct predetermined password from the user, the enter meal doses official screen 3906 and meal doses official screen 3908 may be displayed. The user may decide to access the advanced screen 3912, and upon doing so, the advanced screen 3912 will allow the user to double check the CGM Insulin levels and change the speed of the of the insulin pump. In screen 3906 and screen 3908, the user is provided the option to have the meal keypad on or off. If the user selects to have the keypad on, then an option may be provided for the user to choose the max dose limit. If the user decides to choose the max dose limit, the official max dose limit screen 3910 is displayed, where the user may enter up to 10 units of the dose. The provided number of units is then stored in the model predictive control component 116 for further regulation of the glucose level.

Figure 40:
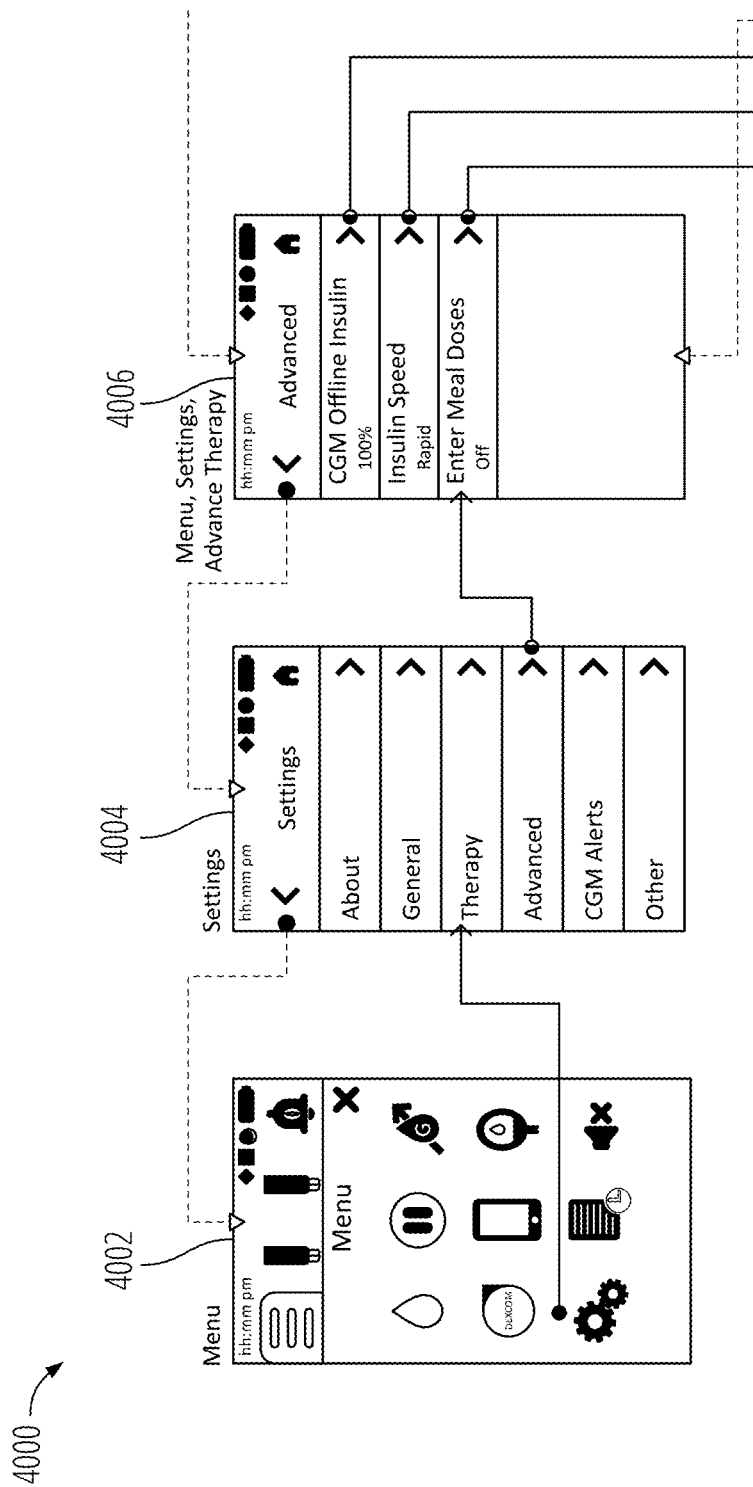
FIG. 40 is a series of screen displays showing a user activating meal dosage on an ambulatory device.

FIG. 40 illustrates a plurality of screens 4000 that may be produced by the ambulatory medical device 3602. Upon activating the ambulatory medical device 3602, the initial menu screen 4002 may be displayed. In the menu screen 4002, options regarding functionalities of the ambulatory medical device 3602 is provided. The list of functionalities may cover all the aspects of the ambulatory medical device 3602. The user may access and control many aspects of the device by choosing the setting option. The setting option will allow the user to further assess and regulate the adjustable functionalities of the ambulatory medical device 3602. Upon selecting the setting option, the setting screen 4004 may be displayed and the user may select the advanced setting option. Upon selecting the advanced option, the advanced setting screen 4006 is displayed, and the user is provided the option to double check the CGM insulin levels and change the speed of the of the insulin pump. The user may speed up the process or slow down the process depending on the regulation stats that are provided by the model predictive control component 3624.

Figure 41:
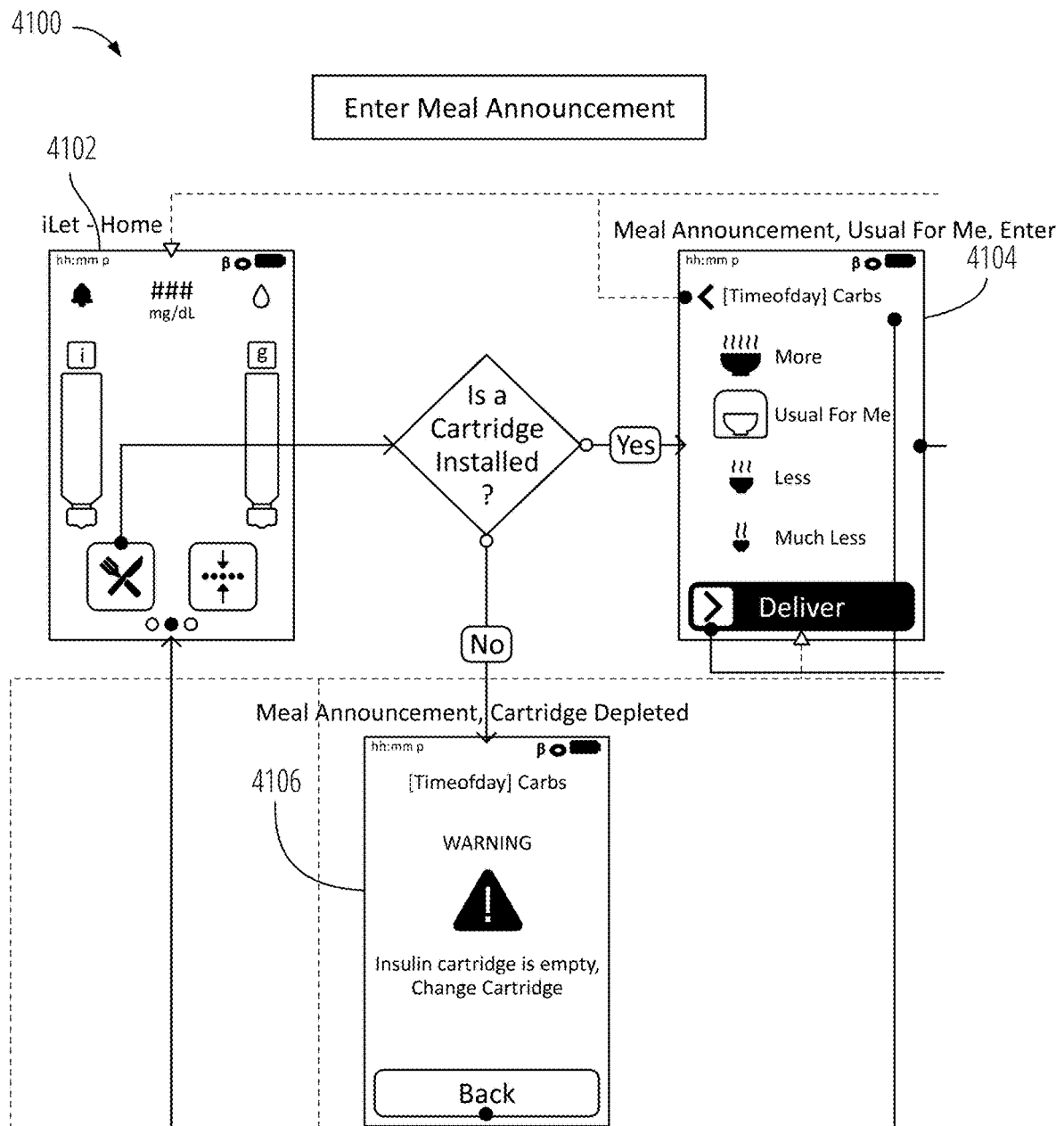
FIG. 41 is a series of screen displays showing a user activating meal announcement on an ambulatory device.

FIG. 41 illustrates a plurality of screens 4100 that may be produced by the ambulatory medical device 3602. The plurality of screens 4100 is the process that a user may take in order to enter meal announcements. The home screen 4102 provides information and stats regarding the cartridge of the ambulatory medical device 3602. The user may select the meal button with or without an installation of a new cartridge. If a user selects the meal button without installing a new cartridge, the ambulatory device 3602 will display the warning screen 4106, where the user is warned that the insulin cartridge is empty, and the device further advises the user to change the cartridge. However, if a new cartridge is already installed and the food button is pressed, the ambulatory medical device 3602 will display the carbs screen 4104, where the user is provided the option to choose a meal dose option. The carbs screen 4104 allows the user to provide subjective information regarding the food that is to be digested. This subjective data provided by the user is further stored in the model predictive control component 3624 for further regulation of the glucose level.

Figure 42:
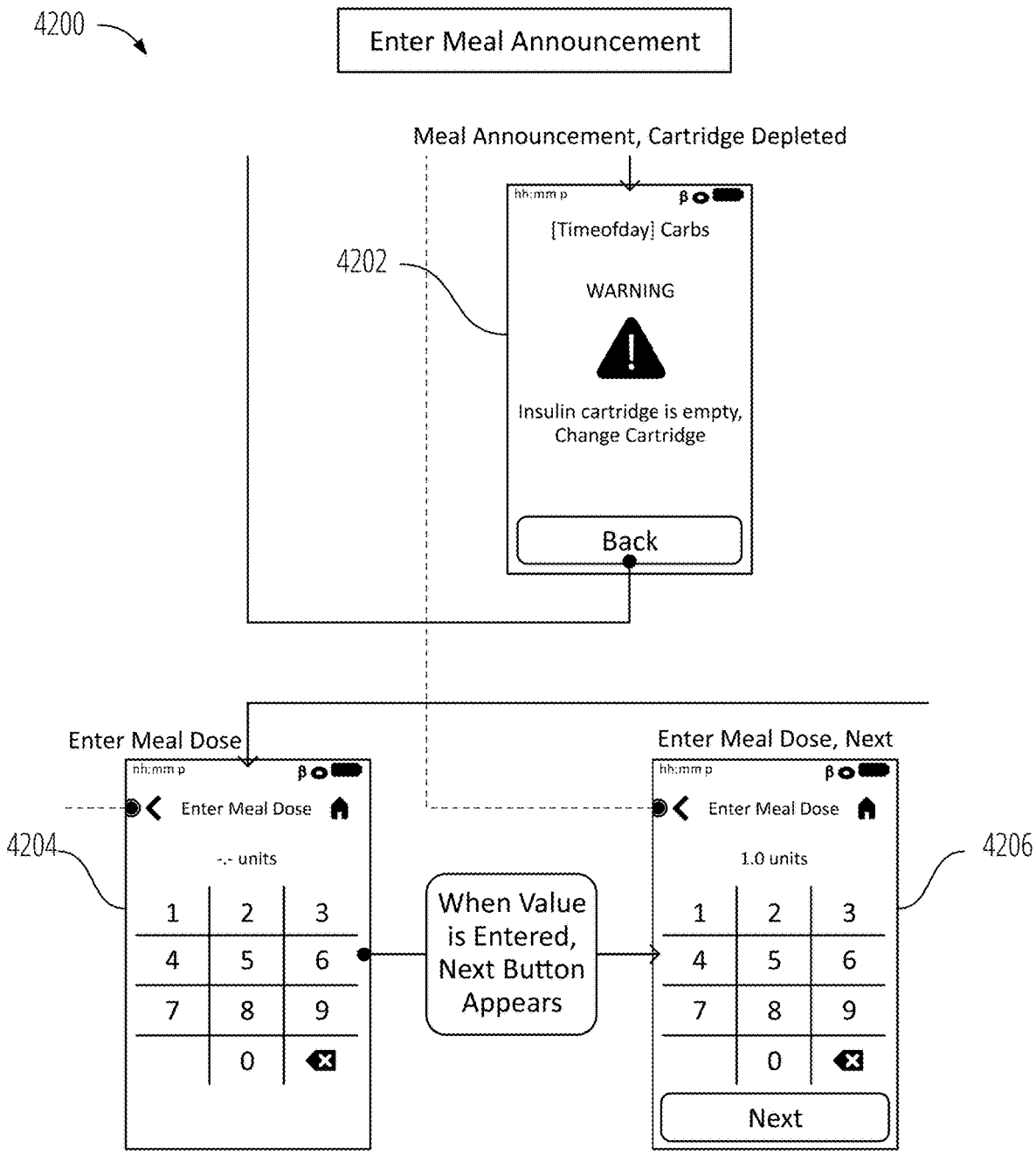
FIG. 42 is a series of screen displays showing a user inputting the total number of units on an ambulatory device.

FIG. 42 illustrates a plurality of screens 4200 that may be produced by the ambulatory medical device 3602. The plurality of screens 4200 demonstrates the process of the user being alerted about the empty cartridge and having the option to replace the cartridge and further enter the meal doses. Warning screen 4202 alerts the user that the insulin cartridge is empty and the fact that it needs to be replaced. Upon replacing the cartridge, screens 4204 and 4206 will be displayed. Screen 4204 is initially displayed, and a user may enter a specified dose for each meal on a numerical pad. Upon inserting a numerical specified dose, screen 4206 is displayed where a next button is provided for the user to further complete the therapy change. The numerical specified dose is further stored in the model predictive control component 3624 for further regulation of the glucose level.

FIG. 43 illustrates a plurality of screens 4300 that may be produced by the ambulatory medical device 3602. Upon selecting the delivery request, a user may cancel the delivery of the medicaments prior to the completion of the delivery. The ambulatory medical device 3602 displays a countdown prior to delivery. The initial countdown screen 4302 is proceeded by the secondary countdown screen 4306. During these countdown screens, a cancel button is provided for the user to cancel the therapy change. During the initial countdown screen 4302 or the secondary countdown screen 4306, the user may cancel the delivery at any time. By swiping the cancel button, the user may officially stop the delivery of the therapy change. If the user does not cancel, the therapy change may be delivered successfully. Furthermore, the time and the amount of the therapy change delivery is stored in the model predictive control component 3624 for further regulation of the glucose level. However, if the user decides to cancel the delivery, the delivery will be canceled and the screen 4304 will be provided. Once the delivery cancelation is requested and the screen 4304 is displayed, upon pressing the ok button, the ambulatory medical device 3602 will display a lock screen 4308 and take the time to officially cancel the therapy change request.

Figure 44:
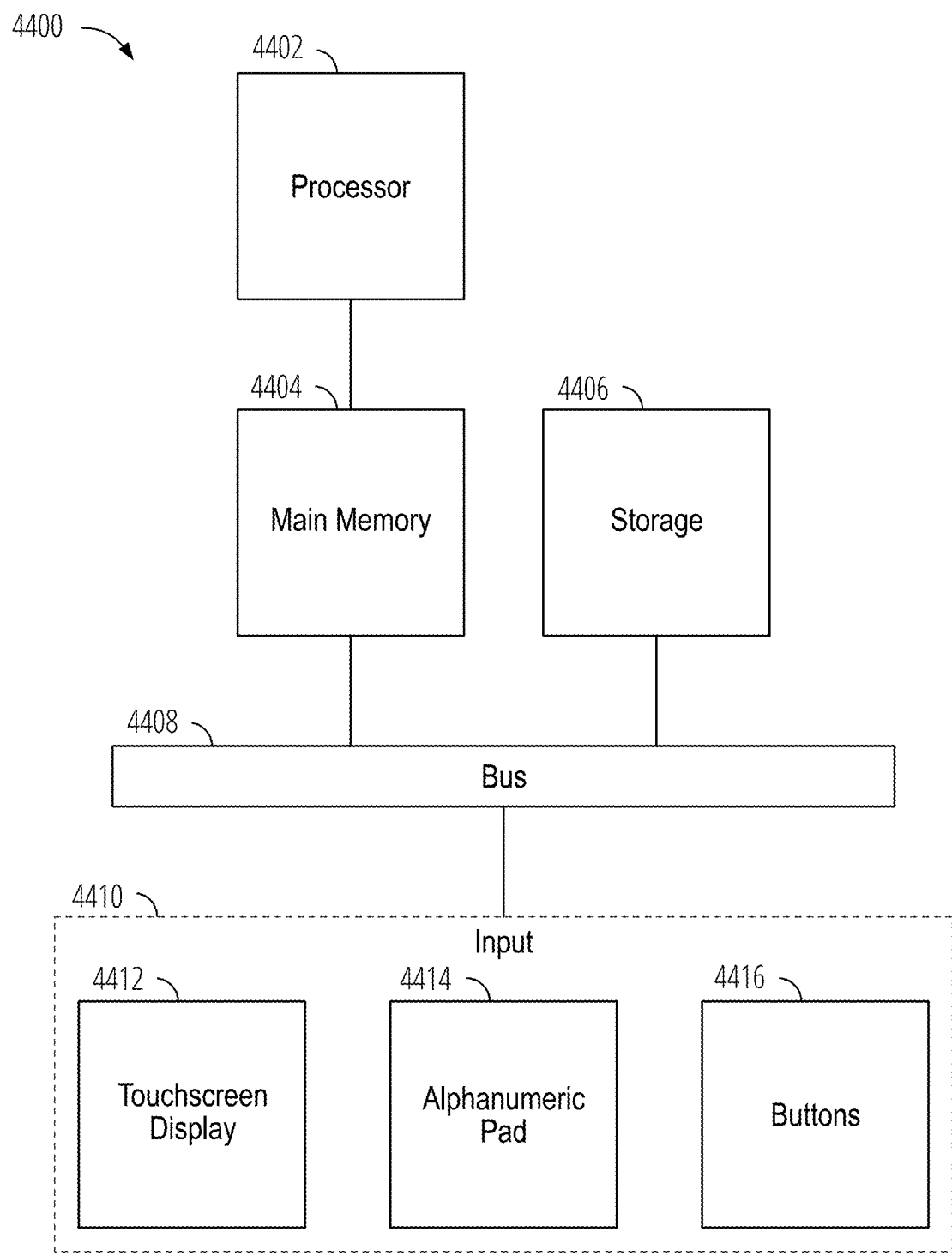
FIG. 44 is a schematic illustrating a computer system that can be implemented in various embodiments of the described subject matter.

FIG. 44 is a block diagram illustrating a computer system 4400 that may be implemented in the various embodiments in the described subject matter. The computer system 4400 includes a processor 4402, main memory 4404, storage 4406, a bus 4408, and input 4410. The processor 4402 may be one or more processors. The processor 4402 executes instructions that are communicated to the processor through the main memory 4404. The main memory 4404 feeds instructions to the processor 4402. The main memory 4404 is also connected to the bus 4408. The main memory 4404 may communicate with the other components of the computer system through the bus 4408. Instructions for the computer system 4400 are transmitted to the main memory 4404 through the bus 4408. Those instructions may be executed by the processor 4402. Executed instructions may be passed back to the main memory 4404 to be disseminated to other components of the computer system 4400. The storage 4406 may hold large amounts of data and retain that data while the computer system 4400 is unpowered. The storage 4406 is connected to the bus 4408 and can communicate data that the storage holds to the main memory 4404 through the bus 4408.

The processor 4402 may be any type of general purpose processor including, but not limited to a central processing unit ("CPU"), a graphics processing unit ("GPU"), a complex programmable logic device ("CPLD"), a field programmable gate array ("FPGA"), or an application-specific integrated circuit ("ASIC"). One embodiment of the computer system 4400 in the ambulatory medical device 100 features a CPU as the processor 4402. However, embodiments may be envisioned for the computer system of the ambulatory medical device 100 that incorporate other types of processors 4402.

The main memory 4404 can be any type of main memory that can communicate instructions to the processor 4402 and receive executed instructions from the processor 4402. Types of main memory 4404 include but are not limited to random access memory ("RAM") and read only memory ("ROM"). In one embodiment, the computer system 4400 incorporates RAM as the form of main memory 4404 to communicate instructions to the processor 4402 and receive executed instructions from the processor 4402. Other embodiments may be envisioned that incorporate other types of main memory 4404 in the computer system 4400.

The storage 4406 can be any type of computer storage that can receive data, store data, and transmit data to the main memory 4404 via the bus 4408. Types of storage 4406 that can be used in the computer system 4400 include, but are not limited to, magnetic disk memory, optical disk memory, and flash memory. In one embodiment, flash memory is used as the storage 4406 in the computer system 4400 of the AMD 100. Other embodiments that use other types of storage 4406 for the computer system 4400 may be envisioned.

The bus 4408 connects the internal components of the computer system 4400. The bus 4408 may include a multitude of wires that are connected to the components of the computer system 4400. The wires of the bus 4408 may differ based on the components of the computer system 4400 to which the bus 4408 connects. In various embodiments, the bus 4408 connects the processor 4402 to the main memory 4404. In various embodiments, the processor 4402 is directly connected to the main memory 4404.

The input 4410 of the computer system 4400 includes a touchscreen display 4412, an alphanumeric pad 4414, and buttons 4416. The touchscreen display 4412 may both produce output and accept input. The touchscreen display can generate user input signals corresponding to user inputs. A touchscreen controller can receive the user input signals. The touchscreen display can display user interface screens generated by the computer system 4400 as discussed herein (for example, critical status information interface screens. The bus 4408 may be coupled to the touchscreen display 4412 to produce visual output. The touchscreen display 4412 may also accept input via capacitive touch, resistive touch, or other touch technology. The input surface of the touchscreen display 4412 can register the position of touches on the surface. Some types of touchscreen display 4412 can register multiple touches at once. The alphanumeric pad 4414 includes a multitude of keys with numerical, alphabetical, and symbol characters. Signals from the alphanumeric pad 4414 are communicated by the bus 4408 to the main memory 4404. Keys of the alphanumeric pad 4414 may be capacitive or mechanical. In some embodiments, the alphanumeric pad 4414 is displayed on the touchscreen display 4412. Buttons 4416, such as the wake button 120, may be capacitive, mechanical, or other types of input buttons. The wake interface may include one or more of the embodiments described herein with respect to the wake interface 506 of FIG. 5B.

The input 4410 may be a user interface module as disclosed with respect to, for example, the user interface module 608 of FIG. 6 and input components 3612 of FIG. 36. The user interface module may include any type of user interface controller for providing a user interface as discussed herein. The user interface may be provided on a display 4412 of the computer system 4400 (e.g., an AMD 100), or may be transmitted to a display of an electronic device in communication with the computer system 4400 (e.g., an AMD 100, 500). In some cases, the user interface controller may be a touchscreen controller that is configured to output display signals configured to generate one or more user interface screens on a touchscreen. Further, the touchscreen controller may be configured to receive user input signals corresponding to user interaction with the touchscreen.

In some embodiments, the input 4410 includes a voice recognition sensor (e.g., a speaker, a microphone, or the like) for receiving a voice/verbal command, as described herein. In this case, a controller of the user interface may be configured to output a sound or voice that is prestored via the speaker. Further, the controller for the voice recognition can be configured to receive user input signals corresponding to a sound or voice.

Supply Ordering

A subject may require many doses of medicament and it can be advantageous to allow a subject to order the medicament directly from and/or via the medicament pump or related system. In some embodiments, the system may be able to track the amount of medicament usage and automatically detect when additional medicament may be needed. Systems and methods described herein can be effective at determining an amount of total remaining medicament and generating a user alert that indicates that additional supply of medicament may be necessary. This may prevent supply shortage and avoid health emergencies. Additionally, or alternatively, as described in more detail the attached Appendix, the system may be able to determine that a number of remaining supplies (e.g., infusion sets, analyte sensors, etc.) is below a reordering threshold and generate a user prompt. The system may receive a request for additional infusion sets and transmit a purchase order for the additional infusion sets.

Figure 45:
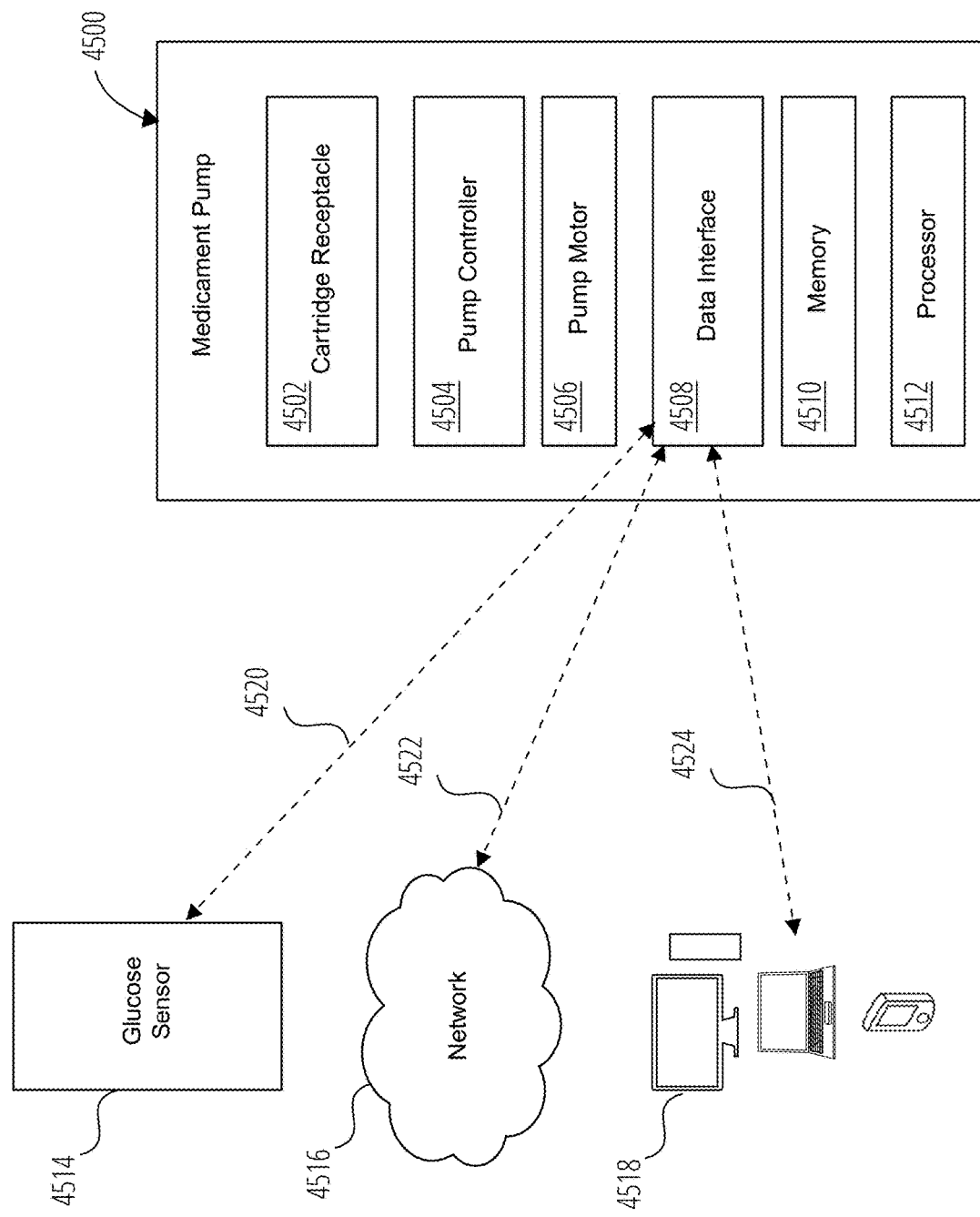
FIG. 45 is a schematic illustrating an example ambulatory medicament pump that is configured to evaluate the need for additional supply of medicament and/or enable modification of glucose level control therapy delivered to a subject via a remote computing environment.

FIG. 45 is a schematic illustrating an example ambulatory medicament pump 4500 that is configured to determine an amount of total remaining medicament and/or to generate a user alert configured to indicate that additional supply of medicament may be necessary. The medicament pump 4500 may be an ambulatory medicament pump. The medicament pump 4500 and/or other components described herein, such as elements described with respect to FIG. 29, FIG. 32, FIG. 34, and FIG. 36. The medicament pump 4500 includes a cartridge receptacle 4502, a pump controller 4504, a pump motor 4506, a data interface 4508, a non-transitory memory 4510, and an electronic hardware processor 4512. The cartridge receptacle 4502, may include a removable cartridge or medicament reservoir where a medicament is stored.

The medicament pump 4500 can be any medical device that a subject (e.g., a user) may carry around and use with the approval of a medical professional. The medicament pump 4500 may correspond to and/or share certain functionality with one or more devices described herein, such as the ambulatory medical device 3602 or therapy delivering component 3608 described above with respect to FIG. 36. There are many different types of ambulatory medicament pumps 4500. In one embodiment, the medicament pump 4500 is an insulin and/or glucagon infusion device for subjects that have Type I diabetes. Ambulatory medicament pumps 4500 allow subjects the freedom to receive medical care in any setting at their convenience.

However, supplies need to be dependably available to a subject or else an emergency may arise. For example, if a medicament (e.g., insulin, glucagon, etc.) is not available when needed, a subject's glucose level may increase uncontrollably. This can be a dangerous scenario. Having sufficient supply on hand is a critical component to proper care, and the medicament pump 4500 described herein may allow for supplies to be ordered in a timely manner.

The medicament pump 4500 can include a data interface 4508, which may be physically connected with the medicament pump 4500, wirelessly connected, connected via a cloud-based computer system, and/or connected in any other way. The pump controller 4504 is configured to direct or eject medicament from a medicament reservoir to the subject (e.g., to a subcutaneous depot of the subject) using the pump motor 4506 or other pump mechanism. In some examples, the medicament pump 4500 includes a medicament ordering control element (not shown), which may allow user input and/or provide feedback to a user.

The processor 4512 is part of a computing system that performs the computing functions for the medicament pump 4500. The processor 4512 may be a single processor or may be made up of several processors. The processor 4512 may perform the computing functions for a single medicament pump 4500 or many ambulatory medicament pumps 4500. The processor 4512 receives signals from the pump motor 4506, the pump controller 4504, and/or from the data interface 4508. The processor 4512 also transmits signals to the pump motor 4506 and/or the pump controller 4504, which may be via the data interface 4508. In some examples, the data interface 4508 may comprise a wireless data interface.

The subject is any individual that uses the medicament pump 4500. In some embodiments the subject is an individual with diabetes that requires a periodic infusion of insulin or glucagon to maintain healthy glucose levels. In various embodiments, the medicament pump 4500 infuses insulin and/or glucagon into the subject. The subject may transport the medicament pump 4500. Thus, as the subject moves around, there is a danger that the subject will be away from medical supplies and/or those who can provide the necessary therapy if the subject becomes low on supply.

The medicament pump 4500 can include therapy delivery components, such as the pump motor 4506. The therapy delivery components may include one or more elements of an infusion pump, such as the pump piston, a cannula, and/or other components as described herein. The therapy delivery components provide medicaments to the subject. Signals received from the processor 4512 are executed by the therapy delivery components, such as the pump motor 4506, to change therapy such as starting, modifying, or stopping a therapy. The therapy delivery components may include a computing component for interpreting and executing instructions from the processor 4512. Thus, the therapy delivery components can follow a program that is controlled by the processor 4512.

The data interface 4508 may be in communication (e.g., wired, wireless) with one or more of a glucose sensor 4514 (e.g., via a glucose sensor connection 4520), with a network 4516 (e.g., via a network connection 4522), and/or with a user device 4518 (e.g., via a user device connection 4524). Each of the connections 4520, 4522, 4524 may be one-way or two-way. The data interface 4508 may also be in communication with other elements of the medicament pump 4500, such as the pump motor 4506, the cartridge receptacle 4502, the cartridge (or medicament reservoir) placed into the cartridge receptacle 4502, and/or the pump controller 4504. The communication with the other elements of the medicament pump 4500 may be via a wired connection. The medicament pump 4500 can include a wireless wide area network modem, which may be a part of the data interface 4508 in some embodiments. The wireless wide area network modem may be configured to provide a wide area network connection. As noted above, the wireless wide area network modem may include a long-term evolution (LTE) modem.

The network 4516 may include any wired network, wireless network, or combination thereof. For example, the network 4516 may be a personal area network, local area network, wide area network, over-the-air broadcast network (e.g., for radio or television), cable network, satellite network, cellular telephone network, or combination thereof. As a further example, the network 4516 may be a publicly accessible network of linked networks, possibly operated by various distinct parties, such as the Internet. In some implementations, the network 4516 may be a private or semi-private network, such as a corporate or university intranet. The network 4516 may include one or more wireless networks, such as a Global System for Mobile Communications (GSM) network, a Code Division Multiple Access (CDMA) network, a Long Term Evolution (LTE) network, or any other type of wireless network. The network 4516 can use protocols and components for communicating via the Internet or any of the other aforementioned types of networks. For example, the protocols used by the network 4516 may include Hypertext Transfer Protocol (HTTP), HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein. The network 4516 may comprise or have access to the "cloud." The network 4516 may include a remote computing environment or other computing hardware.

Various example user devices 4518 are shown in FIG. 45, including a desktop computer, a laptop, and a mobile phone, each provided by way of illustration. In general, the user devices 4518 can be any computing device such as a desktop, laptop or tablet computer, personal computer, tablet computer, wearable computer, server, personal digital assistant (PDA), PDM, hybrid PDA/mobile phone, mobile phone, smartphone, set top box, voice command device, digital media player, and the like. A user device 4518 may execute an application (e.g., a browser, a stand-alone application) that allows a user to access and interact with interactive graphical user interfaces as described herein.

The glucose sensor 4514 may be configured to transmit data to the medicament pump 4500 via the data interface 4508. The data may include a glucose level signal. The glucose level signal can correspond to a glucose level of the subject and/or an indication of a glucose trend. The glucose trend indicates at least a predicted change in the glucose level of the subject. These data may be used, in part, in predicting a rate of usage of medicament by the subject.

In some embodiments, the medicament pump 4500 may include a medicament ordering control element (not shown in FIG. 45), such as a user interface, which may be a graphical user interface. The medicament ordering control element may be integrated into the medicament pump 4500 or may be a separate element. For example, the medicament ordering control element may be integrated with the user device 4518 described above. The user interface may be operatively coupled to the medicament pump 4500 via, for example, the wireless data interface. The user interface can include a touchscreen display. The touchscreen display may display a supply ordering interface for the subject and/or receive subject inputs on the supply ordering interface. Inputs on the touchscreen display may be registered by any touch technology including, but not limited to capacitive and resistive sensing. The touchscreen display may be a part of a mobile computing device, such as a cellular phone, tablet, laptop, computer, or the like (e.g., the user device 4518). The touchscreen display may have a computing component for interpreting and executing instructions from the processor 4512. Thus, the touchscreen display can follow instructions that are directed by the processor 4512. To receive input, the touchscreen display may display buttons, alphanumeric characters, symbols, graphical images, animations, or videos. In some embodiments, the user interface is not a touchscreen display. The user interface may comprise one or more mechanical buttons. The user interface may include an alert generator, such as a light emitter, a speaker, a haptic feedback system, or other sensory alert system.

The medicament pump 4500 may be configured to determine an amount of total remaining medicament in the supply of a subject. The medicament pump 4500 may generate an alert indicating the total remaining medicament. Additionally or alternatively, the medicament pump 4500 may be configured to generate a user alert that indicates that additional supply of medicament may be necessary. In some examples, the medicament pump 4500 can automatically order the additional supply of medicament. Additionally or alternatively, as described in more detail the attached Appendix, the medicament pump 4500 may be able to determine that a number of remaining supplies (e.g., infusion sets, analyte sensors, etc.) is below a reordering threshold and generate a user prompt. The medicament pump 4500 may receive a request for additional infusion sets and transmit a purchase order (e.g., via the medicament ordering control element) for the additional infusion sets.

To determine the amount of total remaining medicament in the supply of a subject, the medicament pump 4500 may undertake a number of actions. For example, the medicament pump 4500 may receive an indication of an amount of initial medicament that is in possession of the subject. The amount of medicament may include an amount that is already in the medicament pump 4500 (e.g., in the cartridge receptacle 4502) as well as an amount of available supply in possession of the subject elsewhere. The amount of available supply of medicament may be received, at least in part, by the subject or other user via the medicament ordering control element. For example, a user may input an amount of supply on hand from the subject. Additionally or alternatively, the medicament pump 4500 may detect an amount of supply that is currently in the medicament pump 4500 (e.g., in the cartridge receptacle 4502).

Determining the amount of initial medicament that is in possession of the subject may include (or be separate from) determining an amount of unusable supply of medicament. The amount of unusable supply of medicament may include any supply of medicament that cannot be safely administered to the subject, such as an amount of medicament that has exceeded an expiration date supplied by a manufacturer of the medicament, an amount of medicament that has exceeded an expiration date received via the medicament ordering control element, and/or an amount of medicament that has been recalled by the manufacturer of the medicament. The expiration date may be determined automatically, such as by estimating the expiration date based on how long the medicament has been in the possession of the subject. Additionally or alternatively, the expiration date may be input by the subject and/or user. The expiration date and/or whether the medicament has been recalled may be based on a batch number or other identifying characteristic of the medicament supply. Based on the determination of the amount of unusable supply of medicament, the medicament pump 4500 may determine an amount of total remaining usable supply of medicament, which may be the total amount of medicament minus the total amount of unusable supply.

The medicament pump 4500 may be able to determine, by a medicament rate determining process, a rate of consumption of medicament. The rate of consumption of medicament may be used to determine how much medicament is used at a particular rate, and this can be used to modify the delivery of medicament remotely. The rate of consumption may be in any units, such as mL/hour, mL/day, cartridges/week, and/or some other reasonable rate of consumption. The rate of consumption may be determined by, for example, determining an amount of medicament ejected from the medicament reservoir and/or an amount inserted into a subject due to operation of the pump motor 4506. Additionally or alternatively, the rate of consumption may be determined by determining an amount of residual medicament remaining in the medicament reservoir during a cartridge replacement procedure. For example, in some cases residual medicament remains in the reservoir and is not ejected from the medicament reservoir. This residual medicament may never be used, may be unusable and/or inaccessible for various reasons (e.g., the medicament is lodged in the lumen between the plunger and the needle), and/or may be ultimately discarded. The medicament pump 4500 may transmit, via the data interface 4508, the rate of consumption of the medicament to the remote electronic device (e.g., the glucose sensor 4514, the network 4516, the user device 4518). The rate of consumption may be based on a set flow rate (e.g., in a hospital, a personal caregiver, etc.) delivered consistently to the subject. The flow rate may be provided in units per time (e.g., seconds, minutes, hours, etc.), volume per time, mass per time, concentration per time, a number of molecules per time, or some other unit designation.

The medicament rate determining process may include at least one of a number of processes. For example, the rate determining process can include a number of turns of a motor. Thus, the system (e.g., the processor 4512) may determine the number of turns of the motor, such as via a known rotational velocity of the motor given a particular current supplied, as well as a time associated with how long the motor has been rotating. The medicament rate determining process can include determining a vapor pressure within the medicament reservoir. This may be accomplished in a variety of ways, such as using a sensor that is fluid communication with an interior of the cartridge receptacle 4502 or with the cartridge. Additionally or alternatively, it may be accomplished based on an electrical resistance realized by the pump motor 4506 or other element of the medicament pump 4500. In some embodiments, the medicament rate determining process includes detecting a volume of medicament within the cartridge such as by using a piston location. The piston location may be determined by a proximity sensor (e.g., optical sensor, capacitive sensor, magnetic sensor, inductance sensor, etc.) and/or by a calculation of the processor of the position of the piston/plunger based on one or more of a length of time the motor has operated, a rate of rotation, and/or a velocity of rotation when operating.

The medicament rate determining process can include determining a number of times a cartridge was installed in the cartridge receptacle 4502. This may be determined in part by a determination by the processor 4512 of the number of times the cartridge receptacle 4502 or the cartridge have been disconnected and/or by a user input of the number of times a cartridge has been installed. In some examples, this number may be estimated based on a passage of time and/or based on a prior known rate of usage by the subject. The estimation may use predictive analytics based on a historical use rate. Additionally or alternatively, the medicament rate determining process can include determining a rate of installation of new cartridges in the cartridge receptacle. This rate may rely on inputs described relating to the determining of the number of number of times a cartridge was installed in the cartridge receptacle 4502, such as determining a number of cartridges installed over a period of time. This may be especially valuable, for example, in medicament pumps 4500 that use pre-filled cartridges.

In some examples, the medicament rate determining process can include receiving from a sensor an amount of existing medicament in the medicament reservoir. The sensor can be any of the sensors described herein, such as a proximity sensor. The sensor may include, for example, a mass sensor and/or an optical sensor. The medicament rate determining process can include determining a location of the piston, such as a position within the medicament reservoir.

In some embodiments, the medicament rate determining process includes estimating a rate of use of medicament by the subject. This rate may be estimated, for example, by receiving an input by the user. The input may include the estimated rate itself or it may include a component of the estimated rate. Any other factor(s) in the estimated rate may be estimated by the processor 4512. Such factors may include a period of time over which the medicament was used, a number of cartridges installed, a rate of delivery and/or consumption of medicament, a glucose level of the subject, and/or other factors.

With continued reference to FIG. 45, the medicament pump 4500 can further be configured to determine the amount of total remaining medicament. This amount may be based on a function of the amount of initial medicament in possession of the subject and the rate of consumption of the medicament. The function may additionally or alternatively include one or more inputs like the ones described above, such as a period of time over which the medicament was used, a number of cartridges installed, a rate of delivery and/or consumption of medicament, a glucose level of the subject, and/or other factors.

The medicament pump 4500 can identify a threshold amount of medicament and/or amount of usable medicament in possession of the subject. The medicament pump 4500 can determine whether the amount is below that threshold amount. The threshold amount may be based on a certain amount of time remaining before the medicament pump 4500 determines that the subject will be out of medicament. For example, if the threshold amount is configured to be at least a 2 week's supply of medicament and the medicament pump 4500 has determined, based on the indication of the initial amount of medicament in possession of the subject and on the rate of consumption determined by the medicament pump 4500, that the user will likely not have enough medicament after the two week period (absent additional supply), the medicament pump 4500 will determine that the amount of total remaining medicament is below the threshold amount. The amount may refer to a time period (e.g., hours, days, weeks, months, etc.) or a volume (e.g., mL). The threshold amount may be about 1 day, about 2 days, about 3 days, about 4 days, about 5 days, about 6 days, about 7 days, about 8 days, about 9 days, about 10 days, about 14 days, about 15 days, about 20 days, about 25 days, about 28 days, about 30 days, about 31 days, about 35 days, about 5 weeks, about 6 weeks, about 8 weeks, about 10 weeks, about 12 weeks, about 15 weeks, about 16 weeks, about 20 weeks, about 25 weeks, any time within those time values, or fall within a range having any of those time values as endpoints. Additionally or alternatively, the threshold amount may be about 1 mL, about 2 mL, about 3 mL, about 4 mL, about 5 mL, about 7 mL, about 10 mL, about 14 mL, about 15 mL, about 20 mL, about 21 mL, about 25 mL, about 28 mL, about 30 mL, about 36 mL, about 42 mL, about 45 mL, about 48 mL, about 50 mL, about 55 mL, about 60 mL, about 66 mL, about 72 mL, about 90 mL, any value therein, or fall within any range having endpoints therein. In some examples the amount is measured in "units", each of which is approximately equal to 0.01 mL.

If it determines that the amount of the total remaining medicament is below the threshold amount, the medicament pump 4500 can generate (e.g., automatically) a user alert that indicates that additional supply of medicament may be necessary. The alert may include any type of alert. For example, the alert may be a visual alert (e.g., a light or changing light), an audible alert (e.g., a beep or series of beeps), a haptic or vibration alert, an email alert, a text alert, or any other type of alert. In some cases, the user alert is dismissible and/or may be snoozed by the user.

Alerts may vary based on when falling below the threshold amount was detected, the time of day, or the detected activity of a subject (e.g., sleep, abnormal activity, or elevated activity, such as exercise). The alert frequency may be for a static time period (e.g., every 5 hours) or may ramp towards more frequency (e.g., every 5 hours for 1 to 3 reminders, every 4 hours for 3 to 6 reminders, etc.), or may change based on time of day (e.g., snooze alerts during sleeping hours for non-urgent alerts), etc.

In some cases, generating the alert may further include contacting a manufacturer, a healthcare provider (e.g., clinician), and/or a care provider (e.g., family member). Generating the alert may include ordering replacement parts. In some cases, the alert may instruct a subject or user on how to repair the ambulatory medical device.

The alert may prompt the subject (and/or other user) to order additional medicament supply. The alert can provide an amount of supply that may be ordered, a recommended amount of supply to be ordered, and/or an indication of the estimated time remaining before the current supply will expire and/or be exhausted.

The medicament pump 4500 can be configured to receive a request for the additional supply of medicament. The request may be made by a user via user interaction with a medicament ordering control element, such as one described herein. The request may be made via a gesture, such as a movement of the eye and/or finger. In some examples, the input is received via a touchscreen interface. In some examples, the touchscreen interface is part of a separate device, such as a user device 4518 and/or the glucose sensor 4514 described herein. The request may include an amount of supply, a record of the current available supply (e.g., total supply, total usable supply) and/or some other value. In some examples, the medicament pump 4500 can propose to the user an amount to be ordered that may be confirmed or declined by the user.

Once the request is received, the medicament pump 4500 can transmit, via the data interface 4508, the request to the remote electronic device. The request may be done wirelessly. The remote electronic device may include one or more of the user device 4518, the network 4516, and/or the glucose sensor 4514. In some examples, the transmission notifies the manufacturer and/or supplier that new supply has been requested and the order may be immediately initiated.

In some embodiments, the medicament pump 4500 can receive, via the data interface 4508, a confirmation signal from the remote electronic device that the request generated by the user input was received by the remote electronic device. The confirmation signal may serve as a type of record of the request and may include an amount requested, an expected and/or estimated delivery time, an option to expedite delivery, an option to submit another request, and/or other data. The medicament pump 4500 may generate a success alert based on the received confirmation signal that the request for the additional supply of medicament was successfully received by the remote electronic device. The success alert may be provided via the medicament ordering control element or through another device.

The medicament pump 4500 may receive (e.g., based on the confirmation signal) a request to order additional medicament supply. The request may be made via user interaction with the medicament ordering control element. In response to receiving the request to order additional medicament supply, the medicament pump 4500 can transmit, via the data interface 4508, a purchase order for additional medicament to the remote electronic device.

As noted above, the medicament pump 4500 may indicate that additional supply of medicament may be necessary. For example, the processor 4512 may determine that the subject will run out of medicament before the estimated delivery date of the medicament. Additionally or alternatively, the medicament pump 4500 may determine that the additional supply is not enough to provide sufficient medicament to the subject for a specified time period, such as a time period specified by the user. In response to one or more of these determinations, the medicament pump 4500 may prompt the subject to authorize a purchase of the additional supply of medicament and/or expedite the delivery of the medicament supply. The medicament pump 4500 can receive, for example via the medicament ordering control element, a command to authorize a purchase of the additional supply of medicament and/or the expediting of the purchase. The medicament pump 4500 may prompt the subject to select a time period for which the additional supply of medicament is desired, and it may receive, e.g., via the medicament ordering control element, a selected time period from the user for which the additional supply of medicament is desired. In response to receiving the selected time period, the medicament pump 4500 can transmit (e.g., automatically), via the data interface 4508, the selected time period for which the additional supply of medicament is desired to the remote electronic device. Additionally or alternatively, the medicament pump 4500 may allow the user to select an amount of additional supply, modify a delivery location(s), and/or set a priority for a particular batch.

In some embodiments, as noted above, the medicament pump 4500 can receive an indication of an expected quantity of medicament to be used for one or more periods of time. In response to this, the medicament pump 4500 can prompt the subject to acquire the expected quantity of medicament to be used for one or more periods of time. For example, a user may select automatic delivery of medicament of a certain amount every couple of weeks or months. Additionally or alternatively, the medicament pump 4500 may automatically determine a time by which a supply of replacement medicament should be ordered. The user can select regular shipment days, times, locations, etc. The medicament pump 4500 can receive, e.g., via the medicament ordering control element, a command to acquire the expected quantity of medicament to be used for one of the one or more periods of time and transmit the command to acquire the expected quantity of medicament to be used for one of the one or more periods of time and/or to acquire the quantity of determined replacement medicament. The medicament pump 4500 may transmit the command to a medical supplier, a manufacturer, a healthcare provider, and/or some other recipient.

Figure 46:
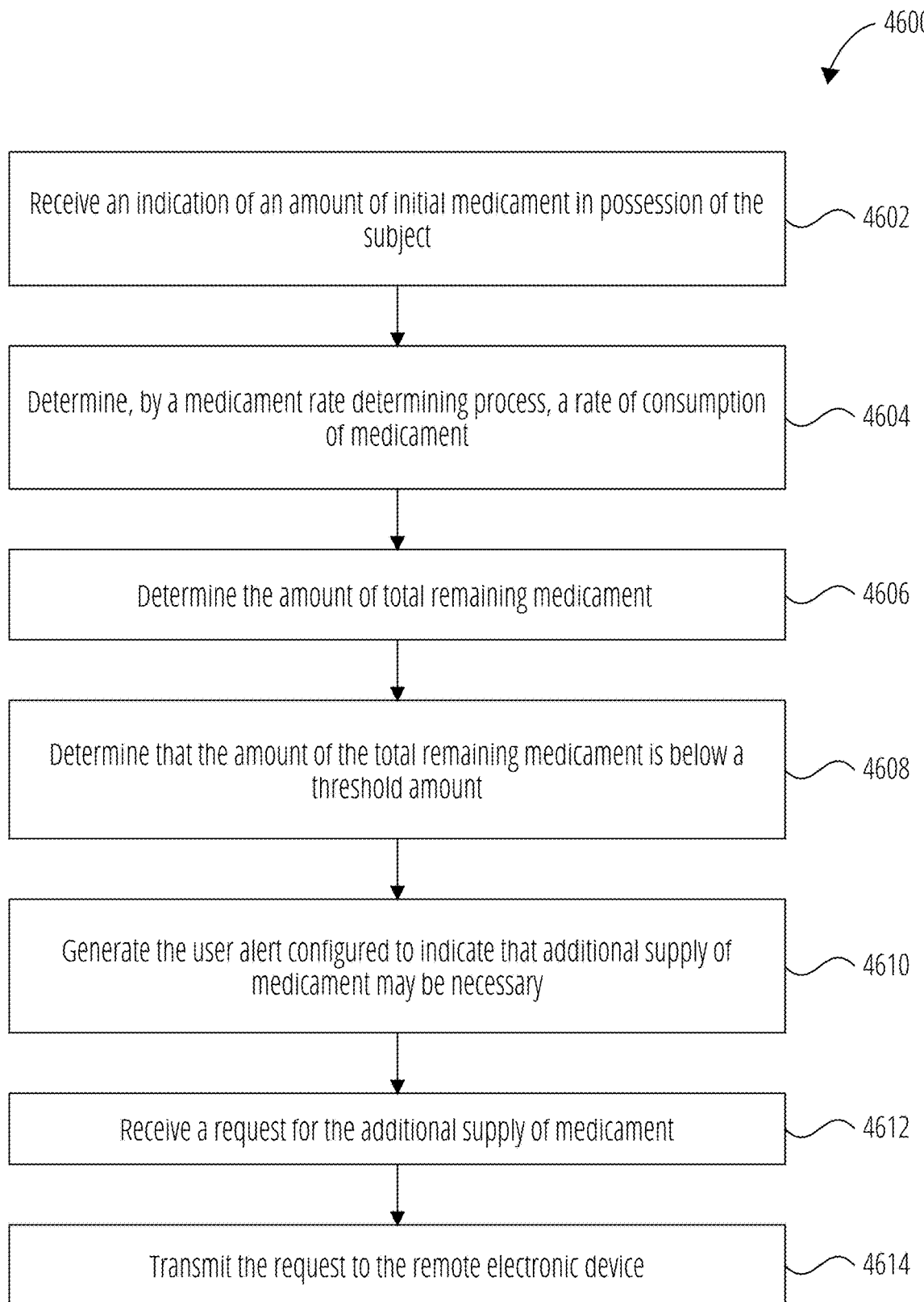
FIG. 46 is a flow chart flow diagram illustrating an example method that may be used by an AMD to determine an amount of total remaining medicament and/or to generate a user alert configured to indicate that additional supply of medicament may be necessary.

FIG. 46 is a flow chart flow diagram illustrating an example method that may be used by an AMD to determine an amount of total remaining medicament and/or to generate a user alert configured to indicate that additional supply of medicament may be necessary. The method 4600 may be performed by a medicament pump, such as a medicament pump 4500 described herein. At block 4602, the system receives an indication of an amount of initial medicament in possession of the subject. At block 4604, the system determines, by a medicament rate determining process, a rate of consumption of medicament. At block 4606, the system determines the amount of total remaining medicament (e.g., total usable medicament). At block 4608, the system determines that the amount of the total remaining medicament is below a threshold amount. At block 4610, the system generates the user alert configured to indicate that additional supply of medicament may be necessary. At block 4612, the system receives a request for the additional supply of medicament. At block 4614, the system transmit the request to the remote electronic device. Other steps and/or features may be included, such as those described in relation to the medicament pump 4500 and/or other systems/devices described above.

In some embodiments, a method may include ordering via a remote electronic device or computing system, such as one described herein. The system may provide an indication of an amount of initial medicament in possession of a subject. The system can determine, by a medicament rate determining process, a rate of consumption of medicament. The medicament rate determining process can include estimating an amount of time that has passed since a previous shipment of medicament. For example, the system may estimate a particular rate of usage of medicament and, based on a previously known amount of medicament on hand, the system can estimate an amount of time before the medicament supply is exhausted. The system may determine the amount of total remaining medicament based on a function of the amount of initial medicament in possession of the subject and the rate of consumption of the medicament. The system may determine that the amount of the total remaining medicament is below a threshold amount and, in response to determining that the amount of the total remaining medicament is below the threshold amount, automatically generate a user alert. The user alert may be transmitted to a user device, such as a medicament ordering control element, and the alert may indicate that additional supply of medicament may be necessary. In some embodiments, the system may receive a request for the additional supply of medicament. Additionally or alternatively, the system may automatically generate the request for the additional supply of medicament. The system can transmit the request to a target entity, such as an entity that manufacturers the medicament or an entity that stores the medicament.

Remote Therapy Modification

Providing glucose control therapy, such as glucose level control therapy, generally requires in-person change requests. For example, a subject who requires an updated therapy delivery may need to initiate a change request on the pump directly. Often this requires another individual to be present. For example, if the subject is a child, then an adult, such as a parent, a school nurse, a doctor, or some other individual, may need to initiate the request and/or approve the request. This may involve a basic meal request or may be an urgent or critical situation where additional/less medicament is needed. This requirement to have another individual present has been, at best, cumbersome or annoying for the subject and the other individuals involved. However, more critically, it can create a potential hazard for the subject who may need the updated therapy delivered. Receiving too much and/or too little of a medicament (e.g., insulin) can potentially dangerous. Additionally or alternatively, receiving the right amount of medicament at the wrong time (e.g., too late) can be similarly problematic or even dangerous.

Meal announcements and other therapy changes have generally been performed on ambulatory medicament pumps directly and/or on a remote control system coupled to a medicament pump via a short-range wireless connection (e.g., BLE, etc.). However, structural and logistical problems have existed for allowing such control to be beyond mere short-range control. Systems and methods described herein offer solutions to such problems.

As described herein, meal announcements and other changes to glucose control therapy can be made remotely via more distant connections. In some examples, a parent or other individual (e.g., adult) may be able to make a meal announcement or other therapy change via a user device (e.g., a smartphone), which may be able to connect to the ambulatory medicament pump via a long-range wireless data interface (e.g., a Long-Term Evolution (LTE) modem, etc.). In some embodiments, a subject (e.g., a child) can additionally or alternatively request a meal announcement from the ambulatory medicament pump and another individual (e.g., a parent, doctor, nurse) can approve remotely. In some embodiments, the system includes an interface that asks the subject to take a photo of the plate. This may promote easier and more accurate meal announcements and approvals of the same.

Meal announcements are not the only changes that may be available in the embodiments described herein. In some cases, a subject or other individual may want to pause or stop delivery of therapy. This may be particularly relevant during activities (e.g., swimming, sports, where delivery is not possible, not possible, not comfortable, or otherwise not preferred.

In some scenarios, the remote therapy delivery can supply critical updates to a subject's therapy during an emergency situation. For example, the subject may receive a counter-regulatory dose if, for example, a glucose sensor (e.g., a CGM) is offline and the subject is unresponsive. In some embodiments, the system can trace a level of glucose level in the subject's body. A subject may require many doses of medicament and it can be advantageous to allow a subject to order the medicament directly from and/or via the medicament pump or related system.

With continued reference to FIG. 45, in some cases, the ambulatory medicament pump 4500 may be configured to transmit a request to modify glucose control therapy delivered to a subject via a remote computing environment.

In some cases, changes of delivery of therapy may need to be made remotely. For example, if a proper amount of medicament (e.g., insulin, glucagon, etc.) is not delivered when needed, a subject's glucose level may increase or decrease uncontrollably. This can be a dangerous scenario. Having the ability to control the amount of delivered medicament may be a very important component to proper care, and the medicament pump 4500 and related systems described herein may allow for better control, including remote control, of therapy delivery.

In some examples, the medicament pump 4500 includes a therapy modification control element (not shown), which may allow user input and/or provide feedback to a user.

In some embodiments, as the subject moves around, there is a danger that the subject will be away from those who can provide the necessary therapy changes if the subject needs it.

The data interface 4508 may be in communication (e.g., wired, wireless) with one or more of a glucose sensors 4514 (e.g., via a glucose sensor connection 4520 with a network 4516 (e.g., via a network connection 4522)), and/or with a user device 4518 (e.g., via a user device connection 4524)). Each of the connections of the glucose sensor connection 4520, network connection 4522, user device connection 4524 may be one-way or two-way. The data interface 4508 may also be in communication with other elements of the medicament pump 4500, such as the pump motor 4506, the cartridge receptacle 4502 (or the cartridges within the cartridge receptacle 4502), and/or the pump controller 4504. The communication with the other elements of the medicament pump 4500 may be via a wired connection.

In some embodiments, the medicament pump 4500 may include a therapy modification control element (not shown in FIG. 45), such as a user interface, which may be a graphical user interface. The therapy modification control element may be integrated into the medicament pump 4500 or may be a separate element. For example, the therapy modification control element may be integrated with the user device 4518 described above. The user interface may be operatively coupled to the medicament pump 4500 via, for example, the wireless data interface. In some cases, the touchscreen display may display a therapy modification interface for modifying therapy the subject and/or for receiving subject inputs on the therapy modification interface.

The medicament pump 4500 can transmit a request to modify glucose control therapy (e.g., glucose control therapy) that is delivered to the subject to a remote electronic device, such as a remote computing environment. The request can be requested via the therapy modification control element.

In some embodiments, the medicament pump 4500 may receive an indication that the request to modify therapy is approved. The indication may be a type of confirmation signal. In response to the indication that the request to modify the glucose control therapy is approved, the medicament pump 4500 can instruct the pump controller to modify the glucose control therapy delivered to the subject. The modified glucose control therapy may include an increase in medicament, a decrease in medicament, a temporary modification, a permanent modification, a modified pattern of therapy delivery, and/or some other modification.

In some embodiments, the medicament pump 4500 can transmit a connection confirmation signal to the remote electronic device. The connection confirmation signal can initiate a determination that a wireless wide area network data connection exists between the data interface and the remote electronic device. However, in some embodiments, the medicament pump 4500 must receive a return confirmation signal to confirm that the proper wireless connection exists. Accordingly, the medicament pump 4500 may receive (e.g., via the wireless data interface) a return confirmation signal from the remote computing environment. The return confirmation signal can indicate that the wireless wide area network data connection exists between the wireless data interface and the remote electronic device. Once the return confirmation signal is received, the medicament pump 4500 can determine that the wireless wide area network data connection exists between the wireless data interface and the remote electronic device. Confirmation of the wide-area wireless connection can allow for the transmission of the dose control signal. In some embodiments, simple wireless connections are insufficient, but rather a wide-area network connection must first be established.

A subject may request to modify the glucose control therapy via the medicament pump 4500 (e.g., via a user interface coupled to the medicament pump 4500). Based on this request and on the determination that the wireless wide area network data connection exists, the medicament pump 4500 can then transmit, via the wireless data interface, a confirmation signal to the remote electronic device. The confirmation signal can indicate to the medicament pump 4500 and/or to the subject that the request to modify the glucose control therapy was successfully received.

In some embodiments, the medicament pump 4500 can transmit a third-party alert to the remote electronic device. The third-party alert may be based at least in part on the modification of the glucose control therapy delivery. The third-party alert can include one or more of a variety of alerts. For example, the third-party alert may indicate that the modification of the glucose control therapy delivery was successful. Additionally or alternatively, the third-party alert may include one or more details of the therapy change, such as an attribute of the glucose control therapy delivery as modified.

As noted above, the medicament pump 4500 may include a user interface that receives the request to modify the glucose control therapy. The user interface may be coupled to the medicament pump 4500 via a wired or wireless data connection. The medicament pump 4500 can generate (e.g., for display) on the user interface a user alert based on the modification of the glucose control therapy delivery. The user alert may include one or more of a variety of alerts. For example, the user alert may include an indication that the modification of the glucose control therapy delivery was successful. Additionally or alternatively, the user alert may include an attribute of the glucose control therapy delivery as modified. Other alerts are possible.

The medicament pump 4500 may include a connection verification system that is in communication with the processor 4512 and/or the data interface 4508. The connection verification system can determine that the wireless wide area network data connection exists between the data interface 4508 and the remote electronic device. This determination may be based on a confirmation signal, such as the connection confirmation signal described herein.

In some embodiments, the medicament pump 4500 is configured to transmit a report to the remote electronic device (or another remote electronic device). The report may be based on the modification of the glucose control therapy delivery and may be stored at the remote computing environment. The report may explain one or more details of the modification of glucose control therapy. For example, the report may include a time of the modification, an amount of the modified glucose control therapy, an amount of the original glucose control therapy, The medicament rate determining process can include determining a number of times a cartridge was installed in the cartridge receptacle 4502. This may be determined in part by a determination by the processor 4512 of the number of times the cartridge receptacle 4502 has been disconnected and/or by a user input of the number of times a cartridge has been installed. In some examples, this number may be estimated based on a passage of time and/or based on a prior known rate of usage by the subject. The estimation may use predictive analytics based on a historical use rate. Additionally or alternatively, the medicament rate determining process can include determining a rate of installation of new cartridges in the cartridge receptacle. This rate may rely on inputs described relating to the determining of the number of number of times a cartridge was installed in the cartridge receptacle 4502, such as determining a number of cartridges installed over a period of time. This may be especially valuable, for example, in medicament pumps medicament pump 4500 that use pre-filled cartridges.

If the medicament pump 4500 determines that the therapy delivery (e.g., amount and/or rate of medicament delivery) is below or above a threshold amount, the medicament pump 4500 can generate (e.g., automatically) a user alert that indicates that additional delivery of medicament may be necessary. As with other alerts described herein, the user alert may include any type of alert.

Alerts may vary based on when amount and/or rate of medicament delivery is determined to be below or rising above the threshold amount was detected, the time of day, or the detected activity of a subject (e.g., sleep, abnormal activity, or elevated activity, such as exercise). As described above, the alert frequency may be for a static time period (e.g., every 5 hours) or may ramp towards more frequency (e.g., every 5 hours for 1 to 3 reminders, every 4 hours for 3 to 6 reminders, etc.), or may change based on time of day (e.g., snooze alerts during sleeping hours for non-urgent alerts), etc.

The alert may prompt the subject (and/or other user) to modify the therapy that is delivered to the subject. The alert can recommend an amount of therapy to be delivered and/or an indication of an estimated time before the current level of therapy raises an urgent or critical medical situation.

Once the request for modifying the therapy delivered to the subject is received, the medicament pump 4500 can transmit, via the data interface 4508, the request to any remote electronic device, such as the network 4516. The request may be done wirelessly. The remote electronic device may include one or more of the user device 4518, the network 4516, and/or the glucose sensor 4514.

In some embodiments, the medicament pump 4500 can receive, via the data interface 4508, a confirmation signal from the remote electronic device that the user input was received by the remote electronic device. The confirmation signal may serve as a type of record of the request and may include an amount of medicament delivered, a beginning time of the medicament delivery, an end time of the medicament delivery, the rate of medicament delivery, details of the previous medicament delivery (e.g., total medicament delivered, rate of delivery, time of start of previous medicament delivery), and/or some other aspect. The medicament pump 4500 may generate a success alert based on the received confirmation signal that the request for the modification of delivery of medicament was successfully received by the remote electronic device. The success alert may be provided via the therapy modification control element or through another device.

Figure 47:
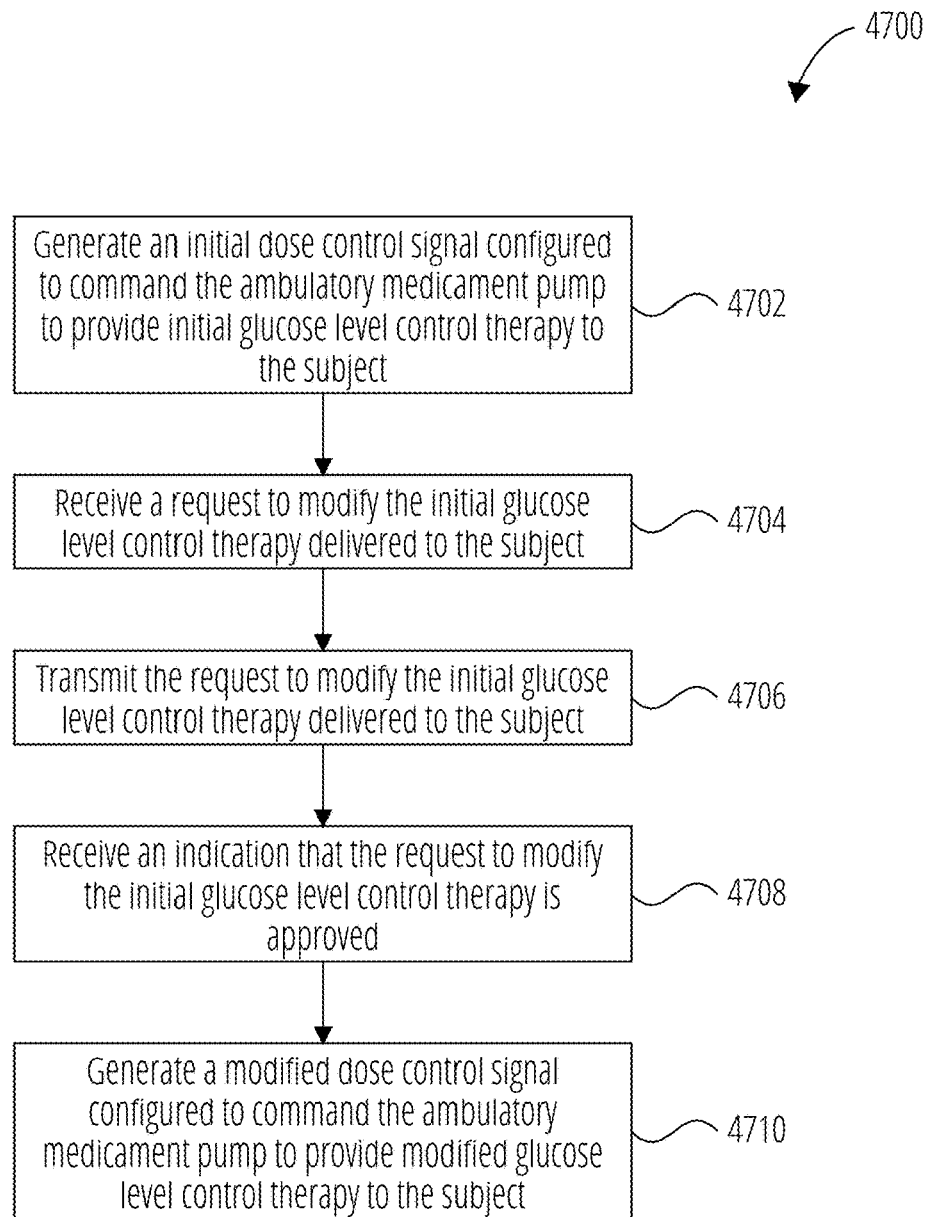
FIG. 47 is a flow chart flow diagram illustrating an example method that may be used by a medicament pump to modify glucose level control therapy delivered by an ambulatory medicament pump to a subject.

FIG. 47 is a flow chart flow diagram illustrating an example method 4700 that may be used by a medicament pump to modify glucose control therapy delivered by an ambulatory medicament pump to a subject. The ambulatory medicament pump may be disposable. The method 4700 may be performed by a medicament pump, such as a medicament pump 4500 described herein. At block 4702, the system generates an initial dose control signal. The initial dose control signal is configured to command the ambulatory medicament pump to provide initial glucose control therapy to the subject. At block 4704, the system receives (e.g., via user interaction with a therapy modification control element) a request to modify the initial glucose control therapy delivered to the subject. At block 4706, the system transmits to a remote computing environment the request to modify the initial glucose control therapy delivered to the subject. The transmission may be via a wireless wide area network data interface that is in communication with an electronic processor of the ambulatory medicament pump. At block 4708, the system receives, via the wireless wide area network data interface, an indication that the request to modify the initial glucose control therapy is approved. At block 4710, the system generates a modified dose control signal in response to the indication that the request to modify the initial glucose control therapy is approved. The modified dose control signal commands the ambulatory medicament pump to provide modified glucose control therapy to the subject.

In some embodiments, the method includes transmitting a connection confirmation signal to the remote computing environment. The connection confirmation signal initiates a determination that a wireless wide area network data connection exists between the wireless wide area network data interface and the remote computing environment. Additionally or alternatively, the system receives a return confirmation signal from the remote computing environment. The return confirmation signal indicates that the wireless wide area network data connection exists between the wireless wide area network data interface and the remote computing environment. Based on the return confirmation signal, the system determines that the wireless wide area network data connection exists between the wireless wide area network data interface and the remote computing environment. Based on the request to modify the initial glucose control therapy and on the determination that the wireless wide area network data connection exists, the system transmits a confirmation signal to the remote computing environment. The confirmation signal indicates that the request to modify the glucose control therapy was successfully received. Sending and receiving data to and from the system may be via a wireless wide area network data interface. Other aspects of the method may be performed as described with relation to the functionality of the medicament pump 4500 and/or other systems described above.

Figure 48:
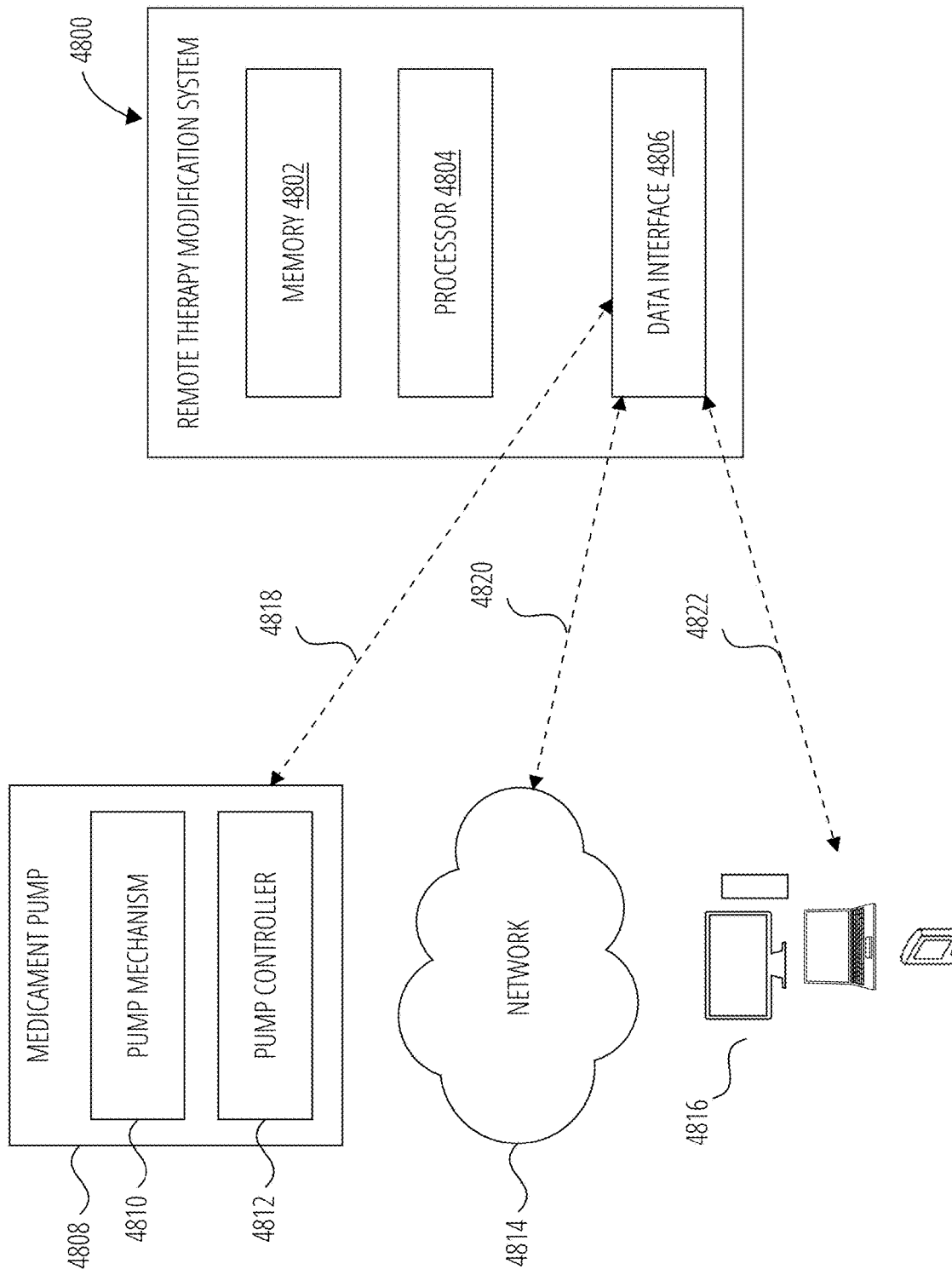
FIG. 48 is a flow chart flow diagram illustrating an example method that may be used by a remote therapy modification system to generate commands to remotely modify glucose level control therapy delivered to a subject by an ambulatory medicament pump.

FIG. 48 shows an example remote therapy modification system 4800 that is configured to generate commands to remotely modify glucose control therapy delivered to a subject by a medicament pump 4808. The remote therapy modification system 4800 includes a non-transitory memory 4802, an electronic hardware processor 4804, and a data interface 4806. The data interface 4806 may include a wireless and/or wired data interface. The data interface 4806 can include a short-range wireless data interface.

The data interface 4806 may be in communication (e.g., wired, wireless) with one or more of a medicament pump 4808 (e.g., via a medicament pump connection 4818), with a network 4814 (e.g., via a network connection 4820), and/or a user device 4816 (e.g., via a user device connection 4822). Each of the connections 4818, 4820, 4822 may be one-way or two-way. The data interface 4806 may include functionality described above with respect to the data interface 4508.

The medicament pump 4808 may be any medicament pump described herein, such as the pump AMD 100 and/or pump 212. The pump controller 4812 is configured to direct medicament from a medicament reservoir to the subject using the pump mechanism 4810.

The data interface 4806 may be able to communicate (e.g., wirelessly, via wired connection) with a medicament pump 4808, a network 4814, and/or a user device 4816 via respective connections 4818, 4820, 4822. The data interface 4806 can communicate with the medicament pump 4808, such as via a wireless connection. The medicament pump 4808 can include a pump mechanism 4810 and a pump controller 4812. In some embodiments, the data interface 4806 communicates with the pump controller 4812 of the medicament pump 4808.

The network 4814 may include any wired network, wireless network, or combination thereof. The network 4814 may include one or more features of the network 4516 described above. For example, the network 4814 may include a remote computing environment. The user device 4816 may be any user device described above, such as the user device 4518.

The remote therapy modification system 4800 may be configured to store a plurality of pump controller decoding profiles corresponding to respective pump controllers. The remote therapy modification system 4800 can be configured to select a pump controller decoding profile from a plurality of pump controller decoding profiles. The pump controller profile can be configured to operate with a particular pump, with a brand of pump, and/or with a different grouping of pump.

The remote therapy modification system 4800 can be configured to determine a status of the medicament pump 4808, such as a status of the pump controller 4812. The remote therapy modification system 4800 can receive, via the data interface 4806, an encoded pump status signal from the pump controller 4812. The encoded pump status signal can include data corresponding to an availability of the ambulatory medicament pump to deliver medicament to the subject. For example, the pump status signal can indicate that the medicament pump 4808 is ready to deliver glucose control therapy to a subject (e.g., that the medicament pump 4808 is operatively connected to the subject). The remote therapy modification system 4800 can additionally or alternatively receive an encoded medicament delivery signal from the pump controller pump controller 4812. The encoded medicament delivery signal can include data corresponding to an amount of medicament dosed to the subject.

Each pump controller decoding profile can be configured to decode various data from the medicament pump 4808. For example, the decoding profile can be configured to decode an encoded pump status signal, an encoded medicament delivery signal, encoded therapy data (e.g., glucose control therapy data), encoded glucose control parameter data, an encoded glucose level of the subject, encoded data indicating a glucose trend, and/or other encoded data. The glucose trend can indicate a predicted change in the glucose level of the subject over a time period and/or at a given time. The encoded therapy data can contain therapy data, such as described herein. The glucose control parameter data can include one or more glucose control parameters, which may include any glucose control parameter described herein. The selected pump controller decoding profile can correspond to the pump controller 4812 that is operatively coupled to the medicament pump 4808. Using the selected pump controller decoding profile(s), the remote therapy modification system 4800 can decode the corresponding encoded data. In some embodiments, the remote therapy modification system 4800 can calculate the dose control signal using a control algorithm (described above) that is configured to calculate regular correction boluses of glucose control agent in response to at least the glucose level of the subject.

In some embodiments, in order to properly transmit the decoded data to the pump controller 4812 (e.g., for instructions on delivering glucose control therapy) of the corresponding medicament pump 4808, the remote therapy modification system 4800 can proceed to encode the data so that it can be read by the corresponding pump controller 4812. Note that the remote therapy modification system 4800 may receive encoded data from a first medicament pump and may transmit encoded data to a second medicament pump. Like with the pump controller decoding profiles, the remote therapy modification system 4800 may have stored thereon one or more of a plurality of pump controller encoding profiles. The remote therapy modification system 4800 can select a pump controller encoding profile from the plurality of pump controller encoding profiles. The selected pump controller encoding profile can correspond to the respective pump controller 4812. The pump controller encoding profile can be configured to encode the therapy data, the glucose control parameter data, the dose control signal, and/or any other data that may be transmitted to the pump controller 4812.

The remote therapy modification system 4800 may determine that the medicament pump 4808 is ready to deliver medicament to the subject. In some embodiments, the remote therapy modification system 4800 can encode a dose control signal for commanding the medicament pump 4808 to administer glucose control therapy (e.g., using the pump mechanism 4810) via infusion of glucose control agent into the subject.

In some embodiments, the remote therapy modification system 4800 can transmit via the data interface 4806 data to a graphical user interface. For example, the remote therapy modification system 4800 may transmit a glucose level of the subject, glucose control therapy data (e.g., a time and/or amount of delivered medicament), one or more glucose control parameters, an indication of the glucose trend of the subject, and/or other similar data to the graphical user interface for display. Additionally or alternatively, the data may be transmitted to a remote device, such as a user device 4816 and/or the network 4814, via a corresponding connection 4820, 4822.

As noted above, the remote therapy modification system 4800 can receive, store, and/or transmit one or more glucose control parameters to the one or more devices illustrated, such as the medicament pump 4808 (e.g., the medicament pump to be replaced, a replacement medicament pump), the user device 4816, and/or the network 4814. As described above, example glucose control parameters can include a variety of parameters. A non-exhaustive list of such glucose control parameters includes, but is not limited to: an insulin decay rate constant associated with a decay rate of insulin at a subcutaneous depot of the subject, a clearance time associated with an estimate of an amount of time for a bolus of insulin to be utilized by the subject, an insulin rise rate constant associated with a rise rate of insulin in blood of the subject after a bolus of insulin, a value (e.g., half-life value) associated with when a concentration of insulin in blood plasma of the subject reaches a threshold concentration (e.g., half, maximum) in the blood plasma, a weight of the subject, an age of the subject, a learned parameter (e.g., via a control algorithm described herein), glucose level data of the subject, a model parameter associated with a pharmacokinetic (PK) model, a health state of the subject (e.g., sick, pregnant, etc.), a parameter associated with an activity level of the subject, an aspect of a diet of the subject (e.g., smoker), a basal rate of insulin delivered to the subject, a correction factor, a carbohydrate ratio associated with the subject, a glucagon control parameter, demographic information associated with the subject, a sensitivity constant associated with the subject's sensitivity to a glucose level or bolus of medicament, or any other parameter that may be used in calculating a dose control signal, such as those described herein. Other parameters may be included, such as those with reference to the control algorithm above.

The remote therapy modification system 4800 can receive and/or store various data related to an amount of insulin on board and/or a value used in a pharmacokinetic (PK) model of the control algorithm described above. The remote therapy modification system 4800 may be configured to execute the control algorithm in some embodiments. The glucose control therapy data may include the amount of insulin on board and/or the value used in the PK model.

In some embodiments, the remote therapy modification system 4800 may include a therapy modification control element (not shown in FIG. 48), such as the therapy modification control element described above. The therapy modification control element may be integrated into the remote therapy modification system 4800 or may be a separate element. For example, the therapy modification control element may be integrated with the user device 4518 described above. The user interface may be operatively coupled to the remote therapy modification system 4800 via, for example, the wireless data interface. The user interface can include a touchscreen display. Other features of the therapy modification control element are described above.

The medicament pump 4808 can receive, for example via user interaction with the therapy modification control element described above, a request to remotely modify glucose control therapy that is delivered to the subject by the medicament pump. In some embodiments, the request to remotely modify glucose control therapy may be done via an automated system. For example, the system may receive automated therapy modification via a remote computing device, such as the network 4814 and/or the user device 4816. The automated system may run a machine algorithm that automatically determines a new dose control signal based on learned factors associated with the subject. Modifying the glucose control therapy can include modifying one or more offsets, targets, times, and/or setpoints. For example, the modification may include a change in meal rise and/or a meal rise range. The meal rise change may be in mg/dL. The remote therapy modification system 4800 can modify a snack size (e.g., a threshold of carbs above which a meal rise is triggered), an offset time (e.g., a length of time after a bolus before begin of significant reduction in glucose levels), and/or an acting time (e.g., time when insulin is delivered to reduce glucose). The remote therapy modification system 4800 may modify a target range of glucose level of the subject, an amount and/or ratio of carbohydrates covered by insulin, and/or an insulin sensitivity.

Modifying therapy may include initiating and/or administering therapy. In some embodiments, modifying therapy can include administering an emergency response. For example, the remote therapy modification system 4800 may transmit an instruction to provide a rescue glucagon bolus via the medicament pump 4808 in an emergency. The modified therapy (e.g., the emergency response) can be based on a location of the subject, a movement of the subject (e.g., tracked by the medicament pump 4808 and/or the remote therapy modification system 4800), etc. In some embodiments, modification of therapy can include changing control parameters or providing a bolus.

In some embodiments, the remote therapy modification system 4800 can develop recommendations for modifications to the glucose control therapy. For example, as noted above, in some embodiments the remote therapy modification system 4800 can employ machine learning to develop a learned understanding of the likely needs of the subject based, for example, on historical trends or other historical data accessed by the remote therapy modification system 4800. In some embodiments the remote therapy modification system 4800 can transmit (e.g., to a user device 4816, the medicament pump 4808) a recommended modification that a subject or other user can accept or reject.

The remote therapy modification system 4800 can receive a connection confirmation signal from a remote electronic device (e.g., a remote computing environment). The connection confirmation signal can indicate that a wireless wide area network data connection exists between the remote electronic device and the medicament pump 4808. It may be beneficial to confirm an establishment of a wide area network because the remote therapy modification system 4800 can be sure that the data to be transmitted is available to be transmitted via, for example, the internet.

In response to receiving the request to modify the glucose control therapy and receiving the connection confirmation signal, the remote therapy modification system 4800 can transmit a remote therapy modification command to the remote electronic device. The remote therapy modification command can modify the glucose control therapy delivered to the subject via the ambulatory medicament pump. In some embodiments, the remote therapy modification command comprises an updated dose control signal.

Additionally or alternatively, the remote therapy modification system 4800 can receive a modification verification signal from the remote electronic device. The modification verification signal can indicate whether the glucose control therapy delivered by the ambulatory medicament pump was successfully modified. If the modification verification signal is confirmatory, then the modification verification signal indicates that the updated glucose control therapy was successfully modified. Additionally or alternatively, if the modification verification signal is a denial signal, then the modification verification signal can transmit that the modification of therapy was unsuccessful. In some embodiments, in response to the modification verification signal being a denial signal, the remote therapy modification system 4800 may manually and/or automatically transmit a second remote therapy modification command. Additionally or alternatively, the remote therapy modification system 4800 may transmit an error signal to a remote electronic device (e.g., the user device 4816, the network 4814) if a threshold number of modification verification signals (e.g., two, three, four, five) are denial signals.

In some embodiments, the remote therapy modification system 4800 can receive the remote therapy modification request from the medicament pump. The modification request may designate that the request to modify the glucose control therapy delivered via the medicament pump. For example, it may be advantageous for the subject to be able to make and transmit the modification directly from the medicament pump. This can allow the subject, who may be a child or someone who requires supervision from a responsible adult, to have more control over their own therapy.

The remote therapy modification system 4800 may be able to transmit a subject alert to the remote electronic device. The subject alert may be based at least in part on the modification of the glucose control therapy delivery. The subject alert can indicate one or more details of the therapy modification. These details may then be accessible to a responsible adult and can provide a better flow of communication to a caretaker or other responsible adult. The subject alert may, for example, include an indication that the modification of the glucose control therapy delivery was successful. Additionally or alternatively, the subject alert can include an attribute of the glucose control therapy delivery as modified. The attribute of the glucose control therapy may be any attribute related to the modified glucose control therapy, such as those described above. For example, the attribute could include one or more of a therapy offset, a therapy target, a time/duration, and/or a therapy setpoint, such as those described herein. The remote therapy modification system 4800 can generate for display (e.g., on the therapy modification control element, on a remote electronic device) a user alert. The user alert may be based on the modification of the therapy delivery. The user alert can include an indication that the modification of the therapy delivery was successful. Additionally or alternatively, the user alert may include an attribute of the therapy delivery as modified. The user alert may be transmitted to a remote electronic device, such as the user device 4816, which may be where a request for therapy change was originated by the user. The subject alert may be transmitted to the medicament pump 4808 or an associated device where the subject may be alerted.

Additionally or alternatively, the remote therapy modification system 4800 may transmit a report to a remote computing environment, such as the network 4814. The remote computing environment may include one or more details of the modified therapy. The report may include a time stamp of when the therapy was modified, for example. The report may be configured for storage at the remote computing environment. Additionally or alternatively, the report may be configured to store a history of therapy modification that has been issued for the subject and/or to the medicament pump 4808. In some embodiments, the report may include details of the person who requested the modification of therapy.

Figure 49:
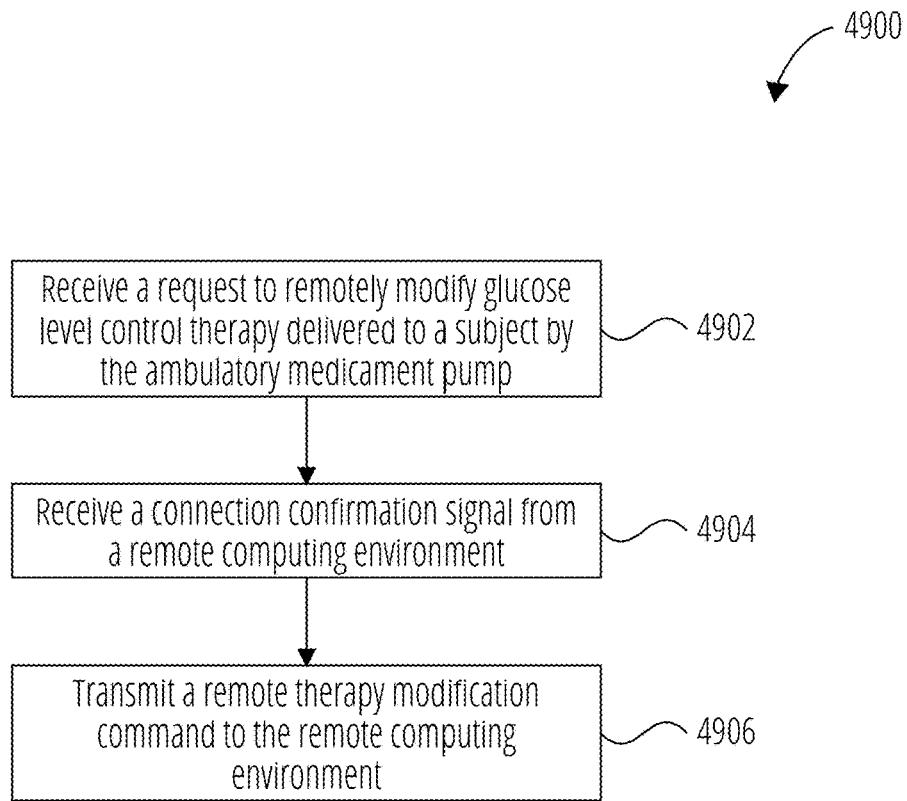
FIG. 49 is a flow chart flow diagram illustrating an example method that may be used by a remote therapy modification system to modify glucose level control therapy delivered by an ambulatory medicament pump to a subject.

FIG. 49 shows a flow diagram illustrating an example method 4900 that may be used by a remote therapy modification system (e.g., the remote therapy modification system 4800) to generate commands to remotely modify glucose control therapy delivered to a subject by an ambulatory medicament pump. The system can receive a request to remotely modify glucose control therapy delivered to a subject by the ambulatory medicament pump at block 4902. At block 4904 the system receives a connection confirmation signal from a remote computing environment. At block 4906, the system transmits a remote therapy modification command to the remote computing environment. The remote therapy modification command may be configured to modify the glucose control therapy delivered to the subject via the ambulatory medicament pump. In some embodiments, the remote therapy modification command instructs a modified dose control signal to the ambulatory medicament pump. In some embodiments, the system receives an indication that the request to modify the initial glucose control therapy is approved. The system may generate a modified dose control signal that is configured to command the ambulatory medicament pump to provide modified glucose control therapy to the subject.

In some embodiments, the method 4900 includes receiving the remote therapy modification request from the ambulatory medicament pump. The modification request can designate that the request to modify the glucose control therapy be delivered via the ambulatory medicament pump. In some embodiments, the system transmits a subject alert to the remote computing environment. The subject alert may be based at least in part on the modification of the glucose control therapy delivery. The subject alert may include one or more details, such as is described above.

Example Glucose level control System

Figure 50:
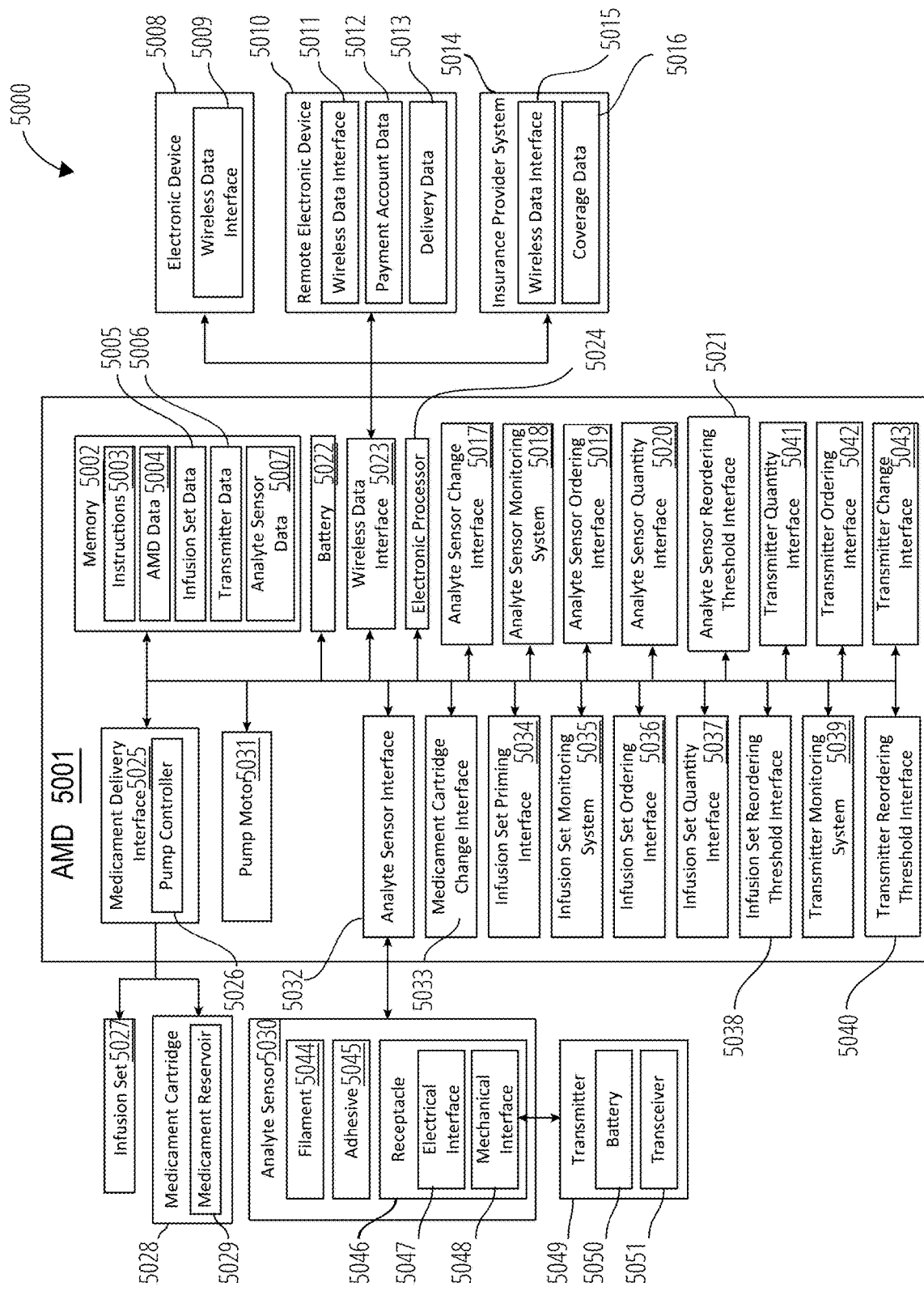
FIG. 50 shows a block diagram of another example glucose level control system.

FIG. 50 illustrates a block diagram of features of a glucose level control system (GLCS) 5000 that may include an example AMD 5001. The AMD 5001, as described elsewhere here, can include more or less features than those illustrated. The AMD 5001 can include those features described and/or illustrated in reference to other AMDs or GLCSes herein. In some embodiments, the AMD 5001 may not include, for example, a pump motor 5031 to function as some GLCSes discussed herein (e.g., in communication with an AMP or to direct administration of medicament via a dose recommendation or dose output). One or more of the AMD 5001, electronic device 5008, remote electronic device 5010, and/or insurance provider system 5014 can be referred to as a system (e.g., glucose level control system). The glucose level control system 5000 or components thereof can include more or less features as shown and described, including incorporating those features described in reference to other features described or shown herein.

The AMD 5001 can include one or more systems for delivering medicament to a patient for therapy. For example, the AMD 5001 can include a medicament delivery interface 5025 that is configured to mechanically connect to an infusion set 5027 and medicament cartridge 5028. The medicament delivery interface 5025 can operatively couple a pump motor 5031 to a medicament reservoir 5029 of the medicament cartridge 5028 that contains a medicament (e.g., insulin, glucagon, etc.). The pump motor 5031 can provide a motive force to direct the medicament from the medicament reservoir 5029 and through the infusion set 5027 such that medicament is delivered beneath the skin of the subject (e.g., to a subcutaneous depot of the subject) for treatment. The medicament delivery interface 5025 can include a coupler or interface connection, that can releasably couple to the medicament cartridge 5028 such that a depleted medicament cartridge 5028 can be conveniently replaced by a new medicament cartridge 5028 with medicament. In some variants, the AMD 5001 can include a cavity or reservoir that is configured to hold a medicament without the medicament being held within a cartridge—e.g., cartridges being emptied into the cavity or reservoir. The infusion set 5027 can include a needle, cannula, insertion device (e.g., spring-loaded tool to insert the set), etc. The infusion set 5027 can be an angled or straight type set. The infusion set 5027 can be an insulin infusion set and/or a glucagon infusion set. In some variants, the infusion set 5027 can be a two-channel infusion set that can deliver insulin and glucagon.

The AMD 5001 can include an analyte sensor interface 5032 that can interface (e.g., facilitate communication) with an analyte sensor 5030 (e.g. with a transceiver). As described elsewhere herein, the analyte sensor 5030 can monitor a subject's glucose level, blood insulin level, etc. The analyte sensor 5030 can include a thin wire or filament 5044 that is configured to be inserted under the skin of the subject. The analyte sensor 5030 can be coupled to the subject and the thin wire or filament 5044 adhered (e.g., taped) to the subject's skin when inserted therein via an adhesive 5045. The analyte sensor 5030 can include a receptacle 5046 that can receive a transmitter 5049. The receptacle 5046 can include an electrical interface 5047 and/or mechanical interface 5048 configured to interface with the transmitter 5049. The electrical interface 5047 can communicate data and/or conduct current between the transmitter 5049 and the analyte sensor 5030. A current can be applied to the thin wire or filament 5044 from a battery 5050 of the transmitter 5049 by way of the electrical interface 5047. The electrical properties resulting from the applied current can be measured in the interstitial fluid in subcutaneous tissue. By way of correlations, the measured resistance can be used to determine the levels of glucose. The mechanical interface 5048 can facilitate the coupling of the transmitter 5049 to the receptacle 5046 and analyte sensor 5030. The transmitter 5049 can have a transceiver 5051 (e.g., Bluetooth) to communicate data, such as the measured resistance, to the AMD 5001 via one of the data transmission techniques described herein. The analyte sensor 5030 can include a processor and micro-controller. Analyte sensors 5030 may need to be periodically replaced (e.g., every 7-10 days), which can be due to deteriorating performance and/or sanitation. The transmitter 5049 may need to be periodically replaced (e.g., every 14-28 days), which can be due to deteriorating performance. The transmitter 5049 can be decoupled from a given analyte sensor 5030 and coupled to a new analyte sensor 5030 due to the longer life of use of the transmitter 5049.

The AMD 5001 can include a memory 5002, which can be the same as or similar to the main memory 616 and/or storage 618. The memory 5002 can refer to multiple types of memory. The memory 5002 can be any type of memory that can store instructions and communicate them to an electronic processor 5024 and receive executed instructions from the electronic processor 5024. The memory 5002 can include random access memory ("RAM") and/or read-only memory ("ROM"). The memory 5002 can be any type of computer storage that can receive data, store data, and transmit data to other features and/or components of the AMD 5001. Types of memory 5002 can include, but are not limited to, magnetic disk memory, optical disk memory, flash memory and the like. The electronic processor 5024 can be the same as or similar to the processor 614. The electronic processor 5024 may be any type of general-purpose processing unit ("CPU"). In some variants, multiple electronic processors can be included, such as, but not limited to, complex programmable logic devices ("CPLDs"), field programmable gate arrays ("FPGAs"), application-specific integrated circuits ("ASICs") or the like.

The memory 5002 can include instructions 5003 executable by the electronic processor 614. The instructions 5003 can be executed to perform the methods, tasks, processes, actions, analysis, etc. described herein. The memory 5002 can store AMD data 5004. The AMD data 5004 can include information regarding the AMD 5001 such as battery level, manufacturer's warranty information, status, usage information, etc. The memory 5002 can include infusion set data 5005 such as usage data, data regarding remaining infusion sets, data regarding an initial quantity of infusion sets, average usage period (e.g., use life) for an infusion set, etc. The infusion set data 5005 can be used to determine when the subject should reorder additional infusion sets. The memory 5002 can include transmitter data 5006 such as usage data, data regarding remaining transmitters, data regarding an initial quantity of transmitters, average usage period (e.g., use life) of transmitter, etc. The transmitter data 5006 can be used to determine when the subject should reorder additional transmitters. The memory 5002 can include analyte sensor data 5007 such as usage data, data regarding remaining analyte sensors, data regarding an initial quantity of analyte sensors, average usage period (e.g., use life) of an analyte sensor, etc. The analyte sensor data 5007 can be used to determine when the subject should reorder additional analyte sensors. The AMD data 5004, infusion set data 5005, transmitter data 5006, and/or analyte sensor data 5007 can be processed (e.g., analyzed) by any of the AMD 5001, electronic device 5008, and/or remote electronic device 5010. For example, in some variants, the AMD 5001 can communicate the AMD data 5004, infusion set data 5005, transmitter data 5006, and/or analyte sensor data 5007 to the electronic device 5008 and/or remote electronic device 5010 for processing (e.g., analyzing) to make any of the determinations or recommendations described herein (e.g., when to order additional supplies, how much to order, reordering thresholds, etc.).

The AMD 5001 can include a battery 5022. The battery 5022 can be rechargeable or replaceable with disposable batteries.

The AMD 5001 can include a wireless data interface 5023 that facilitates communication between the AMD 5001 and an electronic device 5008 (e.g., smart phone, laptop, desktop, tablet, smart wearable device, etc.), remote electronic device 5010 (e.g., remote computing environment), and/or insurance provider system 5014 (e.g., remote computing environment of an insurance provider associated with the subject). The electronic device 5008 can include a wireless data interface 5009 to facilitate communication. The remote electronic device 5010 can include a wireless data interface 5011 to facilitate communication. The insurance provider system 5014 can include a wireless data interface 5015 to facilitate communication. The AMD 5001, electronic device 5008, remote electronic device 5010, insurance provider system 5014, as described herein, can each include a transceiver to facilitate communication. In some variants, the AMD 5001 can communicate directly with the electronic device 5008, remote electronic device 5010, and/or insurance provider system 5014. In some variants, the AMD 5001 can communicate to one or more of the electronic device 5008, remote electronic device 5010, and/or insurance provider system 5014 by way of an intermediary device. For example, the AMD 5001 may communication with the insurance provider system 5014 by way of the remote electronic device 5010. The communication between the AMD 5001, electronic device 5008, remote electronic device 5010, and/or insurance provider system 5014 can be performed using at least any of the communication techniques described herein. In some variants, data, which can include instructions, purchase orders, etc., can be communicated between the AMD 5001, electronic device 5008, remote electronic device 5010, and/or insurance provider system 5014.

As described herein, the electronic device 5008 can be the subject's or another individual's that is involved in providing therapy to the patient. The electronic device 5008 can receive data from the AMD 5001, which can include infusion set data, analyte sensor data, transmitter data, therapy data, instructions, requests, etc. In some variants, the electronic device 5008 can send instructions to the AMD 5001, which can include instructions to alter therapy delivered by the AMD 101, prompt(s) to change an infusion set 5027, transmitter 5049, and/or analyte sensor 5030, prompt(s) to order additional infusion sets 5027, transmitters 5049, and/or analyte sensors 5030, etc. In some variants, the electronic device 5008 can perform the processes, methods, actions, tasks, analysis, etc. described herein (e.g., establishing reordering thresholds, analyzing usage data, etc.).

As described herein, the remote electronic device 5010 can be a remote computing environment. The remote electronic device 5010 can receive orders for additional infusion sets, analyte sensors, and/or transmitters from the AMD 5001 and/or electronic device 5008. The remote electronic device 5010 can facilitate fulfillment of purchase orders for additional infusion sets, analyte sensors, and/or transmitters. In some variants, the remote electronic device 5010 can facilitate fulfillment of purchase orders for a new AMD 5001. The remote electronic device 5010 can include payment account data 5012 for the subject, which can include data related to a credit account, debit account, checking account, etc., such that the subject or an individual involved in providing therapy to the subject can send an order from the AMD 5001 or electronic device 5008 to the remote electronic device 5010, and the remote electronic device 5010 can automatically charge costs to fulfil the purchase order to the subject using the payment account data 5012. In some variants, the remote electronic device 5010 can include delivery data 5013, which can include delivery information for the subject (e.g., the subject's delivery address), estimated shipping time from a fulfillment center to the subject's delivery address, historical data regarding the quantity of infusion sets and/or analyte sensors delivered to the subject, etc. In some variants, historical data regarding the quantity of infusion sets and/or analyte sensors delivered to the subject can be used to determine the initial number of infusion sets and/or analyte sensors in possession of the subject. In some variants, the remote electronic device 5010 can perform the processes, methods, actions, tasks, analysis, etc. described herein (e.g., establishing reordering thresholds, analyzing usage data, etc.).

The insurance provider system 5014 can be a remote computing environment. The insurance provider system 5014 can be affiliated with an insurance provider of the subject. The insurance provider system 5014 can include coverage data 5016 associated with the subject which can include information related to the insurance coverage for the subject. In some variants, the remote electronic device 5010 can communicate an order for additional infusion sets, analyte sensors, and/or an AMD to the insurance provider system 5014. The insurance provider system 5014 can reference the coverage data 5016 for the subject to determine the amount of the cost of the order that the insurance provider will cover. The insurance provider system 5014 can communicate the cost covered by the insurance provider to the remote electronic device 5010. The remote electronic device 5010 can charge the remainder of the cost, not covered by the insurance provider, to the subject or caretaker of the subject using the payment account data 5012 associated with the subject. In some variants, the remote electronic device 5010 can send instructions to the electronic device 5008 and/or AMD 5001 to request authorization to charge of the remainder of the cost, not covered by the insurance provider, to the payment account data 5012 associated with the subject. In some variants, the remote electronic device 5010 can automatically charge the remainder of the cost, not covered by the insurance provider, using the payment account data 5012 associated with the subject. In some variants, the AMD 5001 and/or the electronic device 5008 can directly communicate with insurance provider system 5014. In some variants, the AMD 5001 and/or electronic device 5008 can indirectly communicate with the insurance provider system 5014. In some variants, the remote electronic device 5010 can receive and analyze usage data, which can include usage data for infusion sets, transmitters, and/or analyte sensors, to determine whether the subject should order more infusion sets, transmitters, and/or analyte sensors to avoid therapy disruptions. If the subject should order more infusion sets, transmitters, and/or analyte sensors, the remote electronic device 5010 can send instructions to the electronic device 5008 and/or AMD 5001 to provide a prompt to order more infusion sets, transmitters, and/or analyte sensors.

The AMD 5001 can include an infusion set monitoring system 5035. The infusion set monitoring system 5035 can monitor the status of an infusion set 5027 operatively connected to the AMD 5001 via the medicament delivery interface 5025. The infusion set monitoring system 5035 can monitor the infusion set 5027 to detect failures of the infusion set 5027. The infusion set monitoring system 5035 can detect a failure of the infusion set 5027 and the electronic processor 5024 in communication with the non-transitory memory can execute the specific computer-executable instructions 5003 to receive via the infusion set monitoring system 5035 an infusion set failure alert, which can indicate that an infusion set 5027 operatively connected to the AMD 5001 has a failure. For example, the infusion set monitoring system 5035 can detect an occlusion in the infusion set 5027 such that the infusion set failure alert includes an occlusion alert. The infusion set monitoring system 5035 can include a sensor that can detect that medicament is not flowing from the medicament reservoir 5029 at a rate that correlates to the motive force provided by the pump motor 5031, which can be indicative of an occlusion. The infusion set monitoring system 5035 can include a sensor that can detect if an infusion set 5027 is or is not operatively connected to the medicament delivery interface 5025.

The AMD 5001 can include an analyte sensor monitoring system 5018. The analyte sensor monitoring system 5018 can monitor the analyte sensor 5030. The analyte sensor monitoring system 5018 can monitor the analyte sensor 5030 to detect failures of the analyte sensor 5030. The analyte sensor monitoring system 5018 can detect a failure of the analyte sensor 5030 and the electronic processor 5024 in communication with the non-transitory memory can execute the specific computer-executable instructions 5003 to receive via the analyte sensor monitoring system 5018 an analyte sensor failure alert, which can indicate that an analyte sensor 5030 operatively connected to the AMD 5001 has a failure. For example, the analyte sensor monitoring system 5018 can determine that communication between the analyte sensor 5030 and AMD 5001 is irregular (e.g., disruptions in communication) to detect a failure. In another example, the analyte sensor monitoring system 5018 can detect that the performance (e.g., sensitivity) of the analyte sensor 5030 has decayed to an unacceptable level, indicating a failure.

The AMD 5001 can include a transmitter monitoring system 5039. The transmitter monitoring system 5039 can monitor the transmitter 5049 in communication with the AMD 5001. The transmitter monitoring system 5039 can monitor the transmitter 5049 to detect failures of the transmitter 5049. The transmitter monitoring system 5039 can detect a failure of the transmitter 5049 and the electronic processor 5024, in communication with the non-transitory memory, can execute the specific computer-executable instructions 5003 to receive via the transmitter monitoring system 5039 a transmitter failure alert, which can indicate that a transmitter 5049 operatively connected to the AMD 5001 has a failure. For example, the transmitter monitoring system 5039 can determine that communication between the transmitter 5049 and AMD 5001 is irregular (e.g., disruptions in communication) to detect a failure. In another example, the transmitter monitoring system 5039 can detect that the performance of the transmitter 5049 has decayed to an unacceptable level, indicating a failure (e.g., the electrical connection between the electrical interface 5047 and the battery 5050 is deficient).

The electronic processor 5024 in communication with the non-transitory memory can execute the specific computer-executable instructions to receive an indication of a number of initial infusion sets, transmitters, and/or analyte sensors in possession of the subject. The AMD 5001 can include an infusion set quantity interface 5037. The user (e.g., subject or another individual that assists in providing therapy to the subject) can input a number of initial infusion sets in possession of the subject by way of the infusion set quantity interface 5037. The AMD 5001 can include an analyte sensor quantity interface 5020. The user can input a number of initial analyte sensors in possession of the subject by way of the analyte sensor quantity interface 5020. The AMD 5001 can include a transmitter quantity interface 5041. The user can input a number of initial transmitters in possession of the subject by way of the transmitter quantity interface 5041. In some variants, the infusion set quantity interface 5037, analyte sensor quantity interface 5020, and/or transmitter quantity interface 5041 can be a graphical user interface on a touchscreen display (e.g., the touchscreen display 504) of the AMD 5001. In some variants, the infusion set quantity interface 5037, analyte sensor quantity interface 5020, and/or transmitter quantity interface 5041 can include buttons, switches, an alphanumeric pad, etc. to enable the user to input the number of initial infusion sets and/or analyte sensors. In some variants, the user can input the number of infusion sets, analyte sensors, and/or transmitters by way of the infusion set quantity interface 5037, analyte sensor quantity interface 5020, and/or transmitter quantity interface 5041 upon receipt of a delivery of infusion sets and/or analyte sensors. In some variants, the number of initial infusion sets, analyte sensors, and/or transmitters can be determined based on delivery data 5013, which can include historical data regarding the number of infusion sets, analyte sensors, and/or transmitters delivered to the subject. In some variants, the number of initial number of infusion sets, analyte sensors, and/or transmitters can be determined based on purchase orders associated with the subject. In some variants, the initial number of infusion sets, analyte sensors, and/or transmitters can be provided by the remote electronic device 5010.

The electronic processor 5024 in communication with the non-transitory memory can execute the specific computer-executable instructions to monitor a usage of infusion sets over a period by receiving at least one of a plurality of infusion set change indications during the period. The receipt of an infusion set change indication can indicate that an infusion set has been used or is no longer viable—decreasing the number of remaining infusion sets available to the subject to provide therapy.

For example, the receipt of an electronic cartridge change request can be indicative of an infusion set change indication. The changing of a medicament cartridge 5028 can be accompanied by changing an infusion set 5027 operatively connected to the AMD 5001. In some variants, the changing of a medicament cartridge 5028 must be accompanied by changing an infusion set 5027 operatively connected to the AMD 5001. Accordingly, the AMD 5001 can include a medicament cartridge change interface 5033 that the user interacts with to make an electronic cartridge change request to change a medicament cartridge 5028 operatively coupled to the AMD 5001. The user can interact with the medicament cartridge change interface 5033 to make an electronic cartridge change request and then operatively connect a new medicament cartridge 5028 to the AMD 5001. The electronic cartridge change request can indicate an infusion set change indication, prompting the AMD 5001 and/or another feature of the glucose level control system 5000 to decrease the estimated number of remaining infusion sets in possession of the subject. The medicament cartridge change interface 5033 can be a graphical user interface on a touchscreen display (e.g., the touchscreen display) of the AMD 5001. In some variants, the medicament cartridge change interface 5033 can include buttons, switches, an alphanumeric pad, etc. to enable the user to make an electronic cartridge change request.

In another example, the receipt of an electronic infusion set priming request can be indicative of an infusion set change indication. The changing of an infusion set can be accompanied by a priming of the infusion set. In some variants, a new infusion set operatively connected to the AMD 5001 must be primed before delivering medicament to the subject. Accordingly, the AMD 5001 can include an infusion set priming interface 5034. After a new infusion set 5027 is operatively connected to the medicament delivery interface 5025, the user can interact with the infusion set priming interface 5034 to make an electronic infusion set priming request to prime the infusion set 5027 to fill the cannula thereof with medicament— removing air from the line—in preparation for delivering medicament to the subject via the infusion set 5027. Making an electronic infusion set priming request can result in the pump controller 5026 commanding the pump motor 5031 to provide a motive force to move medicament from within the medicament reservoir 5029 of the medicament cartridge 5028 to fill the cannula of the infusion set 5027—removing air from the line—in preparation for delivering medicament to the subject. The electronic infusion set priming request can indicate an infusion set change indication, prompting the AMD 5001 to decrease the estimated number of remaining infusion sets in possession of the subject by one. The infusion set priming interface 5034 can be a graphical user interface on a touchscreen display (e.g., the touchscreen display 504) of the AMD 5001. In some variants, the infusion set priming interface 5034 can include buttons, switches, an alphanumeric pad, etc.

In another example, the receipt of an infusion set failure alert can be indicative of an infusion set change indication. The failure of an infusion set connected to the medicament delivery interface 5025 may be (or sometimes must be) accompanied by the replacement of the failed infusion set. As described herein, the AMD 5001 can include an infusion set monitoring system 5035 that can monitor an infusion set 5027 connected to the AMD 5001. The infusion set monitoring system 5035 can detect a failure of the infusion set 5027 resulting in an infusion set failure alert, indicating that the infusion set 5027 connected to the medicament delivery interface 5025 has a failure. The infusion set failure alert can indicate an infusion set change indication, prompting the AMD 5001 to decrease the estimated number of remaining infusion sets in possession of the subject. An example failure can be an occlusion in the infusion set 5027 (e.g., occlusion in the cannula). As such, the infusion set monitoring system 5035 can detect an occlusion in the infusion set 5027 such that the infusion set failure alert includes an occlusion alert. The infusion set monitoring system 5035 can include a sensor that can detect that medicament is not flowing from the medicament reservoir 5029 at a rate that correlates to the motive force provided by the pump motor 5031, which can be indicative of an occlusion. Another example failure can be an unintentional decoupling of the infusion set 5027 from the medicament delivery interface 5025. The infusion set monitoring system 5035 can include a sensor that can detect if an infusion set 5027 is or is not operatively connected to the medicament delivery interface 5025 such that an unintentional decoupling of the infusion set 5027 from the medicament delivery interface 5025 can result in an infusion set failure alert.

The electronic processor 5024 in communication with the non-transitory memory can execute the specific computer-executable instructions to monitor a usage of analyte sensors over a period by receiving at least one of a plurality of analyte sensor change indications during the period. The receipt of an analyte sensor change indication can indicate that an analyte sensor has been used or is no longer viable—decreasing the number of remaining analyte sensors available to the subject to provide therapy.

For example, the receipt of an electronic analyte sensor change request can be indicative of an analyte sensor change indication. The AMD 5001 can include an analyte sensor change interface 5017 that the user can interact with to make an analyte sensor change request to change an analyte sensor 5030 operatively connected to the AMD 5001. In some variants, the interaction with the analyte sensor change interface 5017 to make an analyte sensor change request can initiate communication between a new analyte sensor 5030 and the analyte sensor interface 5032 (e.g., pair the new analyte sensor 5030 and the AMD 5001). The analyte sensor change interface 5017 can be a graphical user interface on a touchscreen display (e.g., the touchscreen display 504) of the AMD 5001. In some variants, the analyte sensor change interface 5017 can include buttons, switches, an alphanumeric pad, etc.

In another example, the receipt of an analyte sensor failure alert can be indicative of an analyte sensor change indication. The failure of an analyte sensor 5030 operatively connected to the AMD 5001 may require replacement of the failed analyte sensor 5030. As described herein, the AMD 5001 can include an analyte sensor monitoring system 5018 that can monitor an analyte sensor 5030 operatively connected to the AMD 5001. The analyte sensor monitoring system 5018 can detect a failure of the analyte sensor 5030 resulting in an analyte sensor failure alert, indicating that the analyte sensor 5030 connected to the AMD 5001 has a failure. The analyte sensor failure alert can indicate an analyte sensor change indication, prompting the AMD 5001 or remote electronic device 5010 to decrease the estimated number of remaining analyte sensors in possession of the subject. For example, the analyte sensor monitoring system 5018 can determine that communication between the analyte sensor 5030 and AMD 5001 is irregular (e.g., disruptions in communication) to detect a failure. In another example, the analyte sensor monitoring system 5018 can detect that the performance (e.g., sensitivity) of the analyte sensor 5030 has decayed to an unacceptable level, indicating a failure.

In another example, the receipt of an analyte expiration alert can be indicative of an analyte sensor change indication—indicating that an analyte sensor in possession of the subject is no longer viable for use thereby reducing the number of initial analyte sensors. The AMD 5001 and/or electronic device 5008 can receive the analyte sensor expiration alert or an indication thereof from the remote electronic device 5010. The analyte expiration alert can indicate that an analyte sensor has expired or has passed or is at an expiration threshold (e.g., within one month of expiration). In some variants, the remote electronic device 5010 can include expiration data regarding the analyte sensors. The remote electronic device 5010 can send an indication of the analyte sensor expiration alert based on a correlation of a ship date of the analyte sensor with an expiration date of the analyte sensor (e.g., 6 months after shipping). The remote electronic device 5010 can send an indication of the analyte sensor expiration alert based on electronic expiration information associated with an analyte sensor in possession of the subject. The remote electronic device 5010, in some variants, can send electronic expiration information to the AMD 5001.

The electronic processor 5024 in communication with the non-transitory memory can execute the specific computer-executable instructions to monitor a usage of transmitters over a period by receiving at least one of a plurality of transmitter change indications during the period. The receipt of transmitter change indication can indicate that transmitter has been used or is no longer viable—decreasing the number of remaining transmitters available to the subject to provide therapy.

For example, the receipt of an electronic transmitter change request can be indicative of a transmitter change indication. The AMD 5001 can include a transmitter change interface 5043 that the user can interact with to make a transmitter change request to change transmitter 5049 operatively connected to (e.g., in communication with) the AMD 5001. In some variants, the interaction with the transmitter change interface 5043 to make an transmitter change request can initiate communication between a new transmitter 5049 and the analyte sensor interface 5032 (e.g., pair the new transmitter 5049 and the AMD 5001). The transmitter change interface 5043 can be a graphical user interface on a touchscreen display (e.g., the touchscreen display 504) of the AMD 5001 or electronic device 5008. In some variants, the transmitter change interface 5043 can include buttons, switches, an alphanumeric pad, etc.

In another example, the receipt of a transmitter failure alert can be indicative of transmitter change indication. The failure of a transmitter 5049 operatively connected to (e.g., in communication with) the AMD 5001 may require replacement of the failed transmitter 5049. As described herein, the AMD 5001 can include a transmitter monitoring system 5039 that can monitor a transmitter 5049 operatively connected to the AMD 5001. The transmitter monitoring system 5039 can detect a failure of the transmitter 5049 resulting in a transmitter failure alert, indicating that the transmitter 5049 connected to the AMD 5001 has a failure. The transmitter sensor failure alert can indicate a transmitter change indication, prompting the AMD 5001, electronic device 5008, or remote electronic device 5010 to decrease the estimated number of remaining transmitters in possession of the subject. For example, the transmitter monitoring system 5039 can determine that communication between the transmitter 5049 and AMD 5001 is irregular (e.g., disruptions in communication) to detect a failure, among other indicators.

In another example, the receipt of a transmitter expiration alert can be indicative of a transmitter change indication—indicating that a transmitter in possession of the subject is no longer viable for use—thereby reducing the number of viable transmitters in possession of the subject. The AMD 5001 can receive the transmitter sensor expiration alert or an indication thereof from the remote electronic device 5010. The analyte expiration alert can indicate that a transmitter has expired or has passed or is at an expiration threshold (e.g., within one month of expiration). In some variants, the remote electronic device 5010 can include expiration data regarding the transmitters. The remote electronic device 5010 can send an indication of the transmitter expiration alert based on a correlation of a ship date of the transmitter with an expiration date of the transmitter (e.g., 6 months after shipping). The remote electronic device 5010 can send an indication of the transmitter expiration alert based on electronic expiration information associated with a transmitter in possession of the subject. The remote electronic device 5010, in some variants, can send electronic expiration information to the AMD 5001.

As described herein, the AMD 5001 can monitor the usage of infusion sets, analyte sensors, and/or transmitters to facilitate prompting the order of additional infusions sets, analyte sensors, and/or transmitters to avoid disruptions in therapy. As described herein, the AMD 5001 can monitor a usage of infusion sets, analyte sensors, and/or transmitters over a period by receiving at least one of a plurality of infusion set change indications, analyte set change indications, and/or transmitter indications during the period. The infusion set change indications, analyte set change indications, and/or transmitter set indications can include at least those indicated above. The AMD 5001, by way of execution of the instructions 5003 on the electronic processor 5024, can determine an estimate of remaining infusion sets, analyte sensors, and/or transmitters in possession of the subject at the end of the period based on the number of initial infusion sets, analyte sensors, and/or transmitters and the usage of infusion sets, analyte sensors, and/or transmitters as indicated by the change indications. The number of initial infusion sets, analyte sensors, and/or transmitters can be received as described herein. In some variants, the estimated number of remaining infusion sets can be determined based on the number of initial infusion sets less the number of infusion set change indications received over the period. Similarly, in some variants, the estimated number of remaining analyte sensor can be determined based on the number of initial analyte sensors less the number of analyte sensor change indications received over the period. Similarly, in some variants, the estimated number of remaining transmitters can be determined based on the number of initial transmitters less the number of transmitter change indications received over the period.

The AMD 5001 can include an infusion set reordering threshold interface 5038, analyte sensor reordering threshold interface 5021, and/or transmitter reordering threshold interface 5040 with which the user may interact to set a reordering threshold for infusion sets, analyte sensors, and/or transmitters. The infusion set reordering threshold interface 5038, analyte sensor reordering threshold interface 5021, and/or transmitter reordering threshold interface 5040 can be a graphical user interfaces on a touchscreen display (e.g., the touchscreen display 504) of the AMD 5001. In some variants, the infusion set reordering threshold interface 5038, analyte sensor reordering threshold interface 5021, and/or transmitter reordering threshold interface 5040 can include buttons, switches, an alphanumeric pad, etc. to enable the user to set an infusion set reordering threshold, analyte sensor reordering threshold, and/or transmitter reordering threshold. In some variants, the reordering threshold can be preset. In some variants, the reordering thresholds for the infusion sets, analyte sensors, and/or transmitters can vary based on the usage of the infusion sets, analyte sensors, and/or transmitters over the period (e.g., a higher usage may raise the reordering threshold such that the subject maintains a larger supply of equipment to avoid disruptions in therapy). In some variants, the reordering thresholds for the infusion sets, analyte sensors, and/or transmitters can be preset by an individual involved in administering therapy to the subject (e.g., clinician). In some variants, the reordering thresholds can be determine by the AMD 5001, electronic device 5008, and/or remote electronic device 5010. In some variants, an automatic reordering threshold for the infusion sets, analyte sensors, and/or transmitters can be established, via any manner disclosed herein, that if reached can prompt the automatic reorder of infusion sets, analyte sensors, and/or transmitters to avoid disruptions in therapy. The automatic reordering threshold can be lower than the reordering threshold.

The AMD 5001, electronic device 5008, and/or remote electronic device 5010 can determine that the estimate of remaining infusion sets falls below the infusion set reordering threshold, and in response, automatically generate a prompt including an infusion set ordering interface 5036. The infusion set ordering interface 5036 can indicate to the user that the estimated number of remaining infusion sets has fallen below the infusion set reordering threshold and/or prompt the user to order additional infusion sets to avoid therapy disruption. In some variants, the infusion set ordering interface 5036 can recommend order quantities based on the monitored infusion set usage and ask for authorization to complete an order. In some variants, the infusion set ordering interface 5036 may prompt the user to indicate a period for which additional infusion sets are desired (e.g., 1 month, 2 months, 3 months, 4 months, 5 months, etc.). Based on the monitored usage of infusion sets by the subject, the AMD 5001, electronic device 5008, and/or remote electronic device 5010 can determine the estimated number of additional infusion sets that correspond to a desired period. For example, the monitored usage of infusion sets may indicate that, on average, the subject replaces an infusion set every three days. Accordingly, the AMD 5001, electronic device 5008, and/or remote electronic device 5010 can determine that a one month supply of additional infusion sets is about ten. In some variants, a percentage of additional infusion sets can be added to the determined quantity, such as 10%, to further ensure no therapy disruption. In the preceding example, a 10% increase would prompt the AMD 5001, electronic device 5008, and/or remote electronic device 5010 to determine that a one month supply of additional infusion sets is about eleven. As such, the user can indicate a duration desired (e.g., 1 month) and the AMD 5001, electronic device 5008, and/or remote electronic device 5010 can facilitate ordering a corresponding quantity of infusion sets based on usage data. In some variants, the AMD 5001, electronic device 5008, and/or remote electronic device 5010 can indicate the quantity of infusion sets that corresponds to the desired duration period and/or the estimated cost. The AMD 5001, in some variants, can indicate the portion of the cost covered by the subject's insurance by way of direct or indirect communication with the insurance provider system 5014, which can be via the electronic device 5008 and/or remote electronic device 5010.

The AMD 5001, electronic device 5008, and/or remote electronic device 5010 can determine that the estimate of remaining analyte sensors falls below the analyte sensor reordering threshold, and in response, automatically generate a prompt including an analyte sensor ordering interface 5019. The analyte sensor ordering interface 5019 can indicate to the user that the estimated number of remaining analyte sensors has fallen below the analyte sensor reordering threshold and/or prompt the user to order additional analyte sensors to avoid therapy disruptions. In some variants, the analyte sensor ordering interface 5019 can recommend order quantities based on the monitored usage of analyte sensors and ask for authorization to complete an order. In some variants, the analyte sensor ordering interface 5019 may prompt the user to indicate a period for which additional analyte sensors are desired (e.g., 1 month, 2 months, 3 months, 4 months, 5 months, etc.). Based on the monitored usage of analyte sensors by the subject, the AMD 5001, electronic device 5008, and/or remote electronic device 5010 can determine the estimated number of additional analyte sensors that correspond to a desired period. For example, the monitored usage of analyte sensors may indicate that, on average, the subject replaces an analyte sensor every 10 days. Accordingly, the AMD 5001, electronic device 5008, and/or remote electronic device 5010 can determine that a one month supply of additional analyte sensors is about three. In some variants, an extra analyte sensor or percentage of analyte sensors can be added to the determined quantity to further ensure no therapy disruption. In the preceding example, an extra analyte sensor would prompt the AMD 5001, electronic device 5008, and/or remote electronic device 5010 to determine that a one month supply of additional analyte sensors is about four. As such, the user can indicate a duration desired (e.g., 1 month) and the AMD 5001, electronic device 5008, and/or remote electronic device 5010 can facilitate ordering a corresponding quantity of analyte sensors based on usage data. In some variants, the AMD 5001 can indicate the quantity of analyte sensors that corresponds to the desired duration period and/or the estimated cost. The AMD 5001, in some variants, can indicate the portion of the cost covered by the subject's insurance by way of direct or indirect communication with the insurance provider system 5014, which can be via the electronic device 5008 and/or remote electronic device 5010.

The AMD 5001, electronic device 5008, and/or remote electronic device 5010 can determine that the estimate of remaining transmitters falls below the transmitter reordering threshold, and in response, automatically generate a prompt including a transmitter ordering interface 5042. The transmitter ordering interface 5042 can indicate to the user that the estimated number of remaining transmitters has fallen below the transmitter reordering threshold and/or prompt the user to order additional transmitters to avoid therapy disruptions. In some variants, the transmitter ordering interface 5042 can recommend order quantities based on the monitored usage of transmitters and ask for authorization to complete an order. In some variants, the transmitter ordering interface 5042 may prompt the user to indicate a period for which additional transmitters are desired (e.g., 1 month, 2 months, 3 months, 4 months, 5 months, etc.). Based on the monitored usage of transmitters by the subject, the AMD 5001, electronic device 5008, and/or remote electronic device 5010 can determine the estimated number of additional transmitters that correspond to a desired period. For example, the monitored usage of infusion sets may indicate that, on average, the subject replaces a transmitter every 14 days. Accordingly, the AMD 5001, electronic device 5008, and/or remote electronic device 5010 can determine that a one month supply of additional analyte sensors is about two. In some variants, an extra transmitter or percentage of transmitters can be added to the determined quantity to further ensure no therapy disruption. In the preceding example, an extra transmitter would prompt the AMD 5001, electronic device 5008, and/or remote electronic device 5010 to determine that a one month supply of additional transmitters is about three. As such, the user can indicate a duration desired (e.g., 1 month) and the AMD 5001, electronic device 5008, and/or remote electronic device 5010 can facilitate ordering a corresponding quantity of transmitters based on usage data. In some variants, the AMD 5001 can indicate the quantity of transmitters that corresponds to the desired duration period and/or the estimated cost. The AMD 5001, in some variants, can indicate the portion of the cost covered by the subject's insurance by way of direct or indirect communication with the insurance provider system 5014, which can be via the electronic device 5008 and/or remote electronic device 5010.

In some variants, the reordering threshold for infusion sets, analyte sensors, and/or transmitters can be raised or lowered based on the monitored usage of infusion sets and/or analyte sensors. For example, a higher usage of infusion sets, transmitters, and/or analyte sensors may raise the reordering threshold to avoid therapy disruptions and a lower usage of infusion sets, transmitters, and/or analyte sensors may lower the reordering threshold. In some variants, the reordering threshold for infusion sets, transmitters, and/or analyte sensors can be raised or lowered based on expected fulfillment times. For example, an expected quick fulfillment of analyte sensor, transmitters, and/or infusion sets may lower the reorder threshold while a slower fulfillment of analyte sensors, transmitters and/or infusion sets may raise the reorder threshold. In some variants, a reordering threshold for infusion sets, transmitters, and/or analyte sensors can be determined by the AMD 5001, remote electronic device 5010, and/or electronic device 5008. In some variants, the reordering threshold for infusion sets, transmitters, and/or analyte sensors based on the usage of the infusion sets and/or analyte sensors for a period and the estimate of remaining infusion sets and/or analyte sensors in possession of the subject at the end of the period.

The user can interact with the infusion set ordering interface 5036, analyte sensor ordering interface 5019, and/or transmitter ordering interface 5042 to submit a request to order additional infusion sets and/or analyte sensors. In response to the submission of the request to order additional infusion sets, transmitters, and/or analyte sensors, the AMD 5001 can communicate a purchase order to electronic device 5008, remote electronic device 5010, and/or insurance provider system 5014. In some variants, the AMD 5001, electronic device 5008, and/or remote electronic device 5010 can determine the number of initial infusion sets, transmitters, and/or analyte sensors based on one or more transmitted purchase orders for additional analyte sensors, transmitters, and/or infusion sets.

In some variants, the interfaces that involve user interaction, as described herein, can be provided to the user on the AMD 5001 and/or electronic device 5008.

Figure 51:
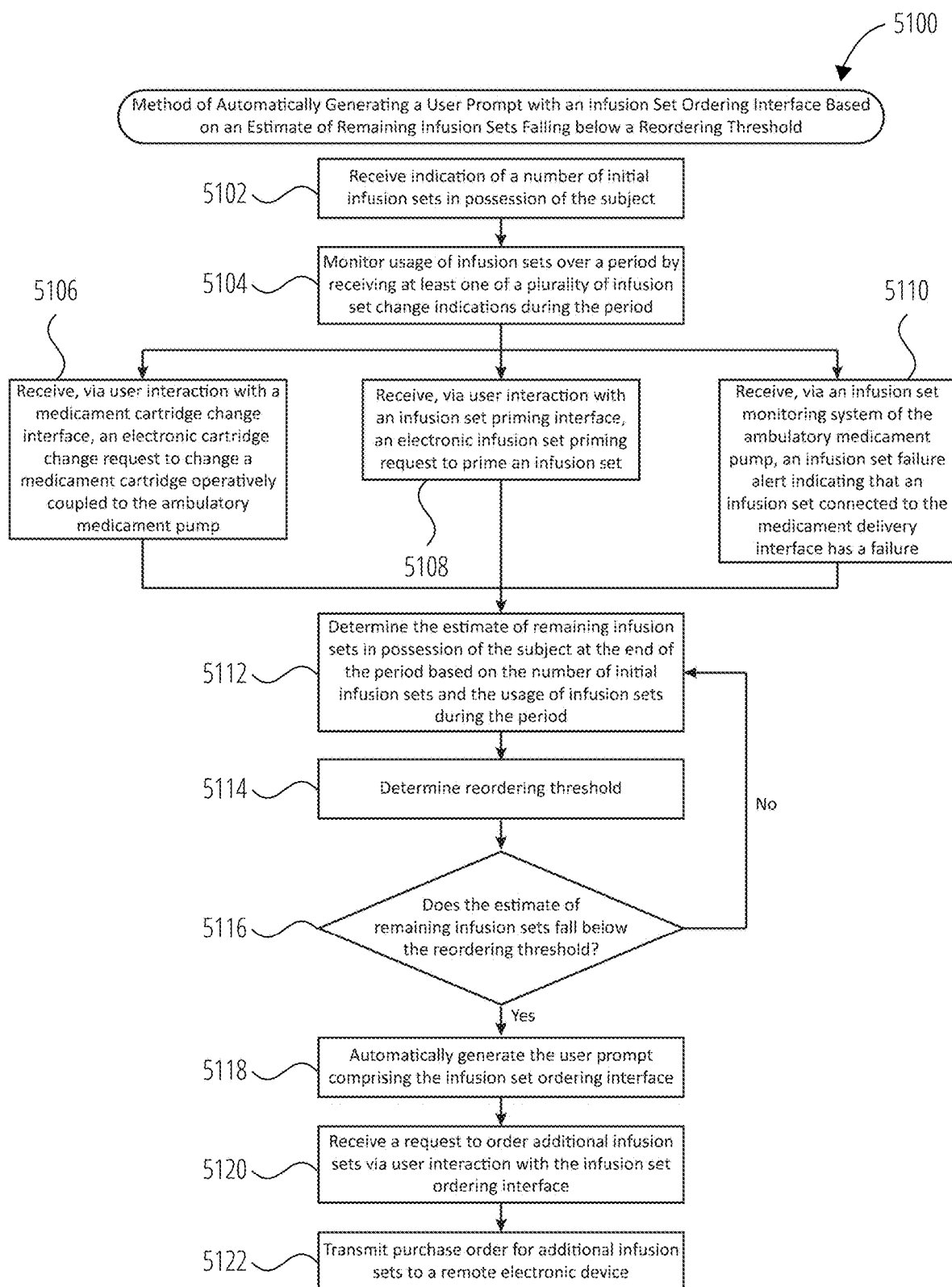
FIG. 51 shows a method of automatically generating a user prompt with an infusion set ordering interface based on an estimate of remaining infusion sets falling below a reordering threshold.

Example Method of Automatically Generating a User Prompt with an Infusion Set Ordering Interface FIG. 51 is a flow diagram depicting an example method 5100 of automatically generating a user prompt with an infusion set ordering interface based on an estimate of remaining infusion sets falling below a reordering threshold. The flow diagram is provided for the purpose of facilitating description of aspects of some embodiments. The diagram does not attempt to illustrate all aspects of the disclosure and should not be considered limiting.

At block 5102, the system can receive an indication of a number of initial infusion sets in possession of the subject. The electronic processor 5024 in communication with the non-transitory memory can execute the specific computer-executable instructions to receive an indication of a number of initial infusion sets in possession of the subject. The AMD 5001 or electronic device 5008 can include an infusion set quantity interface 5037. The user can input a number of initial infusion sets in possession of the subject by way of the infusion set quantity interface 5037. In some variants, the remote electronic device 5010 can include delivery data 5013 that can include historical delivery data regarding the number of infusion sets delivered to the subject that can be communicated to the AMD 5001 to indicate a number of initial infusion sets in possession of the subject. In some variants, the number of initial infusion sets can be determined based on one or more transmitted purchase orders for a number of additional infusion sets.

At block 5104, the system can monitor the usage of infusion sets over a period by receiving at least one of a plurality of infusion set change indications during the period. The electronic processor 5024 in communication with the non-transitory memory can execute the specific computer-executable instructions to monitor the usage of infusion sets over a period by receiving at least one of a plurality of infusion set change indications during the period. The infusion set change indications can at least include receipt of an electronic cartridge change request (described in reference to block 5106), electronic infusion set priming request (described in reference to block 5108), and/or an infusion set failure alert (described in reference to block 5110).

At block 5106, the system can receive, via user interaction with a medicament cartridge change interface, an electronic cartridge change requests to change a medicament cartridge operatively coupled to the ambulatory medicament pump.

The AMD 5001 can include a medicament cartridge change interface 5033 that the user interacts with to make an electronic cartridge change request to change a medicament cartridge 5028 operatively coupled to the AMD 5001. The user can interact with the medicament cartridge change interface 5033 to make an electronic cartridge change request and then operatively connect a new medicament cartridge 5028 to the AMD 5001. The electronic cartridge change request can indicate an infusion set change indication, prompting the AMD 5001 to decrease the estimated number of remaining infusion sets in possession of the subject by one.

At block 5108, the system can receive, via user interaction with an infusion set primping interface, an electronic infusion set priming request to prime an infusion set. The AMD 5001 can include an infusion set priming interface 5034. After a new infusion set 5027 is operatively connected to the medicament delivery interface 5025, the subject or another individual can interact with the infusion set priming interface 5034 to make an electronic infusion set priming request to prime the infusion set 5027 to fill the cannula thereof with medicament—removing air from the line—in preparation for delivering medicament to the subject via the infusion set 5027. The electronic infusion set priming request can indicate an infusion set change indication, prompting the AMD 5001 to decrease the estimated number of remaining infusion sets in possession of the subject.

At block 5110, the system can receive, via an infusion set monitoring system of the ambulatory medicament pump, an infusion set failure alert indicating that an infusion set connected to the medicament delivery interface has a failure. The AMD 5001 can include an infusion set monitoring system 5035 that can monitor an infusion set 5027 connected to the AMD 5001. The infusion set monitoring system 5035 can detect a failure of the infusion set 5027 resulting in an infusion set failure alert, indicating that the infusion set 5027 connected to the medicament delivery interface 5025 has a failure. The infusion set failure alert can indicate an infusion set change indication, prompting the AMD 5001 to decrease the estimated number of remaining infusion sets in possession of the subject by one.

At block 5112, the system can determine the estimate of remaining infusion sets in possession of the subject at the end of the period based on the number of initial infusion sets and the usage of infusion sets during the period. The electronic processor 5024 in communication with the non-transitory memory can execute the specific computer-executable instructions to determine the estimate of remaining infusion sets in possession of the subject at the end of the period based on the number of initial infusion sets and the usage of infusion sets during the period. In some variants, the AMD 5001, electronic device 5008, and/or remote electronic device can make this determination. As described herein, the foregoing infusion set change indications can indicate a decrease of the estimated remaining infusion sets in possession of the subject. Accordingly, the initial number of infusion sets subtracted by the number of infusion set change indications can indicate the estimated remaining number of infusion sets in possession of the subject.

At block 5114, the system can determine the reordering threshold based on usage of infusion sets during the period. As described herein, the AMD 5001 can include an infusion set reordering threshold interface 5038 with which the user may interact to set a reordering threshold for infusion sets. For example, the user may indicate, by way of the infusion set reordering threshold interface 5038, that the reordering threshold for infusion sets is a specific quantity (e.g., ten). In some variants, the user may indicate, by way of the infusion set reordering threshold interface 5038, that the reordering threshold for infusion sets is a duration of time (e.g., one month). The system can analyze the subject's infusion set data 5005 to determine the quantity of infusion sets corresponding to the duration of time indicated by the user. For example, the system may determine that the subject, on average, replaces an infusion set every three days. Accordingly, the system can determine that ten infusion sets corresponds to the one month duration threshold indicated by the user such that ten infusion sets is the reordering threshold for infusion sets. In some variants, the reordering threshold for infusion sets can be raised or lowered based on the monitored usage of infusion sets. For example, a higher usage of infusion sets may raise the reordering threshold to avoid therapy disruption due to a lack of infusion sets. As described herein, the reordering threshold, in some variants, can be raised or lowered based on estimated fulfillment times (e.g., the time after the user submits a purchase order until the order is delivered to the subject).

At decision state 5116, the system can ask if the estimate of remaining infusion sets falls below the reordering threshold. The electronic processor 5024 in communication with the non-transitory memory can execute the specific computer-executable instructions to determine if the estimate of remaining infusion sets falls below the reordering threshold. If the estimate of remaining infusion sets does not fall below the reordering threshold, the process proceeds to block 5112. If the estimate of remaining infusion sets does fall below the reordering threshold, the process proceeds to block 5118.

At block 5118, the system can automatically generate a user prompt that includes an infusion set ordering interface. The electronic processor 5024 in communication with the non-transitory memory can execute the specific computer-executable instructions to generate a user prompt that can include an infusion set ordering interface 5036 that can indicate to the user that the estimated number of remaining infusion sets has fallen below the infusion set reordering threshold and/or prompt the user to order additional infusion sets to avoid therapy disruption. In some variants, the infusion set ordering interface 5036 can recommend order quantities based on the monitored infusion set usage. In some variants, the infusion set ordering interface 5036 may prompt the subject or individual to indicate a period for which additional infusion sets are desired (e.g., 1 month, 2 months, 3 months, 4 months, 5 months, etc.). Based on the monitored usage of infusion sets by the subject, the system can determine the estimated number of additional infusion sets that correspond to a desired period. As such, the user can indicate a duration desired (e.g., 1 month) and the AMD 5001 can facilitate ordering a corresponding quantity of infusion sets based on usage data. In some variants, the AMD 5001 and/or electronic device 5008 can indicate the quantity of infusion sets that corresponds to the desired duration period and/or the estimated cost. The AMD 5001 and/or electronic device 5008, in some variants, can indicate the portion of the cost covered by the subject's insurance by way of direct or indirect communication with the insurance provider system 5014.

At block 5120, the system can receive a request to order additional infusion sets via user interaction with the infusion set ordering interface. The electronic processor 5024 in communication with the non-transitory memory can execute the specific computer-executable instructions to receive, via user interaction with the infusion set ordering interface 5036, a request to order additional infusion sets.

At block 5122, the system can transmit a purchase order for additional infusion sets to a remote electronic device 5010. In response to receiving the request to order additional infusion sets, the electronic processor 5024 in communication with the non-transitory memory can execute the specific computer-executable instructions to transmit the purchase order for additional infusion sets to the remote electronic device 5010. As described herein, the remote electronic device 5010 can include payment account data 5012 associated with the subject that can be automatically billed to cover the cost of the purchase order. As described herein, the remote electronic device 5010 can be in communication with an insurance provider system 5014. The remote electronic device 5010 can communicate with the insurance provider system 5014 to bill the insurance provider for the portion or all of the cost of the purchase order to be covered by the insurance provider based on the subject's coverage data 5016. In some variants, additional infusion sets can be automatically ordered when the estimated number of remaining infusion sets falls below the reordering threshold.

Figure 52:
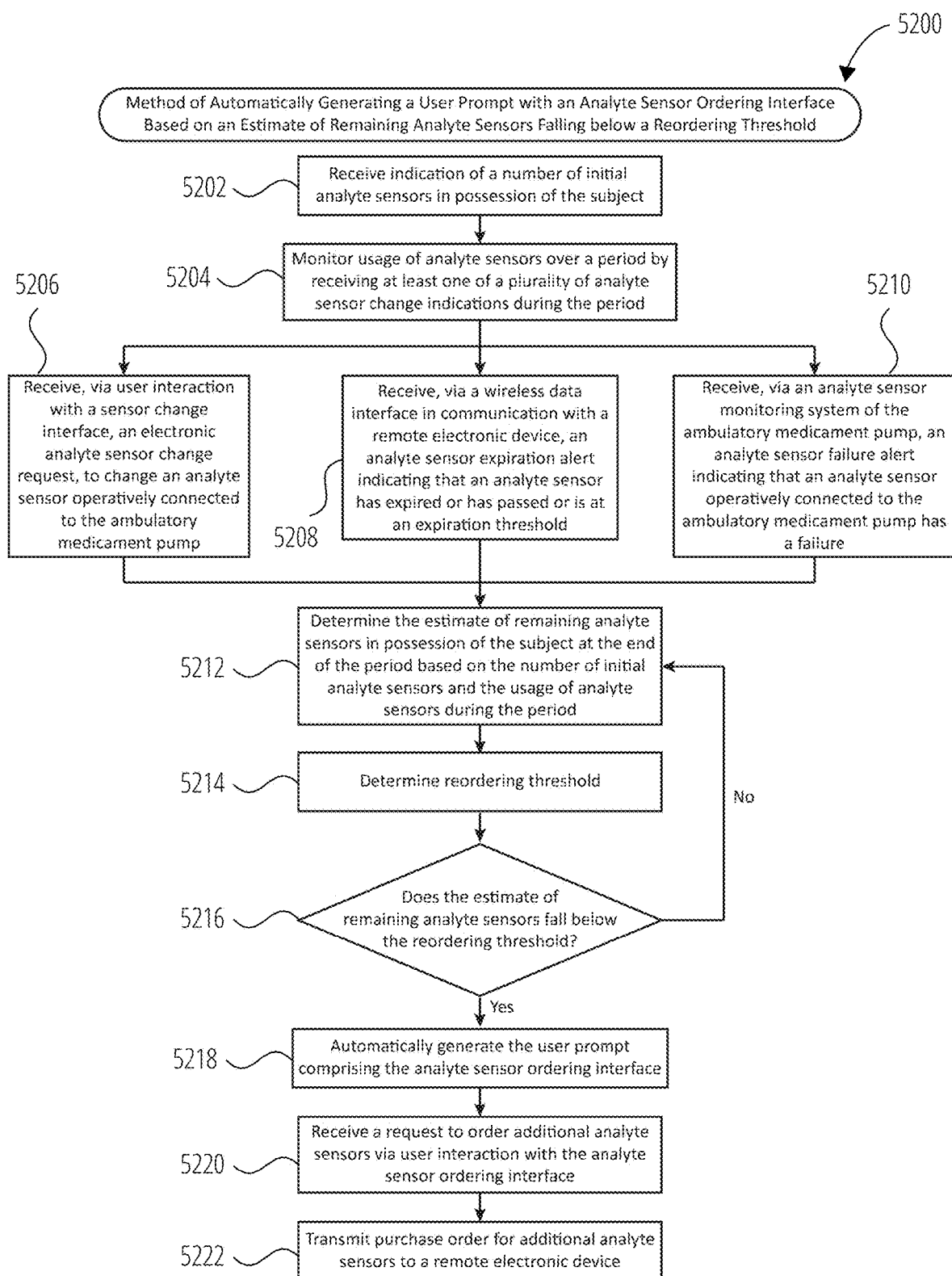
FIG. 52 shows a method of automatically generating a user prompt with an analyte sensor ordering interface based on an estimate of remaining analyte sensors falling below a reordering threshold.

Example Method of Automatically Generating a User Prompt with an Analyte Sensor Ordering Interface FIG. 52 is a flow diagram depicting an example method 5200 of automatically generating a user prompt with an analyte sensor ordering interface based on an estimate of remaining analyte sensors falling below a reordering threshold. The flow diagram is provided for the purpose of facilitating description of aspects of some embodiments. The diagram does not attempt to illustrate all aspects of the disclosure and should not be considered limiting.

At block 5202, the system can receive an indication of a number of initial analyte sensors in possession of the subject. The electronic processor 5024 in communication with the non-transitory memory can execute the specific computer-executable instructions to receive an indication of a number of initial analyte sensors in possession of the subject. The AMD 5001 or electronic device 5008 can include an analyte sensor quantity interface 5020. The user can input a number of initial analyte sensors in possession of the subject by way of the analyte sensor quantity interface 5020. In some variants, the remote electronic device 5010 can include delivery data 5013 that can include historical delivery data regarding the number of analyte sensors delivered to the subject that can be communicated to the AMD 5001 to indicate a number of initial analyte sensors in possession of the subject. In some variants, the number of initial analyte sensors can be determined based on one or more transmitted purchase orders for a number of additional analyte sensors.

At block 5204, the system can monitor the usage of analyte sensors over a period by receiving at least one of a plurality of analyte sensor change indications during the period. The electronic processor 5024 in communication with the non-transitory memory can execute the specific computer-executable instructions to monitor the usage of analyte sensors over a period by receiving at least one of a plurality of analyte sensor change indications during the period. The analyte sensor change indications can at least include receipt of an electronic analyte sensor change request (described in reference to block 5206), receipt of an analyte sensor expiration alert (described in reference to block 5208), and/or an analyte sensor failure alert (described in reference to block 5210).

At block 5206, the system can receive, via user interaction with an analyte sensor change interface, an electronic analyte sensor change request to change an analyte sensor operatively coupled to the ambulatory medicament pump. The AMD 5001 can include an analyte sensor change interface 5017 that the user can interact with to make an electronic analyte sensor change request to change an analyte sensor operatively coupled to the AMD 5001. The user can interact with the analyte sensor change interface 5017 to make an electronic analyte sensor change request and operatively connect a new analyte sensor 5030 to the AMD 5001. The electronic analyte sensor change request can indicate an analyte sensor change indication, prompting the AMD 5001 to decrease the estimated number of remaining analyte sensors in possession of the subject by one.

At block 5208, the system can receive, via the wireless data interface in communication with a remote electronic device, an analyte sensor expiration alert indicating that an analyte sensor has expired or has passed or is at an expiration threshold. The receipt of the analyte sensor expiration alert can indicate an analyte sensor change indication—indicating that an analyte sensor in possession of the subject is no longer viable for use thereby reducing the number of initial analyte sensors. The AMD 5001 can receive the analyte sensor expiration alert or an indication thereof from the remote electronic device 5010. In some variants, the electronic device 5008 can receive the analyte sensor expiration alert or an indication thereof from the remote electronic device 5010. The analyte expiration alert can indicate that an analyte sensor has expired or has passed or is at an expiration threshold (e.g., within one month of expiration). In some variants, the remote electronic device 5010 can include expiration data regarding the analyte sensors. The remote electronic device 5010 can send an indication of the analyte sensor expiration alert based on a correlation of a ship date of the analyte sensor with an expiration date of the analyte sensor (e.g., 6 months after shipping). The remote electronic device 5010 can send an indication of the analyte sensor expiration alert based on electronic expiration information associated with an analyte sensor in possession of the subject. The remote electronic device 5010, in some variants, can send electronic expiration information to the AMD 5001.

At block 5210, the system can receive, via an analyte sensor monitoring system of the ambulatory medicament pump, an analyte sensor failure alert indicating that an analyte sensor operatively connected to the AMD 5001 has a failure. The AMD 5001 can include an analyte sensor monitoring system 5018 that can monitor an analyte sensor 5030 connected to the AMD 5001. The analyte sensor monitoring system 5018 can detect a failure of the analyte sensor 5030 resulting in an analyte sensor failure alert, indicating that the analyte sensor 5030 connected to the AMD 5001 has a failure. The analyte sensor failure alert can indicate an analyte sensor change indication, prompting the AMD 5001 to decrease the estimated number of remaining analyte sensors in possession of the subject by one.

At block 5212, the system can determine the estimate of remaining analyte sensors in possession of the subject at the end of the period based on the number of initial analyte sensors and the usage of analyte sensors during the period. The electronic processor 5024 in communication with the non-transitory memory can execute the specific computer-executable instructions to determine the estimate of remaining analyte sensors in possession of the subject at the end of the period based on the number of initial analyte sensors and the usage of analyte sensors during the period. In some variants, the AMD 5001, electronic device 5008, and/or remote electronic device 5010 can determine the estimate of remaining analyte sensors in possession of the subject. As described herein, the foregoing analyte sensor change indications can indicate a decrease of the estimated remaining analyte sensors in possession of the subject. Accordingly, the initial number of analyte sensors subtracted by the number of analyte sensor change indications can indicate the estimated remaining number of analyte sensors in possession of the subject.

At block 5214, the system can determine the reordering threshold based on usage of analyte sensors during the period. As described herein, the AMD 5001 can include an analyte sensor reordering threshold interface 5021 with which the user may interact to set a reordering threshold for analyte sensors. For example, the user may indicate, by way of the analyte sensor reordering threshold interface 5021, that the reordering threshold for analyte sensors is a specific quantity (e.g., ten). In some variants, the user may indicate, by way of the analyte sensor reordering threshold interface 5021, that the reordering threshold for analyte sensors is a duration of time (e.g., one month). The system can analyze the subject's analyte sensor data 5007 to determine the quantity of analyte sensors corresponding to the duration of time indicated by the user. For example, the system may determine that the subject, on average, replaces an analyte sensor every ten days. Accordingly, the system can determine that three analyte sensors corresponds to the one month duration threshold indicated by the user such that three analyte sensors is the reordering threshold for analyte sensors. In some variants, the reordering threshold for analyte sensors can be raised or lowered based on the monitored usage of analyte sensors. For example, a higher usage of analyte sensors may raise the reordering threshold to avoid therapy disruption due to a lack of analyte sensors. As described herein, the reordering threshold, in some variants, can be raised or lowered based on estimated fulfillment times (e.g., the time after the user submits a purchase order until the order is delivered to the subject).

At decision state 5216, the system can ask if the estimate of remaining analyte sensors falls below the reordering threshold. The electronic processor 5024 in communication with the non-transitory memory can execute the specific computer-executable instructions to determine if the estimate of remaining analyte sensors falls below the reordering threshold. If the estimate of remaining analyte sensors does not fall below the reordering threshold, the process proceeds to block 5212. If the estimate of remaining analyte sensors does fall below the reordering threshold, the process proceeds to block 5218.

At block 5218, the system can automatically generate a user prompt that includes an analyte sensor ordering interface 5019. The electronic processor 5024 in communication with the non-transitory memory can execute the specific computer-executable instructions to generate a user prompt that can include an analyte sensor ordering interface 5019 that can indicate to the user that the estimated number of remaining analyte sensors has fallen below the analyte sensor reordering threshold and/or prompt the user to order additional analyte sensors to avoid therapy disruption. In some variants, the analyte sensor ordering interface 5019 can recommend order quantities based on the monitored analyte sensor usage. In some variants, the analyte sensor ordering interface 5019 may prompt the subject or individual to indicate a period for which additional analyte sensors are desired (e.g., 1 month, 2 months, 3 months, 4 months, 5 months, etc.). Based on the monitored usage of analyte sensors by the subject, the system can determine the estimated number of additional analyte sensors that correspond to a desired period. As such, the user can indicate a duration desired (e.g., 1 month) and the AMD 5001 can facilitate ordering a corresponding quantity of analyte sensors based on usage data. In some variants, the AMD 5001 can indicate the quantity of analyte sensors that corresponds to the desired duration period and/or the estimated cost. The AMD 5001, in some variants, can indicate the portion of the cost covered by the subject's insurance by way of direct or indirect communication with the insurance provider system 5014.

At block 5220, the system can receive a request to order additional analyte sensors via user interaction with the analyte sensor ordering interface. The electronic processor 5024 in communication with the non-transitory memory can execute the specific computer-executable instructions to receive, via user interaction with the analyte sensor ordering interface 5019, a request to order additional analyte sensors.

At block 5222, the system can transmit a purchase order for additional analyte sensors to a remote electronic device. In response to receiving the request to order additional analyte sensors, the electronic processor 5024 in communication with the non-transitory memory can execute the specific computer-executable instructions to transmit the purchase order for additional analyte sensors to the remote electronic device 5010. As described herein, the remote electronic device 5010 can include payment account data 5012 associated with the subject that can be automatically billed to cover the cost of the purchase order. As described herein, the remote electronic device 5010 can be in communication with an insurance provider system 5014. The remote electronic device 5010 can communicate with the insurance provider system 5014 to bill the insurance provider for the portion or all of the cost of the purchase order to be covered by the insurance provider based on the subject's coverage data 5016. In some variants, additional analyte sensors can be automatically ordered when the estimated number of remaining analyte sensors falls below the reordering threshold.

Figure 53:
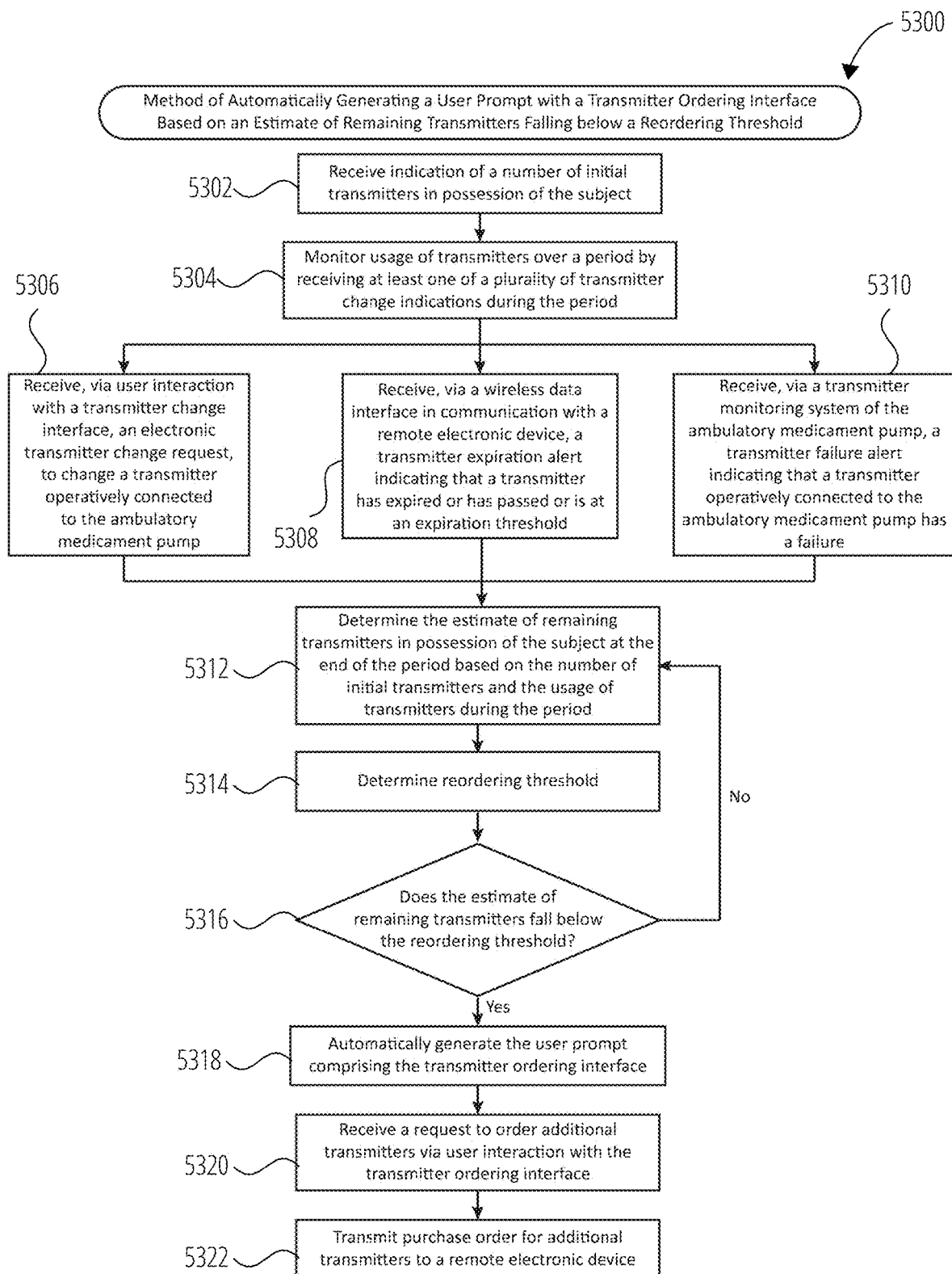
FIG. 53 shows a method of automatically generating a user prompt with a transmitter ordering interface based on an estimate of remaining transmitters falling below a reordering threshold.

Example Method of Automatically Generating User Prompt with a Transmitter Ordering Interface FIG. 53 is a flow diagram depicting an example method 5300 of automatically generating a user prompt with transmitter ordering interface based on an estimate of remaining transmitters falling below a reordering threshold. The flow diagram is provided for the purpose of facilitating description of aspects of some embodiments. The diagram does not attempt to illustrate all aspects of the disclosure and should not be considered limiting.

At block 5302, the system can receive an indication of a number of initial transmitters in possession of the subject. The electronic processor 5024 in communication with the non-transitory memory can execute the specific computer-executable instructions to receive an indication of a number of initial transmitters in possession of the subject. The AMD 5001 or electronic device 5008 can include a transmitter quantity interface 5041. The user can input a number of initial transmitters in possession of the subject by way of the transmitter quantity interface 5041. In some variants, the remote electronic device 5010 can include delivery data 5013 regarding the number of transmitters delivered to the subject, which can be communicated to the AMD 5001 and/or electronic device 5008 to indicate a number of initial transmitters in possession of the subject. In some variants, the number of initial transmitters can be determined based on one or more transmitted purchase orders for a number of additional transmitters.

At block 5304, the system can monitor the usage of transmitters over a period by receiving at least one of a plurality of transmitter change indications during the period. The electronic processor 5024 in communication with the non-transitory memory can execute the specific computer-executable instructions to monitor the usage of transmitters over a period by receiving at least one of a plurality of transmitter change indications during the period. The transmitter change indications can at least include receipt of an electronic transmitter change request (described in reference to block 5306), transmitter expiration alert (described in reference to block 5308), and/or a transmitter failure alert (described in reference to block 5310).

At block 5306, the system can receive, via user interaction with a transmitter change interface, an electronic transmitter sensor change request to change a transmitter operatively connected to (e.g., in communication with) the AMD 5001. The AMD 5001 or electronic device 5008 can include a transmitter change interface 5043 that the user can interact with to make an electronic transmitter change request to change a transmitter operatively connected to (e.g., in communication with) the AMD 5001. The user can make the electronic transmitter change request and operatively connect a new transmitter to the AMD 5001. The electronic transmitter change request can indicate a transmitter change indication, which can decrease the estimated number of remaining transmitters in possession of the subject.

At block 5308, the system can receive, via the wireless data interface in communication with a remote electronic device, a transmitter expiration alert indicating that a transmitter has expired or has passed or is at an expiration threshold. The receipt of the transmitter expiration alert can indicate a transmitter change indication—indicating that transmitter in possession of the subject is no longer viable for use, thereby reducing the number of viable transmitters in possession of the subject. The AMD 5001 and/or electronic device 5008 can receive the transmitter expiration alert or an indication thereof from the remote electronic device 5010. In some variants, the electronic device 5008 can receive the transmitter expiration alert or an indication thereof from the remote electronic device 5010. The transmitter expiration alert can indicate that a transmitter has expired or has passed or is at an expiration threshold (e.g., within one month of expiration). In some variants, the remote electronic device 5010 can include expiration data regarding the transmitters. The remote electronic device 5010 can send an indication of the transmitter expiration alert based on a correlation of a ship date of the transmitter with an expiration date of the transmitter (e.g., 6 months after shipping). The remote electronic device 5010 can send an indication of the transmitter expiration alert based on electronic expiration information associated with a transmitter in possession of the subject. The remote electronic device 5010, in some variants, can send electronic expiration information to the AMD 5001 and/or electronic device 5008.

At block 5310, the system can receive, via the transmitter monitoring system 5039 of the AMD 5001, a transmitter failure alert indicating that a transmitter operatively connected to the AMD 5001 has a failure. The AMD 5001 can include transmitter monitoring system 5039 that can monitor transmitter 5049 operatively connected to (e.g., in communication with) the AMD 5001. The transmitter monitoring system 5039 can detect a failure of the transmitter resulting in a transmitter failure alert, indicating that the transmitter operatively connected to (e.g., in communication with) the AMD 5001 has a failure. The transmitter failure alert can indicate a transmitter change indication, prompting a decrease of the estimated number of remaining transmitters in possession of the subject.

At block 5312, the system can determine the estimate of transmitters in possession of the subject at the end of the period based on the number of initial transmitters and the usage of transmitters during the period. The electronic processor 5024 in communication with the non-transitory memory can execute the specific computer-executable instructions to determine the estimate of remaining transmitters in possession of the subject at the end of the period based on the number of initial transmitters and the usage of transmitters during the period. The AMD 5001, electronic device 5008, and/or remote electronic device 5010 can determine the estimated number of transmitters in possession of the subject. As described herein, the transmitter change indications can indicate a decrease of the estimated remaining transmitters in possession of the subject. Accordingly, the initial number of transmitters subtracted by the number of transmitter change indications can indicate the estimated remaining number of transmitters in possession of the subject.

At block 5314, the system can determine the reordering threshold. As described herein, the AMD 5001 and/or electronic device 5008 can include a transmitter reordering threshold interface 5040 with which the user may interact to set a reordering threshold for transmitters. For example, the user may indicate, by way of the transmitter reordering threshold interface 5040, that the reordering threshold for transmitters is a specific quantity (e.g., ten). In some variants, the user may indicate, by way of the transmitter reordering threshold interface 5040, that the reordering threshold for analyte sensors is a duration of time (e.g., one month). The system can analyze the subject's usage of transmitters to determine the quantity of transmitters corresponding to the duration of time indicated by the user. For example, the system may determine that the subject, on average, replaces a transmitter every fourteen days. Accordingly, the system can determine that two transmitters corresponds to the one month duration threshold indicated by the user such that two transmitters is the reordering threshold for transmitters. In some variants, the reordering threshold for transmitters can be raised or lowered based on the monitored usage of transmitters. For example, a higher usage of transmitters may raise the reordering threshold to avoid therapy disruption due to a lack of transmitters. As described herein, the reordering threshold, in some variants, can be raised or lowered based on estimated fulfillment times (e.g., the time after the user submits a purchase order until the order is delivered to the subject). In some variants, the reordering threshold can be determined algorithmically, which can be via the remote electronic device 5010, electronic device 5008, and/or AMD 5001.

At decision state 5316, the system can ask if the estimate of remaining transmitters falls below the reordering threshold. The electronic processor 5024 in communication with the non-transitory memory can execute the specific computer-executable instructions to determine if the estimate of remaining transmitters falls below the reordering threshold. If the estimate of remaining transmitters does not fall below the reordering threshold, the process proceeds to block 5312. If the estimate of remaining transmitters does fall below the reordering threshold, the process proceeds to block 5318. In some variants, the system can automatically send a purchase order for additional transmitters if the estimate of remaining transmitters falls below the reordering threshold. In some variants, the system can automatically send a purchase order for additional transmitters if the estimate of remaining transmitters falls below an automatic reordering threshold, which can be different than the reordering threshold.

At block 5318, the system can automatically generate a user prompt that includes a transmitter ordering interface 5042. The electronic processor 5024 in communication with the non-transitory memory can execute the specific computer-executable instructions to generate a user prompt that can include the transmitter ordering interface 5042 that can indicate to the user that the estimated number of remaining transmitters has fallen below the transmitter reordering threshold and/or prompt the user to order additional transmitters to avoid therapy disruption. In some variants, the transmitter ordering interface 880 can recommend order quantities based on the monitored transmitter usage. In some variants, the transmitter ordering interface 5042 may prompt the subject or individual to indicate a period for which additional transmitters are desired (e.g., 1 month, 2 months, 3 months, 4 months, 5 months, etc.). Based on the monitored usage of transmitters by the subject, the system can determine the estimated number of additional transmitters that correspond to a desired period. As such, the user can indicate a duration desired (e.g., 1 month) and the AMD 5001, electronic device 5008, and/or remote electronic device 5010 can facilitate ordering a corresponding quantity of transmitters based on usage data. In some variants, the AMD 5001 and/or electronic device 5008 can indicate to the user the quantity of transmitters that corresponds to the desired duration period and/or the estimated cost. The AMD 5001 and/or electronic device 5008, in some variants, can indicate the portion of the cost covered by the subject's insurance by way of direct or indirect communication with the insurance provider system 5014.

At block 5320, the system can receive a request to order additional transmitters via user interaction with the transmitter ordering interface 5042. The electronic processor 5024 in communication with the non-transitory memory can execute the specific computer-executable instructions to receive, via user interaction with the transmitter ordering interface 5042, a request to order additional transmitters.

At block 5322, the system can transmit a purchase order for additional transmitters to the remote electronic device. In response to receiving the request to order additional transmitters, the electronic processor 5024 in communication with the non-transitory memory can execute the specific computer-executable instructions to transmit the purchase order for additional transmitters to the remote electronic device 5010. As described herein, the remote electronic device 5010 can include payment account data 5012 associated with the subject that can be automatically billed to cover the cost of the purchase order. As described herein, the remote electronic device 5010 can be in communication with an insurance provider system 5014. The remote electronic device 5010 can communicate with the insurance provider system 5014 to bill the insurance provider for the portion or all of the cost of the purchase order to be covered by the insurance provider based on the subject's coverage data 5016. As described herein, in some variants, additional transmitters can be automatically ordered when the estimated number of remaining transmitters falls below the reordering threshold.

Example Method of Monitoring a Usage of Infusion Sets

Figure 54:
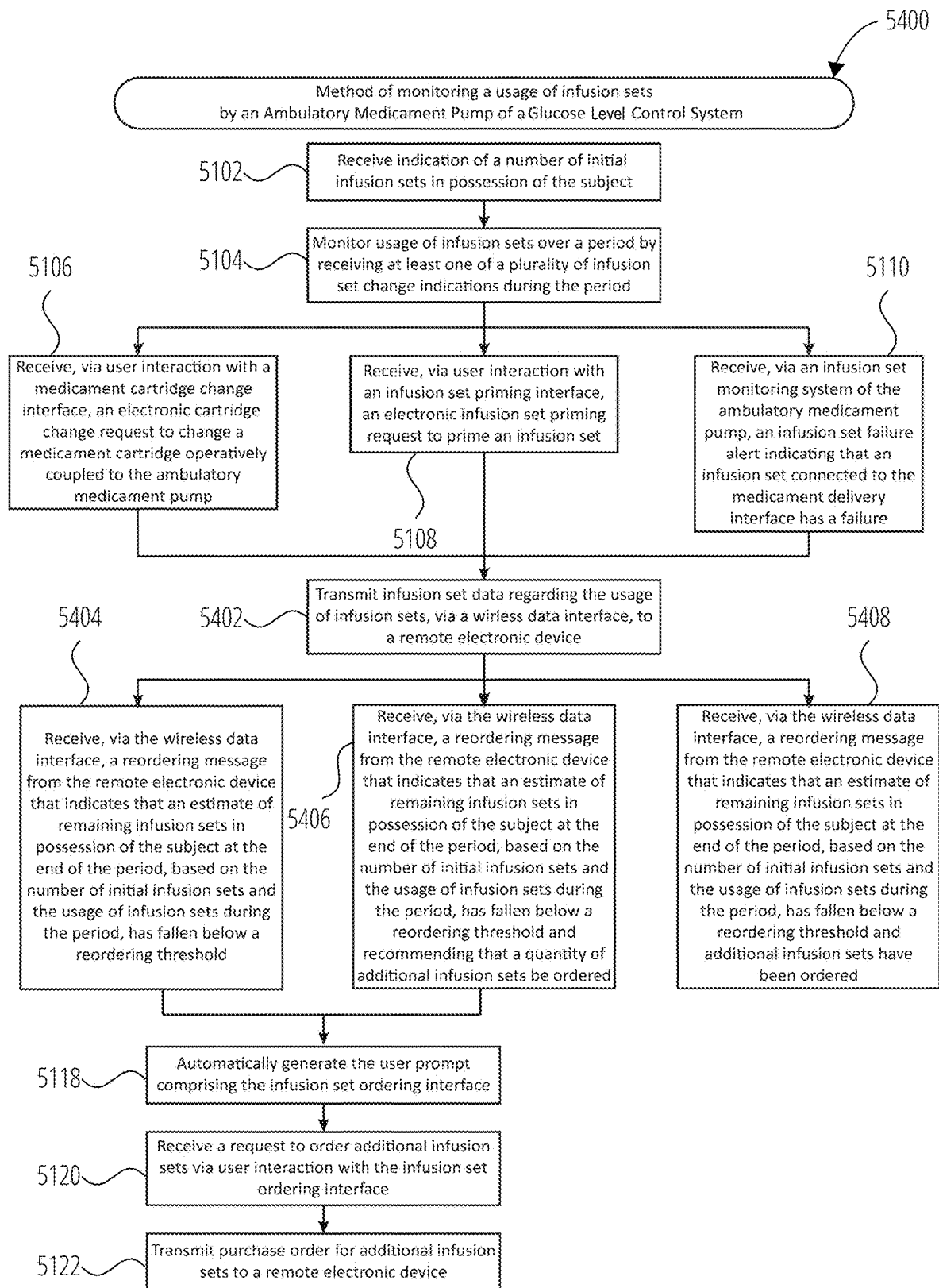
FIG. 54 shows a method of monitoring a usage of infusion sets by an ambulatory medical device (e.g., ambulatory medicament pump) of a glucose level control system, transmitting data regarding the usage of infusion sets, and receiving a reordering message from a remote electronic device.

FIG. 54 is a flow diagram depicting an example method 5400 of monitoring a usage of infusion sets by the AMD 5001 of the glucose level control system 5000. The flow diagram is provided for the purpose of facilitating description of aspects of some embodiments. The diagram does not attempt to illustrate all aspects of the disclosure and should not be considered limiting.

Blocks 5102, 5104, 5106, 5108 and 5110 can be the same as described in reference to FIG. 51.

At block 5402, the system, specifically the AMD 5001 and/or electronic device 5008, can transmit infusion set data, amongst other data (e.g., initial infusion sets), regarding the usage of infusion sets over the period of time, via a wireless data interface, to the remote electronic device 5010 The data can be transmitted using any technique described herein.

At block 5404, the system, via a wireless data interface, can receive a reordering message from the remote electronic device 5008. The reordering message can indicate that an estimate of remaining infusion sets in possession of the subject at the end of the period, based on the number of initial infusion sets and the usage of infusion sets during the period, has fallen below a reordering threshold. The remote electronic device 5010 can make this determination as described herein.

At block 5406, the system, via a wireless data interface, can receive a reordering message from the remote electronic device 5010. The reordering message can indicate that an estimate of remaining infusion sets in possession of the subject at the end of the period, based on the number of initial infusion sets and the usage of infusion sets during the period, has fallen below a reordering threshold. The reordering message can recommend a quantity of additional infusion sets to be ordered, which can be determined algorithmically (e.g., based on the usage data of infusion sets).

Blocks 5118, 5120, and 5122 can be the same as described in reference to FIG. 51.

At block 5408, the system, via a wireless data interface, can receive a reordering message from the remote electronic device 5010 that indicates that an estimate of remaining infusion sets in possession of the subject at the end of the period, based on the number of initial infusion sets and the usage of infusion sets during the period, has fallen below a reordering threshold and additional infusion sets have been ordered. As described herein, in some variants, determining that the estimated number of remaining infusion sets in the possession of the subject at the end of the period falling below the reordering threshold, can trigger an automatic ordering of additional infusion sets to avoid disruptions in therapy. In some variants, the automatic ordering of additional infusion sets can be triggered when the estimated number of remaining infusion sets in possession of the subject at the end of the period falls below an automatic reordering threshold, which can be different than the reordering threshold.

Example Method of Monitoring a Usage of Analyte Sensors

Figure 55:
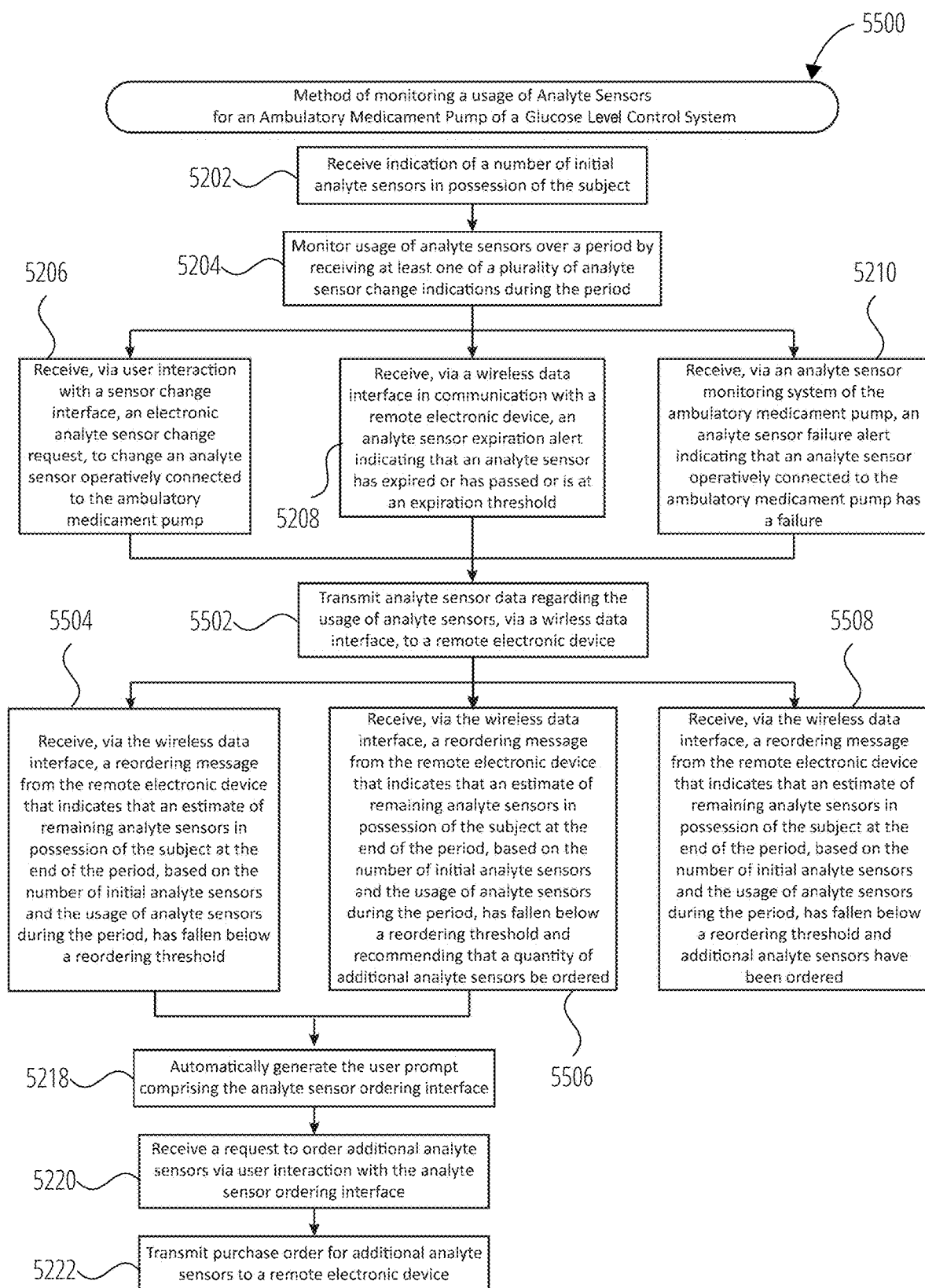
FIG. 55 shows a method of monitoring a usage of analyte sensors by an ambulatory medical device (e.g., ambulatory medicament pump) of a glucose level control system, transmitting data regarding the usage of analyte sensors, and receiving a reordering message from a remote electronic device.

FIG. 55 is a flow diagram depicting an example method 5500 of monitoring a usage of analyte sensors for the AMD 5001 of the glucose level control system 5000. The flow diagram is provided for the purpose of facilitating description of aspects of some embodiments. The diagram does not attempt to illustrate all aspects of the disclosure and should not be considered limiting.

Blocks 5202, 5204, 5206, 5208, and 5210 can be the same as described in reference to FIG. 52.

At block 5502, the system, specifically the AMD 5001 and/or electronic device 5008, can transmit analyte sensor data regarding the usage of analyte sensors over the period of time, via a wireless data interface, to the remote electronic device 5010. The data can be transmitted using any technique described herein.

At block 5504, the system, via a wireless data interface, can receive a reordering message from the remote electronic device 5010. The reordering message can indicate that an estimate of remaining analyte sensors in possession of the subject at the end of the period, based on the number of initial analyte sensors and the usage of analyte sensors during the period, has fallen below a reordering threshold, which can be determined by the remote electronic device 5010 (e.g., remote computing environment). This can be determined algorithmically as described herein.

At block 5506, the system, via a wireless data interface, can receive a reordering message from the remote electronic device 5010. The reordering message can indicate that an estimate of remaining analyte sensors in possession of the subject at the end of the period, based on the number of initial analyte sensors and the usage of analyte sensors during the period, has fallen below a reordering threshold, which can be determined by the remote electronic device 5010 (e.g., remote computing environment). The reordering message can recommend a quantity of additional analyte sensors to be ordered, which can be determined algorithmically (e.g., based on the usage data of analyte sensors) as described herein.

Blocks 5218, 5220, and 5222 can be the same as described in reference to FIG. 52.

At block 5508, the system, via a wireless data interface, can receive a reordering message from the remote electronic device 5010 that indicates that an estimate of remaining analyte sensors in possession of the subject at the end of the period, based on the number of initial analyte sensors and the usage of analyte sensors during the period, has fallen below a reordering threshold and additional analyte sensors have been ordered. As described herein, in some variants, determining that the estimated number of remaining analyte sensors in the possession of the subject at the end of the period falling below or reaching the reordering threshold, can trigger an automatic ordering of additional analyte sensors to avoid disruptions in therapy, which can be performed by the remote electronic device 5010. In some variants, the automatic ordering of additional analyte sensors is triggered when the estimated number of remaining analyte sensors in possession of the subject at the end of the period falls below or reaches an automatic reordering threshold, which can be different than the reordering threshold.

Example Method of Monitoring a Usage of Transmitters

Figure 56:
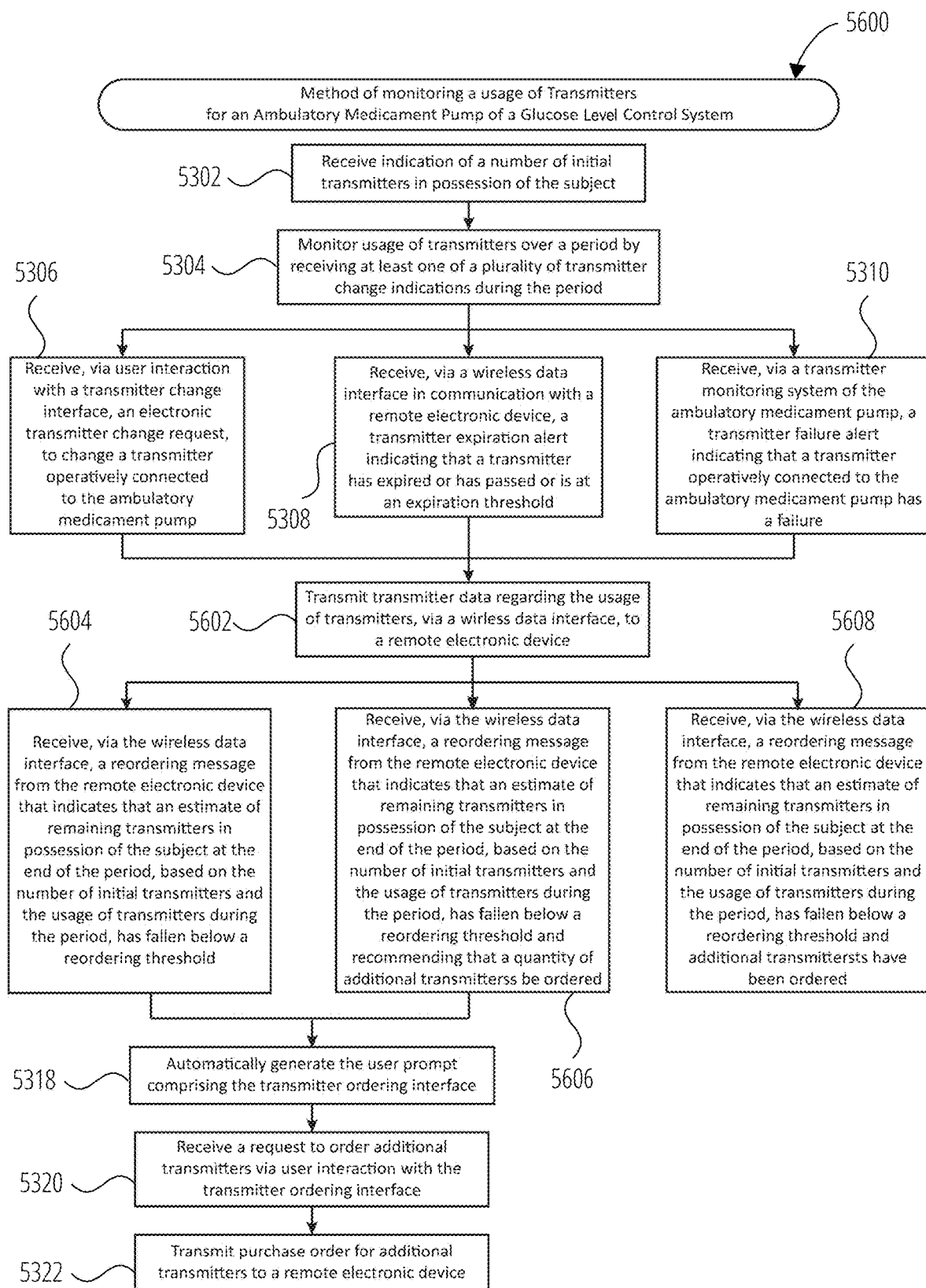
FIG. 56 shows a method of monitoring a usage of transmitters by an ambulatory medical device (e.g., ambulatory medicament pump) of a glucose level control system, transmitting data regarding the usage of transmitters, and receiving a reordering message from a remote electronic device.

FIG. 56 is a flow diagram depicting an example method 5600 of monitoring a usage of transmitters for the AMD 5001 of the glucose level control system 5000. The flow diagram is provided for the purpose of facilitating description of aspects of some embodiments. The diagram does not attempt to illustrate all aspects of the disclosure and should not be considered limiting.

Blocks 5302, 5304, 5306, 5308, and 5310 can be the same as described in reference to FIG. 53.

At block 5602, the system, specifically the AMD 5000 and/or electronic device 5008, can transmit transmitter data, amongst other data (e.g., initial transmitters), regarding the usage of transmitters over the period of time, via a wireless data interface, to the remote electronic device 5010. The data can be transmitted using any technique described herein.

At block 5604, the system, via a wireless data interface, can receive a reordering message from the remote electronic device 5010. The reordering message can indicate that an estimate of remaining transmitters in possession of the subject at the end of the period, based on the number of initial transmitters and the usage of transmitters during the period, has fallen below a reordering threshold, which can be determined by the remote electronic device 5010 (e.g., remote computing environment). This can be determined algorithmically as described herein.

At block 5606, the system, via a wireless data interface, can receive a reordering message from the remote electronic device 5010. The reordering message can indicate that an estimate of remaining transmitters in possession of the subject at the end of the period, based on the number of initial transmitters and the usage of transmitters during the period, has fallen below a reordering threshold, which can be determined by the remote electronic device 5010 (e.g., remote computing environment). The reordering message can recommend a quantity of additional transmitters to be ordered, which can be determined algorithmically (e.g., based on the usage data of transmitters) as described herein.

Blocks 5318, 5320, and 5322 can be the same as described in reference to FIG. 53.

At block 5608, the system, via a wireless data interface, can receive a reordering message from the remote electronic device 5010 that indicates that an estimate of remaining transmitters in possession of the subject at the end of the period, based on the number of initial transmitters and the usage of transmitters during the period, has fallen below a reordering threshold and additional transmitters have been ordered. As described herein, in some variants, determining that the estimated number of remaining transmitters in the possession of the subject at the end of the period falling below or reaching the reordering threshold, can trigger an automatic ordering of additional transmitters to avoid disruptions in therapy, which can be performed by the remote electronic device 5010. In some variants, the automatic ordering of additional transmitters can be triggered when the estimated number of remaining transmitters in possession of the subject at the end of the period falls below or reaches an automatic reordering threshold, which can be different than the reordering threshold.

Generating and Sharing Aggregate Reports

In some cases, a computing system 5704 (e.g., a computing system in a patient data network) may be configured to receive therapy data from a plurality of glucose level control systems (GLCSes) providing glucose control therapy to a group of subjects and generate aggregate therapy reports comprising data and information usable for evaluating a performance of the GLCSes providing glucose control therapy to the group of subjects and/or a quality of the resulting glycemic control of the group of subjects. IN some cases, the computing system 5704 may include one or more features described above with respect to host computing system 704. For example, the computing system 5704 may exchange date with one or more GLCSes (e.g., AMDs such as AMD 100 or AMD 600), via data links (e.g., wireless data links) described with respect FIG. 7. An aggregate therapy report may be referred to herein "aggregate report". Further, the computing system 5704 may be configured to provide access to previously generated aggregate reports or generate customized aggregate reports, upon receiving report requests from eligible users. In various implementations, a GLCS may comprise an ambulatory medical device (AMD) such as glucose level control systems 200*a*, 200*b*, 200*c*, 200*d*, AMD 600, AMD 100, or AMD 702 described above with respect to FIG. 1A-FIG. 1C, FIG. 2A-FIG. 2D, FIG. 6, and FIG. 7. In some cases, a GLCS may include a medicament pump configured to deliver a medicament to a subject upon receiving a dose control signal from a controller (e.g., control and computing module 610) to control a glucose level of the subject.

Glucose control therapy may comprise delivering one or more volumes of a regulatory or a counter-regulatory medicament (e.g., insulin or/and glucagon) to a subject using an injection set via an injection site on subject's body. As described above, a GLCS from the plurality of GLCSes may deliver a medicament dose based at least in part on the glucose level data decoded from glucose level signals received from a glucose sensor. In some cases, a controller (e.g., the control and computing module 610) of the GLCS may use a control algorithm with a set of control parameters to determine a medicament dose and a medicament delivery time based on glucose level data. Subsequently, the controller may generate a dose control signal that causes the delivery of the determined medicament dose at the medicament delivery time to the subject. As such, is some cases, the GLCS may autonomously or semi-autonomously control a glucose level of the subject.

In some cases, the group of subjects may be a plurality of subjects selected by a healthcare provider, manufacturer, or a payer. In some cases, the group of subjects may be associated with a medical office, health care provider, health center, or a payer (e.g., a health insurance provider). In some cases, the group of subjects may receive care from the same healthcare provider, may have the same health insurance, or may receive glucose control therapy from a specific type of GLCS or GLCSes using a specific algorithm. In some cases, the group of subjects may include a plurality of subgroups of subjects. Subjects in different subgroups may be from different age groups, receive glucose control therapy from different types of GLCSes, from GLCSes using different values of control parameters, or from GLCSes using different control algorithms. In some examples, the group of subjects may include 10, 50, 100, 500, or 1000 subjects.

In some cases, the aggregate report may be used by health professionals and researchers to better understand the impact of different values of control parameters, and/or evaluate various protocols and methods used to manage glycemic control of group of subjects receiving glucose therapy from the plurality of GLCSes. In some cases, the aggregate report may be used by a health care provider to monitor and improve the glycemic control of a group of subjects associated with a health center. For example, a health care provider may use an aggregate report to make a decision regarding a increasing or lowering a glucose level set point of the GLCS used by a subject.

In some cases, the health professional may use a first aggregate report generated for the group of subjects receiving therapy from a first type of GLCS and a second aggregate report generated for the same group of subjects receiving therapy from a second type of GLCS, to select the first type of GLCS or the second type of GLCS for providing therapy to the group of subjects. In some cases, a health care provider may use one or more aggregate reports to compare the performance of a type of GLCS providing glucose control therapy to a subject under his care, to the performance of the same type of GLCS obtained from a trial study.

In some cases, a payer may use multiple aggregate reports associated with multiple GLCSes, to select one or more GLCSes that will be covered by an insurance policy. For example, the payer may use the first and the second aggregate reports to select the first type of GLCS or the second type of GLCS as the GLCS that will be covered by an insurance policy (e.g., a policy offered to the subjects associated with a health center).

Further, an aggregate report may be used to: compare glycemic control of subjects receiving glucose control therapy from bi-hormonal GLCSes to those receiving glucose control therapy from mono-hormonal GLCSes, compare glycemic control of subjects receiving glucose control therapy from GLCSes using a first set of control parameters to those receiving glucose control therapy from GLCSes using a second set of control parameters, compare glycemic control of subjects receiving glucose control therapy from GLCSes using a first control algorithm to those receiving glucose control therapy from GLCSes using a second control algorithm, or compare glycemic control of subjects from different age groups, or different ethnical groups. In various implementations, an aggregate report may be used for other types of comparative studies and assessments.

Figure 57:
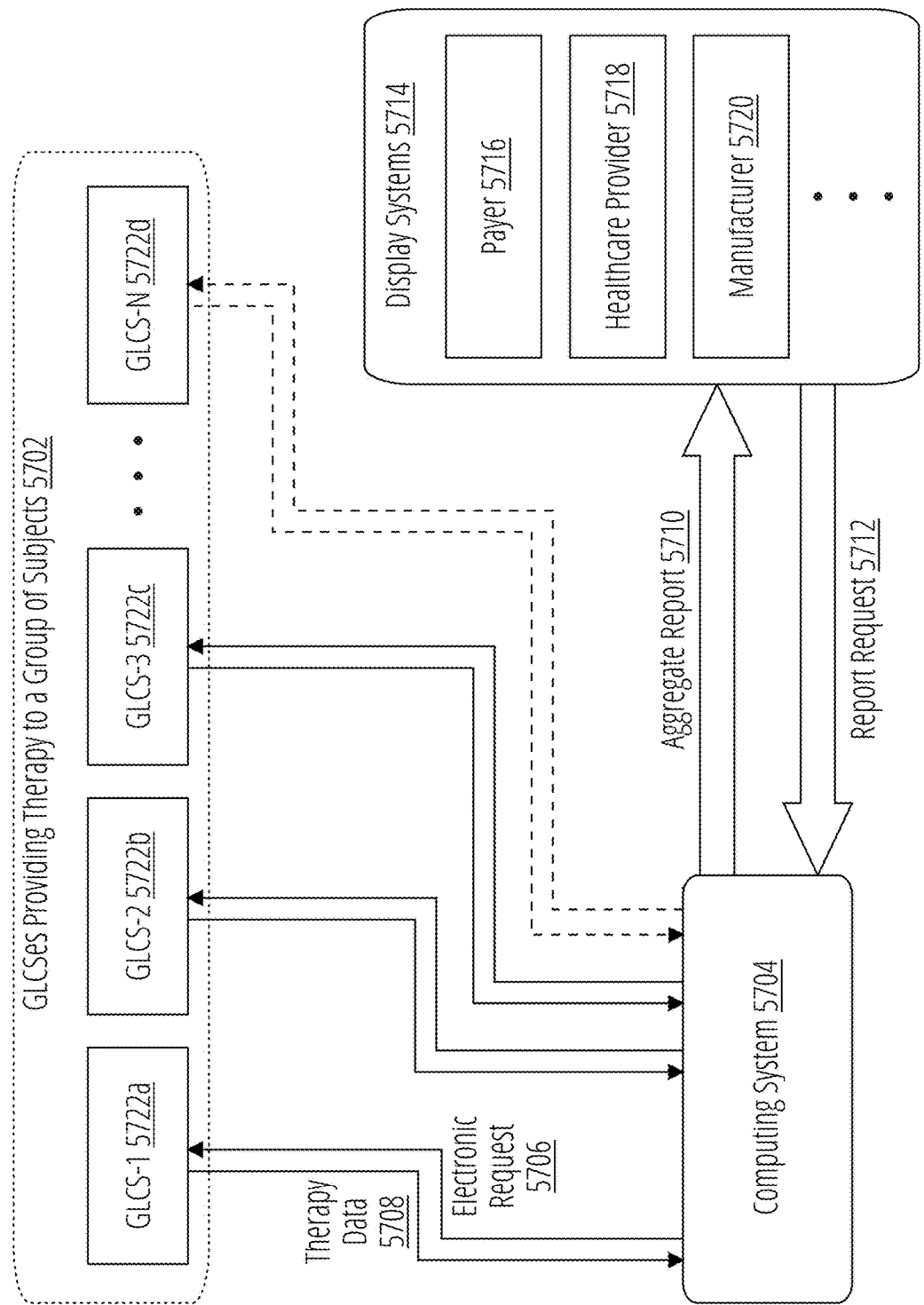
FIG. 57 illustrates a block diagram of an example system for generating aggregate reports based on therapy data received from a plurality of Glucose Level Control Systems (GLCSes) to a plurality of subjects, and sharing the aggregate reports with a display system.

FIG. 57 illustrates a block diagram of an example system for generating and sharing aggregate reports related to glucose control therapy provided to a group of subjects by a plurality of GLCSes 5702, and the resulting glycemic control of the subjects. In some cases, an aggregate report may be generated by the computing system 5704 using therapy data received from a plurality of GLCSes 5702 providing glucose control therapy to the group of subjects. In some cases, the computing system 5704 may receive the therapy data from GLCSes 5702 in response to sending electronic requests to the GLCSes 5702. For example, the computing system 5704 may send an electronic request 5706 to the GLCS-1 5722a of the plurality of GLCSes 5702 that provides glucose therapy to a subject who belongs to the group of subjects. The electronic requests may be sent via a wired or a wireless data connection between the computing system 5704 and the GLCS-1 5722a. In some cases, a wireless data connection may be a direct end-to-end data connection (e.g., based on LTE standard).

In response to receiving the electronic request 5706, the GLCS-1 5722a may send therapy data 5708 to the computing system 5704 via the same data connection though with the electronic request was received or another wired or wireless data connection.

In some cases, GLCS-1 5722a may comprise the AMD 600 that provides therapy to the subject 622 and the therapy data may be stored data in a memory of the AMD 600 (e.g., memory 616).

In some cases, the group of subjects may include N subjects and the computing system 5704 may send N separate electronic requests wherein each electronic request is sent to a GLCS of the plurality of GLCSes 5702. N can be between 2, and 10, 10 and 50, 50 and 100, 100 and 500, or 500 and 1000 or other values.

The computing system 5704 may send the N electronic requests within a data request period. In some embodiments, the data request period may be provided by a payer, a healthcare provider, or a manufacturer, and can be stored in a memory of the computing system 5704. The data request period may be a time period between sending a first electronic request (e.g., to the GLCS-1 5722a) and a last electronic request (e.g., to the GLCS-N 5722d). The data request period may be few hours, a day, or one week.

In some cases, the computing system 5704 may send the electronic requests simultaneously or sequentially. In some cases, the computing system 5704 may send the electronics requested to different GLCSes at different times. For example, a first electronic request 5706 may be send to the GLCS-1 5722a at a first time, a second electronic request may be sent to GLCS-2 5722b at a second time and a third electronic request may be sent to GLCS-3 5722c at a third time where the first, second and third times are distributed over the data request period.

In some cases, multiple electronic requests may be sent to a single GLCS. For example, if therapy data is not received from GLCS-1 5722a within a waiting period after sending the electronic request 5706, the computing system 5704 may send another electronic request to the GLCS-1 5722a. In some cases, the computing system 5704 may continue sending electronic requests to the GLCS-1 5722a until receiving the therapy data 5708 or an electronic response indicating that the therapy data cannot be provided. In some cases, if therapy data is not received from the GLCS-1 5722a within the data request period, the therapy data associated with GLCS-1 5722a may be excluded from the aggregate report.

Therapy data may comprise data received or collected by the GLCS-1 5722a and/or stored in a memory of the GLCS-1 5722a. In some cases, the therapy data may be a requested portion of the data received or collected by the GLCS-1 5722a and/or stored in a memory of the GLCS-1 5722a. In some implementation, therapy data may comprise data associated with glycemic control of a subject in the group of subjects (e.g., the subject 622) receiving glucose control therapy from GLCS-1 5722a), data associated with glucose control therapy delivered to the subject, or pump usage data. In some cases, therapy data may comprise clinically relevant data generated, measured, recorded, or received by the GLCS-1 5722a. In some embodiments, therapy data may comprise supplementary data. In some cases, supplementary data may include demographic or physiological information about the subject (e.g., age, ethnicity, sex, weight, geographic location, and the like). In various implementations, therapy data may comprise any data or information generated by or stored in a GLCS usable for administering glucose control therapy and/or evaluating the performance of the GLCS or glycemic control of the subject.

In some cases, data associated with glycemic control of the subject (or glycemic control data) may comprise data associated with the glucose levels decoded from glucose level signals received from the analyte (or glucose) sensor 620 that is operatively connected to the subject 622. For example, data associated with glycemic control of the subject may comprise: glucose level data (e.g., glucose levels of the subject 622 decoded from glucose level signals), a time period during which glucose levels were within a set range (e.g., a glucose level range provided by the health care provider, manufacturer or a payer), a time period during which glucose levels were above a maximum glucose level of a set range, a time period during which glucose levels were less than a minimum glucose level of a set range, a number of glucose levels smaller than the minimum glucose level of a set range during an evaluation period, a number of glucose levels larger than the maximum glucose level of a set range during the evaluation period, a mean, an average and/or a standard deviation of glucose levels of the subject 622, measured during the evaluation period.

In some cases, the set ranges, as well as the maximum glucose level and the minimum glucose level of a set range, may be predetermined values (e.g., subject specific predetermined values, age specific predetermined values, or group specific predetermined values) stored in a memory of the GLCS-1 5722a. In some such cases, these predetermined values may be provided by the subject 622, a payer, a manufacturer, or a health care provider. In some case, an evaluation period may be a period provided by a user, the subject, a payer, a manufacturer or a healthcare provider. In some cases, the evaluation period may be a time period received from the computing system 5704. In some examples, the computing system 5704 may determine the evaluation period based at least in part on the data stored in in the computing system 5704 (e.g., previous therapy reports). In various implementations, the evaluation period may be one week, one month, three months, four months, six months, or shorter or longer periods. In some cases, the average glucose level or standard deviation of glues levels may be determined by the controller (e.g., control and computing module 610) of a GLCS (e.g., AMD 600) based on glucose level signals received during the evaluation period.

In some cases, data associated with glucose control therapy delivered to the subject 622 (or glucose control therapy data) may comprise: medicament types delivered to the subject 622, amounts of a medicament delivered to the subject, total daily doses of each medicament (e.g., insulin or glucagon) delivered to the subject, a number and/or doses medicament boluses delivered to the subject, distribution of medicament doses delivered throughout a time period, and/or percentages of total daily doses delivered as basal, correction, or meal doses.

In some implementations, pump usage data may comprise: a daily number of meal announcements received by the GLCS-1 5722a, a daily number of medicament bolus or medicament burst requests received by the GLCS-1 5722a, time intervals between infusion set changes announcements received by the GLCS-1 5722a, a total number of meal announcements received from a subject or a user, a total number of bolus or medicament burst requested, a total number of infusion set replacements, recorded by the GLCS-1 5722a or announced/indicated by the subject, time intervals between medicament cartridge changes, or a user interaction with a user interface of the glucose level control system, during the evaluation period. In some cases, pump usage data may include pump connectivity data associated with availability of medicament administration (also known as channel availability). For example, connectivity data may include time intervals during which: the GLCS-1 5722a is disconnected from the infusion set, the infusion set is disconnected from the subject, or a volume of a medicament left in a medicament reservoir is not sufficient for providing the required glucose therapy, or time periods during which the first glucose level control system could not deliver glucose control therapy to the subject for other reasons. In some examples, an infusion set change may be announced by the user (e.g., via a user interaction with a user interface of the GLCS). In some examples, the GLCS may detected an infusion set change, and record as part of the usage data.

In some implementations, the pump usage data may include: a basal rate of insulin delivery requested or adjusted by the user or the subject, a daily (or total) number and/or dosage of bolus insulin delivery (e.g., user-initiated bolus deliveries), a daily (or total) number and/or values of carbohydrate ratios and/or insulin sensitivity factors provided by the subject or the user, or a daily (or total) number and/or values of adjustments made (by the user or the subject) to a control parameter, during the evaluation period. In some cases, pump usage data may include data associated with a user interaction with a user interface of the glucose level control system. For example, a daily (or total) number of alarms snoozed by the user, during the evaluation period.

In various implementations, a value or a change of a GLCS parameter related to delivery of the medicament to the subject, may be saved by the GLCS as data associated with glucose control therapy delivered to the subject if it is controlled or adjusted by the GLCS, or as usage data if it is provided by the user, e.g., via an interaction with a user interface of the GLCS. For examples, a number of medicament doses delivered to the subject in response to user requests, may be considered pump usage data, while a number of medicament doses delivered to the subject based on a time and dose determined by the GLCS, may be considered glucose control therapy data.

In some cases, a medicament burst may comprise delivering a medicament burst associated with a meal or with a time period during which the subject does not receive therapy from the GLCS-1 5722a. For example, a medicament burst (e.g., a G burst) may comprise a volume of glucagon delivered to the subject before the subject is disconnected from the GLCS-1 5722a for a period.

In some cases, therapy data may comprise raw therapy data received by the GLCS-1 5722a and stored in a memory of the GLCS-1 5722a. For example, raw therapy data may include glucose levels, the times at which the glucose levels were received, doses of medicament delivered to the subject, the times at which the medicament doses were delivered, and the times at which the infusion set were replaced. In some cases, therapy data may comprise processed therapy data generated by the GLCS-1 5722a using the raw therapy data and reference values (e.g., evaluation period, set ranges of measured glucose level, and the like) stored in the GLCS-1 5722a (e.g., predetermined values or evaluation period). For example, processed therapy data may include: the time period during which glucose levels were within a set range, average glucose level of the subject, the number of recorded meal announcements during the evaluation period, total daily doses of insulin or glucagon delivered, and the like.

In some cases, in addition to glucose level data, the therapy data may include additional physiological data associated with a health condition of the subject. In some cases, the additional physiological data may be collected by the GLCS-1 5722a using one or more sensors other than the analyte sensor (e.g., glucose sensor) glucose sensor 620 (e.g., heart rate sensor, temperature sensor, oxygen level sensor, and the like). In some examples, the therapy data may further include any type of data that may be obtained by the GLCS-1 5722a directly or via an intermediary electronic device (e.g., a heart rate sensor, blood pressure sensor, or other types of sensors). For example, GLCS-1 5722a may receive data corresponding to a location the subject (e.g., from a GPS system) or a level activity of the subject (e.g., from a motion sensor).

In some embodiments, the GLCS-1 5722a may send raw therapy data to the computing system 5704 and the computing system may generate processed therapy data using the raw therapy data received from the GLCS-1 5722a and reference values stored in the computing system 5704.

In some cases, the electronic request may include a device ID (e.g., an IP address, a serial number or the like) associated with the GLCS-1 5722a, and request information associated with the therapy data. Up on receiving the electronic request and verifying that the device ID included in the electronic request matches with the device ID of the GLCS-1 5722a, a controller (e.g., control and computing module 610) of the GLCS-1 5722a may send the therapy data based at least in part on the request information.

Request information may include instructions and/or information usable for selecting and/or generating the therapy data. In some cases, the request information may indicate the requested portion of data (e.g., raw therapy data) stored in the GLCS-1 5722a, that is requested by the computing system 5704. In some cases, the GLCS-1 5722a may use the information and/or the instructions included in the request information to generate therapy data (e.g., processed therapy data) by processing a portion of raw therapy data (e.g., glucose level data) stored in a memory of GLCS-1 5722a. In some cases, the request information may include a time interval associated with the requested portion of the therapy data that is requested by the computing system 5704 or is required to generate therapy data requested by the computing system 5704. In some cases, the request information may include the evaluation period and/or a time interval over which a statistical parameter (average glucose level) is calculated.

In some examples, the request information may include codes (e.g., hexadecimal codes), indicating a type and/or a portion of raw or processed therapy data that should be generated and/or transferred to the computing system 5704. For example, a code may indicate that the computing system 5704 is requesting a total number of meal announcements, a total number of infusion set replacements recorded during the evaluation period, an average glucose level data calculated over an evaluation period, or other types or processed therapy data. In some cases, where processed therapy data is requested by the computing system 5704, the code may further indicate a time interval (e.g., the evaluation period) that may be used by the control and computing module 610) to generate a requested value. For example, the control and computing module 610 of a GLCS may calculate the total number of meal announcements, total number of infusion set replacements, and average glucose level of the subject, over the time interval indicated by the code.

In some cases, the computing system 5704 may send the electronic request and receive the therapy data via a data connection established with the GLCS-1 5722a. In some cases, the data connection may be a direct end-to-end data connection (e.g., via the wireless wide area network). In some cases, the data connection may be a secure data connection. In some cases, the computing system 5704 may use an asymmetric key pair to securely receive the therapy data. For example, the computing system 5704 may send a public key to the GLCS-1 5722a where the public key is associated with a private key stored in the computing system 5704. The GLCS-1 5722a may use the public key to encrypt the therapy data and transmit the encrypted therapy data to the computing system 5704 via the data connection. Upon receiving the encrypted therapy data, the computing system 5704 may use the private key to decrypt the therapy data. Alternatively, or in addition, a shared secret may be determined for the computing system 5704 and the GLCS-1 5722a. The GLCS-1 5722a may use the shared secret to encrypt the therapy data, and transfer the encrypted therapy data to the computing system 5704.

In some cases, the computing system 5704 may open or provide a port to the GLCS-1 5722a enabling the GLCS-1 5722a to connect to the identified port and transfer the therapy data to the computing system 5704 via the identified port. Further, transferring therapy data may include the computing system 5704 sending an acknowledgement packet that the transfer request is approved or permitted. The GLCS-1 5722a may transfer the data in response to approval by the computing system 5704 to transfer the therapy data. In some cases, the approval may be based on the computing system 5704 confirming user account information (e.g., such as a username and/or password).

Upon receiving the therapy data 5708, the computing system 5704 may process at least a portion of the therapy data received from a GLCS of the plurality of GLCSes 5702, to determine values of one or more biometric parameters for the subject who receives therapy from the corresponding GLCS using a model (e.g., a kinetic model). A biometric parameter may be a related to one or more parameters whose values are included in the therapy data (e.g., raw therapy data). In some examples, the biometric parameter can be an estimated level of Hemoglobin A1c (eHbA1c), insulin sensitivity, insulin-to-carbohydrate ratio, insulin correction factor, or other biometric parameters that may be estimated or calculated using therapy data. In some cases, a value of a biometric parameter may be included in the received therapy data. For example, the GLCS may process raw therapy data to generate the value of one or biometric parameters and transmit the corresponding values to the computing system 5704 as processed therapy data. In some embodiments, the computing system 5704 may process raw therapy data received from a GLCS to determine values of parameters other than biometric parameters; for example, an average glucose level of the subject over the evaluation period, a total daily dose of insulin or glucagon delivered to the subject, total number of medicament bursts delivered to the subject, and the like.

After receiving therapy data from all the GLCSes 5702 providing therapy to the group of subjects, the computing system 5704 may generate aggregate therapy data and aggregate biometric parameter data by compiling therapy data received from the GLCSes 5702 and data generated by processing the raw therapy data received from the GLCSes 5702. The aggregate therapy data and aggregate biometric parameters data may be collectively referred to as subject data. Aggregate therapy data may comprise: a list, a table, a spreadsheet, or other types of data storage and management formats that may be used to store and process the therapy data, biometric parameter data, data generated by processing raw therapy data, times and time intervals associated with the therapy data, the corresponding device IDs, information related to the subject associated with each portion of therapy data and the like. Aggregate biometric parameter data may comprise, a list or table that includes all the biometric parameter data, the model or parameter values used to determine the biometric parameter data, the corresponding device ID or device information, information related to the subject associated with the therapy data and the like.

In various implementations, the computing system 5704 may anonymize the therapy data received from each GLCS before generating aggregate therapy data and aggregate biometric parameter data. In some cases, raw or processed therapy data received from a GLCS can be anonymized data.

Subsequently, the computing system 5704 may use reference data stored in a memory of the computing system 5704, aggregate therapy data and aggregate biometric parameter data associated with the group of subjects, to generate a comparative assessment of various aspects of therapy provided by the GLCSes 5702 to the subjects in the group of subjects and the resulting glycemic controls of the subjects. In some implementations, the computing system 5704 may evaluate a quality of the glycemic control of the subjects with reference to one or more glycemic control criteria. In some cases, the computing system 5704 may use aggregate therapy and/or biometric data to evaluate a model (e.g., a kinetic model) used by the GLCSes 5702, a model-predictive control (MPC) algorithm used by the GLCSes, a configuration, a setting, or a feature of the GLCSes 5702, or an infusion set used by the GLCSes 5702.

The computing system 5704 may generate one or more aggregate reports using the outcomes of the comparative assessments and evaluations and store them in a memory of the computing system 5704. The aggregate reports may be anonymized reports without any personal information (e.g., name, address, insurance ID, medical information, and the like) associated with the subjects in the group of subjects associated with the aggregate report. In some cases, the computing system 5704 may transmit the aggregate report (e.g., a copy of the aggregate report) to an electronic system (e.g., a display system, another computing system, a mobile electronic device, and the like). For example, a display system of the display system 5714 may send a report request 5712 to the computing system 5704 and the computing system 5704 may transmit a copy of the aggregate report 5710 to the display system in response to receiving the report request 5712. In some cases, upon receiving a report request 5712 from the display system, the computing system 5704 may permit the user to observe the aggregate report 5710 using the display system without transferring the copy of the aggregate report 5710 to the display system. In some cases, display system 5714 may comprise a display system of a payer 5716 (e.g., an insurance provider), a display system of a healthcare provider 5718, or a display system of a manufacturer (e.g., a manufacturer of the GLCSes 5702). The display system 5714 may comprise remote systems separate from the computing system 5704. In some cases, the display system 5714 may include display systems in a networked computing environment associated with the computing system 5704.

In some implementations, the computing system 5704 may automatically generate an aggregate report upon receiving therapy data from all GLCSes providing therapy to a group of subjects. In some implementations, the computing system 5704 may generate an aggregate report upon receiving the report request from the electronic system, based at least in part on the information included in the report request. In yet other implementations, the computing system 5704 may generate a customized aggregate report upon receiving a customized report request from the electronic system, based at least in part on the information included in the customized report request.

Figure 58:
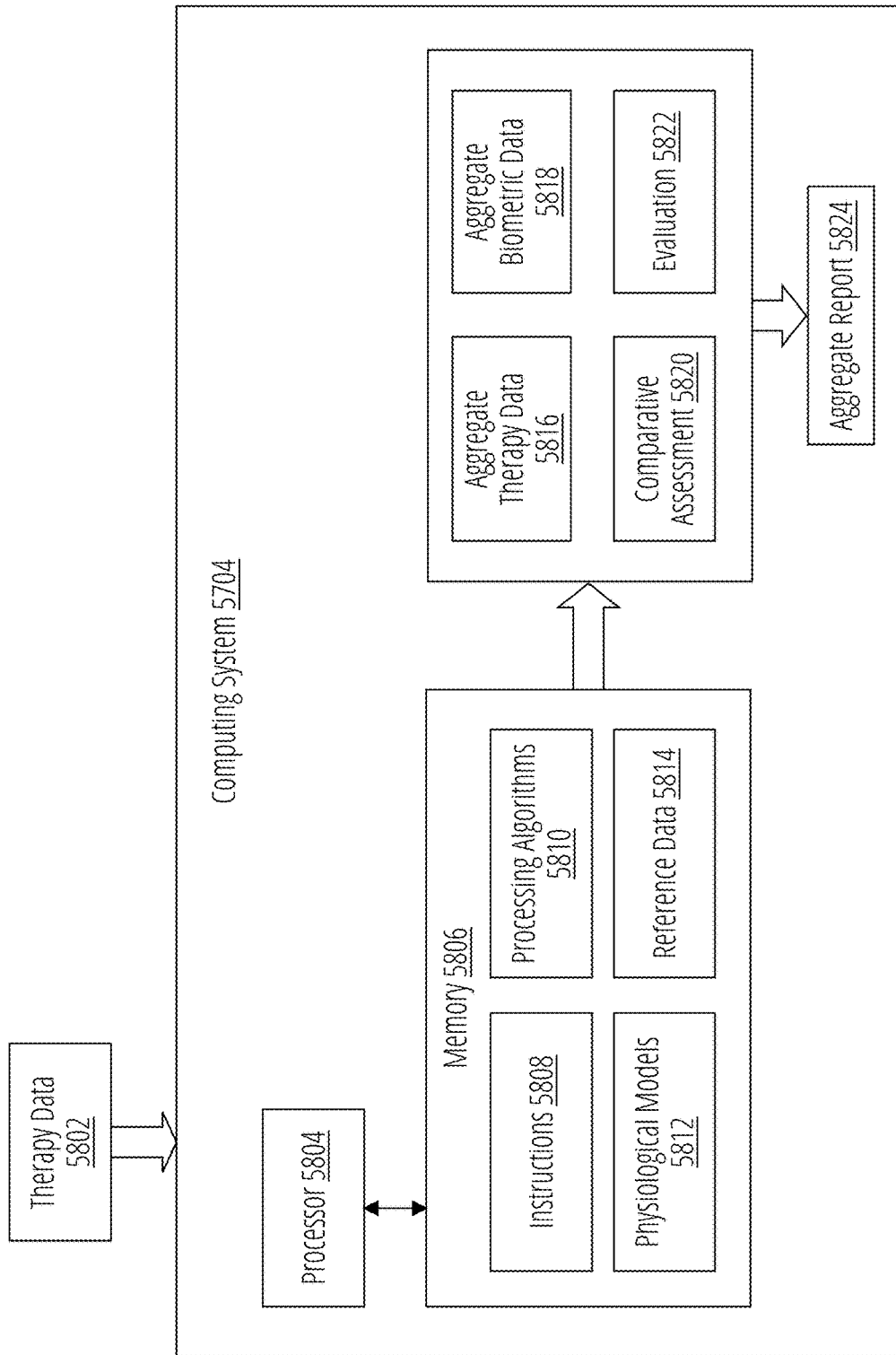
FIG. 58 illustrates a block diagram of an example computing system that generates an aggregate report based therapy data received from a plurality of GLCSes.

FIG. 58 illustrates a block diagram of an example computing system 5704 that generates an aggregate report 5824 using therapy data 5802 received from the plurality of GLCSes 5702. The therapy data 5802 may comprise the therapy data associated with subjects in the group of subjects receiving therapy (e.g., glucose control therapy) from the plurality of GLCSes 5702. The computing system 5704 may include at least one electronic processor 5804 (e.g., electronic hardware processor) and at least one memory 5806 (e.g., a non-transitory memory) that is in communication with the electronic processor 5804. The processor 5804 executes specific computer-executable instructions 5808 stored in the memory 5806 to process therapy data 5708 received from the plurality of GLCSes 5702 providing therapy to a group of subjects and to generate the aggregate report 5824. The processor 5804 may process the therapy data 5802 using processing algorithms 5810, physiological models 5812, and reference data 5814, stored in the memory 5806, to generate the aggregate report 5824. In some cases, therapy data 5802 may be stored in the memory 5806 before being processed by the processor 5804. In some implementations, the processor 5804 may process the therapy data 5802 using processing algorithms 5810, reference data 5814, and physiological models 5812 to generate aggregate therapy data 5816, aggregate biometric data 5818, a comparative assessment 5820, and/or an evaluation 5822. Subsequently, the processor 5804 may generate an aggregate report 5824 that includes a representation of the aggregate therapy data 5816, aggregate biometric data 5818, the comparative assessment 5820 and the evaluation 5822, for example, in the form of tables, graphs, charts, histograms, textual data and the like.

The processor 5804 may use the physiological models 5812 to generate biometric data comprising biometrical parameters determined for subjects in the group of subjects. In some cases, biometric data may include value of one or more parameters (e.g., biometric parameters) generated using raw therapy data. In some embodiments, the processor

5804 may use a physiological model of the physiological models 5812 and a portion of the therapy data 5802 to determine a value of a biometric parameter for a subject. In some cases, the physiological model may include one or more subject specific parameters. In some such cases, the processor 5804 may use a value of a subject specific model parameter in the physiological model to estimate the value of the corresponding biometric parameter for a subject. The values of the subject specific model parameters for each subject in the group of subjects may be stored in the memory 5806. In these implementations the processor 5804 may access the values of the subject specific model parameters for each subject using the device ID of GLCS from which the therapy data is received. In some implementations, the values of the subject specific model parameters for a subject may be included in the therapy data (e.g., therapy data 5708) received from the GLCS that provides glucose control therapy to the subject. In some cases, the processor 5804 may use subgroup specific parameter values or group specific parameter values in place of subject specific parameters to determine the values of the biometric parameters for a subgroup of subjects or a group of subjects, respectively. In some examples, a subgroup specific parameter value or a group specific parameter value can be the average value of a parameter (e.g., a biometric parameter) calculated by averaging over the values associated with subjects in corresponding subgroups or groups. Subgroup specific parameter values or the group specific parameter values may be stored in a memory (e.g., memory 5806) of the computing system 5704.

Examples of a biometric parameter may include but not limited to: estimated Hemoglobin A1c (eHbA1c), insulin sensitivity, insulin-to-carbohydrate ratio, and insulin correction factor. In various embodiments, a model (e.g., a physiological model) may be used to estimate a value of a biometric parameter for a subject based on therapy data received from the GLCS that provides therapy to the subject. For example, data associated with glucose level of the subject and data associated with meal announcements recorded by the GLCS, may be used to calculate insulin sensitivity, insulin-to-carbohydrate ratio, and/or insulin correction factor for the subject.

In some cases, a biometric parameter is a control parameter used by the control algorithm of the GLCS that controls the delivery of medicament to the subject. The computing system 5704 may use a physiological model and measured values of glucose level included in the therapy data, to estimate the control parameter for a subject in the group of subjects. For example, the computing system may use a Pharmacokinetic (PK) model (e.g., a bi-exponential PK model), to estimate a rate of absorption or accumulation of subcutaneously administered insulin in the subject's bloods and/or a decay rate of the insulin level in the subject's blood. In some cases, the control parameter is a peak time of absorption of insulin (Tmax), starting from the time that a subcutaneous dose is delivered, and the computing system 5704 may use the PK model and therapy data to estimate Tmax as a biometric parameter for a subject in the group of subjects. The methods of estimating Tmax based on PK model are described in the International Patent Application PCT/US2020/054130 titled "Blood Glucose Control System" filed on Oct. 2, 2020, and the corresponding publication WO 2021/067856, published on Apr. 8, 2021, the content of which are hereby incorporated by reference in its entirety.

In some cases, the physiological model may comprise a kinetic model for estimating subject's HbA1c level indicating an amount of glucose attached to the hemoglobin in subject's blood. For example, the processor may use the measured glucose levels received from the GLCS-1 5722a (included in therapy data 5708), and the values of subject specific model parameters, subgroup parameters or group parameters to determine an estimated HbA1c value (eHbA1c) for the subject receiving glucose control therapy from the GLCS-1 5722a.

In some implementations, processing algorithms 5810 may include aggregation algorithms, statistical algorithms, comparative algorithms, or evaluation algorithms. In some cases, the processor 5804 may use an aggregation algorithm to generate aggregate therapy data and aggregate biometric data from therapy data 5802 and biometric data respectively. For example, the aggregation algorithm may be used to generate one or more table or matrices that include glycemic control data, glucose control therapy data and pump usage data associated with subjects in the group of subjects receiving therapy from the GLCSes 5702. In some examples, the data in each table or matrix may be sorted based on times or diurnal periods associated with the corresponding portion of therapy data. In some cases, the therapy data associated with different subgroups of subjects may be included in different parts of the table or matrix. In some cases, the aggregate therapy data 5816 may aggregate raw therapy data and/or aggregate processed therapy data.

In some cases, the processor 5804 may use statistical algorithms for statistical analysis of the therapy data. In some cases, the statistical analysis of the therapy data may include determining the statistical characteristics of a portion of therapy/biometric data or aggregate therapy/biometric data associated with the therapy data 5802. In some cases, the processor 5804 may use the reference data 5814 to determine the corresponding statistical characteristics using the statistical algorithms. In some examples, a statistical algorithm may be used to determine the mean glucose level for each subject in the group of subjects and generate a histogram for a subgroup of subjects that represents a number of subjects in the subgroup having mean glucose levels within a glucose level interval of a plurality of glucose level intervals. The mean glucose level may be calculated over a specified time period (e.g., a diurnal period, a day, or a week), or over the evaluation period. In some cases, the glucose level intervals may be equal intervals resulting from dividing a mean glucose level range into M intervals. In some examples, the mean glucose level range can be 120 mg/dl (milligram per deciliters) to 280 mg/dl, 100 mg/dl to 300 mg/dl, or 80 mg/dl to 320 mg/dl. In some examples, M can be larger than 20, larger than 50, or larger than 100, and a mean glucose level interval can be form 0.5 mg/dl to 10 mg/dl. In some cases, the glucose level intervals may be predetermined intervals (e.g., provided by an HCP, a payer or a manufacturer) stored in the memory 5806. In some such cases, the glucose level intervals may be included in the reference data 5814. The computing system 5704 may receive the mean glucose level range, the value of M, or the glucose level intervals from a display system of the display system 5714. The statistical algorithm may be used to calculate a standard deviation and/or variance for the glucose levels associated with subjects in a group of subjects or a subgroup of subjects during a specific time period (e.g., a diurnal period, a day, or a week), or over the evaluation period. In some cases, the specific period is a time interval within the evaluation period (e.g., provided by a user via a display system). Subsequently, the computing system 5704 may use the calculated glucose level standard deviations to generate a histogram showing a distribution of the calculated glucose level standard deviation. In some cases, the computing system 5704 may determine a number or a percentage of subjects having a mean glucose level larger than a set glucose level, smaller than a set glucose level, or within a set glucose level range. In some examples, the set glucose level, or the set glucose level range may be values stored in a memory (e.g., memory 5806) of the computing system 5704. In some examples, the set glucose level, or the set glucose level range may be included in the reference data 5814. In some cases, the set glucose level or the set glucose level range may be values received from a display system, a healthcare provider, a payer, or a manufacturer.

In some cases, the processor 5804 may use comparative algorithms and, the therapy/biometric data, aggregate therapy/biometric data, and/or the statistical characteristics of the therapy/biometric data (e.g., determined by a statistical algorithm) to generate a comparative assessment 5820.

In some cases, the comparative assessment may comprise a comparison of various aspects of the glucose therapy control provided to the group of subjects and the resulting glycemic control, with target values associated with of glycemic control.

In some cases, the comparative assessment may comprise a comparison of glycemic control of different subgroups of the subjects in the group of subjects resulting from glucose control therapy provided by the corresponding GLCSes. In some cases, the comparison of glycemic control of different subgroups of the subjects may be with respect to target values associated with of glycemic control. The target values associated with glycemic control may include an average glucose level, an average glucose level variation, a normal glucose level range, or an average eHbA1c. In some examples, the target values may be stored in a memory (e.g., memory 5806) of the computing system 5704. In some cases, the target values may be included in reference data 5814. In some cases, the target values may be values received from a display system (e.g., a display system of display system 5714), a healthcare provider, a payer, or a manufacturer.

For example, the processor 5804 may use a comparative algorithm to determine a number or a percentage of subjects in a group of subjects whose mean or average glucose level during the evaluation period or a time period within the evaluation period, were within a set glucose level range, e.g., selected by a healthcare provider or a payer and stored in a memory of the computing system 5704. In some cases, the set glucose level range may be included in the reference data. In some cases, the set glucose level range may be included in a report request or customized report request received from a display system. The set glucose level range may be associated with one or more clinical studies, manufacturer's recommendations, or American Diabetes Association (ADA) targets for monitoring glycemic control.

As another example, the processor 5804 may use a comparative algorithm to compare the glycemic control of subjects in a first subgroup of subjects with subjects in a second subgroup of subjects. In some cases, the first and the second subgroups of subjects may receive glucose control therapy from different types of GLCSes or same type of GLCS with different glucose control settings (e.g., different values of control parameters). In some cases, the first and the second subgroup of subjects may use different glucose control methods. In some cases, glucose control methods may include: manual control (where the GLCS delivers glucose therapy upon receiving an input from the subject), automatic mono-hormonal control (where the GLCS delivers glucose therapy using a regulatory hormone, e.g., insulin, using a glucose control algorithm and glucose level data received from a glucose sensor), or automatic bi-hormonal control (where the GLCS delivers glucose therapy using a regulatory hormone and an anti-regulatory hormone, e.g., glucagon, using a glucose control algorithm and glucose level data received from a glucose sensor).

In some examples, the comparative assessment may include determining a total daily range of a biometric parameter (e.g., Hemoglobin A1c) and/or the mean glucose level and comparing them with reference values or set values. Reference of set values, may be received from a display system, of stored in the memory 5806 of the computing system 5704 as reference data (e.g., reference data provided by a healthcare provider or a payer).

In some cases, the processor 5804 may use an evaluation algorithm, to generate an evaluation. The evaluation may include an evaluation of a quality of the glycemic control of one or more subject in a group of subjects or in a subgroup of subjects. The computing system 5704 may generate the evaluation based on the outcomes of the statistical analysis, the comparative assessment, and one or more evaluation criteria. Evaluation criteria may be included in reference data and stored in a memory (e.g., memory 5806) of the computing system 5704. In some cases, evaluation criteria may be included in a report request or customized report request received from a display system. An evaluation criterion may be a criterion of a payer, a healthcare provider, a manufacturer, or a health association. In some cases, an evaluation criterion may be associated with a clinical study. In some examples, the payer's criteria may include one or more of A1C level 7, A1C level 8, A1C level 9 or HEVIS criteria. In some cases, the evaluation may indicate the performance of a control algorithm or a configuration, used by the GLCSes providing therapy to the group of subjects. In some cases, the evaluation may indicate the performance of an infusion set used to deliver glucose control therapy to the group of subjects. In some cases, the evaluation criterion may comprise glycemic control criterion associated with the glycemic control of a subject (e.g., a mean or average daily glucose level, a daily or weekly percentage of periods associated with hypoglycemia or hyperglycemia, and the like). In such cases, the evaluation may include an evaluation of the quality of the glycemic control of one or more subjects with reference to the glycemic control criterion. For example, the computing system 5704 may use an evaluation algorithm to evaluate the quality of glycemic control of the subjects in a group of subjects that receive glucose control therapy from a specific type of GLCS by comparing an average daily period during which the glucose level of group of subjects is within a set range with a set daily period to determine a performance of the specific type of GLCS. In some cases, the commuting system may compare a standard deviation of the distribution of glucose level variations of subjects within a set period with a set standard deviation, to determine a performance of the specific type of GLCS. In some cases, the set range, and the set standard deviation, can be values promised by a manufacturer of the specific type of GLCS. In some cases, the set range, set daily period, and the set standard deviation may be associated with one or more clinical studies, manufacturer's recommendations, or ADA targets for monitoring glycemic control.

In some such cases, the evaluation may be usable to verify that performance of the specific type of GLCS is consistent with a promised performance by a manufacturer of the GLCS. In some cases, the set daily period, set range, set period and set standard deviation, can be values provided by a healthcare provider or a payer. The set daily period, set range, set period and set standard deviation, can be values stored in the computing system 5704 (e.g., included in the reference data) or values included in a report request or a customized report request.

In some cases, the glycemic control criterion may be associated with an expected range for a mean or average daily glucose level or a biometric parameter. In some cases, the glycemic control criterion may be associated with a percentage (e.g., a daily or a weekly percentage) of time periods during which the average value of the glucose level, or the biometric parameter were within the expected range. The expected range can be a custom range selected by a healthcare provider or a payer, and stored in a memory of the computing system 5704. In some cases, the expected range may be associated with one or more clinical studies, manufacturer's recommendations, or ADA targets for monitoring glycemic control. In some cases, the expected range may be included in reference data 5814. In some cases, the expected range may be included in a report request 5712 or customized report request received from a display system.

In some cases, the processor 5804 may use a machine learning algorithm (e.g., a deep learning algorithms), to identify a specific glycemic control behavior in the therapy data 5802 aggregate therapy data 5816, biometric data, or aggregate biometric data 5818. The specific glycemic control behavior may be used to generate the evaluation and/or may be included in the aggregate report. For example, the aggregate report may include a histogram representing a percentage of subjects from the group of subjects whose glycemic control behavior was substantially matched with the specific glycemic control behavior. The specific glycemic control behavior may be associated with reference data 5814. In some cases, the specific glycemic control behavior may be provided by a healthcare provides, a payer or a manufacturer. In some cases, the specific glycemic control behavior may be associated with a clinical study.

In some cases, the computing system 5704 may evaluate the performance of subjects in a group of subjects with respect to controlling their glucose level by managing the GLCSes from which they receive glucose level control therapy. In these cases, the processor 5804 may use an evaluation algorithm to select a subgroup of subjects having similar physiological characteristics and similar histories of glycemic control, who received glucose control therapy from same type of GLCS, but with different user controllable parameters or settings. The evaluation algorithm may compare the glycemic control of subjects in the subgroup and categorize subjects in the subgroup based on their glycemic control to determine a performance of subjects.

In some implementations, reference data may include data associated with a payer criteria, data associated with one or more clinical studies or data associated with a recommendation by: a manufacturer, a health association, a health care professional, or American Diabetes Association (ADA). In some examples reference data may include set glucose levels, set glucose level ranges, evaluation criteria, target mean glucose level and/or target values associated with of glycemic control. In these examples, the reference data may include data associated with a trial study.

In some examples, a target or a target range value of a parameter (e.g., a target glucose level range) may be associated with an ADA goal for glucose control therapy or customizable goals set or recommended by a health care provider, a manufacturer, or a payer. For example, the target glucose level range may be determined by a payer, a manufacturer or a healthcare provider based on an average age or a common health condition of the subjects in the group of subjects.

In some cases, a portion of the reference data 5814 may be used to generate the comparative assessment 5820 and the evaluation 5822. In some examples, the portion of the reference data 5814 may be selected by based on a reference data filter. For example, a reference data filter may filter the reference data 5814 by demographic identifiers, usage correlations, and other parameters. In some cases, a reference data filter may be included in the report request 5712 send by a display system. In some cases, different data filters may be used to generate different aggregate reports. In some example, a report request generated by a user via a display system may include instructions to select a portion of the reference data 5814 or exclude a portion of reference data 5814.

In some cases, the computing system 5704 may determine a distribution of the subjects based on a parameter associated with the glycemic control of the subject. The parameter can be an average time within a diurnal period during which the mean glucose level of the subject is within a set range, above a set range, or below a set range. In some cases, the parameter can be a biometric parameter (e.g., eHbA1c). The computing system may determine a number or a percentage of subjects in a group of subjects with a mean or average value of the parameter within a set range. The set range can be a range selected by a healthcare provider or a payer and stored in a memory of the computing system 5704. In some cases, the set range may be included in reference data. In some cases, the set range may be included in a report request or customized report request received from a display system. In some cases, the set range may be associated with one or more clinical studies, manufacturer's recommendations, or ADA targets for monitoring glycemic control.

The aggregate report 5824 may include charts, histograms, plots, time-series, tables, and/or textual information representing aggregate therapy data 5816, aggregate biometric data 5818, the comparative assessment and/or the evaluation of the glycemic control of the group of subjects.

In some cases, the aggregate report 5824 may include charts, tables or textual information representing a breakdown of the reference data used for generating the comparative assessment based on race, income, gender, birthplace, or residence location of a plurality of subjects associated with the reference data.

In some cases, the aggregate report 5824 may include charts, histograms, plots, or tables representing a breakdown of the pump usage data based on a characteristic of the first and the second usage data.

In some cases, the aggregate report 5824 may include charts, histograms, plots or tables representing a number of meal announcement per day, time periods (e.g., daily or, weekly time periods) during which an average glucose level of the subjects has been within one or more set ranges (including time-in-range associated with a glucose level range identified as normal by a healthcare provider, a manufacturer or a payer), standard deviation of the measured glucose level of the group of subjects within different time periods during the evaluation period, average glucose level of different subgroups in the group of subjects during the evaluation period or during one or more time periods within the evaluation period, and the like. For example, the aggregate report may include a histogram illustrating the number of subjects whose time-in-range are within a time interval of a plurality of time intervals.

In some implementations, the aggregate report 5824 may include charts, histograms, plots, or tables representing an evaluation generated by the computing system 5704 associated with one or more evaluation criterion. For example, an aggregate report may include a chart, a histogram, a plot, or a table that illustrates the outcomes of an evaluation based on a glycemic control criterion indicating a quality of glucose level control for a group of subjects. Healthcare providers and/or payers, may use such aggregate report to compare the performance of a type of GLCS that was used by the group of subjects with a target performance (e.g., a performance promised by the manufacturer of the GLCS, a desired performance based on clinical studies, and the like).

In some cases, the processor 5804 may anonymize the aggregate therapy data 5816, aggregate biometric data 5818, the comparative assessment and the evaluation of the glycemic control, before generating the aggregate report 5824. In such cases, the corresponding charts, histograms, plots, time-series, tables, and/or textual information may be anonymized.

In some cases, the subjects whose clinical parameters are outside an expected or target value, may be highlighted in the aggregate report. For examples, all subjects whose average glucose levels during a diurnal period is above or below a set range may be highlighted in the aggregate report. In some cases, behaviors (e.g., high or low number of meal announcements) or device performances (e.g., high occlusion rate) which may be leading to the abnormal outcomes, are highlighted in the aggregate report 5824.

In some embodiments, an aggregate report may be an interactive aggregate report where the user can modify a content of the aggregate report via a user interface of the display system. In some examples, a user may use the user interface to change a parameter used to generate a comparative assessment, an evaluation, a graphical or textual representation of the aggregate therapy data, aggregate biometric data. For example, the user may interactively change a plot that represents basal dose delivery over a period to a plot that represents correction dose delivery or meal dose delivery over the period. As another example, a user (e.g., a healthcare provider) may generate and manipulate one or more graphical representations to make a comparison between the impact of delivering therapy via basal doses, correction doses and meal doses on the glycemic control of a group or subgroup of subjects.

In some cases, the user may be able to vary the time interval, or a parameter range (e.g., glucose level range) associated with a plot. In some cases, the user may interactively select and change the portion of reference data used to generate the aggregate report 5824 (e.g., reference data used to generate he comparative assessment or the customized evaluation represented in the report). For example, the user may select the reference data based on demographic identifies and/or usage correlations. In some cases, the user may generate a comparison between the glycemic control of a subject in the group of subjects and other subjects in the group of subjects. For example, a health care provider may access a report that plots a distribution that was found in the clinical trial and compares to a single patient and to other patients under his/her care.

In some cases, a user (e.g., a payer) may select subgroup of subjects and generate a histogram representing a mean or average glucose level of the subgroup of subjects measured over an evaluation period. In some cases, the subgroup of subjects may include subjects that were receiving glucose control therapy from the same type of GLCS, and the histograms may be used to evaluate the performance the GLCS.

In some cases, the group of subjects may include two or more subgroups where a subgroup of subjects receive identical glucose therapy (e.g., from a specific type GLCS with the same settings an control parameter values), while glucose control therapy provided to the subjects in other subgroups may be different (e.g., different glucose control therapy may be used, different GLCSes may be used to provide glucose control therapy, or different setting or control parameter values may be used by the GLCSes). In some examples, a subgroup may control their glucose level using a manual mode where GLCS delivers glucose therapy upon receiving a user input and another subgroup may receive automated glucose control therapy where the GLCS delivers glucose therapy based on glucose level data received from a glucose sensor and using a control algorithm. In some examples, the group of subjects may receive automated glucose control therapy from a specific type of GLCS however the GLCSes providing therapy to a first subgroup may use a first setting while the GLCSes providing to a second subgroup may use a second setting. In some examples, the group of subjects may receive automated glucose control therapy from one type of GLCS, however the GLCSes providing glucose control therapy to a first subgroup may use first values of control parameters, while the GLCSes providing glucose control therapy to a second subgroup may use second values of the control parameters. Thus, the aggregate report may be used to compare the quality of glucose control therapy provided by different GLCSes, to evaluate the impact of one or more GLCS settings on the quality of glucose control, or to evaluate the impact of different values of control parameters on the quality of glucose control.

Figure 59:
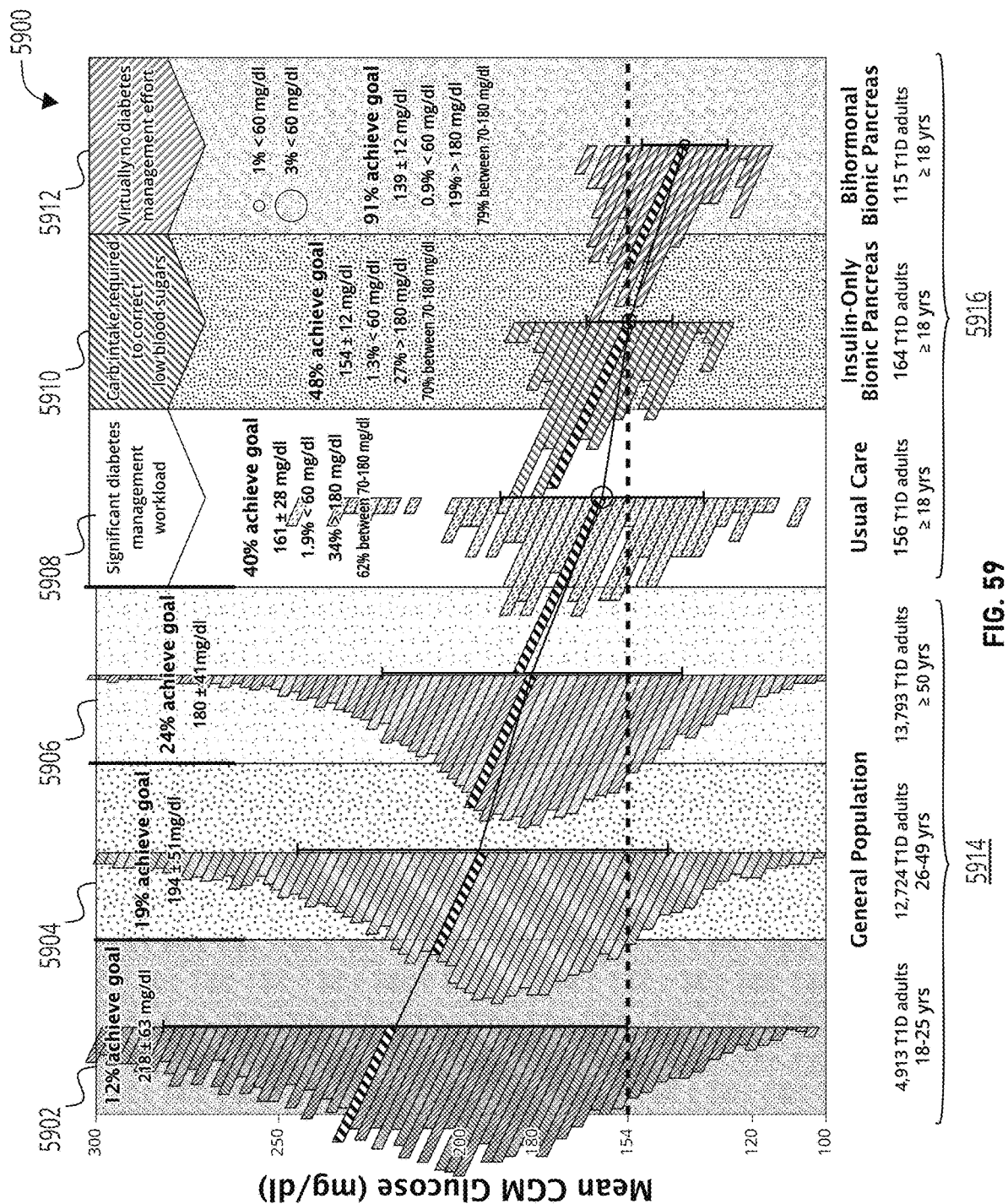
FIG. 59 shows an example aggregate report that generated by the computing system shown in FIG. 9.

FIG. 59 shows an example aggregate report 5900 generated by the computing system 5704 in a patient data network. The aggregate report 5900 may be an example of the aggregate report 5824 generated by the computing system 5704 using therapy data 5708 received from a plurality of GLCSes 5702 providing therapy to a group of subjects.

The aggregate report 5900 includes several mean glucose histograms each indicating a distribution of a mean value of glucose level associated with a group of subjects. The mean value of glucose level for a subject of the group of subjects may be calculated based on glucose levels decoded from glucose level signals received from a glucose sensor (e.g., a CGM sensor) operatively connected to the subject. In some cases, the mean glucose level may comprise mean glucose level in an interstitial fluid expressed in milligram per deciliter (mg/dl). In some cases, the mean glucose level may be proportional to a glucose concentration in subject's blood. The glucose level signals used for calculating the mean glucose level for the subject may be received during the evaluation period.

In the example shown in FIG. 59, the group of subjects includes three subgroups of subjects. A first subgroup of subjects may control their glucose level manually, for example, they use a glucose monitor and test strips to measure their glucose level and manually inject insulin to their body using a syringe, or an insulin pump (e.g., via an infusion set). In some examples, the insulin pump, used by a subject in the first subgroup, may receive glucose level signals from a glucose sensor (e.g., a CGM sensor) that is operatively connect to the subject and display the corresponding glucose level on a display (e.g., touch screen display). Alternatively, the glucose sensor may transmit the glucose level signal to an electronic device (e.g., a smart watch, a smart phone, or the like) of the subject. In these examples, the subject may read his/her glucose level via a display of the insulin pump or the electronic and use the insulin pump to inject insulin to his/her body. The delivery time and the dose of insulin (or glucagon) delivered to a subject in the first subgroup, are determined by the subject or an authorized user (e.g., a guardian or parent) based on the glucose level measured manually using a glucose monitor and a test strip or automatically by a glucose sensor.

A second subgroup of subjects may receive automated or on-line glucose control therapy from mono-hormonal GLCSes that deliver a regulatory hormone (e.g., insulin). A third subgroup of subjects may receive automated glucose control therapy from bihormonal GLCSes that deliver both regulatory and counter-regulatory hormones (e.g., insulin and glucagon). A dose and a delivery time of insulin or glucagon delivered to a subject in the second or third group may be determined by a controller of the GLCS based on glucose level data received from a glucose sensor operatively connected to the subject and using a control algorithm executed by the GLCS. In the aggregate report 5900, the subjects in the first, second, and third subgroups, may be 18 years old or older.

The aggregate report 5900 has two sections 5914/5916 where each section includes three mean glucose level histograms associated with mean glucose levels of subjects in the group of subjects. The first section 5914 includes aggregate therapy data for comparing glycemic control of subjects in different age groups, and the second section 5916 includes aggregate therapy data for comparing glycemic control of subjects who receive glucose control therapy using different control methods (e.g., manual control, automatic control) and/or receive glucose control therapy using different combination of medicaments.

The histograms 5902/5904/5906 included in the first section 5914, illustrate mean glucose histograms for subjects from different age groups. The first histogram 5902 illustrates the distribution of the mean glucose level for subjects between 18-25 years old, the second histogram 5904 illustrates the distribution of the mean glucose level for subjects between 26-49 years old, and the third histogram 5906 illustrates the distribution of the mean glucose level for subjects older than 50 years. The subjects in any age group may be from any of the subgroups described above and therefore may have used different medicament or control methods for glucose control therapy. The first section 5914 of the aggregate report 5900 also includes a percentage of the subjects that have achieved a glucose therapy goal associated with the corresponding age group and a median value of the mean glucose level indicated by the histogram are shown. The glucose therapy goal for each age group may comprise a reference value (e.g., included in the reference data) provided, for example, by a healthcare provider or a payer, or received from a display system.

The histograms 5908/5910/5912 included in the second section 5916, illustrate mean glucose histograms for subjects from different subgroups described above. The first histogram 5908 illustrates the distribution of the mean glucose level for subjects in first subgroup, the second histogram 5910 illustrates the distribution of the mean glucose level for subjects in the second subgroup, and the third histogram 5912 illustrates the distribution of the mean glucose level for the third subgroup. The second section 5916 of the aggregate report 5900 also includes a percentage of the subjects that have achieved a glucose therapy goal and a median value of the mean glucose level indicated by the histogram are shown. The glucose therapy goal may comprise a reference value (e.g., included in the reference data) provided, for example, by a healthcare provider or a payer. The percentage of the subjects in each age group that have achieved a glucose therapy goal is an example of a comparative assessment that may be used to quantify the impact of age on the glycemic control of subjects.

In addition, the second section 5916 of the aggregate report 5900 includes a first percentage of the subjects whose mean glucose level is below a first reference value (e.g., 60 mg/dl), a second percentage of the subjects whose mean glucose level is above a second reference value (e.g., 180 mg/dl) and a third percentage of the subjects whose mean glucose level his within a reference range (e.g., 70-180 mg/dl). The first reference value can be a lower limit and the first percentage may indicate the ratio of the subjects experiencing hypoglycemia during the evaluation period. The second reference value can be an upper limit and the second percentage may indicate the ratio of the subjects experiencing hyperglycemia during the evaluation period. The reference range may comprise a target range and the first percentage may indicate the ratio of the subjects whose mean glucose level stayed within the target range. In some cases, the target range, lower limit, upper limit and other references values used to generate the aggregate report can be associated with an ADA goal for therapy, clinical study results, or a customized values set by a healthcare provider or a payer. The percentage of the subjects in each subgroup that have achieved a glucose therapy goal is an example of a comparative assessment that may be used to quantify the impact of a control method on the glycemic control of a subject.

Example Embodiments

Figure 60:
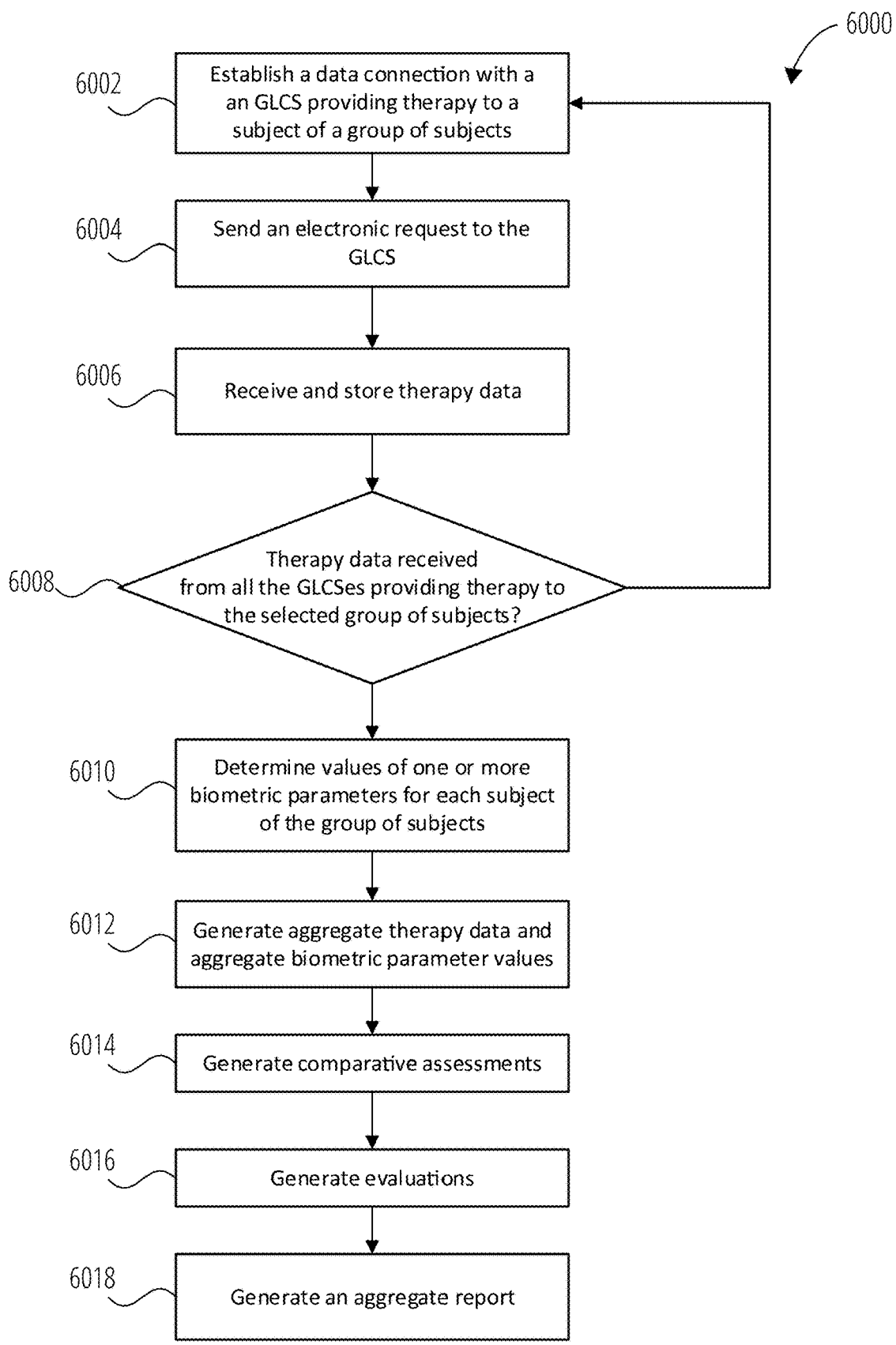
FIG. 60 is a flow diagram showing an example of a process for generating an aggregate report based on therapy data received from a plurality of GLCSes.

FIG. 60 is a flow diagram showing an example of a computer-implemented method or process 6000 that may be used by the computing system 5704 shown in FIG. 58 to generate the aggregate report 5824 or the example aggregate report 5900. The steps below may be performed by the processor 5804 of the computing system 5704 by executing specific computer-executable instructions stored in a non-transitory memory (e.g., a memory 5806 of the computing system 5704) that is in communication with the processor 5804.

The process 6000 begins at block 6002 where the computing system 5704 establishes a data connection with an GLCS (e.g., GLCS-1 5722a) of the GLCSes 5702 providing therapy to a subject from the group of subjects receiving glucose control therapy from the GLCSes 5702. In some cases, the data connection can be a wired or wireless data connection. Further, the data connection can be a digital or analog data connection. In some cases, the data connection can be a direct end-to-end data connection (e.g., an end-to-end data connection based on LTE standard). The data connection can be a secure data connection (e.g., an encrypted data connection). In some cases, the group of subjects may be selected by a healthcare provider, manufacturer, or a payer. In some cases, the group of subjects may be associated with a health clinic selected by a healthcare provider, manufacturer, or a payer.

At block 6004 the computing system 5704 sends an electronic request 5706 to the GLCS-1 5722a via the data connection established at block 6002. In some cases, the electronic request 5706 may include information that uniquely identifies the GLCS-1 5722a (e.g., an IP address, a serial number, or the like). Further, the electronic request 5706 may include information usable by the GLCS-1 5722a to verify that the computing system 5704 is authorized to receive therapy data from the GLCS-1 5722*a*. The electronic request may cause the GLCS-1 5722*a* to transmit therapy data stored in a memory of the GLCS-1 5722*a* to the computing system 5704 over the established data connection. In some cases, the GLCS-1 5722*a* may select and/or generate the therapy data 5708 based at least in part on the information encoded in the electronic request.

At block 6006, the computing system 5704 may receive the therapy data 5708 (e.g., the requested therapy data indicated by the electronic request) from the GLCS-1 5722*a* and store the received therapy data in a memory (e.g., a non-transitory memory). The received therapy data 5708 may include data associated with glycemic control of the subject, data associated with glucose control therapy delivered to the subject, or pump usage data. The therapy data can raw or processed therapy data (e.g., data processed by the GLCS-1 5722*a*).

In some implementations, the received therapy data 5708 may be encrypted therapy data. For example, the computing system 5704 may send a public key to the GLCS-1 5722*a* and GLCS-1 5722*a* may use the public key to encrypt the therapy data. In some examples, the public key may be included in the electronic request. Subsequently, the computing system 5704 may use a private key associated with the public key to decrypt the received encrypted therapy data.

In some implementations, the GLCS-1 5722*a* may anonymize the therapy data 5708 before sending it to the computing system 5704. For example, the GLCS-1 5722*a* may remove any code or information that may be used to identify the subject receiving therapy from the GLCS-1 5722*a*.

At decision block 6008, the computing system 5704 may determine whether therapy data 5708 has been received from all GLCSs in the group of GLCSes 5702 providing therapy to a subject in the group of subjects.

If at the decision block 6008, if the computing system 5704 determines that therapy data has not been received from a GLCS providing therapy to a subject in the group of subjects, the process may return to block 6002 where the computing system 5704 establishes a data connection with the GLCS, whose therapy data is missing, to obtain therapy data from that GLCS using the steps described with respect to block 6004, 6006 and 6008.

If at the decision block 6008, the computing system 5704 determines that therapy data has been received from all GLCSes 5702 providing therapy to a subject in the group of subjects, the process may proceed to block 6010.

At block 6010, the computing system 5704 may determine values of one or more biometric parameters for each subject based at least in part on the therapy data received from a GLCS that provides therapy to that subject. The biometric parameters may be associated with a health condition of the subject. In some cases, the biometric parameters may include one or more of estimated Hemoglobin A1c (eHbA1c) estimated using the measured glucose level of the subject received from the GLCS-1 5722*a* and a kinetic model for estimating HbA1c stored in a memory of the computing system 5704.

In some examples, biometric parameters may include any parameter calculated or derived based on analyzing or manipulating the raw therapy data received from the GLCS-1 5722*a*.

At block 6012 the computing system 5704 may process the received therapy data 5708 and the determined values of the 5816 biometric parameters for subjects in the group of subjects, to generate aggregate therapy data and aggregate biometric data 5818. Aggregate therapy data 5816 may include aggregate glycemic control data, aggregate glucose control therapy data, or aggregate pump usage data.

At block 6014 the computing system 5704 may generate comparative assessments based on reference data 5814, aggregate therapy data 5816 and/or aggregate biometric data 5818. Reference data may comprise reference values associated with the one or more biometric parameters and/or therapy data. In some examples, the reference values may be associated with a payer, a clinical study. In some examples, the references values may be associated with recommendation by a manufacturer, a health association, or a health care professional.

The comparative assessment may include assessment of one or more clinical outcomes based at least in part on a kinetic model used by the GLCSs, a model-predictive control (MPC) algorithm used by the GLCSs and/or a configuration of the GLCSs.

In some cases, the computing system 5704 may generate the comparative assessment by performing a statistical analysis, or a cross-correlation analysis using aggregate pump usage data. For example, comparative assessment may include determining a range of total daily dose of medicament delivered, a mean value of the Hemoglobin A1c determined based on aggregate biometric parameter data, a mean glucose level, or the like.

At block 6016, the computing system 5704 may generate one or more evaluations indicative of the quality of the glycemic control of the subjects in the group of subjects with reference to a glycemic control criterion.

In some cases, the evaluation may indicate the performance of a control algorithm or a configuration, used by the GLCSs providing therapy to the group of subjects. In some cases, the evaluation may indicate the performance of an infusion set used to deliver glucose control therapy to the group of subjects.

At block 6018, the computing system 5704 may generate the aggregate report 5824 based at least in part on a comparative assessment generated at block 6014 and/or an evaluation generated at block 6016. In some cases, the aggregate report may include data, charts, histograms, plots, or tables usable for evaluating a quality of the glycemic control of one or more subjects in the group of subjects each receiving glucose control therapy via a GLCS. In some cases, the GLCSs may be identical, or share a common feature (e.g., a control algorithm). In such case, the aggregate report may be usable for evaluating a performance of a specific type of GLCS, or the performance of the common feature of the GLCS.

The aggregate report may include charts, histograms, plots, tables, or textual data representing the aggregate therapy data, the aggregate physiological parameter data, a comparative assessment, and/or an evaluation.

In some cases, the aggregate report may further include charts, histograms, plots, tables, or textual data representing a breakdown of the aggregate therapy data, the aggregate physiological parameter data, a comparative assessment, and/or an evaluation data based on age, ethnicity of subgroups of subjects in the group of subjects, or a protocol/method used for glucose control therapy during the evaluation period.

In some cases, the aggregate report may further include charts, histograms, plots, tables, or textual data representing a breakdown of the reference data based on race, income, gender, birthplace, or residence location of subgroups of subjects in the group of subjects.

In some cases, the aggregate report may include charts, histograms, plots, tables, or textual data representing a breakdown of the pump usage data based on a characteristic of the pump usage data. For example, a histogram may represent a distribution associated with a daily number of meal announcement or time periods between infusion set changes.

Figure 61:
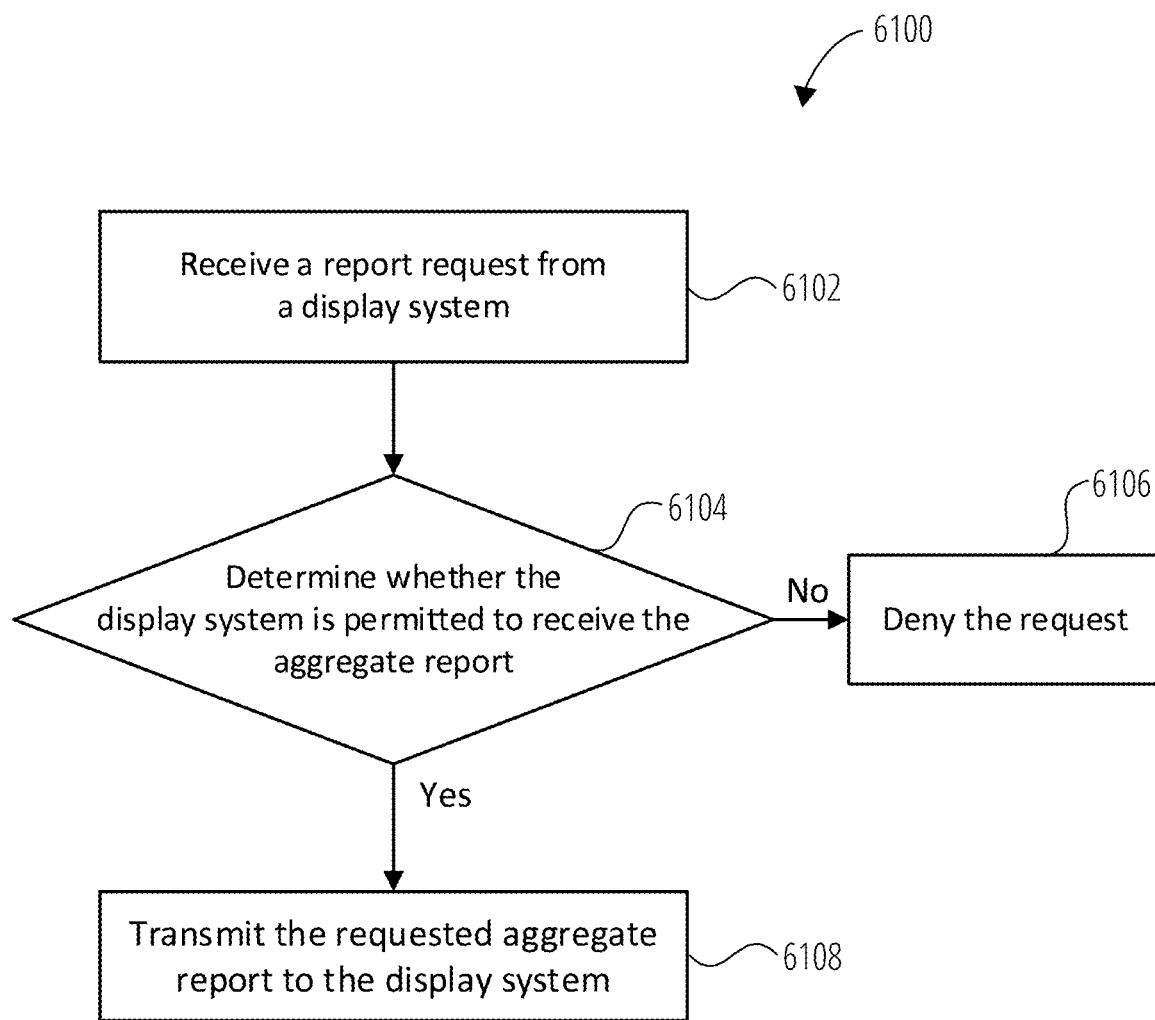
FIG. 61 is a flow diagram showing an example of a process for sharing an aggregate therapy report with a display system.

FIG. 61 is a flow diagram showing an example of a computer-implemented method or process 6100 that may be used by the computing system 5704 to send an aggregate report (e.g., aggregate report 5824) to a display system (e.g., a display system of display system 5714). The steps below may be performed by a processor of the computing system 5704 by executing specific computer-executable instructions stored in a non-transitory memory of the computing system 5704 system 5704 that is in communication with the processor.

The process 6100 begins at block 6102 where the computing system 5704 receives a report request from a display system. In some cases, the display system may be a display system of a remote computing device. In some cases, the remote computing device may be a computing device (e.g., a laptop, a smart phone, or a table) of a: medical practitioner (e.g., such as a doctor, nurse, physician's assistant, etc.), an authorized user (e.g., a researcher, a trainer, and the like), a healthcare provider, a payer (e.g., a health insurance company), or a manufacturer (e.g., the manufacturer of the GLCSs that provide therapy to the group of subjects). In some examples, the display system and the computing system 5704 may be part of the same patient data network. In some examples, the display system and the computing system 5704 may be part of the different patient data networks.

In some embodiments, the computing system 5704 may receive the report request via a data connection (e.g., a data connection) stablished between the display system and the computing system 5704. In some such embodiments, the data connection may be a wireless data connection (e.g., a connection via wide area network, local areas network). In some examples, the data connection may be a connection based on LTE standard. In some examples, the data connection may be a connection via an intermediary electronic device. In some cases, the data connection may be a secure data connection (e.g., an encrypted data connection).

The report request may be a request to receive or view an aggregate report stored in the computing system 5704. The aggregate report may have been generated by the computing system 5704. In some cases, the report request may comprise an account identifier associated with a user of the display who generates the report request. In some cases, the account identifier may include a name, unique identifier (e.g., social security number), an email, an address, a phone number, account information for the user at the networked-computing environment, or any other identifying information. In some cases, the report request may include device identifier (e.g., an IP address, a serial number, or the like) associated with the display system.

The report request may further include a report identifier associated with the requested aggregate report. For example, a plurality of reports associated with different groups of subjects may be stored in the computing system 5704 and the report identifier may be usable by the computing system 5704, to find, select, and/or display the requested report. In some cases, a group of subjects may use the same type of GLCS and/or the same therapy settings (e.g., control parameter values) for glucose control therapy.

At the decision block 6104 the computing system 5704 determines whether the display system or the user of who generated the report request is permitted or authorized to receive, access or view the requested aggregated report indicated in the report identifier based at least in part on the report request. In some cases, different authorization levels may be required to access different reports. In some cases, the permissions of an account or a display system to access and/or receive an aggregate report may be granted and/or modified by a healthcare provider, a payer, a manufacturer, an administrator of the computing system 5704 or the corresponding patient network. For example, a healthcare provider may access an account at a patient network and provide one or more identifiers associated with a user or a display to give them permission to access the aggregate reports stored on the computing system 5704.

If at the decision block 6104 the computing system 5704 determines that the display system or the user who generated the report request is not permitted or authorized to receive, access, or view the aggregate report, the computing system 5704 may proceed to block 6106 where the computing system 5704 denies the request and notifies the user that the request has been rejected.

If at the decision block 6104 the computing system 5704 determines that the display system or the user who generates the report request is permitted or authorized to receive, access or view the aggregate report, the process proceeds to block 6108 where the computing system 5704 transmits the aggregate report (e.g., a copy of the aggregate report) to the display system where the user can view and/or save the report in a local memory of the display system or in a mobile storage devise (e.g., a USB drive, a CD and the like). The computing system 5704 may transmit a copy of the aggregate report over a secure data connection such as an encrypted data connection (e.g., created by using asymmetric key pairs to encrypt the data transmitted, or using a shared secret). In some cases, the data connection used to transmit the report the display system may be different from the data connection used to receive the report request.

In some embodiments, at block 6108 the computing system 5704 may allow the user to view the aggregate report via the display system without transferring the copy of the aggregate report to the display system. In such embodiments, the user may not be able to save a copy of the aggregate report on a local device. Further, in some such embodiments, the computing system may use the device identifier associated with the display system, or the account identifier associated with the user, included in the report request to determine an access period during which the aggregate report may be viewed by the user and/or received by the display system.

In some cases, the report request may not include a report identifier. In some such cases, the computing system 5704 may automatically select or generate an aggregate report based on the account identifier associated with the report request. For example, when a report request is received from a payer, the computing system may select generate an aggregate report that includes distribution of mean glucose level for a group of subjects. As another example, when a report request is received from a health care provider, the computing system 5704 may access a report that includes glucose level distributions from a clinical trial and generate a comparative assessment associated to a single patient and to other patients of the health care provider.

In some embodiments, the computing system 5704 may generate a customized aggregate report, e.g., in response to receiving a customized report request. In these implementations, the computing system 5704 may generate an aggregate report using therapy data stored in a memory of the display system (e.g., a display system of the display systems) and the information included in a corresponding customized report request received from the display system.

Figure 62:
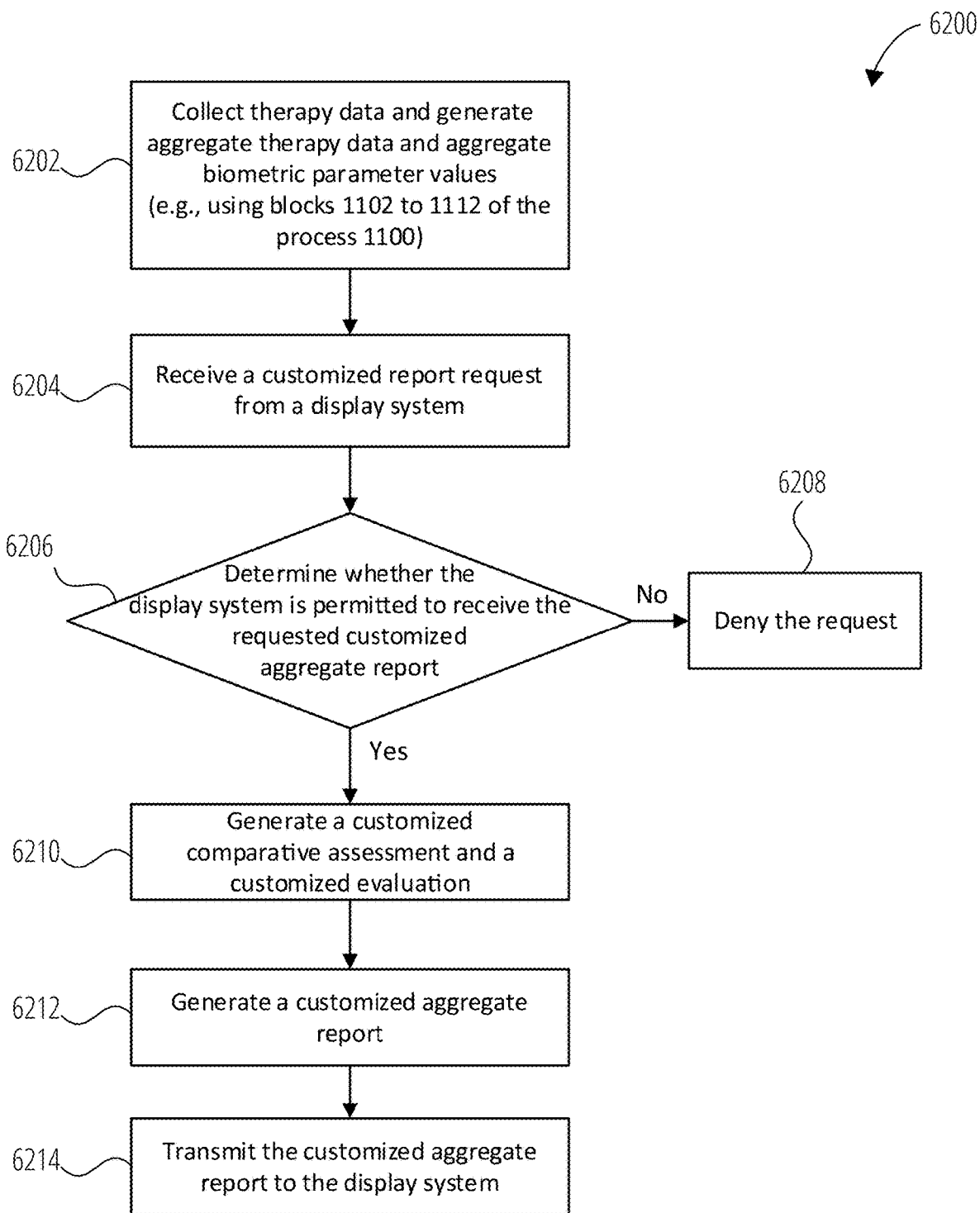
FIG. 62 is a flow diagram showing an example of a process for generating and sharing a customized aggregate therapy report in response to a customized report request received from a display system.

FIG. 62 is a flow diagram showing an example of a computer-implemented method or process 6200 that may be used by the computing system 5704 to generate and send a customized aggregate report to a display system (e.g., a display system of display system 5714). The steps below may be performed by a processor of the computing system 5704 by executing specific computer-executable instructions stored in a non-transitory memory of the computing system 5704 that is in communication with the processor.

The process 6200 begins at block 6202 where the computing system 5704 collects therapy data from AMDs providing therapy to a group of subjects and generates aggregate therapy data and aggregate biometric parameter values using the steps described above with respect to block 6002 to block 6012 of the computer-implemented process 6000. The computing may store the aggregate therapy data and aggregate biometric parameter values in a memory of the computing system 5704. The process 6200 may include one or more embodiments described with respect to process 6000 and/or process 6100.

At block 6204, the computing system 5704 may receive a customized report request from the display device.

A customized report request may include a device identifier (e.g., a serial number or an IP address) and/or a user identifier (e.g., an account ID, or a passcode) of the display system and information (e.g., instructions and data) usable for generating the customized aggregate report. In some embodiments, the customized report request may include data and instructions for selectin a portion of the aggregate therapy data, a portion of the aggregate biometric data and a portion of the reference data stored in the memory of the computing system 5704. In some cases, the customized report request may include information usable for selecting or identifying a group of subjects and the portion of the selected portion of the aggregate therapy data and the aggregate biometric data may be associated with the selected or identified group of subjects. For example, the customized report request may include an age range, a residence area, or information for identifying a health clinic, a health provider or an insurance company associated with the group of subjects. In some cases, the customized report request may include information usable for selecting a group of GLCSes and the portion of the selected portion of the aggregate therapy data and the aggregate biometric data may be associated with the selected group of GLCSs. For example, the customized report request may include a type of GLCS, a setting used by a GLCS, or information for identifying a health clinic, a health provider or an insurance company associated with the group of GLCSs. In some embodiments, the customized report request may include instructions for generating the customized aggregate report using the selected portions of aggregate therapy data, aggregate biometric data, and reference data. In some cases, the customized report request may include a category or type of data that may be included in the aggregate report. In some cases, a category or type of data may comprise outcomes of the statistical analysis, the comparative assessment, or the evaluation performed by the computing system. In some cases, a category or type of data may comprise aggregate therapy data or aggregate biometric data. Further, the customized report request may include a type of comparative assessment, and/or a type of evaluation (e.g., an evaluation based on average glucose level, number of infusion set changes, number of therapy deliveries in a time period, and the like) that may be used to generate the aggregate report. In some cases, the customized report request may include a value of a parameter used in the selected comparative assessment, statistical analysis, and/or evaluation. In some cases, the customized report request may include a value of a parameter used in estimating a biometric parameter. In some cases, the customized report request may include a type of graphical or textual representation (e.g., a plot, a histogram, a table, and the like) that may be used to represent the requested data in the aggregate report. In some examples, the report request may include information for selecting and highlighting a portion of data in the graphs, table, and/or other graphical and textual representations of the requested information.

At the decision block 6206 the computing system 5704 determines whether the display system or the user that generated the customized report request is permitted or authorized to request a customized aggregate report based on the device identifier and/or account identifier included in the customized report request. In some cases, different authorization levels may be required to generate and/or access different customized aggregate reports. In some cases, the computing system many use the device identifier and/or the user identifier to identify a portion of the aggregate therapy data and/or a portion of the aggregate biometric data that may be used to the customized aggregate report. In some cases, different authorization levels may be required to access different customized aggregate reports and different portions of the stored therapy data. In some cases, the permissions of a user or a display system to request and receive a customized aggregate report may be granted and/or modified by a healthcare provider, a payer, a manufacturer, an administrator of the computing system 5704 or the corresponding patient network. For example, a healthcare provider may access an account at a patient network and provide one or more identifiers associated with a user or a display to give them permission to generate certain customized aggregate reports based on the therapy data or a portion of the therapy data.

If at the decision block 6206 the computing system 5704 determines that the customized report request is received from a user or display system that is not permitted or authorized to generate, receive, and view the customized aggregate report, the computing system 5704 may proceed to block 6208 where the computing system 5704 denies the request and notifies the user that the request has been rejected.

If at the decision block 6206 the computing system 5704 determines that the display system or the user who generates the customized report request is permitted or authorized to generate and receive and view the customized aggregate report, the process proceeds to block 6210 where the computing system 5704 generates a customized comparative assessment and a customized evaluation based at least in part on the information included in the customized report request.

A block 6212 the computing system generates the customized aggregate report using the therapy data, customized comparative assessment, customized evaluation, aggregate therapy data, and/or aggregate biometric data, and the information included in the customized report request.

At block 6214 the display system may transmit the customized aggregate report (e.g., a copy of the customized aggregate report) to the display system where the user can view and/or save the report in a local memory of the display system or in a mobile storage devise (e.g., a USB drive, a CD and the like). The computing system 5704 may transmit the customized aggregate report over a secure data connection such as an encrypted data connection (e.g., created by using asymmetric key pairs to encrypt the data transmitted, or using a shared secret). In some cases, the data connection used to transmit the report the display system may be different from the data connection used to receive the customized report request. In some cases, the computing system 5704 may allow the user to view the customized aggregate report via the display system without transmitting the customized aggregate report to the display system.

In some cases, the subjects whose clinical parameters are outside the expected values may be highlighted in the customized aggregate report. In some cases, the computing system 5704 may identify behaviors (e.g., high or low number of meal announcements) or GLCS performance (e.g., high occlusion rate) which may be abnormal, and highlight them in the customized aggregate report. In some such cases, the expected values, abnormal behaviors, and/or abnormal GLCS performance, may be included in the customized report request.

In some embodiments, a customized report may include plots (e.g., histograms) representing a comparison between reference data from a clinical study and a therapy data associated with a subject identified based on the customized report request. In some case, such plots may help a healthcare provider to determine whether the glycemic control of the subject by the GLCS is consistent with the outcomes of the clinical study.

In some embodiments, the computing system 5704 may generate an interactive customized aggregate report and allow a user to modify the customized aggregate report via a user interface of the display system. In some examples, a user (e.g., a healthcare provider or a payer) may request a customized aggregate report and use the display system to tweak a parameter used to generate a comparative assessment, an evaluation, a graphical or textual representation of the aggregate therapy data, aggregate biometric data. For example, the user may interactively change a plot that represents basal dose delivery over a time period to a plot that represents correction dose delivery over time period or meal dose delivery over time period. In some cases, the user may be able to vary the time interval, or a parameter range (e.g., glucose level range) associated with a plot. In some cases, the user may interactively select and change the portion of reference data used to generate the customized aggregate report (e.g., reference data used to generate the customized comparative assessment or the customized evaluation represented in the report). For example, the user may select the reference data based on demographic identifies and/or usage correlations.

In some embodiments, a healthcare provider may send a customized report request to the computing system 5704 to generate a customized aggregate report that includes a comparison between a subject in a selected group of subjects and other subjects in the selected group of subjects.

A user may generate customized aggregate report that include data and graphical representations described above with respect to the interactive aggregate report and for the same type of evaluation and analysis.

Voice Activate Therapy Control

Providing glucose control therapy, such as glucose level control therapy, generally requires regular delivery of medicament. For example, in a healthcare context, a healthcare provider may need to set a rate of medicament delivery to a subject. This rate may need to be regularly and/or frequently adjusted in response to a variety of factors. For instance, a subject may require additional insulin delivery after food intake.

In some cases, a subject will receive a basal rate of medicament. For example, a subject may receive a regular or basal rate of insulin to maintain a desired a glucose level or a blood sugar level. This basal rate may be set by a healthcare provider, such as a nurse or a doctor. The basal rate may need to be modified as needed. The modifications may need to be made in response to changes to a user's consumption pattern or other factor. For example, the basal rate may need to be modified in response to food intake announcement. The basal dose can be generated using a basal control algorithm such as discussed above. Food intake announcements are not the only changes that may cause modifications to the basal rate. In some cases, the therapy delivered (e.g., the basal rate) may need to be paused or stopped. This may be particularly relevant during activities.

In addition, glucose control therapy generally requires in-person change requests. For example, a subject who requires an updated therapy delivery may need to initiate a change request on the pump directly. In some cases, a subject or other individual may want to pause or stop delivery of therapy. This may be particularly relevant during activities (e.g., swimming, sports, where delivery is not possible, not possible, not comfortable, or otherwise not preferred).

In some circumstances, a user is limited to manual operations which require direct contact. Medicament pumps sometimes may be equipped with non-contact operations. For example, the subject or user can start or modify (pause or stop) therapy delivered to the subject via user interaction, e.g., via a gesture, such as a movement of the eye and/or finger, or via a touchscreen interface. The medicament pump can be configured to receive a request for modifying the therapy delivered to the subject. The request may be made by a user via user interaction with a therapy modification control element. The request may be made via a gesture, such as a movement of the eye and/or finger. In some examples, the input is received via a touchscreen interface. Details of gesture-based control is disclosed in U.S. patent application Ser. No. 17/062,356.

In some circumstances, a user is completely limited to a manual operation, whether direct contact or non-direct contact. A user may be even limited to any gesture motion, eye movement, etc. due to, e.g., driving, health problems, injury, or any activities that limit body motion. Accordingly, in various embodiments of the present disclosure, the therapy delivery can be controlled by a recognized voice/verbal command via user interaction. A voice activated control can allow a user or subject in this case to control the therapy when there is a limit in motion. That is, when a user is driving, is injured, or is in any situation in which mobility is limited, such that gesture or touch input cannot be provided, a voice recognition can be activated to control an ambulatory medical device (AMD) having a medicament pump.

Voice control operation also known as hands free operation is indeed widely used in various applications. For instance, hands free operation of phones while driving and voice activation for home use devices (e.g., Amazon Echo, Google Home, etc.) have brought convenience to users. Further, the voice/verbal command allows a user to remotely control devices using a smart device. For example, a user can control a function of an AC unit in a house using a smart portable device of the user anywhere inside or even outside the house. Such operation can be adapted to control the therapy delivery via the AMD or via a user device communicating with the AMD.

In various embodiments, the smart device can be any device having smart functions as well known. For example, a smart device is an electronic device, generally connected to other devices or networks via different wireless protocols such as Bluetooth, Zigbee, NFC, Wi-Fi, LiFi, 5G, etc., that can operate to some extent interactively and autonomously. Several notable types of smart devices are smartphones, smart vehicles, smart thermostats, smart doorbells, smart locks, smart refrigerators, phablets and tablets, smartwatches, smart bands, smart key chains, false and others. In certain embodiments, the smart device can be wirelessly connected to the AMD having the medicament pump through, e.g., BLE or LTE. In some examples, the smart device has an LTE connection, which connected to a cloud service (e.g., a cloud based computing network or system 708) then connected to the AMD through NB LTE. Alternatively, the smart device can be connected through Wi-Fi to a TCP-IP link to the cloud service.

In addition or alternatively, the smart device may have a skill or app that interfaces with the cloud service, or have a direct connection to the AMD. In various cases, a user having any of the above-described smart device (e.g., a smart phone) can communicate with and control the AMD via one of available wireless protocols by manipulating buttons or touch screen of the smart device and/or gesture input or verbal input to the smart device. In various embodiments, the medicament pump of the AMD or AMD may be a smart device having smart functions as discussed herein, including voice recognition, authentication, command, etc. Alternatively, any other system or user devices described herein may be implemented with smart functions as discussed herein, including voice recognition, authentication, command, etc.

As described herein, food intake announcements and other changes to glucose control therapy can be made verbally and/or remotely via more distant connections. In some examples, a parent or other individual (e.g., adult) may be able to make food intake announcement or other therapy change via a user device (e.g., a smartphone), which may be able to connect to the medicament pump via a long-range wireless data interface (e.g., a Long-Term Evolution (LTE) modem, etc.). In some embodiments, a subject (e.g., a child) can additionally or alternatively request a food intake announcement from the medicament pump and another individual (e.g., a parent, doctor, nurse) can approve remotely, based on authenticated user lists.

Figure 63:
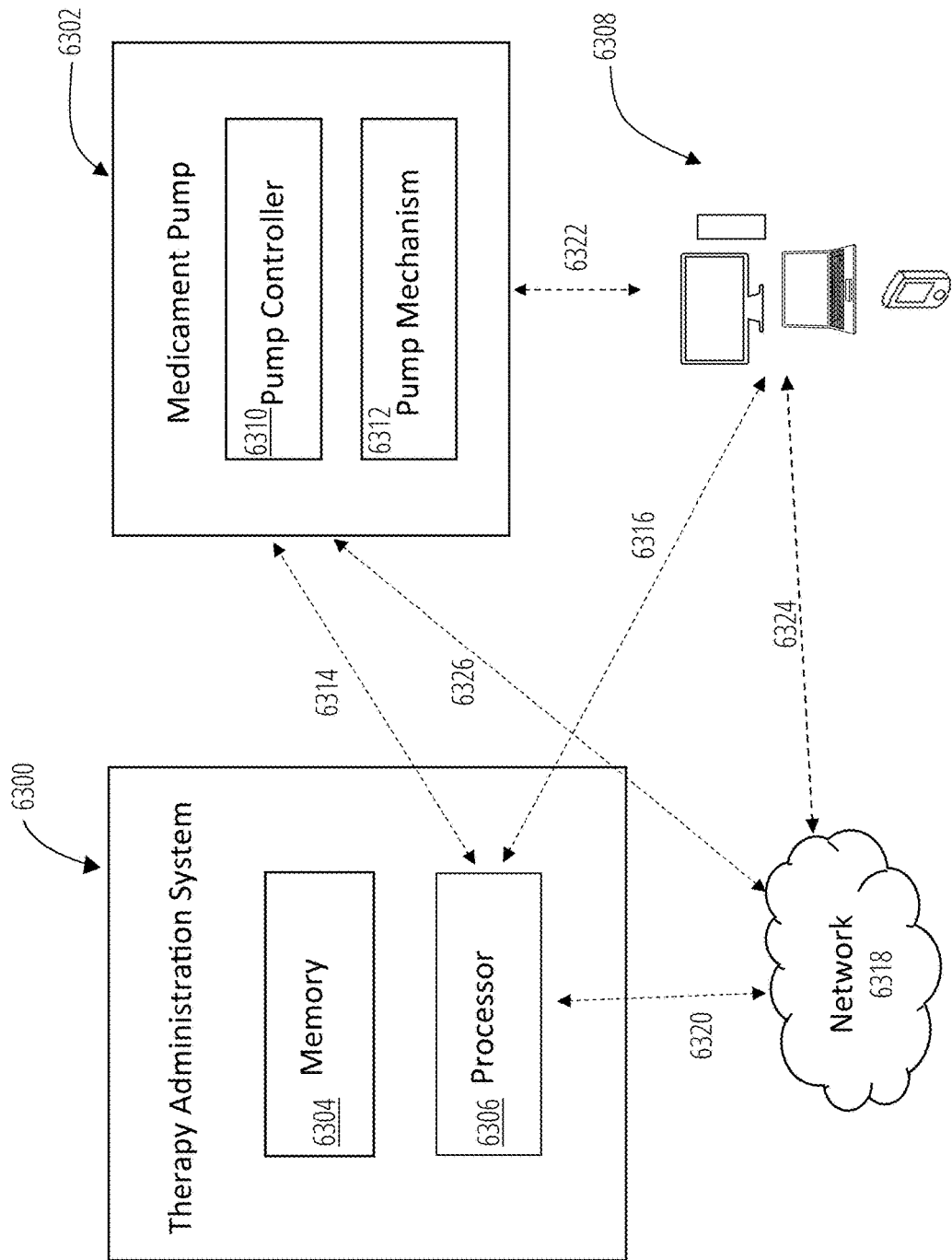
FIG. 63 is an example therapy administration system configured to manage glucose level control therapy delivered to a subject by an ambulatory medicament pump using a verbal command.

FIG. 63 shows an example therapy administration system configured to transmit a request to modify glucose control therapy delivered to a subject via verbal communication between an ambulatory medical device and a user (e.g., subject) via a voice activated user-interface. "Modify" may refer to its plain and ordinary meaning, and may include adjusting, updating, complementing, temporarily overriding, or permanently overriding the manual therapy instruction. The therapy administration system 6300 can further communicate with a medicament pump 6302 of an ambulatory medical device (AMD) via wired or wireless connection 6314. The therapy administration system 6300 includes a non-transitory memory 6304 and an electronic hardware processor 6306. The therapy administration system 6300 may be a remote computing system as discussed herein. The therapy administration system 6300 may further include a data or network interface (not shown) comprising a wireless and/or wired data interface. The data interface can include a short-range wireless data interface. As discussed herein, networks or network connections can include data or network interfaces.

Additionally or alternatively, the therapy administration system 6300 can be in communication with a network 6318 (e.g., via a network connection 6320). In some examples, the therapy administration system 6300 may establish a communication channel with the computing system whether a local or remote computing system. This communication channel may be an encrypted channel. Further the communication channel may be a direct end-to-end connection between the therapy administration system 6300 and the computing system. Once the communication channel is established, the therapy administration system 6300 may transmit control signal data to a computing system.

The therapy administration system 6300 may be in communication (e.g., wired, wireless) with the medicament pump 6302 and a user device 6308. For instance, a user device 6308 can be in communication with the processor 6306 via a voice-user connection 6316 which may be one-way or two-way. The data interface may also be in communication with other elements of the medicament pump 6302, such as the pump mechanism 6312 and/or the pump controller 6310. The communication with the other elements within the medicament pump 6302 may be via a wired connection. The therapy administration system 6300 can represent one or a plurality of medicament pumps. In some embodiments, for example, the therapy administration system 6300 is in communication with a medicament pump that is to be replaced as well as an additional pump to replace that pump. However, for simplicity, reference to the medicament pump 6302 will represent one or a plurality of medicament pumps.

In certain embodiments, the user device 6308 may directly communicate with the medicament pump 6302 via wireless (or wired) connection 6322. Throughout the disclosure, the terms "user interface" and "user device" may be interchangeably used for certain embodiments. In this case, a user can communicate or control the medicament pump 6302 by inputting a voice command to the user interface of the user device 6308. For example, the user device 6308 is implemented with a voice recognition sensor for recognizing the user's verbal wake up command (e.g., "Hey, Google" when the user's device is a Google enabled device). The user's voice recognition device that is configured to communicate with the medicament pump 6302 triggers a user's command. For example, in case of the google enabled device, after waking up the device (by saying "Hey, Google"), the user can provide a verbal command to execute the functions of the medicament pump 6302 (e.g., "start the therapy delivery"). As described herein, the user device can be implemented in various devices, such as a smart phone, a smart watch, a laptop, a smart speaker, or any other smart device that can communicate with the medicament pump 6302 and have software capability. In various embodiments, the user device 6308 is in communication with the network 6318 (e.g., via a network connection 6324) via with wide area networks (WANs) such as a cellular network transceiver that enables 3G, 4G, 4G-LTE, or 5G. In some embodiments, the medicament pump 6302 may be in communication (wired or wireless) with the network 6318 directly with the network 6318 via connection 6326 or in communication (wired or wireless) with the network 6318 through the therapy administration system 6300 and/or the user device 6308 (e.g., via connection 6314 and/or connection 6324). In some examples, the network communication may be via a Narrowband Long-Term Evolution (NB-LTE), a Narrowband Internet-of-Things (NB-IoT), or a Long-Term Evolution Machine Type Communication (LTE-MTC) communication connection with the wireless wide area network. In some embodiments, any other system such as the therapy administration system 6300 or the medicament pump 6302 described herein may be implemented with smart functions as discussed herein, including voice recognition, authentication, command, etc. In this case, the therapy administration system 6300 or the medicament pump 6302 is configured as a smart device having smart functions and communicates with the network 6318.

Figure 84:
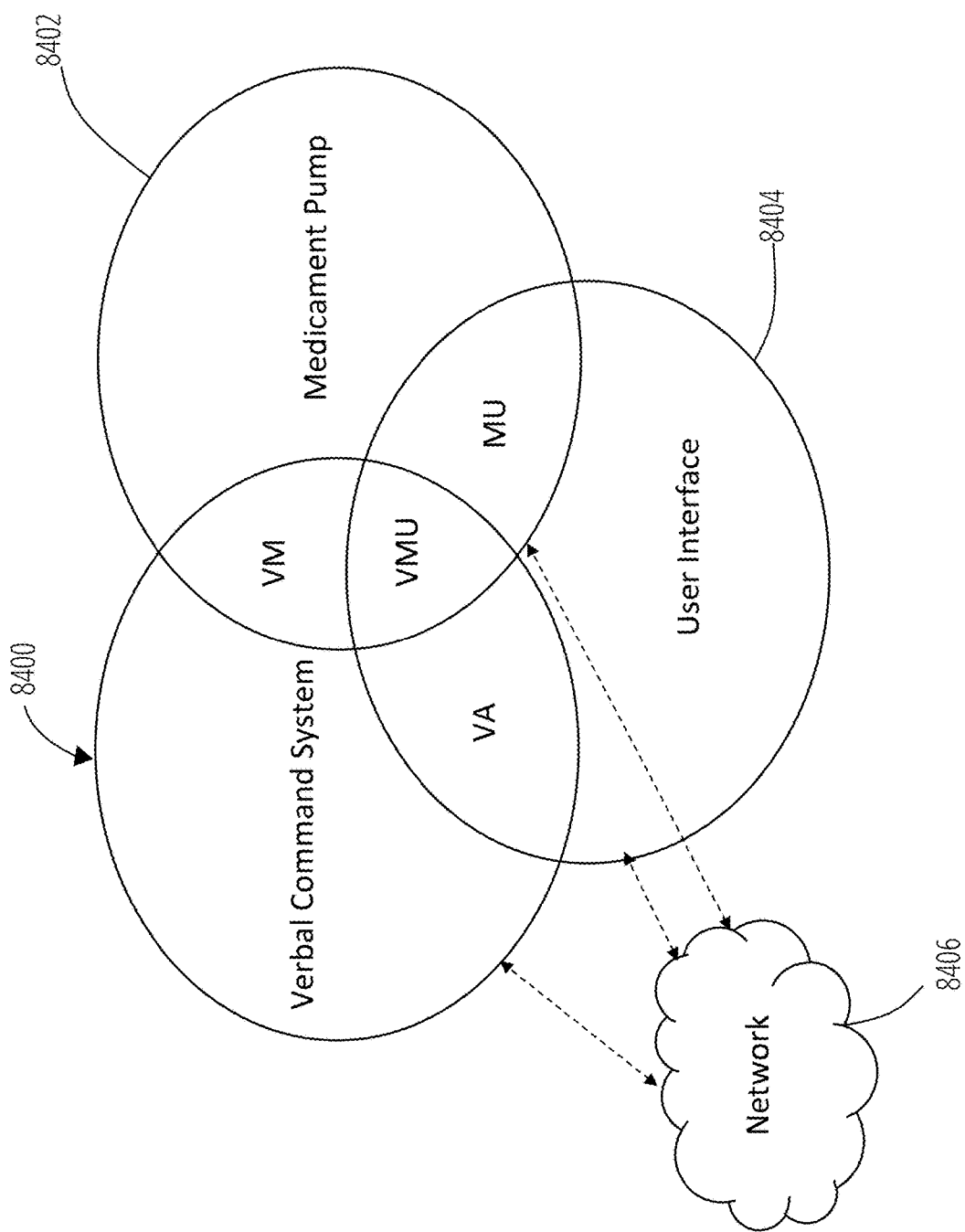
FIG. 84 is a diagram illustrating an exemplary connection relationship between each system for verbal communication, a medicament pump, and a user interface.

The communication/connection between the therapy administration system 6300, the network 6318, the medicament pump 6302, and the user device 6308 is not limited to above. Each element may directly and/or indirectly communicate with each other. FIG. 84 is a diagram illustrating an exemplary connection relationship between each of a system for verbal communication, a medicament pump, and a user interface. In this case, for example, a verbal command system 8400 (or the therapy administration system 6300) may communicate directly or only with a user interface 8404 (e.g., connection "VA"), and may communicate directly or only with a medicament pump 8402 (e.g., connection "VM"). Alternatively or additionally, the therapy administration system 6300 may communicate with the user interface 8404 and the medicament pump 8402 (e.g., connection "VMU").

In addition or alternatively, the medicament pump 8402 may communicate directly or only with the user interface 8404 (connection "MU"). In some examples, the verbal command system 8400, the medicament pump 8402, and the user interface 8404 can be implemented as one device having all the functions of each element (the verbal command system 8400, the medicament pump 8402, and the user interface 8404). That is, the medicament pump 8402 may be configured to receive and execute the verbal command of a user and provide a verbal output (e.g., an alarm, a request of user's input, therapy reports, etc.). Furthermore, the verbal command system 8400 may be integrated into the medicament pump 8402 as one control unit and/or integrated into the user interface 8404 as one control unit.

In some examples, the therapy administration system 6300 may be a medicament pump (e.g., medicament pump 6302) itself. The therapy administration system 6300 may have hardware device configurations of the therapy administration system 6300 as well as the medicament pump 6302 to perform all the functions as discussed herein. In this case, the verbal command system 8400 of FIG. 84, which corresponds to the therapy administration system 6300, and the medicament pump 8402 of FIG. 84, which corresponds to the medicament pump 6302, may be completely overlap to each other (i.e., "VM" portion entirely overlap with the verbal command system 8400 and the medicament pump 8402). For instance, the therapy administration system 6300 may include a voice recognition sensor for receiving and recognizing a voice and perform the described operations of the therapy administration system 6300.

Additionally, the therapy administration system 6300 can be configured to perform the functions of the medicament pump such as receiving a verbal command and controlling the therapy delivery to the user. Alternatively or additionally, the therapy administration system 6300 may incorporate or may be a user interface (e.g., user device 6308) itself, which may correspond to "VA" of FIG. 84. That is, the therapy administration system 6300 may be configured as an interface for allowing direct interaction with a user (e.g., receiving a verbal command, outputting a confirmation signal, etc.). In some examples, the therapy administration system 6300 may one hardware device implementing a medicament pump and a user interface/device, which corresponds to "VMU" of FIG. 84. In that case, the therapy administration system 6300 is configured to perform all the functions of the therapy administration system 6300 as well as those of the medicament pump 6302 and the user device 6308 as discussed herein. The configurations described herein are merely examples and not limited thereto. In some examples, the medicament pump 6302 may include or may be the user device 6308, which corresponds to "MU" of FIG. 84. In this case, the medicament pump 6302 can perform all the functions of the medicament pump 6302 as well as the user device 6308 as discussed herein.

The medicament pump 6302 may be any medicament pump described herein, such as the pump 100 and/or pump 212. The medicament pump 6302 may be an ambulatory medicament pump. In some embodiments, the medicament pump 6302 is a medicament pump coupled to the subject during in-patient therapy delivery. The pump controller 6310 is configured to direct medicament from a medicament reservoir to the subject using the pump mechanism 6312. In some embodiments, the medicament pump 6302 is an insulin and/or glucagon infusion device for subjects that have Type I diabetes. Ambulatory medical medicament pumps 6302 allow subjects the freedom to receive medical care in any setting at their convenience.

However, changes of delivery of therapy may sometimes need to be made remotely or without user's manual operation of, e.g., touching, any types of gesture motion, etc. For example, if a proper amount of medicament (e.g., insulin, glucagon, etc.) is not delivered when needed, a subject's glucose level may increase or decrease uncontrollably. This can be a dangerous scenario. Having the ability to control the amount of delivered medicament may be a very important component to proper care, and the medicament pump 6302 and related systems described herein may allow for better control, including hands free control, of therapy delivery.

The pump controller 6310 is part of a computing system that performs the computing functions for the medicament pump 6302. The pump controller 6310 may be a single processor or may be made up of several processors. The pump controller 6310 may perform the computing functions for a single medicament pump 6302 or many medicament pumps 6302.

Various example user devices 6308 are shown in FIG. 63, including a desktop computer, a laptop, and a mobile phone, each provided by way of illustration only. In general, the user devices 6308 can be any computing device such as a desktop, laptop or tablet computer, personal computer, tablet computer, wearable computer, server, personal digital assistant (PDA), PDM, hybrid PDA/mobile phone, mobile phone, smartphone, set top box, voice command device, digital media player, and the like. A user device 6308 may execute an application (e.g., a browser, a stand-alone application) that allows a user to access and interact with interactive graphical user interfaces as described herein.

In some embodiments, the medicament pump 6302 may include a therapy modification control element (not shown), such as a user interface, which may be a graphical user interface. The therapy modification control element may be integrated into the medicament pump 6302 or may be a separate element. For example, the therapy modification control element may be integrated with the user device 6308 described above. The user interface may be operatively coupled to the medicament pump 6302 via, for example, the wireless data interface or voice-user interface. The user interface can include a touchscreen display. The touchscreen display may display a therapy modification interface for modifying therapy the subject and/or for receiving subject inputs on the therapy modification interface. Inputs on the touchscreen display may be registered by any touch technology including, but not limited to capacitive and resistive sensing. The touchscreen display may be a part of a mobile computing device, such as a cellular phone, tablet, laptop, computer, or the like (e.g., the user device 6308). The user interface may further comprise one or more mechanical buttons. The user interface may include an alert generator, such as a light emitter, a speaker, a haptic feedback system, or other sensory alert system.

The network 6318 may include any wired network, wireless network, or combination thereof. For example, the network 6318 may be a personal area network, local area network, wide area network, over-the-air broadcast network (e.g., for radio or television), cable network, satellite network, cellular telephone network, or combination thereof. As a further example, the network 6318 may be a publicly accessible network of linked networks, possibly operated by various distinct parties, such as the Internet. In some implementations, the network 6318 may be a private or semi-private network, such as a corporate or university intranet. The network 4524 may include one or more wireless networks, such as a Global System for Mobile Communications (GSM) network, a Code Division Multiple Access (CDMA) network, a Long Term Evolution (LTE) network, or any other type of wireless network. The network 6318 can use protocols and components for communicating via the Internet or any of the other aforementioned types of networks. For example, the protocols used by the network 6318 may include Hypertext Transfer Protocol (HTTP), HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein. The network 6318 may comprise the "cloud." The network 6318 may include a remote computing environment.

Figure 64:
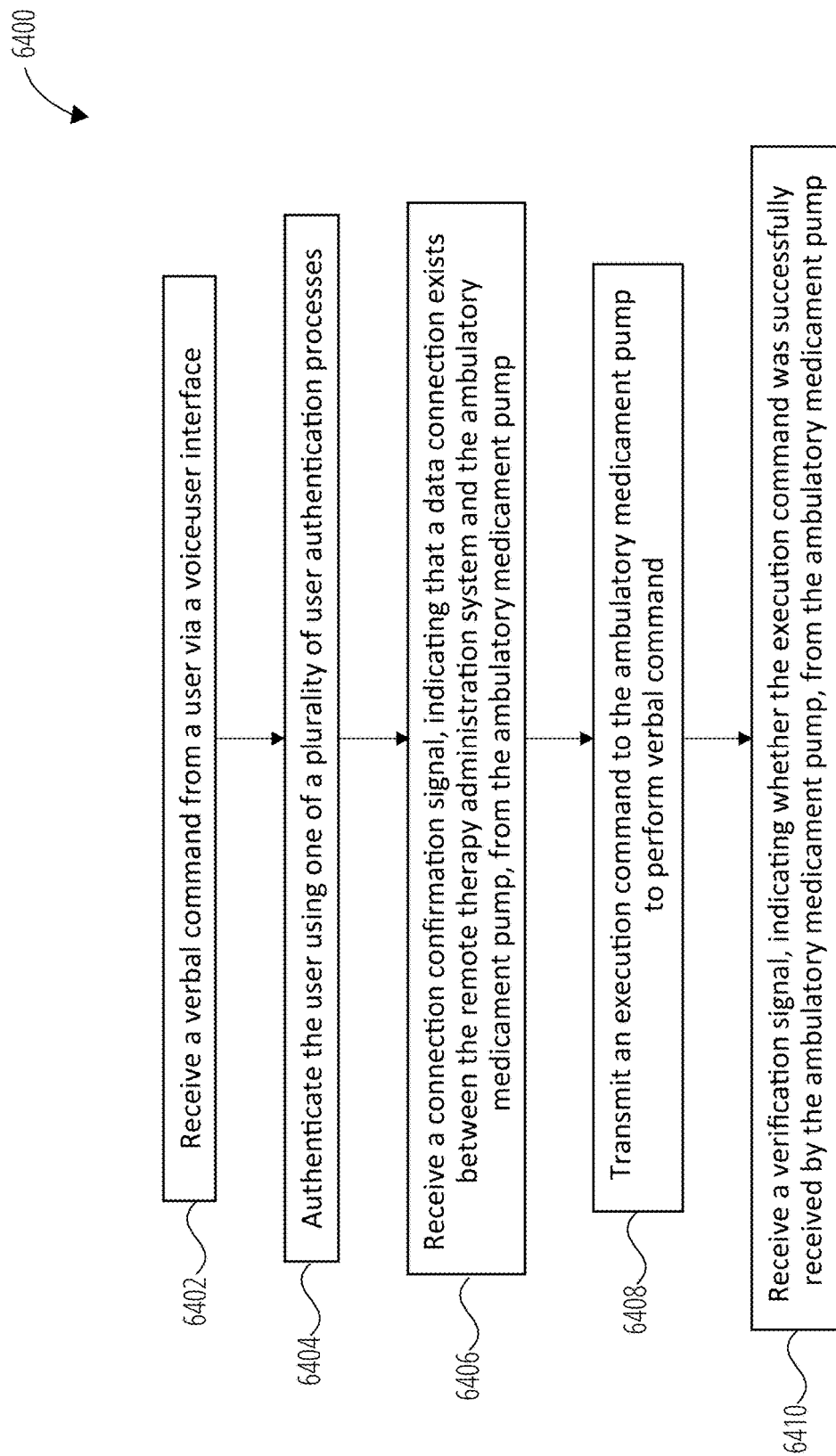
FIG. 64 shows a flow diagram illustrating an example method that may be used by a control system to manage glucose level control therapy delivered to a subject by an ambulatory medicament pump using a verbal command.

FIG. 64 shows a flow diagram illustrating an example method 6400 that may be used by a therapy administration system to manage glucose level control therapy delivered to a subject by a medicament pump using a verbal command. At block 6402, the therapy administration system 6300 receives a verbal command from a user. At block 6404, the therapy administration system 6300 authenticates the user using at least one of a plurality of user authentication processes. At block 6406, the therapy administration system 6300 receives a connection confirmation signal from the medicament pump 6302. The connection confirmation signal indicates indicating that a data connection exists between the remote therapy administration system and the medicament pump. At block 6408, the therapy administration system 6300 transmits an execution command to the medicament pump 6302 to perform the verbal command. Finally, at verbal command, the therapy administration system 6300 receives a verification signal from the medicament pump 6302. The verification signal indicates whether the execution command was successfully received by the medicament pump.

Figure 65:
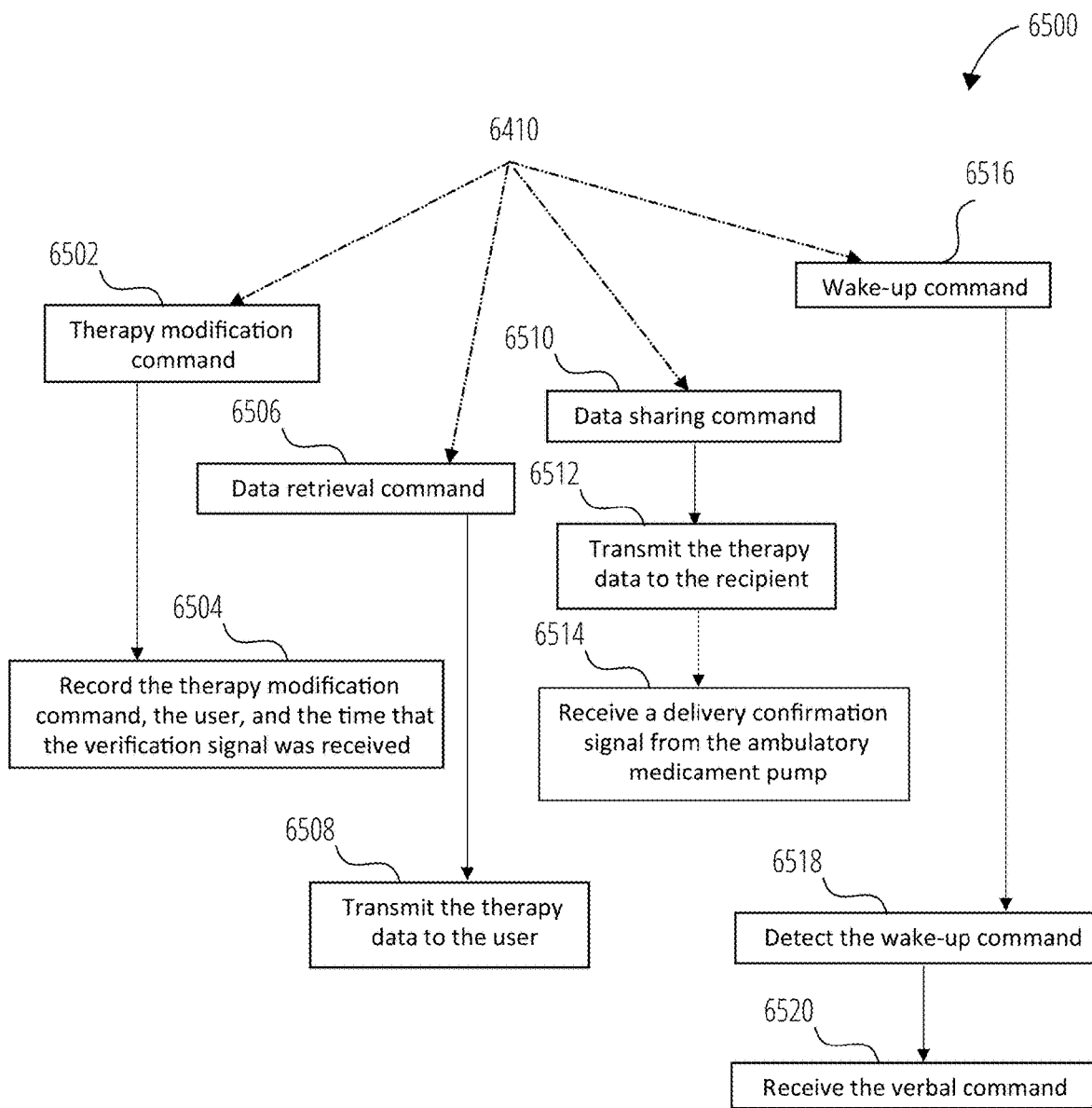
FIG. 65 shows a flow diagram illustrating an example method of controlling a therapy administration system when a verbal command is a specific command among various commands.

FIG. 65 shows a flow diagram illustrating an example method 6500 of controlling a therapy administration system when a verbal command is a specific command among various commands.

Referring to FIG. 64 and FIG. 65, at block 6402, the therapy administration system 6300 may be configured to receive a verbal command from a user. The verbal command includes a therapy modification command (block 6502) that is to administer a medicament, to modify a medicament dose, or to modify a medicament dose calculation factor. In some examples, when the therapy modification command is received, information on the therapy modification command, the user, and the time that the verification signal was received are recorded (block 6504).

The verbal command can further include a data retrieval command (block 6506), a data sharing command (block 6510), a wake-up command (block 6516), and a medicament dose calculation command. When the verbal command is the data retrieval command (block 6506), therapy data can be retrieved from the non-transitory memory, the medicament pump, or a remote computing environment. The retrieved data can be transmitted to the user (block 6508). Here, the therapy data can be transmitted to the user via a voice-user interface. In some examples, the user device 6308 may be the voice-user interface and have a voice-activated function.

When the verbal command is the data sharing command (block 6510), the therapy data can be retrieved from the non-transitory memory 6304, the medicament pump 6302, or the remote computing environment. The data sharing command includes a request for therapy data and a recipient. The therapy data then can be transmitted to the user via a network interface (block 6512). The network interface may be the data interface described herein which can be wirelessly connected, connected via a cloud-based computer system, and/or connected in any other way. The wireless wide area network modem may be configured to provide a wide area network connection. As described throughout the disclosure, the wireless wide area network modem may include a long-term evolution (LTE) modem. If the requested therapy data was successfully transmitted to the user, the therapy administration system 6300 may receive a delivery confirmation signal from the medicament pump 6302 (block 6514).

When the verbal command is a wake-up command received from a user (block 6516), a wake signal that activates the AMD may be generated and detected (block 6518). That is, the user can wake or unlock the AMD by interacting with the voice-user interface. Once the AMD is waken-up by the user's verbal command, other verbal commands, e.g., the medicament dose calculation command, the data sharing command, or the like, can be received from the user (block 6520).

Figure 66:
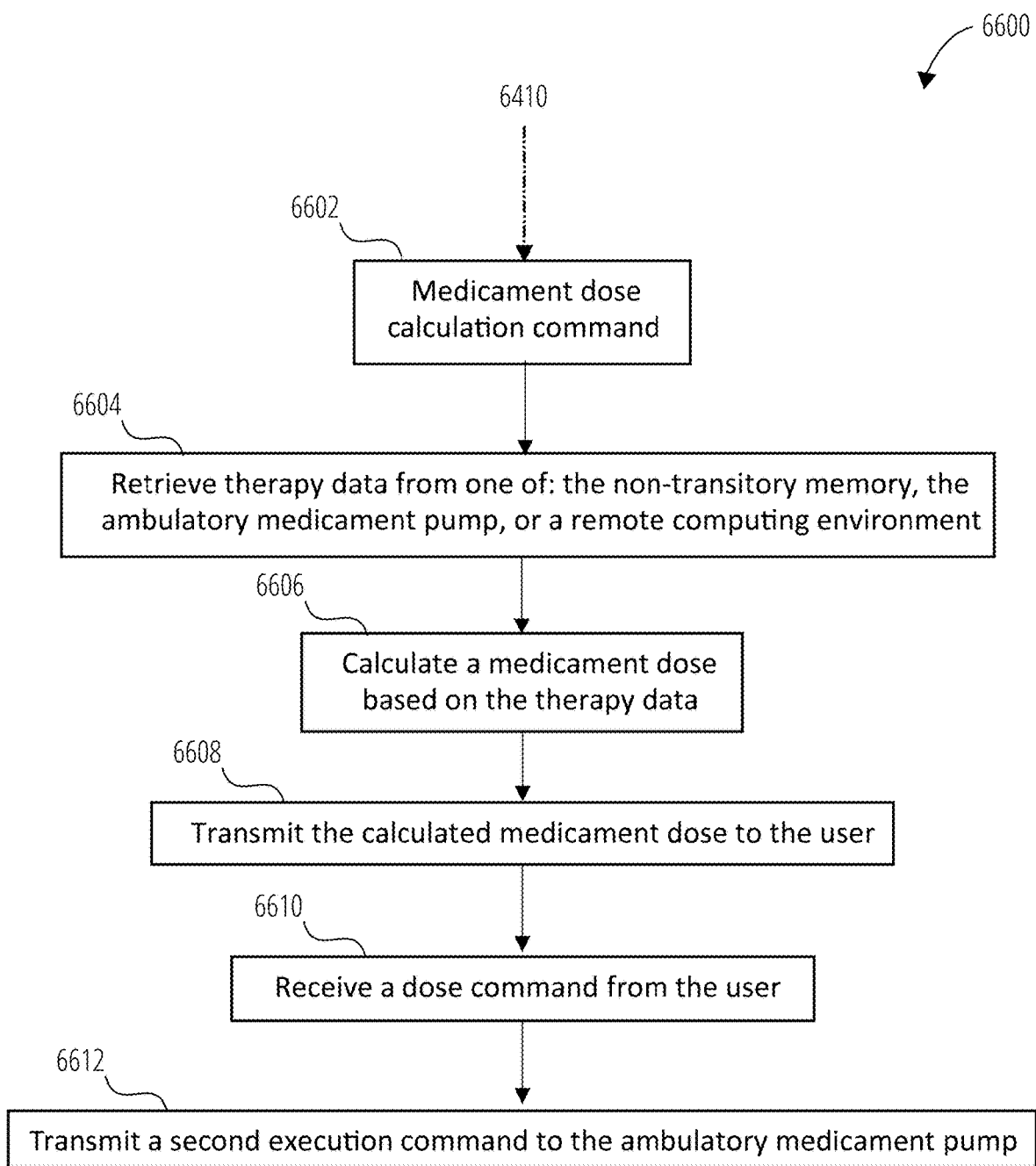
FIG. 66 shows a flow diagram illustrating an example method of controlling a therapy administration system when a verbal command is a medicament dose calculation command

FIG. 66 shows a flow diagram illustrating another example method 6600 of controlling a therapy administration system when a verbal command is a medicament dose calculation command. When the verbal command is a medicament dose calculation command at block 6602, therapy data can be retrieved from the non-transitory memory, the medicament pump, or a remote computing environment (not shown), for example, a cloud computing service, that connects to the medicament pump 6302 via a direct or indirect electronic data connection (block 6604). A medicament dose is calculated based on the therapy data at block 6606 and transmitted to the user at block 6608. At block 6610, the user may send a dose command to the therapy administration system 6300.

Additionally, a second execution command can be transmitted to the medicament pump 6302 to administer the calculated medicament dose to the user (subject) at block 6612. In some cases, the execution command to administer the calculated medicament dose is the execution command discussed herein (e.g., not a second execution command). As described herein in various embodiments, a confirmation of the user may be requested before performing the execution command such as administering the medicament dose to the user. In certain embodiments, the therapy administration system 6300 requires a user confirmation before the therapy change can be executed. Alternatively, the confirmation command may be feedback on the verbal command. If the execution command is successfully executed, the therapy administration system 6300 may or may not provide a response. However, if the command was unsuccessfully executed, the therapy administration system 6300 may provide explanation via, for example, the user device 6308 of the reasons or causes behind the unsuccessful execution. The explanation may be any one or more alarms, status, and/or execution indications discussed herein. The explanation may be output in the form of sound, display, haptic, etc. via the user device 6308, or through the medicament pump 6302.

When the verbal command is the medicament dose calculation command as described above, the therapy data can be retrieved in a similar way applied for the data sharing command. In some embodiments, a medicament dose can be calculated based on the therapy data. The calculated medicament dose can be transmitted to the user via the voice-user interface. The calculated medicament dose can be used as a dose command for the user to request to administer the calculated medicament dose. In certain embodiments, a user can input a dose command via the voice-user interface. The dose command may be a request to administer the calculated medicament dose. When the dose command is received from the user, the therapy administration system 6300 may transmit a second execution command to the medicament pump 6302 to administer the calculated medicament dose.

Figure 67:
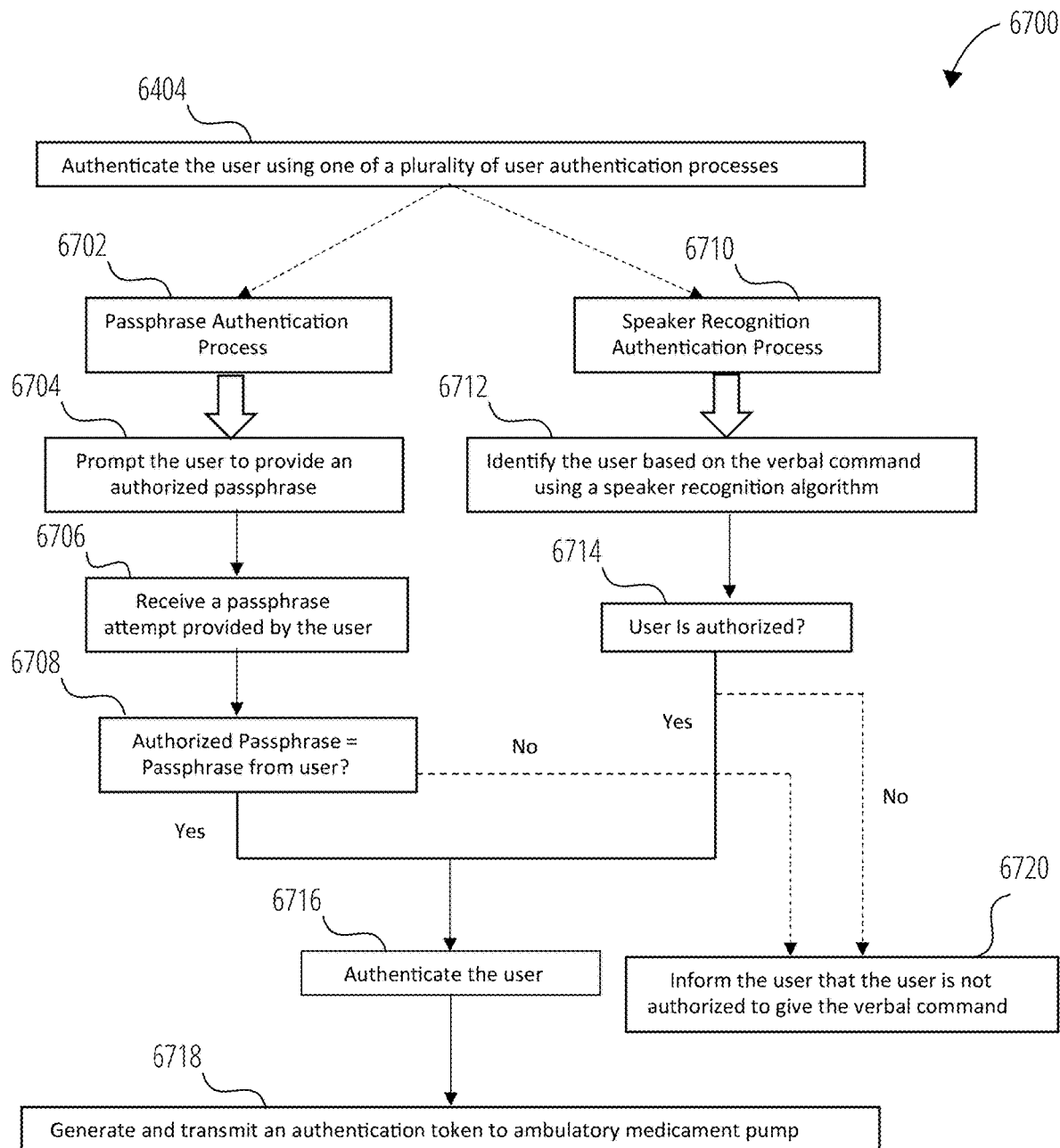
FIG. 67 shows a flow diagram illustrating an example method of controlling a therapy administration system for authenticating a user based on a verbal command.

In some embodiments, once a verbal command has been received by a user, the therapy administration system 6300 may authenticate the user using at least one of a plurality of user authentication processes at block 6404. The authentication processes may be a passphrase authentication process. For instance, referring to FIG. 67 which shows a flow diagram illustrating an example method 6700 of controlling a therapy administration system for authenticating a user based on a verbal command (block 6404), when a verbal command is received via the voice-user interface, the therapy administration system 6300 may request the user to provide an authorized passphrase at blocks 6702 and 6704. The user may provide a passphrase at block 6706. The therapy administration system 6300 then determines whether the provided passphrase matches the authorized passphrase stored in database (e.g., cloud) at block 6708. In certain embodiments, login information may be tied to customer account database stored on platform servers to meet security requirements for providing access to confidential healthcare information. If the user provided passphrase matches the authorized passphrase, the therapy administration system 6300 authenticates the user at block 6716. However, if the user provided passphrase does not match the authorized passphrase, the therapy administration system 6300 may inform the user that the user is not authorized to give the verbal command at block 6720. In some examples, only authorized users can have access to one or more medicament pumps 6302. In some embodiments, the medicament pump 6302 can have multiple authorized users. In addition, adults (e.g., age 18 or over) can have different access privileges than kids. That is, based on authorization level, different access can be allowed to authorized users.

In certain embodiments, to provide user access to one or more therapy change controls of an AMD without putting the health of a subject at risk, access to therapy change controls may be managed using a plurality of safe access levels for the AMD where a safe access level corresponds to selected control parameters that can be modified by a user or a subject who is qualified for the corresponding safe access level. In some examples, access to the selected control parameters may be allowed by enabling the corresponding therapy change controls in the AMD (e.g., activating or displaying one or more therapy change control elements on a touchscreen user interface).

In some cases, safe access levels may be categorized based on the capacity of a user for modifying control parameters without causing harm or increasing the risk of harmful effects to the subject. For example, safe access levels may be defined based on age, training, experience, and the like. In other cases, safe access levels may be defined or categorized based on a therapy history of the subject.

Additional embodiments relating to determining safe access levels that can be combined with one or more embodiments of the present disclosure are described in U.S. Provisional Application No. 63/169,112, which was filed on Mar. 31, 2021 and is titled "AMBULATORY MEDICAMENT PUMP WITH SAFE ACCESS CONTROL," the disclosure of which is hereby incorporated by reference in its entirety herein for all purposes.

In some cases, the authentication process can be performed by various user devices. For example, if a user has a smart phone (or a smart watch) and a smart speaker paired with the therapy administration system 6300, the user may authenticate via either the smart phone or smart speaker. In some cases, only one device can be used for authentication. For example, only the user's designated smart phone has authorization for authentication process so that the authentication can be done only using the specific user defined device. In some cases, any pair devices can be used for verbal authentication. Further, in some cases, one user device may be used for authentication with limited verbal command functions while another user device may be used for authentication with full verbal command functions. For example, a user can use a smart phone to authenticate and voice control the medicament pump 6302 for changing, e.g., name of the pump. The user can use, e.g., a laptop to authenticate and voice control the medicament pump 6302 for any implemented verbal command functions.

In certain embodiments, the therapy administration system 6300 can authenticate the user using a speaker recognition or voiceprint authentication process at block 6710. The speaker recognition authentication process may include identifying the user based on the verbal command using a speaker recognition algorithm (block 6712). If it is determined that the user is authorized to give the verbal command using the speaker recognition algorithm at block 6714, the therapy administration system 6300 authenticate the user (block 6716). On the other hand, if it is determined that the user is not authorized to give the verbal command, the therapy administration system 6300 can inform the user that the user is not authorized to give the verbal command at block 6720. In some examples, the speaker recognition algorithm may be any one of a hidden Markov model, a Gaussian mixture model, a pattern matching algorithm, a neural network, or a frequency estimation algorithm.

When the user is authenticated to give a verbal command, an authentication token may be generated and transmitted to the AMD at block 6718. The authentication token may provide a validity period such that the user is authorized for a certain period of time, for example, one hour, one day, or one week. In some examples, the validity period can be set by the user via the voice-user interface. For instance, the therapy administration system 6300 may request the user to set the validity period via the voice-user interface.

Referring back to FIG. 64, once the user is authenticated using any of the described authentication processes, the therapy administration system 6300 may receive a connection confirmation signal from the medicament pump 6302 at block 6406. The connection signal may be a signal indicating that there is a data connection between the therapy administration system 6300 and the medicament pump 6302. In some embodiments, the therapy administration system 6300 and the medicament pump 6302 can be connected via a remote connection to remotely control the medicament pump 6302 for therapy delivery to a subject. For instance, medicament pumps may be directly and/or on a remote control system coupled to a medicament pump via a short-range wireless connection (e.g., BLE, etc.). However, structural and logistical problems have existed for allowing such control to be beyond mere short-range control.

In some embodiments, the medicament pump 6302 can transmit a connection confirmation signal to the remote electronic device. The connection confirmation signal can initiate a determination that a wireless wide area network data connection exists between the data interface and the remote electronic device. However, in some embodiments, the medicament pump 6302 receives a return confirmation signal to confirm that the proper wireless connection exists. Accordingly, the medicament pump 6302 may receive (e.g., via the wireless data interface) a return confirmation signal from the remote computing environment. The return confirmation signal can indicate that the wireless wide area network data connection exists between the wireless data interface and the remote electronic device. Once the return confirmation signal is received, the medicament pump 6302 can determine that the wireless wide area network data connection exists between the wireless data interface and the remote electronic device. Confirmation of the wide-area wireless connection can allow for the transmission of the dose control signal. In some embodiments, simple wireless connections are insufficient, but rather a wide-area network connection should first be established.

In some examples, the medicament pump 6302 may be connected with various user devices 6308. The user device 6308 may be a user's mobile terminal with voice recognition enabled such as Siri or Google. In some examples, the medicament pump 6302 may be connected with a smart speaker such as Amazon Echo, Apple Homepod, Google Home, or the like. The smart speaker or user's mobile terminal (e.g., smart phone) may be configured with any one or more of voice recognition software using voice queries interacting with recognized voice or verbal commands. The medicament pump 6302 may be wirelessly paired or connected with the user device 6308. This could be a BLE, LTE, Wi-fi, other TCP/IP, etc. connection. A pairing process could be unique to the platform (e.g., Amazon, Apple, etc.). User authentication as described herein can be performed between platform and cloud.

In certain embodiments, a user's smart device may be paired with one device (e.g., user's medicament pump 6302) such that any verbal commands from the authorized user would automatically be delivered to the paired device. Alternatively, the smart device could be paired with multiple the medicament pumps 6302 and the therapy administration system 6300 needs to identify the particular the medicament pump 6302 for executing commands. In some examples, one the medicament pump 6302 may be paired to multiple smart devices. The process of identifying the pump when there is more than one pump is disclosed throughout the disclosure in more detail.

After the user is authenticated and the connection confirmation signal is received, at block 6408, the therapy administration system 6300 transmits an execution command to the medicament pump 6302 to perform the verbal command. In certain embodiments, the therapy administration system 6300 may enable a group of authorized verbal commands associated with the user based on the authentication of the user. The therapy administration system 6300 then transmits the execution command once the verbal command is determined to be enabled for the particular user, and the connection confirmation signal is received. On the other hand, if the verbal command is not enabled or disabled for the particular user, the therapy administration system 6300 may inform, via the voice-user interface, the user that the user is not authorized to give the verbal command.

In some embodiments, the authentication of the user as discussed herein verifies the user's identity and determines which group the user is part of, belongs to, or is associated with (e.g., the user is categorize into a particular or corresponding group). The therapy administration system 6300 determines whether the verbal command is enabled for the particular group that the user is associated with. The therapy administration system 6300 then transmits the execution command once the verbal command is determined to be enabled for the user's particular group, and the connection confirmation signal is received. On the other hand, if the verbal command is not enabled or disabled for the user based on, for example, the user's particular group categorization, the therapy administration system 6300 may inform, via the voice-user interface, the user that the user is not authorized to give the verbal command. The therapy administration system 6300 can inform the user in various way, for example, by providing explanation through the voice-user interface. In some examples, the therapy administration system 6300 informs the user that the user is not authorized by outputting a specific sound (e.g., beeping, song, music, or prerecorded voice) having a specific pattern and/or for a certain period of time (1 second, 1 minute, etc.).

In certain embodiments, the connected or paired user device/interface may accept various execution commands. For example, therapy modification can be requested via a verbal command and executed once authorized. The acceptable execution commands can further include requesting for medicament pump or subject status information (e.g., BG level, insulin/glucagon level, charge level, software version, configuration status, order status), changing pump settings (e.g., setpoint, exercise announcement, food intake announcement), sharing therapy data (e.g., export data, upload to server/cloud, transfer to healthcare provider, transfer to customer service), authenticating a user. Further, software update, including initiating downloading, and installing, can be executed via a voice command. A user can further initiate therapy delivery, or pause, resume, or stop the delivery. As also described throughout the disclosure, the executable verbal commands include calculating bolus of food intake (carbs), delivering the calculated bolus, calculating correction bolus, setting basal rate, carb ratio, and/or correction factor, setting a temporary basal rate, setting an insulin action time, stopping or aborting the execution command, confirming the therapy, delivery, checking a battery level of the pump, checking user's insulin level, checking active alarms, requesting alarm information, acknowledging alarm or any other alarm-related actions permitted by remote action from, e.g., a user's smart device, ordering supplies or confirming supply levels of, e.g., medicament, cartridges, infusion sets, requesting to notify the time to reorder supply, calculating current supply amount, requesting to notify abnormal supply usage, checking eVG, etc.

In certain embodiments, after the execution command has been transmitted, the therapy administration system 6300 may receive a verification signal from the medicament pump 6302 (see block 6410 of FIG. 64). The verification signal indicates whether the execution command was successfully received by the medicament pump. If the verification signal is confirmatory, then the verification signal indicates that the verbal command received from a user was successfully executed. Additionally or alternatively, if the verification signal is a denial signal, then the verification signal can transmit that the execution was unsuccessful. In some embodiments, in response to the verification signal being a denial signal, the therapy administration system 6300 may manually and/or automatically transmit a second execution command. Additionally or alternatively, the therapy administration system 6300 may transmit an error signal to a user device if a threshold number of modification verification signals (e.g., two, three, four, five) are denial signals. In response to receiving the verification signal from the medicament pump 6302, the therapy administration system 6300 may announce that the verbal command was performed.

In some embodiment, when the verbal command is a therapy modification command (see block 6502 of FIG. 65), the therapy modification command, the user, and the time that the verification signal was received may be recorded upon receiving the verification signal from the medicament pump 6302 (see block 6504 of FIG. 65).

As described herein, the therapy administration system 6300 may transmit the execution command when the verbal command is enabled, and the connection confirmation signal is received from the medicament pump 6302. The verbal command may be enabled when or after a user is authenticated. After the user is authenticated and the connection confirmation signal is received, the therapy administration system 6300 may request the user to confirm the verbal command. Once the confirmation command is received from the user, the therapy administration system 6300 may transmit the execution command to the medicament pump 6302.

In some examples, when the verbal command and the connection confirmation signal are received, the user's device (e.g., a smart phone, a smart speaker, or the like) may output when the execution command is performed or selected. For example, the user's device may output, via a voice-activated interface, which medicament pump 6302 is selected or which medicament pump 6302 is available or not available to use when there are more than one medicament pumps. Further, the therapy administration system 6300 may prompt to request for user confirmation before executing the command such as therapy change. The confirmation command may be feedback on command. The therapy administration system 6300 attempts to perform the execution command upon receiving the user's confirmation command. The therapy administration system 6300 then sends a response indicating success or failure.

In various examples, the smart device can have a skill or application that interfaces with the cloud service. The smart device could have a direct connection to the medicament pump 6302. The smart device can be configured with voice recognition to ensure that an authorized person is requesting therapy changes, settings change, and/or requesting status. In some cases, the smart device can be configured to annunciate alarms, therapy status, and/or pump status. The smart device may require a voiceprint authentication prior to annunciation. Alarms can be indicated with a visual indicator on the smart device. For instance, the therapy administration system 6300 may detect an alarm condition and generate an alarm that may be provided to the subject. In some cases, the therapy data may trigger an automatic response by the computing system. For example, the AMD may determine that a medicament or another disposable is running low based on the received data and may automatically reorder the medicament or the disposable.

In some embodiments of the AMD, an alarm status indicator may be presented to the user via the user interface. The alarm status indicator can be an alert message or an alert symbol. The alarm status indicator may be related to a configuration change made by a user, a change in the status of the AMD not related to a user input, or the condition of the subject (e.g., detected by the subject sensor). In some examples, the alert message is output by sound in various forms (beeping, music sound, etc.).

In some cases, the AMD may be operating as intended, but the condition of the subject may not satisfy a desired level of health. In either case, it is generally desirable to generate an alarm to inform the subject and/or one or more users of the condition of the ambulatory medicament device and/or the subject. Moreover, it is desirable to track the alarm until the condition that caused the alarm is resolved. Further, it is desirable to issue different types of alarms for different conditions to enable a subject or user to easily distinguish the severity of the condition that triggered the alarm. The user may be a subject receiving medicament or therapy, or may be another user, such as a clinician or healthcare provider, or a parent or guardian. In some examples, the volume and length of the sound may vary based on the severity of alarm. For example, when an alarm has a high severity so that it is necessary to notify the user, the volume of the sound may be higher than an alarm with a low severity. Alternatively, the length of the sound may be longer or shorter based on the severity of the alarm, in a way of delivering the alert message through the voice-user interface.

The AMD of the present disclosure may include an alarm system configured to monitor the ambulatory medicament device and/or the subject, and to generate an alarm when it is determined that a condition has been detected that satisfies an alarm condition. In some examples, the alarm system that may organize a list of alarms, notifying a user of these alarms, and allowing the user to acknowledge alarms.

In some embodiments, the alarm system may comprise a plurality of sensors that monitor the AMD or the subject, a monitoring system interface that receives the data from sensors, and alarm generation module that process the received data and generate alarms if an alarm condition is met. In some examples, the monitoring system interface and the alarm generation module are implemented using one or more hardware processors and machine readable. In some examples, the monitoring system interface and the alarm generation module are separate hardware modules.

Additional embodiments relating to determining a severity of an alarm condition and annunciating the alarm based at least in part on the severity of the alarm condition that can be combined with one or more embodiments of the present disclosure are described in U.S. Provisional Application No. 62/911,017, which was filed on Oct. 4, 2019 and is titled "ALARM SYSTEM AND METHOD IN A DRUG INFUSION DEVICE."

Figure 68:
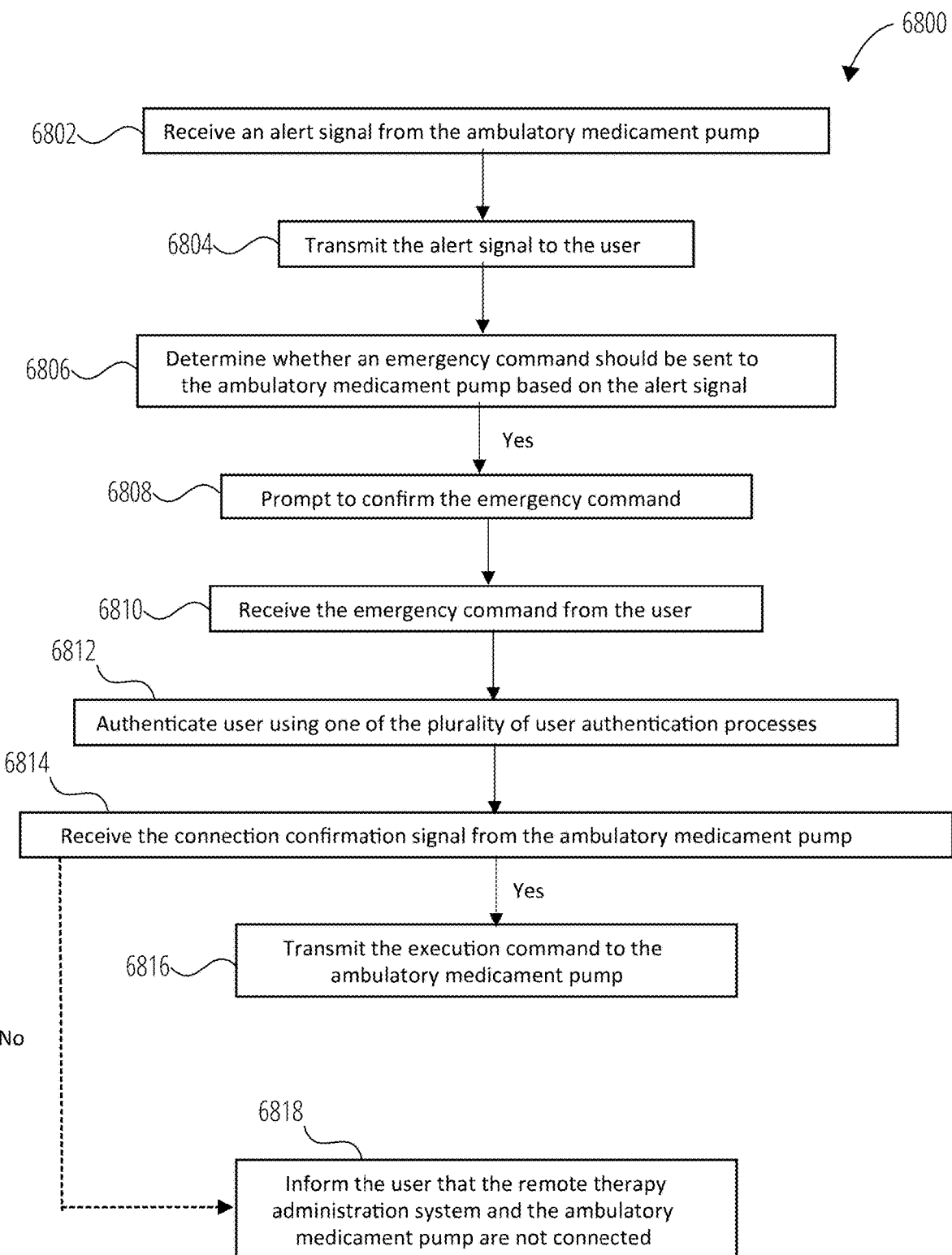
FIG. 68 shows a flow diagram illustrating an example method of controlling a therapy administration system when an alert signal is generated.

FIG. 68 shows a flow diagram illustrating an example method 6800 of controlling a therapy administration system when an alert signal is generated. In certain embodiments, when an alert signal is received from the medicament pump at block 6802, the alert signal can be notified to the user via the voice-user interface at block 6804. As described herein, the alert signal may be generated for indicating any one of a low battery level of the medicament pump, a high glucose level (e.g., blood sugar level) of the user, a low glucose level of the user, a low medicament level, or that the therapy administration system and the medicament pump are disconnected.

Based on the alert signal, the therapy administration system 6300 determine whether an emergency command should be sent to the medicament pump 6302 at block 6806. If "Yes" at block 6806, that is, it is necessary to send an emergency command, the therapy administration system 6300 prompt the user to confirm the emergency command at block 6808 before executing the command. Additionally, the user then may be authenticated using one of the plurality of user authentication processes described herein, at block 6812. The connection confirmation signal may be further received from the medicament pump at block 6814. Upon determining that the user is authenticated, and the connection is confirmed, the therapy administration system 6300 transmits the execution command to the medicament pump to perform the emergency command at block 6816. On the other hand, if the connection confirmation signal is not generated and/or the user is not authenticated, the therapy administration system 6300 may inform the user with one or more of the situations at block 6818. In some examples, the connection confirmation signal is not received from the medicament pump 6302, the therapy administration system 6300 may inform the user, via the voice-user interface, that the remote therapy administration system and the medicament pump are not connected. In some cases, the alert signal may be muted for a predetermined time until the user acknowledges the alert.

In certain implementations, the method 6800 may further include determining that the therapy data or other data received from the AMD satisfy an alert threshold condition. In these implementations, it is determined that the therapy data or other data received from the AMD satisfy an alert threshold condition, the computing system may send an alert to one or more display systems designated to receive alerts from the computing system. Additional embodiments relating to determining alert conditions and generating an alert based on the alert conditions that can be combined with one or more embodiments of the present disclosure are described in U.S. Provisional Application No. 63/168,203, which was filed on Mar. 30, 2021 and is titled "IN-PATIENT BLOOD GLUCOSE CONTROL SYSTEM," the disclosure of which is hereby incorporated by reference.

Figure 69:
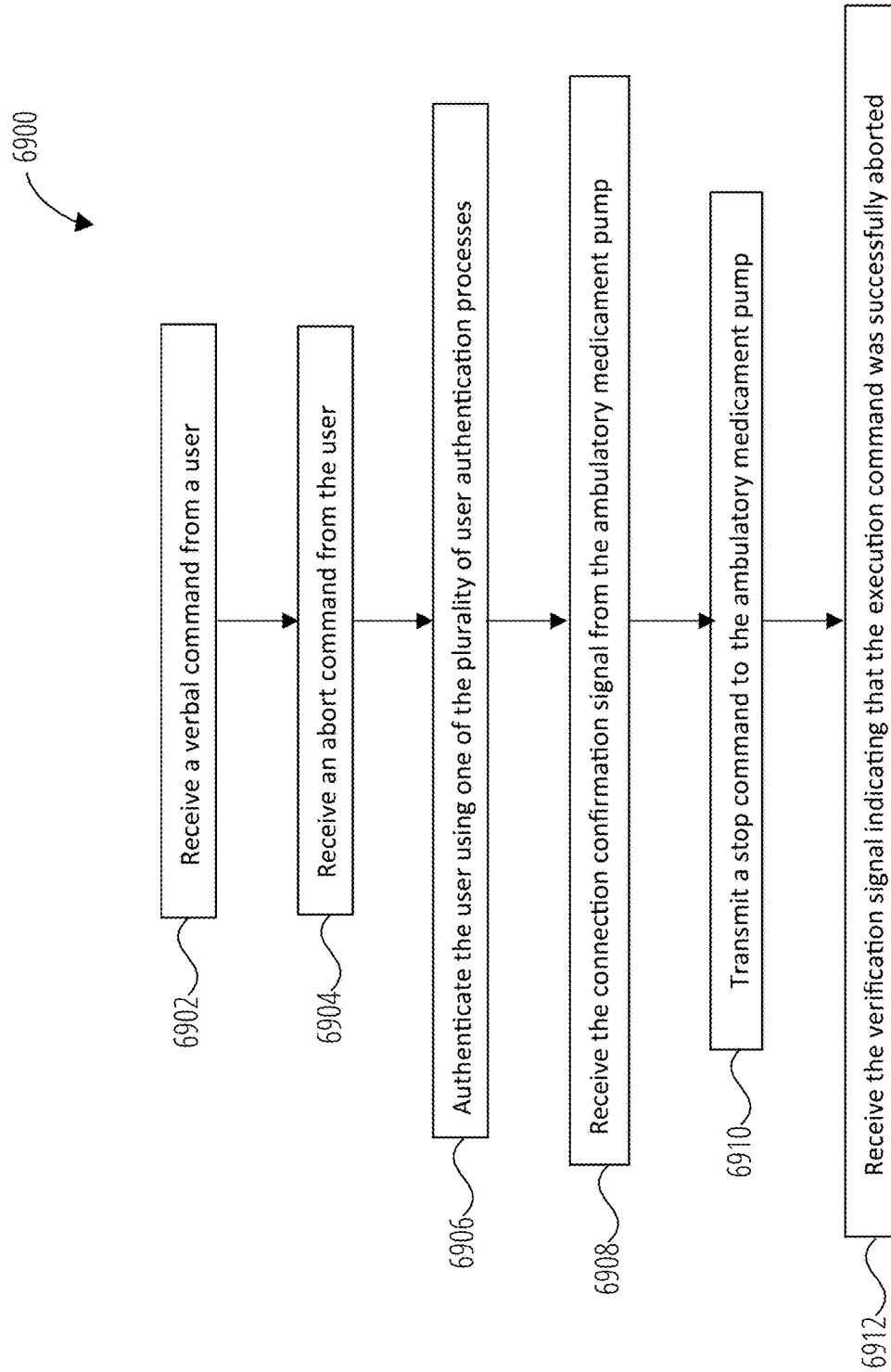
FIG. 69 shows a flow diagram illustrating an example method of controlling a therapy administration system when a verbal command includes an abort command.

In certain embodiments, the user may request to abort the command that has been input by the user. FIG. 69 shows a flow diagram illustrating an example method 6900 of controlling a therapy administration system when a verbal command includes an abort command. At block 6902, the therapy administration system 6300 receives a verbal command from a user. Then, the therapy administration system 6300 may, immediately or after a certain period of time, receive a command from the user to abort the verbal command at block 6904. As described herein, once the abort command has been received, the user authentication process can be performed using any one of the described authentication processes at block 6906. Additionally, the connection confirmation signal is received from the medicament pump at block 6908. Upon authenticating the user and receiving the connection confirmation signal, the therapy administration system 6300 transmits a stop command to the medicament pump 6302 at block 6910. When the pump has been stopped performing the execution command according to the abort command, the therapy administration system 6300 receives a verification signal indicating that the execution command was successfully aborted at block 6912.

In some embodiments, the verbal command may be a request to set up the medicament pump 6302 by a user. When such a request is received, the therapy administration system 6300 may request the user to name the medicament pump among one or more medicament pumps 6302. The user can provide the name for the medicament pump via the voice-user interface. The user can provide names for one or more medicament pumps that the user may want to operate.

In some embodiments, when the user provides a verbal command, the therapy administration system 6300 may request the user to select one or more medicament pumps to receive the verbal command. The user can provide the name of the specific pump, in which the name was set by the user. The therapy administration system 6300 then authenticate the user to confirm that the user providing the verbal command can be authorized to voice control the selected medicament pump 6302.

In various embodiments, the medicament pump 6302 can be connected to the therapy administration system 6300 by a broadband cellular network, a local wireless network, or a personal area network.

Figure 70:
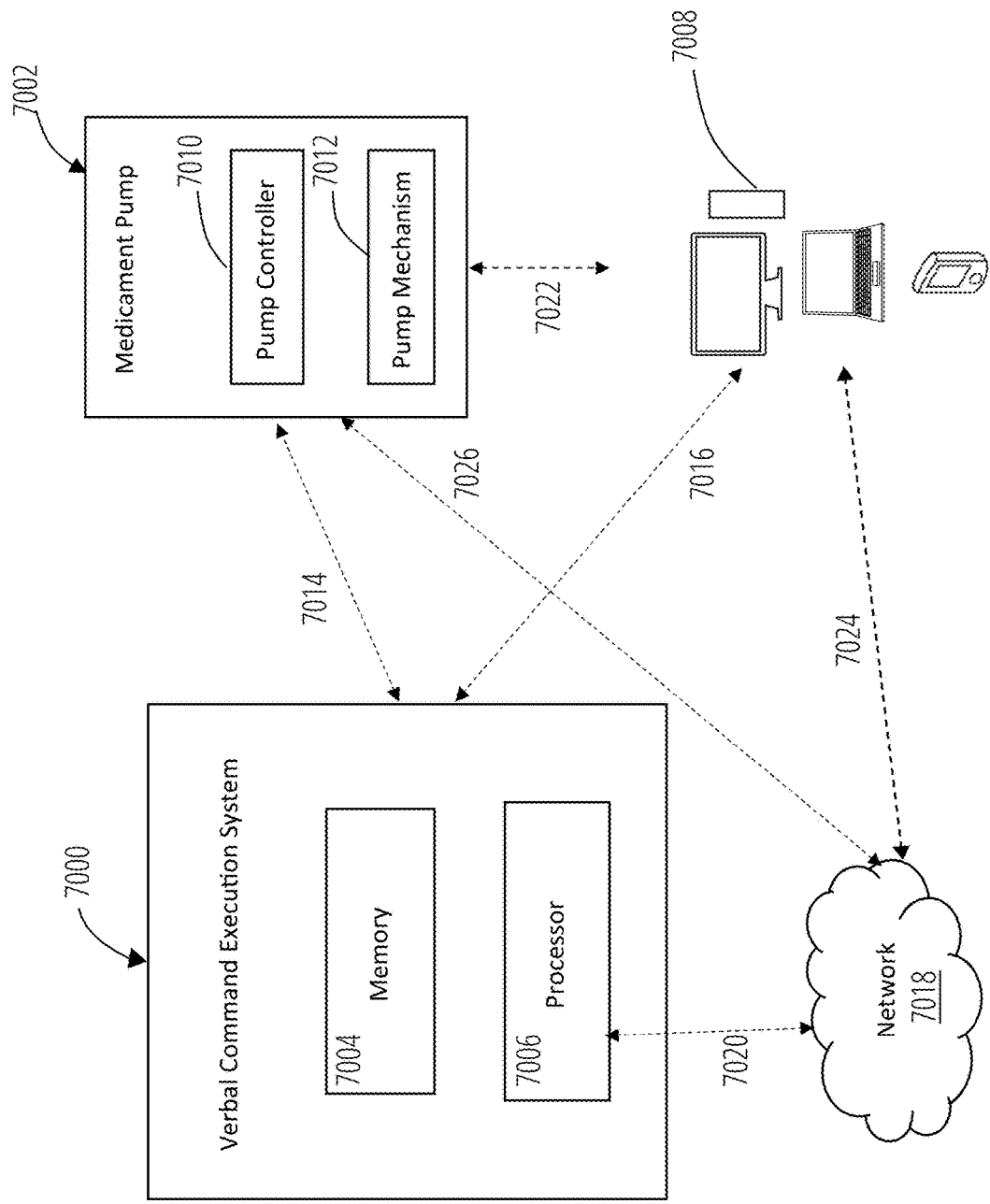
FIG. 70 shows an example system configured to manage execution of a command by an ambulatory medicament pump using a verbal command.

FIG. 70 shows a verbal command execution system 7000 configured to manage execution of a command by a medicament pump using a verbal command. Similar to the therapy administration system 6300, the verbal command execution system 7000 includes a memory a non-transitory memory 7004 and an electronic hardware processor 7006. The verbal command execution system 7000 may be a remote computing system as discussed herein. The verbal command execution system 7000 may further includes a data interface (not shown) comprising a wireless and/or wired data interface. The data interface can include a short-range wireless data interface. As discussed herein, networks or network connections can include data or network interfaces.

Additionally or alternatively, the verbal command execution system 7000 can be in communication with a network 7018 (e.g., via a network connection 7020). The verbal command execution system 7000 may be in communication via connection 7014, 7016 (e.g., wired, wireless) with the medicament pump 7002 and a user device 7008. For instance, a user device 7008 can be in communication with the processor 7006 via a voice-user connection 7016 which may be one-way or two-way. The data interface may also be in communication with other elements of the medicament pump 7002, such as the pump mechanism 7012 and/or the pump controller 7010. The detailed description and function of each element similarly correspond to each element of the therapy administration system 6300 of FIG. 63. Thus, the detailed description can be referred to the description of FIG. 63.

In certain embodiments, the user device 7008 may directly communicate with the medicament pump 7002 via wireless (or wired) connection 7022, as similarly described in FIG. 63. In this case, a user can communicate or control the medicament pump 6302 by inputting a voice command to the user interface of the user device 6308. In various embodiments, the user device 7008 is in communication with the network 7018 (e.g., via a network connection 7024)

via with wide area networks (WANs) such as a cellular network transceiver that enables 3G, 4G, 4G-LTE, or 5G. In some embodiments, the medicament pump 7002 may be in communication (wired or wireless) with the network 7018 directly with the network 7018 via connection 7026 or in communication (wired or wireless) with the network 7018 through the verbal command execution system 7000 and/or the user device 7008 (e.g., via connection 7014 and/or connection 7024). In some examples, the network communication may be via a Narrowband Long-Term Evolution (NB-LTE), a Narrowband Internet-of-Things (NB-IoT), or a Long-Term Evolution Machine Type Communication (LTE-MTC) communication connection with the wireless wide area network.

The communication between each system (the verbal command execution system 7000, the medicament pump 7002, and the user device 7008) may be variously configured as illustrated in FIG. 84. That is, as similarly described in connection with FIG. 63, the verbal command execution system 7000, the medicament pump 7002, and the user device 7008 may individually connected to each other. Alternatively, two or more of the verbal command execution system 7000, the medicament pump 7002, and the user device 7008 may be integrated as one element and configured to perform all the functions, as similarly described in connection with FIG. 63 above. The detailed description can be found throughout the disclosure in relation to the verbal command system 8400, the user interface 8404, and the medicament pump 8402 of FIG. 84.

In various embodiments, the user devices 7008 can be any smart device that a user can operate manually or verbally, as described herein. As an example, the user device 7008 may be a smart phone, a smart watch, a laptop, a smart speaker, or any other smart device that can communicate with the medicament pump 7002 and have software capability. In some embodiments, any other system such as the verbal command execution system 7000 or the medicament pump 7002 described herein may be implemented with smart functions as discussed herein, including voice recognition, authentication, command, etc. In this case, the therapy administration verbal command execution system 7000 or the medicament pump 7002 can be configured as a smart device having smart functions and communicates with the network 7018.

Figure 71:
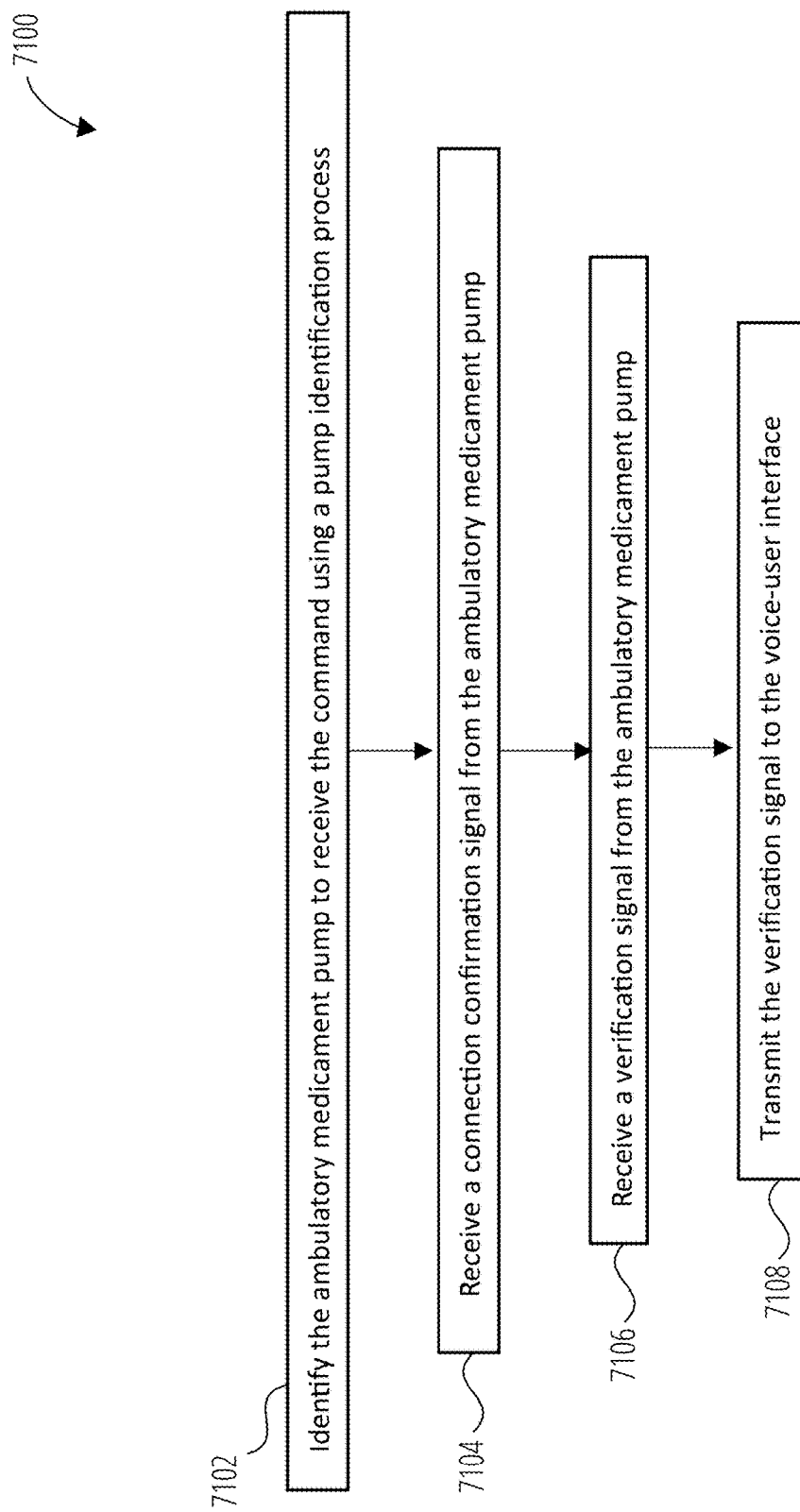
FIG. 71 shows a flow diagram illustrating an example method of managing execution of a verbal command by an ambulatory medicament pump.

FIG. 71 shows a flow diagram illustrating an example method 7100 of controlling the verbal command execution system 7000 to manage execution of a verbal command by a medicament pump. At block 7102, the verbal command execution system 7000 may identify the medicament pump 7002 to receive the command using a pump identification process. At block 7104, the verbal command execution system 7000 receives a connection confirmation signal from the medicament pump 7002. The connection confirmation signal can indicate that a data connection exists between the hardware processor 7006 and the medicament pump 7002. At block 7106, a verification signal is received from the medicament pump 7002. The verification signal indicates whether the medicament pump 7002 has received the command. Then, at block 7108, the verification signal is sent to the voice-user interface. The verification signal may further indicate that the medicament pump 7002 successfully performed the verbal command. In some cases, the verbal command execution system 7000 can record the command, an identity of the user, and a time that the verification signal was received, when the verification signal is received from the medicament pump 7002.

Figure 72:
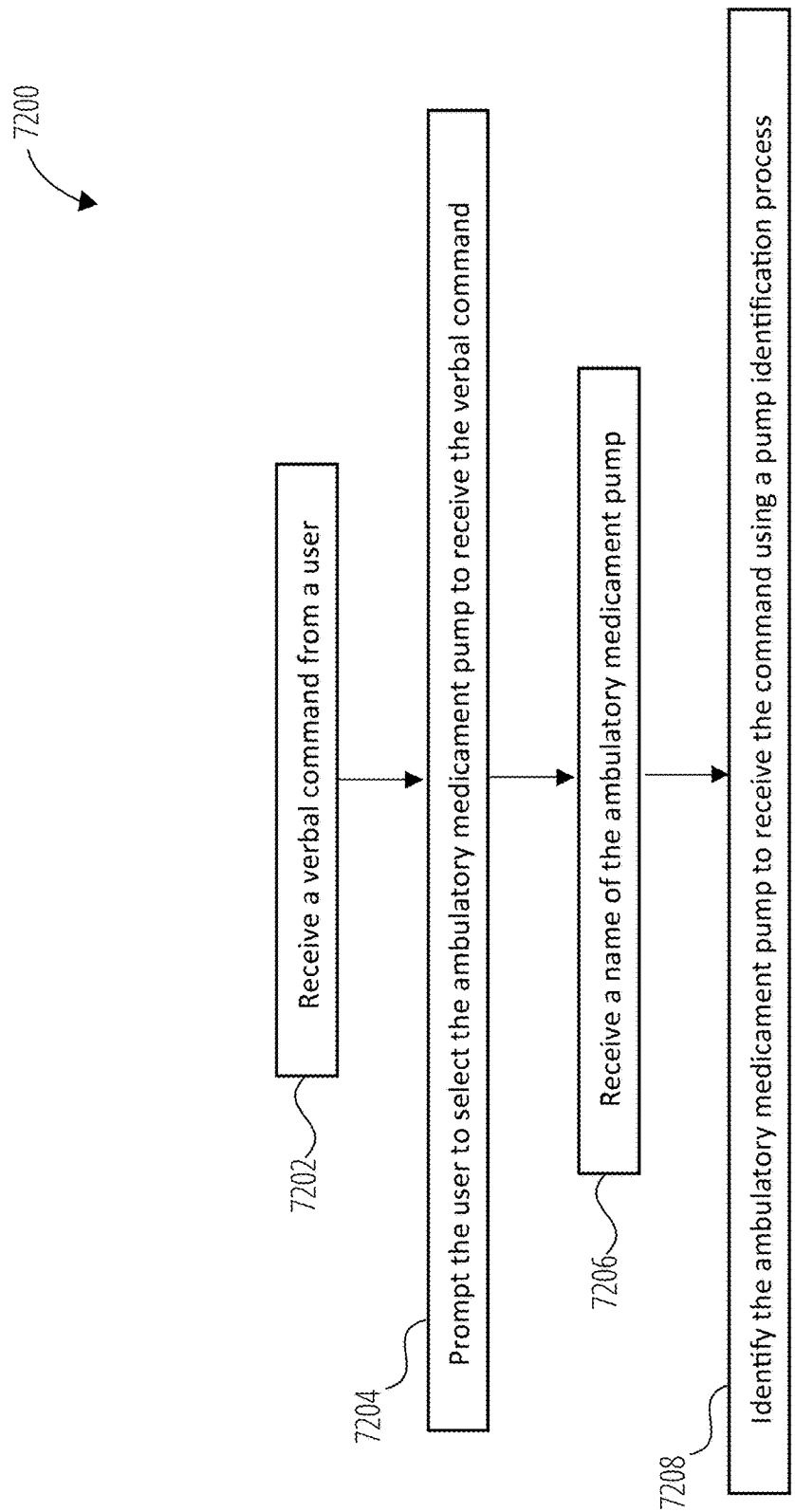
FIG. 72 shows a flow diagram illustrating an example method of managing execution of a verbal command to identify an ambulatory medicament pump for receiving a verbal command.

FIG. 72 shows a flow diagram illustrating an example method 7200 of managing execution of a verbal command to identify an ambulatory medicament pump for receiving a verbal command. In some embodiments, when the verbal command has been received (block 7202), a user may be asked to select a particular medicament pump to receive the verbal command (block 7204). For example, the user may have more than one pump or may have just replaced an old pump. In some cases, the verbal command execution system 7000 may be paired with more than one pump such that a user needs to specify the pump to be controlled. In certain embodiments, a user may give a name of the specific pump via the voice-user interface (block 7206). The name may be set previously by the user. Alternately, the user may provide unique identification information of the specific pump. The verbal command execution system 7000 then identifies and confirms which pump to receive user's verbal command (block 7208).

Similar to the therapy administration system 6300 which can authenticate the user, the verbal command execution system 7000 also authenticates the user using one of a plurality of authentication processes. The authentication can be valid for a validity period of time which may be one hour, one day, or one week. Alternatively, the validity period is set by the authenticated user using a verbal command. For some examples, the verbal command execution system 7000 may ask the user to define and receive a duration of the validity period via the voice-user interface.

In certain embodiments, the authenticated user or users can be added to a list of authorized users. In certain cases, only authorized users can have access to control the AMD by a verbal communication. In some examples, children may be authenticated, e.g., a passphrase was leaked. However, if the children are not added in the list of authorized users, limited access may be given to the children.

Figure 73:
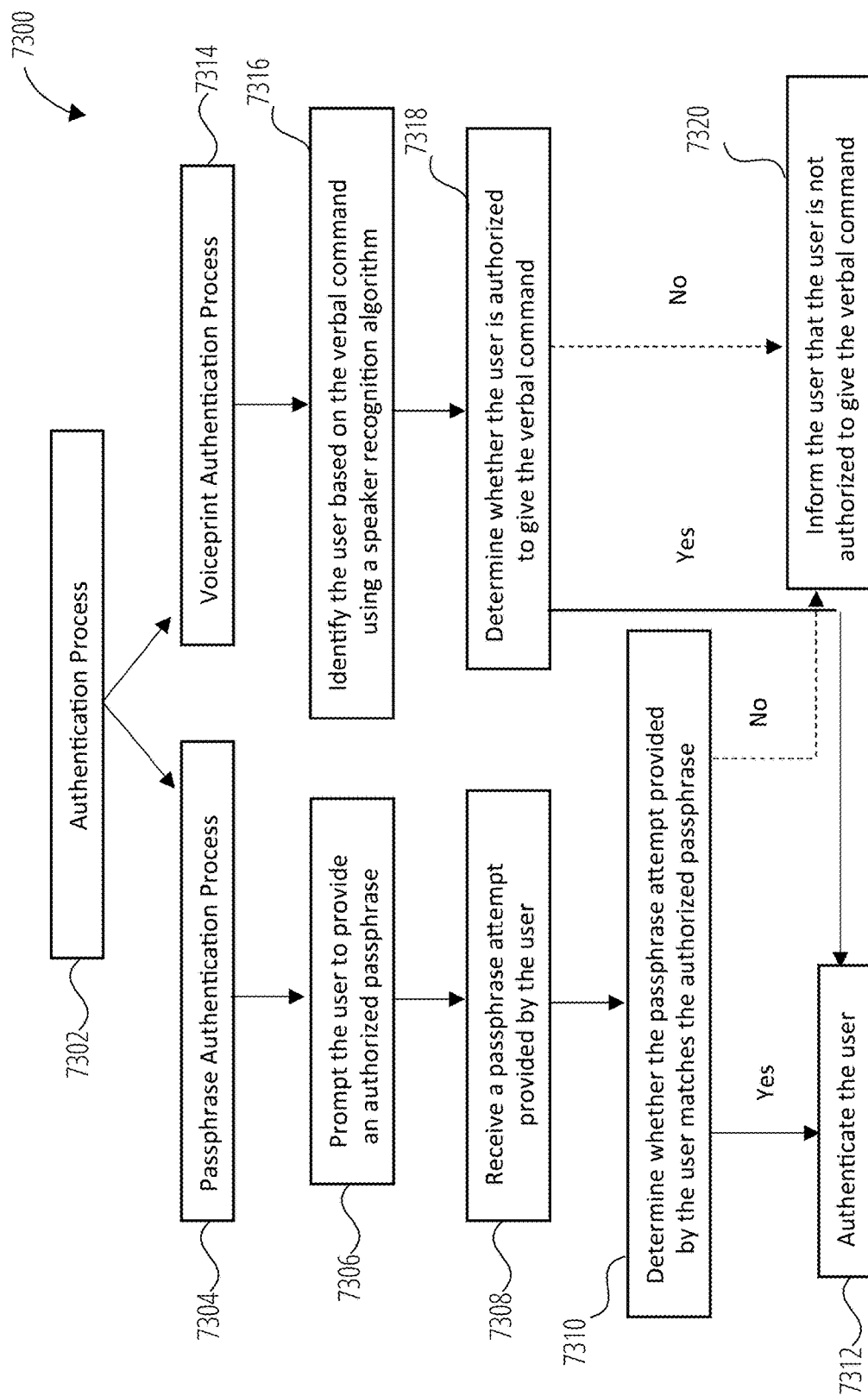
FIG. 73 shows a flow diagram illustrating an example method managing execution of a verbal command for authenticating a user based on a verbal command.

In more detail, referring to FIG. 73, which shows a flow diagram illustrating an example method 7300 managing execution of a verbal command for authenticating a user based on a verbal command, a user may be asked to provide an authorized passphrase (blocks 7304 and 7306). After receiving a verbal passphrase from the user (block 7308), the verbal command execution system 7000 determines whether the verbal passphrase of the user matches the authorized passphrase (block 7310). If "Yes" at block 7310, the user is authenticated (block 7312). If "No" at block 7310, on the other hand, the verbal command execution system 7000 informs the user that the user is not authorized to give the verbal command (block 7320).

In some embodiments, the user authentication processes are a voiceprint or speaker recognition authentication process (block 7314). In this case, when the verbal command execution system 7000 receives a verbal command from a user, the verbal command execution system 7000 identifies the user based on the verbal command using a speaker recognition algorithm (block 7316). The verbal command execution system 7000 then determines whether the user is authorized to give the verbal command (block 7318). The speaker recognition algorithm may be a hidden Markov model, a Gaussian mixture model, a pattern matching algorithm, a neural network, or a frequency estimation algorithm. If "Yes" at block 7318, the user is authenticated (block 7312). If "No" at block 7318, on the other hand, the verbal command execution system 7000 informs the user that the user is not authorized to give the verbal command (block 7320). The authenticated user or users can be added to a list of authorized users, as described herein.

Figure 74:
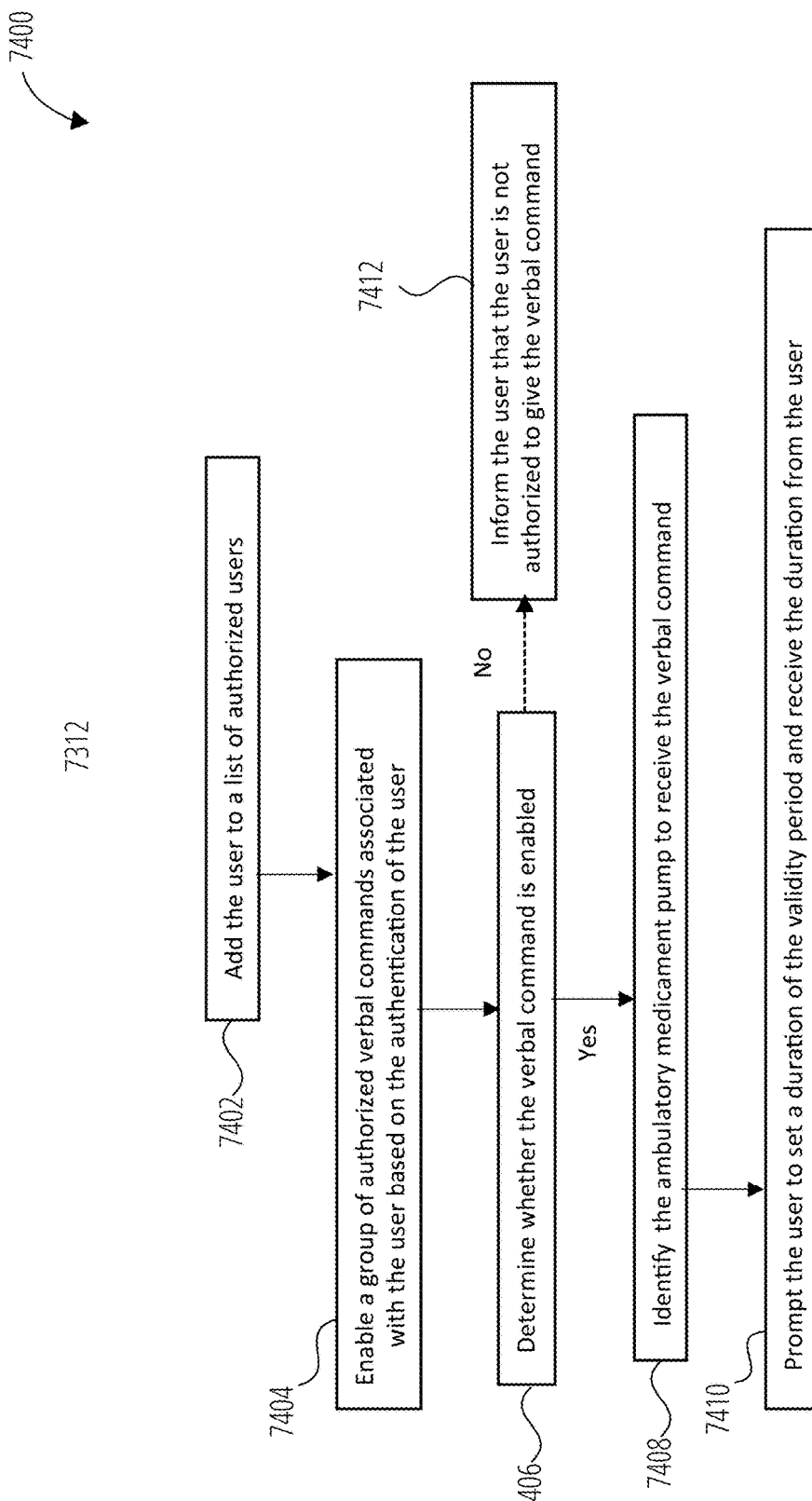
FIG. 74 shows a flow diagram illustrating an example method of controlling a therapy administration system when a user is authenticated.

In some embodiments, the verbal command execution system 7000 can enable a group of authorized verbal commands associated with the user based on the authentication of the user. That is, referring to method 7400 of FIG. 74, once the user is authenticated at block 7312, the authenticated user can be added to the authorized users' list at block 7402. The authentication of the user verifies the user's identity using at least one of the user authentication processes (e.g., verbal passphrase, speaker recognition, etc.). At block 7404, the verbal command execution system 7000 determines whether the verbal command is enabled. Upon determining that the verbal command is enabled at block 7406, the verbal command execution system 7000 identifies the medicament pump to receive the verbal command at block 7408. The group of authorized commands is enabled during a validity period (one hour, one day, or one week). Alternatively, the user can set a duration of the validity period via the voice-user interface at block 7410.

Additionally or alternatively, an authorization token may be generated when a user is authenticated. The authorization token may be valid for a specific period of time (one hour, one day, or one week). Similarly, the validity period of time for the authorization token can be set by the user via the voice-user interface. On the other hand, if it is determined that the verbal command is disabled, the verbal command execution system 7000 informs the user that the user is not authorized to give the verbal command at block 7412.

In various embodiments, the verbal command execution system 7000 transmits an execution command to the medicament pump 7002 to perform the verbal command when various conditions are satisfied. The conditions include authenticating a user or users.

Figure 75:
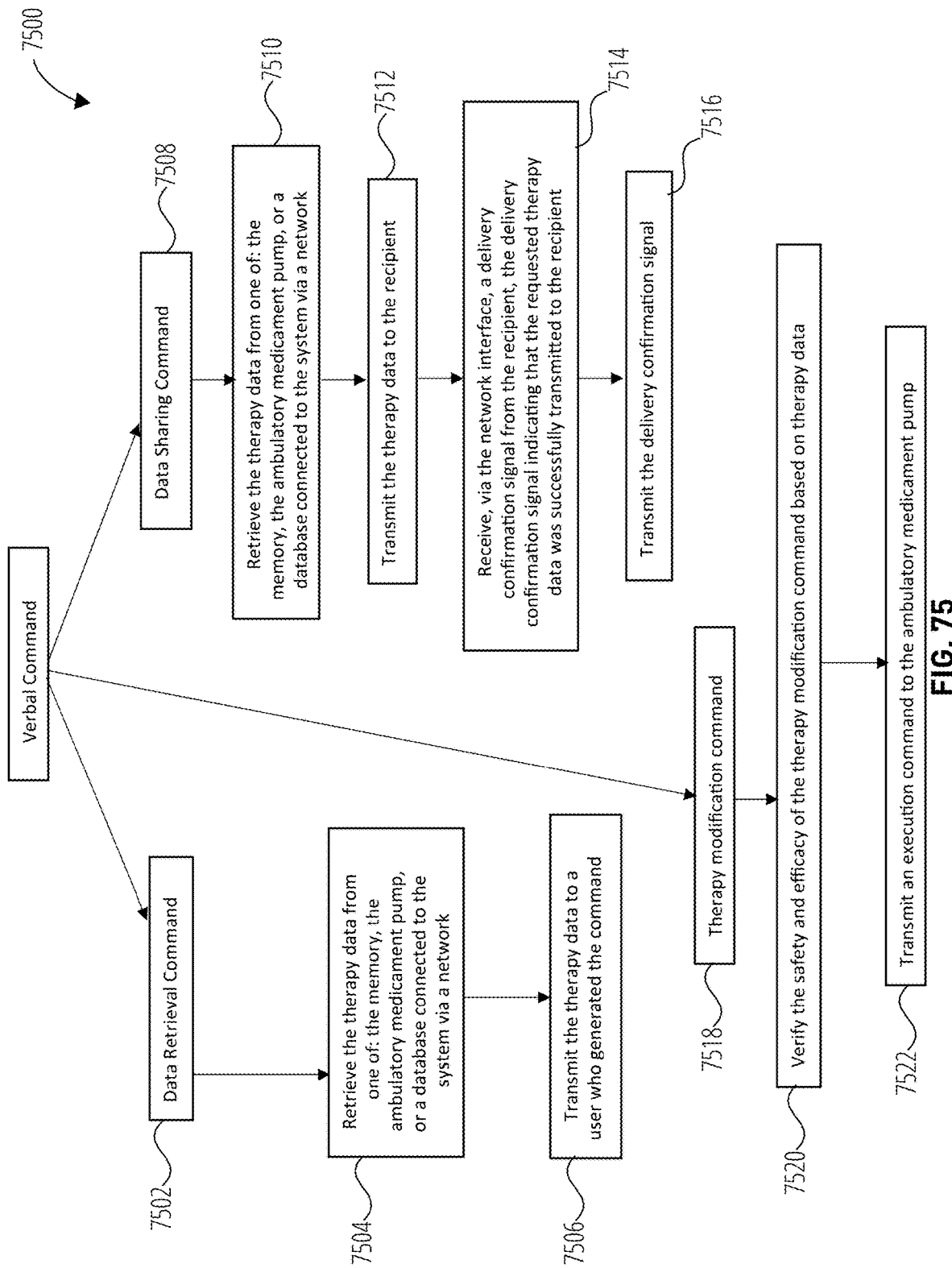
FIG. 75 shows a flow diagram illustrating an example method of controlling a verbal command execution system when a verbal command is a specific command among various commands.

FIG. 75 illustrates a flow diagram illustrating an example method 7500 of controlling a verbal command execution system when a verbal command is a specific command among various commands. The verbal command can be various commands that the user can verbally input. In certain embodiments, the verbal command includes a therapy modification command, a data retrieval command, a data sharing command, a medicament dose calculation command, etc. When the verbal command is a therapy modification command (block 7518), the verbal command execution system 7000 verifies the safety and efficacy of the therapy modification command based on therapy data at block 7520. The therapy modification command is for administering a medicament, modifying a medicament dose, or modifying a medicament dose calculation factor. The medicament can be insulin, glucagon, a bolus dose, or a Gburst dose. The medicament dose calculation factor may be a basal medicament rate, a carbohydrate ratio, a correction factor, or an insulin action time. Once the confirmation signal has been sent by the medicament pump 7002, the verbal command execution system 7000 transmits an execution command to the medicament pump 7002 to perform the therapy modification command at block 7522.

As described in various embodiments, the ambulatory medical device (AMD) having the medicament pump 7002 can provide life-saving treatment to subjects or subjects by delivering one or more medicaments (e.g., insulin and/or glucagon) to a subject or a subject. In some cases, the verbal command execution system 7000 may receive an indication to administer to a subject in place of the calculated dose of insulin. The verbal command execution system 7000 may further receive an indication that a subject is consuming or will consume food. The indication may include a type of food to be consumed and an estimate of the quantity of food or carbohydrates to be consumed (e.g., less than usual, a usual amount, more than usual, 30-40 grams of carbohydrates, 45-60 grams of carbohydrates, etc.). Based on the indication, or food intake announcement, the verbal command execution system 7000 may calculate an amount of insulin to administer to the subject. The calculation may be based on an insulin to carbohydrate ratio provided by a clinician and/or determined by the automated glucose level control system. Moreover, the calculation may be based at least in part on a history of glucose level measurements for the subject when consuming particular food. The subject or user as described herein can trigger the medicament pump 7002 for therapy delivery or modify the dose amount. The verbal command execution system 7000 of the embodiments is configured to allow administering or modifying the therapy delivery by user's voice input considering the calculated insulin dose.

In some embodiments, the verbal command is a data retrieval command comprising a request for therapy data (block 7502 of FIG. 75). The therapy data may be any one of battery level of the medicament pump, an insulin level of the user, a glucagon level of the user, a glucose level of the user, a blood sugar level of the user, an A1C level of the user, an eAG level of the user, an amount of a medicament stored by the medicament pump, or a medical history of the user. At block 7504, such therapy data is retrieved from one of: the memory, the medicament pump, or a database connected to the system via a network. At block 7506, the therapy data is transmitted to a user who generated the command via the voice-user interface.

In some embodiments, the verbal command is a data sharing command (block 7508 of FIG. 75). In this case, at block 7510, the verbal command execution system 7000 retrieves therapy data from one of the memory, the medicament pump, or a database connected to the system via a network. At block 7512, the therapy data to a recipient (e.g., user). Then at block 7514, the verbal command execution system 7000 receives a delivery confirmation signal from the recipient via the network interface. The delivery confirmation signal can indicate that the requested therapy data was successfully transmitted to the recipient. The delivery confirmation signal is then transmitted at block 7516.

Figure 76:
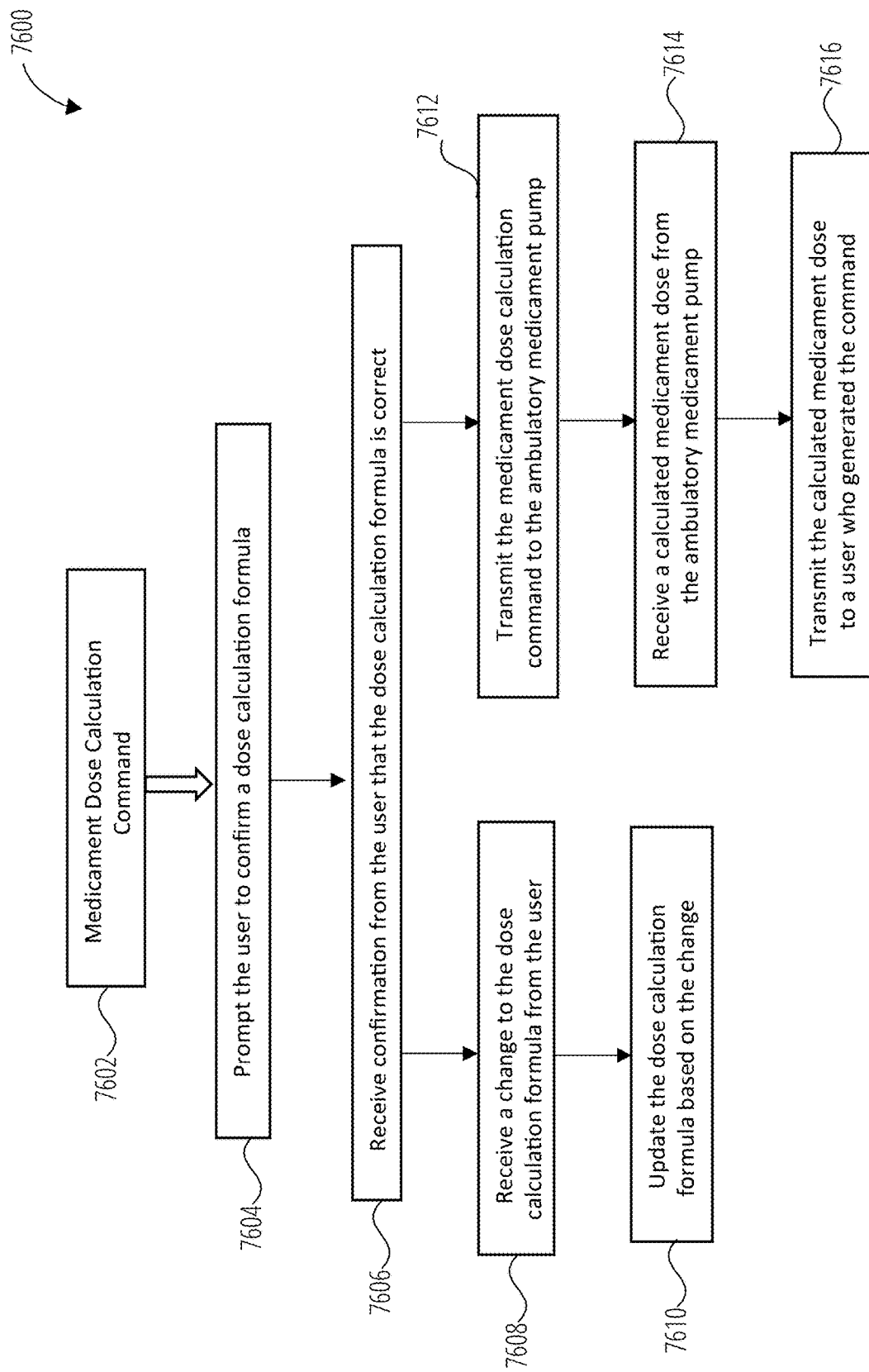
FIG. 76 shows a flow diagram illustrating an example method of controlling a therapy administration system when a verbal command is a medicament dose calculation command.

FIG. 76 shows a flow diagram illustrating an example method of controlling a therapy administration system when a verbal command is a medicament dose calculation command. In this case, the verbal command execution system 7000 prompts a user to confirm a dose calculation formula. Then, the verbal command execution system 7000 receives confirmation from the user that the dose calculation formula is correct at block 7606. In some embodiments, the verbal command execution system 7000 receives a change to the dose calculation formula from the user at block 7608. The verbal command execution system 7000 then updates the dose calculation formula based on the change at block 7610. Here, the change includes at least one updated medicament dose calculation factor. The method of controlling a therapy administration system when a verbal command is a medicament dose calculation command may further include transmitting the medicament dose calculation command to the medicament pump at block 7612. The verbal command execution system 7000, via the voice-user interface, receives a calculated medicament dose from the medicament pump at block 7614, and transmits the calculated medicament dose to a user who generated the command at block 7616.

Figure 77:
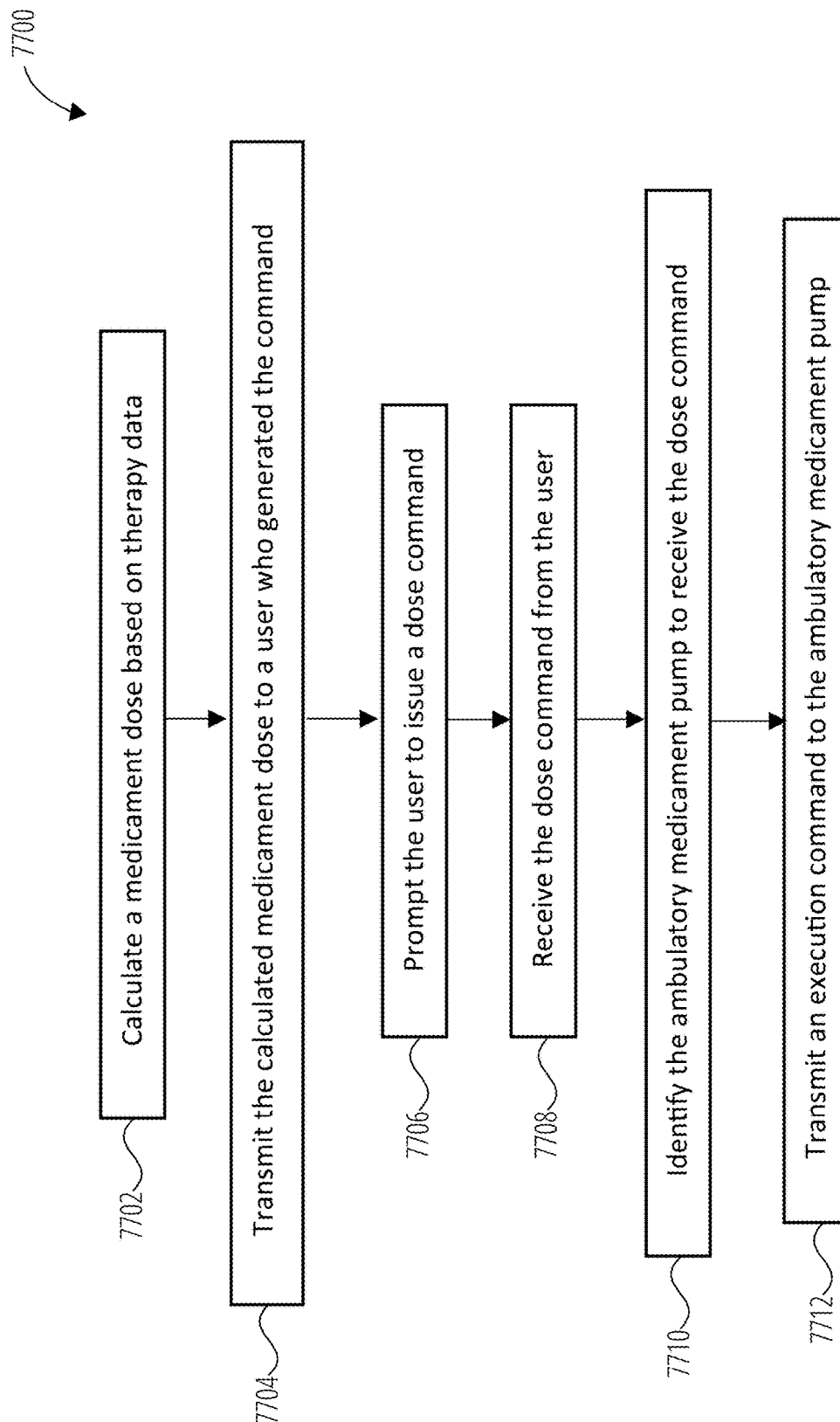
FIG. 77 shows a flow diagram illustrating another example method of controlling a therapy administration system when a verbal command is a medicament dose calculation command.

Additionally, referring to FIG. 77 (process 7700), after the verbal command execution system 7000 receives the confirmation at block 7606, the verbal command execution system 7000 may calculate a medicament dose based on therapy data at block 7702. The therapy data can be stored in the memory, the medicament pump, or a database connected to the system via a network. The calculated medicament dose is then transmitted to a user who generated the command at block 7704. The verbal command execution system 7000 then prompts the user to issue a dose command of requesting to administer the calculated medicament dose at block 7706. In response to receiving the dose command, the verbal command execution system 7000 identifies the medicament pump 7002 to receive the dose command at block 7710. The process of identifying the pump has been described throughout the disclosure, e.g., by naming each pump by the user. At block 7712, in response to receiving the dose command, the verbal command execution system 7000 transmits an execution command to the identified medicament pump 7002 to perform the dose command.

Alternatively, the dose command can be directly requested by the user via the voice-user interface. In this case, the verbal command execution system 7000 identifies the medicament pump 7002 to receive the dose command. Once the pump is identified, the verbal command execution system 7000 transmits an execution command to the identified medicament pump 7002 to perform the dose command.

Figure 78:
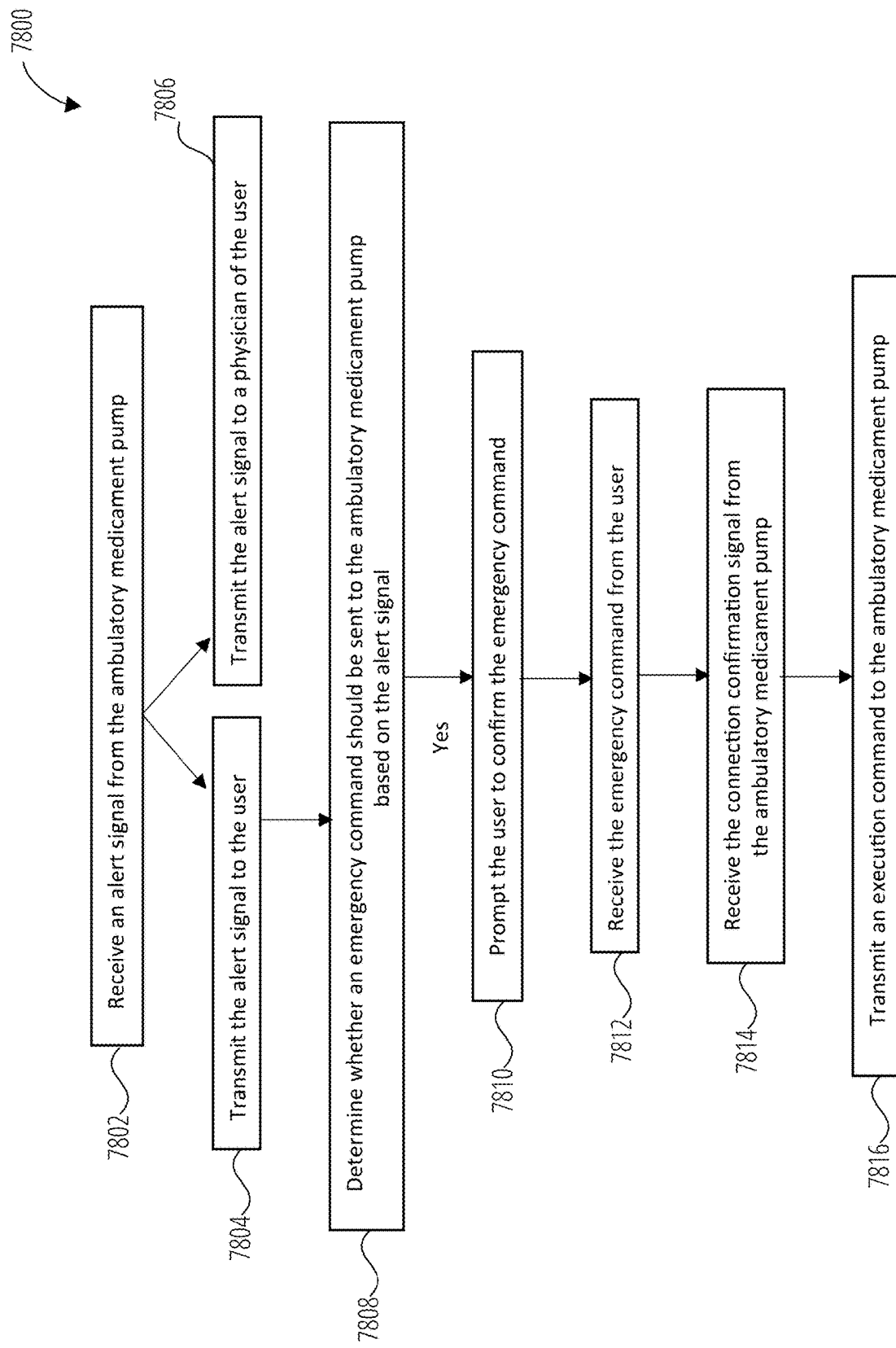
FIG. 78 Shows a flow diagram illustrating an example method of controlling a therapy administration system when there is an alert signal.

FIG. 78 shows a flow diagram illustrating an example method 7800 of controlling a therapy administration system when there is an alert signal. At block 7802, an alert signal (e.g., alert messages, alert signals, and the like) is received from the medicament pump. The alert signal is then transmitted to the user via the voice-user interface at block 7804. The alert signal indicates, for example, a low battery level of the medicament pump, a high glucose level (e.g., a blood sugar level) of the user, a low glucose level of the user, a low medicament level, or that the system and the medicament pump are disconnected.

In some cases, the alert signal can be transmitted to a physician of the user at block 7806. After the alert signal has been transmitted to the user, and/or the physician, the verbal command execution system 7000 determines whether an emergency command should be sent to the medicament pump based on the alert signal at block 7808. If it is determined that an emergency command should be sent at block 7808, the verbal command execution system 7000 prompts the user to confirm the emergency command at block 7810. The verbal command execution system 7000 can receive the emergency command from the user at block 7812. The verbal command execution system 7000 can further receive a connection confirmation signal from the medicament pump at block 7814. Then, the verbal command execution system 7000 transmits an execution command to the medicament pump to perform the emergency command at block 7816. The connection confirmation signal, as described herein, indicates that a data connection exists between the hardware processor 7006 and the medicament pump 7002. Alternatively or additionally, when it is determined that the emergency command should be sent to the medicament pump at block 7808, the verbal command execution system 7000 may receive the connection confirmation signal via the network interface before transmitting the execution command.

In various embodiments, the connection confirmation signal is not received from the medicament pump, the verbal command execution system 7000 informs the user that the system and the medicament pump are not connected. In this case, the verbal command execution system 7000 does not transmit the execution command to the medicament pump 7002.

In some embodiments, the verbal command execution system 7000 may receive an abort command from the user to abort, stop, or pause the verbal command. In this case, the verbal command execution system 7000 identifies the medicament pump to receive the abort command. The verbal command execution system 7000 then transmits a stop command to the identified medicament pump 7002 to abort execution of the verbal command. When the execution command is successfully aborted, a verification signal may be sent from the medicament pump 7002. In various embodiments, the medicament pump can be identified by naming each pump especially when there are multiple pumps. A user can name each pump via the voice-user interface without manually typing in.

In certain embodiments, the verbal command execution system 7000 can generate a therapy report and transmit to a user via the voice-user interface. The therapy report may include at least one of: a list of commands executed by the medicament pump, a basal medicament rate, one or more medicament dose calculation levels, a glucose level (e.g., a blood sugar level) of the user, an A1C level of the user, an eAG level of the user, a glucagon level of the user, a battery level of the medicament pump, or an amount of medicament stored by the medicament pump.

In some cases, the verbal command execution system 7000 may receive therapy data via the voice-user interface or a network interface. The therapy data may be a medicament dose, a medicament basal rate, a medicament dose calculation factor, an alert trigger, or a medical history of the user. In some examples, the therapy data comprises dose or dosage data corresponding to one or more doses of medicament provided by the ambulatory medical device to the subject. Further, the therapy data may comprise subject data corresponding to a medical or physiological state of the subject as determined by the ambulatory medical device.

In other examples, the data provided to computing system may include any type of data that may be measured or obtained by the ambulatory medical device and may include a record of therapy provided by the ambulatory medical device. For example, the data may include a time that therapy was provided, an amount of medicament provided as part of the therapy, a measure of one or more vital signs of the subject, a measure of glucose levels at different times for the subject, a location of the subject, and the like.

In some cases, the therapy data may be used to track the use of disposables, such as insulin or other medicament, or insulin pump site kits. In some cases, the computing system may automatically order or reorder disposables at a particular time based on tracking the use of the disposable. Alternatively, or in addition, the reordering of the disposables may be initiated or performed from the ambulatory medical device (e.g., via a wireless wide area network or via a local connection through a separate electronic device). In some examples, the data, therapy data and/or the therapy report may be stored in a memory of the computing system and/or at a storage of the networked-computing environment.

In some examples, a therapy report based at least in part on the therapy data may be generated by the computing system. The therapy report may comprise time-series therapy data relating to the therapy delivered by the ambulatory medical device over a particular time period. In some examples, the therapy report may be sent to AMD wherein the subject can see the report via a voice user interface (e.g., a speaker).

In certain implementations, the method may further include determining that the therapy data or other data received from the AMD satisfy an alert threshold condition.

In these implementations, it is determined that the therapy data or other data received from the AMD satisfy an alert threshold condition, the computing system may send an alert to one or more display systems designated to receive alerts from the computing system. In some examples, alert threshold condition may be associated with the health condition of the subject. For example, alert threshold condition may include subject's glucose level (e.g., blood sugar level) is above or below a set value (hyperglycemia or hypoglycemia). In some examples the alert threshold condition may be associated with the operation of the AMD. For example, alert threshold condition may include the rate of therapy (e.g., the rate at which insulin is provided to a subject) being above or below a set value.

In some cases, the verbal command execution system 7000 may periodically generate therapy reports based on a regular schedule. Alternatively, or in addition, the data may be received in response to a command or when the ambulatory medical device determines it is within a certain location. In some cases, the verbal command execution system 7000 may automatically generate the therapy report after a time period set by the user. The time period can be one of daily, weekly, or monthly.

Additional embodiments relating to therapy data and therapy report that can be combined with one or more embodiments of the present disclosure are described in U.S. Provisional Application No. 63/157,541, which was filed on Mar. 5, 2021 and is titled "REMOTE MODIFICATION OF THERAPY DELIVERED BY AMBULATORY MEDICAMENT PUMP," the disclosure of which is hereby incorporated by reference in its entirety herein for all purposes.

Figure 79:
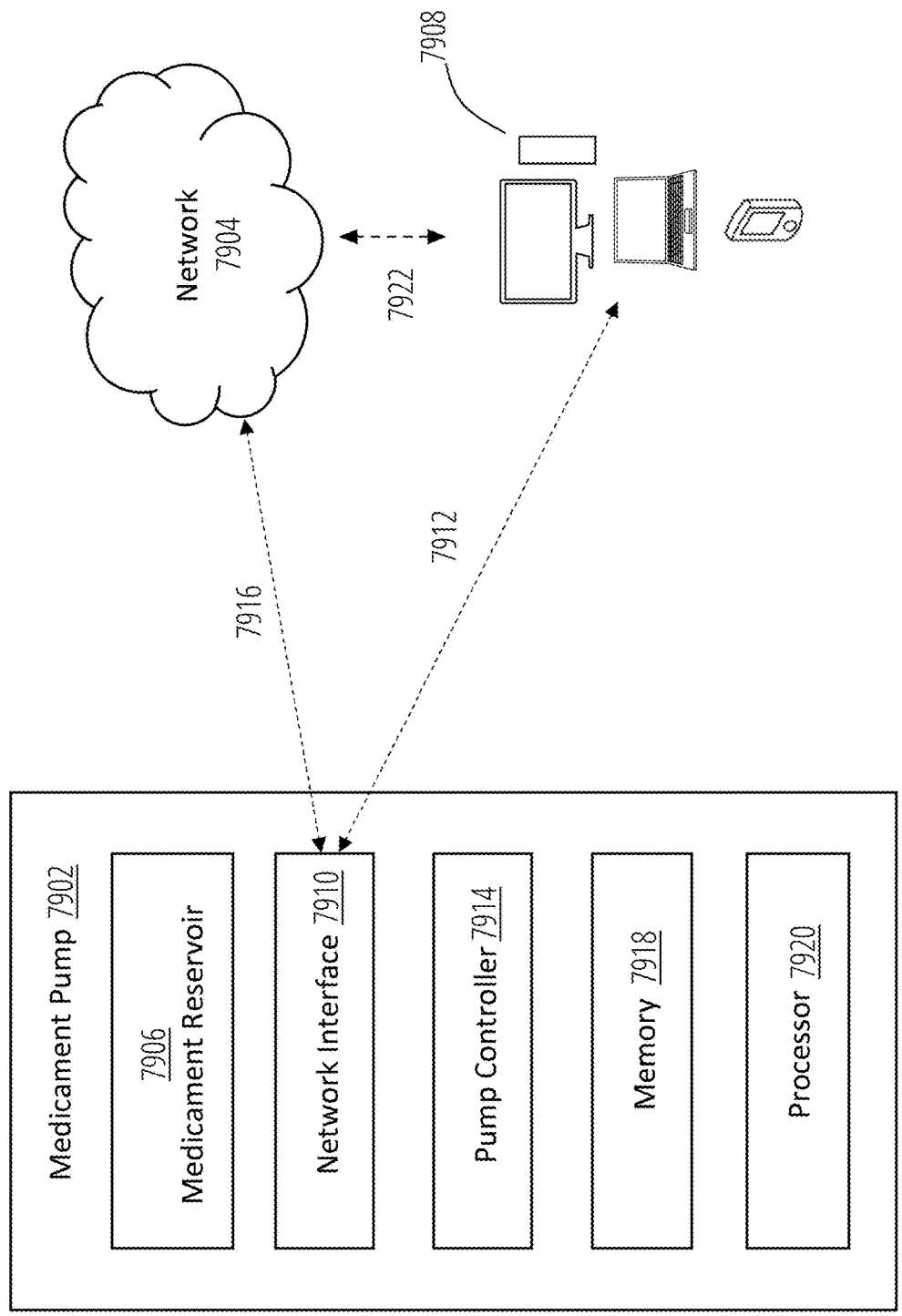
FIG. 79 is a schematic illustrating an example ambulatory medicament pump that is configured to transmit a request to modify glucose level control therapy delivered to a subject via a verbal command.

FIG. 79 is a schematic illustrating an example ambulatory medicament pump that is configured to transmit a request to modify glucose level control therapy delivered to a subject via a verbal command. The medicament pump 7902 may be an ambulatory medicament pump. The medicament pump 7902 includes a medicament reservoir 7906, a network interface 7910, a pump controller 7914, a non-transitory memory 7918, and an electronic hardware processor 7920.

The medicament pump 7902 can be any medical device that a subject (e.g., a user) may carry around and use with the approval of a medical professional. The medicament pump 7902 may correspond to and/or share certain functionality with one or more devices described herein. There are many different types of medicament pumps 7902. In some embodiments, the medicament pump 7902 is an insulin and/or glucagon infusion device for subjects that have Type I diabetes. Ambulatory medicament pumps 7902 allow subjects the freedom to receive medical care in any setting at their convenience.

The medicament pump 7902 can include a data network interface 7910, which may be physically connected with the medicament pump 7902, wirelessly connected, connected via a cloud-based computer system, and/or connected in any other way. The pump controller 7914 is configured to direct medicament from the medicament reservoir 7906 to the subject using a pump motor or other pump mechanism. In some examples, the medicament pump 7902 includes a therapy modification control element (not shown), which may allow user input and/or provide feedback to a user. The components of the medicament pump 7902 are similar to the medicament pump 6302 of FIG. 63 or medicament pump 7002 of FIG. 70. That is, in various embodiments, the medicament pump 7902 enables therapy delivery into the subject using the components as described herein (pump mechanism, reservoir, memory, controller, etc.).

The medicament pump 7902 may communicate with a network 7904 that includes any wired network, wireless network, or combination thereof, via a network connection 7916. For example, the network 7904 may be a personal area network, local area network, wide area network, over-the-air broadcast network (e.g., for radio or television), cable network, satellite network, cellular telephone network, or combination thereof. The network 7904 may include one or more wireless networks, such as a Global System for Mobile Communications (GSM) network, a Code Division Multiple Access (CDMA) network, a Long Term Evolution (LTE) network, or any other type of wireless network. The network 7904 can use protocols and components for communicating via the Internet or any of the other aforementioned types of networks. For example, the protocols used by the network 7904 may include Hypertext Transfer Protocol (HTTP), HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein. The network 7904 may comprise or have access to the "cloud." The network 7904 may include a remote computing environment. As discussed herein, networks or network connections can include data or network interfaces.

Similar to FIG. 63 and FIG. 70, various example user devices 7908 are shown in FIG. 79, including a desktop computer, a laptop, and a mobile phone, each provided by way of illustration. The user device 7908 can execute an application (e.g., a browser, a stand-alone application) that allows a user to access and interact with interactive user interfaces as described herein. Similar to the user device 6308 of FIG. 63 and the user device 7008 of FIG. 70, the user device 7908 can be any device configured for smart functions (e.g., voice activation technology).

In some embodiments, the medicament pump 7902 and the user device 7908 are connected via a connection 7912. For instance, the user device 7908 may be a network enabled device communicating with the medicament pump 7902 wirelessly or via a wired. The medicament pump 7902 may directly communicate with the network 7904 (via a connection 7916) or indirectly communicate with the network 7904 via the user device 7908 (via a connection 7912). In certain example, the medicament pump 7902 may be implemented as a smart device for receiving a verbal command, without communicating with the user device 7908. In some example, the user device 7908 may communicate with the network 7904 via a connection 7922 similarly to the configurations of FIG. 63 and FIG. 79.

In certain embodiments, the medicament pump 7902 and the user device 7908 may be integrated into one device as described in FIG. 84. In this case, the integrated device can be configured to perform the functions of the medicament pump 7902 and the user device 7908 (e.g., receiving a verbal command, executing the verbal command, etc.). In some cases, the user device 7908 can be any smart device having various smart functions implemented for a user to operate as discussed herein, including voice recognition, authentication, command, etc. Alternatively, or in addition, the medicament pump 7902 may be configured as a smart device implemented with smart functions as discussed herein, including voice recognition, authentication, command, etc.

Figure 80:
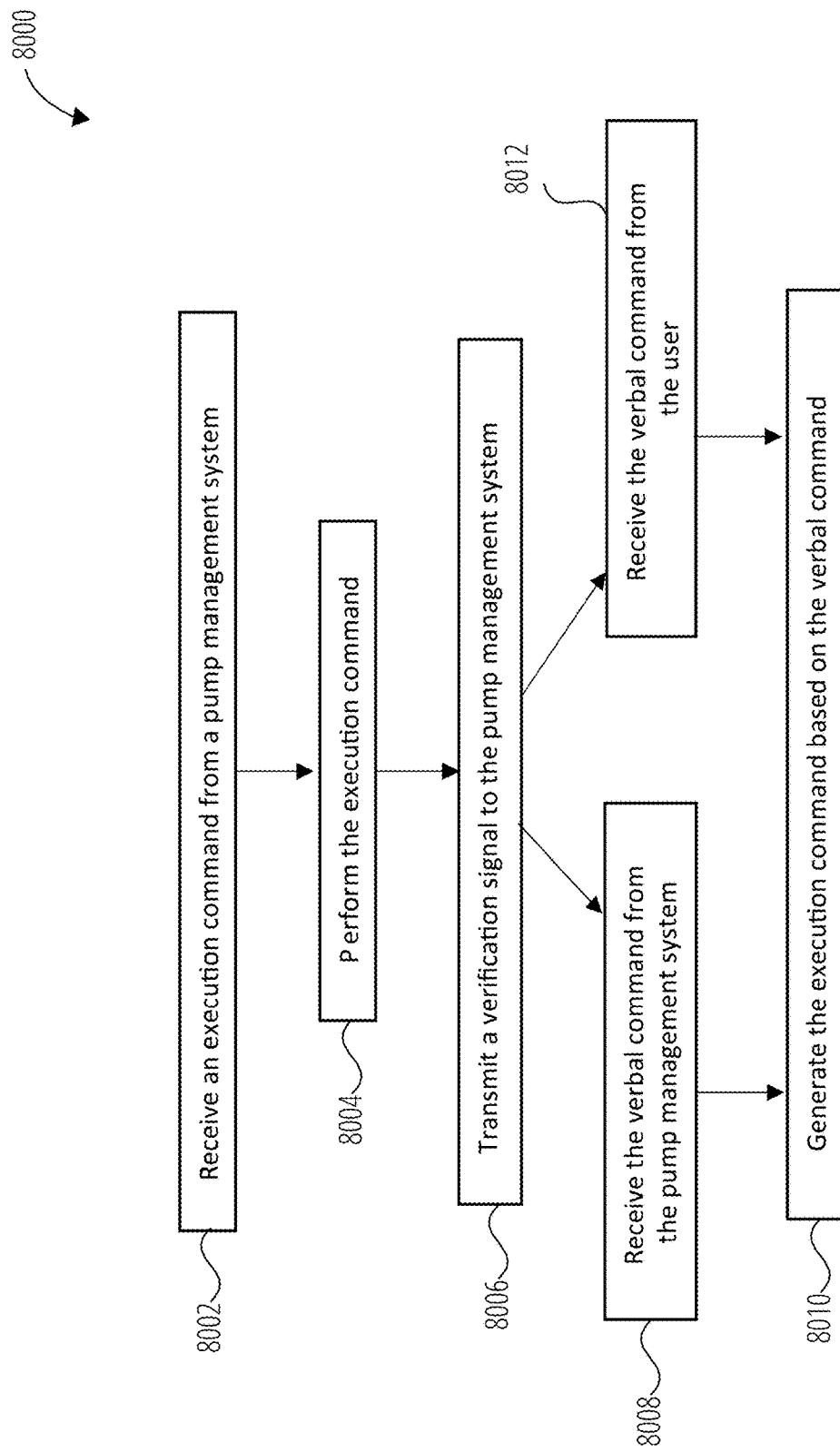
FIG. 80 shows a flow diagram illustrating an example method of controlling an ambulatory medicament pump of FIG. 79 to execute a glucose level control system command.

FIG. 80 shows a flow diagram illustrating an example method 8000 of controlling a medicament pump of FIG. 79 to execute a glucose level control system command. The method 8000 may be performed by a medicament pump, such as a medicament pump 7902 described herein. At block 8002, the medicament pump 7902 may receive an execution command from a pump management system via a network interface. The execution command may be computer executable instructions to perform a verbal command of a user. At block 8004, the execution command can be performed. The medicament pump 7902 then transfers a verification signal to the pump management system if the execution command is successfully performed at block 8006.

In various embodiments, the medicament pump 7902 is connected to the pump management system by a broadband cellular network, a local wireless network, a personal area network, or a direct electrical connection. Such that, the medicament pump 7902 can receive the verbal command of the user from the pump management system at block 8008. Alternatively, the medicament pump 7902 can receive the verbal command directly from the user via user interaction with the voice-user interface at block 8012. The medicament pump 7902 then generates the execution command based on the verbal command at block 8010 received from the pump management system or directly from the user.

In some examples, the medicament pump 7902 includes a microphone configured to receive the verbal command from the user. The medicament pump 7902 may further include a speaker configured to transmit outputs from the voice-user interface to the user.

Figure 81:
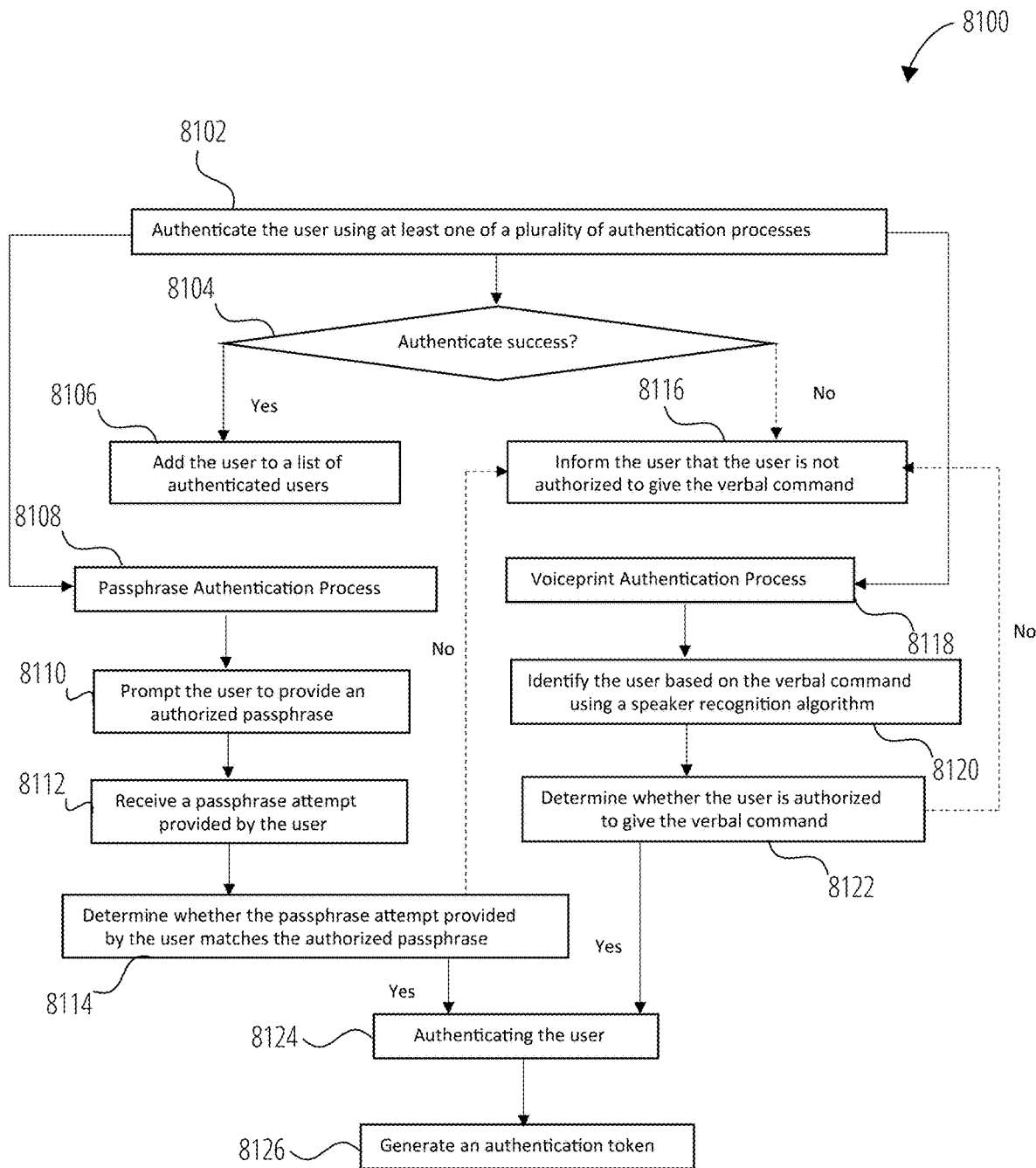
FIG. 81 shows a flow diagram illustrating an example method of controlling a therapy administration system when there is an alert signal.

Referring to process 8100 in FIG. 81, in various embodiments, the pump management system authenticates the user using at least one of a plurality of authentication processes as described herein at block 8102. For example, the plurality of authentication processes include a passphrase authentication process and a voiceprint authentication process. In case of the passphrase authentication at block 8108, the pump management system that is in communication with the medicament pump prompts the user to provide an authorized passphrase at block 8110. Then, the pump management system authenticates the user when the user provided passphrase matches the authorized passphrase (blocks 8110, 8112, 8114 and 8124). If the user provided passphrase does not match the authorized passphrase, the pump management system informs the user that the user is not authorized to give the verbal command via the voice-user interface at block 8116.

In some examples, the authenticated user or users can be added to a list of authenticated users at block 8106. In some cases, the pump management system may generate an authentication token in response to authenticating the user at block 8126. The authentication token is valid during a validity period (e.g., one hour, one day, or one week). Alternatively, the pump management system may ask the user to define the duration of the validity period via the voice-user interface.

In certain embodiments, the pump management system may transmit a confirmation request to the pump management system similar to the therapy administration system 6300 or the verbal command execution system 7000 as described herein. The pump management system may pump management system once the confirmation request is received. Additionally, the pump management system may prompt the user to confirm the verbal command before executing the verbal command.

The described processes of the pump management system to execute a glucose level control system command are similarly disclosed for the therapy administration system 6300 or the verbal command execution system 7000.

In some cases, the method of controlling a medicament pump may further record the command, the identity of a user, and a time that the execution command was successfully executed.

Figure 82:
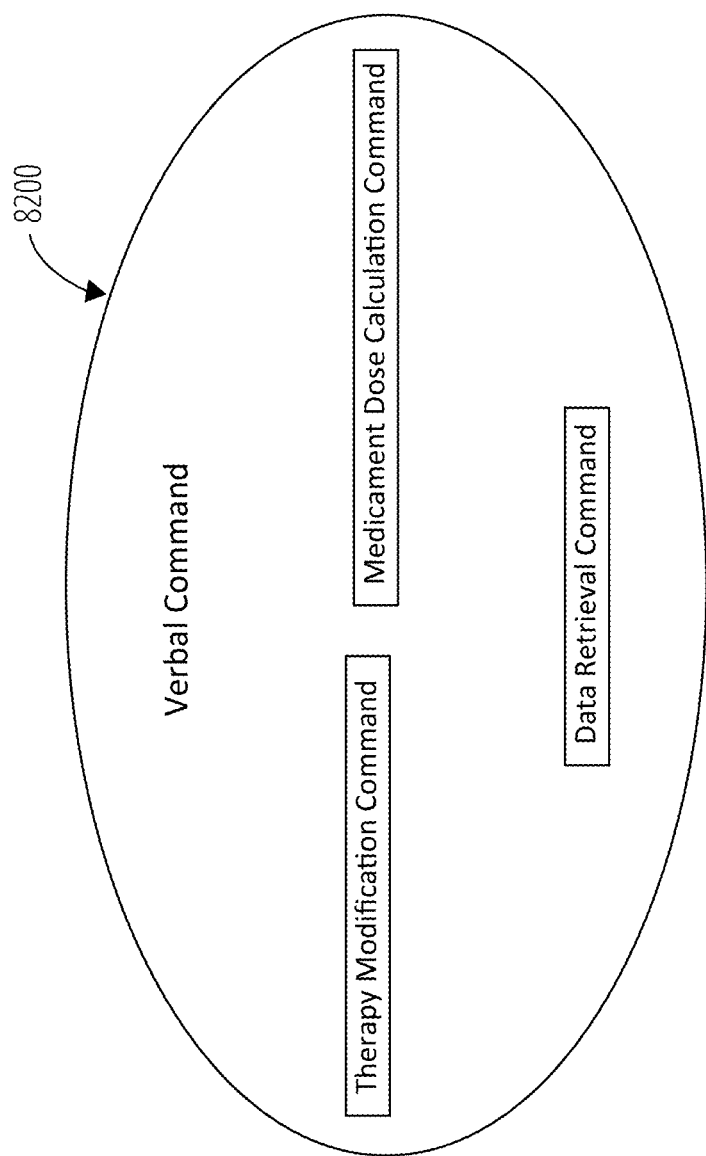
FIG. 82 is a diagram illustrating an example verbal command for modifying glucose level control therapy delivered.

In various embodiments, the verbal command 8200 is one or more of a therapy modification command, a data retrieval command, and a medicament dose calculation command as shown in FIG. 82. In case of the therapy modification command, the pump management system administers a medicament or modify a medicament dose. The medicament is one of insulin, glucagon, a bolus dose, or a Gburst dose. In some examples, the pump management system instructs the pump controller 7914 to execute the therapy modification command. In some example, the therapy modification command may modify a medicament calculation factor. the medicament dose calculation factor includes a basal medicament rate, a carbohydrate ratio, a correction factor, or an insulin action time. Additionally, the pump management system verifies the safety and efficacy of the therapy modification command based on therapy data before executing the verbal command.

In case of the data retrieval command, therapy data is requested. As an example, the therapy data can be a battery level of the medicament pump, an insulin level of the user, a glucagon level of the user, a glucose level or a blood sugar level of the user, an A1C level of the user, an eAG level of the user, an amount of a medicament stored by the medicament pump, or a medical history of the user. The therapy data is then transmitted to the pump management system. Herein, the therapy data may be retrieved from the pump management system or a database connected to the pump via a network as described previously in detail.

Figure 83:
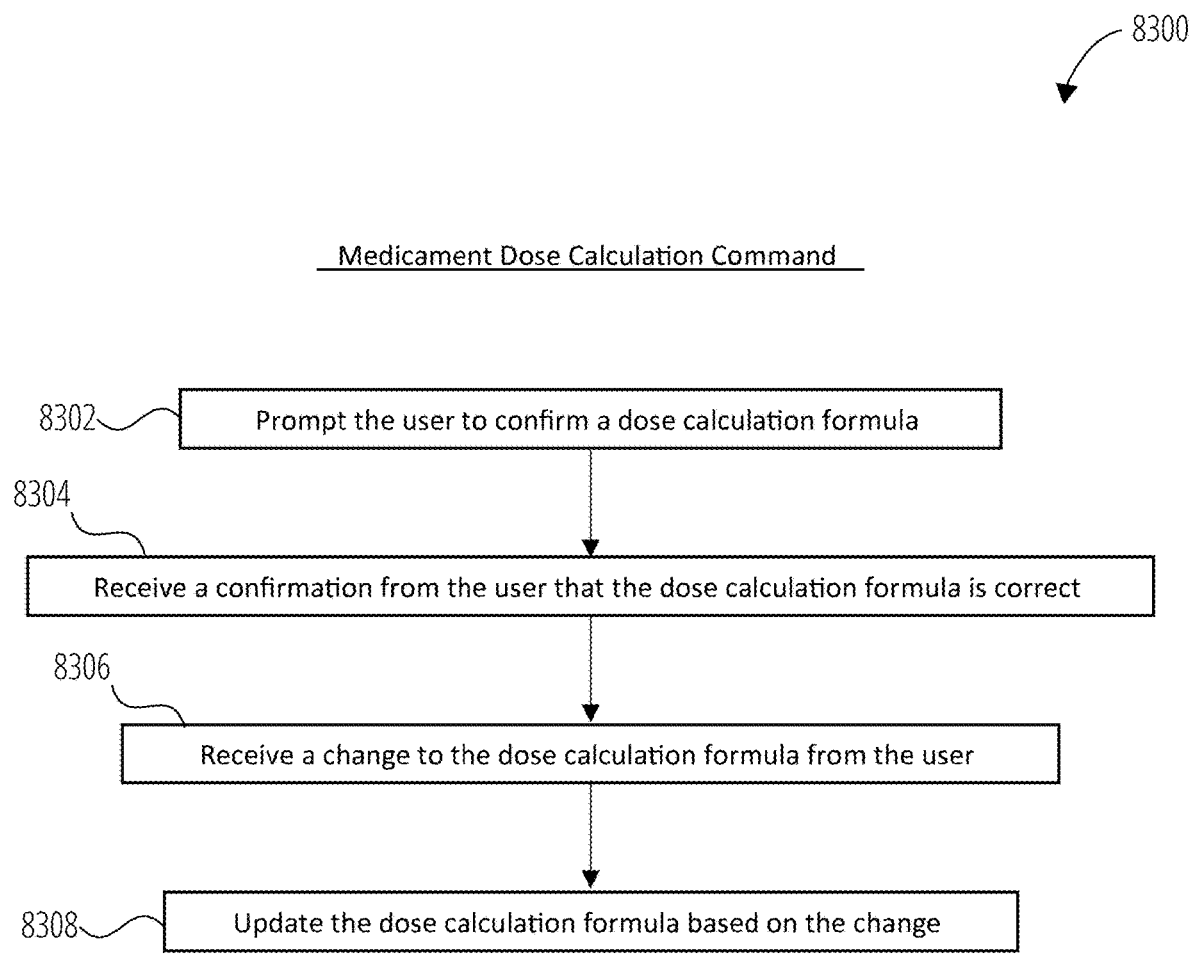
FIG. 83 shows a flow diagram illustrating an example method of controlling an ambulatory medicament pump when a verbal command is a medicament dose calculation command.

FIG. 83 shows a flow diagram illustrating an example method 8300 of controlling a medicament pump when a verbal command is a medicament dose calculation command. In case of the medicament dose calculation command, the pump asks the user to confirm a dose calculation formula via the voice-user interface at block 8302. The pump then receives a confirmation from the user that the dose calculation formula is correct at block 8304. At block 8306, the pump may receive a change to the dose calculation formula from the user via the voice-user interface. Here, the change includes at least one updated medicament dose calculation factor. Then, at block 8308, the pump updates the dose calculation formula based on the change. In some examples, the medicament dose can be calculated based on therapy data and transmitted to the user. The therapy data may be retrieved from the non-transitory memory, the pump management system, or a database connected to the medicament pump via a network. In some cases, the pump may ask the user to issue a dose command to administer the calculated medicament dose. The pump then instructs the pump controller to administer the dose.

In administering the calculated dose, an alert signal may be generated to inform the user via the voice-user interface. Similar to other control processes described herein, the alert signal indicates a low battery level of the medicament pump, a high glucose level (e.g., blood sugar level) of the user, a low glucose level of the user, a low medicament level, or that the system and the medicament pump are disconnected.

The medicament pump 7902 of FIG. 79 can further generate an alert signal the user and/or the physician of the user. Based on the severity of the alert signal, the medicament pump 7902 can further prompt the user to confirm and execute an emergency command. The process of generating and performing the alert signal can be similarly performed with reference to the method 6800 of FIG. 68 and the method 7800 of FIG. 78.

Furthermore, the medicament pump 7902 of FIG. 79 performs an abort process when an abort command has been received by a user via the voice-user interface, similar to method 6900 of FIG. 69. In some cases, therapy data and therapy report can be generated by the medicament pump 7902 of FIG. 79 similar to the therapy administration system 6300 or the verbal command execution system 7000 described herein.

As described herein in connection with FIG. 63, FIG. 70, and FIG. 79, FIG. 84 is a diagram illustrating an exemplary connection relationship between each of a system for verbal communication, a medicament pump, and a user interface. That is, each system can communicate with each other and/or can be integrated into one or two systems to perform all the necessary functions described herein. As also described throughout the disclosure, the verbal command system 8400 (or the therapy administration system 6300 or the verbal command execution system 7000) and the medicament pump 8402 (or the medicament pump 6302 or the medicament pump 7002) can be integrated into one device (VM) configured to perform all the functions thereof as discussed herein, including voice recognition, authentication, command, etc. For example, the medicament pump 8402 may be configured to receive a verbal command and perform the authentication process, confirmation process, etc., and finally execute the verbal command. In further example, the verbal command system 8400 (or the therapy administration system 6300 or the verbal command execution system 7000), the medicament pump 8402 (or the medicament pump 6302 or the medicament pump 7002) and the user interface 8404 (or the user device 6308 or the user device 7008) may be integrated into one device (VMU). In this case, the medicament pump 8402 having all the functions of the verbal command system 8400 and the user interface 8404 may function as a smart device for receiving a user verbal command. Alternatively or in addition, the medicament pump 8402 (or the medicament pump 6302, the medicament pump 7002, or the medicament pump 7902) and the user interface 8404 (or the user device 6308, the user device 7008, or the user devices 7908) may be integrated into one device (MU). Furthermore, the verbal command system 8400 (or the therapy administration system 6300 or the verbal command execution system 7000) and the user interface 8404 (or the user device 6308 or the user device 7008) may be integrated into one device (VA). Each of the devices can communicate directly and/or indirectly with the network 8406, whether as in an integrated device or as individually. In various embodiments, as also described throughout the disclosure, the verbal command system 8400 may correspond to each of the therapy administration system 6300 of FIG. 63 and the verbal command execution system 7000 of FIG. 70. That is, the therapy administration system 6300 can be integrated with the medicament pump 6302 and/or the user device 6308, and the verbal command execution system 7000 can be integrated with the medicament pump 7002 and the user device 7008. Similarly, the medicament pump 7902 of FIG. 79 may correspond to the medicament pump 8402, such that the medicament pump 7902 can be integrated with the user device 7908. The configurations and the connection relationships are however not limited to the description herein, but any other configuration and relationships can be achieved.

Additional device or system can be added to control any of the devices (e.g., the verbal command system 8400, the medicament pump 8402, the user interface/device 8404, and the network 8406) in FIG. 84 to communicate with them. For example, a healthcare provider (e.g. physician) may have an interface communicating with the user interface 8404 of a subject (e.g., patient) or communicating with the medicament pump 8402 of the user to remotely and/or verbally control the therapy setting or delivery to the subject. Alternatively, the interface of the healthcare provider may communicate with the verbal command system 8400 via a network connection (wirelessly) that communicates with the user interface 8404 or the medicament pump 8402. The healthcare provider may communicate a plurality of medicament pumps or verbal command systems of one or more patients, such that one physician (or nurse) can communicate the AMD of various patients. That is, FIG. 84 is merely one exemplary embodiment such that any other possible connections for enabling the verbal command can be configured. In various embodiments, the configurations and connection relationships of FIG. 84 can be correspondingly applied to the configurations of FIG. 63, FIG. 70, and FIG. 79.

Example Embodiments

Some additional nonlimiting examples of embodiments discussed above are provided below. These should not be read as limiting the breadth of the disclosure in any way.

Example 1: An ambulatory medicament pump configured to determine an amount of total remaining medicament and to generate a user alert configured to indicate that additional supply of medicament may be necessary, the ambulatory medicament pump comprising: a cartridge receptacle configured to receive a cartridge comprising a medicament reservoir and to secure the cartridge to the cartridge receptacle, wherein the medicament reservoir is configured to contain an amount of the medicament; a pump controller configured to command to direct the medicament from the medicament reservoir to a subject; a pump motor configured to eject the medicament from the medicament reservoir; a wireless data interface configured to connect to a remote electronic device; a non-transitory memory configured to store specific computer-executable instructions; and a hardware processor in communication with the non-transitory memory and configured to execute the specific computer-executable instructions to at least: receive an indication of an amount of initial medicament in possession of the subject; determine, by a medicament rate determining process, a rate of consumption of medicament; determine the amount of total remaining medicament based on a function of the amount of initial medicament in possession of the subject and the rate of consumption of the medicament; determine that the amount of the total remaining medicament is below a threshold amount; in response to determining that the amount of the total remaining medicament is below the threshold amount, automatically generate the user alert configured to indicate that additional supply of medicament may be necessary; and transmit, via the wireless data interface, a request for the additional supply of medicament to the remote electronic device.

Example 2: The ambulatory medicament pump of example 1, further comprising a medicament ordering control element configured to receive the request for the additional supply of medicament.

Example 3: The ambulatory medicament pump of example 2, wherein the indication of the amount of initial medicament in possession of the subject is received via the medicament ordering control element.

Example 4: The ambulatory medicament pump of example 2 or 3, wherein the user alert is indicated via the medicament ordering control element.

Example 5: The ambulatory medicament pump of example 4, wherein the hardware processor is further configured to execute the specific computer-executable instructions to at least: receive, via user interaction with the medicament ordering control element, the request to order additional supply of medicament; and in response to receiving the request to order additional supply of medicament, transmit, via the wireless data interface, a purchase order for additional supply of medicament to the remote electronic device.

Example 6: The ambulatory medicament pump of example 4 or 5, wherein the hardware processor is further configured to execute the specific computer-executable instructions to at least: in response to generation of the user alert configured to indicate that additional supply of medicament may be necessary, prompt the subject to authorize a purchase of the additional supply of medicament; and receive, via the medicament ordering control element, a command to authorize a purchase of the additional supply of medicament.

Example 7: The ambulatory medicament pump of any one of examples 4 to 6, wherein the hardware processor is further configured to execute the specific computer-executable instructions to at least: in response to generation the user alert configured to indicate that additional supply of medicament may be necessary, prompt the subject, via the medicament ordering control element, to select a time period for which the additional supply of medicament is desired; receive, via the medicament ordering control element, a selected time period for which the additional supply of medicament is desired; and in response to receiving the selected time period for which the additional supply of medicament is desired, transmit, via the wireless data interface, the selected time period for which the additional supply of medicament is desired to the remote electronic device.

Example 8: The ambulatory medicament pump of any one of examples 4 to 7, wherein the hardware processor is further configured to execute the specific computer-executable instructions to at least: receive, via the wireless data interface, an indication of an expected quantity of medicament to be used for one or more periods of time; in response to receiving the indication of the expected quantity of medicament to be used for one or more periods of time, prompt the subject to acquire the expected quantity of medicament to be used for one or more periods of time; receive, via the medicament ordering control element, a command to acquire the expected quantity of medicament to be used for one of the one or more periods of time; and in response to receiving the command to acquire the expected quantity of medicament to be used for one of the one or more periods of time, transmit, via the wireless data interface, the command to acquire the expected quantity of medicament to be used for one of the one or more periods of time to a medical supplier, a manufacturer, or a healthcare provider.

Example 9: The ambulatory medicament pump of any one of examples 4 to 8, wherein the hardware processor is further configured to execute the specific computer-executable instructions to at least: determine, based on the rate of the consumption of the medicament, a time by which a supply of replacement medicament should be ordered; based on the time by which the supply of replacement medicament should be ordered, prompt the subject to acquire a quantity of replacement medicament before the time; receive, via the medicament ordering control element, a command to acquire the quantity of replacement medicament; and in response to receiving the command to acquire the command to acquire the quantity of replacement medicament, transmit, via the wireless data interface, the command to acquire the quantity of replacement medicament to a medical supplier, a manufacturer, or a healthcare provider.

Example 10: The ambulatory medicament pump of any one of examples 1 to 9, wherein the remote electronic device comprises computing hardware in a network-connected computing environment, and wherein the request for the additional supply of medicament is transmitted to the computing hardware.

Example 11: The ambulatory medicament pump of example 10, wherein determining that the amount of the total remaining medicament is below the threshold amount comprises receiving an indication from the computing hardware that the total remaining medicament is below the threshold amount.

Example 12: The ambulatory medicament pump of example 10 or 11, wherein receiving the indication of the amount of initial medicament in possession of the subject comprises receiving the indication from the computing hardware.

Example 13: The ambulatory medicament pump of any one of examples 10 to 12, wherein the medicament rate determining process comprises receiving an indication from the computing hardware.

Example 14: The ambulatory medicament pump of any one of examples 2 to 13, wherein the hardware processor is further configured to execute the specific computer-executable instructions to at least: determine an amount of unusable supply of medicament; and based on the determination of the amount of unusable supply of medicament, determine an amount of total remaining usable medicament less than the total remaining medicament.

Example 15. The ambulatory medicament pump of example 14, wherein the hardware processor is further configured to execute the specific computer-executable instructions to at least: in response to determining that the amount of the total remaining usable medicament is below a threshold amount, automatically generate the user alert configured to indicate that additional supply of medicament may be necessary.

Example 16: The ambulatory medicament pump of example 14 or 15, wherein the amount of unusable supply of medicament comprises at least one of: medicament that has exceeded an expiration date supplied by a manufacturer of the medicament, medicament that has exceeded an expiration date received via the medicament ordering control element, or medicament that has been recalled by the manufacturer of the medicament.

Example 17: The ambulatory medicament pump of any one of examples 14 to 16, wherein determining the amount of unusable supply of medicament comprises estimating an expiration date of at least some of the amount of the total remaining medicament.

Example 18: The ambulatory medicament pump of any one of examples 1 to 17, wherein determining the rate of consumption of the medicament comprises: determining an amount of medicament ejected from the medicament reservoir due to operation of the pump motor; and determining an amount of residual medicament remaining in the medicament reservoir during a cartridge replacement procedure, wherein the residual medicament comprises medicament not ejected from the medicament reservoir.

Example 19: The ambulatory medicament pump of any one of examples 1 to 18, wherein the hardware processor is further configured to execute the specific computer-executable instructions to at least: receive, via the wireless data interface, a confirmation signal from the remote electronic device, the confirmation signal configured to indicate that the request for the additional supply of medicament was received by the remote electronic device; and generate a success alert configured to indicate that the request for the additional supply of medicament was successfully received by the remote electronic device.

Example 20: The ambulatory medicament pump of any one of examples 1 to 19, wherein the medicament rate determining process comprises determining a number of turns of a motor.

Example 21: The ambulatory medicament pump of any one of examples 1 to 20, wherein the medicament rate determining process comprises at least one of determining a vapor pressure within the medicament reservoir or detecting a volume of medicament using a piston location.

Example 22: The ambulatory medicament pump of any one of examples 1 to 21, wherein the medicament rate determining process comprises at least one of determining a number of times a cartridge was installed in the cartridge receptacle or a rate of installation of new cartridges in the cartridge receptacle.

Example 23: The ambulatory medicament pump of any one of examples 1 to 22, wherein the medicament rate determining process comprises receiving from a sensor an amount of existing medicament in the medicament reservoir.

Example 24: The ambulatory medicament pump of any one of examples 1 to 23, wherein the medicament rate determining process comprises determining a location of a piston.

Example 25: The ambulatory medicament pump of any one of examples 1 to 24, wherein the medicament rate determining process comprises estimating a rate of use of medicament.

Example 26: The ambulatory medicament pump of any one of examples 1 to 25, wherein the hardware processor is further configured to execute the specific computer-executable instructions to at least: transmit, via the wireless data interface, the rate of consumption of the medicament to the remote electronic device.

Example 27: The ambulatory medicament pump of any one of examples 1 to 26, wherein the hardware processor is configured to execute the specific computer-executable instructions to at least: receive, via the wireless data interface from the remote electronic device, an indication of the total remaining medicament.

Example 28: The ambulatory medicament pump of any one of examples 1 to 27, wherein determining the rate of consumption of the medicament comprises determining a number of cartridges used over a period of time.

Example 29: The ambulatory medicament pump of any one of examples 1 to 28, wherein the hardware processor is further configured to execute the specific computer-executable instructions to at least: receive, via user interaction with a medicament ordering control element, a request for the additional supply of medicament.

Example 30: The ambulatory medicament pump of any one of examples 1 to 29, wherein the hardware processor is further configured to execute the specific computer-executable instructions to at least: in response to determining that the amount of the total remaining medicament is below the threshold amount, automatically transmit, via the wireless data interface, the request for the additional supply of medicament to the remote electronic device.

Example 31: An ambulatory medicament pump configured to transmit a request to modify glucose level control therapy delivered to a subject via a remote computing environment, the ambulatory medicament pump comprising: a medicament reservoir configured to store medicament to be delivered as therapy to a subject by the ambulatory medicament pump; a pump controller configured to command to direct the medicament from the medicament reservoir to the subject via the ambulatory medicament pump; a wireless data interface configured to connect to the remote computing environment via a network connection comprising a wide area network; a non-transitory memory configured to store specific computer-executable instructions; and a hardware processor in communication with the non-transitory memory and configured to execute the specific computer-executable instructions to at least: transmit, via the wireless data interface, the request to modify glucose level control therapy delivered to the subject to the remote computing environment; receive, via the wireless data interface, an indication that the request to modify therapy is approved; and in response to the indication that the request to modify the glucose level control therapy is approved, instruct the pump controller to modify the glucose level control therapy delivered to the subject.

Example 32: The ambulatory medicament pump of example 31, wherein the hardware processor is further configured to execute the specific computer-executable instructions to at least: transmit, via the wireless data interface, a connection confirmation signal to the remote computing environment, the connection confirmation signal configured to initiate a determination that a wireless wide area network data connection exists between the wireless data interface and the remote computing environment; receive, via the wireless data interface, a return confirmation signal from the remote computing environment, the return confirmation signal configured to indicate that the wireless wide area network data connection exists between the wireless data interface and the remote computing environment; based on the return confirmation signal, determine that the wireless wide area network data connection exists between the wireless data interface and the remote computing environment; and based on the request to modify the glucose level control therapy and on the determination that the wireless wide area network data connection exists, transmit, via the wireless data interface, a confirmation signal to the remote computing environment, the confirmation signal configured to indicate that the request to modify the glucose level control therapy was successfully received.

Example 33: The ambulatory medicament pump of example 31 or 32, wherein the hardware processor is further configured to execute the specific computer-executable instructions to at least: transmit a third-party alert to the remote computing environment based at least in part on the modification of the glucose level control therapy delivery, the third-party alert comprising indication of at least (i) that the modification of the glucose level control therapy delivery was successful and (ii) an attribute of the glucose level control therapy delivery as modified.

Example 34: The ambulatory medicament pump of any one of examples 31 to 33, further comprising a user interface configured to receive the request to modify the glucose level control therapy.

Example 35: The ambulatory medicament pump of example 34, wherein the hardware processor is further configured to execute the specific computer-executable instructions to at least: generate for display on the user interface a user alert based at least in part on the modification of the glucose level control therapy delivery, the user alert comprising an indication of at least (i) that the modification of the glucose level control therapy delivery was successful and (ii) an attribute of the glucose level control therapy delivery as modified.

Example 36: The ambulatory medicament pump of any one of examples 32 to 35, further comprising a connection verification system in communication with the hardware processor, the connection verification system configured to determine, based on the return confirmation signal, that the wireless wide area network data connection exists between the wireless data interface and the remote computing environment.

Example 37: The ambulatory medicament pump of any one of examples 31 to 36, wherein the hardware processor is further configured to execute the specific computer-executable instructions to at least: transmit a report to the remote computing environment based at least in part on the modification of the glucose level control therapy delivery, the report configured to be stored at the remote computing environment.

Example 38: The ambulatory medicament pump of any one of examples 31 to 37, comprising a wireless wide area network modem.

Example 39: The ambulatory medicament pump of example 38, wherein the wireless wide area network modem comprises the wireless data interface, the wireless wide area network modem configured to provide the network connection comprising a wide area network.

Example 40: The ambulatory medicament pump of example 38 or 39, wherein the wireless wide area network modem comprises a long-term evolution (LTE) modem.

Example 41: A method for modifying glucose level control therapy delivered by an ambulatory medicament pump to a subject, the method comprising: by an electronic processor of a glucose level control system executing instructions stored on non-transitory memory connected to the electronic processor: generating an initial dose control signal configured to command the ambulatory medicament pump to deliver initial glucose level control therapy to the subject; receiving, via user interaction with a therapy modification control element, a request to modify the initial glucose level control therapy delivered to the subject; transmitting to a remote computing environment, via a wireless wide area network data interface in communication with the electronic processor, the request to modify the initial glucose level control therapy delivered to the subject; receiving, via the wireless wide area network data interface, an indication that the request to modify the initial glucose level control therapy is approved; and in response to the indication that the request to modify the initial glucose level control therapy is approved, generating a modified dose control signal configured to command the ambulatory medicament pump to provide modified glucose level control therapy to the subject.

Example 42: The method of example 41, further comprising: transmitting, via the wireless wide area network data interface, a connection confirmation signal to the remote computing environment, the connection confirmation signal configured to initiate a determination that a wireless wide area network data connection exists between the wireless wide area network data interface and the remote computing environment; receiving, via the wireless wide area network data interface, a return confirmation signal from the remote computing environment, the return confirmation signal configured to indicate that the wireless wide area network data connection exists between the wireless wide area network data interface and the remote computing environment; based on the return confirmation signal, determining that the wireless wide area network data connection exists between the wireless wide area network data interface and the remote computing environment; and based on the request to modify the initial glucose level control therapy and on the determination that the wireless wide area network data connection exists, transmitting, via the wireless wide area network data interface, a confirmation signal to the remote computing environment, the confirmation signal configured to indicate that the request to modify the glucose level control therapy was successfully received.

Example 43: The method of example 41 or 42, further comprising: transmitting a third-party alert to the remote computing environment based at least in part on the modification of the glucose level control therapy delivery, the third-party alert comprising indication of at least (i) that the modification of the initial glucose level control therapy delivery was successful and (ii) an attribute of the glucose level control therapy delivery as modified.

Example 44: The method of any one of examples 41 to 43, further comprising, via a user interface configured to receive the request to modify the glucose level control therapy: generating for display on the user interface a user alert based at least in part on the modification of the glucose level control therapy delivery, the user alert comprising an indication of at least (i) that the modification of the initial glucose level control therapy delivery was successful and (ii) an attribute of the glucose level control therapy delivery as modified.

Example 45: The method of any one of examples 41 to 44, further comprising: transmitting a report to the remote computing environment based at least in part on the modification of the initial glucose level control therapy delivery, the report configured to be stored at the remote computing environment.

Example 46: The method of any one of examples 41 to 45, wherein transmitting to the remote computing environment comprises transmitting via a wide area network.

Example 47: The method of any one of examples 41 to 46, wherein transmitting to the remote computing environment comprises transmitting via a long-term evolution (LTE) modem integrated with the ambulatory medicament pump.

Example 48: A remote therapy modification system configured to generate commands to remotely modify glucose level control therapy delivered to a subject by an ambulatory medicament pump, the remote therapy modification system comprising: a non-transitory memory configured to store specific computer-executable instructions; and a hardware processor in communication with the non-transitory memory and configured to execute the specific computer-executable instructions to at least: receive, via user interaction with a therapy modification control element, a request to remotely modify glucose level control therapy delivered to the subject by the ambulatory medicament pump; receive, via a network interface, a connection confirmation signal from a remote computing environment, the connection confirmation signal indicating that a wireless wide area network data connection exists between the remote computing environment and the ambulatory medicament pump; in response to receiving the request to modify the glucose level control therapy and receiving the connection confirmation signal, transmit, via the network interface, a remote therapy modification command to the remote computing environment, the remote therapy modification command configured to modify the glucose level control therapy delivered to the subject via the ambulatory medicament pump; and receive, via the network interface, a modification verification signal from the remote computing environment, the modification verification signal indicating whether the glucose level control therapy delivered by the ambulatory medicament pump was successfully modified.

Example 49: The remote therapy modification system of example 48, wherein the hardware processor is further configured to execute the specific computer-executable instructions to at least: receive, via the network interface, the remote therapy modification request from the ambulatory medicament pump, the modification request designating that the request to modify the glucose level control therapy be delivered via the ambulatory medicament pump.

Example 50: The remote therapy modification system of example 48 or 49, wherein the hardware processor is further configured to execute the specific computer-executable instructions to at least: transmit a subject alert to the remote computing environment based at least in part on the modification of the glucose level control therapy delivery, the subject alert comprising an indication of at least (i) that the modification of the glucose level control therapy delivery was successful and (ii) an attribute of the glucose level control therapy delivery as modified.

Example 51: The remote therapy modification system of any one of examples 48 to 50, further comprising the therapy modification control element configured to receive the remote glucose level control therapy modification request.

Example 52: The remote therapy modification system of any one of examples 48 to 51, wherein the hardware processor is further configured to execute the specific computer-executable instructions to at least: generate for display on the therapy modification control element a user alert based at least in part on the modification of the glucose level control therapy delivery, the user alert comprising an indication of at least (i) that the modification of the therapy delivery was successful and (ii) an attribute of the therapy delivery as modified.

Example 53: The remote therapy modification system of any one of examples 48 to 52, further comprising a connection verification system in communication with the hardware processor, the connection verification system configured to determine, based on the connection confirmation signal, that the wireless wide area network data connection exists between the network interface and the remote computing environment.

Example 54: The remote therapy modification system of any one of examples 48 to 53, wherein the hardware processor is further configured to execute the specific computer-executable instructions to at least: transmit a report to the remote computing environment based at least in part on the modification of the glucose level control therapy delivery, the report configured to be stored at the remote computing environment.

Example 55: The remote therapy modification system of any one of examples 48 to 54, comprising a wireless wide area network modem.

Example 56: The remote therapy modification system of example 55, wherein the wireless wide area network modem comprises the network interface, the wireless wide area network modem configured to provide the network connection comprising a wide area network.

Example 57: The remote therapy modification system of any one of examples 48 to 56, wherein the request to remotely modify glucose level control therapy delivered to the subject by the ambulatory medicament pump is received via user interaction with a therapy modification control element.

Example 58: A method for generating commands to remotely modify glucose level control therapy delivered to a subject by an ambulatory medicament pump, the method comprising: by an electronic processor executing instructions stored on non-transitory memory connected to the electronic processor: receiving a request to remotely modify therapy delivered to the subject by the ambulatory medicament pump; receiving, via a network interface, a connection confirmation signal from a remote computing environment, the connection confirmation signal indicating that a wireless wide area network data connection exists between the remote computing environment and the ambulatory medicament pump; in response to receiving the request to modify the glucose level control therapy and receiving the connection confirmation signal, transmitting, via the network interface, a remote therapy modification command to the remote computing environment, the remote therapy modification command configured to modify the glucose level control therapy delivered to the subject via the ambulatory medicament pump; and receiving, via the network interface, a modification verification signal from the remote computing environment, the modification verification signal indicating whether the glucose level control therapy delivered by the ambulatory medicament pump was successfully modified.

Example 59: The method of example 58, further comprising: receiving, via the network interface, the remote therapy modification request from the ambulatory medicament pump, the modification request designating that the request to modify the glucose level control therapy be delivered via the ambulatory medicament pump.

Example 60: The method of example 58 or 59, further comprising: transmitting a subject alert to the remote computing environment based at least in part on the modification of the glucose level control therapy delivery, the subject alert comprising an indication of at least (i) that the modification of the glucose level control therapy delivery was successful and (ii) an attribute of the glucose level control therapy delivery as modified.

Example 61: An ambulatory medicament pump configured to automatically generate a user prompt comprising an infusion set ordering interface based on an estimate of remaining infusion sets falling below a reordering threshold, the ambulatory medicament pump comprising: a medicament delivery interface comprising a pump controller configured to command to direct a medicament from the ambulatory medicament pump to a subcutaneous depot of a subject via an infusion set; a non-transitory memory configured to store specific computer-executable instructions; and an electronic processor in communication with the non-transitory memory and configured to execute the specific computer-executable instructions to at least: receive an indication of a number of initial infusion sets in possession of the subject; monitor a usage of infusion sets over a period by receiving at least one of a plurality of infusion set change indications during the period, wherein the plurality of infusion set change indications comprises: an electronic cartridge change request, received via user interaction with a medicament cartridge change interface, to change a medicament cartridge operatively coupled to the ambulatory medicament pump; an electronic infusion set priming request, received via user interaction with an infusion set priming interface, to prime an infusion set; and an infusion set failure alert, received via an infusion set monitoring system of the ambulatory medicament pump, indicating that an infusion set connected to the medicament delivery interface has a failure; determine the estimate of remaining infusion sets in possession of the subject at the end of the period based on the number of initial infusion sets and the usage of infusion sets during the period; determine that the estimate of remaining infusion sets falls below the reordering threshold; in response to determining that the estimate of remaining infusion sets falls below the reordering threshold, automatically generate the user prompt comprising the infusion set ordering interface; receive, via user interaction with the infusion set ordering interface, a request to order additional infusion sets; and in response to receiving the request to order additional infusion sets, transmit a purchase order for additional infusion sets.

Example 62: The ambulatory medicament pump of example 61, wherein the medicament delivery interface operatively couples a pump motor to a medicament reservoir of the medicament cartridge containing the medicament, the pump motor being configured to provide motive force to direct the medicament through the infusion set.

Example 63: The ambulatory medicament pump of example 61 or 62, wherein the medicament is disposed in a medicament reservoir of the medicament cartridge configured to couple to the medicament delivery interface.

Example 64: The ambulatory medicament pump of any one of examples 61 to 63, wherein the purchase order for additional infusion sets is transmitted to a remote electronic device.

Example 65: The ambulatory medicament pump of example 64, further comprising a wireless data interface configured to facilitate communication with the remote electronic device.

Example 66: The ambulatory medicament pump of example 64 or 65, wherein the remote electronic device is a portable electronic device.

Example 67: The ambulatory medicament pump of any one of examples 64 to 66, wherein the remote electronic device is a remote computing environment.

Example 68: The ambulatory medicament pump of any one of examples 64 to 67, wherein the remote electronic device comprises payment account data associated with the subject, and wherein the remote electronic device is configured to automatically process payment for the purchase order using the payment account data associated with the subject.

Example 69: The ambulatory medicament pump of any one of examples 64 to 68, wherein the remote electronic device is in communication with an insurance provider system associated with the subject, and wherein the remote electronic device is configured to automatically send the purchase order to the insurance provider system for processing.

Example 70: The ambulatory medicament pump of example 69, wherein the remote electronic device comprises payment account data associated with the subject, and wherein the remote electronic device is configured to automatically process payment for the purchase order using the payment account data associated with the subject and data provided by the insurance provider system.

Example 71: The ambulatory medicament pump of any one of examples 61 to 70, wherein the number of initial infusion sets is input via an infusion set quantity interface.

Example 72: The ambulatory medicament pump of any one of examples 61 to 71, wherein the electronic processor is further configured to execute the specific computer-executable instructions to at least: receive one or more delivery indications from a remote device that are indicative of initial infusion sets delivered to the subject; and determine, based on the one or more delivery indications, the number of initial infusion sets delivered to the subject.

Example 73: The ambulatory medicament pump of any one of examples 61 to 72, wherein the electronic processor is further configured to execute the specific computer-executable instructions to at least: determine the number of initial infusion sets based on one or more transmitted purchase orders for additional infusion sets.

Example 74: The ambulatory medicament pump of any one of examples 61 to 73, wherein the electronic processor is further configured to execute the specific computer-executable instructions to at least: receive, via user interaction with a reordering threshold interface, an indication of the reordering threshold.

Example 75: The ambulatory medicament pump of any one of examples 61 to 74, wherein the electronic processor is further configured to execute the specific computer-executable instructions to at least: receive an indication of the reordering threshold from a remote electronic device.

Example 76: The ambulatory medicament pump of any one of examples 61 to 75, wherein the electronic processor is further configured to execute the specific computer-executable instructions to at least: determine the reordering threshold based on the usage of infusion sets during the period and the estimate of remaining infusion sets in possession of the subject at the end of the period, wherein the reordering threshold is higher for a higher usage of infusion sets during the period compared to the reordering threshold for a lower usage of infusion sets during the period.

Example 77: The ambulatory medicament pump of any one of examples 61 to 76, wherein the electronic processor is further configured to execute the specific computer-executable instructions to at least: receive, via a wireless data interface, an indication from a remote electronic device of the reordering threshold, wherein the reordering threshold is determined by the remote electronic device algorithmically.

Example 78: The ambulatory medicament pump of any one of examples 61 to 77, wherein the electronic processor is further configured to execute the specific computer-executable instructions to at least determine the reordering threshold algorithmically.

Example 79: The ambulatory medicament pump of any one of examples 61 to 78, wherein the electronic processor is further configured to execute the specific computer-executable instructions to at least: in response to determining that the estimate of remaining infusion sets falls below the reordering threshold, transmit the purchase order for additional infusion sets.

Example 80: The ambulatory medicament pump of any one of examples 61 to 79, wherein the electronic processor is further configured to execute the specific computer-executable instructions to at least: determine that the estimate of remaining infusion sets falls below an automatic reordering threshold; and in response to determining that the estimate of remaining infusion sets falls below the automatic reordering threshold, transmit the purchase order for the additional infusion sets.

Example 81: The ambulatory medicament pump of example 80, wherein the automatic reordering threshold is different than the reordering threshold.

Example 82: The ambulatory medicament pump of any one of examples 61 to 81, wherein the request to order additional infusion sets comprises a duration period, and wherein the electronic processor is further configured to execute the specific computer-executable instructions to at least: determine a quantity of additional infusion sets that corresponds to the duration period based on the usage of infusion sets during the period.

Example 83: The ambulatory medicament pump of any one of examples 61 to 82, wherein the electronic processor is further configured to execute the specific computer-executable instructions to at least: determine a quantity of additional infusion sets that corresponds to a duration period based on the usage of infusion sets during the period; and indicate, via the infusion set ordering interface, the duration period and the quantity of additional infusion sets that corresponds thereto.

Example 84: The ambulatory medicament pump of any one of examples 61 to 83, wherein the infusion set is an insulin infusion set.

Example 85: The ambulatory medicament pump of any one of examples 61 to 84, wherein the infusion set is a glucagon infusion set.

Example 86: The ambulatory medicament pump of any one of examples 61 to 85, wherein the infusion set is a two-channel infusion set configured to deliver insulin and glucagon.

Example 87: The ambulatory medicament pump of any one of examples 61 to 86, wherein the infusion sets are insulin or glucagon infusion sets.

Example 88: The ambulatory medicament pump of example 87, wherein the electronic processor is further configured to execute the specific computer-executable instructions to at least: automatically generate the user prompt comprising the infusion set ordering interface for the insulin and/or glucagon infusion sets; receive, via user interaction with the infusion set ordering interface, a request to order additional insulin and/or glucagon infusion sets; and in response to receiving the request to order additional insulin and/or glucagon infusion sets, transmit the purchase order for additional insulin and/or glucagon infusion sets.

Example 89: The ambulatory medicament pump of any one of examples 61 to 88, wherein the infusion set failure alert comprises an occlusion alert, and wherein the failure is an occlusion.

Example 90: A method of transmitting a purchase order for additional infusion sets for an ambulatory medicament pump from a glucose level control system, the method comprising: by an electronic processor of the glucose level control system executing specific computer-executable instructions stored in a non-transitory memory in communication with the electronic processor: receiving an indication of a number of initial infusion sets in possession of a subject; monitoring a usage of infusion sets over a period by receiving at least one of a plurality of infusion set change indications during the period, wherein the plurality of infusion set change indications comprises: receiving, via user interaction with a medicament cartridge change interface, an electronic cartridge change request to change a medicament cartridge operatively coupled to the ambulatory medicament pump; receiving, via user interaction with an infusion set priming interface, an electronic infusion set priming request to prime an infusion set; and receiving, via an infusion set monitoring system of the ambulatory medicament pump, an infusion set failure alert indicating that an infusion set connected to a medicament delivery interface has a failure; determining an estimate of remaining infusion sets in possession of the subject at the end of the period based on the number of initial infusion sets and the usage of infusion sets during the period; determining that the estimate of remaining infusion sets falls below a reordering threshold; in response to determining that the estimate of remaining infusion sets falls below the reordering threshold, automatically generating a user prompt comprising an infusion set ordering interface; receiving, via user interaction with the infusion set ordering interface, a request to order additional infusion sets; and in response to receiving the request to order additional infusion sets, transmitting a purchase order for additional infusion sets.

Example 91: The method of example 90, wherein the purchase order for additional infusion sets is transmitted to a remote electronic device.

Example 92: The method of example 91, wherein the purchase order for additional infusion sets is transmitted to the remote electronic device via a wireless data interface.

Example 93: The method of example 91 or 92, wherein the remote electronic device is a remote computing environment.

Example 94: The method of any one of examples 91 to 93, wherein the remote electronic device is configured to automatically process payment for the purchase order using payment account data associated with the subject.

Example 95: The method of any one of examples 91 to 94, wherein the remote electronic device is in communication with an insurance provider system associated with the subject and is configured to automatically send the purchase order to the insurance provider system for processing.

Example 96: The method of example 95, wherein the remote electronic device comprises payment account data associated with the subject, and wherein the remote electronic device is configured to automatically process payment for the purchase order using payment account data associated with the subject and coverage data associated with the subject provided by the insurance provider system.

Example 97: The method of any one of examples 90 to 96, further comprising receiving, via an infusion set quantity interface, the number of initial infusion sets.

Example 98: The method of any one of examples 90 to 97, further comprising receiving one or more delivery indications from a remote electronic device that are indicative of initial infusion sets delivered to the subject; and determining, based on the one or more delivery indications, the number of initial infusion sets delivered to the subject.

Example 99: The method of any one of examples 90 to 98, further comprising, receiving, via user interaction with a reordering threshold interface, an indication of the reordering threshold.

Example 100: The method of any one of examples 90 to 99, further comprising, receiving, via a remote electronic device, an indication of the reordering threshold.

Example 101: The method of any one of examples 90 to 100, further comprising determining the reordering threshold based on the usage of infusion sets during the period and the estimate of remaining infusion sets in possession of the subject at the end of the period, wherein the reordering threshold is higher for a higher usage of infusion sets during the period compared to the reordering threshold for a lower usage of infusion sets during the period.

Example 102: The method of any one of examples 90 to 101, wherein the request to order additional infusion sets comprises a duration period.

Example 103: The method of example 102, further comprising determining a quantity of additional infusion sets that corresponds to the duration period based on the usage of infusion sets during the period.

Example 104: The method of any one of examples 90 to 103, further comprising determining a quantity of additional infusion sets that corresponds to a duration period based on the usage of infusion sets during the period; and indicating the quantity of additional infusion sets that corresponds to the duration period via the infusion set ordering interface.

Example 105: The method of any one of examples 90 to 104, wherein the infusion set is an insulin infusion set.

Example 106: The method of any one of examples 90 to 104, wherein the infusion set is a glucagon infusion set.

Example 107: The method of any one of examples 90 to 104, wherein the infusion set is a two-channel infusion set configured to deliver insulin and glucagon.

Example 108: The method of any one of examples 90 to 104, wherein the infusion sets are insulin and/or glucagon infusion sets.

Example 109: The method of any one of examples 90 to 104, wherein the infusion set ordering interface is configured to facilitate ordering insulin and/or glucagon infusion sets.

Example 110: The method of any one of examples 90 to 109, wherein the infusion set failure alert comprises an occlusion alert, and wherein the failure is an occlusion.

Example 111: The method of any one of examples 90 to 110, further comprising receiving, via a wireless data interface, an indication from a remote electronic device of the reordering threshold, wherein the reordering threshold is determined by the remote electronic device algorithmically.

Example 112: The method of any one of examples 90 to 110, further comprising determining the reordering threshold algorithmically.

Example 113: The method of any one of examples 90 to 112, further comprising transmitting the purchase order for additional infusion sets in response to determining that the estimate of remaining infusion sets falls below the reordering threshold.

Example 114: The method of any one of examples 90 to 113, further comprising determining that the estimate of remaining infusion sets falls below an automatic reordering threshold; and in response to determining that the estimate of remaining infusion sets falls below the automatic reordering threshold, transmitting the purchase order for additional infusion sets.

Example 115: The method of example 114, wherein the automatic reordering threshold is different than the reordering threshold.

Example 116: The method of any one of examples 90 to 115, wherein the request to order additional infusion sets comprises a duration period, and wherein the method further comprises determining a quantity of additional infusion sets that corresponds to the duration period based on the usage of infusion sets during the period.

Example 117: The method of any one of examples 90 to 115, further comprising determining a quantity of additional infusion sets that corresponds to a duration period based on the usage of infusion sets during the period; and indicating, via the infusion set ordering interface, the duration period and the quantity of additional infusion sets that correspond thereto.

Example 118: The method of any one of examples 90-105 or 110-117, wherein the infusion set is an insulin infusion set.

Example 119: The method of any one of examples 90-104, 106 or 110-118, wherein the infusion set is a glucagon infusion set.

Example 120: The method of any one of examples 90-104, 107 or 110-119, wherein the infusion set is a two-channel infusion set configured to deliver insulin and glucagon.

Example 121: The method of any one of examples 90-104 or 107-120, wherein the infusion sets are insulin or glucagon infusion sets.

Example 122: An ambulatory medicament pump configured to automatically generate a user prompt comprising an analyte sensor ordering interface based on an estimate of remaining analyte sensors falling below a reordering threshold, the ambulatory medicament pump comprising: an analyte sensor interface configured to facilitate communication with an analyte sensor; a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial analyte sensors in possession of a subject; monitor a usage of analyte sensors over a period by receiving at least one of a plurality of analyte sensor change indications during the period, wherein the plurality of analyte sensor change indications comprises: an electronic analyte sensor change request, received via user interaction with a sensor change interface, to change an analyte sensor operatively connected to the ambulatory medicament pump; an analyte sensor expiration alert, received from the remote electronic device via the wireless data interface, indicating that an analyte sensor has expired or has passed an expiration threshold; and an analyte sensor failure alert, received via an analyte sensor monitoring system of the ambulatory medicament pump, indicating that an analyte sensor operatively connected to the ambulatory medicament pump has a failure; determine the estimate of remaining analyte sensors in possession of a subject at the end of the period based on the number of initial analyte sensors and the usage of analyte sensors during the period; determine that the estimate of remaining analyte sensors falls below the reordering threshold; in response to determining that the estimate of remaining analyte sensors falls below the reordering threshold, automatically generate the user prompt comprising the analyte sensor ordering interface; receive, via user interaction with the analyte sensor ordering interface, a request to order additional analyte sensors; and in response to receiving the request to order additional analyte sensors, transmit a purchase order for additional analyte sensors.

Example 123: The ambulatory medicament pump of example 122, wherein the purchase order for additional analyte sensors is transmitted to the remote electronic device.

Example 124: The ambulatory medicament pump of example 122 or 123, wherein the remote electronic device is a portable electronic device.

Example 125: The ambulatory medicament pump of example 122 or 123, wherein the remote electronic device is a remote computing environment.

Example 126: The ambulatory medicament pump of any one of examples 122 to 125, wherein the remote electronic device comprises payment account data associated with the subject, and wherein the remote electronic device is configured to automatically process payment for the purchase order using the payment account data associated with the subject.

Example 127: The ambulatory medicament pump of any one of examples 122 to 126, wherein the remote electronic device is in communication with an insurance provider system associated with the subject, and wherein the remote electronic device is configured to automatically send the purchase order to the insurance provider system for processing.

Example 128: The ambulatory medicament pump of example 127, wherein the remote electronic device comprises payment account data associated with the subject, and wherein the remote electronic device is configured to automatically process payment for the purchase order using the payment account data associated with the subject and coverage data provided by the insurance provider system.

Example 129: The ambulatory medicament pump of any one of examples 122 to 128, wherein the number of initial analyte sensors is input via an analyte sensor quantity interface.

Example 130: The ambulatory medicament pump of any one of examples 122 to 129, wherein the electronic processor is further configured to execute the specific computer-executable instructions to at least: receive one or more delivery indications from a remote device that are indicative of initial analyte sensors delivered to the subject; and determine, based on the one or more delivery indications, the number of initial analyte sensors delivered to the subject.

Example 131: The ambulatory medicament pump of any one of examples 122 to 130, wherein the electronic processor is further configured to execute the specific computer-executable instructions to at least: determine the number of initial analyte sensors based on one or more transmitted purchase orders for additional analyte sensors.

Example 132: The ambulatory medicament pump of any one of examples 122 to 131, wherein the electronic processor is further configured to execute the specific computer-executable instructions to at least: receive, via user interaction with an analyte reordering threshold interface, an indication of the reordering threshold.

Example 133: The ambulatory medicament pump of any one of examples 122 to 132, wherein the electronic processor is further configured to execute the specific computer-executable instructions to at least: receive an indication of the reordering threshold from a remote electronic device.

Example 134: The ambulatory medicament pump of any one of examples 122 to 133, wherein the electronic processor is further configured to execute the specific computer-executable instructions to at least: determine the reordering threshold based on the usage of analyte sensors during the period and the estimate of remaining analyte sensors in possession of the subject at the end of the period, wherein the reordering threshold is higher for a higher usage of analyte sensors during the period compared to the reordering threshold for a lower usage of analyte sensors during the period.

Example 135: The ambulatory medicament pump of any one of examples 122 to 134, wherein the electronic processor is further configured to execute the specific computer-executable instructions to at least: receive, via a wireless data interface, an indication from a remote electronic device of the reordering threshold, wherein the reordering threshold is determined by the remote electronic device algorithmically.

Example 136: The ambulatory medicament pump of any one of examples 122 to 134, wherein the electronic processor is further configured to execute the specific computer-executable instructions to at least determine the reordering threshold algorithmically.

Example 137: The ambulatory medicament pump of any one of examples 122 to 134, wherein the electronic processor is further configured to execute the specific computer-executable instructions to at least: in response to determining that the estimate of remaining analyte sensors falls below the reordering threshold, transmit the purchase order for additional analyte sensors.

Example 138: The ambulatory medicament pump of any one of examples 122 to 134, wherein the electronic processor is further configured to execute the specific computer-executable instructions to at least: determine that the estimate of remaining analyte sensors falls below an automatic reordering threshold; and in response to determining that the estimate of remaining analyte sensors falls below the automatic reordering threshold, transmit the purchase order for the additional analyte sensors.

Example 139: The ambulatory medicament pump of example 138, wherein the automatic reordering threshold is different than the reordering threshold.

Example 140: The ambulatory medicament pump of any one of examples 122 to 139, wherein the request to order additional analyte sensors comprises a duration period, and wherein the electronic processor is further configured to execute the specific computer-executable instructions to at least: determine a quantity of additional analyte sensors that corresponds to the duration period based on the usage of analyte sensors during the period.

Example 141: The ambulatory medicament pump of any one of examples 122 to 140, wherein the electronic processor is further configured to execute the specific computer-executable instructions to at least: determine a quantity of additional analyte sensors that corresponds to a duration period based on the usage of analyte sensors during the period; and indicate, via the analyte sensor ordering interface, the quantity of additional analyte sets that corresponds to the duration period.

Example 142: The ambulatory medicament pump of any one of examples 122 to 141, wherein the analyte sensor is a glucose sensor.

Example 143: The ambulatory medicament pump of any one of examples 122 to 142, wherein the analyte sensor is an insulin sensor.

Example 144: The ambulatory medicament pump of any one of examples 122 to 143, wherein the electronic processor is further configured to execute the specific computer-executable instructions to at least: determine that a new analyte sensor is in communication with the ambulatory medicament pump; in response to determining that the new analyte sensor is in communication with the ambulatory medicament pump, monitor a duration of use of the new analyte sensor; determine that the duration of use of the new analyte sensor has reached a threshold; and in response to determining that the duration of use of the new analyte sensor has reached a threshold, generate an alert prompting a user to replace the analyte sensor.

Example 145: The ambulatory medicament pump of any one of examples 122 to 144, wherein the remote electronic device sends an indication of the analyte sensor expiration alert based on a correlation of a ship date of the analyte sensor with an expiration date of the analyte sensor.

Example 146: The ambulatory medicament pump of any one of examples 122 to 145, wherein the remote electronic device sends an indication of the analyte sensor expiration alert based on electronic expiration information associated with an analyte sensor.

Example 147: The ambulatory medicament pump of any one of examples 122 to 146, wherein the analyte sensor expiration alert is electronic expiration information associated with an analyte sensor.

Example 148: A method of transmitting a purchase order for additional analyte sensors from a glucose level control system, the method comprising: by an electronic processor of the glucose level control system executing specific computer-executable instructions stored in a non-transitory memory in communication with the electronic processor: receiving an indication of a number of initial analyte sensors in possession of a subject; monitoring a usage of analyte sensors over a period by receiving at least one of a plurality of analyte sensor change indications during the period, wherein the plurality of analyte sensor change indications comprises: receiving, via user interaction with a sensor change interface, an electronic analyte sensor change request, to change an analyte sensor operatively connected to an ambulatory medicament pump of the glucose level control system; receiving, via a wireless data interface in communication with a remote electronic device, an analyte sensor expiration alert indicating that an analyte sensor has expired or has passed or is at an expiration threshold; and receiving, via an analyte sensor monitoring system of the ambulatory medicament pump, an analyte sensor failure alert indicating that an analyte sensor operatively connected to the ambulatory medicament pump has a failure; determining an estimate of remaining analyte sensors in possession of the subject at the end of the period based on the number of initial analyte sensors and the usage of analyte sensors during the period; determining that the estimate of remaining analyte sensors falls below a reordering threshold; in response to determining that the estimate of remaining analyte sensors falls below the reordering threshold, automatically generating a user prompt comprising an analyte sensor ordering interface; receiving, via user interaction with the analyte sensor ordering interface, a request to order additional analyte sensors; and in response to receiving the request to order additional analyte sensors, transmitting a purchase order for additional analyte sensors.

Example 149: The method of example 148, wherein the purchase order for additional analyte sensor is transmitted to the remote electronic device.

Example 150: The method of example 149, wherein the purchase order for additional analyte sensors is transmitted to the remote electronic device via the wireless data interface.

Example 151: The method of any one of examples 148 to 150, wherein the remote electronic device is a remote computing environment.

Example 152: The method of any one of examples 148 to 151, wherein the remote electronic device is configured to automatically process payment for the purchase order using payment account data associated with the subject.

Example 153: The method of any one of examples 148 to 152, wherein the remote electronic device is in communication with an insurance provider system associated with the subject and is configured to automatically send the purchase order to the insurance provider system for processing.

Example 154: The method of example 153, wherein the remote electronic device comprises payment account data associated with the subject, and wherein the remote electronic device is configured to automatically process payment for the purchase order using payment account data associated with the subject and coverage data provided by the insurance provider system.

Example 155: The method of any one of examples 148 to 154, further comprising receiving, via an analyte sensor quantity interface, the number of initial analyte sensors.

Example 156: The method of any one of examples 148 to 155, further comprising receiving one or more delivery indications from a remote electronic device that are indicative of initial analyte sensors delivered to the subject; and determining, based on the one or more delivery indications, the number of initial analyte sensors delivered to the subject.

Example 157: The method of any one of examples 148 to 156, further comprising, receiving, via user interaction with a reordering threshold interface, an indication of the reordering threshold.

Example 158: The method of any one of examples 148 to 157, further comprising, receiving, via a remote electronic device, an indication of the reordering threshold.

Example 159: The method of any one of examples 148 to 158, further comprising determining the reordering threshold based on the usage of analyte sensors during the period and the estimate of remaining analyte sensors in possession of the subject at the end of the period, wherein the reordering threshold is higher for a higher usage of analyte sensors during the period compared to the reordering threshold for a lower usage of analyte sensors during the period.

Example 160: The method of any one of examples 148 to 159, further comprising receiving, via a wireless data interface, an indication from a remote electronic device of the reordering threshold, wherein the reordering threshold is determined by the remote electronic device algorithmically.

Example 161: The method of any one of examples 148 to 160, further comprising determining the reordering threshold algorithmically.

Example 162: The method of any one of examples 148 to 161, further comprising transmitting the purchase order for additional analyte sensors in response to determining that the estimate of remaining analyte sensors falls below the reordering threshold.

Example 163: The method of any one of examples 148 to 162, further comprising determining that the estimate of remaining analyte sensors falls below an automatic reordering threshold; and transmitting the purchase order for additional analyte sensors in response to determining that the estimate of remaining analyte sensors falls below the automatic reordering threshold.

Example 164: The method of example 163, wherein the automatic reordering threshold is different than the reordering threshold.

Example 165: The method of any one of examples 148 to 164, wherein the request to order additional analyte sensors comprises a duration period.

Example 166: The method of example 165, further comprising determining a quantity of additional analyte sensors that corresponds to the duration period based on the usage of analyte sensors during the period.

Example 167: The method of any one of examples 148 to 166, further comprising determining a quantity of additional analyte sensors that corresponds to a duration period based on the usage of analyte sensors during the period; and indicating the quantity of additional analyte sensors that corresponds to the duration period via the analyte sensor ordering interface.

Example 168: The method of any one of examples 148 to 167, wherein the analyte sensor is an insulin sensor.

Example 169: The method of any one of examples 148 to 167, wherein the analyte sensor is a glucose sensor.

Example 170: The method of any one of examples 148 to 167, wherein the analyte sensor is an insulin and glucose sensor.

Example 171: The method of any one of examples 148 to 170, wherein the analyte sensor ordering interface is configured to facilitate ordering insulin sensors and/or glucose sensors.

Example 172: An ambulatory medicament pump configured to monitor a usage of infusion sets over a period by receiving at least one of a plurality of infusion set change indications during the period, the ambulatory medicament pump comprising: a medicament delivery interface comprising a pump controller configured to command to direct a medicament from the ambulatory medicament pump to a subcutaneous depot of a subject via an infusion set; a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial infusion sets in possession of the subject; monitor a usage of infusion sets over a period by receiving at least one of a plurality of infusion set change indications during the period, wherein the plurality of infusion set change indications comprises: an electronic cartridge change request, received via user interaction with a medicament cartridge change interface, to change a medicament cartridge operatively coupled to the ambulatory medicament pump; an electronic infusion set priming request, received via user interaction with an infusion set priming interface, to prime an infusion set; and an infusion set failure alert, received via an infusion set monitoring system of the ambulatory medicament pump, indicating that an infusion set connected to the medicament delivery interface has a failure; and transmit infusion set data regarding the usage of infusion sets, via the wireless data interface, to the remote electronic device.

Example 173: The ambulatory medicament pump of example 172, wherein the remote electronic device is a remote computing environment.

Example 174: The ambulatory medicament pump of example 172 or 173, wherein the electronic processor is further configured to execute the specific computer-executable instructions to at least: receive, via the wireless data interface, a reordering message from the remote electronic device that indicates that an estimate of remaining infusion sets in possession of the subject at the end of the period, based on the number of initial infusion sets and the usage of infusion sets during the period, has fallen below a reordering threshold.

Example 175: The ambulatory medicament pump of example 174, wherein the electronic processor is further configured to execute the specific computer-executable instructions to at least: in response to receiving the reordering message from the remote electronic device, automatically generate a user prompt comprising an infusion set ordering interface; receive, via user interaction with the infusion set ordering interface, a request to order additional infusion sets; and in response to receiving the request to order additional infusion sets, transmit a purchase order for additional infusion sets.

Example 176: The ambulatory medicament pump of example 172 or 173, wherein the electronic processor is further configured to execute the specific computer-executable instructions to at least: receive, via the wireless data interface, a reordering message from the remote electronic device that indicates that an estimate of remaining infusion sets in possession of the subject at the end of the period, based on the number of initial infusion sets and the usage of infusion sets during the period, has fallen below a reordering threshold and recommending that a quantity of additional infusion sets be ordered.

Example 177: The ambulatory medicament pump of example 176, wherein the electronic processor is further configured to execute the specific computer-executable instructions to at least: in response to receiving the reordering message from the remote electronic device, automatically generate a user prompt comprising an infusion set ordering interface that provides at least the recommended quantity of additional infusion sets to be ordered; receive, via user interaction with the infusion set ordering interface, a request to order the recommended quantity of additional infusion sets; and in response to receiving the request to order the recommended quantity of additional infusion sets, transmit a purchase order for the recommended quantity of additional infusion sets.

Example 178: The ambulatory medicament pump of example 176 or 177, wherein the recommended quantity of additional infusion sets is based at least in part on the usage of the infusion sets over the period of time.

Example 179: The ambulatory medicament pump of example 176 or 177, wherein the recommended quantity of additional infusion sets is preset.

Example 180: The ambulatory medicament pump of example 176 or 177, wherein the recommended quantity of additional infusion sets is set by an individual involved in administering therapy to the subject.

Example 181: The ambulatory medicament pump of any one of examples 172 to 180, wherein the electronic processor is further configured to execute the specific computer-executable instructions to at least: receive, via the wireless data interface, a reordering message from the remote electronic device that indicates that an estimate of remaining infusion sets in possession of the subject at the end of the period, based on the number of initial infusion sets and the usage of infusion sets during the period, has fallen below a reordering threshold and additional infusion sets have been ordered.

Example 182: The ambulatory medicament pump of example 181, wherein the remote electronic device comprises payment account data associated with the subject, and wherein the remote electronic device is configured to automatically process payment for the ordered additional infusion sets using the payment account data associated with the subject.

Example 183: The ambulatory medicament pump of any one of examples 177 to 180, wherein the remote electronic device is in communication with an insurance provider system associated with the subject, and wherein the remote electronic device is configured to automatically send the purchase order to the insurance provider system for processing.

Example 184: The ambulatory medicament pump of example 183, wherein the remote electronic device comprises payment account data associated with the subject, and wherein the remote electronic device is configured to automatically process payment for the recommended quantity of additional infusion sets using the payment account data associated with the subject and data provided by the insurance provider system.

Example 185: The ambulatory medicament pump of any one of examples 172 to 185, wherein the number of initial infusion sets is input via an infusion set quantity interface.

Example 186: The ambulatory medicament pump of any one of examples 172 to 184, wherein the number of initial infusion sets is received via the wireless data interface from the remote electronic device.

Example 187: The ambulatory medicament pump of example 186, wherein the number of initial infusion sets is provided by the remote electronic device based on received purchase orders and/or delivery data.

Example 188: The ambulatory medicament pump of any one of examples 172 to 187, wherein the infusion set comprises an insulin infusion set.

Example 189: The ambulatory medicament pump of any one of examples 172 to 188, wherein the infusion set comprises a glucagon infusion set.

Example 190: The ambulatory medicament pump of any one of examples 172 to 189, wherein the infusion set comprises a two-channel infusion set configured to deliver insulin and glucagon.

Example 191: The ambulatory medicament pump of any one of examples 172 to 190, wherein the infusion set failure alert comprises an occlusion alert, and wherein the failure is an occlusion.

Example 192: A method of monitoring a usage of infusion sets by an ambulatory medicament pump of a glucose level control system, the method comprising: by an electronic processor of the glucose level control system executing specific computer-executable instructions stored in a non-transitory memory in communication with the electronic processor: receiving an indication of a number of initial infusion sets in possession of a subject; monitoring a usage of infusion sets over a period by receiving at least one of a plurality of infusion set change indications during the period, wherein the plurality of infusion set change indications comprises: receiving, via user interaction with a medicament cartridge change interface, an electronic cartridge change request to change a medicament cartridge operatively coupled to the ambulatory medicament pump; receiving, via user interaction with an infusion set priming interface, an electronic infusion set priming request to prime an infusion set; and receiving, via an infusion set monitoring system of the ambulatory medicament pump, an infusion set failure alert indicating that an infusion set has a failure; and transmitting infusion set data regarding the usage of infusion sets, via a wireless data interface, to a remote electronic device.

Example 193: The method of example 192, wherein the remote electronic device is a remote computing environment.

Example 194: The method of example 192 or 193, further comprising receiving, via the wireless data interface, a reordering message from the remote electronic device that indicates that an estimate of remaining infusion sets in possession of the subject at the end of the period, based on the number of initial infusion sets and the usage of infusion sets during the period, has fallen below a reordering threshold.

Example 195: The method of example 194, further comprising: automatically generating a user prompt comprising an infusion set ordering interface in response to receiving the reordering message from the remote electronic device; receiving, via user interaction with the infusion set ordering interface, a request to order additional infusion sets; and transmitting a purchase order for additional infusion sets in response to receiving the request to order additional infusion sets.

Example 196: The method of example 192 or 193, further comprising receiving, via the wireless data interface, a reordering message from the remote electronic device that indicates that an estimate of remaining infusion sets in possession of the subject at the end of the period, based on the number of initial infusion sets and the usage of infusion sets during the period, has fallen below a reordering threshold and recommending that a quantity of additional infusion sets be ordered.

Example 197: The method of example 196, further comprising: automatically generating a user prompt comprising an infusion set ordering interface that provides at least the recommended quantity of additional infusion sets to be ordered in response to receiving the reordering message from the remote electronic device; receiving, via user interaction with the infusion set ordering interface, a request to order the recommended quantity of additional infusion sets; and transmitting a purchase order for the recommended quantity of additional infusion sets in response to receiving the request to order the recommended quantity of additional infusion sets.

Example 198: The method of example 196 or 197, wherein the recommended quantity of additional infusion sets is based at least in part on the usage of the infusion sets over the period of time.

Example 199: The method of example 196 or 197, wherein the recommended quantity of additional infusion sets is preset.

Example 200: The method of example 196 or 197, wherein the recommended quantity of additional infusion sets is set by an individual involved in administering therapy to the subject.

Example 201: The method of example 192 or 193, further comprising receiving, via the wireless data interface, a reordering message from the remote electronic device that indicates that an estimate of remaining infusion sets in possession of the subject at the end of the period, based on the number of initial infusion sets and the usage of infusion sets during the period, has fallen below a reordering threshold and additional infusion sets have been ordered.

Example 202: The method of any one of examples 192 to 201, wherein the remote electronic device comprises payment account data associated with the subject that is configured to be used to automatically process payment for a purchase order.

Example 203: The method of any one of examples 197 to 200, wherein the remote electronic device is in communication with an insurance provider system associated with the subject, and wherein the remote electronic device is configured to automatically send the purchase order to the insurance provider system for processing.

Example 204: The method of example 203, wherein the remote electronic device comprises payment account data associated with the subject, and wherein the remote electronic device is configured to automatically process payment for the purchase order using the payment account data associated with the subject and data provided by the insurance provider system.

Example 205: An ambulatory medicament pump configured to monitor a usage of analyte sensors over a period by receiving at least one of a plurality of infusion set change indications during the period, the ambulatory medicament pump comprising: an analyte sensor interface configured to facilitate communication with an analyte sensor; a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial analyte sensors in possession of a subject; monitor a usage of analyte sensors over a period by receiving at least one of a plurality of analyte sensor change indications during the period, wherein the plurality of analyte sensor change indications comprises: an electronic analyte sensor change request, received via user interaction with a sensor change interface, to change an analyte sensor operatively connected to the ambulatory medicament pump; an analyte sensor expiration alert, received from the remote electronic device via the wireless data interface, indicating that an analyte sensor has expired or has passed or is at an expiration threshold; and an analyte sensor failure alert, received via an analyte sensor monitoring system of the ambulatory medicament pump, indicating that an analyte sensor operatively connected to the ambulatory medicament pump has a failure; and transmit analyte sensor data regarding the usage of the analyte sensors, via the wireless data interface, to the remote electronic device.

Example 206: The ambulatory medicament pump of example 205, wherein the remote electronic device is a remote computing environment.

Example 207: The ambulatory medicament pump of example 205 or 206, wherein the electronic processor is further configured to execute the specific computer-executable instructions to at least: receive, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold.

Example 208: The ambulatory medicament pump of example 207, wherein the electronic processor is further configured to execute the specific computer-executable instructions to at least: in response to receiving the reordering message from the remote electronic device, automatically generate a user prompt comprising an analyte sensor ordering interface; receive, via user interaction with the analyte sensor ordering interface, a request to order additional sensors; and in response to receiving the request to order additional sensors, transmit a purchase order for additional analyte sensors.

Example 209: The ambulatory medicament pump of example 205 or 206, wherein the electronic processor is further configured to execute the specific computer-executable instructions to at least: receive, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and recommending that a quantity of additional analyte sensors be ordered.

Example 210: The ambulatory medicament pump of example 209, wherein the electronic processor is further configured to execute the specific computer-executable instructions to at least: in response to receiving the reordering message from the remote electronic device, automatically generate a user prompt comprising an analyte sensor ordering interface that provides at least the recommended quantity of additional analyte sensors to be ordered; receive, via user interaction with the analyte sensor ordering interface, a request to order the recommended quantity of additional analyte sensors; and in response to receiving the request to order the recommended quantity of additional analyte sensors, transmit a purchase order for the recommended quantity of additional analyte sensors.

Example 211: The ambulatory medicament pump of example 209 or 210, wherein the recommended quantity of additional analyte sensors is based at least in part on the usage of the analyte sensors over the period of time.

Example 212: The ambulatory medicament pump of example 209 or 210, wherein the recommended quantity of additional analyte sensors is preset.

Example 213: The ambulatory medicament pump of example 209 or 210, wherein the recommended quantity of additional analyte sensors is set by an individual involved in administering therapy to the subject.

Example 214: The ambulatory medicament pump of example 205 or 206, wherein the electronic processor is further configured to execute the specific computer-executable instructions to at least: receive, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and additional analyte sensors have been ordered.

Example 215: The ambulatory medicament pump of example 214, wherein the remote electronic device comprises payment account data associated with the subject, and wherein the remote electronic device is configured to automatically process payment for the ordered additional analyte sensors using the payment account data associated with the subject.

Example 216: The ambulatory medicament pump of any one of examples 209 to 213, wherein the remote electronic device is in communication with an insurance provider system associated with the subject, and wherein the remote electronic device is configured to automatically send the order for recommended quantity of additional analyte sensors to the insurance provider system for processing.

Example 217: The ambulatory medicament pump of example 216, wherein the remote electronic device comprises payment account data associated with the subject, and wherein the remote electronic device is configured to automatically process payment for the recommended quantity of additional analyte sensors using the payment account data associated with the subject and data provided by the insurance provider system.

Example 218: The ambulatory medicament pump of any one of examples 205 to 217, wherein the analyte sensor is an insulin sensor.

Example 219: The ambulatory medicament pump of any one of examples 205 to 217, wherein the analyte sensor is a glucose sensor.

Example 220: The ambulatory medicament pump of any one of examples 205 to 219, wherein the remote electronic device sends an indication of the analyte sensor expiration alert based on a correlation of a ship date of the analyte sensor with an expiration date of the analyte sensor.

Example 221: The ambulatory medicament pump of any one of examples 205 to 219, wherein the remote electronic device sends an indication of the analyte sensor expiration alert based on electronic expiration information associated with an analyte sensor.

Example 222: The ambulatory medicament pump of any one of examples 205 to 219, wherein the analyte sensor expiration alert is electronic expiration information associated with an analyte sensor.

Example 223: A method of monitoring a usage of analyte sensors for an ambulatory medicament pump of a glucose level control system, the method comprising: by an electronic processor of the glucose level control system executing specific computer-executable instructions stored in a non-transitory memory in communication with the electronic processor: receiving an indication of a number of initial analyte sensors in possession of a subject; monitoring a usage of analyte sensors over a period by receiving at least one of a plurality of analyte sensor change indications during the period, wherein the plurality of analyte sensor change indications comprises: receiving, via user interaction with a sensor change interface, an electronic analyte sensor change request, to change an analyte sensor operatively connected to the ambulatory medicament pump; receiving, from a remote electronic device via a wireless data interface, an analyte sensor expiration alert, indicating that an analyte sensor has expired or has passed or is at an expiration threshold; and receiving, via an analyte sensor monitoring system of the ambulatory medicament pump, an analyte sensor failure alert indicating that an analyte sensor operatively connected to the ambulatory medicament pump has a failure; and transmitting analyte sensor data regarding the usage of analyte sensors, via the wireless data interface, to the remote electronic device.

Example 224: The method of example 223, wherein the remote electronic device is a remote computing environment.

Example 225: The method of example 223 or 224, further comprising receiving, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold.

Example 226: The method of example 225, further comprising: automatically generating a user prompt comprising an analyte sensor ordering interface in response to receiving the reordering message from the remote electronic device; receiving, via user interaction with the analyte sensor ordering interface, a request to order additional analyte sensors; and transmitting a purchase order for additional analyte sensors in response to receiving the request to order additional analyte sensors.

Example 227: The method of example 223 or 224, further comprising receiving, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and recommending that a quantity of additional analyte sensors be ordered.

Example 228: The method of example 227, further comprising: automatically generating a user prompt comprising an analyte sensor ordering interface that provides at least the recommended quantity of additional analyte sensors to be ordered in response to receiving the reordering message from the remote electronic device; receiving, via user interaction with the analyte sensor ordering interface, a request to order the recommended quantity of additional analyte sensors; and transmitting a purchase order for the recommended quantity of additional analyte sensors in response to receiving the request to order the recommended quantity of additional analyte sensors.

Example 229: The method of example 227 or 228, wherein the recommended quantity of additional analyte sensors is based at least in part on the usage of the analyte sensors over the period of time.

Example 230: The method of example 227 or 228, wherein the recommended quantity of additional analyte sensors is preset.

Example 231: The method of example 227 or 228, wherein the recommended quantity of additional analyte sensors is set by an individual involved in administering therapy to the subject.

Example 232: The method of example 223 or 224, further comprising receiving, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and additional analyte sensors have been ordered.

Example 233: The method of any one of examples 223 to 232, wherein the remote electronic device comprises payment account data associated with the subject that is configured to be used to automatically process payment for a purchase order of additional analyte sensors.

Example 234: The method of any one of examples 223 to 232, wherein the remote electronic device is in communication with an insurance provider system associated with the subject, and wherein the remote electronic device is configured to automatically send a purchase order for additional analyte sensors to the insurance provider system for processing.

Example 235: The method of example 234, wherein the remote electronic device comprises payment account data associated with the subject, and wherein the remote electronic device is configured to automatically process payment for the purchase order for additional analyte sensors using the payment account data associated with the subject and data provided by the insurance provider system.

Example 236: The ambulatory medicament pump of any one of examples 223 to 235, wherein the remote electronic device sends an indication of the analyte sensor expiration alert based on a correlation of a ship date of the analyte sensor with an expiration date of the analyte sensor.

Example 237: The ambulatory medicament pump of any one of examples 223 to 235, wherein the remote electronic device sends an indication of the analyte sensor expiration alert based on electronic expiration information associated with an analyte sensor.

Example 238: The ambulatory medicament pump of any one of examples 223 to 235, wherein the analyte sensor expiration alert is electronic expiration information associated with an analyte sensor.

Example 239: An ambulatory medicament pump configured to automatically generate a user prompt comprising a transmitter ordering interface based on an estimate of remaining transmitters falling below a reordering threshold, the ambulatory medicament pump comprising: an analyte sensor interface configured to facilitate communication with a transmitter operatively connected to an analyte sensor; a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial transmitters in possession of a subject; monitor a usage of transmitters over a period by receiving at least one of a plurality of transmitter change indications during the period, wherein the plurality of transmitter change indications comprises: an electronic transmitter change request, received via user interaction with a transmitter change interface, to change a transmitter in communication with the ambulatory medicament pump; a transmitter expiration alert, received from the remote electronic device via the wireless data interface, indicating that a transmitter has expired or has passed or is at an expiration threshold; and a transmitter failure alert, received via a transmitter monitoring system of the ambulatory medicament pump, indicating that the transmitter in communication with the ambulatory medicament pump has a failure; determine the estimate of remaining transmitters in possession of a subject at the end of the period based on the number of initial transmitters and the usage of transmitters during the period; determine that the estimate of remaining transmitters falls below the reordering threshold; in response to determining that the estimate of remaining transmitters falls below the reordering threshold, automatically generate the user prompt comprising the transmitter ordering interface; receive, via user interaction with the transmitter ordering interface, a request to order additional transmitters; and in response to receiving the request to order additional transmitters, transmit a purchase order for additional transmitters to the remote electronic device.

Example 240: The ambulatory medicament pump of example 239, wherein the remote electronic device sends an indication of the transmitter expiration alert based on a correlation of a ship date of the analyte sensor with an expiration date of the analyte sensor.

Example 241: The ambulatory medicament pump of example 239 or 240, wherein the remote electronic device sends an indication of the transmitter expiration alert based on electronic expiration information associated with an analyte sensor.

Example 242: The ambulatory medicament pump of any one of examples 239 to 241, wherein the transmitter expiration alert is electronic expiration information associated with an analyte sensor.

Example 243: An ambulatory medicament pump configured to monitor a usage of transmitters over a period by receiving at least one of a plurality of transmitter change indications during the period, the ambulatory medicament pump comprising: a analyte sensor interface configured to facilitate communication with a transmitter operatively connected to an analyte sensor; a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial transmitters in possession of a subject; monitor a usage of transmitters over a period by receiving at least one of a plurality of transmitter change indications during the period, wherein the plurality of transmitter change indications comprises: an electronic transmitter change request, received via user interaction with a transmitter change interface, to change a transmitter in communication with the ambulatory medicament pump; a transmitter expiration alert, received from the remote electronic device via the wireless data interface, indicating that a transmitter has expired or has passed or is at an expiration threshold; and a transmitter failure alert, received via a transmitter monitoring system of the ambulatory medicament pump, indicating that the transmitter in communication with the ambulatory medicament pump has a failure; transmit transmitter data regarding the usage of transmitters, via the wireless data interface, to a remote electronic device.

Example 244: The ambulatory medicament pump of example 243, wherein the remote electronic device is a remote computing environment.

Example 245: The ambulatory medicament pump of example 243 or 244, wherein the electronic processor is further configured to execute the specific computer-executable instructions to at least: receive, via the wireless data interface, a reordering message from the remote electronic device that indicates that an estimate of remaining transmitters in possession of the subject at the end of the period, based on the number of initial transmitters and the usage of transmitters during the period, has fallen below a reordering threshold.

Example 246: The ambulatory medicament pump of example 245, wherein the electronic processor is further configured to execute the specific computer-executable instructions to at least: in response to receiving the reordering message from the remote electronic device, automatically generate a user prompt comprising a transmitter ordering interface; receive, via user interaction with the transmitter ordering interface, a request to order additional transmitters; and in response to receiving the request to order additional transmitters, transmit a purchase order for additional transmitters.

Example 247: The ambulatory medicament pump of example 243 or 244, wherein the electronic processor is further configured to execute the specific computer-executable instructions to at least: receive, via the wireless data interface, a reordering message from the remote electronic device that indicates that an estimate of remaining transmitters in possession of the subject at the end of the period, based on the number of initial transmitters and the usage of transmitters during the period, has fallen below a reordering threshold and recommending that a quantity of additional transmitters be ordered.

Example 248: The ambulatory medicament pump of example 247, wherein the electronic processor is further configured to execute the specific computer-executable instructions to at least: in response to receiving the reordering message from the remote electronic device, automatically generate a user prompt comprising a transmitter ordering interface that provides at least the recommended quantity of additional transmitters to be ordered; receive, via user interaction with the transmitter ordering interface, a request to order the recommended quantity of additional transmitters; and in response to receiving the request to order the recommended quantity of additional transmitters, transmit a purchase order for the recommended quantity of additional transmitters.

Example 249: The ambulatory medicament pump of example 247 or 248, wherein the recommended quantity of additional transmitters is based at least in part on the usage of the transmitters over the period of time.

Example 250: The ambulatory medicament pump of example 247 or 248, wherein the recommended quantity of additional transmitters is preset.

Example 251 The ambulatory medicament pump of example 247 or 248, wherein the recommended quantity of additional transmitters is set by an individual involved in administering therapy to the subject.

Example 252: The ambulatory medicament pump of example 243 or 244, wherein the electronic processor is further configured to execute the specific computer-executable instructions to at least: receive, via the wireless data interface, a reordering message from the remote electronic device that indicates that an estimate of remaining transmitters in possession of the subject at the end of the period, based on the number of initial transmitters and the usage of transmitters during the period, has fallen below a reordering threshold and additional transmitters have been ordered.

Example 253: The ambulatory medicament pump of example 252, wherein the remote electronic device comprises payment account data associated with the subject, and wherein the remote electronic device is configured to automatically process payment for the ordered additional transmitters using the payment account data associated with the subject.

Example 254: The ambulatory medicament pump of any one of examples 243 to 252, wherein the remote electronic device is in communication with an insurance provider system associated with the subject, and wherein the remote electronic device is configured to automatically send the recommended quantity of additional transmitters to the insurance provider system for processing.

Example 255: The ambulatory medicament pump of example 254, wherein the remote electronic device comprises payment account data associated with the subject, and wherein the remote electronic device is configured to automatically process payment for the recommended quantity of additional transmitters using the payment account data associated with the subject and data provided by the insurance provider system.

Example 256: The ambulatory medicament pump of any one of examples 243 to 255, wherein the remote electronic device sends an indication of the transmitter expiration alert based on a correlation of a ship date of the transmitter with an expiration date of the transmitter.

Example 257: The ambulatory medicament pump of any one of examples 243 to 255, wherein the remote electronic device sends an indication of the transmitter expiration alert based on electronic expiration information associated with a transmitter.

Example 258: The ambulatory medicament pump of any one of examples 243 to 255, wherein the transmitter expiration alert is electronic expiration information associated with a transmitter.

Example 259: A method of transmitting a purchase order for additional transmitters from a glucose level control system, the method comprising: by an electronic processor of the glucose level control system executing specific computer-executable instructions stored in a non-transitory memory in communication with the electronic processor: receiving an indication of a number of initial transmitters in possession of a subject; monitoring a usage of transmitters over a period by receiving at least one of a plurality of transmitter change indications during the period, wherein the plurality of transmitter change indications comprises: receiving, via user interaction with a transmitter change interface, an electronic transmitter change request, to change a transmitter in communication with an ambulatory medicament pump of the glucose level control system; receiving, via a wireless data interface in communication with a remote electronic device, a transmitter expiration alert, indicating that transmitter has expired or has passed or is at an expiration threshold; and receiving, via a transmitter monitoring system of the ambulatory medicament pump, a transmitter failure alert indicating that a transmitter in communication with the ambulatory medicament pump has a failure; determining an estimate of remaining transmitters in possession of the subject at the end of the period based on the number of initial transmitters and the usage of transmitters during the period; determining that the estimate of remaining transmitters falls below a reordering threshold; in response to determining that the estimate of remaining transmitters falls below the reordering threshold, automatically generating a user prompt comprising a transmitter ordering interface; receiving, via user interaction with the transmitter ordering interface, a request to order additional transmitters; and in response to receiving the request to order additional transmitters, transmitting a purchase order for additional transmitters.

Example 260: The method of example 259, wherein the remote electronic device sends an indication of the transmitter expiration alert based on a correlation of a ship date of the analyte sensor with an expiration date of the analyte sensor.

Example 261: The method of example 259, wherein the remote electronic device sends an indication of the transmitter expiration alert based on electronic expiration information associated with an analyte sensor.

Example 262: The method of example 259, wherein the transmitter expiration alert is electronic expiration information associated with an analyte sensor.

Example 263: A method of monitoring a usage of transmitters for an ambulatory medicament pump of a glucose level control system, the method comprising: by an electronic processor of the glucose level control system executing specific computer-executable instructions stored in a non-transitory memory in communication with the electronic processor: receiving an indication of a number of initial transmitters in possession of a subject; monitoring a usage of transmitters over a period by receiving at least one of a plurality of transmitter change indications during the period, wherein the plurality of transmitter change indications comprises: receiving, via user interaction with a transmitter change interface, an electronic transmitter change request, to change a transmitter in communication with the ambulatory medicament pump; receiving, via a wireless data interface in communication with a remote electronic device, a transmitter expiration alert, indicating that transmitter has expired or has passed or is at an expiration threshold; and receiving, via a transmitter monitoring system of the ambulatory medicament pump, a transmitter failure alert indicating that a transmitter in communication with the ambulatory medicament pump has a failure; and transmitting transmitter data regarding the usage of transmitters, via the wireless data interface, to the remote electronic device.

Example 264: The method of example 263, wherein the remote electronic device is a remote computing environment.

Example 265: The method of example 263 or 264, further comprising receiving, via the wireless data interface, a reordering message from the remote electronic device that indicates that an estimate of remaining transmitters in possession of the subject at the end of the period, based on the number of initial transmitters and the usage of transmitters during the period, has fallen below a reordering threshold.

Example 266: The method of example 265, further comprising: automatically generating a user prompt comprising transmitter ordering interface in response to receiving the reordering message from the remote electronic device; receiving, via user interaction with the transmitter ordering interface, a request to order additional transmitters; and transmitting a purchase order for additional transmitters in response to receiving the request to order additional transmitters.

Example 267: The method of example 263 or 264, further comprising receiving, via the wireless data interface, a reordering message from the remote electronic device that indicates that an estimate of remaining transmitters in possession of the subject at the end of the period, based on the number of initial transmitters and the usage of transmitters during the period, has fallen below a reordering threshold and recommending that a quantity of additional transmitters be ordered.

Example 268: The method of example 267, further comprising: automatically generating a user prompt comprising a transmitter ordering interface that provides at least the recommended quantity of additional transmitters to be ordered in response to receiving the reordering message from the remote electronic device; receiving, via user interaction with the transmitter ordering interface, a request to order the recommended quantity of additional transmitters; and transmitting a purchase order for the recommended quantity of additional transmitters in response to receiving the request to order the recommended quantity of additional transmitters.

Example 269: The method of example 267 or 268, wherein the recommended quantity of additional transmitters is based at least in part on the usage of the transmitters over the period of time.

Example 270: The method of example 267 or 268, wherein the recommended quantity of additional transmitters is preset.

Example 271: The method of example 267 or 268, wherein the recommended quantity of additional transmitters is set by an individual involved in administering therapy to the subject.

Example 272: The method of example 263 or 264, further comprising receiving, via the wireless data interface, a reordering message from the remote electronic device that indicates that an estimate of remaining transmitters in possession of the subject at the end of the period, based on the number of initial transmitters and the usage of transmitters during the period, has fallen below a reordering threshold and additional transmitters have been ordered.

Example 273: The method of any one of examples 263 to 272, wherein the remote electronic device comprises payment account data associated with the subject that is configured to be used to automatically process payment for a purchase order of additional transmitters.

Example 274: The method of any one of examples 263 to 272, wherein the remote electronic device is in communication with an insurance provider system associated with the subject, and wherein the remote electronic device is configured to automatically send a purchase order for additional transmitters to the insurance provider system for processing.

Example 275: The method of example 274, wherein the remote electronic device comprises payment account data associated with the subject, and wherein the remote electronic device is configured to automatically process payment for the purchase order for additional transmitters using the payment account data associated with the subject and data provided by the insurance provider system.

Example 276: The ambulatory medicament pump of any one of examples 263 to 275, wherein the remote electronic device sends an indication of the transmitter expiration alert based on a correlation of a ship date of the transmitter with an expiration date of the transmitter.

Example 277: The ambulatory medicament pump of any one of examples 263 to 275, wherein the remote electronic device sends an indication of the transmitter expiration alert based on electronic expiration information associated with a transmitter.

Example 278: The ambulatory medicament pump of any one of examples 263 to 275, wherein the transmitter expiration alert is electronic expiration information associated with a transmitter.

Example 279: A computer-implemented method of generating an aggregate report, wherein the aggregate report is usable for evaluating a quality of the glycemic control of one or more subjects receiving glucose control therapy via a glucose level control system, the computer-implemented method comprising: by an electronic processor of a computing system in a patient data network, wherein the electronic processor executes specific computer-executable instructions stored in a non-transitory memory in communication with the electronic processor, establishing a first data connection to a first glucose level control system providing glucose therapy to a first subject; sending a first electronic request to the first glucose level control system, wherein the first electronic request causes the first glucose level control system to transmit first therapy data stored on the first glucose level control system to the computing system over the first data connection; receiving, via the first data connection, first therapy data, wherein the first therapy data comprises data associated with glycemic control of the first subject, data associated with glucose control therapy delivered to the first subject, and first pump usage data; establishing a second data connection to a second glucose level control system providing glucose therapy to a second subject; sending a second electronic request to the second glucose level control system, wherein the second electronic request causes the second glucose level control system to transmit second therapy data stored on the second glucose level control system to the computing system over the second data connection; receiving, via the second data connection, second therapy data, wherein the second therapy data comprises data associated with glycemic control of the second subject, data associated with glucose control therapy delivered to the second subject, and second pump usage data; determining first values of one or more biometric parameters based at least in part on the first therapy data and second values of one or more biometric parameters based at least in part on the second therapy data, wherein the one or more biometric parameters are associated with a health condition; generating a comparative assessment based on (1) reference data comprising reference values associated with the one or more biometric parameters and/or the first and the second therapy data and (2) subject data, wherein the subject data comprises at least one of: aggregate biometric parameter data comprising the first and second values of the one or more biometric parameters, or aggregate therapy data comprising the first and the second therapy data; and generating the aggregate report based at least in part on the comparative assessment, wherein the aggregate report comprises at least one evaluation, wherein the at least one evaluation is indicative of the quality of the glycemic control of the first subject and the second subject with reference to at least one glycemic control criterion.

Example 280: The computer-implemented method of example 279, wherein the glucose control therapy delivered to the first subject comprises one or more volumes of medicament delivered to the first subject via the first glucose level control system.

Example 281: The computer-implemented method of example 279 or 280, wherein the patient data network comprises a local storage of patient data or a cloud storage.

Example 282: The computer-implemented method of any one of examples 279 to 281, wherein the data associated with glycemic control of the first subject comprises: glucose level data received from a glucose sensor operatively connected to the first subject; one or more time periods during which one or more measured glucose levels of the first subject were within a set range; one or more time periods during which one or more measured glucose levels of the first subject were above a maximum glucose level of the set range; one or more time periods during which one or more measured glucose levels of the first subject were less than a minimum glucose level of the set range; or one or more average glucose levels of the first subject determined over an evaluation period.

Example 283: The computer-implemented method of any one of examples 279 to 282, wherein the data associated with glucose control therapy delivered to the first subject comprises at least one of: amounts of insulin delivered to the first subject, amounts of glucagon delivered to the first subject, total daily doses of insulin delivered to the first subject, total daily doses of glucagon delivered to the first subject, a number of insulin boluses delivered to the first subject, wherein the insulin boluses are associated with meals or with a period of time during which the first subject does not receive therapy from the first glucose level control system, a number of counter-regulatory agent boluses delivered to the first subject, wherein the counter-regulatory agents boluses are associated with physical activity of the first subject or with a period of time during which the first subject does not receive therapy from the first glucose level control system, or medicament types delivered to the first subject, wherein the medicament types comprise insulin or glucagon.

Example 284: The computer-implemented method of any one of examples 279 to 283, wherein the first pump usage data comprises at least one of: a daily number of meal announcements received by the first glucose level control system, time intervals between infusion set changes, time intervals between medicament cartridge changes, a user interaction with a user interface of the glucose level control system, or time periods during which the first glucose level control system could not deliver glucose control therapy to the first subject.

Example 285: The computer-implemented method of any one of examples 279 to 284, wherein determining the first values of one or more biometric parameters comprises determining the first values of one or more biometric parameters using a kinetic model.

Example 286: The computer-implemented method of example 285, wherein the biometric parameters comprise estimated Hemoglobin A1c (eHbA1c), and the kinetic model provides an estimate of HbA1c from a measured glucose level of the subject.

Example 287: The computer-implemented method of any one of examples 279 to 286, wherein generating the comparative assessment comprises determining total daily range, Hemoglobin A1c or mean glucose level.

Example 288: The computer-implemented method of any one of examples 279 to 287, wherein determining the first values of one or more biometric parameters comprises determining the first values of one or more biometric parameters using raw therapy data.

Example 289: The computer-implemented method of any one of examples 279 to 288, wherein generating the comparative assessment comprises performing one or more statistical analysis.

Example 290: The computer-implemented method of any one of examples 279 to 289, wherein generating the comparative assessment comprises a cross-correlation analysis using the first and the second pump usage data to determine subject-specific pump usage.

Example 291: The computer-implemented method of any one of examples 279 to 290, wherein the at least one evaluation comprises evaluation of a kinetic model, a configuration, a feature of the first glucose level control system, or an evaluation of an infusion set used to deliver glucose control therapy to first subject.

Example 292: The computer-implemented method of any one of examples 279 to 291, wherein generating the comparative assessment comprises performing an assessment of one or more clinical outcomes based at least in part on: the first and the second therapy data, a kinetic model used by the first glucose level control system, and/or a configuration of the first glucose level control system, or a kinetic model used by the second glucose level control system, and/or a configuration of the second glucose level control system.

Example 293: The computer-implemented method of any one of examples 279 to 292, wherein the aggregate report further comprises: one or more charts, histograms, plots or tables representing: the aggregate therapy data, the aggregate biometric parameter data, the comparative assessment, the at least one evaluation, or one or more charts or tables representing a breakdown of the reference data used for generating the comparative assessment based on race, income, gender, birthplace, or residence location of a plurality of subjects associated with the reference data.

Example 294: The computer-implemented method of example 293, wherein the one or more charts, histograms, plots or tables representing the aggregate therapy data comprises a breakdown of the first and the second pump usage data based on a characteristic of the first and the second pump usage data.

Example 295: The computer-implemented method of any one of examples 279 to 293, wherein the reference data is stored in a non-transitory memory of the computing system and the reference data comprises: data associated with one or more clinical studies, data associated with a recommendation by a manufacturer, data associated with a recommendation by a health association, data associated with a recommendation by a health care professional, or data associated with a payer criterion.

Example 296: The computer-implemented method of example 295, wherein the payer criterion comprise one or more of A1C level 7, A1C level 8, A1C level 9 or HEVIS criterion.

Example 297: The computer-implemented method of any one of examples 279 to 296, wherein the first and the second data connections are wireless connections via a WAN, a LAN, or a Bluetooth link.

Example 298: The computer-implemented method of any one of examples 279 to 297, wherein the first and the second data connections are secure data connections.

Example 299: The computer-implemented method of any one of examples 279 to 298, wherein the computing system is a computing system of a healthcare provider, a health care professional or a manufacturer and wherein the computing system is connected to the patient data network.

Example 300: The computer-implemented method of any one of examples 279 to 299, wherein the first subject and the second subject belong to a group of subjects selected by a healthcare provider, manufacturer or a payer.

Example 301: The computer-implemented method of any one of examples 279 to 300, further comprising: receiving a report request from a display system to access the aggregate report, wherein the report request comprises an account identifier associated with a user who generates the report request; determining whether an account associated with the account identifier is permitted to view the aggregate report; and responsive to determining that the account is permitted to view the aggregate report, transmitting the aggregate report to the display system.

Example 302: The computer-implemented method of example 301, wherein the display system is a display system of a remote computing device.

Example 303: The computer-implemented method of example 302, wherein the remote computing device is a remote computing device of a health insurance company or a healthcare provider.

Example 304: The computer-implemented method of any one of examples 301 to 303, wherein transmitting the aggregate report to the display system comprises transmitting the aggregate report to the display system via a secure data connection.

Example 305: The computer-implemented method of any one of examples 301 to 304, wherein generating the aggregate report comprises anonymizing the subject data.

Example 306: The computer-implemented method of any one of examples 301 to 304, wherein the report request is a customized report request.

Example 307: A computing system included in a patient data network, wherein the computing system is configured to generate an aggregate report, wherein the aggregate report is usable for evaluating a quality of the glycemic control of one or more subjects receiving glucose control therapy via a glucose level control system, the computing system comprising: a memory configured to store specific computer-executable instructions; and a hardware processor in communication with the memory and configured to execute the specific computer-executable instructions to at least: establish a first data connection to a first glucose level control system; send a first electronic request to the first glucose level control system, wherein the first electronic request causes the first glucose level control system to transmit first therapy data stored on the first glucose level control system to the computing system over the first data connection; receive, via the first data connection, the first therapy data, wherein the first therapy data comprises data associated with a glycemic control of a first subject, a glucose control therapy delivered to the first subject, and first pump usage data; establish a second data connection to a second glucose level control system; send a second electronic request, to the second glucose level control system, wherein the second electronic request causes the second glucose level control system to transmit second therapy data stored on the second glucose level control system to the computing system over the second data connection; receive, via the second data connection, a second therapy data from the second glucose level control system, wherein the second therapy data comprises data associated with a glycemic control of a second subject, a glucose control therapy delivered to the second subject, and second pump usage data; determine first values of one or more biometric parameters based at least in part on the first therapy data and second values of one or more biometric parameters based at least in part on the second therapy data, wherein the one or more biometric parameters are associated with a health condition; generate a comparative assessment based on (1) reference data comprising reference values associated with the one or more biometric parameters and/or the first and the second therapy data and (2) subject data, wherein the subject data comprises at least one of: aggregate biometric parameter data comprising the first and second values of the one or more biometric parameters; or aggregate therapy data comprising the first and second therapy data; and generate the aggregate report based at least in part on the comparative assessment, wherein the aggregate report comprises at least one evaluation, wherein the at least one evaluation is indicative of the quality of the glycemic control of the first subject and the second subject with reference to at least one glycemic control criterion.

Example 308: The computing system of example 307, wherein the glucose control therapy delivered to the first subject comprises one or more volumes of medicament delivered to the first subject via the first glucose level control system.

Example 309: The computing system of example 307 or 308, wherein the patient data network comprises a local storage of patient data or a cloud storage.

Example 310: The computing system of any one of examples 307 to 309, wherein the data associated with glycemic control of the first subject comprises: glucose level data received from a glucose sensor operatively connected to the first subject, one or more time periods during which one or more measured glucose levels of the first subject were within a set range, one or more time periods during which one or more measured glucose levels of the first subject were above a maximum glucose level of the set range, one or more time periods during which one or more measured glucose levels of the first subject were less than a minimum glucose level of the set range, and one or more average glucose levels of the first subject determined over an evaluation period.

Example 311: The computing system of any one of examples 307 to 310, wherein the data associated with glucose control therapy delivered to the first subject comprises at least one of: amounts of insulin delivered to the first subject, amounts of glucagon delivered to the first subject, total daily doses of insulin delivered to the first subject, total daily doses of glucagon delivered to the first subject, a number of insulin boluses delivered to the first subject, wherein the insulin boluses are associated with meals or with a period of time during which the first subject does not receive therapy from the first glucose level control system, a number of counter-regulatory agent boluses delivered to the first subject, wherein the counter-regulatory agent boluses are associated with physical activity of the first subject or with a period of time during which the first subject does not receive therapy from the first glucose level control system, or medicament types delivered to the first subject, wherein the medicament types comprise insulin or glucagon.

Example 312: The computing system of any one of examples 307 to 311, wherein the first pump usage data comprises: a daily number of meal announcements received by the first glucose level control system, time intervals between infusion set changes, time intervals between medicament cartridge changes, a user interaction with a user interface of the first glucose level control system, or time periods during which the first glucose level control system could not deliver glucose control therapy to the first subject.

Example 313: The computing system of any one of examples 307 to 312, wherein the hardware processor is configured to execute the specific computer-executable instructions to determine the first and the second values of one or more biometric parameters using a kinetic model.

Example 314: The computing system of any one of examples 307 to 313, wherein the biometric parameter is an estimated level of Hemoglobin A1c (eHbA1c) and the kinetic model is for estimating HbA1c from a measured glucose level of the subject.

Example 315: The computing system of any one of examples 307 to 314, wherein the hardware processor is configured to execute the specific computer-executable instructions to determine the first values of one or more biometric parameters using raw therapy data.

Example 316: The computing system of any one of examples 307 to 315, wherein the hardware processor is configured to execute the specific computer-executable instructions to generate the comparative assessment by performing one or more statistical analysis.

Example 317: The computing system of any one of examples 307 to 316, wherein the hardware processor is configured to execute the specific computer-executable instructions to generate the comparative assessment by performing a cross-correlation analysis using the first and the second pump usage data to determine subject-specific pump usage.

Example 318: The computing system of any one of examples 307 to 317, wherein the hardware processor is configured to execute the specific computer-executable instructions to generate the comparative assessment by determining total daily range, Hemoglobin A1c or mean glucose level.

Example 319: The computing system of any one of examples 307 to 318, wherein the at least one evaluation comprises evaluation of a kinetic model, a configuration, a feature of the first glucose level control system, or an evaluation of an infusion set used to deliver glucose control therapy to first subject.

Example 320: The computing system of any one of examples 307 to 319, wherein the hardware processor is configured to execute the specific computer-executable instructions to generate the comparative assessment by performing an assessment of one or more clinical outcomes based at least in part on: the first and the second therapy data, a model kinetic model used by the first glucose level control, and/or a configuration of the first glucose level control system, or a model kinetic model used by the first glucose level control, and/or a configuration of the second glucose level control system.

Example 321: The computing system of any one of examples 307 to 320, wherein the aggregate report further comprises: one or more charts, histograms, plots or tables representing: the aggregate therapy data, the aggregate biometric parameter data, the comparative assessment, the at least one evaluation, or one or more charts or tables representing a breakdown of the reference data used for generating the comparative assessment based on race, income, gender, birthplace, or residence location of a plurality of subjects associated with the reference data.

Example 322: The computing system of example 321, wherein the one or more charts, histograms, plots or tables representing the aggregate therapy data comprises a breakdown of the first and the second pump usage data based on a characteristic of the first and the second pump usage data.

Example 323: The computing system of any one of examples 307 to 322, wherein the reference data is stored in a non-transitory memory of the computing system and the reference data comprises: data associated with one or more clinical studies, data associated with a recommendation by a manufacturer, data associated with a recommendation by a health association, data associated with a recommendation by a health care professional, or data associated with a payer criterion.

Example 324: The computing system of example 323, wherein the payer criterion comprises one or more of A1C level 7, A1C level 8, A1C level 9 or HEVIS criterion.

Example 325: The computing system of any one of examples 307 to 324, wherein the first and the second data connections are wireless connections via a WAN or a LAN.

Example 326: The computing system of any one of examples 307 to 325, wherein the first and the second data connections are secure data connections.

Example 327: The computing system of any one of examples 307 to 326, wherein the computing system is a computing system of a healthcare provider, a health care professional or a manufacturer and wherein the computing system is connected to the patient data network.

Example 328: The computing system of any one of examples 307 to 327, wherein the first subject and the second subject belong to a group of subjects selected by a healthcare provider or a manufacturer.

Example 329: The computing system of any one of examples 307 to 328, wherein the hardware processor is further configured to execute the specific computer-executable instructions to: receive a report request from a display system to access the aggregate report, wherein the report request comprises an account identifier associated with a user who generates the report request; determine whether an account associated with the account identifier is permitted to view the aggregate report; and responsive to determining that the account is permitted to view the aggregate report, transmit the aggregate report to the display system.

Example 330: The computing system of example 329, wherein the display system is a display system of a remote computing device.

Example 331: The computing system of example 330, wherein the remote computing device is a remote computing device of a health insurance company or healthcare provider.

Example 332: The computing system of any one of examples 329 to 331, wherein report request is generated by a user of the display system.

Example 333: The computing system of any one of examples 329 to 332, wherein the display system transmits the aggregate report to the display system via a secure data connection.

Example 334: The computing system of any one of examples 329 to 333, wherein the hardware processor is further configured to execute the specific computer-executable instructions to anonymize the subject data before generating the aggregate report.

Example 335: The computing system of any one of examples 329 to 334, wherein the report request comprises a customized report request.

Example 336: A therapy administration system configured to manage glucose level control therapy delivered to a subject by an ambulatory medicament pump, the therapy administration system comprising: a non-transitory memory configured to store specific computer-executable instructions; and a hardware processor in communication with the non-transitory memory and configured to execute the specific computer executable instructions to at least: receive, via user interaction with a voice-user interface, a verbal command from a user; authenticate the user using at least one of a plurality of user authentication processes; receive a connection confirmation signal from the ambulatory medicament pump, the connection confirmation signal indicating that a data connection exists between the therapy administration system and the ambulatory medicament pump; in response to authenticating the user and receiving the connection confirmation signal, transmit an execution command to the ambulatory medicament pump, the execution command comprising computer-executable instructions to perform the verbal command; and receive a verification signal from the ambulatory medicament pump, the verification signal indicating whether the execution command was successfully received by the ambulatory medicament pump.

Example 337: The therapy administration system of example 336, wherein the plurality of user authentication processes comprises a passphrase authentication process, and wherein the hardware processor is further configured to execute the specific computer executable instructions to at least: in response to receiving the verbal command, authenticate the user using the passphrase authentication process by: prompting the user, via the voice-user interface, to provide an authorized passphrase; receiving, via user interaction with the voice-user interface, a passphrase attempt provided by the user; determining whether the passphrase attempt provided by the user matches the authorized passphrase; and in response to determining that the passphrase attempt provided by the user and the authorized passphrase match, authenticating the user.

Example 338: The therapy administration system of example 336 or 337, wherein the plurality of user authentication processes comprises a speaker recognition authentication process, and wherein the hardware processor is further configured to execute the specific computer executable instructions to at least: authenticate the user using the speaker recognition authentication process by: identifying the user based on the verbal command using a speaker recognition algorithm; determining whether the user is authorized to give the verbal command; and in response to determining that the user is authorized to give the verbal command, authenticating the user.

Example 339: The therapy administration system of example 338, wherein the speaker recognition algorithm is one of: a hidden Markov model, a Gaussian mixture model, a pattern matching algorithm, a neural network, or a frequency estimation algorithm.

Example 340: The therapy administration system of any one of examples 336 to 339, wherein the hardware processor is further configured to execute the specific computer executable instructions to at least: enable a group of authorized verbal commands associated with the user based on the authentication of the user, wherein the authentication of the user verifies the user's identity using at least one of the user authentication processes; determine whether the verbal command is enabled; and in response to determining the verbal command is enabled and receiving the connection confirmation signal from the ambulatory medicament pump, transmit the execution command to the ambulatory medicament pump.

Example 341: The therapy administration system of example 340, wherein the hardware processor is further configured to execute the specific computer executable instructions to at least: in response to determining that the verbal command is disabled, inform the user, via the voice-user interface, that the user is not authorized to give the verbal command.

Example 342: The therapy administration system of example 340 or 341, wherein the group of authorized verbal commands is enabled during a validity period.

Example 343: The therapy administration system of example 342, wherein the validity period is one hour, one day, or one week.

Example 344: The therapy administration system of any one of examples 336 to 343, wherein the hardware processor is further configured to execute the specific computer executable instructions to at least: in response to authenticating the user, generate an authorization token; and in response to authenticating the user and receiving the connection confirmation signal, transmit the authentication token to the ambulatory medicament pump.

Example 345: The therapy administration system of example 344, wherein the authentication token is valid during a validity period.

Example 346: The therapy administration system of example 345, wherein the validity period is one hour, one day, or one week.

Example 347: The therapy administration system of any one of examples 336 to 346, wherein the hardware processor is further configured to execute the specific computer executable instructions to at least: in response to the user failing one of the plurality of user authentication processes, inform the user, via the voice-user interface, that the user is not authorized to give the verbal command.

Example 348: The therapy administration system of any one of examples 336 to 347, wherein the hardware processor is further configured to execute the specific computer executable instructions to at least: in response to authenticating the user and receiving the connection confirmation signal, prompt the user, via the voice-user interface, to confirm the verbal command; receive, via the voice-user interface, a confirmation command from the user; and in response to receiving the confirmation command and the connection confirmation signal, transmit the execution command to the ambulatory medicament pump.

Example 349: The therapy administration system of any one of examples 336 to 348, wherein the verbal command is a therapy modification command, the therapy modification command configured to administer a medicament, modify a medicament dose, or modify a medicament dose calculation factor.

Example 350: The therapy administration system of example 349, wherein the hardware processor is further configured to execute the specific computer executable instructions to at least: in response to receiving the verification signal from the ambulatory medicament pump, record the therapy modification command, the user, and a time that the verification signal was received.

Example 351: The therapy administration system of any one of examples 336 to 350, wherein the verbal command is a data retrieval command.

Example 352: The therapy administration system of any one of examples 336 to 351, wherein the hardware processor is further configured to execute the specific computer executable instructions to at least: transmit, via the voice-user interface, therapy data to the user.

Example 353: The therapy administration system of example 352, wherein the hardware processor is further configured to execute the specific computer executable instructions to at least: retrieve the therapy data from one of: the non-transitory memory, the ambulatory medicament pump, or a remote computing environment.

Example 354: The therapy administration system of any one of examples 336 to 353, wherein the verbal command is a data sharing command, the data sharing command comprising a request for therapy data and a recipient.

Example 355: The therapy administration system of example 354, wherein the hardware processor is further configured to execute the specific computer executable instructions to at least: transmit, via a network interface, the therapy data to the recipient; and receive, via the network interface, a delivery confirmation signal from the ambulatory medicament pump, the delivery confirmation signal indicating that the requested therapy data was successfully transmitted to the recipient.

Example 356: The therapy administration system of any one of examples 352 to 355, wherein the hardware processor is further configured to execute the specific computer executable instructions to at least: retrieve the therapy data from one of: the non-transitory memory, the ambulatory medicament pump, or a remote computing environment.

Example 357: The therapy administration system of any one of examples 336 to 356, wherein the verbal command is a medicament dose calculation command.

Example 358: The therapy administration system of example 357, wherein the hardware processor is further configured to execute the specific computer executable instructions to at least: retrieve therapy data from one of: the non-transitory memory, the ambulatory medicament pump, or a remote computing environment; calculate a medicament dose based on the therapy data; and transmit, via the voice-user interface, the calculated medicament dose to the user.

Example 359: The therapy administration system of example 358, wherein the hardware processor is further configured to execute the specific computer executable instructions to at least: receive, via the voice-user interface, a dose command from the user, the dose command comprising a request to administer the calculated medicament dose; and transmit a second execution command to the ambulatory medicament pump, the second execution command comprising computer-executable instructions to administer the calculated medicament dose.

Example 360: The therapy administration system of example 358 or 359, wherein the hardware processor is further configured to execute the specific computer executable instructions to at least: retrieve the therapy data from one of: the non-transitory memory, the ambulatory medicament pump, or a remote computing environment; calculate a medicament dose based on the therapy data; and transmit the execution command to the ambulatory medicament pump, the execution command comprising computer-executable instructions to administer the calculated medicament dose.

Example 361: The therapy administration system of any one of examples 336 to 360, wherein the verbal command comprises a wake-up command, and wherein the hardware processor is further configured to execute the specific computer executable instructions to at least: detect, via the voice-user interface, the wake-up command; and in response to detecting the wake-up command, receive the verbal command.

Example 362: The therapy administration system of any one of examples 336 to 361, wherein the hardware processor is further configured to execute the specific computer executable instructions to at least: receive an alert signal from the ambulatory medicament pump; and transmit, via the voice-user interface, the alert signal to the user.

Example 363: The therapy administration system of example 362, wherein the alert signal indicates one of: a low battery level of the ambulatory medicament pump, a high glucose level of the user, a low glucose level of the user, a low medicament level, or that the therapy administration system and the ambulatory medicament pump are disconnected.

Example 364: The therapy administration system of example 362 or 363, wherein the hardware processor is further configured to execute the specific computer executable instructions to at least: determine whether an emergency command should be sent to the ambulatory medicament pump based on the alert signal; in response to determining that the emergency command should be sent to the ambulatory medicament pump, prompt the user, via the voice-user interface, to confirm the emergency command; receive, via the voice-user interface, the emergency command from the user; authenticate the user using one of the plurality of user authentication processes; receive the connection confirmation signal from the ambulatory medicament pump; and in response to receiving the connection confirmation signal and authenticating the user, transmit the execution command to the ambulatory medicament pump, wherein the execution command comprises computer-executable instructions to perform the emergency command.

Example 365: The therapy administration system of any one of examples 336 to 364, wherein the hardware processor is further configured to execute the specific computer executable instructions to at least: in response to not receiving the connection confirmation signal from the ambulatory medicament pump, inform the user, via the voice-user interface, that the therapy administration system and the ambulatory medicament pump are not connected.

Example 366: The therapy administration system of any one of examples 336 to 365, wherein the hardware processor is further configured to execute the specific computer executable instructions to at least: in response to receiving the verification signal from the ambulatory medicament pump, announce, via the voice-user interface, that the verbal command was performed.

Example 367: The therapy administration system of any one of examples 336 to 366, wherein the hardware processor is further configured to execute the specific computer executable instructions to at least: receive, via the voice-user interface, an abort command from the user; authenticate the user using one of the plurality of user authentication processes; receive the connection confirmation signal from the ambulatory medicament pump; in response to receiving the connection confirmation signal and authenticating the user, transmit a stop command to the ambulatory medicament pump, the stop command configured to abort the execution command; and receiving the verification signal from the ambulatory medicament pump, wherein the verification signal indicates that the execution command was successfully aborted.

Example 368: The therapy administration system of any one of examples 336 to 367, wherein the hardware processor is further configured to execute the specific computer executable instructions to at least: receive, via the voice-user interface, a request to set up the ambulatory medicament pump from the user; prompt the user, via the voice-user interface, to name the ambulatory medicament pump; and receive, via the voice-user interface, a name for the ambulatory medicament pump.

Example 369: The therapy administration system of example 368, wherein the hardware processor is further configured to execute the specific computer executable instructions to at least: in response to receiving the verbal command, prompt the user, via the voice-user interface, to select at least one of a plurality of ambulatory medicament pumps to receive the verbal command; receive, via the voice-user interface, the name of the ambulatory medicament pump; and in response to receiving the name of the ambulatory medicament pump, authenticating the user using at least one of the plurality of user authentication processes.

Example 370: The therapy administration system of any one of examples 336 to 369, wherein the ambulatory medicament pump is connected to the hardware processor by one of: a broadband cellular network, a local wireless network, or a personal area network.

Example 371: A system configured to manage execution of a command, provided verbally by a user via a voice-user interface, by an ambulatory medicament pump, the system comprising: a non-transitory memory configured to store specific computer-executable instructions; and a hardware processor in communication with the non-transitory memory and configured to execute the specific computer executable instructions to at least: identify the ambulatory medicament pump to receive the verbal command using a pump identification process; receive a connection confirmation signal from the ambulatory medicament pump, the connection confirmation signal indicating that a data connection exists between the hardware processor and the ambulatory medicament pump; receive a verification signal from the ambulatory medicament pump, the verification signal indicating whether the ambulatory medicament pump received the command; and transmit the verification signal to the voice-user interface.

Example 372: The system of example 371, wherein the ambulatory medicament pump is connected to the system by one of: a broadband cellular network, a local wireless network, a personal area network, or a direct electrical connection.

Example 373: The system of example 371 or 372, wherein the voice-user interface is connected to the system by one of: a broadband cellular network, a local wireless network, a personal area network, or a direct electrical connection.

Example 374: The system of any one of examples 371 to 373, wherein the hardware processor is further configured to execute the specific computer executable instructions to at least: receive, via user interaction with the voice-user interface, the verbal command from the user.

Example 375: The system of example 374, wherein the hardware processor is further configured to execute the specific computer executable instructions to at least: in response to receiving the verbal command, prompt the user, via the voice-user interface, to select the ambulatory medicament pump to receive the verbal command; receive, via the voice-user interface, a name of the ambulatory medicament pump; and identify the ambulatory medicament pump receive the verbal command based on the name.

Example 376: The system of any one of examples 371 to 375, wherein the voice-user interface or a device associated with the voice-user interface is configured to authenticate the user using at least one of a plurality of authentication processes, and wherein the hardware processor is further configured to execute the specific computer executable instructions to at least: receive an authentication token generated by the voice-user interface or the device associated with the voice-user interface.

Example 377: The system of example 376, wherein the authentication token is valid during a validity period.

Example 378: The system of example 377, wherein the validity period is one hour, one day, or one week.

Example 379: The system of example 377 or 378, wherein the hardware processor is further configured to execute the specific computer executable instructions to at least: prompt the user, via the voice-user interface, to define a duration of the validity period; and receive, via the voice-user interface, the duration provided by the user.

Example 380: The system of any one of examples 371 to 379, wherein the hardware processor is further configured to execute the specific computer executable instructions to at least: authenticate the user using at least one of a plurality of user authentication processes.

Example 381: The system of example 380, wherein the hardware processor is further configured to execute the specific computer executable instructions to at least: in response to authenticating the user, add the user to a list of authorized users.

Example 382: The system of example 380 or 381, wherein the hardware processor is further configured to execute the specific computer executable instructions to at least: in response to the user failing one of the plurality of user authentication processes, inform the user, via the voice-user interface, that the user is not authorized to give the verbal command.

Example 383: The system of any one of examples 380 to 382, wherein the plurality of user authentication processes comprises a passphrase authentication process, and wherein the hardware processor is further configured to execute the specific computer executable instructions to at least: authenticate the user using the passphrase authentication process by: prompting the user, via the voice-user interface, to provide an authorized passphrase; receiving, via user interaction with the voice-user interface, a passphrase attempt provided by the user; determine whether the passphrase attempt provided by the user matches the authorized passphrase; and in response to determining that the passphrase attempt provided by the user and the authorized passphrase match, authenticating the user.

Example 384: The system of any one of examples 380 to 383, wherein the plurality of user authentication processes comprises a voiceprint authentication process, and wherein the hardware processor is further configured to execute the specific computer executable instructions to at least: authenticate the user using the voiceprint authentication process by: identifying the user based on the verbal command using a speaker recognition algorithm; determining whether the user is authorized to give the verbal command; and in response to determining that the user is authorized to give the verbal command, authenticating the user.

Example 385: The system of example 384, wherein the speaker recognition algorithm is one of: a hidden Markov model, a Gaussian mixture model, a pattern matching algorithm, a neural network, or a frequency estimation algorithm.

Example 386: The system of any one of examples 380 to 385, wherein the hardware processor is further configured to execute the specific computer executable instructions to at least: enable a group of authorized verbal commands associated with the user based on the authentication of the user, wherein the authentication of the user verifies the user's identity using at least one of the user authentication processes; determine whether the verbal command is enabled; and in response to determining that the verbal command is enabled, identifying the ambulatory medicament pump to receive the verbal command.

Example 387: The system of example 386, wherein the group of authorized commands is enabled during a validity period.

Example 388: The system of example 387, wherein the validity period is one hour, one day, or one week.

Example 389: The system of example 387 or 388, wherein the hardware processor is further configured to execute the specific computer executable instructions to at least: prompt the user, via the voice-user interface, to set a duration of the validity period; and receive, via the voice-user interface, the duration from the user.

Example 390: The system of any one of examples 371 to 389, wherein the hardware processor is further configured to execute the specific computer executable instructions to at least: in response to determining that the verbal command is disabled, inform the user, via the voice-user interface, that the user is not authorized to give the verbal command.

Example 391: The system of any one of examples 371 to 390, wherein the hardware processor is further configured to execute the specific computer executable instructions to at least: in response to authenticating the user, generate an authorization token.

Example 392: The system of example 391, wherein the authentication token is valid during a validity period.

Example 393: The system of example 392, wherein the validity period is one hour, one day, or one week.

Example 394: The system of example 392 or 393, wherein the hardware processor is further configured to execute the specific computer executable instructions to at least: prompt the user, via the voice-user interface, to define a duration of the validity period; and receive, via the voice-user interface, the duration from the user.

Example 395: The system of any one of examples 371 to 394, wherein the hardware processor is further configured to execute the specific computer executable instructions to at least: prompt the user, via the voice-user interface, to confirm the verbal command; and receive, via the voice-user interface, a confirmation command from the user.

Example 396: The system of any one of examples 371 to 395, wherein the hardware processor is further configured to execute the specific computer executable instructions to at least: transmit an execution command to the ambulatory medicament pump, the execution command comprising computer-executable instructions to perform the verbal command.

Example 397: The system of any one of examples 371 to 396, wherein the verification signal indicates that the ambulatory medicament pump successfully performed the verbal command, and the hardware processor is further configured to execute the specific computer executable instructions to at least: in response to receiving the verification signal from the ambulatory medicament pump, record the command, an identity of the user, and a time that the verification signal was received.

Example 398: The system of any one of examples 371 to 397, wherein the verbal command is a therapy modification command, the therapy modification command configured to administer a medicament, modify a medicament dose, or modify a medicament dose calculation factor.

Example 399: The system of example 398, wherein the medicament is one of: insulin, glucagon, a bolus dose, or a Gburst dose.

Example 400: The system of example 398 or 399, wherein the medicament dose calculation factor is one of: a basal medicament rate, a carbohydrate ratio, a correction factor, or an insulin action time.

Example 401: The system of any one of examples 398 to 400, wherein the hardware processor is further configured to execute the specific computer executable instructions to at least: verify the safety and efficacy of the therapy modification command based on therapy data; and in response to receiving the confirmation signal from the ambulatory medicament pump, transmit an execution command to the ambulatory medicament pump, the execution command comprising computer executable instructions to perform the therapy modification command.

Example 402: The system of any one of examples 371 to 401, wherein the verbal command is a data retrieval command comprising a request for therapy data.

Example 403: The system of example 402, wherein the therapy data is one of: a battery level of the ambulatory medicament pump, an insulin level of the user, a glucagon level of the user, a glucose level of the user, an A1C level of the user, an eAG level of the user, an amount of a medicament stored by the ambulatory medicament pump, or a medical history of the user.

Example 404: The system of example 402 or 403, wherein the hardware processor is further configured to execute the specific computer executable instructions to at least: retrieve the therapy data from one of: the memory, the ambulatory medicament pump, or a database connected to the system via a network; and transmit, via the voice-user interface, the therapy data to a user who generated the command.

Example 405: The system of any one of examples 371 to 404, wherein the verbal command is a data sharing command, the data sharing command comprising a request for therapy data and a recipient.

Example 406: The system of example 405, wherein the hardware processor is further configured to execute the specific computer executable instructions to at least: retrieve the therapy data from one of: the memory, the ambulatory medicament pump, or a database connected to the system via a network; transmit, via a network interface, the therapy data to the recipient; receive, via the network interface, a delivery confirmation signal from the recipient, the delivery confirmation signal indicating that the requested therapy data was successfully transmitted to the recipient; and transmit, via the voice-user interface, the delivery confirmation signal.

Example 407: The system of any one of examples 371 to 406, wherein the verbal command is a medicament dose calculation command.

Example 408: The system of example 407, wherein the hardware processor is further configured to execute the specific computer executable instructions to at least: prompt the user, via the voice-user interface, to confirm a dose calculation formula; and receive, via the voice-user interface, confirmation from the user that the dose calculation formula is correct.

Example 409: The system of example 408, wherein the hardware processor is further configured to execute the specific computer executable instructions to at least: receive, via the voice-user interface, a change to the dose calculation formula from the user, wherein the change includes at least one updated medicament dose calculation factor; and update the dose calculation formula based on the change.

Example 410: The system of any one of examples 407 to 409, wherein the hardware processor is further configured to execute the specific computer executable instructions to at least: transmit the medicament dose calculation command to the ambulatory medicament pump; receive a calculated medicament dose from the ambulatory medicament pump, the medicament dose calculated based on therapy data; and transmit, via the voice-user interface, the calculated medicament dose to a user who generated the command.

Example 411: The system of example 407, wherein the hardware processor is further configured to execute the specific computer executable instructions to at least: calculate a medicament dose based on therapy data, wherein the therapy data is stored in one of: the memory, the ambulatory medicament pump, or a database connected to the system via a network; and transmit, via the voice-user interface, the calculated medicament dose to a user who generated the command.

Example 412: The system of example 410 or 411, wherein the hardware processor is further configured to execute the specific computer executable instructions to at least: prompt the user, via the voice-user interface, to issue a dose command, the dose command comprising a request to administer the calculated medicament dose; and in response to receiving the dose command, identify the ambulatory medicament pump to receive the dose command.

Example 413: The system of example 412, wherein the hardware processor is further configured to execute the specific computer executable instructions to at least: in response to receiving the dose command, transmit an execution command to the ambulatory medicament pump, the execution command comprising computer-executable instructions to perform the dose command.

Example 414: The system of example 410 or 411, wherein the hardware processor is further configured to execute the specific computer executable instructions to at least: receive, via the voice-user interface, a dose command from the user, the dose command comprising a request to administer the calculated medicament dose; and in response to receiving the dose command, identify the ambulatory medicament pump to receive the dose command.

Example 415: The system of example 414, wherein the hardware process further is configured to execute the specific computer executable instructions to at least: in response to receiving the dose command, transmit an execution command to the ambulatory medicament pump, the execution command comprising computer-executable instructions to perform the dose command.

Example 416: The system of any one of examples 410 to 415, wherein the hardware processor is further configured to execute the specific computer executable instructions to at least: calculate a medicament dose based on therapy data, wherein the therapy data is stored in a database connected to the system via a network; and transmit an execution command to the ambulatory medicament pump, the execution command comprising computer-executable instructions to administer the calculated medicament dose.

Example 417: The system of any one of examples 371 to 416, wherein the hardware processor is further configured to execute the specific computer executable instructions to at least: receive an alert signal from the ambulatory medicament pump; and transmit, via the voice-user interface, the alert signal to the user.

Example 418: The system of example 417, wherein the alert signal indicates one of: a low battery level of the ambulatory medicament pump, a high glucose level of the user, a low glucose level of the user, a low medicament level, or that the system and the ambulatory medicament pump are disconnected.

Example 419: The system of example 417 or 418, wherein the hardware processor is further configured to execute the specific computer executable instructions to at least: transmit, via a network interface, the alert signal to a physician of the user.

Example 420: The system of any one of examples 417 to 419, wherein the hardware processor is further configured to execute the specific computer executable instructions to at least: determine whether an emergency command should be sent to the ambulatory medicament pump based on the alert signal; in response to determining that the emergency command should be sent to the ambulatory medicament pump, prompt the user, via the voice-user interface, to confirm the emergency command; receive, via the voice-user interface, the emergency command from the user; receive the connection confirmation signal from the ambulatory medicament pump; and transmit, via a network interface, an execution command to the ambulatory medicament pump, wherein the execution command comprises computer-executable instructions to perform the emergency command.

Example 421: The system of any one of examples 417 to 420, wherein the hardware processor is further configured to execute the specific computer executable instructions to at least: determine whether an emergency command should be sent to the ambulatory medicament pump based on the alert signal; in response to determining that the emergency command should be sent to the ambulatory medicament pump, receive, via a network interface, the connection confirmation signal from the ambulatory medicament pump; and in response to receiving the connection confirmation signal from the ambulatory medicament pump, transmit, an execution command to the ambulatory medicament pump, wherein the execution command comprises computer-executable instructions to perform the emergency command.

Example 422: The system of any one of examples 371 to 421, wherein the hardware processor is further configured to execute the specific computer executable instructions to at least: in response to not receiving the connection confirmation signal from the ambulatory medicament pump, inform the user, via the voice-user interface, that the system and the ambulatory medicament pump are not connected.

Example 423: The system of any one of examples 371 to 422, wherein the hardware processor is further configured to execute the specific computer executable instructions to at least: receive, via the voice-user interface, an abort command from the user, the abort command configured to abort the verbal command; and in response to receiving the abort command, identify the ambulatory medicament pump to receive the abort command.

Example 424: The system of example 423, wherein the hardware processor is further configured to execute the specific computer executable instructions to at least: in response to receiving the abort command, transmit, a stop command to the ambulatory medicament pump comprising computer executable instructions to abort execution of the verbal command; and receive the verification signal from the ambulatory medicament pump, wherein the verification signal indicates that the execution command was successfully aborted.

Example 425: The system of any one of examples 371 to 424, wherein the hardware processor is further configured to execute the specific computer executable instructions to at least: receive, via the voice-user interface, a request to set up the ambulatory medicament pump from the user; prompt the user, via the voice-user interface, to name the ambulatory medicament pump; and receive, via the voice-user interface, a name for the ambulatory medicament pump.

Example 426: The system of any one of examples 371 to 425, wherein the hardware processor is further configured to execute the specific computer executable instructions to at least: receive therapy data comprising one or more of: a medicament dose, a medicament basal rate, a medicament dose calculation factor, an alert trigger, or a medical history of the user.

Example 427: The system of example 426, wherein the therapy data is received through one of: the voice-user interface or a network interface.

Example 428: The system of any one of examples 371 to 427, wherein the hardware processor is further configured to execute the specific computer executable instructions to at least: generate a therapy report; and transmit, via the voice-user interface, the therapy report to the user.

Example 429: The system of example 428, wherein the therapy report includes at least one of: a list of commands executed by the ambulatory medicament pump, a basal medicament rate, one or more medicament dose calculation levels, a glucose level of the user, an A1C level of the user, an eAG level of the user, a glucagon level of the user, a battery level of the ambulatory medicament pump, or an amount of medicament stored by the ambulatory medicament pump.

Example 430: The system of example 428 or 429, wherein the hardware processor is further configured to execute the specific computer executable instructions to at least: automatically generate the therapy report after a time period set by the user, wherein the time period is one of: daily, weekly, or monthly.

Example 431: An ambulatory medicament pump configured to execute a glucose level control system command provided by a user via a voice-user interface, the ambulatory medicament pump comprising: a medicament reservoir configured to store medicament to be delivered as therapy to a subject by the ambulatory medicament pump; a pump controller configured to command to direct the medicament from the medicament reservoir to the subject; a non-transitory memory configured to store specific computer-executable instructions; and a hardware processor in communication with the non-transitory memory and configured to execute the specific computer-executable instructions to at least: receive, via a network interface, an execution command from a pump management system, the execution command comprising computer executable instructions to perform a verbal command; perform the execution command; and transmit, via the network interface, a verification signal to the pump management system, the verification signal indicating that the execution command was successfully performed.

Example 432: The ambulatory medicament pump of example 431 wherein the ambulatory medicament pump is connected to the pump management system by one of: a broadband cellular network, a local wireless network, a personal area network, or a direct electrical connection.

Example 433: The ambulatory medicament pump of example 431 or 432, wherein the hardware processor is further configured to execute the specific computer-executable instructions to at least: receive the verbal command from the pump management system; and generate the execution command based on the verbal command.

Example 434: The ambulatory medicament pump of any one of examples 431 to 433, wherein the hardware processor is further configured to execute the specific computer-executable instructions to at least: receive, via user interaction with the voice-user interface, the verbal command from the user.

Example 435: The ambulatory medicament pump of any one of examples 431 to 434, wherein the ambulatory medicament pump further comprises a microphone configured to receive the verbal command from the user.

Example 436: The ambulatory medicament pump of any one of examples 431 to 435, wherein the ambulatory medicament pump further comprises a speaker configured to transmit outputs from the voice-user interface to the user.

Example 437: The ambulatory medicament pump of any one of examples 431 to 436, wherein the pump management system is configured to authenticate the user using at least one of a plurality of user authentication processes, and wherein the hardware processor is further configured to execute the specific computer-executable instructions to at least: receive an authentication token generated by the pump management system.

Example 438: The ambulatory medicament pump of example 437, wherein the authentication token is valid during a validity period.

Example 439: The ambulatory medicament pump of example 438, wherein the validity period is one hour, one day, or one week.

Example 440: The ambulatory medicament pump of example 438 or 439, wherein the hardware processor is further configured to execute the specific computer-executable instructions to at least: prompt the user, via the voice-user interface, to define a duration of the validity period; and receive, via the voice-user interface, the duration provided by the user.

Example 441: The ambulatory medicament pump of any one of examples 431 to 440, wherein the hardware processor is further configured to execute the specific computer-executable instructions to at least: authenticate the user using at least one of a plurality of user authentication processes.

Example 442: The ambulatory medicament pump of example 441, wherein the hardware processor is further configured to execute the specific computer-executable instructions to at least: in response to authenticating the user, add the user to a list of authenticated users.

Example 443: The ambulatory medicament pump of example 441 or 442, wherein the hardware processor is further configured to execute the specific computer-executable instructions to at least: in response to the user failing the at least one of the plurality of user authentication processes, inform the user, via the voice-user interface, that the user is not authorized to give the verbal command.

Example 444: The ambulatory medicament pump of any one of examples 441 to 443, wherein the plurality of authentication processes comprises a passphrase authentication process, and wherein the hardware processor is further configured to execute the specific computer-executable instructions to at least: authenticate the user using the passphrase authentication process by: prompting the user, via the voice-user interface, to provide an authorized passphrase; receiving, via user interaction with the voice-user interface, a passphrase attempt provided by the user; determine whether the passphrase attempt provided by the user matches the authorized passphrase; and in response to determining that the passphrase attempt provided by the user and the authorized passphrase match, authenticating the user.

Example 445: The ambulatory medicament pump of any one of examples 441 to 444, wherein the plurality of user authentication processes comprises a voiceprint authentication process, and wherein the hardware processor is further configured to execute the specific computer-executable instructions to at least: authenticate the user using the voiceprint authentication process by: identifying the user based on the verbal command using a speaker recognition algorithm; determining whether the user is authorized to give the verbal command; and in response to determining that the user is authorized to give the verbal command, authenticating the user.

Example 446: The ambulatory medicament pump of example 445, wherein the speaker recognition algorithm is one of: a hidden Markov model, a Gaussian mixture model, a pattern matching algorithm, a neural network, or a frequency estimation algorithm.

Example 447: The ambulatory medicament pump of any one of examples 431 to 446, wherein the hardware processor is further configured to execute the specific computer-executable instructions to at least: enable a group of authorized verbal commands associated with the user based on an authentication of the user, wherein the authentication of the user verifies the user's identity using at least one of a plurality of user authentication processes; determine whether the verbal command is enabled; and in response to determining that the verbal command is enabled, generate the execution command based on the verbal command.

Example 448: The ambulatory medicament pump of example 447, wherein the group of authorized commands is enabled during a validity period.

Example 449: The ambulatory medicament pump of example 448, wherein the validity period is one hour, one day, or one week.

Example 450: The ambulatory medicament pump of example 448 or 449, wherein the hardware processor is further configured to execute the specific computer-executable instructions to at least: prompt the user, via the voice-user interface, to set a duration of the validity period; and receive, via the voice-user interface, the duration from the user.

Example 451: The ambulatory medicament pump of any one of examples 431 to 450, wherein the hardware processor is further configured to execute the specific computer executable instructions to at least: in response to determining that the verbal command is disabled, inform the user, via the voice-user interface, that the user is not authorized to give the command.

Example 452: The ambulatory medicament pump of any one of examples 452 to 451, wherein the hardware processor is further configured to execute the specific computer-executable instructions to at least: in response to authenticating the user, generate an authentication token.

Example 453: The ambulatory medicament pump of example 452, wherein the authentication token is valid during a validity period.

Example 454: The ambulatory medicament pump of example 453, wherein the validity period is one hour, one day, or one week.

Example 455: The ambulatory medicament pump of example 453 or 454, wherein the hardware processor is further configured to execute the specific computer-executable instructions to at least: prompt the user, via the voice-user interface, to define a duration of the validity period; and receive, via the voice-user interface, the duration provided by the user.

Example 456: The ambulatory medicament pump of any one of examples 431 to 455, wherein the hardware processor is further configured to execute the specific computer-executable instructions to at least: transmit a confirmation request to the pump management system; receive a confirmation signal from the pump management system; and in response to receiving the confirmation signal, perform the execution command.

Example 457: The ambulatory medicament pump of any one of examples 431 to 456, wherein the hardware processor is further configured to execute the specific computer-executable instructions to at least: prompt the user, via the voice-user interface, to confirm the verbal command; and receive, via the voice-user interface, a confirmation from the user.

Example 458: The ambulatory medicament pump of any one of examples 431 to 457, wherein the hardware processor is further configured to execute the specific computer-executable instructions to at least: record the command, the identity of a user, and a time that the execution command was successfully executed.

Example 459: The ambulatory medicament pump of any one of examples 431 to 458, wherein the verbal command is a therapy modification command, the therapy modification command configured to one of: administer a medicament or modify a medicament dose.

Example 460: The ambulatory medicament pump of example 459, wherein the medicament is one of insulin, glucagon, a bolus dose, or a Gburst dose.

Example 461: The ambulatory medicament pump of example 459 or 460, wherein the hardware processor is further configured to execute the specific computer-executable instructions to at least: perform the execution command by: instructing the pump controller to execute the therapy modification command.

Example 462: The ambulatory medicament pump of any one of examples 431 to 461, wherein the verbal command is a therapy modification command, the therapy modification command configured to modify a medicament calculation factor.

Example 463: The ambulatory medicament pump of example 462, wherein the medicament calculation factor is one of: a basal medicament rate, a carbohydrate ratio, a correction factor, or an insulin action time.

Example 464: The ambulatory medicament pump of any one of examples 459 to 463, wherein the hardware processor is further configured to execute the specific computer-executable instructions to at least: verify the safety and efficacy of the therapy modification command based on therapy data; and in response to verifying the safety and efficacy of the command, performing the execution command.

Example 465: The ambulatory medicament pump of example 464, wherein the verbal command is a data retrieval command comprising a request for the therapy data.

Example 466: The ambulatory medicament pump of example 465, wherein the therapy data is one of: a battery level of the ambulatory medicament pump, an insulin level of the user, a glucagon level of the user, a glucose level of the user, an A1C level of the user, an eAG level of the user, an amount of a medicament stored by the ambulatory medicament pump, or a medical history of the user.

Example 467: The ambulatory medicament pump of any one of examples 464 to 466, wherein the therapy data is stored on the non-transitory memory, and wherein the hardware processor is further configured to execute the specific computer-executable instructions to at least: perform the execution command by: transmitting the therapy data to the pump management system.

Example 468: The ambulatory medicament pump of any one of examples 464 to 467, wherein the therapy data is stored on the non-transitory memory, and wherein the hardware processor is further configured to execute the specific computer-executable instructions to at least: perform the execution command by: transmitting, via the voice-user interface, the therapy data to the user.

Example 469: The ambulatory medicament pump of any one of examples 464 to 466, wherein the hardware processor is further configured to execute the specific computer-executable instructions to at least: retrieve the therapy data from the pump management system or a database connected to the pump via a network; and transmit, via the voice-user interface, the therapy data to the user.

Example 470: The ambulatory medicament pump of any one of examples 431 to 469, wherein the verbal command is a medicament dose calculation command.

Example 471: The ambulatory medicament pump of example 470, wherein the hardware processor is further configured to execute the specific computer-executable instructions to at least: prompt the user, via the voice-user interface to confirm a dose calculation formula; and receive, via the voice-user interface, a confirmation from the user that the dose calculation formula is correct.

Example 472: The ambulatory medicament pump of example 471, wherein the hardware processor is further configured to execute the specific computer-executable instructions to at least: receive, via the voice-user interface, a change to the dose calculation formula from the user, wherein the change includes at least one updated medicament dose calculation factor; and update the dose calculation formula based on the change.

Example 473: The ambulatory medicament pump of any one of examples 464 to 472, wherein the hardware processor is further configured to execute the specific computer-executable instructions to at least: perform the execution command by: calculating the medicament dose based on therapy data; and transmitting, via the voice-user interface the calculated medicament dose to the user.

Example 474: The ambulatory medicament pump of any one of examples 464 to 473, wherein the hardware processor is further configured to execute the specific computer-executable instructions to at least: perform the execution command by: retrieving the therapy data from one of: the non-transitory memory, the pump management system, or a database connected to the ambulatory medicament pump via a network.

Example 475: The ambulatory medicament pump of example 473, wherein the hardware processor is further configured to execute the specific computer-executable instructions to at least: prompt the user, via the voice-user interface, to issue a dose command, the dose command comprising a request to administer the calculated medicament dose; and in response to receiving the dose command, instruct the pump controller to administer the dose.

Example 476: The ambulatory medicament pump of any one of examples 464 to 472, wherein the hardware processor is further configured to execute the specific computer-executable instructions to at least: perform the execution command by: calculating the medicament dose based on the therapy data; and administering the calculated dose.

Example 477: The ambulatory medicament pump of any one of examples 431 to 476, wherein the hardware processor is further configured to execute the specific computer-executable instructions to at least: generate an alert signal; and transmit the alert signal, via the voice-user interface, to the user.

Example 478: The ambulatory medicament pump of example 477, wherein the alert signal indicates one of: a low battery level of the ambulatory medicament pump, a high glucose level of the user, a low glucose level of the user, a low medicament level, or that the system and the ambulatory medicament pump are disconnected.

Example 479: The ambulatory medicament pump of example 477 or 478, wherein the hardware processor is further configured to execute the specific computer-executable instructions to at least: transmit, via a network interface, the alert signal to a physician of the user.

Example 480: The ambulatory medicament pump of any one of examples 477 to 479, wherein the hardware processor is further configured to execute the specific computer-executable instructions to at least: receive an emergency command from the pump management system; and perform the execution command by: executing the emergency command.

Example 481: The ambulatory medicament pump of any one of examples 477 to 480, wherein the hardware processor is further configured to execute the specific computer-executable instructions to at least: determine whether an emergency command should be executed; in response to determining that the emergency command should be executed, prompt the user, via the voice-user interface, to confirm the emergency command; receive, via the voice-user interface, the emergency command from the user; and perform the execution command by: executing the emergency command.

Example 482: The ambulatory medicament pump of any one of examples 431 to 481, wherein the hardware processor is further configured to execute the specific computer-executable instructions to at least: receive a stop command from the pump management system; in response to receiving the stop command, abort the execution command; and transmit the verification signal to the pump management system, the verification signal indicating that the execution command was successfully aborted.

Example 483: The ambulatory medicament pump of any one of examples 431 to 482, wherein the hardware processor is further configured to execute the specific computer-executable instructions to at least: receive, via the voice-user interface, an abort command from the user, the abort command configured to abort the execution command; in response to receiving the abort command, abort the execution command; and transmit the verification signal to the pump management system, the verification signal indicating that the execution command was successfully aborted.

Example 484: The ambulatory medicament pump of any one of examples 431 to 483, wherein the hardware processor is further configured to execute the specific computer-executable instructions to at least: receive, via the voice-user interface, a request to set up the ambulatory medicament pump from the user; prompt the user, via the voice-user interface, to name the ambulatory medicament pump; and receive, via the voice-user interface, a name for the ambulatory medicament pump.

Example 485: The ambulatory medicament pump of any one of examples 431 to 484, wherein the hardware processor is further configured to execute the specific computer-executable instructions to at least: receive therapy data comprising one or more of: a medicament dose, a medicament basal rate, a medicament dose calculation factor, an alert trigger, or a medical history of the user.

Example 486: The ambulatory medicament pump of example 485, wherein the therapy data is received through one of: the voice-user interface or a network interface.

Example 487: The ambulatory medicament pump of any one of examples 431 to 486, wherein the hardware processor is further configured to execute the specific computer-executable instructions to at least: generate a therapy report; and transmit the therapy report to the pump management system.

Example 488: The ambulatory medicament pump of example 487, wherein the hardware processor is further configured to execute the specific computer-executable instructions to at least: transmit the therapy report, via the voice-user interface, to the user.

Example 489: The ambulatory medicament pump of example 487 or 488, wherein the therapy report includes at least one of: a list of commands executed by the ambulatory medicament pump, a basal medicament rate, one or more medicament dose calculation levels, a glucose level of the user, an A1C level of the user, an eAG level of the user, a glucagon level of the user, a battery level of the ambulatory medicament pump, or an amount of medicament stored by the ambulatory medicament pump.

Example 490: The ambulatory medicament pump of any one of examples 487 to 489, wherein the hardware processor is further configured to execute the specific computer executable instructions to at least: automatically generate the therapy report after a time period set by the user, wherein the time period is one of: daily, weekly, or monthly.

Example 491: A glucose level control system configured to determine an amount of total remaining medicament and to generate a user alert configured to indicate that additional supply of medicament may be necessary, the glucose level control system comprising: a wireless data interface configured to connect to a remote electronic device; a non-transitory memory configured to store specific computer-executable instructions; and a hardware processor in communication with the non-transitory memory and configured to execute the specific computer-executable instructions to at least: receive an indication of an amount of initial medicament in possession of a subject; determine, by a medicament rate determining process, a rate of consumption of medicament; determine the amount of total remaining medicament based on a function of the amount of initial medicament in possession of the subject and the rate of consumption of the medicament; determine that the amount of the total remaining medicament is below a threshold amount; in response to determining that the amount of the total remaining medicament is below the threshold amount, automatically generate the user alert configured to indicate that additional supply of medicament may be necessary; and transmit, via the wireless data interface, a request for the additional supply of medicament to the remote electronic device.

Example 492: The glucose level control system of example 491, wherein glucose level control system further comprises an ambulatory medicament pump, the ambulatory medicament pump comprising a reservoir configured to store medicament to be delivered as therapy to a subject by the ambulatory medicament pump.

Example 493: The glucose level control system of example 491 or 492, further comprising any one of the features of any one of examples 1 to 30.

Example 494: A glucose level control system configured to transmit a request to modify glucose control therapy administered to a subject via a remote computing environment, the glucose level control system comprising: a wireless data interface configured to connect to the remote computing environment via a network connection comprising a wide area network; a non-transitory memory configured to store specific computer-executable instructions; and a hardware processor in communication with the non-transitory memory and configured to execute the specific computer-executable instructions to at least: transmit, via the wireless data interface, the request to modify glucose control therapy administered to the subject to the remote computing environment; receive, via the wireless data interface, an indication that the request to modify therapy is approved; and in response to the indication that the request to modify the glucose control therapy is approved, modify the glucose control therapy administered to the subject.

Example 495: The glucose level control system of example 494, wherein glucose level control system further comprises an ambulatory medicament pump, the ambulatory medicament pump comprising a reservoir configured to store medicament to be delivered as therapy to a subject by the ambulatory medicament pump.

Example 496: The glucose level control system of example 494 or 495, further comprising any one of the features of any one of examples 31 to 40.

Example 497: A method for modifying glucose control therapy administered by a glucose level control system to a subject, the method comprising: by an electronic processor of a glucose level control system executing instructions stored on non-transitory memory connected to the electronic processor: generating an initial dose output configured to for administration of initial glucose control therapy to the subject; receiving, via user interaction with a therapy modification control element, a request to modify the initial glucose control therapy administered to the subject; transmitting to a remote computing environment, via a wireless wide area network data interface in communication with the electronic processor, the request to modify the initial glucose control therapy administered to the subject; receiving, via the wireless wide area network data interface, an indication that the request to modify the initial glucose control therapy is approved; and in response to the indication that the request to modify the initial glucose control therapy is approved, generating a modified dose output for administration of modified glucose control therapy to the subject.

Example 498: The method of example 497, further comprising delivering the initial glucose control therapy and the modified glucose control therapy via an ambulatory medicament pump.

Example 499: The method of example 497 or 498, further comprising any one of the features of any one of examples 41 to 47.

Example 500: A remote therapy modification system configured to generate commands to remotely modify glucose control therapy administered to a subject by a glucose level control system, the remote therapy modification system comprising: a non-transitory memory configured to store specific computer-executable instructions; and a hardware processor in communication with the non-transitory memory and configured to execute the specific computer-executable instructions to at least: receive, via user interaction with a therapy modification control element, a request to remotely modify glucose control therapy administered to the subject by the glucose level control system; receive, via a network interface, a connection confirmation signal from a remote computing environment, the connection confirmation signal indicating that a wireless wide area network data connection exists between the remote computing environment and the glucose level control system; in response to receiving the request to modify the glucose control therapy and receiving the connection confirmation signal, transmit, via the network interface, a remote therapy modification command to the remote computing environment, the remote therapy modification command configured to modify the glucose control therapy administered to the subject via the glucose level control system; and receive, via the network interface, a modification verification signal from the remote computing environment, the modification verification signal indicating whether the glucose control therapy administered by the glucose level control system was successfully modified.

Example 501: The glucose level control system of example 500, wherein glucose level control system further comprises an ambulatory medicament pump configured to deliver the glucose control therapy.

Example 502: The glucose level control system of example 500 or 501, further comprising any one of the features of any one of examples 48 to 57.

Example 503: A method for generating commands to remotely modify glucose control therapy administered to a subject by a glucose level control system, the method comprising: by an electronic processor executing instructions stored on non-transitory memory connected to the electronic processor: receiving a request to remotely modify therapy administered to the subject by the glucose level control system; receiving, via a network interface, a connection confirmation signal from a remote computing environment, the connection confirmation signal indicating that a wireless wide area network data connection exists between the remote computing environment and the glucose level control system; in response to receiving the request to modify the glucose control therapy and receiving the connection confirmation signal, transmitting, via the network interface, a remote therapy modification command to the remote computing environment, the remote therapy modification command configured to modify the glucose control therapy administered to the subject via the glucose level control system; and receiving, via the network interface, a modification verification signal from the remote computing environment, the modification verification signal indicating whether the glucose control therapy administered by the glucose level control system was successfully modified.

Example 504: The method of example 503, further comprising delivering the glucose control therapy via an ambulatory medicament pump.

Example 505: The method of example 503 or 504, further comprising any one of the features of any one of examples 58 to 60.

Example 506: A glucose level control system configured to automatically generate a user prompt comprising an infusion set ordering interface based on an estimate of remaining infusion sets falling below a reordering threshold, the glucose level control system comprising: a non-transitory memory configured to store specific computer-executable instructions; and an electronic processor in communication with the non-transitory memory and configured to execute the specific computer-executable instructions to at least: receive an indication of a number of initial infusion sets in possession of a subject; monitor a usage of infusion sets over a period by receiving at least one of a plurality of infusion set change indications during the period, wherein the plurality of infusion set change indications comprises: an electronic cartridge change request, received via user interaction with a medicament cartridge change interface, to change a medicament cartridge; an electronic infusion set priming request, received via user interaction with an infusion set priming interface, to prime an infusion set; and an infusion set failure alert indicating that the infusion set has a failure; determine the estimate of remaining infusion sets in possession of the subject at the end of the period based on the number of initial infusion sets and the usage of infusion sets during the period; determine that the estimate of remaining infusion sets falls below the reordering threshold; in response to determining that the estimate of remaining infusion sets falls below the reordering threshold, automatically generate the user prompt comprising the infusion set ordering interface; receive, via user interaction with the infusion set ordering interface, a request to order additional infusion sets; and in response to receiving the request to order additional infusion sets, transmit a purchase order for additional infusion sets.

Example 507: The glucose level control system of example 506, wherein glucose level control system further comprises an ambulatory medicament pump, the ambulatory medicament pump comprising a medicament delivery interface comprising a pump controller configured to command to direct a medicament from the ambulatory medicament pump to a subcutaneous depot of the subject via the infusion set.

Example 508: The glucose level control system of example 506 or 507, further comprising any one of the features of any one of examples 61 to 89.

Example 509: A method of transmitting a purchase order for additional infusion sets from a glucose level control system, the method comprising: by an electronic processor of the glucose control system executing specific computer-executable instructions stored in a non-transitory memory in communication with the electronic processor: receiving an indication of a number of initial infusion sets in possession of a subject; monitoring a usage of infusion sets over a period by receiving at least one of a plurality of infusion set change indications during the period, wherein the plurality of infusion set change indications comprises: receiving, via user interaction with a medicament cartridge change interface, an electronic cartridge change request to change a medicament cartridge; receiving, via user interaction with an infusion set priming interface, an electronic infusion set priming request to prime an infusion set; and receiving an infusion set failure alert indicating that the infusion set has a failure; determining an estimate of remaining infusion sets in possession of the subject at the end of the period based on the number of initial infusion sets and the usage of infusion sets during the period; determining that the estimate of remaining infusion sets falls below a reordering threshold; in response to determining that the estimate of remaining infusion sets falls below the reordering threshold, automatically generating a user prompt comprising an infusion set ordering interface; receiving, via user interaction with the infusion set ordering interface, a request to order additional infusion sets; and in response to receiving the request to order additional infusion sets, transmitting a purchase order for additional infusion sets.

Example 510: The method of example 509, wherein the medicament cartridge is connected to an ambulatory medicament pump of the glucose level control system.

Example 511: The method of example 509 or 510, further comprising any one of the features of any one of examples 90 to 121.

Example 512: A glucose level control system configured to automatically generate a user prompt comprising an analyte sensor ordering interface based on an estimate of remaining analyte sensors falling below a reordering threshold, the glucose level control system comprising: a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial analyte sensors in possession of a subject; monitor a usage of analyte sensors over a period by receiving at least one of a plurality of analyte sensor change indications during the period, wherein the plurality of analyte sensor change indications comprises: an electronic analyte sensor change request, received via user interaction with a sensor change interface, to change an analyte sensor; an analyte sensor expiration alert, received from the remote electronic device via the wireless data interface, indicating that the analyte sensor has expired or has passed an expiration threshold; and an analyte sensor failure alert indicating that the analyte sensor has a failure; determine the estimate of remaining analyte sensors in possession of a subject at the end of the period based on the number of initial analyte sensors and the usage of analyte sensors during the period; determine that the estimate of remaining analyte sensors falls below the reordering threshold; in response to determining that the estimate of remaining analyte sensors falls below the reordering threshold, automatically generate the user prompt comprising the analyte sensor ordering interface; receive, via user interaction with the analyte sensor ordering interface, a request to order additional analyte sensors; and in response to receiving the request to order additional analyte sensors, transmit a purchase order for additional analyte sensors.

Example 513: The glucose level control system of example 512, wherein the analyte sensor is connected to an ambulatory medicament pump of the glucose level control system.

Example 514: The glucose level control system of example 512 or 513, further comprising any one of the features of any one of examples 122 to 147.

Example 515: A method of transmitting a purchase order for additional analyte sensors from a glucose level control system, the method comprising: by an electronic processor of the glucose level control system executing specific computer-executable instructions stored in a non-transitory memory in communication with the electronic processor: receiving an indication of a number of initial analyte sensors in possession of a subject; monitoring a usage of analyte sensors over a period by receiving at least one of a plurality of analyte sensor change indications during the period, wherein the plurality of analyte sensor change indications comprises: receiving, via user interaction with a sensor change interface, an electronic analyte sensor change request, to change an analyte sensor; receiving, via a wireless data interface in communication with a remote electronic device, an analyte sensor expiration alert indicating that the analyte sensor has expired or has passed or is at an expiration threshold; and receiving an analyte sensor failure alert indicating that the analyte sensor has a failure; determining an estimate of remaining analyte sensors in possession of the subject at the end of the period based on the number of initial analyte sensors and the usage of analyte sensors during the period; determining that the estimate of remaining analyte sensors falls below a reordering threshold; in response to determining that the estimate of remaining analyte sensors falls below the reordering threshold, automatically generating a user prompt comprising an analyte sensor ordering interface; receiving, via user interaction with the analyte sensor ordering interface, a request to order additional analyte sensors; and in response to receiving the request to order additional analyte sensors, transmitting a purchase order for additional analyte sensors.

Example 516: The method of example 515, wherein the analyte sensor is connected to an ambulatory medicament pump of the glucose level control system.

Example 517: The method of example 515 or 516, further comprising any one of the features of any one of examples 148 to 171.

Example 518: A glucose level control system configured to monitor a usage of infusion sets over a period by receiving at least one of a plurality of infusion set change indications during the period, the glucose level control system comprising: a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial infusion sets in possession of a subject; monitor a usage of infusion sets over a period by receiving at least one of a plurality of infusion set change indications during the period, wherein the plurality of infusion set change indications comprises: an electronic cartridge change request, received via user interaction with a medicament cartridge change interface, to change a medicament cartridge; an electronic infusion set priming request, received via user interaction with an infusion set priming interface, to prime an infusion set; and an infusion set failure alert indicating that the infusion set has a failure; and transmit infusion set data regarding the usage of infusion sets, via the wireless data interface, to the remote electronic device.

Example 519: The glucose level control system of example 518, wherein glucose level control system further comprises an ambulatory medicament pump, the ambulatory medicament pump comprising a medicament delivery interface comprising a pump controller configured to command to direct a medicament from the ambulatory medicament pump to a subcutaneous depot of the subject via the infusion set.

Example 520: The glucose level control system of example 518 or 519, further comprising any one of the features of any one of examples 172 to 191.

Example 521: A method of monitoring a usage of infusion sets by a glucose level control system, the method comprising: by an electronic processor of the glucose level control system executing specific computer-executable instructions stored in a non-transitory memory in communication with the electronic processor: receiving an indication of a number of initial infusion sets in possession of a subject; monitoring a usage of infusion sets over a period by receiving at least one of a plurality of infusion set change indications during the period, wherein the plurality of infusion set change indications comprises: receiving, via user interaction with a medicament cartridge change interface, an electronic cartridge change request to change a medicament cartridge; receiving, via user interaction with an infusion set priming interface, an electronic infusion set priming request to prime an infusion set; and receiving an infusion set failure alert indicating that the infusion set has a failure; and transmitting infusion set data regarding the usage of infusion sets, via a wireless data interface, to a remote electronic device.

Example 522: The method of example 521, wherein the infusion set is connected to an ambulatory medicament pump of the glucose level control system.

Example 523: The method of example 521 or 522, further comprising any one of the features of any one of claims 192 to 204.

Example 524: A glucose level control system configured to monitor a usage of analyte sensors over a period by receiving at least one of a plurality of analyte sensor change indications during the period, the glucose level control system comprising: a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial analyte sensors in possession of a subject; monitor a usage of analyte sensors over a period by receiving at least one of a plurality of analyte sensor change indications during the period, wherein the plurality of analyte sensor change indications comprises: an electronic analyte sensor change request, received via user interaction with a sensor change interface, to change an analyte sensor; an analyte sensor expiration alert, received from the remote electronic device via the wireless data interface, indicating that the analyte sensor has expired or has passed or is at an expiration threshold; and an analyte sensor failure alert indicating that the analyte sensor has a failure; and transmit analyte sensor data regarding the usage of the analyte sensors, via the wireless data interface, to the remote electronic device.

Example 525: The system of example 524, wherein the analyte sensor is connected to an ambulatory medicament pump of the glucose level control system.

Example 526: The system of example 524 or 525, further comprising any one of the features of any one of examples 205 to 222.

Example 527: A method of monitoring a usage of analyte sensors for a glucose level control system, the method comprising: by an electronic processor of the glucose level control system executing specific computer-executable instructions stored in a non-transitory memory in communication with the electronic processor: receiving an indication of a number of initial analyte sensors in possession of a subject; monitoring a usage of analyte sensors over a period by receiving at least one of a plurality of analyte sensor change indications during the period, wherein the plurality of analyte sensor change indications comprises: receiving, via user interaction with a sensor change interface, an electronic analyte sensor change request, to change an analyte sensor; receiving, from a remote electronic device via a wireless data interface, an analyte sensor expiration alert, indicating that the analyte sensor has expired or has passed or is at an expiration threshold; and receiving an analyte sensor failure alert indicating that the analyte sensor has a failure; and transmitting analyte sensor data regarding the usage of analyte sensors, via the wireless data interface, to a remote electronic device.

Example 528: The method of example 527, wherein the analyte sensor is connected to an ambulatory medicament pump of the glucose level control system.

Example 529: The method of example 527 or 528, further comprising any one of the features of any one of examples 223 to 238.

Example 530: A glucose level control system configured to automatically generate a user prompt comprising a transmitter ordering interface based on an estimate of remaining transmitters falling below a reordering threshold, the glucose level control system comprising: a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial transmitters in possession of a subject; monitor a usage of transmitters over a period by receiving at least one of a plurality of transmitter change indications during the period, wherein the plurality of transmitter change indications comprises: an electronic transmitter change request, received via user interaction with a transmitter change interface, to change a transmitter connected to an analyte sensor; a transmitter expiration alert, received from the remote electronic device via the wireless data interface, indicating that the transmitter has expired or has passed or is at an expiration threshold; and a transmitter failure alert indicating that the transmitter has a failure; determine the estimate of remaining transmitters in possession of a subject at the end of the period based on the number of initial transmitters and the usage of transmitters during the period; determine that the estimate of remaining transmitters falls below the reordering threshold; in response to determining that the estimate of remaining transmitters falls below the reordering threshold, automatically generate the user prompt comprising the transmitter ordering interface; receive, via user interaction with the transmitter ordering interface, a request to order additional transmitters; and in response to receiving the request to order additional transmitters, transmit a purchase order for additional transmitters to the remote electronic device.

Example 531: The glucose level control system of example 530, wherein the transmitter is connected to an ambulatory medicament pump of the glucose level control system.

Example 532: The glucose level control system of example 530 or 531, further comprising any one of the features of any one of examples 239 to 242.

Example 533: A glucose level control system configured to monitor a usage of transmitters over a period by receiving at least one of a plurality of transmitter change indications during the period, the glucose level control system comprising: a wireless data interface configured to facilitate communication with a remote electronic device; a non-transitory memory configured to store specific computer-executable instructions; and an electronic processor in communication with the non-transitory memory and configured to execute the specific computer-executable instructions to at least: receive an indication of a number of initial transmitters in possession of a subject; monitor a usage of transmitters over a period by receiving at least one of a plurality of transmitter change indications during the period, wherein the plurality of transmitter change indications comprises: an electronic transmitter change request, received via user interaction with a transmitter change interface, to change a transmitter connected to an analyte sensor; a transmitter expiration alert, received from the remote electronic device via the wireless data interface, indicating that the transmitter has expired or has passed or is at an expiration threshold; and a transmitter failure alert indicating that the transmitter has a failure; and transmit transmitter data regarding the usage of transmitters, via the wireless data interface, to the remote electronic device.

Example 534: The glucose level control system of example 533, wherein the transmitter is connected to an ambulatory medicament pump of the glucose level control system.

Example 535: The glucose level control system of example 533 or 534, further comprising any one of the features of any one of examples 243 to 258.

Example 536: A method of transmitting a purchase order for additional transmitters from a glucose level control system, the method comprising: by an electronic processor of the glucose level control system executing specific computer-executable instructions stored in a non-transitory memory in communication with the electronic processor: receiving an indication of a number of initial transmitters in possession of a subject; monitoring a usage of transmitters over a period by receiving at least one of a plurality of transmitter change indications during the period, wherein the plurality of transmitter change indications comprises: receiving, via user interaction with a transmitter change interface, an electronic transmitter change request, to change a transmitter in communication with the glucose level control system; receiving, via a wireless data interface in communication with a remote electronic device, a transmitter expiration alert, indicating that the transmitter has expired or has passed or is at an expiration threshold; and receiving a transmitter failure alert indicating that the transmitter has a failure; determining an estimate of remaining transmitters in possession of the subject at the end of the period based on the number of initial transmitters and the usage of transmitters during the period; determining that the estimate of remaining transmitters falls below a reordering threshold; in response to determining that the estimate of remaining transmitters falls below the reordering threshold, automatically generating a user prompt comprising a transmitter ordering interface; receiving, via user interaction with the transmitter ordering interface, a request to order additional transmitters; and in response to receiving the request to order additional transmitters, transmitting a purchase order for additional transmitters.

Example 537: The method of example 536, wherein the transmitter is connected to an ambulatory medicament pump of the glucose level control system.

Example 538: The method of example 536 or 537, further comprising any one of the features of any one of examples 259 to 262.

Example 539: A method of monitoring a usage of transmitters for a glucose level control system, the method comprising: by an electronic processor of the glucose level control system executing specific computer-executable instructions stored in a non-transitory memory in communication with the electronic processor: receiving an indication of a number of initial transmitters in possession of a subject; monitoring a usage of transmitters over a period by receiving at least one of a plurality of transmitter change indications during the period, wherein the plurality of transmitter change indications comprises: receiving, via user interaction with a transmitter change interface, an electronic transmitter change request, to change a transmitter in communication with the glucose level control system; receiving, via a wireless data interface in communication with a remote electronic device, a transmitter expiration alert, indicating that the transmitter has expired or has passed or is at an expiration threshold; and receiving a transmitter failure alert indicating that the transmitter has a failure; and transmitting transmitter data regarding the usage of transmitters, via the wireless data interface, to the remote electronic device.

Example 540: The method of example 539, wherein the transmitter is connected to an ambulatory medicament pump of the glucose level control system.

Example 541: The method of example 539 or 540, further comprising any one of the features of any one of examples 263 to 278.

Example 542: A computer-implemented method of generating an aggregate report, wherein the aggregate report is usable for evaluating a quality of glycemic control of one or more subjects receiving glucose control therapy via a glucose level control system, the computer-implemented method comprising: by an electronic processor of a computing system in a patient data network, wherein the electronic processor executes specific computer-executable instructions stored in a non-transitory memory in communication with the electronic processor, establishing a first data connection to a first glucose level control system providing glucose therapy to a first subject; sending a first electronic request to the first glucose level control system, wherein the first electronic request causes the first glucose level control system to transmit first therapy data stored on the first glucose level control system to the computing system over the first data connection; receiving, via the first data connection, first therapy data, wherein the first therapy data comprises data associated with glycemic control of the first subject and data associated with glucose control therapy administered to the first subject; establishing a second data connection to a second glucose level control system providing glucose therapy to a second subject; sending a second electronic request to the second glucose level control system, wherein the second electronic request causes the second glucose level control system to transmit second therapy data stored on the second glucose level control system to the computing system over the second data connection; receiving, via the second data connection, second therapy data, wherein the second therapy data comprises data associated with glycemic control of the second subject and data associated with glucose control therapy administered to the second subject; determining first values of one or more biometric parameters based at least in part on the first therapy data and second values of one or more biometric parameters based at least in part on the second therapy data, wherein the one or more biometric parameters are associated with a health condition; generating a comparative assessment based on (1) reference data comprising reference values associated with the one or more biometric parameters and/or the first and the second therapy data and (2) subject data, wherein the subject data comprises at least one of: aggregate biometric parameter data comprising the first and second values of the one or more biometric parameters, or aggregate therapy data comprising the first and the second therapy data; and generating the aggregate report based at least in part on the comparative assessment, wherein the aggregate report comprises at least one evaluation, wherein the at least one evaluation is indicative of the quality of the glycemic control of the first subject and the second subject with reference to at least one glycemic control criterion.

Example 543: The method of example 542, wherein the first therapy data comprises first pump usage data and the second therapy data comprises second pump usage data.

Example 544: The method of example 542 or 543, further comprising any one of the features of any one of examples 279 to 306.

Example 545: A computing system included in a patient data network, wherein the computing system is configured to generate an aggregate report, wherein the aggregate report is usable for evaluating a quality of glycemic control of one or more subjects receiving glucose control therapy via a glucose level control system, the computing system comprising: a memory configured to store specific computer-executable instructions; and a hardware processor in communication with the memory and configured to execute the specific computer-executable instructions to at least: establish a first data connection to a first glucose level control system; send a first electronic request to the first glucose level control system, wherein the first electronic request causes the first glucose level control system to transmit first therapy data stored on the first glucose level control system to the computing system over the first data connection; receive, via the first data connection, the first therapy data, wherein the first therapy data comprises data associated with a glycemic control of a first subject and a glucose control therapy administered to the first subject; establish a second data connection to a second glucose level control system; send a second electronic request, to the second glucose level control system, wherein the second electronic request causes the second glucose level control system to transmit second therapy data stored on the second glucose level control system to the computing system over the second data connection; receive, via the second data connection, a second therapy data from the second glucose level control system, wherein the second therapy data comprises data associated with a glycemic control of a second subject and a glucose control therapy administered to the second subject; determine first values of one or more biometric parameters based at least in part on the first therapy data and second values of one or more biometric parameters based at least in part on the second therapy data, wherein the one or more biometric parameters are associated with a health condition; generate a comparative assessment based on (1) reference data comprising reference values associated with the one or more biometric parameters and/or the first and the second therapy data and (2) subject data, wherein the subject data comprises at least one of: aggregate biometric parameter data comprising the first and second values of the one or more biometric parameters; or aggregate therapy data comprising the first and second therapy data; and generate the aggregate report based at least in part on the comparative assessment, wherein the aggregate report comprises at least one evaluation, wherein the at least one evaluation is indicative of the quality of the glycemic control of the first subject and the second subject with reference to at least one glycemic control criterion.

Example 546: The computing system of example 545, wherein the first therapy data comprises first pump usage data and the second therapy data comprises second pump usage data.

Example 547: The computing system of example 545 or 546, further comprising any one of the features of any one of examples 307 to 335.

Example 548: A therapy administration system configured to manage glucose control therapy administered to a subject by a glucose level control system, the therapy administration system comprising: a non-transitory memory configured to store specific computer-executable instructions; and a hardware processor in communication with the non-transitory memory and configured to execute the specific computer-executable instructions to at least: receive, via user interaction with a voice-user interface, a verbal command from a user; authenticate the user using at least one of a plurality of user authentication processes; receive a connection confirmation signal from the glucose level control system, the connection confirmation signal indicating that a data connection exists between the therapy administration system and the glucose level control system; in response to authenticating the user and receiving the connection confirmation signal, transmit an execution command to the glucose level control system, the execution command comprising computer-executable instructions to perform the verbal command; and receive a verification signal from the glucose level control system, the verification signal indicating whether the execution command was successfully received by the glucose level control system.

Example 549: The therapy administration system of example 548, wherein the glucose level control system comprises an ambulatory medicament pump configured to deliver medicament to a subject.

Example 550: The therapy administration system of example 548 or 549, further comprising any one of the features of any one of examples 336 to 370.

Example 551: A system configured to manage execution of a command, provided verbally by a user via a voice-user interface, by a glucose level control system, the system comprising: a non-transitory memory configured to store specific computer-executable instructions; and a hardware processor in communication with the non-transitory memory and configured to execute the specific computer-executable instructions to at least: identify the glucose level control system to receive the command using a glucose level control system identification process; receive a connection confirmation signal from the glucose level control system, the connection confirmation signal indicating that a data connection exists between the hardware processor and the glucose level control system; receive a verification signal from the glucose level control system, the verification signal indicating whether the glucose level control system received the command; and transmit the verification signal to the voice-user interface.

Example 552: The system of example 551, wherein the glucose level control system comprises an ambulatory medicament pump configured to deliver medicament to a subject.

Example 553: The system of example 551 or 552, further comprising any one of the features of any one of examples 371 to 430.

Example 554: A glucose level control system configured to execute a glucose level control system command provided by a user via a voice-user interface, the glucose level control system comprising: a non-transitory memory configured to store specific computer-executable instructions; and a hardware processor in communication with the non-transitory memory and configured to execute the specific computer-executable instructions to at least: receive, via a network interface, an execution command from a glucose level control system management system, the execution command comprising computer executable instructions to perform a verbal command; perform the execution command; and transmit, via the network interface, a verification signal to the glucose level control system management system, the verification signal indicating that the execution command was successfully performed.

Example 555: The glucose level control system of example 554, wherein glucose level control system comprises an ambulatory medicament pump, the ambulatory medicament pump comprising a medicament reservoir configured to store medicament to be delivered as therapy to a subject by the ambulatory medicament pump.

Example 556: The glucose level control system of example 554 or 555, further comprising any one of the features of any one of examples 431 to 490.

Terminology

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware. Further, the computing system may include, be implemented as part of, or communicate with an automated glucose level control system, an ambulatory medicament system, or an ambulatory medical device.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Many variations and modifications may be made to the above-described embodiments, the elements of which are to be understood as being among other acceptable examples. All such modifications and variations are intended to be included herein within the scope of this disclosure.

What is claimed is:

1. An ambulatory medicament pump configured to monitor a usage of analyte sensors over a period by receiving at least one of a plurality of analyte sensor change indications during the period, the ambulatory medicament pump comprising:
   an analyte sensor interface configured to facilitate communication with an analyte sensor;
   a wireless data interface configured to facilitate communication with a remote electronic device;
   a non-transitory memory configured to store specific computer-executable instructions; and
   an electronic processor in communication with the non-transitory memory and configured to execute the specific computer-executable instructions to at least:
      receive an indication of a number of initial analyte sensors in possession of a subject;
      monitor a usage of analyte sensors over a period by receiving at least one of a plurality of analyte sensor change indications during the period, wherein the plurality of analyte sensor change indications comprises:
         an electronic analyte sensor change request, received via user interaction with a sensor change interface, to change an analyte sensor operatively connected to the ambulatory medicament pump;
         an analyte sensor expiration alert, received from the remote electronic device via the wireless data interface, indicating that an analyte sensor has expired or has passed or is at an expiration threshold; and
         an analyte sensor failure alert, received via an analyte sensor monitoring system of the ambulatory medicament pump, indicating that an analyte sensor operatively connected to the ambulatory medicament pump has a failure; and
      transmit analyte sensor data regarding the usage of the analyte sensors, via the wireless data interface, to the remote electronic device.

2. The ambulatory medicament pump of claim 1, wherein the remote electronic device is a remote computing environment.

3. The ambulatory medicament pump of claim 1, wherein the electronic processor is further configured to execute the specific computer-executable instructions to at least:
   receive, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold.

4. The ambulatory medicament pump of claim 3, wherein the electronic processor is further configured to execute the specific computer-executable instructions to at least:
   in response to receiving the reordering message from the remote electronic device, automatically generate a user prompt comprising an analyte sensor ordering interface;
   receive, via user interaction with the analyte sensor ordering interface, a request to order additional sensors; and
   in response to receiving the request to order additional sensors, transmit a purchase order for additional analyte sensors.

5. The ambulatory medicament pump of claim 1, wherein the electronic processor is further configured to execute the specific computer-executable instructions to at least:

receive, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and recommending that a quantity of additional analyte sensors be ordered.

6. The ambulatory medicament pump of claim 5, wherein the recommended quantity of additional analyte sensors is based at least in part on the usage of analyte sensors over the period of time.

7. The ambulatory medicament pump of claim 1, wherein the electronic processor is further configured to execute the specific computer-executable instructions to at least:

receive, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and additional analyte sensors have been ordered.

8. The ambulatory medicament pump of claim 7, wherein the remote electronic device comprises payment account data associated with the subject, and wherein the remote electronic device is configured to automatically process payment for the ordered additional analyte sensors using the payment account data associated with the subject.

9. The ambulatory medicament pump of claim 1, wherein one or more of the analyte sensors are insulin sensors or glucose sensors.

10. The ambulatory medicament pump of claim 1, wherein the remote electronic device sends an indication of the analyte sensor expiration alert based on a correlation of a ship date of one of the analyte sensors with an expiration date of the analyte sensor.

11. The ambulatory medicament pump of claim 1, wherein the remote electronic device sends an indication of the analyte sensor expiration alert based on electronic expiration information associated with one or more of the analyte sensors.

12. The ambulatory medicament pump of claim 1, wherein the analyte sensor expiration alert comprises electronic expiration information associated with one or more of the analyte sensors.

13. A method of monitoring a usage of analyte sensors for an ambulatory medicament pump of a glucose level control system, the method comprising:

by an electronic processor of a glucose level control system executing specific computer-executable instructions stored in a non-transitory memory in communication with the electronic processor:

receiving an indication of a number of initial analyte sensors in possession of a subject;
monitoring a usage of analyte sensors over a period by receiving at least one of a plurality of analyte sensor change indications during the period, wherein the plurality of analyte sensor change indications comprises:
receiving, via user interaction with a sensor change interface, an electronic analyte sensor change request, to change an analyte sensor operatively connected to an ambulatory medicament pump;
receiving, from a remote electronic device via a wireless data interface, an analyte sensor expiration alert, indicating that an analyte sensor has expired or has passed or is at an expiration threshold; and
receiving, via an analyte sensor monitoring system of the ambulatory medicament pump, an analyte sensor failure alert indicating that an analyte sensor operatively connected to the ambulatory medicament pump has a failure; and
transmitting analyte sensor data regarding the usage of analyte sensors, via the wireless data interface, to the remote electronic device.

14. The method of claim 13, further comprising receiving, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold.

15. The method of claim 14, further comprising:
automatically generating a user prompt comprising an analyte sensor ordering interface in response to receiving the reordering message from the remote electronic device;
receiving, via user interaction with the analyte sensor ordering interface, a request to order additional analyte sensors; and
transmitting a purchase order for additional analyte sensors in response to receiving the request to order additional analyte sensors.

16. The method of claim 13, further comprising receiving, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and recommending that a quantity of additional analyte sensors be ordered.

17. The method of claim 16, wherein the recommended quantity of additional analyte sensors is preset.

18. The method of claim 13, wherein the remote electronic device comprises payment account data associated with the subject that is configured to be used to automatically process payment for a purchase order of additional analyte sensors.

19. The method of claim 13, wherein the remote electronic device is in communication with an insurance provider system associated with the subject, and wherein the remote electronic device is configured to automatically send a purchase order for additional analyte sensors to the insurance provider system for processing.

20. The method of claim 19, wherein the remote electronic device comprises payment account data associated with the subject, and wherein the remote electronic device is configured to automatically process payment for the purchase order for additional analyte sensors using the payment account data associated with the subject and data provided by the insurance provider system.

21. A glucose level control system configured to monitor a usage of analyte sensors over a period by receiving at least one of a plurality of analyte sensor change indications during the period, the glucose level control system comprising:
a wireless data interface configured to facilitate communication with a remote electronic device;

a non-transitory memory configured to store specific computer-executable instructions; and
an electronic processor in communication with the non-transitory memory and configured to execute the specific computer-executable instructions to at least:
  receive an indication of a number of initial analyte sensors in possession of a subject;
  monitor a usage of analyte sensors over a period by receiving at least one of a plurality of analyte sensor change indications during the period, wherein the plurality of analyte sensor change indications comprises:
    an electronic analyte sensor change request, received via user interaction with a sensor change interface, to change an analyte sensor;
    an analyte sensor expiration alert, received from the remote electronic device via the wireless data interface, indicating that an analyte sensor has expired or has passed or is at an expiration threshold; and
    an analyte sensor failure alert indicating that an analyte sensor has a failure; and
  transmit analyte sensor data regarding the usage of the analyte sensors, via the wireless data interface, to the remote electronic device.

22. The glucose level control system of claim 21, wherein one of the analyte sensors is connected to an ambulatory medicament pump of the glucose level control system.

23. The glucose level control system of claim 21, wherein the electronic processor is further configured to execute the specific computer-executable instructions to at least:
  receive, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and recommending that a quantity of additional analyte sensors be ordered.

24. The glucose level control system of claim 23, wherein the electronic processor is further configured to execute the specific computer-executable instructions to at least:
  in response to receiving the reordering message from the remote electronic device, automatically generate a user prompt comprising an analyte sensor ordering interface that provides at least the recommended quantity of additional analyte sensors to be ordered;
  receive, via user interaction with the analyte sensor ordering interface, a request to order the recommended quantity of additional analyte sensors; and
  in response to receiving the request to order the recommended quantity of additional analyte sensors, transmit a purchase order for the recommended quantity of additional analyte sensors.

25. The glucose level control system of claim 23, wherein the recommended quantity of additional analyte sensors is set by an individual involved in administering therapy to the subject.

26. The glucose level control system of claim 24, wherein the remote electronic device is in communication with an insurance provider system associated with the subject, and wherein the remote electronic device is configured to automatically send the purchase order for recommended quantity of additional analyte sensors to the insurance provider system for processing.

27. A method of monitoring a usage of analyte sensors for a glucose level control system, the method comprising:
  by an electronic processor of a glucose level control system executing specific computer-executable instructions stored in a non-transitory memory in communication with the electronic processor:
  receiving an indication of a number of initial analyte sensors in possession of a subject;
  monitoring a usage of analyte sensors over a period by receiving at least one of a plurality of analyte sensor change indications during the period, wherein the plurality of analyte sensor change indications comprises:
    receiving, via user interaction with a sensor change interface, an electronic analyte sensor change request, to change an analyte sensor;
    receiving, from a remote electronic device via a wireless data interface, an analyte sensor expiration alert, indicating that an analyte sensor has expired or has passed or is at an expiration threshold; and
    receiving an analyte sensor failure alert indicating that an analyte sensor has a failure; and
  transmitting analyte sensor data regarding the usage of analyte sensors, via the wireless data interface, to the remote electronic device.

28. The method of claim 27, wherein one of the analyte sensors is connected to an ambulatory medicament pump of the glucose level control system.

29. The method of claim 27, further comprising receiving, via the wireless data interface, a reordering message from the remote electronic device that indicates that an estimate of remaining analyte sensors in possession of the subject at the end of the period, based on the number of initial analyte sensors and the usage of analyte sensors during the period, has fallen below a reordering threshold and additional analyte sensors have been ordered.

30. The method of claim 29, further comprising:
  automatically generating a user prompt comprising an analyte sensor ordering interface that provides at least a recommended quantity of additional analyte sensors to be ordered in response to receiving the reordering message from the remote electronic device;
  receiving, via user interaction with the analyte sensor ordering interface, a request to order the recommended quantity of additional analyte sensors; and
  transmitting a purchase order for the recommended quantity of additional analyte sensors in response to receiving the request to order the recommended quantity of additional analyte sensors.

* * * * *